US010179806B2

(12) United States Patent
Garcia-Sastre et al.

(10) Patent No.: US 10,179,806 B2
(45) **Date of Patent: *Jan. 15, 2019**

(54) INFLUENZA VIRUS VACCINES AND USES THEREOF

(71) Applicant: Icahn School of Medicine at Mount Sinai, New York, NY (US)

(72) Inventors: Adolfo Garcia-Sastre, New York, NY (US); Anice C. Lowen, Decatur, GA (US); Peter Palese, New York, NY (US); John Steel, Decatur, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/616,615

(22) Filed: Jun. 7, 2017

(65) Prior Publication Data

US 2018/0002385 A1 Jan. 4, 2018

Related U.S. Application Data

(63) Continuation of application No. 13/638,148, filed as application No. PCT/US2011/030441 on Mar. 30, 2011, now Pat. No. 9,708,373.

(60) Provisional application No. 61/319,137, filed on Mar. 30, 2010.

(51) Int. Cl.

| | |
|---|---|
| ***A61K 39/00*** | (2006.01) |
| ***A61K 39/12*** | (2006.01) |
| ***C07K 14/11*** | (2006.01) |
| ***A61K 39/145*** | (2006.01) |
| ***C07K 14/005*** | (2006.01) |

(52) U.S. Cl.

CPC .............. *C07K 14/11* (2013.01); *A61K 39/12* (2013.01); *A61K 39/145* (2013.01); *C07K 14/005* (2013.01); *A61K 2039/5256* (2013.01); *A61K 2039/5258* (2013.01); *C07K 2319/00* (2013.01); *C12N 2760/16022* (2013.01); *C12N 2760/16034* (2013.01)

(58) Field of Classification Search

CPC .. A61K 2300/00; A61K 39/12; A61K 39/145; A61K 39/42; A61K 35/76; A61K 2039/6075; A61K 39/00; A61K 2039/5254; C07K 14/005; C07K 16/1018; C07K 2317/33; C07K 2317/24; C07K 14/11; C12N 2760/16134; C12N 7/00; C12N 2760/16121; C12N 2760/16122; C12N 2760/16171; C12N 15/62; C12N 2760/16034; C12N 2760/16111; C12N 2760/16151; C12N 15/86

See application file for complete search history.

(56) References Cited

U.S. PATENT DOCUMENTS

| | | | |
|---|---|---|---|
| 5,182,192 | A | 1/1993 | Steplewski et al. |
| 5,413,923 | A | 5/1995 | Kucherlapati et al. |
| 5,545,806 | A | 8/1996 | Lonberg et al. |
| 5,569,825 | A | 10/1996 | Lonberg et al. |
| 5,571,709 | A | 11/1996 | Devauchelle et al. |
| 5,573,916 | A | 11/1996 | Cheronis et al. |
| 5,589,174 | A | 12/1996 | Okuno et al. |
| 5,625,126 | A | 4/1997 | Lonberg et al. |
| 5,631,350 | A | 5/1997 | Okuno et al. |
| 5,633,425 | A | 5/1997 | Lonberg et al. |
| 5,661,016 | A | 8/1997 | Lonberg et al. |
| 5,820,871 | A | 10/1998 | Palese et al. |
| 5,854,037 | A | 12/1998 | Palese et al. |
| 5,885,793 | A | 3/1999 | Griffiths et al. |
| 5,916,771 | A | 6/1999 | Hon et al. |
| 6,001,634 | A | 12/1999 | Palese et al. |
| 6,165,476 | A | 12/2000 | Strom et al. |
| 6,337,070 | B1 | 1/2002 | Okuno et al. |
| 6,720,409 | B2 | 4/2004 | Okuno et al. |
| 6,867,293 | B2 | 3/2005 | Andrews et al. |
| 6,887,699 | B1 | 5/2005 | Palese et al. |
| 6,942,861 | B2 | 9/2005 | McKee et al. |
| 7,566,458 | B2 | 7/2009 | Yang et al. |
| 8,367,077 | B2 | 2/2013 | Zurbriggen et al. |
| 8,603,467 | B2 | 12/2013 | Chen et al. |
| 8,673,314 | B2 | 3/2014 | Garcia-Sastre et al. |
| 8,828,406 | B2 | 9/2014 | Garcia-Sastre et al. |
| 9,051,359 | B2 | 6/2015 | Garcia-Sastre et al. |
| 9,175,069 | B2 | 11/2015 | Garcia-Sastre et al. |
| 9,371,366 | B2 | 6/2016 | Garcia-Sastre et al. |
| 9,452,211 | B2 | 9/2016 | Meijberg et al. |
| 9,701,723 | B2 | 7/2017 | Garcia-Sastre et al. |
| 9,707,288 | B2 | 7/2017 | Schrader |
| 9,708,373 | B2 | 7/2017 | Garcia-Sastre et al. |
| 9,849,172 | B2 | 12/2017 | Garcia-Sastre et al. |
| 2002/0164770 | A1 | 11/2002 | Hoffman |
| 2003/0134338 | A1 | 7/2003 | Makarocskiy |
| 2004/0002061 | A1 | 1/2004 | Kawaoka |
| 2005/0009008 | A1 | 1/2005 | Robinson et al. |
| 2005/0042229 | A1 | 2/2005 | Yang et al. |

(Continued)

FOREIGN PATENT DOCUMENTS

| | | |
|---|---|---|
| CA | 2121559 | 10/1994 |
| CA | 2718923 | 9/2009 |

(Continued)

OTHER PUBLICATIONS

Bianchi et al., 2005, "Universal influenza B vaccine based on the maturational cleavage site of the hemagglutinin precursor", Journal of Virology; 79(12):7380-7388.

(Continued)

*Primary Examiner* — Rachel B Gill

(57) ABSTRACT

Provided herein are influenza hemagglutinin stem domain polypeptides, compositions comprising the same, vaccines comprising the same and methods of their use.

27 Claims, 11 Drawing Sheets

Figure 4A:
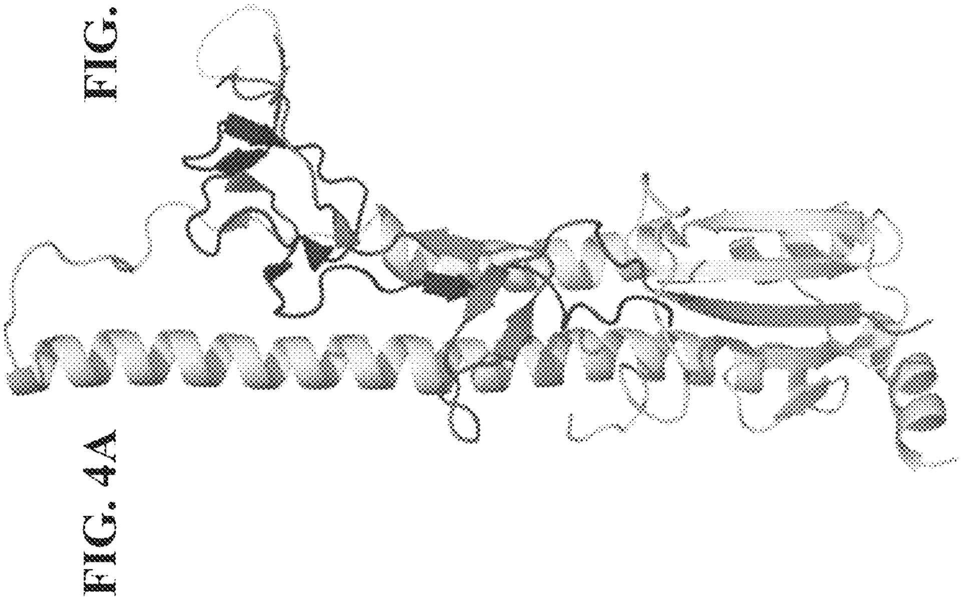

Specification includes a Sequence Listing.

(56) References Cited

U.S. PATENT DOCUMENTS

| | | | |
|---|---|---|---|
| 2005/0048074 | A1 | 3/2005 | Cardineau et al. |
| 2005/0064391 | A1 | 3/2005 | Segal et al. |
| 2005/0106178 | A1 | 5/2005 | O'hagan et al. |
| 2005/0201946 | A1 | 9/2005 | Friede et al. |
| 2006/0008473 | A1 | 1/2006 | Yang et al. |
| 2006/0280754 | A1 | 12/2006 | Garry et al. |
| 2007/0020238 | A1 | 1/2007 | Baltimore et al. |
| 2007/0036809 | A1 | 2/2007 | Michl et al. |
| 2008/0019998 | A1 | 1/2008 | Wang et al. |
| 2008/0032921 | A1 | 2/2008 | Alexander et al. |
| 2008/0152657 | A1 | 6/2008 | Horowitz et al. |
| 2008/0176247 | A1 | 7/2008 | Chou et al. |
| 2009/0081255 | A1 | 3/2009 | Bublot et al. |
| 2009/0291472 | A1 | 11/2009 | Lu et al. |
| 2009/0304730 | A1 | 12/2009 | Amon et al. |
| 2009/0304739 | A1 | 12/2009 | Rappouli et al. |
| 2009/0311265 | A1 | 12/2009 | Van Den Brink et al. |
| 2009/0311669 | A1 | 12/2009 | Kawaoka |
| 2010/0184192 | A1 | 7/2010 | Smith et al. |
| 2010/0297165 | A1 | 11/2010 | Berzofsky et al. |
| 2010/0297174 | A1 | 11/2010 | Garcia-Sastre et al. |
| 2011/0027270 | A1 | 2/2011 | Garcia-Sastre et al. |
| 2011/0111494 | A1 | 5/2011 | Hill et al. |
| 2011/0182938 | A1 | 7/2011 | Weiner et al. |
| 2012/0039898 | A1 | 2/2012 | Throsby et al. |
| 2012/0122185 | A1 | 5/2012 | Palese et al. |
| 2012/0189658 | A1 | 7/2012 | Couture et al. |
| 2012/0244183 | A1 | 9/2012 | Garcia-Sastre et al. |
| 2013/0129747 | A1 | 5/2013 | Schraeder |
| 2013/0129761 | A1 | 5/2013 | Garcia-Sastre et al. |
| 2013/0209499 | A1 | 8/2013 | Garcia-Sastre et al. |
| 2014/0170163 | A1 | 6/2014 | Garcia-Sastre et al. |
| 2014/0193484 | A1 | 7/2014 | Bertholet Girardin et al. |
| 2014/0328875 | A1 | 11/2014 | Garcia-Sastre et al. |
| 2015/0132330 | A1 | 5/2015 | Garcia-Sastre et al. |
| 2015/0239960 | A1 | 8/2015 | Garcia-Sastre et al. |
| 2015/0297712 | A1 | 10/2015 | Garcia-Sastre et al. |
| 2015/0299270 | A1 | 10/2015 | Galarza et al. |
| 2015/0335729 | A1 | 11/2015 | Garcia-Sastre et al. |
| 2016/0022806 | A1 | 1/2016 | Weiner et al. |
| 2016/0038585 | A1 | 2/2016 | Dormitzer et al. |
| 2016/0355553 | A1 | 12/2016 | Meijberg et al. |
| 2016/0361408 | A1 | 12/2016 | Garcia-Sastre et al. |
| 2016/0362455 | A1 | 12/2016 | Meijberg et al. |
| 2016/0376347 | A1 | 12/2016 | Saelens et al. |
| 2017/0327565 | A1 | 11/2017 | Schrader |
| 2018/0002385 | A1 | 1/2018 | Garcia-Sastre et al. |
| 2018/0008696 | A1 | 1/2018 | Palese et al. |

FOREIGN PATENT DOCUMENTS

| | | | |
|---|---|---|---|
| EP | 0621339 | A2 | 10/1994 |
| EP | 2 540 312 | A1 | 1/2013 |
| JP | A-H7-89992 | | 4/1995 |
| JP | 2004-258814 | | 9/2004 |
| JP | 2006-347922 | | 12/2006 |
| JP | A-2008-249712 | | 10/2008 |
| JP | 2011-057653 | | 3/2011 |
| JP | 2012-530499 | A | 12/2012 |
| WO | WO 1984/000687 | A1 | 3/1984 |
| WO | WO 1992/001047 | | 1/1992 |
| WO | WO 1994/009136 | | 4/1994 |
| WO | WO 1994/016109 | | 7/1994 |
| WO | WO 1994/017826 | | 8/1994 |
| WO | WO 1995/034324 | | 12/1995 |
| WO | WO 1996/033735 | | 10/1996 |
| WO | WO 1996/034096 | | 10/1996 |
| WO | WO 97/40161 | | 10/1997 |
| WO | WO 1997/040177 | | 10/1997 |
| WO | WO 1998/024893 | | 6/1998 |
| WO | WO 2007/045674 | | 4/2007 |
| WO | WO 2007/064802 | | 6/2007 |
| WO | WO 2007/103322 | | 9/2007 |
| WO | WO 2007/134327 | A2 | 11/2007 |
| WO | WO 2008/005777 | | 1/2008 |
| WO | WO 2008/028946 | A2 | 3/2008 |
| WO | WO 2008/032219 | | 3/2008 |
| WO | WO 2009/009876 | | 1/2009 |
| WO | WO 2009/012489 | A1 | 1/2009 |
| WO | WO 2009/025770 | A2 | 2/2009 |
| WO | WO 2009/036157 | A1 | 3/2009 |
| WO | WO 2009/068992 | A1 | 6/2009 |
| WO | WO 2009/076778 | | 6/2009 |
| WO | WO 2009/079259 | A2 | 6/2009 |
| WO | WO 2009/092038 | | 7/2009 |
| WO | WO 2009/121004 | A2 | 10/2009 |
| WO | WO 2009/150532 | A1 | 12/2009 |
| WO | WO 2009/156405 | | 12/2009 |
| WO | WO 2010/003235 | | 1/2010 |
| WO | WO 2010/036948 | | 4/2010 |
| WO | WO 2010/117786 | A1 | 10/2010 |
| WO | WO 2010/130636 | | 11/2010 |
| WO | WO 2010/138564 | A1 | 12/2010 |
| WO | WO 2010/148511 | A1 | 12/2010 |
| WO | WO 2011/014645 | | 2/2011 |
| WO | WO 2011/044152 | | 4/2011 |
| WO | WO 2011/087092 | | 7/2011 |
| WO | WO 2011/103453 | A1 | 8/2011 |
| WO | WO 2011/111966 | | 9/2011 |
| WO | WO 2011/123495 | | 10/2011 |
| WO | WO 2012/009790 | | 1/2012 |
| WO | WO 2013/043729 | | 3/2013 |
| WO | WO 2013/079473 | | 6/2013 |
| WO | WO 2014/159960 | | 1/2014 |
| WO | WO 2014/099931 | | 6/2014 |
| WO | WO 2014/152841 | | 9/2014 |
| WO | WO 2015/199564 | A1 | 12/2015 |
| WO | WO 2016/118937 | A1 | 7/2016 |
| WO | WO 2016/205347 | A1 | 12/2016 |
| WO | WO 2017/210445 | A1 | 12/2017 |
| WO | WO 2017/218624 | A1 | 12/2017 |

OTHER PUBLICATIONS

Database Geneseq "Influenza A virus hemagglutinin protein, H1PR8", Accession No. AJG95109, dated Nov. 15, 2007.

Ekiert et al., 2009, "Antibody recognition of a highly conserved influenza virus epitope", Science; 324(5924):246-251.

Gerhard et al., 2006, "Prospects for universal influenza virus vaccine", Emerging Infectious Diseases; 12(4):569-574.

Graves et al., 1983, "Preparation of influenza virus subviral particles lacking the HA1 subunit of hemagglutinin: unmasking of cross-reactive HA2 determinants," Virology, 126(1):106-116.

Horvath et al., 1998, "Hemagglutinin-based multipeptide construct elicits enhanced protective immune response in mice against influenza A virus infection", Immunology Letters; 60(2/03):127-136.

International Search Report of International application No. PCT/US2011/025467, dated Oct. 19, 2011.

International Search Report of International application No. PCT/US2010/036170, dated Aug. 17, 2010.

International Search Report of International application No. PCT/US11/30441, dated Jul. 13, 2011.

International Search Report of International application No. PCT/US2010/029202, dated Aug. 24, 2010.

Kashyap et al., 2008, "Combinatorial antibody libraries from survivors of the Turkish H5N1 avian influenza outbreak reveal virus neutralization strategies", Proc Natl Acad Sci USA; 105:5986-5991.

Kistner et al., 2007, "Cell culture (Vero) derived whole virus (H5N1) vaccine based on wild-type virus strain induces cross-protective immune responses", Vaccine; 25(32):6028-6036.

Landry et al., 2008, "Three-dimensional structure determines the pattern of CD4+ T-cell epitope dominance in influenza virus hemagglutinin", Journal of Virology; 82(3):1238-1248.

Leroux-Roels, et al., 2008, "Broad Glade 2 cross-reactive immunity induced by an adjuvanted clade 1 rH5N1 pandemic influenza vaccine", PLOS One; 3(2):1-5.

Lowen et al. 2009, "Blocking interhost transmission of influenza virus by vaccination in the guinea pig model", Journal of Virology; 83(7):2803-2818.

(56) References Cited

OTHER PUBLICATIONS

Marasco et al., 2007, "The growth and potential of human antiviral monoclonal antibody therapeutics", Nat Biotechnol; 25(12):1421-1434.
Mo et al., 2003, "Coexpression of complementary fragments of CIC-5 and restoration of chloride channel function in a Dent's disease mutation", Am J Physiol Cell Physiol; 286:C79-C89.
Mok et al., 2008, "Enhancement of the CD8<+> T cell response to a subdominant epitope respiratory.syncytial virus by deletion of an immunodominant epitope", Vaccine; 26(37):4775-4782.
Okuno et al., 1993, "A common neutralizing epitope conserved between the hemagglutinins of influenza A virus H1 and H2 strains," J. Virol., 67(5):2552-2558.
Okuno et al., 1994, "Protection against the mouse-adapted A/FM/1/47 strain of influenza A virus in mice by a monoclonal antibody with cross-neutralizing activity among H1 and H2 strains," J. Virol., 68(1):517-520.
Sagawa et al., 1996, "The immunological activity of a deletion mutant of influenza virus haemagglutinin lacking the globular region", J Gen Virol; 77:1483-1487.
Simmons et al., 2007, "Prophylactic and therapeutic efficacy of human monoclonal antibodies against H5N1 influenza", PLOS Medicine; 4(5):928-936.
Steel et al., 2010, "Influenza Virus Vaccine Based on the Conserved Hemagglutinin Stalk Domain," mBIO, 1(1):1-9, pii: e00018-10.
Sui et al., 2009, "Structural and functional bases for broad-spectrum neutralization of avian and human.influenza A viruses", Nat Struct Mol Biol; 16(3):265-273.
Thoennes et al., 2008, "Analysis of residues near the fusion peptide in the influenza hemagglutinin structure for roles in triggering membrane fusion", Virology; 370(2):403-414.
Throsby et al., 2008, "Heterosubtypic neutralizing monoclonal antibodies cross-protective against H5N1 and H1N1 recovered from human IgM+ memory B cells", PLoS ONE; 3(12):e3942.
Vanlandschoot et al., 1998, "An antibody which binds to the membrane-proximal end of influenza virus haemagglutinin (H3 subtype) inhibits the low-pH-induced conformational change and cell-cell fusion but does not neutralize virus", Journal of General Virology; 79:1781-1791.
Wang et al., 2009, "Characterization of cross-reactive antibodies against the influenza virus hemagglutinin", American Society for Virology 28$^{th}$ Annual Meeting, University of British Columbia, Vancouver, BC, Canada dated Jul. 11-15, 2009; Abstract W30-6.
Wang et al., 2009, "Universal epitopes of influenza virus hemagglutinins?", Nature Structural and Molecular Biology; 16(3):233-234.
Wang et al., 2010, "Broadly protective monoclonal antibodies against H3 influenza viruses following sequential immunization with different hemagglutinins", PLOS Pathogens; 6(2):1-9.
Written Opinion of International application No. PCT/US2010/036170, dated Aug. 17, 2010.
Written Opinion of International application No. PCT/US2011/25467, dated Oct. 19, 2011.
Written Opinion of International application No. PCT/US2010/029202, dated Aug. 24, 2010.
Written Opinion of International application No. PCT/US11/30441, dated Jul. 13, 2011.
Babai et al., 2011, "A novel loposomal influenza vaccine (influsome-vac) containing hemagglutinin-neuraminidase and IL-2 or GM-CSF induces protective anti-neuraminidase antibodies cross-reacting with a wide specrum of incluenza A viral strains", Vaccine, Elsevier Ltd, GB, 20(3-4): 505-515.
Horimoto et al. 2003, "Generation of influenza A viruses with chimeric (type A/B) hemagglutinins " J.Virol, 77(14): 8031-8038.
International Search Report of International Application No. PCT/US2012/56122, dated Feb. 19, 2013.
International Search Report of International Application No. PCT/US2013/75697, dated Apr. 28, 2014.
Pica et al. 2012, "Hemagglutinin stalk antibodies elicited by the 2009 pandemic influenza virus as a mechanism for the extinction of seasonal H1N1 viruses." PNAS. 109(7): 2573-2578.
Santak et al. 2012, "Old and new ways to combat human influenza virus". Periodicum Biologororum 114(2): 221-234.
Wang et al., 2010, "Vaccination with a synthetic peptide from the influenza virus hemagglutinin provides protection agaisnt distinct viral subtypes". PNAS. 107(44): 18979-18984.
Zamarin et al. 2006, "Influenza A virus PB1-F2 protein contributes to viral pathogenesis in mice". J Virol. 80(16):7976-7983.
Written Opinion of International application No. PCT/US2012/056122, dated Mar. 20, 2014.
Written Opinion of International application No. PCT/US2013/75697, dated Apr. 28, 2014.
Gocnik et al., 2008, "Antibodies Induced by the HA2 Glycopolypeptide of Influenza Virus Haemagglutinin Improve Recovery from Influenza A Virus Infection," J Gen Virol., 89:958-967.
Gould et al., 1987, "Mouse H-2k-Restricted Cytotoxic T Cells Recognize Antigenic Determinants in.Both the HA1 and HA2 Subunits of the Influenza A/PR/8/34 Hemagglutinin," J. Exp. Med., 166:693-701.
Roberts et al., 1993, "Role of conserved glycosylation sites in maturation and transport of influenza A virus hemagglutinin," J Virol, 67(6):3048-3060.
Schneeman et al., 2012, "A Virus-Like Particle That Elicits Cross-Reactive Antibodies to the Conserved Stem of Influenza Virus Hemagglutinin," J. Virol., 86(21): 11686-22697.
Song et al., 2007, "Influenza A Virus Hemagglutinin Protein, H1PR8," GENESEQ, XP002595511.
Stephenson et al., 2005, "Cross-Reactivity to Highly Pathogenic Avian Influenza H5N1 Viruses after Vaccination with Nonadjuvanted and MF59-Adjuvanted Influenza A/Duck/Singapore/97 (H5N3) Vaccine: A Potential Priming Strategy," The Journal oflnfectious Diseases; 191:1210-1215.
Vareckova et al., 2008, "HA2-specific monoclonal antibodies as tools for differential recognition of influenza A virus antigenic subtypes," Virus Research, 132:181-186.
Berry, 2007, "Cross-reactive MAb to the binding domain of botulinum neurotoxin A, B, and E developed using a sequential immunization strategy: anti-botulinum neurotoxin", Hybridoma, 26(6).
Chen et al., 2011, "Vaccine design of hemagglutinin glycoprotein against influenza", Trends in Biotechnology, 29(9):426-434.
Copeland et al., 2005, "Functional chimeras of human immunodeficiency virus type 1 Gp120 and influenza A virus (H3) hemagglutinin", Journal of Virology; 79:6459-6471.
Corti et al., 2011, "A neutralizing antibody selected from plasma cells that binds to group 1 and group 2 influenza A hemagglutinins", Science. 333(6044):850-856.
D'Aoust et al., 2008, "Influenza virus-like particles produced by transient expression in Nicotiana benthaminana induce a protective immune response against a lethal viral challenge in mice", J. Plant Biotechnology, 6(9):930-940.
Eda et al., 2006, "Sequential immunization with V3 peptides from primary human immunodeficiency virus type 1 produces cross-neutralizing antibodies against primary isolates with a matching narrow-neutralization sequence motif" J Virol, 80(11):5552-5562.
Ekiert et al., 2011, "A highly conserved neutralizing epitope on group 2 influenza A viruses", Science 333:843-850.
Ekiert et al., 2012, "Cross-neutralization of influenza A viruses mediated by a single antibody loop", Nature, 489:526-532.
Flandorfer et al., 2003, "Chimeric Influenza A Viruses with a Functional Influenza B Virus Neuraminidase or Hemagglutinin", J. Virol., 77(17):9116-9123.
Fodor et al., 1999, "Rescue of influenza A virus from recombinant DNA", J Virol 73:9679-9682.
Fujii et al., 2002, "Selective incorporation of influenza virus RNA segments into virions", Proc. Natl. Acad. Sci. USA 100:2002-2007.
Gao & Palese, 2009, "Rewiring the RNAs of influenza virus to prevent reassortment", PNAS 106:15891-15896.
Gao et al., 2013, "Human infection with a novel avian-origin influenza A(H7N9) virus", N. Engl. J. Med. 368:1888-1897.
Garcia-Sastre et al., 1994, "Introduction of foreign sequences into the genome of influenza A virus", Dev. Biol. Stand, 82:237-246.
García-Sastre et al., 1994, "Use of a mammalian internal ribosomal entry site element for expression of a foreign protein by a transfectant influenza virus", J. Virol. 68:6254-6261.

(56) References Cited

OTHER PUBLICATIONS

Gibbs et al., 2001, "Recombination in the hemagglutinin gene of the 1918 Spanish Flu". Science, 293(5536):1842-1845.
Goff et al., 2013, "Adjuvants and immunization strategies to induce influenza virus hemagglutinin stalk.antibodies", PLoS One 8:e79194.
Hai et al., 2008, "Influenza B virus NS1-truncated mutants: live-attenuated vaccine approach", J Virol 82:10580-10590.
Hai et al., 2011, "A reassortment-incompetent live attenuated influenza virus vaccine for protection against pandemic virus strains", Journal of virology 85:6832-6843.
Hai et al., 2012, "Influenza viruses expressing chimeric hemagglutinins: globular head and stalk domains derived from different subtypes", J. Virol. 86:5774-5781.
Krammer et al., 2010, "Trichoplusia ni cells (High Five) are highly efficient for the production of influenza A virus-like particles: a comparison of two insect cell lines as production platforms for influenza vaccines", Mol Biotechnol; 45:226-34.
Krammer et al., 2012, "A carboxy-terminal trimerization domain stabilizes conformational epitopes on the stalk domain of soluble recombinant hemagglutinin substrates", PLoS One. 7:e43603.doi:10.1371/journal.pone.0043603.
Krammer et al., 2013, "Chimeric hemagglutinin influenza virus vaccine constructs elicit broadly protective stalk-specific antibodies", J. Virol. 87:6542-6550.
Krammer et al., 2013, "Influenza virus hemagglutinin stalk-based antibodies and vaccines", Current Opinion in Virology 3:521-530.
Krause et al., 2012, "Human monoclonal antibodies to pandemic 1957 H2N2 and pandemic 1968 H3N2 influenza viruses", J. Virol. 86:6334-6340.
Lee et al., 2012, "Heterosubtypic antibody recognition of the influenza virus hemagglutinin receptor binding site enhanced by avidity", Proc. Natl. Acad. Sci. U.S.A. 109:17040-17045.
Li et al., 1992, "Influenza A virus transfectants with chimaeric haemagglutinins containing epitopes from different subytpes", Journal of Virology, 67:399-404.
Igarashi et al.: 2008, "Genetically destined potentials for N-linked glycosylation of influenza virus hemagglutinin" Virology, 376:323-329.
Margine et al., 2013, "H3N2 influenza virus infection induces broadly reactive hemagglutinin stalk antibodies in humans and mice", J. Virol. 87:4728-4737.
Miller et al., 2013, "1976 and 2009 H1N1 influenza virus vaccines boost anti-hemagglutinin stalk antibodies in humans", J. Infect. Dis. 207:98-105.
Neumann et al., 1999, "Generation of influenza A viruses entirely from cloned cDNAs", PNAS 96:9345-9350.
Ott et al., 2000. The Adjuvant MF59: A 10-Year Perspective, p. 211-228. In O'Hagan DT (ed.), Vaccine Adjuvants, vol. 42. Springer.
Papanikolopoulou et al., 2004, "Formation of highly stable chimeric trimers by fusion of an adenovirus fiber shaft fragment with the foldon domain of bacteriophage t4 fibritin", J. Biol. Chem. 279(10):8991-8998.
Pleschka et al., 1996, "A plasmid-based reverse genetics system for influenza A virus", J Virol 70:4188-92.
Ponomarenko et al., "B-Cell Epitope Prediction" Chap. 35 in Structural Bioinformatics, 2nd Edition, Gu and Bourne. Editors; 2009 John Wiley & Sons. Inc. pp. 849-879.
Reid et al., Hemagglutinin [Influenza A virus (A/South Carolina/1/1918(H1N1))]. GenBank Acc. No. AAD17229.1. Dep. Oct. 11, 2000.
Rudikoff et al., Single amino acid substitution altering antigen-binding specificity. Proc Nat Acad Sci U S A. 1982; 79(6): I 979-83.
Salem, 2000, "In vivo acute depletion of CD8(+) T cells before murine cytomegalovirus infection upregulated innate antiviral activity of natural killer cells", Int. J. Immunopharmacol. 22:707-718.
Schulze, 1997, "Effects of Glycosylation on the Properites and Functions of Influenza Virus Hemagglutinin", The Journal of Infectious Diseases, 176(S1):S24-S28.
Shoji et al., 2008, "Plant-expressed HA as a seasonal influenza vaccine candidate", Vaccine, 26(23):2930-2934.
Stech et al., 2005, "A new approach to an influenza live vaccine: modification of the cleavage site of hemagglutinin", Nature Med. 11(6):683-689.
Stevens et al., 2006, "Structure and Receptor Specificity of the Hemagglutinin from an H5N1 Influenza Virus" Science, 312:404-409.
Strobel et al., 2000, "Efficient Expression of the Tumor-Associated Antigen MAGE-3 in Human Dendritic Cells, Using an Avian Influenza Virus Vector", Human Gene Therapy 11:2207-2218.
Sui et al.. 2009, "Structural and functional bases for broad-spectrum neutralization of avian and human influenza A viruses", Nat Struct Mol Biol; 16(3):265-273; Supplementary Information.
Tamura et al., 1998, "Definition of amino acid residues on the epitope responsible for recognition by influenza A virus H1-specific, H2-specific, and H1- and H2-cross-reactive murine cytotoxic T-lymphocyte clones", J. Virol. 72:9404-9406.
Tan et al., 2012, "A pan-H1 anti-hemagglutinin monoclonal antibody with potent broad-spectrum efficacy in vivo", J. Virol. 86:6179-6188.
Tao et al., 2009, "Enhanced protective immunity against H5N1 influenza virus challenge by vaccination with DNA expressing a chimeric hemagglutinin in combination with an MHC class I-restricted epitope of nucleoprotein in mice", Antiviral research. 2009; 81(3); 253-260.
Thomson et al., 2012, "Pandemic H1N1 Influenza Infection and Vaccination in Humans Induces Cross-Protective Antibodies that Target the Hemagglutinin Stem", Front. Immunol. 3:87.
Vigerust et al., 2007, "N-Linked Glycosylation Attenuates H3N2 Influenza Viruses", Journal of Virology, 81(16): 8593-8600.
Webby et al., 2010, Hemagglutinin [Influenza A virus (A/Brisbane/59/2007(H1N1))]. GenBank Acc. No. ADE28750.1. Dep. Mar. 29, 2010.
Weldon et al., 2010, "Enhanced immunogenicity of stabilized trimeric soluble influenza hemagglutinin", PLoSONE 5(9): e12466.
Wohlbold et al., 2015, "Vaccination with soluble headless hemagglutinin protects mice from challenge with divergent influenza viruses." Vaccine, 33(29):3314-3321.
Wohlbold et al., 2015, "Vaccination with adjuvanted recombinant neuraminidase induces broad heterologous, but not heterosubtypic, cross-protection against influenza virus infection in mice." MBio, 6(2):e02556.
Wrammert et al., 2011, "Broadly cross-reactive antibodies dominate the human B cell response against 2009 pandemic H1N1 influenza virus infection", J. Exp. Med. 208:181-193.
Yang et al., 2006, "Targeting lentiviral vectors to specific cell types in vivo", PNAS 103: 11479-11484.
Yasugi et al., 2013, "Human monoclonal antibodies broadly neutralizing against influenza B virus", PLoS Pathog. 9(2): e1003150.
Yoshida et al., A. Cross-protective potential of a novel monoclonal antibody directed against antigenic site B of the hemagglutinin of influenza A viruses. PLoS Pathog. 2009; 5(3);e1000350.
Zheng, et al., 1996, "Nonconserved nucleotides at the 3' and 5' ends of an influenza A virus RNA play an important role in viral RNA replication", Virology 217:242-251.
Babu et al., 2014, "Live attenuated H7N7 influenza vaccine primes for a vigorous antibody response to inactivated H7N7 influenza vaccine," Vaccine, 32:6798-6804.
Bommakanti et al., 2012, "Design of *Eschericia coli*-Expressed Stalk Domain Immunogens of H1N1 Hemagglutinin That Protect Mice from Lethal Challenge." J. Virol., 86(24):13434-13444.
Boni et al., 2010, "Guidelines for identifying homologous recombination events in influenza A virus", PLoS One, 5(5):e10434.
Boni et al., 2012, "No evidence for intra-segment recombination of 2009 H1N1 influenza virus in swine", Gene, 494(2):242-245.
Bowie, et al., 1990, "Deciphering the Message in Protein Sequences: Tolerance to Amino Acid Substitutions." Science, 247: 1306-1310.
Chen et al., 2016, "Influenza A viruses expressing intra- or intergroup chimeric hemagglutinins", doi:10.1128/JVI.03060-15.
D'Aoust et al., 2010, "The production of hemagglutinin-based virus-like particles in plants: a rapid, efficient and safe response to pandemic influenza", Plant Biotechnology, 8(5):607-619.

(56) References Cited

OTHER PUBLICATIONS

Database GenPept "Hemagglutinin precursor [Contains: Hemagglutinin HA1 chain; Hemagglutinin HA2 chain]",C119 Accession No. P03437, dated Jul. 21, 1986.
Dillon et al., 1992, "Induction of protective class I MHC-restricted CTL in mice by a recombinant influenza vaccine in aluminum hydroxide adjuvant", Vaccine, 10(5):309-318.
Doms RW & Moore JP, 2000, "HIB-1 Membrane Fusion: Targets of Opportunity," JCB, 151(2): F9-F13.
Dunand et al., 2016, "Both Neutralizing and Non-Neutralizing Human H7N9 Influenza Vaccine-Induced Monoclonal Antibodies Confer Protection," Cell Host & Microbe, 19:1-14.
Fleury, et al., 2007, GenBank Acc. No. P03437, Updated Apr. 3, 2007.
Graham et al., 2013, "DNA Vaccine Delivered by a Needle-Free Injection Device Improves Potency of Priming for Antibody and CD8+ TCell Responses after rAd5 Boost in a Randomized Clinical Trial," PLoS ONE, 8(4): 1-11, e59340.
Hallily et al., 2015, "High-Affinity H7 Head and Stalk Domain-Specific Antibody Response to an Inactivated Influenza H7N7 Vaccine After Priming With Live Attenuated Influenza Vaccine," Journal of Infectious Diseases, 212: 1270-1278.
Haynes, 2009, "Influenza virus-like particle vaccines", Expert Rev. Vaccines, 8(4): 435-445.
Impagliazzo et al., 2015, "A stable trimeric influenza hemagglutinin stem as a broadly protective immunogen." Science, 349(6254):1301-1306.
Kanekiyo et al., 2013, "Self-assembling influenza nanoparticle vaccines elicit broadly neutralizing H1N1 antibodies." Nature, 499(7456):102-6.
Kaverin et al., 2004, "Structural Differences Among Hemagglutinins of Influenza A Virus Subtypes Are Reflected in Their Antigenic Architecture: Analysis of H9 Escape Mutants", Journal of Virology, 78(1):240-249.
Khurana et al., 2013, "DNA Priming Prior to Inactivated Influenza A(H5N1) Vaccination Expands the Antibody Epitope Repertoire and Increases Affinity Maturation in a Boost-Interval-Dependent Manner in Adults," Journal of Infectious Disease, 208:413-417.
Krause et al., 2011, "A broadly neutralizing human monoclonal antibody that recognizes a conserved, novel epitope on the globular head of the influenza H1N1 virus hemagglutin", J. Virol., 85(20):10905-10908.
Landry et al., 2010, "Preclinical and Clinical Development of Plant-Made Virus-Like Particle Vaccine against Avian H5N1 Influenza", PLoS One, 5(12):e15559.
Ledgerwood, et al., 2013, "Prime-Boost Interval Matters: A Randomized Phase 1 Study to Identify the Minimum Interval Necessary to Observe the H5 DNA Influenza Vaccine Priming Effect," Journal of Infectious Diseases, 208:418-422.
Lu et al., 2013, "Production and stabilization of the trimeric influenza hemagglutinin stem domain for potentially broadly protective influenza vaccines." PNAS, 111(1):125-130.
Luke et al., 2014, "Improving pandemic H5N1 influenza vaccines by combining different vaccine platforms," Expert Review of Vaccines 13(7):873-883.
Mallajosyula et al., 2014, "Influenza hemagglutinin stem-fragment immunogen elicits broadly neutralizing antibodies and confers heterologous protection" PNAS, 111(25):E2514-23.
Mbawuike et al., 1994, "Influenza A subtype cross-protection after immunization of outbred mice with purified chimeric NS1/HA2 influenza virus protein", Vaccine, 1994: 12(14):1340-1348.
Mett et al., 2008, "A plant-produced influenza subunit vaccine protects ferrets against virus challenge", Influenza and Other Respiratory Viruses, 2(1):33-40.
Nachbagauer et al., 2015, "Hemagglutinin stalk immunity reduces influenza virus replication and transmission in ferrets", J. Virol., doi:10.1128/JVI.02481-15.
Palese P & Shaw M (2007). Orthomyxoviridae: The Viruses and Their Replication. In D.M. Knipe, & P.M. Howley (Eds.), Fields Virology (pp. 1647-1689). Philadelphia, PA: Wolters Kluwer Lippincott Williams & Wilkins.
Robertson, 1987, "Sequence Analysis of the Haemagglutinin of A/Taiwan/1/86, a New Variant of Human Influenza A(H1/N1) Virus," J. Gen. Virol., 68:1205-1208.
Rudenko et al., 2015, "Assessment of immune responses to H5N1 inactivated influenza vaccine among individuals previously primed with H5N2 live attenuated influenza vaccine," Human Vaccines & Immunotherapeutics, 11(12):2839-2848.
Ryder et al., 2016, "Vaccination with VSV-vectored chimeric hemagglutinins protects mice against divergent influenza virus challenge strains", J. Virol., 90(5):2544-2550.
Talaat et al., 2014, "A Live Attenuated Influenza A(H5N1) Vaccine Induces Long-Term Immunity in the Absence of a Primary Antibody Response," Journal of Infectious Disease; 208:1860-1869.
Wei et al., 2010, "Induction of Broadly Neutralizing H1N1 Influenza Antibodies by Vaccination," Science; 329:1060-1064.
Wiley, 1987, "The Structure and Function of the Hemagglutinin Membrane Glycoprotein of Influenza Virus", Ann. Rev. Biochem. 56:365-394.
Winter et al., 1981, "Nucleotide Sequence of the Haemagglutinin Gene of a Human Influenza Virus H1 Subtype" Nature, 292:72-75.
Worobey et al., 2002, "Questioning the Evidence for Genetic Recombination in the 1918 "Spanish Flu" Virus", Science, 296(5566): 211a.
Vanlandschoot et al., 1995. "A fairly conserved epitope on the hemagglutinin of influenza A (H3N2) virus with variable accessibility to neutralizing antibody." Virology, 212(2)526-34.
Yassine et al., 2015, "Hemagglutinin-stem nanoparticles generate heterosubtypic influenza protection" Nat. Med. 21(9):1065-70.
Bommakanti et al., 2010, "Design of an HA2-based *Escherichia coli* expressed influenza immunogen that protects mice from pathogenic challenge", Proc Natl Acad Sci USA, 107:13701-13706.
Bullough et al., 1994, "Structure of influenza haemagglutinin at the pH of membrane fusion." Nature, 371:37-43.
Casali et al., 2008, "Site-directed mutagenesis of the hinge peptide from the hemagglutinin protein: enhancement of the pH-responsive conformational change." Protein Engineering Design & Selection, 21(6):395-404.
Chen et al., 1999, "N- and C-terminal residues combine in the fusion-pH influenza hemagglutinin HA2 subunit to form an N cap that terminates the triple-stranded coiled coil." Proc. Natl. Acad Sci., 91:8967-8972.
Chen et al., 2007, "Influenza Virus Hemagglutinin and Neuraminidase, but Not the Matrix Protein, Are Required for Assembly and Budding of Plasmid-Derived Virus-Like Particles", J. Virol. 81(13):7111-7123.
Chen et al., 2010, "Generation of Live Attenuated Novel Influenza Virus A/California/7/09 (H1N1) Vaccines with High Yield in Embryonated Chicken Eggs." J. Virol. 84(1):44-51.
Cotter et al., 2014, "A Single Amino Acid in the Stalk Region of the H1N1pdm Influenza Virus HA Protein Affects Viral Fusion, Stability and Infectivity." PLoS Pathogens, 10(1):e1003831.
Das et al., 2010, "Glycosylation Focuses Sequence Variation in the Influenza A Virus H1 Hemagglutinin Globular Domain." PLoS Pathogens, 6(11):e1001211.
Doyle et al., 1986, "Analysis of Progressive Deletions of the Transmembrane and Cytoplasmic Domains of Influenza Hemagglutinin", JCB, 103:1193-1204.
Fluzone®, 2009-2010 Fluzone Seasonal influenza vaccine package insert, 2009.
Genbank, NCBI Reference Sequence: YP_163736.1, HA2 [Influenza A virus (A/Puerto Rico/Aug. 1934(H1N1))].
Giddings et al., 2000, "Transgenic plants as factories for biopharmaceuticals", Nature Biotechnology, 18:1151-1155.
Gomord et al., 2005, "Biopharmaceutical production in plants: problems, solutions and opportunities." Trends in Biotechnology, 23(11):559-565.
Horimoto et al., 2004, "Influenza A viruses possessing type B hemagglutinin and neuraminidase: potential as vaccine components." Microbes and Infection, 6(6): 579-583.

(56) References Cited

OTHER PUBLICATIONS

Krammer et al., 2012, "Hemagglutinin stalk-reactive antibodies are boosted following sequential infection with seasonal and pandemic H1N1 influenza virus in mice", J Virol, 86:10302-10307.

Krammer et al., 2014, "Assessment of influenza virus hemagglutinin stalk-based immunity in ferrets", J Virol, 88:3432-3442.

Krammer et al., 2014, "H3 stalk-based chimeric hemagglutinin influenza virus constructs protect mice from H7N9 challenge", J Virol, 88:2340-2343.

Krammer, 2015, "The quest for a universal flu vaccine: headless HA 2.0", Cell Host Microbe, 18:395-397.

Krammer, 2016, "Novel universal influenza virus vaccine approaches", Current Opinion in Virology, 17:95-103.

Lebendiker M. "Purification Protocols." The Wolfson Centre for Applied Structural Biology, http://wolfson.huji.ac.il/purification/Purification_Protocols.html. Apr. 5, 2006.

Lorieau, et al., 2010, "The complete influenza hemagglutinin fusion domain adopts a tight helical hairpin arrangement at the lipid:water interface." PNAS, 107(25):11341-11346.

Margine et al., 2013, "Hemagglutinin stalk-based universal vaccine constructs protect against group 2 influenza A viruses", J Virol, 10435-10446.

Sun et al., 2011, "Glycosylation Site Alteration in the Evolution of Influenza A (H1N1) Viruses." PLoS Pathogens, 6(7):e22844.

Tate et al., 2001, "Specific Sites of N-Linked Glycosylation on the Hemagglutinin of H1N1 Subtype Influenza A Virus Determine Sensitivity to Inhibitors of the Innate Immune Systema nd Virulence in Mice." Journal of Immunology, 187(4):1884-1894.

Tran et al., 2016, "Cryo-electron microscopy structures of chimeric hemagglutinin displayed on a universal influenza vaccine candidate", MBio, 7(2): e00257-16.

Vajdos et al., 2002, "Comprehensive Functional Maps of the Antigenbinding Site of an Anti-ErbB2 Antibody Obtained with Shotgun Scanning Mutagenesis," Journal of Molecular Biology, 320:415-428.

Wang et al., 2007, "Incorporation of High Levels of Chimeric Human Immunodeficiency Virus Envelope Glycoproteins into Virus-Like Particles", J. Virol., 81(20):10869-10878.

Wang et al., 2009, "Glycans on influenza hemagglutinin affect receptor binding and immune response." PNAS, 106(43): 18137-18142.

Wang et al., 2012, "Generation of recombinant pandemic H1N1 influenza virus with the HA cleavable by bromelain and identification of the residues influencing HA bromelain cleavage." Vaccine, 30(4):872-8.

Weis and Brunger, 1990, "Refinement of the Influenza Virus Hemagglutinin by Simulated Annealing." J. Mol. Biol. 212:737-761.

Weis et al., 1988, "Structure of the influenza virus haemagglutinin complexed with its receptor, sialic acid." Nature, 333:426-431.

Wiley and Skehel, 1983, "The three-dimensional structure and antigenic variation of the influenza virus haemagglutinin." Division of Virology, 107-111.

Wiley, 1987, "The Structure and Function of the Hemagglutinin Membrane Glycoprotein of Influenza Virus." Ann. Rev. Biochem., 56:365-94.

Wilson et al., 1981, "Structure of the haemagglutinin membrane glycoprotein of influenza virus at 3 A resolution." Nature, 289:366-373.

Yang et al., 2007, "Immunization by Avian H5 Influenza Hemagglutinin Mutants with Altered Receptor Binding Specificity", Science, 317(5839):825-828.

Yang et al., 2014, "Structural stability of influenza A(H1N1)pdm09 virus hemagglutinins." J. Virol., 88(9):4828-38.

Centers for Disease Control and Prevention Metropolitan Atlanta Congenital Defects Program (CDC MACDP) guidelines. Birth defects and genetic diseases branch 6-digit code for reportable congenital anomalies; http://www.cdc.gov/ncbddd/birthdefects/documents/MACDPcode0807.pdf.

Clementi et al., 2011, "A Human Monoclonal Antibody with Neutralizing Activity against Highly Divergent Influenza Subtypes". PLoS ONE, 6(12):e28001.

Cox and Fukuda, 1998, "Influenza," *Infect.Dis.Clin.North Am*, 12:27-38.

Crotty et al., 2004, "Tracking human antigen-specific memory B cells: a sensitive and generalized ELISPOT system," *J. Immunol. Methods*, 286 (1-2):111-122.

EMA Guideline on the exposure to medicinal products during pregnancy: need for post-authorization data (Doc. Ref. EMEA/CHMP/313666/2005 ) adopted at Community level in May 2006); http://www.ema.europa.eu/docs/en_GB/document_library/Regulatory_and_procedural_guideline/2009/11/WC500011303.pdf.

Gauger et al., 2011, "Enhanced pneumonia and disease in pigs vaccinated with an inactivated human-like (δ-cluster) H1N2 vaccine and challenged with pandemic 2009 H1N1 influenza virus." *Vaccine.*, 29(15):2712-2719.

Goff et al., 2013, "Induction of cross-reactive antibodies to novel H7N9 influenza virus by recombinant Newcastle disease virus expressing a North American lineage H7 subtype hemagglutinin," *J. Virol.*, 87 (14): 8235-40.

Heaton et al., "In Vivo Bioluminescent Imaging of Influenza A Virus Infection and Characterization of Novel Cross-Protective Monoclonal Antibodies," J. Virol. 87(15):8272-8281 (2013).

Hong et al., "Antibody recognition of the pandemic H1N1 Influenza virus hemagglutinin receptor binding site," J. Virol. 87(22):12471-12480 (2013) (Epub Sep. 11, 2013).

International Search Report dated Jun. 26, 2014 for PCT Application No. PCT/US2014/025526, Published as WO 2014/159960.

Izurieta et al., 2000, "Influenza and the rates of hospitalization for respiratory disease among infants and young children," NEJM, 342(4):232-239.

Krammer and Palese, 2013, "Influenza virus hemagglutinin stalk-based antibodies and vaccines," Curr. Opin. Virol., 3, 521-530.

Montplaisir et al., 2009, "Risk of narcolepsy associated with inactivated adjuvanted (AS03) A/H1N1 (2009) pandemic influenza vaccine in Quebec," *PLoS One*, 9 (9): e108489. doi: 10.1371/journal.pone.0108489.

Nachbagauer et al., 2014, "Induction of broadly reactive anti-hemagglutinin stalk antibodies by an H5N1 vaccine in humans," *J. Virol.*, 88 (22): 13260-8.

Nachbagauer et al., 2016, "A chimeric haemagglutinin-based influenza split virion vaccine adjuvanted with AS03 induces protective stalk-reactive antibodies in mice." *Nature Partner Journals* (NPJ) Vaccines, Article No. 16015 (2016) doi:10.1038/npjvaccines.2016.15.

NCT01676402, Clinical Trial, Seasonal Influenza HA DNA With Trivalent Inactivated Vaccine (TIV) Administered ID or IM in Healthy Adults 18-70 Years.

O'Brien MA, Uyeki TM, Shay DK, Thompson WW, Kleinman K, McAdam A, Yu XJ, Platt R, Lieu TA. Incidence of outpatient visits and hospitalizations related to influenza in infants and young children. *Pediatrics*. 2004; 113: 585-93.

Oshima et al., 2011, "Naturally Occurring Antibodies in Humans Can Neutralize a Variety of Influenza Virus Strains, Including H3, H1, H2, and H5". Journal of Virology, 85(21):11048-11057.

Perricone et al., 2013, "Autoimmune/inflammatory syndrome induced by adjuvants (Asia) 2013: Unveiling the pathogenic, clinical and diagnostic aspects," J Autoimmun., 47:1-16.

Sparrow et al., 2016, "Passive immunization for influenza through antibody therapies, a review of the pipeline, challenges, and potential applications." Vaccine, 34: 5442-5448.

Tete et al., 2016, "Dissecting the hemagglutinin head and stalk-specific IgG antibody response in healthcare workers following pandemic H1N1 vaccination," *Nature Partner Journals* (*NPJ*) *Vaccine*, Article No. 16001 doi:10.1038/npjvaccines.2016.1.

Tong et al., 2013. "New world bats harbor diverse influenza A viruses," PLoS Pathog. 9: e1003657.

Vincent et al., 2008, "Failure of protection and enhanced pneumonia with a US H1N2 swine influenza virus in pigs vaccinated with an inactivated classical swine H1N1 vaccine," *Vet Microbiol.*, 126 (4): 310-23.

(56) References Cited

OTHER PUBLICATIONS

WHO World Health Organization Factsheet No. 211. Influenza Nov. 2016. https://www.who.int/mediacentre/factsheets/fs211/en.
Written Opinion dated Jun. 26, 2014 for PCT Application No. PCT/US2014/025526, Published as WO 2014/159960.
Zhang et al., "Crystal structure of the swine-origin A (H1N1)-2009 influenza A virus hemagglutinin (HA) reveals similar antigenicity to that of the 1918 pandemic virus," Protein Cell 1(5):459-467 (2010) (Epub Jun. 4, 2010).
Zhang et al., 2011, "Determination of serum neutralization antibodies against seasonal influenza A strain H3N2 and the emerging strains 2009 H1N1 and avian H5N1". Scandinavian Journal of Infectious Diseases, 43:216-220.
International Search Report of International Application No. PCT/US2017/037384, dated Nov. 3, 2017.
International Search Report of International Application No. PCT/US2016/014640, dated Jun. 3, 2016.
International Search Report of International Application No. PCT/US2016/037595, dated Sep. 15, 2016.
International Search Report of International Application No. PCT/US2017/035479, dated Oct. 25, 2017.
Montgomery et al., "Heterologous and homologous protection against influenza A by DNA vaccination: optimization of DNA vectors," DNA Cell Biol. 12(9):777-783 (1993).
Ni et al, "Structural basis for the divergent evolution of influenza B virus hemagglutinin," Virology 446(1-2):112-122 (2013) (Epub Aug. 27, 2013).
Ohkura et al., "Epitope mapping of neutralizing monoclonal antibody in avian influenza A H5N1 virus hemagglutinin," Biochem. Biophys. Res. Commun. 418(1):38-43 (2012) (Epub Dec. 27, 2011).
Q0PZR5, UniProtKB Accession No. Q0PZR5, Oct. 29, 2014 [online]. [Retrieved on Sep. 2, 2016]. Retrieved from the internet <URL: http://www.uniprot.org/uniprot/Q0PZR5.txt?version=53> Entire document.
Wohlbold et al., "In the Shadow of Hemagglutinin: A Growing Interest in Influenza Viral N euraminidase and Its Role as a Vaccine Antigen," Viruses 6(6):2465-2494 (2014).
Written Opinion of the International Searching Authority for International Application No. PCT/US2017/037384, dated Nov. 3, 2017.
Written Opinion of the International Searching Authority for International Application No. PCT/US2016/014640, dated Jun. 3, 2016.
Written Opinion of the International Searching Authority for International Application No. PCT/US2016/037595, dated Sep. 15, 2016.
Written Opinion of the International Searching Authority for International Application No. PCT/US2017/035479, dated Oct. 25, 2017.
Ermler et al., 2017, "Chimeric Hemagglutinin Constructs Induce Broad Protection against Influenza B Virus Challenge in the Mouse Model". J Virol 91(112): e00286-17.
Rivera et al., "Probing the structure of influenza B hemagglutinin using site-directed mutagenesis," Virology 206(2):787-795 (1995).
Wang et al., "Crystal structure of unliganded influenza B virus hemagglutinin," J Virol. 82(6):3011-3020 (2008) (Epub Jan. 9, 2008).
Extended European Search Report for European Application No. 11763347.9, dated Feb. 2, 2015.
International Preliminary Report on Patentability of International application No. PCT/US11/30441, dated Oct. 2, 2012.

```
                 ▼(Mature residue 1)
H1    MKANLLVLLCALA---------AADADTICIGYHANNSTDTVDTVLEKNVTVTHSVNLLE
H2    --MAIIYLILLFT---------AVRGDQICIGYHSNNSTEKVDTILERNVTVTHAQNILE
H3    MKTIIALSYIFCLALGQDLPGNDNSTATLCLGHHAVPNGTLVKTITDDQIEVTNATELVQ
H4    MLSIVILFLLIAENS----SQNYTGNPVICMGHHAVANGTMVKTLADDQVEVVTAQELVE
H5    -MERIVLLLAIVS---------LVKSDQICIGYHANKSTKQVDTIMEKNVTVTHAQDILE
H6    -MIAIIVVAILAT---------AGRSDKICIGYHANNSTTQIDTILEKNVTVTHSVELLE
H7    MNTQILVFALVAVIPTN--------ADKICLGHHAVSNGTKVNTLTERGVEVVNATETVE
H8    --MEKFIAIAT-LAS-------TNAYDRICIGYQSNNSTDTVNTLIEQNVPVTQTMELVE
H9    -METKAIIAALLMVT-------AANADKICIGYQSTNSTETVDTLTESNVPVTHTKELLH
H10   MYKVVVIIALLGAVKG---------LDRICLGHHAVANGTIVKTLTNEQEEVTNATETVE
H11   -MEKTLLFAAIFL---------CVKADEICIGYLSNNSTDKVDTIIENNVTVTSSVELVE
H12   --MEKFIILSTVLAA-------SFAYDKICIGYQTNNSTETVNTLSEQNVPVTQVEELVH
H13   MALNVIATLTLIS-V-------CVHADRICVGYLSTNSSERVDTLLENGVPVTSSIDLIE
H14   MIALILVALALSHTAYSQITNGTTGNPIICLGHHAVENGTSVKTLTDNHVEVVSAKELVE
H15   MNTQIIVILVLGLSMVK--------SDKICLGHHAVANGTKVNTLTERGVEVVNATETVE
H16   MMIKVLYFLIIVLGR-------YSKADKICIGYLSNNSSDTVDTLTENGVPVTSSVDLVE
                 ▲(Mature resdidue 1)

          ▼(Residue Ap)                        (Residue Cp)▼
H1    DSHNGKLCRLKGIAPLQLGKCNIAGWLLGNPECDPLLPVRSWSYIVETPNSENGICYPGD
H2    KTHNGKLCKLNGIPPLELGDCSIAGWLLGNPECDRLLTVPEWSYIMEKENPRNGLCYPGS
H3    SSSTGKICNN-PHRILDGIDCTLIDALLGDPHCDVFQN-ETWDLFVERSKAFS-NCYPYD
H4    SQNLPELCPS-PLRLVDGQTCDIINGALGSPGCDHLNG-AEWDVFIERPNAVD-TCYPFD
H5    RTHNGKLCSLNGVKPLILRDCSVAGWLLGNPMCDEFLNLPEWLYIVEKDNPINSLCYPGD
H6    NQKEERFCKILKKAPLDLKGCTIEGWILGNPQCDLLLGDQSWSYIVERPTAQNGICYPGV
H7    RTNIPKICSK-GKRTTDLGQCGLLGTITGPPQCDQFLE-FSADLIIERREGND-VCYPGK
H8    TEKHPAYCNTDLGAPLELRDCKIEAVIYGNPKCDIHLKDQGWSYIVERPSAPEGMCYPGS
H9    TEHNGMLCATDLGHPLILDTCTIEGLIYGNPSCDILLGGKEWSYIVERSSAVNGMCYPGN
H10   STNLNKLCMK-GRSYKDLGNCHPVGMLIGTPVCDPHLT-GTWDTLIERENAIA-HCYPGA
H11   TEHTGSFCSINGKQPISLGDCSFAGWILGNPMCDELIGKTSWSYIVEKPNPTNGICYPGT
H12   RGIDPILCGTELGSPLVLDDCSLEGLILGNPKCDLYLNGREWSYIVERPKEMEGVCYPGS
H13   TNHTGTYCSLNGVSPVHLGDCSFEGWIVGNPACTSNFGIREWSYLIEDPAAPHGLCYPGE
H14   TNHTDELCPS-PLKLVDGQDCHLINGALGSPGCDRLQD-TTWDVFIERPTAVD-TCYPFD
H15   ITGIDKVCTK-GKKAVDLGSCGILGTIIGPPQCDLHLE-FKADLIIERRNSSD-ICYPGR
H16   TNHTGTYCSLNGISPIHLGDCSFEGWIVGNPSCATNINIREWSYLIEDPNAPNKFCYPGE
          ▲(Residue Ap)                        (Residue Cp)▲
```

FIG. 1A

```
H1    FIDYEELREQLSSVSSFERFEIFPKESSWPNHNTNGV-TAACSHE-GKSSFYRNLLWLTE
H2    FNDYEELKHLLSSVTHFEKVKILPK-DRWTQHTTTGG-SRACAVS-GNPSFFRNMVWLTK
H3    VPDYASLRSLVAS-S--GTLEFITEGFTW-TGVTQNGGSNACKRGPG-NGFFSRLNWLTK
H4    VPEYQSLRSILAN-N--GKFEFIAEEFQW-NTVKQNGKSGACKRANV-DDFFNRLNWLVK
H5    FNDYEELKYLLSSTNHFEKIRIIPR-SSWSNHDASSGVSSACPYI-GRSSFLRNVVWLIK
H6    LNEVEELKALIGSGERVERFEMFPK-STWTGVDTSSGVTRACPYN-SGSSFYRNLLWIIK
H7    FVNEEALRQILRG-S--GGIDKETMGFTY-SGIRTNGTTSACRRSG--SSFYAEMEWLLS
H8    VENLEELRFVFSSAASYKRIRLFDY-SRWNVTRS--GTSKACNASTGGQSFYRSINWLTK
H9    VENLEELRSLFSSAKSYKRIQIFPD-KTWNVTYS--GTSRACSN-----SFYRSMRWLTH
H10   TINEEALRQKIME-S--GGISKMSTGFTYGSSITSAGTTKACMRNGG-DSFYAELKWLVS
H11   LESEEELRLKFSGVLEFNKFEVFTS-NGWGAVNSGVGVTAACKFG-GSNSFFRNMVWLIH
H12   IENQEELRSLFSSIKKYERVKMFDF-TKWNVTYT--GTSKACNNTSNQGSFYRSMRWLTL
H13   LNNNGELRHLFSGIRSFSRTELIPP-TSWGEVLD--GTTSACRDNTGTNSFYRNLVWFIK
H14   VPDYQSLRSILAS-S--GSLEFIAEQFTW-NGVKVDGSSSACLRGGR-NSFFSRLNWLTK
H15   FTNEEALRQIIRE-S--GGIDKESMGFRY-SGIRTDGATSACKRTV--SSFYSEMKWLSS
H16   LDNNGELRHLFSGVNSFSRTELINP-SKWGNVLD--GVTASCLDR-GASSFYRNLVWIVK

H1    -K-EGSYPKLKNSYVNKKGKEVLVLWGIHHPPNSKEQQNLYQNENAYVSVVTSNYNRRFT
H2    -K-GSNYPIAKGSYNNTSGEQMLIIWGVHHPNDETEQRTLYQNVGTYVSIGTSTLNKRSI
H3    S--GSTYPVLNVTMPNNDNFDKLYIWGVHHPSTNQEQTSLYVQESGRVTVSTRRSQQSII
H4    SD-GNAYPLQNLTKINNGDYARLYIWGVHHPSTSTEQTNLYKNNPGRVTVSTKTSQTSVV
H5    -K-NNTYPTIKRSYNNTNQEDLLILWGIHHPNDAAEQTKLYQNPTTYVSVGTSTLNQRSI
H6    TK-SAAYSVIKGAYNNTGNQPILYFWGVHHPPDTNEQNTLYGSGDRYVRMGTESMNFAKS
H7    NTDNASFPQMTKSYKNTRRESALIVWGIHHSGSTTEQTKLYGSGNKLITVGSSKYHQSFV
H8    KE-PDTYDFNEGAYVNNEDGDIIFLWGIHHPPDTKEQTTLYKNANTLSSVTTNTINRSFQ
H9    K--SNSYPFQNAHYTNNERENILFMWGIHHPPTDTEQTDLYKNADTTTSVTTEDINRTFK
H10   KTKGQNFPQTTNTYRNTDTAEHLIIWGIHHPSSTQEKNDLYGTQSLSISVESSTYQNNFV
H11   -Q-SGTYPVIKRTFNNTKGRDVLIVWGIHHPATLTEHQDLYKKDSSYVAVGSETYNRRFT
H12   K--SGQFPVQTDEYKNTRDSDIVFTWAIHHPPTSDEQVKLYKNPDTLSSVTTVEINRSFK
H13   -K-NTRYPVISKTYNNTTGRDVLVLWGIHHPVSVDETKTLYVNSDPYTLVSTKSWSEKYK
H14   AT-NGNYGPINVTKENTGSYVRLYLWGVHHPSSDNEQTDLYKVATGRVTVSTRSDQISIV
H15   SMNNQVFPQLNQTYRNTRKEPALIVWGVHHSSSLDEQNKLYGTGNKLITVGSSKYQQSFS
H16   -K-DEKYPVIKGDYNNTTGRDVLVLWGIHHPDTETTATNLYVNKNPYTLVSTKEWSKRYE
```

FIG. 1B

```
                                            ▼(Residue Cq)
H1   PEIAERPKVRDQAGRMNYYWTLLKPGDTIIFEANGNLIAPMYAFALSRGFG--------S
H2   PVIATRPKVNGQGGRMEFSWTILDIWDTINFESTGNLIAPEYGFRISKRGS--------S
H3   PNIGSRPWVRGQSSRISIYWTIVKPGDVLVINSNGNLIAPRGYFKMRTG---------KS
H4   PDIGSRPLVRGQSGRVSFYWTIVEPGDLIVFNTIGNLIAPRGHYKLNNQK--------KS
H5   PEIATRPKVNGQSGRMEFFWTILKPNDAINFESNGNFIAPRYAYKIVKKGD--------S
H6   PEIAARPAVNGQRGRIDYYWSILKPGETLNVESNGNLIAPWYAFRFVSTSNK-------G
H7   PSPGTRPQINGQSGRIDFHWLILDPNDTVTFSFNGAFIAPNRASFLR----------GKS
H8   PNIGPRPLVRGQQGRMDYYWGILKRGETLKIRTNGNLIAPEFGYLLKGESYG-------R
H9   PVIGPRPLVNGQQGRIDYYWSVLKPGQTLRIRSNGNLIAPWYGHVLTGESHG-------R
H10  PVVGARPQVNGQSGRIDFHWTLVQPGDNITFSDNGGLIAPSRVSKLT----------GRD
H11  PEINTRPRVNGQAGRMTFYWKIVKPGESITFESNGAFLAPRYAFEIVSVGN--------G
H12  PNIGPRPLVRGQQGRMDYYWAVLKPGQTVKIQTNGNLIAPEYGHLITGKSHG-------R
H13  LETGVRPGYNGQRSWMKIYWSLIHPGEMITFESNGGFLAPRYGYIIEEYGK--------G
H14  PNIGSRPRVRNQSGRISIYWTLVNPGDSIIFNSIGNLIAPRGHYKISKST--------KS
H15  PSPGARPKVNGQAGRIDFHWMLLDPGDTVTFTFNGAFIAPDRATFLRSNAPSGIEYNGKS
H16  LEIGTRIG-DGQRSWMKLYWHLMHPGERIMFESNGGLIAPRYGYIIEKYGT--------G
                                            ▲(Residue Cq)


                 ▼(Residue Aq)                 ▼(Residue Bq)
H1   GIITSNASMHE-CNTKCQTPLGAINSSLPYQNIHPVTIGECPKYVRSAKLRMVTGLRNNP
H2   GIMKTEGTLEN-CETKCQTPLGAINTTLPFHNVHPLTIGECPKYVKSERLVLATGLRNVP
H3   SIMSSDAPIDT-CISECITPNGSIPNDKPFQNVNKITYGACPKYVKQNTLKLATGMRNVP
H4   TILNTAIPIGS-CVSKCHTDKGSLSTTKPFQNISRIAVGDCPRYVKQGSLKLATGMRNIP
H5   AIMKSGLAYGN-CDTKCQTPVGEINSSMPFHNIHPHTIGECPKYVKSDRLVLATGLRNVP
H6   AVFKSNLPIEN-CDATCQTVAGVLRTNKTFQNVSPLWIGECPKYVKSESLRLATGLRNVP
H7   MGIQSDVQVDANCEGECYHSGGTITSRLPFQNINSRAVGKCPRYVKQESLLLATGMKNVP
H8   IIQNEDIPIGN-CNTKCQTYAGAINSSKPFQNASRHYMGECPKYVKKASLRLAVGLRNTP
H9   ILKT-DLNNGN-CVVQCQTEKGGLNTTLPFHNISKYAFGNCPKYVGVKSLKLPVGLRNVP
H10  LGIQSEALIDNSCESKCFWRGGSINTKLPFQNLSPRTVGQCPKYVNQRSLLLATGMRNVP
H11  KLFRSELNIES-CSTKCQTEIGGINTNKSFHNVHRNTIGDCPKYVNVKSLKLATGPRNVP
H12  ILKN-NLPMGQ-CVTECQLNEGVMNTSKPFQNTSKHYIGKCPKYIPSGSLKLAIGLRNVP
H13  RIFQSRIRMSR-CNTKCQTSVGGINTNRTFQNIDKNALGDCPKYIKSGQLKLATGLRNVP
H14  TVLKSDKRIGS-CTSPCLTDKGSIQSDKPFQNVSRIAIGNCPKYVKQGSLMLATGMRNIP
H15  LGIQSDAQIDESCEGECFYSGGTINSPLPFQNIDSRAVGKCPRYVKQSSLPLALGMKNVP
H16  RIFQSGVRMAR-CNTKCQTSLGGINTNKTFQNIERNALGDCPKYIKSGQLKLATGLRNVP
                 ▲(Residue Aq)                 ▲(Residue Bq)
```

FIG. 1C

```
             ▼(HA2 domain starts)
H1    ----SIQSRGLFGAIAGFIEGGWTGMIDGWYGYHHQNEQGSGYAADQKSTQNAINGITNK
H2    ----QIESRGLFGAIAGFIEGGWQGMIDGWYGYHHSNDQGSGYAADKESTQKAIDGITNR
H3    ----EKQTRGLFGAIAGFIENGWEGMIDGWYGFRHQNSEGTGQAADLKSTQAAIDQINGK
H4    ----EKASRGLFGAIAGFIENGWQGLIDGWYGFRHQNAEGTGTAADLKSTQAAIDQINGK
H5    ----QRKKRGLFGAIAGFIEGGWQGMVDGWYGYHHSNEQGSGYAADKESTQKAIDGITNK
H6    ----QIETRGLFGAIAGFIEGGWTGMIDGWYGYHHENSQGSGYAADRESTQKAVDGITNK
H7    EPSKKRKKRGLFGAIAGFIENGWEGLVDGWYGFRHQNAQGEGTAADYKSTQSAIDQITGK
H8    ----SVEPRGLFGAIAGFIEGGWSGMIDGWYGFHHSNSEGTGMAADQKSTQEAIDKITNK
H9    ----AVSSRGLFGAIAGFIEGGWPGLVAGWYGFQHSNDQGVGMAADKGSTQKAIDKITSK
H10   ---EVVQGRGLFGAIAGFIENGWEGMVDGWYGFRHQNAQGTGQAADYKSTQAAIDQITGK
H11   ----AIASRGLFGAIAGFIEGGWPGLINGWYGFQHRDEEGTGIAADKESTQKAIDQITSK
H12   ----QVQDRGLFGAIAGFIEGGWPGLVAGWYGFQHQNAEGTGIAADRDSTQRAIDNMQNK
H13   ----AISNRGLFGAIAGFIEGGWPGLINGWYGFQHQNEQGTGIAADKESTQKAIDQITTK
H14   ----GKQAKGLFGAIAGFIENGWQGLIDGWYGFRHQNAEGTGTAADLKSTQAAIDQINGK
H15   ---EKIRTRGLFGAIAGFIENGWEGLIDGWYGFRHQNAQGQGTAADYKSTQAAIDQITGK
H16   ----SIGERGLFGAIAGFIEGGWPGLINGWYGFQHQNEQGTGIAADKASTQKAINEITTK
             ▲(HA2 domain starts)
```

```
H1    VNTVIEKMNIQFTAVGKEFNKLEKRMENLNKKVDDGFLDIWTYNAELLVLLENERTLDFH
H2    VNSVIEKMNTQFEAVGKEFSNLEKRLENLNKKMEDGFLDVWTYNAELLVLMENERTLDFH
H3    LNRVIEKTNEKFHQIEKEFSEVEGRIQDLEKYVEDTKIDLWSYNAELLVALENQHTIDLT
H4    LNRLIEKTNDKYHQIEKEFEQVEGRIQDLENYVEDTKIDLWSYNAELLVALENQHTIDVT
H5    VNSIIDKMNTRFEAVGKEFNNLERRVENLNKKMEDGFLDVWTYNVELLVLMENERTLDFH
H6    VNSIIDKMNTQFEAVDHEFSNLERRIDNLNKRMEDGFLDVWTYNAELLVLLENERTLDLH
H7    LNRLIEKTNQQFELIDNEFTEVEKQIGNLINWTKDSITEVWSYNAELIVAMENQHTIDLA
H8    VNNIVDKMNREFEVVNHEFSEVEKRINMINDKIDDQIEDLWAYNAELLVLLENQKTLDEH
H9    VNNIIDKMNKQYEVIDHEFNELEARLNMINNKIDDQIQDIWAYNAELLVLLENQKTLDEH
H10   LNRLIEKTNTEFESIESEFSETEHQIGNVINWTKDSITDIWTYNAELLVAMENQHTIDMA
H11   VNNIVDRMNTNFESVQHEFSEIEERINQLSKHVDDSVVDIWSYNAQLLVLLENEKTLDLH
H12   LNNVIDKMNKQFEVVNHEFSEVESRINMINSKIDDQITDIWAYNAELLVLLENQKTLDEH
H13   INNIIDKMNGNYDSIRGEFNQVEKRINMLADRIDDAVTDIWSYNAKLLVLLENDKTLDMH
H14   LNRLIEKTNEKYHQIEKEFEQVEGRIQDLEKYVEDTKIDLWSYNAELLVALENQHTIDVT
H15   LNRLIEKTNKQFELIDNEFTEVEQQIGNVINWTRDSLTEIWSYNAELLVAMENQHTIDLA
H16   INNIIEKMNGNYDSIRGEFNQVEKRINMLADRVDDAVTDIWSYNAKLLVLLENDRTLDLH
```

FIG. 1D

```
H1   DSNVKNLYEKVKSQLKNNAKEIGNGCFEFYHKCDNECMESVRNGTYDYPKYSEESKLNRE
H2   DSNVKNLYDRVRMQLRDNAKELGNGCFEFYHKCDDECMNSVKNGTYDYPKYEEESKLNRN
H3   DSEMNKLFEKTRRQLRENAEDMGNGCFKIYHKCDNACIESIRNGTYDHDVYRDEALNNRF
H4   DSEMNKLFERVRRQLRENAEDKGNGCFEIFHKCDNNCIESIRNGTYDHDIYRDEAINNRF
H5   DSNVNNLYDKVRLQLKDNARELGNGCFEFYHKCDNECMESVRNGTYDYPQYSEEARLNRE
H6   DANVKNLYERVKSQLRDNAMILGNGCFEFWHKCDDECMESVKNGTYDYPKYQDESKLNRQ
H7   DSEMNRLYERVRKQLRENAEEDGTGCFEIFHKCDDDCMASIRNNTYDHSKYREEAMQNRI
H8   DSNVKNLFDEVKRRLSANAIDAGNGCFDILHKCDNECMETIKNGTYDHKEYEEEAKLERS
H9   DANVNNLYNKVKRALGSNAVEDGNGCFELYHKCDDQCMETIRNGTYDRQKYQEESRLERQ
H10  DSEMLNLYERVRKQLRQNAEEDGKGCFEIYHTCDDSCMESIRNNTYDHSQYREEALLNRL
H11  DSNVRNLHEKVRRMLKDNAKDEGNGCFTFYHKCDNKCIERVRNGTYDHKEFEEESKINRQ
H12  DANVRNLHDRVRRVLRENAIDTGDGCFEILHKCDNNCMDTIRNGTYNHKEYEEESKIERQ
H13  DANVKNLHEQVRRELKDNAIDEGNGCFELLHKCNDSCMETIRNGTYDHTEYAEESKLKRQ
H14  DSEMNKLFERVRRQLRENAEDQGNGCFEIFHQCDNNCIESIRNGTYDHNIYRDEAINNRI
H15  DSEMNKLYERVRRQLRENAEEDGTGCFEIFHRCDDQCMESIRNNTYNHTEYRQEALQNRI
H16  DANVRNLHDQVKRALKSNAIDEGDGCFNLLHKCNDSCMETIRNGTYNHEDYREESQLKRQ
```

```
H1   KVDGVKLESMG-IYQILAIYSTVASSLVLLVSLGAISFWMCSNGSLQCRICI
H2   EIKGVKLSNMG-VYQILAIYATVAGSLSLAIMIAGISLWMCSNGSLQCRICI
H3   QIKGVELKSGY--KDWILWISFAISCFLLCVVLLGFIMWACQRGNIRCNICI
H4   QIQGVKLTQGY--KDIILWISFSISCFLLVALLLAFILWACQNGNIRCQICI
H5   EISGVKLESMG-VYQILSIYSTVASSLALAIMIAGLSFWMCSNGSLQCRICI
H6   EIESVKLESLG-VYQILAIYSTVSSSLVLVGLIIAVGLWMCSNGSMQCRICI
H7   QIDPVKLSSGY--KDVILWFSFGASCFLLLAIAMGLVFICVKNGNMRCTICI
H8   KINGVKLEENT-TYKILSIYSTVAASLCLAILIAGGLILGMQNGSCRCMFCI
H9   KIEGVKLESEG-TYKILTIYSTVASSLVLAMGFAAFLFWAMSNGSCRCNICI
H10  NINPVKLSSGY--KDIILWFSFGESCFVLLAVVMGLVFFCLKNGNMRCTICI
H11  EIEGVKLDSSGNVYKILSIYSCIASSLVLAALIMGFMFWACSNGSCRCTICI
H12  KVNGVKLEENS-TYKILSIYSSVASSLVLLLMIIGGFIFGCQNGNVRCTFCI
H13  EIDGIKLKSEDNVYKALSIYSCIASSVVLVGLILSFIMWACSSGNCRFNVCI
H14  KINPVTLTMGY--KDIILWISFSMSCFVFVALILGFVLWACQNGNIRCQICI
H15  MINPVKLSSGY--KDVILWFSFGASCVMLLAIAMGLIFMCVKNGNLRCTICI
H16  EIEGIKLKTEDNVYKVLSIYSCIASSIVLVGLILAFIMWACSNGSCRFNVCI
```

FIG. 1E

H1 MK--ANLLVLLCALAAADAD-------TICIGYHANNSTDTVDTVLEKNVTVTHSVNLLE
H3 MKTIIALSYIFCLALGQDLPGNDNSTATLCLGHHAVPNGTLVKTITDDQIEVTNATELVQ
HB MK---AIIVILMVVTSNADR---------ICTGITSSNSPHVVKTATQGEVNVTGVIPLTT

▼(Cys52,HA1)
H1 DSHNGKLCRLKG-----IAPLQLGKCNIAGWLLGNPECDPLLPVRSWSYIVETPNSENG-
H3 SSSTGKICNNP------HRILDGIDCTLIDALLGDPHCD-VFQNETWDLFVERSKAFS--
HB TPTKSHFANLKGTETRGKLCPKCLNCTDLDVALGRPKCTGKIPSARVSILHEVRPVTSGC
▲(Arg50,B-HA1) ▲(Ala66,B-HA1)▲(Arg80,B-HA1)

H1 ICYPGDFIDYEELREQLSSVSSF--ERFEIFPKESSWPNHNTNGVTAACS-HEGKSSFYR
H3 NCYPYDVPDYASLRSLVASSG----T-LEFITEGFTWTGVTQNGGSNACK-RGPGNGFFS
HB FPIMHDRTKIRQLPNLLRGYEHIRLSTHNVINAENAPGGPYKIGTSGSCPNITNGNGFFA

H1 NLLWLTEKE------GSYPKLKNSYVNKKGKEVLVLWGIHHPPNSKEQQNLYQNENAYVS
H3 RLNWLTKSG------STYPVLNVTMPNNDNFDKLYIWGVHHPSTNQEQTSLYVQESGRVT
HB TMAWAVPKNDKNKTATNPLTIEVPYICTEGEDQITVWGFHSDSETQMAKLYGDSKPQKFT

H1 VVTSNYNRRFTPEIAERPKVRD-----QAGRMNYYWTLLKPGDTIIFEANGNLIAPMYAF
H3 VSTRRSQQSIIPNIGSRPWVRG-----QSSRISIYWTIVKPGDVLVINSNGNLIAPRGYF
HB SSANGVTTHYVSQIGGFPNQTEDGGLPQSGRIVVDYMVQKSGKTGTITYQRGILLPQKVW
(Trp271)▲

H1 ALSRGFGSGIITSNASMHECNTKCQTPLGAINSSLPYQNIHPVTIGECPKYVRSAKLRMV
H3 KMRTGKSS-IMSSDAPIDTCISECITPNGSIPNDKPFQNVNKITYGACPKYVKQNTLKLA
HB CASGRSKV-IKGSLPLIGEADCLHEKYGGLNKSKPYYTGEHAKAIGNCPIWVKTP-LKLA
▲(Ser277,B-HA1)

FIG. 2A

```
                    ▼(HA2 domain starts)
H1   TGLRNNP---SIQSRGLFGAIAGFIEGGWTGMIDGWYGYHHQNEQGSGYAADQKSTQNAI
H3   TGMRNVP---EKQTRGLFGAIAGFIENGWEGMIDGWYGFRHQNSEGTGQAADLKSTQAAI
HB   NGTKYRPPAKLLKERGFFGAIAGFLEGGWEGMIAGWHGYTSHGAHGVAVAADLKSTQEAI
                    ▲(B-HA2 domain starts)

H1   NGITNKVNTVIEKMNIQFTAVGKEFNKLEKRMENLNKKVDDGFLDIWTYNAELLVLLENE
H3   DQINGKLNRVIEKTNEKFHQIEKEFSEVEGRIQDLEKYVEDTKIDLWSYNAELLVALENQ
HB   NKITKNLNSLSELEVKNLQRLSGAMDELHNEILELDEKVDDLRADTISSQIELAVLLSNE

H1   RTLDFHDSNVKNLYEKVKSQLKNNAKEIGNGCFEFYHKCDNECMESVRNGTYDYPKYSEE
H3   HTIDLTDSEMNKLFEKTRRQLRENAEDMGNGCFKIYHKCDNACIESIRNGTYDHDVYRDE
HB   GIINSEDEHLLALERKLKKMLGPSAVEIGNGCFETKHKCNQTCLDRIAAGTFDAGEFSLP

H1   SKLNR-EKVDGVKLESMGIYQILAIYSTVASSLVLLVSLGAISFWMCSNGSLQCRICI
H3   ALNNR-FQIKGVELKSGYKDWILWISFAISCFLLCVVLLGFI-MWACQRGNIRCNICI
HB   TFDSLNITAASLNDDGLDNHTILLYYSTAASSLAVTLMIAIFVVYMVSRDNVSCSICL
```

FIG. 2B

```
1     DRICTGITSS NSPHVVKTAT QGEVNVTGVI PLTTTPTKSH FANLKGTQTR
                                                          ▲(Arg50)

51    GKLCPNCLNC TDLDVALGRP KCMGTIPSAK ASILHEVKPV TSGCFPIMHD
        ▲(Cys54)    ▲(Ala66)      ▲(Arg/Lys80)    ▲(Cys94)

101   RTKIRQLPNL LRGYENIRLS ARNVTNAETA PGGPYIVGTS GSCPNVTNGN
                                                 ▲(Cys143)

151   GFFATMAWAV PKNKTATNPL TVEVPYICTK GEDQITVWGF HSDDETQMVK
                                   ▲(Cys178)

201   LYGDSKPQKF TSSANGVTTH YVSQIGGFPN QAEDEGLPQS GRIVVDYMVQ

                  (Cys272)▼    ▼(Ser277)
251   KPGKTGTIAY QRGVLLPQKV WCASGRSKVI KGSLPLIGEA DCLHEKYGGL
                            ▲(Trp271)

301   NKSKPYYTGE HAKAIGNCPI WVKTPLKLAN GTKYRPPAKL LK
```

FIG. 3

Headless HK68 HA constructs

Headless PR8 HA constructs

Influenza B Headless HA constructs

INFLUENZA VIRUS VACCINES AND USES THEREOF

This application is a continuation of U.S. patent application Ser. No. 13/638,148, filed Jan. 14, 2013, now U.S. Pat. No. 9,708,373, which is a national stage entry of International patent application No. PCT/US2011/030441, filed Feb. 18, 2011, which claims priority benefit of U.S. provisional application No. 61/319,137, filed Mar. 30, 3010, each of which is incorporated herein by reference in its entirety.

This invention was made with government support under AI086061, AI057158, AI070469, and HHSN266200700010C awarded by the National Institutes of Health (NIH). The government has certain rights in the invention.

1. INTRODUCTION

Provided herein are influenza hemagglutinin stem domain polypeptides, compositions comprising the same, vaccines comprising the same and methods of their use.

2. BACKGROUND

Influenza viruses are enveloped RNA viruses that belong to the family of Orthomyxoviridae (Palese and Shaw (2007) Orthomyxoviridae: The Viruses and Their Replication, 5th ed. Fields' Virology, edited by B. N. Fields, D. M. Knipe and P. M. Howley. Wolters Kluwer Health/Lippincott Williams & Wilkins, Philadelphia, USA, p 1647-1689). The natural host of influenza viruses are avians, but influenza viruses (including those of avian origin) also can infect and cause illness in humans and other animal hosts (canines, pigs, horses, sea mammals, and mustelids). For example, the H5N1 avian influenza virus circulating in Asia has been found in pigs in China and Indonesia and has also expanded its host range to include cats, leopards, and tigers, which generally have not been considered susceptible to influenza A (CIDRAP—Avian Influenza: Agricultural and Wildlife Considerations). The occurrence of influenza virus infections in animals could potentially give rise to human pandemic influenza strains.

Influenza A and B viruses are major human pathogens, causing a respiratory disease that ranges in severity from sub-clinical infection to primary viral pneumonia which can result in death. The clinical effects of infection vary with the virulence of the influenza strain and the exposure, history, age, and immune status of the host. The cumulative morbidity and mortality caused by seasonal influenza is substantial due to the relatively high attack rate. In a normal season, influenza can cause between 3-5 million cases of severe illness and up to 500,000 deaths worldwide (World Health Organization (2003) Influenza: Overview; www.who.int). In the United States, influenza viruses infect an estimated 10-15% of the population (Glezen and Couch R B (1978) Interpandemic influenza in the Houston area, 1974-76. N Engl J Med 298: 587-592; Fox et al. (1982) Influenza virus infections in Seattle families, 1975-1979. II. Pattern of infection in invaded households and relation of age and prior antibody to occurrence of infection and related illness. Am J Epidemiol 116: 228-242) and are associated with approximately 30,000 deaths each year (Thompson W W et al. (2003) Mortality Associated with Influenza and Respiratory Syncytial Virus in the United States. JAMA 289: 179-186; Belshe (2007) Translational research on vaccines: influenza as an example. Clin Pharmacol Ther 82: 745-749).

In addition to annual epidemics, influenza viruses are the cause of infrequent pandemics. For example, influenza A viruses can cause pandemics such as those that occurred in 1918, 1957, 1968, and 2009. Due to the lack of pre-formed immunity against the major viral antigen, hemagglutinin (HA), pandemic influenza can affect greater than 50% of the population in a single year and often causes more severe disease than epidemic influenza. A stark example is the pandemic of 1918, in which an estimated 50-100 million people were killed (Johnson and Mueller (2002) Updating the Accounts: Global Mortality of the 1918-1920 "Spanish" Influenza Pandemic Bulletin of the History of Medicine 76: 105-115). Since the emergence of the highly pathogenic avian H5N1 influenza virus in the late 1990s (Claas et al. (1998) Human influenza A H5N1 virus related to a highly pathogenic avian influenza virus. Lancet 351: 472-7), there have been concerns that it may be the next pandemic virus.

An effective way to protect against influenza virus infection is through vaccination; however, current vaccination approaches rely on achieving a good match between circulating strains and the isolates included in the vaccine. Such a match is often difficult to attain due to a combination of factors. First, influenza viruses are constantly undergoing change: every 3-5 years the predominant strain of influenza A virus is replaced by a variant that has undergone sufficient antigenic drift to evade existing antibody responses. Isolates to be included in vaccine preparations must therefore be selected each year based on the intensive surveillance efforts of the World Health Organization (WHO) collaborating centers. Second, to allow sufficient time for vaccine manufacture and distribution, strains must be selected approximately six months prior to the initiation of the influenza season. Often, the predictions of the vaccine strain selection committee are inaccurate, resulting in a substantial drop in the efficacy of vaccination.

The possibility of a novel subtype of influenza A virus entering the human population also presents a significant challenge to current vaccination strategies. Since it is impossible to predict what subtype and strain of influenza virus will cause the next pandemic, current, strain-specific approaches cannot be used to prepare a pandemic influenza vaccine.

3. SUMMARY

In one aspect, provided herein are influenza hemagglutinin stem domain polypeptides. In certain embodiments, the influenza hemagglutinin stem domain polypeptides lack globular head domains as described herein.

While not intending to be bound by any particular theory of operation, it is believed that the globular head domain of an influenza hemagglutinin comprises one or more highly immunogenic regions. These highly immunogenic regions might generate a host immune response. However, the highly immunogenic regions might also vary from strain to strain of influenza virus. Embodiments presented herein are based on, in part, the discovery that residues in influenza hemagglutinin stem domains are relatively conserved and immunogenic, and that antibodies binding to this region may be neutralizing. An influenza hemagglutinin stem domain polypeptide, lacking all or substantially all of an influenza hemagglutinin globular head domain, may be used to generate an immune response to one or more conserved epitopes of the stem domain polypeptide. Removal of the highly immunogenic regions of the globular head domain might expose one or more epitopes of the stem domain polypeptide to a host immune system. In addition, in certain embodiments, elimination of the glycosylation of the influenza hemagglutinin stem domain through alteration of glycosylation sites present therein may render the conserved regions of the stem domain more accessible to the host immune response.

If the one or more epitopes of the stem domain polypeptide are less immunogenic than the highly immunogenic regions of a globular head domain, the absence of a globular head domain in the stem domain polypeptide might allow an immune response against the one or more epitopes of the stem domain polypeptide to develop. Advantageously, since the amino acid sequences of influenza hemagglutinin stem domain polypeptides might be conserved or highly conserved across viral subtypes, an immune response against an influenza hemagglutinin stem domain polypeptide provided herein might cross react with one or more viral subtypes other than the subtype corresponding to the stem domain polypeptide. Accordingly, the influenza hemagglutinin stem domain polypeptides provided herein may be useful for immunogenic compositions (e.g. vaccines) capable of generating immune responses against a plurality of influenza virus strains.

Without being bound by any theory, influenza hemagglutinin stem domain polypeptides described herein are based, in part, on the inventors' discovery of polypeptides that lack the globular head domain of influenza hemagglutinin and maintain the stability of the pre-fusion conformation of influenza hemagglutinin. In one aspect, without being bound by theory, the inventors have discovered that the maintenance of cysteine residues identified as $A_p$ and $A_q$ in influenza hemagglutinin polypeptides in FIG. 1 contributes the stability of the stalk region of influenza hemagglutinin. In another aspect, without being bound by theory, the inventors have discovered that influenza hemagglutinin stem domain polypeptides that maintain the pre-fusion conformation of influenza hemagglutinin polypeptides are more effective at inducing a protective effect in subjects. In certain aspects, the stability of the pre-fusion conformation can be conferred by introducing amino acid substitutions at certain residues, such as HA1 H17Y (H3 numbering).

3.1 Terminology

The terms "about" or "approximate," when used in reference to an amino acid position refer to the particular amino acid position in a sequence or any amino acid that is within five, four, three, two or one residues of that amino acid position, either in an N-terminal direction or a C-terminal direction.

As used herein, the term "about" or "approximately" when used in conjunction with a number refers to any number within 1, 5 or 10% of the referenced number.

The term "amino acid sequence identity" refers to the degree of identity or similarity between a pair of aligned amino acid sequences, usually expressed as a percentage. Percent identity is the percentage of amino acid residues in a candidate sequence that are identical (i.e., the amino acid residues at a given position in the alignment are the same residue) or similar (i.e., the amino acid substitution at a given position in the alignment is a conservative substitution, as discussed below), to the corresponding amino acid residue in the peptide after aligning the sequences and introducing gaps, if necessary, to achieve the maximum percent sequence homology. Sequence homology, including percentages of sequence identity and similarity, are determined using sequence alignment techniques well-known in the art, preferably computer algorithms designed for this purpose, using the default parameters of said computer algorithms or the software packages containing them. Non-limiting examples of computer algorithms and software packages incorporating such algorithms include the following. The BLAST family of programs exemplify a particular, non-limiting example of a mathematical algorithm utilized for the comparison of two sequences (e.g., Karlin & Altschul, 1990, *Proc. Natl. Acad. Sci. USA* 87:2264-2268 (modified as in Karlin & Altschul, 1993, *Proc. Natl. Acad. Sci. USA* 90:5873-5877), Altschul et al., 1990, *J. Mol. Biol.* 215:403-410, (describing NBLAST and XBLAST), Altschul et al., 1997, *Nucleic Acids Res.* 25:3389-3402 (describing Gapped BLAST, and PSI-Blast). Another particular example is the algorithm of Myers and Miller (1988 CABIOS 4:11-17) which is incorporated into the ALIGN program (version 2.0) and is available as part of the GCG sequence alignment software package. Also particular is the FASTA program (Pearson W. R. and Lipman D. J., *Proc. Nat. Acad. Sci. USA,* 85:2444-2448, 1988), available as part of the Wisconsin Sequence Analysis Package. Additional examples include BESTFIT, which uses the "local homology" algorithm of Smith and Waterman (Advances in Applied Mathematics, 2:482-489, 1981) to find best single region of similarity between two sequences, and which is preferable where the two sequences being compared are dissimilar in length; and GAP, which aligns two sequences by finding a "maximum similarity" according to the algorithm of Neddleman and Wunsch (*J. Mol. Biol.* 48:443-354, 1970), and is preferable where the two sequences are approximately the same length and an alignment is expected over the entire length.

"Conservative substitution" refers to replacement of an amino acid of one class is with another amino acid of the same class. In particular embodiments, a conservative substitution does not alter the structure or function, or both, of a polypeptide. Classes of amino acids for the purposes of conservative substitution include hydrophobic (Met, Ala, Val, Leu, Ile), neutral hydrophilic (Cys, Ser, Thr), acidic (Asp, Glu), basic (Asn, Gln, His, Lys, Arg), conformation disrupters (Gly, Pro) and aromatic (Trp, Tyr, Phe).

As used herein, the terms "disease" and "disorder" are used interchangeably to refer to a condition in a subject. In some embodiments, the condition is a viral infection. In specific embodiments, a term "disease" refers to the pathological state resulting from the presence of the virus in a cell or a subject, or by the invasion of a cell or subject by the virus. In certain embodiments, the condition is a disease in a subject, the severity of which is decreased by inducing an immune response in the subject through the administration of an immunogenic composition.

As used herein, the term "effective amount" in the context of administering a therapy to a subject refers to the amount of a therapy which has a prophylactic and/or therapeutic effect(s). In certain embodiments, an "effective amount" in the context of administration of a therapy to a subject refers to the amount of a therapy which is sufficient to achieve one, two, three, four, or more of the following effects: (i) reduce or ameliorate the severity of an influenza virus infection, disease or symptom associated therewith; ii) reduce the duration of an influenza virus infection, disease or symptom associated therewith; (iii) prevent the progression of an influenza virus infection, disease or symptom associated therewith; (iv) cause regression of an influenza virus infection, disease or symptom associated therewith; (v) prevent the development or onset of an influenza virus infection, disease or symptom associated therewith; (vi) prevent the recurrence of an influenza virus infection, disease or symptom associated therewith; (vii) reduce or prevent the spread of an influenza virus from one cell to another cell, one tissue to another tissue, or one organ to another organ; (ix) prevent or reduce the spread of an influenza virus from one subject to another subject; (x) reduce organ failure associated with an influenza virus infection; (xi) reduce hospitalization of a subject; (xii) reduce hospitalization length; (xiii) increase the survival of a subject with an influenza virus infection or disease associated therewith; (xiv) eliminate an influenza virus infection or disease associated therewith; (xv) inhibit or reduce influenza virus replication; (xvi) inhibit or reduce the entry of an influenza virus into a host cell(s); (xviii) inhibit or reduce replication of the influenza virus genome; (xix) inhibit or reduce synthesis of influenza virus proteins; (xx) inhibit or reduce assembly of influenza virus particles; (xxi) inhibit or reduce release of influenza virus particles from a host cell(s); (xxii) reduce influenza virus titer; and/or (xxiii) enhance or improve the prophylactic or therapeutic effect(s) of another therapy.

In certain embodiments, the effective amount does not result in complete protection from an influenza virus disease, but results in a lower titer or reduced number of influenza viruses compared to an untreated subject. In certain embodiments, the effective amount results in a 0.5 fold, 1 fold, 2 fold, 4 fold, 6 fold, 8 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titer of influenza virus relative to an untreated subject. In some embodiments, the effective amount results in a reduction in titer of influenza virus relative to an untreated subject of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs. Benefits of a reduction in the titer, number or total burden of influenza virus include, but are not limited to, less severe symptoms of the infection, fewer symptoms of the infection and a reduction in the length of the disease associated with the infection.

"Hemagglutinin" and "HA" refer to any hemagglutinin known to those of skill in the art. In certain embodiments, the hemagglutinin is influenza hemagglutinin, such as an influenza A hemagglutinin, an influenza B hemagglutinin or an influenza C hemagglutinin. A typical hemagglutinin comprises domains known to those of skill in the art including a signal peptide (optional herein), a stem domain, a globular head domain, a luminal domain (optional herein), a transmembrane domain (optional herein) and a cytoplasmic domain (optional herein). In certain embodiments, a hemagglutinin consists of a single polypeptide chain, such as HA0. In certain embodiments, a hemagglutinin consists of more than one polypeptide chain in quaternary association, e.g. HA1 and HA2. Those of skill in the art will recognize that an immature HA0 might be cleaved to release a signal peptide (approximately 20 amino acids) yielding a mature hemagglutinin HA0. A hemagglutinin HA0 might be cleaved at another site to yield HA1 polypeptide (approximately 320 amino acids, including the globular head domain and a portion of the stem domain) and HA2 polypeptide (approximately 220 amino acids, including the remainder of the stem domain, a luminal domain, a transmembrane domain and a cytoplasmic domain). In certain embodiments, a hemagglutinin comprises a signal peptide, a transmembrane domain and a cytoplasmic domain. In certain embodiments, a hemagglutinin lacks a signal peptide, i.e. the hemagglutinin is a mature hemagglutinin. In certain embodiments, a hemagglutinin lacks a transmembrane domain or cytoplasmic domain, or both. As used herein, the terms "hemagglutinin" and "HA" encompass hemagglutinin polypeptides that are modified by post-translational processing such as signal peptide cleavage, disulfide bond formation, glycosylation (e.g., N-linked glycosylation), protease cleavage and lipid modification (e.g. S-palmitoylation).

"HA1 N-terminal stem segment" refers to a polypeptide segment that corresponds to the amino-terminal portion of the stem domain of an influenza hemagglutinin HA1 polypeptide. In certain embodiments, an HA1 N-terminal stem segment consists of amino acid residues corresponding approximately to amino acids $HA1_{N\text{-}term}$ through $A_p$ of an HA1 domain. $HA1_{N\text{-}term}$ is the N-terminal amino acid of HA1 as recognized by those of skill in the art. $A_p$ is the cysteine residue in the HA1 N-terminal stem segment that forms or is capable of forming a disulfide bond with a cysteine residue in an HA1 C-terminal stem segment. Residue $A_p$ is identified in influenza A hemagglutinin polypeptides in FIG. 1. Exemplary HA1 N-terminal stem segments are described herein. In certain embodiments, an HA1 N-terminal stem segment consists of amino acid residues corresponding approximately to amino acids 1-52 of HA1 from an H3 hemagglutinin. Note that, in this numbering system, 1 refers to the N-terminal amino acid of the mature HA0 protein, from which the signal peptide has been removed.

"HA1 C-terminal stem segment" refers to a polypeptide segment that corresponds to the carboxy-terminal portion of the stem domain of an influenza hemagglutinin HA1 polypeptide. In certain embodiments, an HA1 C-terminal stem segment consists of amino acid residues corresponding approximately to amino acids $A_q$ through $HA1_{C\text{-}term}$ of an HA1 domain. $HA1_{C\text{-}term}$ is the C-terminal amino acid of the HA1 domain as recognized by those of skill in the art. Residue $A_q$ is identified in influenza A hemagglutinin polypeptides in FIG. 1. Exemplary HA1 C-terminal stem segments are described herein. In certain embodiments, an HA1 C-terminal stem segment consists of amino acid residues corresponding approximately to amino acids 277-329 of HA1 from an H3 hemagglutinin. Note that, in this numbering system, 1 refers to the N-terminal amino acid of the mature HA0 protein, from which the signal peptide has been removed.

"HA1 C-terminal short stem segment" refers to a polypeptide segment that corresponds to the carboxyl-terminal portion of the stem domain of an influenza hemagglutinin HA1 polypeptide. In certain embodiments, an HA1 C-terminal short stem segment consists of amino acid residues corresponding approximately to amino acids $B_q$ through $HA1_{C\text{-}term}$ of an HA1 domain. Residue $B_q$ is identified in influenza A hemagglutinin polypeptides in FIG. 1. Exemplary HA1 C-terminal short stem segments are described herein. In certain embodiments, an HA1 C-terminal short stem segment consists of amino acid residues corresponding approximately to amino acids 305-329 of HA1 from an H3 hemagglutinin. Note that, in this numbering system, 1 refers to the N-terminal amino acid of the mature HA0 protein, from which the signal peptide has been removed.

"HA1 N-terminal long stem segment" refers to a polypeptide segment that corresponds to the amino-terminal portion of the stem domain of an influenza hemagglutinin HA1 polypeptide. In certain embodiments, an HA1 N-terminal long stem segment consists of amino acid residues corresponding approximately to amino acids $HA1_{N\text{-}term}$ through $C_p$ of an HA1 domain. $C_p$ is a cysteine residue in the HA1 N-terminal long stem segment that is or is capable of being linked to an alanine residue in an HA1 C-terminal long stem segment. Residue $C_p$ is identified in influenza A hemagglutinin polypeptides in FIG. 1. Exemplary HA1 N-terminal long stem segments are described herein. In certain embodiments, an HA1 N-terminal long stem segment consists of amino acid residues corresponding approximately to amino acids 1-97 of HA1 from an H3 hemagglutinin. Note that, in this numbering system, 1 refers to the N-terminal amino acid of the mature HA0 protein, from which the signal peptide has been removed.

"HA1 C-terminal long stem segment" refers to a polypeptide segment that corresponds to the carboxyl-terminal portion of the stem domain of an influenza hemagglutinin HA1 polypeptide. In certain embodiments, an HA1 C-terminal long stem segment consists of amino acid residues corresponding approximately to amino acids $C_q$ through $HA1_{C\text{-}term}$ of an HA1 domain. $C_q$ is an alanine residue in the HA1 C-terminal long stem segment that is or is capable of being linked to a cysteine residue in an HA1 N-terminal long stem segment. Residue $C_q$ is identified in influenza A hemagglutinin polypeptides in FIG. 1. Exemplary HA1 C-terminal long stem segments are described herein. In certain embodiments, an HA1 C-terminal long stem segment consists of amino acid residues corresponding approximately to amino acids 253-329 of HA1 from an H3 hemagglutinin. Note that, in this numbering system, 1 refers to the N-terminal amino acid of the mature HA0 protein, from which the signal peptide has been removed.

"HA2" refers to a polypeptide domain that corresponds to the HA2 domain of an influenza hemagglutinin polypeptide known to those of skill in the art. In certain embodiments, an HA2 consists of a stem domain, a luminal domain, a transmembrane domain and a cytoplasmic domain (see, e.g., Scheiffle et al., 2007, *EMBO J.* 16(18):5501-5508, the contents of which are incorporated by reference in their entirety). In certain embodiments, an HA2 consists of a stem domain, a luminal domain and a transmembrane domain. In certain embodiments, an HA2 consists of a stem domain and a luminal domain; in such embodiments, the HA2 might be soluble. In certain embodiments, an HA2 consists of a stem domain; in such embodiments, the HA2 might be soluble.

As used herein, the term "heterologous" in the context of a polypeptide, nucleic acid or virus refers to a polypeptide, nucleic acid or virus, respectively, that is not normally found in nature or not normally associated in nature with a polypeptide, nucleic acid or virus of interest. For example, a "heterologous polypeptide" may refer to a polypeptide derived from a different virus, e.g., a different influenza strain or subtype, or an unrelated virus or different species.

As used herein, the term "in combination," in the context of the administration of two or more therapies to a subject, refers to the use of more than one therapy (e.g., more than one prophylactic agent and/or therapeutic agent). The use of the term "in combination" does not restrict the order in which therapies are administered to a subject. For example, a first therapy (e.g., a first prophylactic or therapeutic agent) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

As used herein, the term "infection" means the invasion by, multiplication and/or presence of a virus in a cell or a subject. In one embodiment, an infection is an "active" infection, i.e., one in which the virus is replicating in a cell or a subject. Such an infection is characterized by the spread of the virus to other cells, tissues, and/or organs, from the cells, tissues, and/or organs initially infected by the virus. An infection may also be a latent infection, i.e., one in which the virus is not replicating. In certain embodiments, an infection refers to the pathological state resulting from the presence of the virus in a cell or a subject, or by the invasion of a cell or subject by the virus.

As used herein, the term "influenza virus disease" refers to the pathological state resulting from the presence of an influenza (e.g., influenza A or B virus) virus in a cell or subject or the invasion of a cell or subject by an influenza virus. In specific embodiments, the term refers to a respiratory illness caused by an influenza virus.

As used herein, the phrases "IFN deficient system" or "IFN-deficient substrate" refer to systems, e.g., cells, cell lines and animals, such as pigs, mice, chickens, turkeys, rabbits, rats, etc., which do not produce IFN or produce low levels of IFN (i.e., a reduction in IFN expression of 5-10%, 10-20%, 20-30%, 30-40%, 40-50%, 50-60%, 60-70%, 70-80%, 80-90% or more when compared to IFN-competent systems under the same conditions), do not respond or respond less efficiently to IFN, and/or are deficient in the activity of one or more antiviral genes induced by IFN.

As used herein, the numeric term "log" refers to $\log_{10}$.

As used herein, the phrase "multiplicity of infection" or "MOI" is the average number of infectious virus particles per infected cell. The MOI is determined by dividing the number of infectious virus particles added (ml added×PFU/ml) by the number of cells added (ml added×cells/ml).

As used herein, the term "nucleic acid" is intended to include DNA molecules (e.g., cDNA or genomic DNA) and RNA molecules (e.g., mRNA) and analogs of the DNA or RNA generated using nucleotide analogs. The nucleic acid can be single-stranded or double-stranded.

"Polypeptide" refers to a polymer of amino acids linked by amide bonds as is known to those of skill in the art. As used herein, the term can refer to a single polypeptide chain linked by covalent amide bonds. The term can also refer to multiple polypeptide chains associated by non-covalent interactions such as ionic contacts, hydrogen bonds, Van der Waals contacts and hydrophobic contacts. Those of skill in the art will recognize that the term includes polypeptides that have been modified, for example by post-translational processing such as signal peptide cleavage, disulfide bond formation, glycosylation (e.g., N-linked glycosylation), protease cleavage and lipid modification (e.g. S-palmitoylation).

As used herein, the terms "prevent," "preventing" and "prevention" in the context of the administration of a therapy(ies) to a subject to prevent an influenza virus disease refer to one or more of the following effects resulting from the administration of a therapy or a combination of therapies: (i) the inhibition of the development or onset of an influenza virus disease or a symptom thereof; (ii) the inhibition of the recurrence of an influenza virus disease or a symptom associated therewith; and (iii) the reduction or inhibition in influenza virus infection and/or replication.

As used herein, the terms "purified" and "isolated" when used in the context of a polypeptide (including antibody)

that is obtained from a natural source, e.g., cells, refers to a polypeptide which is substantially free of contaminating materials from the natural source, e.g., soil particles, minerals, chemicals from the environment, and/or cellular materials from the natural source, such as but not limited to cell debris, cell wall materials, membranes, organelles, the bulk of the nucleic acids, carbohydrates, proteins, and/or lipids present in cells. Thus, a polypeptide that is isolated includes preparations of a polypeptide having less than about 30%, 20%, 10%, 5%, 2%, or 1% (by dry weight) of cellular materials and/or contaminating materials. As used herein, the terms "purified" and "isolated" when used in the context of a polypeptide (including antibody) that is chemically synthesized refers to a polypeptide which is substantially free of chemical precursors or other chemicals which are involved in the syntheses of the polypeptide. In a specific embodiment, an influenza hemagglutinin stem domain polypeptide is chemically synthesized. In another specific embodiment, an influenza hemagglutinin stem domain polypeptide is isolated.

As used herein, the terms "replication," "viral replication" and "virus replication" in the context of a virus refer to one or more, or all, of the stages of a viral life cycle which result in the propagation of virus. The steps of a viral life cycle include, but are not limited to, virus attachment to the host cell surface, penetration or entry of the host cell (e.g., through receptor mediated endocytosis or membrane fusion), uncoating (the process whereby the viral capsid is removed and degraded by viral enzymes or host enzymes thus releasing the viral genomic nucleic acid), genome replication, synthesis of viral messenger RNA (mRNA), viral protein synthesis, and assembly of viral ribonucleoprotein complexes for genome replication, assembly of virus particles, post-translational modification of the viral proteins, and release from the host cell by lysis or budding and acquisition of a phospholipid envelope which contains embedded viral glycoproteins. In some embodiments, the terms "replication," "viral replication" and "virus replication" refer to the replication of the viral genome. In other embodiments, the terms "replication," "viral replication" and "virus replication" refer to the synthesis of viral proteins.

"Stem domain polypeptide" refers to a derivative, e.g. an engineered derivative, of a hemagglutinin polypeptide that comprises one or more polypeptide chains that make up a stem domain of hemagglutinin. A stem domain polypeptide might be a single polypeptide chain, two polypeptide chains or more polypeptide chains. Typically, a stem domain polypeptide is a single polypeptide chain (i.e. corresponding to the stem domain of a hemagglutinin HA0 polypeptide) or two polypeptide chains (i.e. corresponding to the stem domain of a hemagglutinin HA1 polypeptide in association with a hemagglutinin HA2 polypeptide). In certain embodiments, a stem domain polypeptide is derived from an influenza hemagglutinin. Engineered stem domain polypeptides can comprise one or more linkers as described below.

As used herein, the terms "subject" or "patient" are used interchangeably to refer to an animal (e.g., birds, reptiles, and mammals). In a specific embodiment, a subject is a bird. In another embodiment, a subject is a mammal including a non-primate (e.g., a camel, donkey, zebra, cow, pig, horse, goat, sheep, cat, dog, rat, and mouse) and a primate (e.g., a monkey, chimpanzee, and a human). In certain embodiments, a subject is a non-human animal. In some embodiments, a subject is a farm animal or pet. In another embodiment, a subject is a human. In another embodiment, a subject is a human infant. In another embodiment, a subject is a human child. In another embodiment, a subject is a human adult. In another embodiment, a subject is an elderly human. In another embodiment, a subject is a premature human infant.

As used herein, the term "premature human infant" refers to a human infant born at less than 37 weeks of gestational age.

As used herein, the term "human infant" refers to a newborn to 1 year old human.

As used herein, the term "human child" refers to a human that is 1 year to 18 years old.

As used herein, the term "human adult" refers to a human that is 18 years or older.

As used herein, the term "elderly human" refers to a human 65 years or older.

The terms "tertiary structure" and "quaternary structure" have the meanings understood by those of skill in the art. Tertiary structure refers to the three-dimensional structure of a single polypeptide chain. Quaternary structure refers to the three dimensional structure of a polypeptide having multiple polypeptide chains.

As used herein, the terms "therapies" and "therapy" can refer to any protocol(s), method(s), compound(s), composition(s), formulation(s), and/or agent(s) that can be used in the prevention or treatment of a viral infection or a disease or symptom associated therewith. In certain embodiments, the terms "therapies" and "therapy" refer to biological therapy, supportive therapy, and/or other therapies useful in treatment or prevention of a viral infection or a disease or symptom associated therewith known to one of skill in the art. In some embodiments, the term "therapy" refers to a nucleic acid encoding an influenza virus hemagglutinin stem domain polypeptide, an influenza virus hemagglutinin stem domain polypeptide, or a vector or composition comprising said nucleic acid encoding an influenza virus hemagglutinin stem domain polypeptide or an influenza hemagglutinin stem domain polypeptide. In some embodiments, the term "therapy" refers to an antibody that specifically binds to an influenza virus hemagglutinin polypeptide or an influenza virus hemagglutinin stem domain polypeptide.

As used herein, the terms "treat," "treatment," and "treating" refer in the context of administration of a therapy(ies) to a subject to treating an influenza virus disease to obtain a beneficial or therapeutic effect of a therapy or a combination of therapies. In specific embodiments, such terms refer to one, two, three, four, five or more of the following effects resulting from the administration of a therapy or a combination of therapies: (i) the reduction or amelioration of the severity of an influenza virus infection or a disease or a symptom associated therewith; (ii) the reduction in the duration of an influenza virus infection or a disease or a symptom associated therewith; (iii) the regression of an influenza virus infection or a disease or a symptom associated therewith; (iv) the reduction of the titer of an influenza virus; (v) the reduction in organ failure associated with an influenza virus infection or a disease associated therewith; (vi) the reduction in hospitalization of a subject; (vii) the reduction in hospitalization length; (viii) the increase in the survival of a subject; (ix) the elimination of an influenza virus infection or a disease or symptom associated therewith; (x) the inhibition of the progression of an influenza virus infection or a disease or a symptom associated therewith; (xi) the prevention of the spread of an influenza virus from a cell, tissue, organ or subject to another cell, tissue, organ or subject; (xii) the inhibition or reduction in the entry of an influenza virus into a host cell(s); (xiii) the inhibition or reduction in the replication of an influenza virus genome;

(xiv) the inhibition or reduction in the synthesis of influenza virus proteins; (xv) the inhibition or reduction in the release of influenza virus particles from a host cell(s); and/or (xvi) the enhancement or improvement the therapeutic effect of another therapy.

As used herein, in some embodiments, the phrase "wild-type" in the context of a virus refers to the types of a virus that are prevalent, circulating naturally and producing typical outbreaks of disease. In other embodiments, the term "wild-type" in the context of a virus refers to a parental virus.

4. BRIEF DESCRIPTION OF THE DRAWINGS

FIG. 1A-FIG. 1E present a sequence alignment by CLUSTALW of representative sequences of 16 subtypes of influenza virus A hemagglutinin (SEQ ID NOS:1-16, respectively).

FIG. 2A and FIG. 2B present a sequence alignment by CLUSTALW of a representative sequence of influenza virus B hemagglutinin (SEQ ID NO:17) aligned with influenza A HK68-H3N2 (SEQ ID NO:3) and PR8-H1N1 (SEQ ID NO:1) hemagglutinins.

FIG. 3 presents a sequence listing of influenza B virus hemagglutinin (SEQ ID NO:17), noting amino acids that constitute boundaries for various N- and C-terminal stem segments and intermediate stem segments described herein.

Figure 4B:
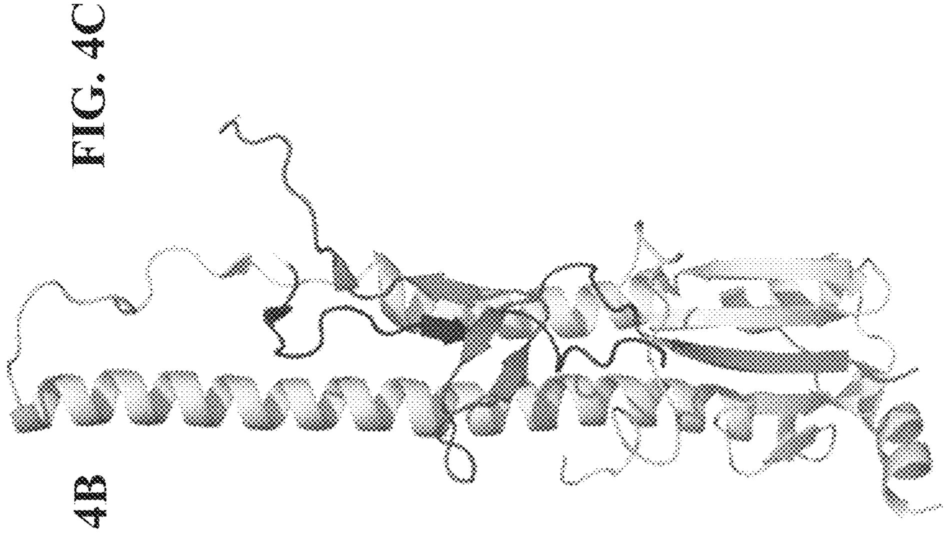
Figure 4C:
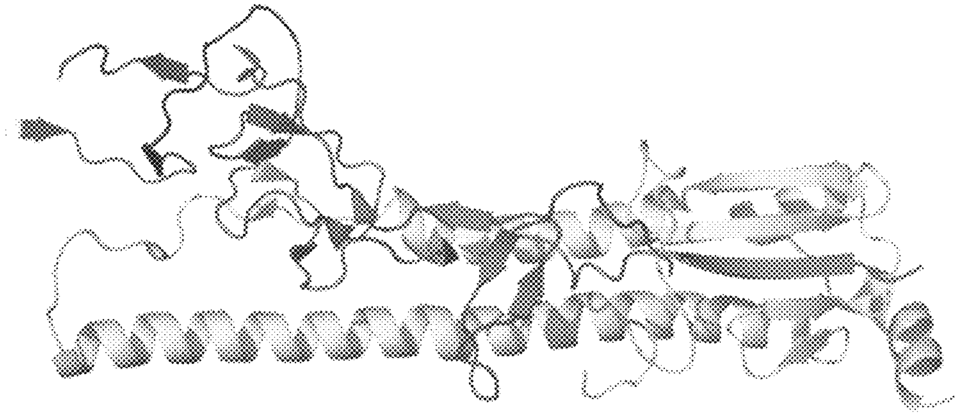

FIG. 4A-FIG. 4C provide putative structures of influenza A HA stem domain polypeptides based on an HK68-H3N2 hemagglutinin protein. FIG. 4A provides the putative structure of an influenza A HA stem domain polypeptide based on an HK68-H3N2 hemagglutinin protein, HA1 N-terminal stem segment SEQ ID NO:36 and C-terminal stem segment SEQ ID NO:52. FIG. 4B provides the putative structure of an influenza A HA short stem domain polypeptide based on an HK68-H3N2 hemagglutinin protein, HA1 N-terminal stem segment SEQ ID NO:36 and C-terminal short stem segment SEQ ID NO:352. FIG. 4C provides the putative structure of an influenza A HA long stem domain polypeptide based on an HK68-H3N2 hemagglutinin protein, HA1 N-terminal long stem segment SEQ ID NO:417 and C-terminal long stem segment SEQ ID NO:433.

Figure 5C:
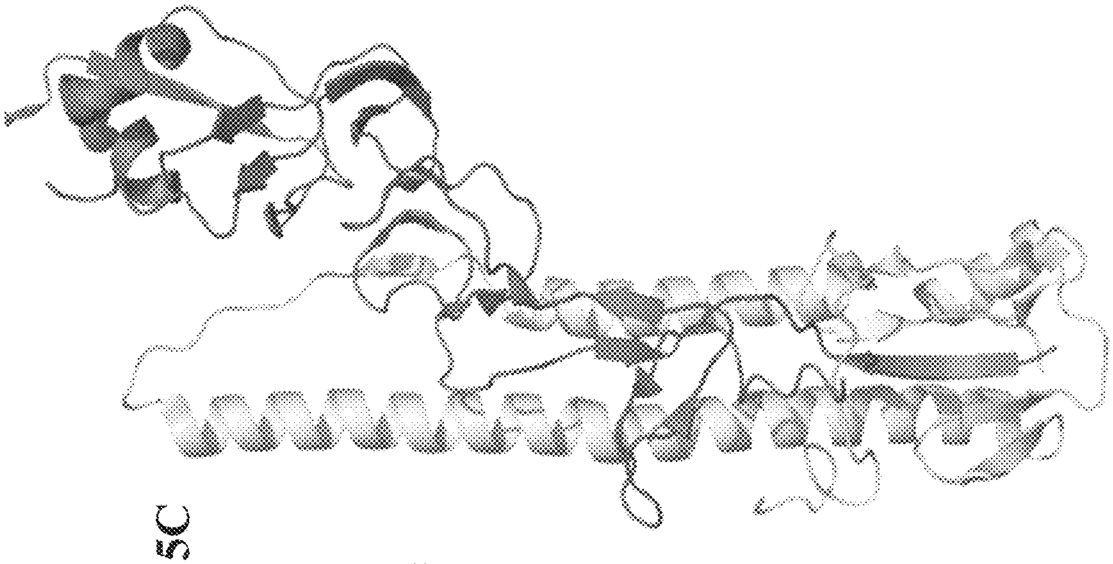
Figure 5B:
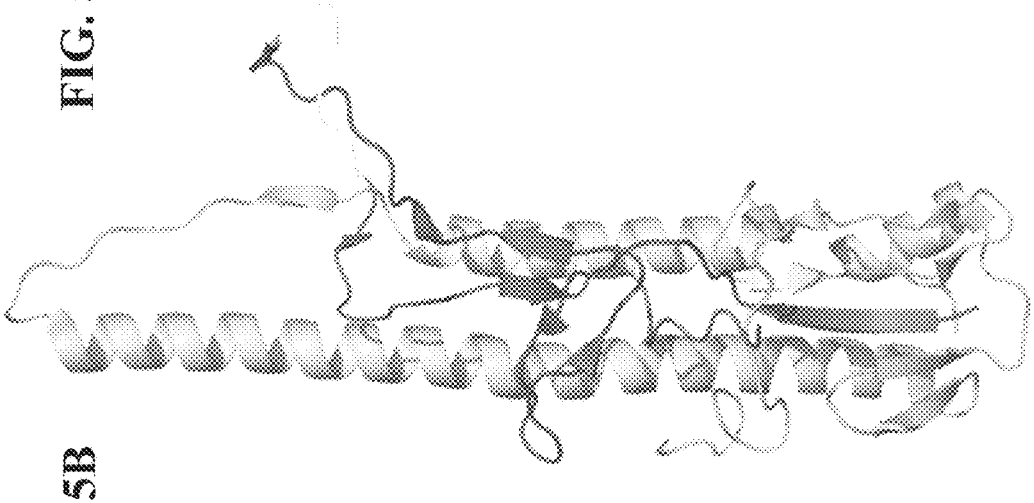
Figure 5A:
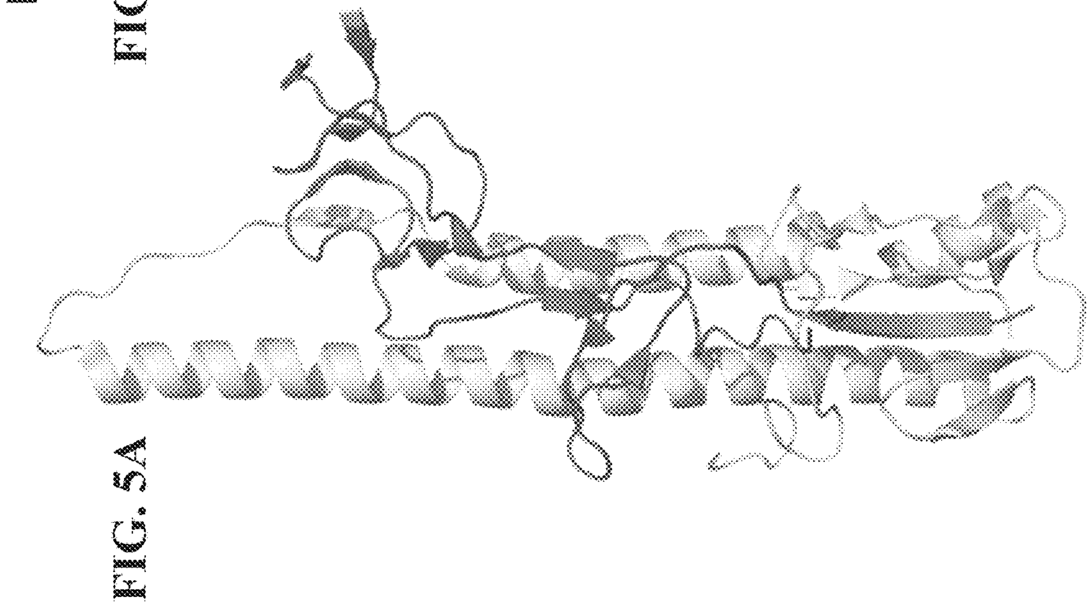

FIG. 5A-FIG. 5C provide putative structures of influenza A HA stem domain polypeptides based on a PR8-H1N1 hemagglutinin protein. FIG. 5A provides the putative structure of an influenza A HA stem domain polypeptide based on a PR8-H1N1 hemagglutinin protein, HA1 N-terminal stem segment SEQ ID NO:18 and C-terminal stem segment SEQ ID NO:34. FIG. 5B provides the putative structure of an influenza A HA short stem domain polypeptide, HA1 N-terminal stem segment SEQ ID NO:18 and C-terminal short stem segment SEQ ID NO:350. FIG. 5C provides the putative structure of an influenza A HA long stem domain polypeptide based on a PR8-H1N1 hemagglutinin protein, HA1 N-terminal long stem segment SEQ ID NO:414 and C-terminal long stem segment SEQ ID NO:430.

Figure 6A:
Figure 6B:
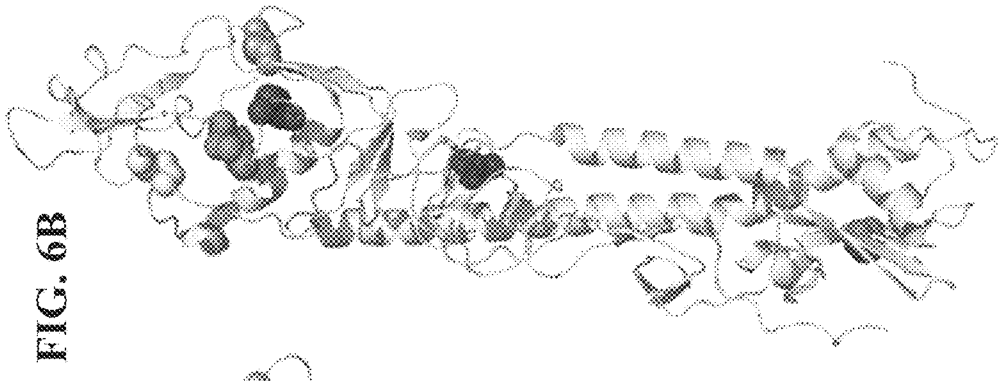
Figure 6C:
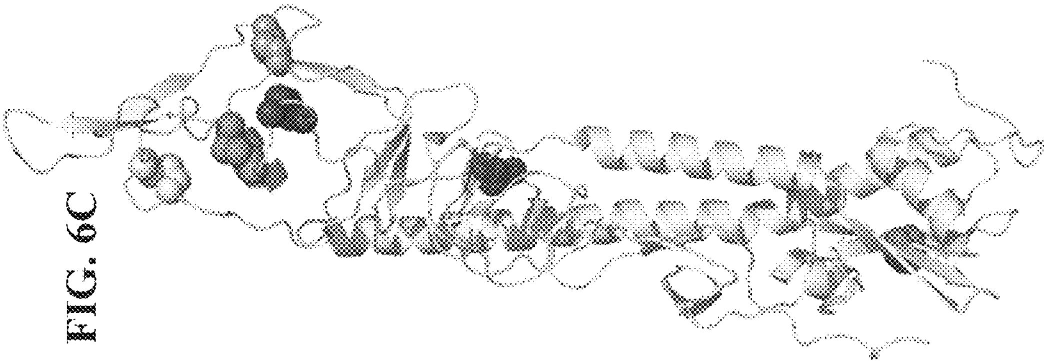
Figure 6D:
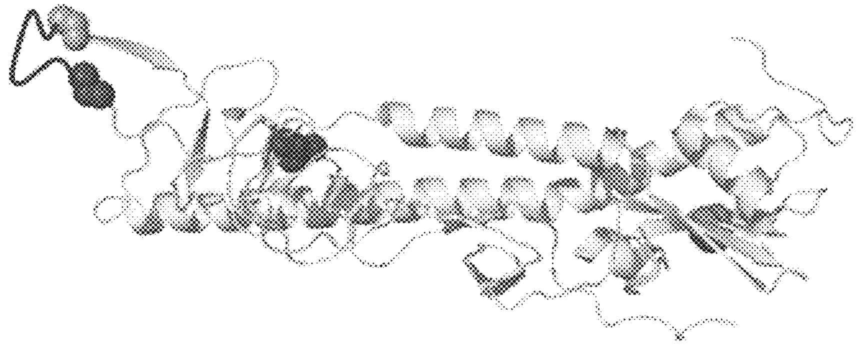

FIG. 6A-FIG. 6D provide putative structures of influenza B HA stem domain polypeptides. FIG. 6A provides a partially headless HA molecule based on the B/Hong Kong/8/73 hemagglutinin protein, in which the first 94 amino acids of the HA1 domain of the HA are retained (SEQ ID NO:550), and where Cys94 is linked directly to Cys143 of the HA1 domain (SEQ ID NO: 553), by means of a linker bridge. FIG. 6B depicts a partially headless HA molecule based on the B/Hong Kong/8/73 hemagglutinin protein, in which the first 178 amino acids of the HA1 domain of the HA are retained (SEQ ID NO:551), and where Cys178 is linked directly to Cys272 of the HA1 domain (SEQ ID NO:554), by means of a linker bridge. FIG. 6C depicts a headless HA molecule based on the B/Hong Kong/8/73 hemagglutinin protein, in which the first 94 amino acids of the HA1 domain of the HA are retained (SEQ ID NO:555), and where Cys94 is linked directly to Cys143 of the HA1 domain, by means of a linker bridge. Amino acids 143 to 178 of the HA1 domain are furthermore retained (SEQ ID NO:556), and Cys178 is linked directly to Cys272 of the HA1 domain (SEQ ID NO:557), by means of a linker bridge. FIG. 6D depicts a headless HA molecule based on the B/Hong Kong/8/73 hemagglutinin protein, in which the first 54 amino acids of the HA1 domain of the HA are retained (SEQ ID NO:552), and where Cys54 is linked directly to Cys272 of the HA1 domain (SEQ ID NO:554), by means of a linker bridge.

5. DETAILED DESCRIPTION

5.1 Polypeptides

Provided herein are influenza hemagglutinin stem domain polypeptides. While not intending to be bound by any particular theory of operation, it is believed that the influenza hemagglutinin stem domain polypeptides are useful for presenting one or more relatively conserved antigenic regions to a host immune system in order to generate an immune response that is capable of cross-reacting with a plurality of influenza strains. Since the one or more antigenic regions are well conserved across influenza hemagglutinin subtypes, such an immune response might cross-react with several subtypes of full-length influenza hemagglutinin polypeptides.

It is believed that full-length influenza hemagglutinin presents several highly antigenic segments in its globular head domain. These highly antigenic segments might be more accessible to a host immune system or more immunogenic in structure, or both. It is believed that a host immune system responds preferentially to these highly immunogenic segments compared to one or more epitopes in the stem domain of an influenza hemagglutinin. Further, since a globular head domain of an influenza hemagglutinin might be variable across subtypes and viral strains, an immune response against one globular head domain subtype might be limited to the specific highly antigenic segments of that globular head domain. Strains with different globular head domains might not cross react with the same immune response. As such, the effectiveness of vaccines presenting hemagglutinin polypeptides might be limited to the specific strains presented in the vaccine. Hence, a given conventional influenza vaccine is likely only effective against the influenza strains predicted to be virulent during a given flu season.

Advantageously, influenza hemagglutinin stem domain polypeptides provided herein might be useful to generate an immune response against multiple influenza strains. The influenza hemagglutinin stem domain polypeptides generally do not comprise the highly antigenic, variable globular head domains of conventional influenza vaccine polypeptides. Thus, they should not generate immune responses limited to the variable segments of the globular head domains. Instead, they present one or more epitopes in the relatively conserved stem domain of influenza hemagglutinin. As such, they might be used to generate a host immune response against multiple influenza strains that carry the relatively conserved epitopes. Accordingly, the influenza hemagglutinin stem domain polypeptides find use as antigens in the compositions, vaccines and methods described in detail below. The influenza hemagglutinin stem domain polypeptides might be useful for generating a host immune response against any one, two, three, four, five, six, seven, eight, nine, ten, eleven, twelve, thirteen, fourteen, fifteen or sixteen known influenza A hemagglutinin subtypes or a later identified influenza A hemagglutinin subtype. The influenza hemagglutinin stem domain polypeptides might also be useful for generating a host immune response against any influenza B hemagglutinin subtype now known or later identified.

Generally, the influenza hemagglutinin stem domain polypeptides provided herein are polypeptides that comprise or consist essentially of the stem domain of an influenza hemagglutinin polypeptide. The stem domain of an influenza hemagglutinin polypeptide is the stem domain that is generally recognized by those of skill in the art.

As is known to those of skill in the art, a full-length influenza hemagglutinin typically comprises an HA1 domain and an HA2 domain. The stem domain is formed by two segments of the HA1 domain and most or all of the HA2 domain. The two segments of the HA1 domain are separated, in primary sequence, by a globular head domain.

In certain embodiments, influenza hemagglutinin stem domain polypeptides comprise little or no globular head domain of an influenza hemagglutinin polypeptide. In certain embodiments, an influenza hemagglutinin stem domain polypeptides is an influenza hemagglutinin that has had its globular head domain deleted by any technique deemed suitable by one of skill in the art.

In certain embodiments, influenza hemagglutinin stem domain polypeptides described herein maintain the cysteine residues identified in influenza hemagglutinin polypeptides as $A_p$ and $A_q$ in FIG. 1. In certain embodiments, influenza hemagglutinin stem domain polypeptides described herein have greater stability at a pH lower than the hemagglutinin of a wild-type influenza viruse (e.g., a pH less than 5.2, less than 5.1, less than 5.0, or less than 4.9, such as 4.8, 4.7, 4.6, 4.5, 4.4, 4.3, 4.2, 4.1, 4.0, 3.9, 3.8, etc.). In particular embodiments, influenza hemagglutinin stem domain polypeptides described herein undergo conformational changes from the pre-fusion to the fusion conformation at a pH lower than the hemagglutinin of wild-type influenza viruses. In some embodiments, influenza hemagglutinin stem domain polypeptides described herein comprise one or more amino acid substitutions, such as HA1 H17Y (H3 numbering) that increases the stability of the polypeptides at a low pH (e.g., a pH of between 4.9 to 5.2, 4.5 to 3.5, 3.5 to 2.5, 2.5 to 1.5, 1.5 to 0.5). The stability of influenza hemagglutinin stem domain polypeptides can be assessed using techniques known in the art, such as sensitivity of the hemagglutinin-molecules to trypsin digestion, as described in, e.g., Thoennes et al., 2008, Virology 370: 403-414.

The influenza hemagglutinin stem domain polypeptides can be prepared according to any technique deemed suitable to one of skill, including techniques described below. In certain embodiments, the stem domain polypeptides are isolated.

In some embodiments, the primary structure of an influenza hemagglutinin stem domain polypeptide comprises, in the following order: an HA1 N-terminal stem segment, a linker, an HA1 C-terminal stem segment and an HA2. In some embodiments, the primary structure of an influenza hemagglutinin stem domain polypeptide comprises, in the following order: an HA1 N-terminal stem segment, a linker, an HA1 C-terminal short stem segment and an HA2. In some embodiments, the primary structure of an influenza hemagglutinin stem domain polypeptide comprises, in the following order: an HA1 N-terminal long stem segment, a linker, an HA1 C-terminal long stem segment and an HA2. In some embodiments, the influenza hemagglutinin stem domain polypeptide comprises in the following order: an HA1 N-terminal stem segment, a linker, an HA1 intermediate stem segment, a second linker, an HA1 C-terminal stem segment and an HA2.

The primary sequence might be formed by a single polypeptide, or it might be formed by multiple polypeptides. Typically, a single polypeptide is expressed by any technique deemed suitable by one of skill in the art. In single polypeptide embodiments, the HA1 segments and the HA2 are in tertiary association. As is known to those of skill in the art, a single HA polypeptide might be cleaved, for example by a protease, under appropriate expression conditions to yield two polypeptides in quaternary association. The cleavage is typically between the HA1 C-terminal stem segment and the HA2. In certain embodiments, provided herein are multiple polypeptide, for example two polypeptide, influenza hemagglutinin stem domains. In multiple polypeptide embodiments, the HA1 segments and HA2 are in quaternary association.

In certain embodiments, an influenza hemagglutinin stem domain polypeptide provided herein is monomeric. In certain embodiments, an influenza hemagglutinin stem domain polypeptide provided herein is multimeric. In certain embodiments, an influenza hemagglutinin stem domain polypeptide provided herein is trimeric. Those of skill in the art will recognize that native influenza hemagglutinin polypeptides are capable of trimerization in vivo and that certain influenza hemagglutinin stem domain polypeptides provided herein are capable of trimerization. In particular embodiments described below, influenza hemagglutinin stem domain polypeptides provided herein comprise trimerization domains to facilitate trimerization.

In certain embodiments, an influenza hemagglutinin stem domain polypeptide comprises a signal peptide. Typically, the signal peptide is cleaved during or after polypeptide expression and translation to yield a mature influenza hemagglutinin stem domain polypeptide. The signal peptide might be advantageous for expression of the influenza hemagglutinin stem domain polypeptides. In certain embodiments, also provided herein are mature influenza hemagglutinin stem domain polypeptides that lack a signal peptide.

Influenza hemagglutinin HA2 typically comprises a stem domain, transmembrane domain and a cytoplasmic domain. In certain embodiments, provided herein are influenza hemagglutinin stem domain polypeptides that comprise an HA2 stem domain, an HA2 luminal domain, an HA2 transmembrane domain and an HA2 cytoplasmic domain. Such influenza hemagglutinin stem domain polypeptides might be expressed as membrane-bound antigens. In certain embodiments, provided herein are influenza hemagglutinin stem domain polypeptides that comprise an HA2 stem domain, an HA2 luminal domain, and an HA2 transmembrane domain but lack some or all of the typical cytoplasmic domain. Such influenza hemagglutinin stem domain polypeptides might be expressed as membrane-bound antigens. In certain embodiments, provided herein are influenza hemagglutinin stem domain polypeptides that comprise an HA2 stem domain and an HA2 luminal domain but lack both an HA2 transmembrane domain and an HA2 cytoplasmic domain. Such influenza hemagglutinin stem domain polypeptides might advantageously be expressed as soluble polypeptides. In certain embodiments, provided herein are influenza hemagglutinin stem domain polypeptides that comprise an HA2 stem domain but lack an HA2 luminal domain, an HA2 transmembrane domain and an HA2 cytoplasmic domain. Such influenza hemagglutinin stem domain polypeptides might advantageously be expressed as soluble polypeptides. In certain embodiments, the influenza hemagglutinin stem domain polypeptides comprise an HA2 stem domain having at least 70%, 75%, 80%, 85%, 90%, 95%, 96% or 98% amino acid sequence identity to an influenza HA2 stem domain known to those of skill in the art. Exemplary known HA2 stem domains from known influenza A and influenza B hemagglutinins are provided in the tables below.

Also provided herein are influenza hemagglutinin stem domain polypeptides comprising deleted forms of HA2 stem domains wherein up to 10, 9, 8, 7, 6, 5, 4, 3, 2 or 1 amino acid residues are deleted from either or both termini of the HA2 stem domain. Further provided herein are influenza hemagglutinin stem domain polypeptides comprising altered forms of HA2 stem domains wherein up to 10, 9, 8, 7, 6, 5, 4, 3, 2 or 1 amino acid residues are conservatively substituted with other amino acids. Further provided are influenza hemagglutinin stem domain polypeptides comprising deleted and altered HA2 stem domains.

In some embodiments, the primary structure of an influenza hemagglutinin stem domain polypeptide comprises, in the following order: an HA1 N-terminal stem segment, a linker, an HA1 C-terminal stem segment and an HA2. The HA1 N-terminal stem segment might be any HA1 N-terminal stem segment recognized by one of skill in the art based on the definition provided herein. Typically, an HA1 N-terminal stem segment corresponds to a polypeptide consisting of the N-terminal amino acid of a mature HA1 (i.e. an HA1 lacking a signal peptide) through the cysteine residue located in sequence at approximately the $52^{nd}$ residue of the HA1. This cysteine residue, termed $A_p$ herein, is generally capable of forming a disulfide bridge with a cysteine residue in the C-terminal stem segment of HA1. Sequences of 16 representative influenza A hemagglutinins are presented in FIG. 1, and residue $A_p$ is identified in each.

In certain embodiments, the HA1 N-terminal stem segment does not end exactly at $A_p$ (e.g., $Cys_{52}$ of an HA1 subunit from an H3 hemagglutinin), but at a residue in sequence and structure vicinity to $A_p$. For example, in certain embodiments, the HA1 N-terminal stem segment ends at $A_{p-1}$, $A_{p-2}$, $A_{p-3}$, or $A_{p-4}$. In other embodiments, the HA1 N-terminal stem segment ends at $A_{p+1}$, $A_{p+2}$, $A_{p+3}$, $A_{p+4}$ or $A_{p+5}$. The end of an HA1 N-terminal stem segment should be selected in conjunction with the end of the HA1 C-terminal stem segment and the linker so that the resulting linked HA1 stem domain is capable of forming a three-dimensional structure similar, as described below, to an influenza hemagglutinin stem domain.

In certain embodiments, the influenza hemagglutinin stem domain polypeptides comprise an HA1 N-terminal stem segment having at least 70%, 75%, 80%, 85%, 90%, 95%, 96% or 98% amino acid sequence identity to an influenza HA1 N-terminal stem segment known to those of skill in the art. Exemplary known HA1 N-terminal stem segments are provided in the tables below.

Also provided herein are influenza hemagglutinin stem domain polypeptides comprising deleted forms of HA1 N-terminal stem segments wherein up to 10, 9, 8, 7, 6, 5, 4, 3, 2 or 1 amino acid residues are deleted from either or both termini of the HA1 N-terminal stem segment. In certain embodiments, provided herein are influenza hemagglutinin stem domain polypeptides that comprise expanded forms of HA1 N-terminal stem segments wherein 1, 2 or 3 residues are added to the C-terminus of the HA1 N-terminal stem segments; these added residues might be derived from the amino acid sequence of a globular head domain adjacent to an HA1 N-terminal stem segment. Further provided herein are influenza hemagglutinin stem domain polypeptides comprising altered forms of HA1 N-terminal stem segments wherein up to 10, 9, 8, 7, 6, 5, 4, 3, 2 or 1 amino acid residues are conservatively substituted with other amino acids. Further provided are influenza hemagglutinin stem domain polypeptides comprising deleted and altered HA1 N-terminal stem segments.

The HA1 C-terminal stem segment might be any HA1 C-terminal stem segment recognized by one of skill in the art based on the definition provided herein. Typically, an HA1 C-terminal stem segment corresponds to a polypeptide consisting of the cysteine residue located in sequence at approximately the $277^{th}$ residue of an HA1 (using H3 numbering) through the C-terminal amino acid of the HA1. This cysteine residue, termed $A_q$ herein, is generally capable of forming a disulfide bridge with cysteine residue $A_p$ in the N-terminal stem segment of HA1. Sequences of 16 representative influenza A hemagglutinins are presented in FIG. 1, and residue $A_q$ is identified in each.

In certain embodiments, the HA1 C-terminal stem segment does not start at $A_q$ (e.g., $Cys_{277}$ of an HA1 subunit from an H3 hemagglutinin), but at a residue in sequence and structure vicinity to $A_q$. For example, in certain embodiments, the HA1 C-terminal stem segment starts at $A_{q-1}$, $A_{q-2}$, $A_{q-3}$, or $A_{q-4}$. In other embodiments, the HA1 C-terminal stem segment starts at $A_{q+i}$, $A_{q+2}$, $A_{q+3}$, $A_{q+4}$ or $A_{q+5}$. The end of an HA1 N-terminal stem segment should be selected in conjunction with the start of the HA1 C-terminal stem segment and the linker so that the resulting HA1 stem domain is capable of forming a three-dimensional structure similar, as described below, to an influenza hemagglutinin.

In certain embodiments, the influenza hemagglutinin stem domain polypeptides comprise an HA1 C-terminal stem segment having at least 70%, 75%, 80%, 85%, 90%, 95%, 96% or 98% amino acid sequence identity to an influenza HA1 C-terminal stem segment known to those of skill in the art. Exemplary known HA1 C-terminal stem segments are provided in the tables below.

In certain embodiments, the end of the N-terminal stem segment is $A_{p-1}$, and the start of the C-terminal stem segment is $A_{q-1}$. In certain embodiments, the end of the N-terminal stem segment is $A_{p-2}$, and the start of the C-terminal stem segment is $A_{q-2}$ In certain embodiments, the end of the N-terminal stem segment is $A_{p-3}$, and the start of the C-terminal stem segment is $A_{q-3}$ In certain embodiments, the end of the N-terminal stem segment is $A_{p-4}$, and the start of the C-terminal stem segment is $A_{q-4}$ In certain embodiments, the end of the N-terminal stem segment is $A_{p-5}$, and the start of the C-terminal stem segment is $A_{q-g}$.

In certain embodiments, the end of the N-terminal stem segment is $A_{p+1}$, and the start of the C-terminal stem segment is $A_{q+1}$ In certain embodiments, the end of the N-terminal stem segment is $A_{p+2}$, and the start of the C-terminal stem segment is $A_{q+2}$ In certain embodiments, the end of the N-terminal stem segment is $A_{p+3}$, and the start of the C-terminal stem segment is $A_{q+3}$ In certain embodiments, the end of the N-terminal stem segment is $A_{p+4}$, and the start of the C-terminal stem segment is $A_{q+4}$ In certain embodiments, the end of the N-terminal stem segment is $A_{p+5}$, and the start of the C-terminal stem segment is $A_{q+5}$.

In certain embodiments, the end of the N-terminal stem segment is $A_{p-1}$, and the start of the C-terminal stem segment is $A_{q+1}$ In certain embodiments, the end of the N-terminal stem segment is $A_{p-2}$, and the start of the C-terminal stem segment is $A_{q+2}$ In certain embodiments, the end of the N-terminal stem segment is $A_{p-3}$, and the start of the C-terminal stem segment is $A_{q+3}$ In certain embodiments, the end of the N-terminal stem segment is $A_{p-4}$, and the start of the C-terminal stem segment is $A_{q+4}$ In certain embodiments, the end of the N-terminal stem segment is $A_{p-5}$, and the start of the C-terminal stem segment is $A_{q+5}$.

In certain embodiments, the end of the N-terminal stem segment is $A_{p+1}$, and the start of the C-terminal stem segment is $A_{q-1}$. In certain embodiments, the end of the N-terminal stem segment is $A_{p+2}$, and the start of the C-terminal stem segment is $A_{q-2}$ In certain embodiments, the end of the N-terminal stem segment is $A_{p+3}$, and the start of the C-terminal stem segment is $A_{q-3}$ In certain embodiments, the end of the N-terminal stem segment is $A_{p+4}$, and the start of the C-terminal stem segment is $A_{q-4}$ In certain embodiments, the end of the N-terminal stem segment is $A_{p+5}$, and the start of the C-terminal stem segment is $A_{q-5}$.

Also provided herein are influenza hemagglutinin stem domain polypeptides comprising deleted forms of HA1 C-terminal stem segments wherein up to 10, 9, 8, 7, 6, 5, 4, 3, 2 or 1 amino acid residues are deleted from either or both termini of the HA1 C-terminal stem segment. In certain embodiments, provided herein are influenza hemagglutinin stem domain polypeptides that comprise expanded forms of HA1 C-terminal stem segments wherein 1, 2 or 3 residues are added to the N-terminus of the HA1 C-terminal stem segments; these added residues might be derived from the amino acid sequence of a globular head domain adjacent to an HA1 C-terminal stem segment. In particular embodiments, if one residue is added to the C-terminal stem segment, then one residue is added to the N-terminal stem segment; if two residues are added to the C-terminal stem segment, then two residues are added to the N-terminal stem segment; if three residues are added to the C-terminal stem segment, then three residues are added to the N-terminal stem segment. Further provided herein are influenza hemagglutinin stem domain polypeptides comprising altered forms of HA1 C-terminal stem segments wherein up to 10, 9, 8, 7, 6, 5, 4, 3, 2 or 1 amino acid residues are conservatively substituted with other amino acids. Further provided are influenza hemagglutinin stem domain polypeptides comprising deleted and altered HA1 C-terminal stem segments.

The influenza hemagglutinin stem domain polypeptides might be based on (i.e. might have sequence identity, as described above) any influenza hemagglutinin known to those of skill or later discovered. In certain embodiments, influenza hemagglutinin stem domain polypeptides are based on an influenza A hemagglutinin. In certain embodiments, the influenza hemagglutinin stem domain polypeptides are based on an influenza A hemagglutinin selected from the group consisting of H1, H2, H3, H4, H5, H6, H7, H8, H9, H10, H11, H12, H13, H14, H15 and H16. In certain embodiments, influenza hemagglutinin stem domain polypeptides are based on an influenza B hemagglutinin, as described in detail below.

The HA1 N-terminal stem segments might be based on (i.e. might have sequence identity, as described above) any HA1 N-terminal stem segments known to those of skill or later discovered. In certain embodiments, the HA1 N-terminal stem segments are based on influenza A HA1 N-terminal stem segments. In certain embodiments, the HA1 N-terminal stem segments are based on an influenza A hemagglutinin selected from the group consisting of H1, H2, H3, H4, H5, H6, H7, H8, H9, H10, H11, H12, H13, H14, H15 and H16. In certain embodiments, the HA1 N-terminal stem segment is selected from SEQ ID NOS:34-49. In certain embodiments, the HA1 N-terminal stem segment is selected from SEQ ID NOS:34-49, each having one amino acid deleted from its C-terminus. In certain embodiments, the HA1 N-terminal stem segment is selected from SEQ ID NOS:34-49, each having two amino acids deleted from its C-terminus. In certain embodiments, the HA1 N-terminal stem segment is selected from SEQ ID NOS:34-49, each having three amino acids deleted from its C-terminus. In certain embodiments, the HA1 N-terminal stem segment is selected from SEQ ID NOS:34-49, each having four amino acids deleted from its C-terminus. In certain embodiments, the HA1 N-terminal stem segment is selected from SEQ ID NOS:34-49, each having five amino acids deleted from its C-terminus. In certain embodiments, the HA1 N-terminal stem segment is selected from SEQ ID NOS:177-224.

The HA1 C-terminal stem segments might be based on (i.e. might have sequence identity, as described above) any HA1 C-terminal stem segments known to those of skill or later discovered. In certain embodiments, the HA1 C-terminal stem segments are based on influenza A HA1 C-terminal stem segments. In certain embodiments, the HA1 C-terminal stem segments are based on an influenza A hemagglutinin selected from the group consisting of H1, H2, H3, H4, H5, H6, H7, H8, H9, H10, H11, H12, H13, H14, H15 and H16. In certain embodiments, the HA1 C-terminal stem segment is selected from SEQ ID NOS:50-65. In certain embodiments, the HA1 C-terminal stem segment is selected from SEQ ID NOS: 50-65, each having one amino acid deleted from its N-terminus. In certain embodiments, the HA1 C-terminal stem segment is selected from SEQ ID NOS: 50-65, each having two amino acids deleted from its N-terminus. In certain embodiments, the HA1 C-terminal stem segment is selected from SEQ ID NOS: 50-65, each having three amino acids deleted from its N-terminus. In certain embodiments, the HA1 C-terminal stem segment is selected from SEQ ID NOS: 50-65, each having four amino acids deleted from its N-terminus. In certain embodiments, the HA1 C-terminal stem segment is selected from SEQ ID NOS: 50-65, each having five amino acids deleted from its N-terminus. In certain embodiments, the HA1 C-terminal stem segment is selected from SEQ ID NOS:226-273.

The HA2 stem domains might be based on (i.e. might have sequence identity, as described above) any HA2 stem domains known to those of skill or later discovered. In certain embodiments, the HA2 stem domains are based on influenza A HA2 stem domains. In certain embodiments, the HA2 stem domains are based on an influenza A hemagglutinin selected from the group consisting of H1, H2, H3, H4, H5, H6, H7, H8, H9, H10, H11, H12, H13, H14, H15 and H16. In certain embodiments, the HA2 stem domain is selected from SEQ ID NOS:66-97.

In embodiments comprising a signal peptide, the signal peptide might be based on any influenza virus signal peptide known to those of skill in the art. In certain embodiments, the signal peptides are based on influenza A signal peptides. In certain embodiments, the signal peptides are based on an influenza A hemagglutinin selected from the group consisting of H1, H2, H3, H4, H5, H6, H7, H8, H9, H10, H11, H12, H13, H14, H15 and H16. In certain embodiments, the signal peptide might be any signal peptide deemed useful to one of skill in the art. In certain embodiments, the signal peptide is selected from SEQ ID NOS:18-33.

In embodiments comprising a luminal domain, the luminal domain might be based on any influenza luminal domain known to those of skill in the art. In certain embodiments, the luminal domains are based on influenza A luminal domains. In certain embodiments, the HA2 luminal domains are based on an influenza A hemagglutinin selected from the group consisting of H1, H2, H3, H4, H5, H6, H7, H8, H9, H10, H11, H12, H13, H14, H15 and H16. In certain embodiments, the luminal domain might be any luminal domain deemed useful to one of skill in the art. In certain embodiments, the luminal domain is selected from SEQ ID NOS: 98-113.

In embodiments comprising a transmembrane domain, the transmembrane domain might be based on any influenza transmembrane domain known to those of skill in the art. In certain embodiments, the transmembrane domains are based on influenza A transmembrane domains. In certain embodiments, the HA2 transmembrane domains are based on an influenza A hemagglutinin selected from the group consisting of H1, H2, H3, H4, H5, H6, H7, H8, H9, H10, H11, H12, H13, H14, H15 and H16. In certain embodiments, the transmembrane domain might be any transmembrane domain deemed useful to one of skill in the art. In certain embodiments, the transmembrane domain is selected from SEQ ID NOS:114-129.

In embodiments comprising a cytoplasmic domain, the cytoplasmic domain might be based on any influenza cytoplasmic domain known to those of skill in the art. In certain embodiments, the cytoplasmic domains are based on influenza A cytoplasmic domains. In certain embodiments, the HA2 cytoplasmic domains are based on an influenza A hemagglutinin selected from the group consisting of H1, H2, H3, H4, H5, H6, H7, H8, H9, H10, H11, H12, H13, H14, H15 and H16. In certain embodiments, the cytoplasmic domain might be any cytoplasmic domain deemed useful to one of skill in the art. In certain embodiments, the cytoplasmic domain is selected from SEQ ID NOS:130-145.

In certain embodiments, one or more of the glycosylation sites in the hemagglutinin stem domain are altered or deleted such that glycosylation at these sites will not occur during processing and maturation of the polypeptide. Those of skill in the art will recognize that influenza HA typically comprises one or more glycosylation sequences (e.g. Asn-Xaa-Ser/Thr/Cys, wherein Xaa is any amino acid other than Pro). In certain embodiments, one or more amino acid residues in a glycosylation sequence is conservatively substituted with an amino acid residue that disrupts the glycosylation sequence. In certain embodiments, one or more amino acid residues in a glycosylation sequence is substituted with any amino acid residue that disrupts the glycosylation sequence. In certain embodiments, one or more asparagine residues in a glycosylation sequence is substituted with alanine. In a particular embodiment, the asparagine at position 38 of an H3 hemagglutinin is changed to an alanine.

Table 1, below, identifies signal peptides, HA1 N-terminal stem segments, HA1 C-terminal stem segments and HA2 domains of influenza A hemagglutinin polypeptides. These signal peptides, stem segments and domains are useful in the polypeptides and methods described herein.

TABLE 1

Exemplary Influenza A Hemagglutinin Sequences

| HA Subtype (Genbank No.) | Signal peptide | HA1 N-terminal Stem Segment | HA1 C-terminal Stem Segment | HA2 Domain |
|---|---|---|---|---|
| H1 PR8-H1N1 (EF467821.1) | MKAN LLVLL CALAA ADA [SEQ ID NO: 18] | DTICIGYHANN STDTVDTVLE KNVTVTHSVN LLEDSHNGKLC [SEQ ID NO: 34] | CNTKCQTPLG AINSSLPYQNI HPVTIGECPKY VRSAKLRMVT GLRNNPSIQSR [SEQ ID NO: 50] | GLFGAIAGFIEGGW TGMIDGWYGYHHQ NEQGSGYAADQKST QNAINGITNKVNTVI EKMNIQFTAVGKEF NKLEKRMENLNKK VDDGFLDIWTYNAE LLVLLENERTLDFH DSNVKNLYEKVKSQ LKNNAKEIGNGCFE FYHKCDNECMESVR NGTYDYPKYSEESK LNREKVDGVKLES MGIYQILAIYSTVAS SLVLLVSLGAISFW MCSNGSLQCRICI [SEQ ID NO: 66] |
| H2 (L11136) | MAIIY LILLFT AVRG [SEQ ID NO: 19] | DQICIGYHSNN STEKVDTILER NVTVTHAQNI LEKTHNGKLC [SEQ ID NO: 35] | CETKCQTPLG AINTTLPFHNV HPLTIGECPKY VKSERLVLAT GLRNVPQIESR [SEQ ID NO: 51] | GLFGAIAGFIEGGW QGMIDGWYGYHHS NDQGSGYAADKEST QKAIDGITNRVNSVI EKMNTQFEAVGKEF SNLEKRLENLNKKM EDGFLDVWTYNAE LLVLMENERTLDFH DSNVKNLYDRVRM QLRDNAKELGNGCF EFYHKCDDECMNS VKNGTYDYPKYEEE SKLNRNEIKGVKLS NMGVYQILAIYATV AGSLSLAIMIAGISL WMCSNGSLQCRICI [SEQ ID NO: 67] |

TABLE 1-continued

Exemplary Influenza A Hemagglutinin Sequences

| HA Subtype (Genbank No.) | Signal peptide | HA1 N-terminal Stem Segment | HA1 C-terminal Stem Segment | HA2 Domain |
|---|---|---|---|---|
| H3<br>HK68-H3N2<br>(EF409245)<br>PDB: 1HGJ | MKTII<br>ALSYIF<br>CLALG<br>[SEQ ID NO: 20] | QDLPGNDNST<br>ATLCLGHHAV<br>PNGTLVKTITD<br>DQIEVTNATEL<br>VQSSSTGKIC<br>[SEQ ID NO: 36] | CISECITPNGSI<br>PNDKPFQNVN<br>KITYGACPKY<br>VKQNTLKLAT<br>GMRNVPEKQTR<br>[SEQ ID NO: 52] | GLFGAIAGFIENGW<br>EGMIDGWYGFRHQ<br>NSEGTGQAADLKST<br>QAAIDQINGKLNRVI<br>EKTNEKFHQIEKEFS<br>EVEGRIQDLEKYVE<br>DTKIDLWSYNAELL<br>VALENQHTIDLTDS<br>EMNKLFEKTRRQLR<br>ENAEDMGNGCFKIY<br>HKCDNACIESIRNGT<br>YDHDVYRDEALNN<br>RFQIKGVELKSGYK<br>DWILWISFAISCFLL<br>CVVLLGFIMWACQR<br>GNIRCNICI<br>[SEQ ID NO: 68] |
| H4<br>(D90302) | MLSIVI<br>LFLLIA<br>ENSS<br>[SEQ ID NO: 21] | QNYTGNPVIC<br>MGHHAVANG<br>TMVKTLADDQ<br>VEVVTAQELV<br>ESQNLPELC<br>[SEQ ID NO: 37] | CVSKCHTDKG<br>SLSTTKPFQNI<br>SRIAVGDCPRY<br>VKQGSLKLAT<br>GMRNIPEKASR<br>[SEQ ID NO: 53] | GLFGAIAGFIENGW<br>QGLIDGWYGFRHQ<br>NAEGTGTAADLKST<br>QAAIDQINGKLNRLI<br>EKTNDKYHQIEKEF<br>EQVEGRIQDLENYV<br>EDTKIDLWSYNAEL<br>LVALENQHTIDVTD<br>SEMNKLFERVRRQL<br>RENAEDKGNGCFEI<br>FHKCDNNCIESIRNG<br>TYDHDIYRDEAINN<br>RFQIQGVKLTQGYK<br>DIILWISFSISCFLLV<br>ALLLAFILWACQNG<br>NIRCQICI<br>[SEQ ID NO: 69] |
| H5<br>(X07826) | MERIV<br>LLLAI<br>VSLVKS<br>[SEQ ID NO: 22] | DQICIGYHAN<br>KSTKQVDTIM<br>EKNVTVTHAQ<br>DILERTHNGKLC<br>[SEQ ID NO: 38] | CDTKCQTPVG<br>EINSSMPFHNI<br>HPHTIGECPKY<br>VKSDRLVLAT<br>GLRNVPQRKKR<br>[SEQ ID NO: 54] | GLFGAIAGFIEGGW<br>QGMVDGWYGYHH<br>SNEQGSGYAADKES<br>TQKAIDGITNKVNSI<br>IDKMNTRFEAVGKE<br>FNNLERRVENLNKK<br>MEDGFLDVWTYNV<br>ELLVLMENERTLDF<br>HDSNVNNLYDKVR<br>LQLKDNARELGNGC<br>FEFYHKCDNECMES<br>VRNGTYDYPQYSEE<br>ARLNREEISGVKLES<br>MGVYQILSIYSTVAS<br>SLALAIMIAGLSFW<br>MCSNGSLQCRICI<br>[SEQ ID NO: 70] |
| H6<br>(D90303) | MIAIIV<br>VAILA<br>TAGRS<br>[SEQ ID NO: 23] | DKICIGYHAN<br>NSTTQIDTILE<br>KNVTVTHSVE<br>LLENQKEERFC<br>[SEQ ID NO: 39] | CDATCQTVAG<br>VLRTNKTFQN<br>VSPLWIGECPK<br>YVKSESLRLA<br>TGLRNVPQIETR<br>[SEQ ID NO: 55] | GLFGAIAGFIEGGW<br>TGMIDGWYGYHHE<br>NSQGSGYAADREST<br>QKAVDGITNKVNSII<br>DKMNTQFEAVDHE<br>FSNLERRIDNLNKR<br>MEDGFLDVWTYNA<br>ELLVLLENERTLDL<br>HDANVKNLYERVK<br>SQLRDNAMILGNGC<br>FEFWHKCDDECMES<br>VKNGTYDYPKYQD<br>ESKLNRQEIESVKLE<br>SLGVYQILAIYSTVS<br>SSLVLVGLIIAVGLW<br>MCSNGSMQCRICI<br>[SEQ ID NO: 71] |

TABLE 1-continued

Exemplary Influenza A Hemagglutinin Sequences

| HA Subtype (Genbank No.) | Signal peptide | HA1 N-terminal Stem Segment | HA1 C-terminal Stem Segment | HA2 Domain |
|---|---|---|---|---|
| H7<br>(M24457) | MNTQI<br>LVFAL<br>VAVIP<br>TNA<br>[SEQ ID<br>NO: 24] | DKICLGHHAV<br>SNGTKVNTLT<br>ERGVEVVNAT<br>ETVERTNIPKIC<br>[SEQ ID NO: 40] | CEGECYHSGG<br>TITSRLPFQNIN<br>SRAVGKCPRY<br>VKQESLLLAT<br>GMKNVPEPSK<br>KRKKR<br>[SEQ ID NO: 56] | GLFGAIAGFIENGW<br>EGLVDGWYGFRHQ<br>NAQGEGTAADYKS<br>TQSAIDQITGKLNRL<br>IEKTNQQFELIDNEF<br>TEVEKQIGNLINWT<br>KDSITEVWSYNAELI<br>VAMENQHTIDLADS<br>EMNRLYERVRKQL<br>RENAEEDGTGCFEIF<br>HKCDDDCMASIRNN<br>TYDHSKYREEAMQ<br>NRIQIDPVKLSSGYK<br>DVILWFSFGASCFLL<br>LAIAMGLVFICVKN<br>GNMRCTICI<br>[SEQ ID NO: 72] |
| H8<br>(D90304) | MEKFI<br>AIATL<br>ASTNAY<br>[SEQ ID<br>NO: 25] | DRICIGYQSNN<br>STDTVNTLIEQ<br>NVPVTQTMEL<br>VETEKHPAYC<br>[SEQ ID NO: 41] | CNTKCQTYAG<br>AINSSKPFQNA<br>SRHYMGECPK<br>YVKKASLRLA<br>VGLRNTPSVEPR<br>[SEQ ID NO: 57] | GLFGAIAGFIEGGWS<br>GMIDGWYGFHHSN<br>SEGTGMAADQKST<br>QEAIDKITNKVNNIV<br>DKMNREFEVVNHEF<br>SEVEKRINMINDKID<br>DQIEDLWAYNAELL<br>VLLENQKTLDEHDS<br>NVKNLFDEVKRRLS<br>ANAIDAGNGCFDIL<br>HKCDNECMETIKNG<br>TYDHKEYEEEAKLE<br>RSKINGVKLEENTT<br>YKILSIYSTVAASLC<br>LAILIAGGLILGMQN<br>GSCRCMFCI<br>[SEQ ID NO: 73] |
| H9<br>(D90305) | METK<br>AIIAAL<br>LMVTA<br>ANA<br>[SEQ ID<br>NO: 26] | DKICIGYQSTN<br>STETVDTLTES<br>NVPVTHTKEL<br>LHTEHNGMLC<br>[SEQ ID NO: 42] | CVVQCQTEKG<br>GLNTTLPFHNI<br>SKYAFGNCPK<br>YVGVKSLKLP<br>VGLRNVPAVS<br>SR<br>[SEQ ID NO: 58] | GLFGAIAGFIEGGWP<br>GLVAGWYGFQHSN<br>DQGVGMAADKGST<br>QKAIDKITSKVNNII<br>DKMNKQYEVIDHEF<br>NELEARLNMINNKI<br>DDQIQDIWAYNAEL<br>LVLLENQKTLDEHD<br>ANVNNLYNKVKRA<br>LGSNAVEDGNGCFE<br>LYHKCDDQCMETIR<br>NGTYDRQKYQEESR<br>LERQKIEGVKLESEG<br>TYKILTIYSTVASSL<br>VLAMGFAAFLFWA<br>MSNGSCRCNICI<br>[SEQ ID NO: 74] |
| H10<br>(M21647) | MYKV<br>VVIIAL<br>LGAVKG<br>[SEQ ID<br>NO: 27] | LDRICLGHHA<br>VANGTIVKTL<br>TNEQEEVTNA<br>TETVESTNLN<br>KLC<br>[SEQ ID NO: 43] | CESKCFWRGG<br>SINTKLPFQNL<br>SPRTVGQCPK<br>YVNQRSLLLA<br>TGMRNVPEVV<br>QGR<br>[SEQ ID NO: 59] | GLFGAIAGFIENGW<br>EGMVDGWYGFRHQ<br>NAQGTGQAADYKS<br>TQAAIDQITGKLNRL<br>IEKTNTEFESIESEFS<br>ETEHQIGNVINWTK<br>DSITDIWTYNAELLV<br>AMENQHTIDMADSE<br>MLNLYERVRKQLR<br>QNAEEDGKGCFEIY<br>HTCDDSCMESIRNN<br>TYDHSQYREEALLN<br>RLNINPVKLSSGYK<br>DIILWFSFGESCFVL<br>LAVVMGLVFFCLKN<br>GNMRCTICI<br>[SEQ ID NO: 75] |

TABLE 1-continued

Exemplary Influenza A Hemagglutinin Sequences

| HA Subtype (Genbank No.) | Signal peptide | HA1 N-terminal Stem Segment | HA1 C-terminal Stem Segment | HA2 Domain |
|---|---|---|---|---|
| H11 (D90306) | MEKTL LFAAIF LCVKA [SEQ ID NO: 28] | DEICIGYLSNN STDKVDTIIEN NVTVTSSVEL VETEHTGSFC [SEQ ID NO: 44] | CSTKCQTEIGG INTNKSFHNV HRNTIGDCPK YVNVKSLKLA TGPRNVPAIASR [SEQ ID NO: 60] | GLFGAIAGFIEGGWP GLINGWYGFQHRDE EGTGIAADKESTQK AIDQITSKVNNIVDR MNTNFESVQHEFSEI EERINQLSKHVDDS VVDIWSYNAQLLVL LENEKTLDLHDSNV RNLHEKVRRMLKD NAKDEGNGCFTFYH KCDNKCIERVRNGT YDHKEFEEESKINR QEIEGVKLDSSGNV YKILSIYSCIASSLVL AALIMGFMFWACS NGSCRCTICI [SEQ ID NO: 76] |
| H12 (D90307) | MEKFII LSTVL AASFAY [SEQ ID NO: 29] | DKICIGYQTNN STETVNTLSEQ NVPVTQVEEL VHRGIDPILC [SEQ ID NO: 45] | CVTECQLNEG VMNTSKPFQN TSKHYIGKCPK YIPSGSLKLAI GLRNVPQVQDR [SEQ ID NO: 61] | GLFGAIAGFIEGGWP GLVAGWYGFQHQN AEGTGIAADRDSTQ RAIDNMQNKLNNVI DKMNKQFEVVNHE FSEVESRINMINSKI DDQITDIWAYNAEL LVLLENQKTLDEHD ANVRNLHDRVRRV LRENAIDTGDGCFEI LHKCDNNCMDTIRN GTYNHKEYEEESKI ERQKVNGVKLEENS TYKILSIYSSVASSL VLLLMIIGGFIFGCQ NGNVRCTFCI [SEQ ID NO: 77] |
| H13 (D90308) | MALN VIATL TLISVC VHA [SEQ ID NO: 30] | DRICVGYLSTN SSERVDTLLEN GVPVTSSIDLIE TNHTGTYC [SEQ ID NO: 46] | CNTKCQTSVG GINTNRTFQNI DKNALGDCPK YIKSGQLKLAT GLRNVPAISNR [SEQ ID NO: 62] | GLFGAIAGFIEGGWP GLINGWYGFQHQNE QGTGIAADKESTQK AIDQITTKINNIIDKM NGNYDSIRGEFNQV EKRINMLADRIDDA VTDIWSYNAKLLVL LENDKTLDMHDAN VKNLHEQVRRELKD NAIDEGNGCFELLH KCNDSCMETIRNGT YDHTEYAEESKLKR QEIDGIKLKSEDNVY KALSIYSCIASSVVL VGLILSFIMWACSSG NCRFNVCI [SEQ ID NO: 78] |
| H14 (M35997) | MIALIL VALAL SHTAYS [SEQ ID NO: 31] | QITNGTTGNPII CLGHHAVENG TSVKTLTDNH VEVVSAKELV ETNHTDELC [SEQ ID NO: 47] | CTSPCLTDKGS IQSDKPFQNVS RIAIGNCPKYV KQGSLMLATG MRNIPGKQAK [SEQ ID NO: 63] | GLFGAIAGFIENGW QGLIDGWYGFRHQ NAEGTGTAADLKST QAAIDQINGKLNRLI EKTNEKYHQIEKEF EQVEGRIQDLEKYV EDTKIDLWSYNAEL LVALENQHTIDVTD SEMNKLFERVRRQL RENAEDQGNGCFEI FHQCDNNCIESIRNG TYDHNIYRDEAINN RIKINPVTLTMGYK DIILWISFSMSCFVF VALILGFVLWACQN GNIRCQICI [SEQ ID NO: 79] |

TABLE 1-continued

Exemplary Influenza A Hemagglutinin Sequences

| HA Subtype (Genbank No.) | Signal peptide | HA1 N-terminal Stem Segment | HA1 C-terminal Stem Segment | HA2 Domain |
|---|---|---|---|---|
| H15 (L43917) | MNTQI IVILVL GLSMV KS [SEQ ID NO: 32] | DKICLGHHAV ANGTKVNTLT ERGVEVVNAT ETVEITGIDKVC [SEQ ID NO: 48] | CEGECFYSGG TINSPLPFQNID SRAVGKCPRY VKQSSLPLAL GMKNVPEKIR TR [SEQ ID NO: 64] | GLFGAIAGFIENGW EGLIDGWYGFRHQN AQGQGTAADYKST QAAIDQITGKLNRLI EKTNKQFELIDNEFT EVEQQIGNVINWTR DSLTEIWSYNAELL VAMENQHTIDLADS EMNKLYERVRRQL RENAEEDGTGCFEIF HRCDDQCMESIRNN TYNHTEYRQEALQN RIMINPVKLSSGYKD VILWFSFGASCVML LAIAMGLIFMCVKN GNLRCTICI [SEQ ID NO: 80] |
| H16 (EU293865) | MMIK VLYFLI IVLGR YSKA [SEQ ID NO: 33] | DKICIGYLSNN SSDTVDTLTEN GVPVTSSVDL VETNHTGTYC [SEQ ID NO: 49] | CNTKCQTSLG GINTNKTFQNI ERNALGDCPK YIKSGQLKLAT GLRNVPSIGER [SEQ ID NO: 65] | GLFGAIAGFIEGGWP GLINGWYGFQHQNE QGTGIAADKASTQK AINEITTKINNIIEKM NGNYDSIRGEFNQV EKRINMLADRVDDA VTDIWSYNAKLLVL LENDRTLDLHDANV RNLHDQVKRALKS NAIDEGDGCFNLLH KCNDSCMETIRNGT YNHEDYREESQLKR QEIEGIKLKTEDNVY KVLSIYSCIASSIVLV GLILAFIMWACSNG SCRFNVCI [SEQ ID NO: 81] |

Table 1A, below, identifies useful HA1 N-terminal stem segments and HA1 C-terminal stem segments for the polypeptides and methods described herein.

TABLE 1A

Exemplary Influenza A Hemagglutinin Sequences

| HA Subtype (Genbank No.) | HA1 N-terminal Stem Segment | HA1 C-terminal Stem Segment |
|---|---|---|
| H1 PR8-H1N1 (EF467821.1) No Cys | DTICIGYHANNSTDTVDT VLEKNVTVTHSVNLLED SHNGKL [SEQ ID NO: 177] | NTKCQTPLGAINSSLPYQNIHPVTIGEC PKYVRSAKLRMVTGLRNNPSIQSR [SEQ ID NO: 226] |
| H1 PR8-H1N1 (EF467821.1) No Cys Δ1 | DTICIGYHANNSTDTVDT VLEKNVTVTHSVNLLED SHNGKL [SEQ ID NO: 178] | TKCQTPLGAINSSLPYQNIHPVTIGECP KYVRSAKLRMVTGLRNNPSIQSR [SEQ ID NO: 227] |
| H1 PR8-H1N1 (EF467821.1) No Cys Δ3 | DTICIGYHANNSTDTVDT VLEKNVTVTHSVNLLED SHNGK [SEQ ID NO: 179] | KCQTPLGAINSSLPYQNIHPVTIGECPK YVRSAKLRMVTGLRNNPSIQSR [SEQ ID NO: 228] |
| H1 PR8-H1N1 (EF467821.1) PR8-CON-A | DTICIGYHANNSTDTVDT VLEKNVTVTHSVNLLED SHNGKLCRLKC [SEQ ID NO: 312] | CKCQTPLGAINSSLPYQNIHPVTIGECP KYVRSAKLRMVTGLRNNPSIQSRG [SEQ ID NO: 313] |
| H1 PR8-H1N1 | DTICIGYHANNSTDTVDT VLEKNVTVTHSVNLLED | CVRSAKLRMVTGLRNNPSIQSRG [SEQ ID NO: 314] |

TABLE 1A-continued

Exemplary Influenza A Hemagglutinin Sequences

| HA Subtype (Genbank No.) | HA1 N-terminal Stem Segment | HA1 C-terminal Stem Segment |
|---|---|---|
| (EF467821.1) PR8-CON-B | SHNGKLC [SEQ ID NO: 34] | |
| H1 PR8-H1N1 (EF467821.1) PR8-CON-C | DTICIGYHANNSTDTVDTVLEKNVTVTHSVNLLEDSHNGKLCRLKGIAPLQLGKCNIAGWLLGNPECDPLLPVRSWSYIVETPNSENGICYPGC [SEQ ID NO: 315] | AFALSRGFGSGIITSNASMHECNTKCQTPLGAINSSLPYQNIHPVTIGECPKYVRSAKLRMVTGLRNNPSIQSRG [SEQ ID NO: 316] |
| H2 (L11136) No Cys | DQICIGYHSNNSTEKVDTILERNVTVTHAQNILEKTHNGKL [SEQ ID NO: 180] | ETKCQTPLGAINTTLPFHNVHPLTIGECPKYVKSERLVLATGLRNVPQIESR [SEQ ID NO: 229] |
| H2 (L11136) No Cys Δ1 | DQICIGYHSNNSTEKVDTILERNVTVTHAQNILEKTHNGKL [SEQ ID NO: 181] | TKCQTPLGAINTTLPFHNVHPLTIGECPKYVKSERLVLATGLRNVPQIESR [SEQ ID NO: 230] |
| H2 (L11136) No Cys Δ3 | DQICIGYHSNNSTEKVDTILERNVTVTHAQNILEKTHNGK [SEQ ID NO: 182] | KCQTPLGAINTTLPFHNVHPLTIGECPKYVKSERLVLATGLRNVPQIESR [SEQ ID NO: 231] |
| H3 HK68-H3N2 (EF409245) PDB: 1HGJ No Cys | QDLPGNDNSTATLCLGHHAVPNGTLVKTITDDQIEVTNATELVQSSSTGKI [SEQ ID NO: 183] | ISECITPNGSIPNDKPFQNVNKITYGACPKYVKQNTLKLATGMRNVPEKQTR [SEQ ID NO: 232] |
| H3 HK68-H3N2 (EF409245) PDB: 1HGJ No Cys Δ1 | QDLPGNDNSTATLCLGHHAVPNGTLVKTITDDQIEVTNATELVQSSSTGKI [SEQ ID NO: 184] | SECITPNGSIPNDKPFQNVNKITYGACPKYVKQNTLKLATGMRNVPEKQTR [SEQ ID NO: 233] |
| H3 HK68-H3N2 (EF409245) PDB: 1HGJ No Cys Δ3 | QDLPGNDNSTATLCLGHHAVPNGTLVKTITDDQIEVTNATELVQSSSTGK [SEQ ID NO: 185] | ECITPNGSIPNDKPFQNVNKITYGACPKYVKQNTLKLATGMRNVPEKQTR [SEQ ID NO: 234] |
| H3 HK68-H3N2 PDB: 1HGJ (EF409245) HK68-CON-A | STATLCLGHHAVPNGTLVKTITDDQIEVTNATELVQSSSTGKIC [SEQ ID NO: 308] | CISECITPNGSIPNDKPFQNVNKITYGACPKYVKQNTLKLATGMRNVPEKQTR [SEQ ID NO: 52] |
| H3 HK68-H3N2 PDB: 1HGJ (EF409245) HK68-CON-B | QDLPGNDNSTATLCLGHHAVPNGTLVKTITDDQIEVTNATELVQSSSTGKIC [SEQ ID NO: 36] | CKYVKQNTLKLATGMRNVPEKQTR [SEQ ID NO: 309] |
| H3 HK68-H3N2 PDB: 1HGJ (EF409245) HK68-CON-C | QDLPGNDNSTATLCLGHHAVPNGTLVKTITDDQIEVTNATELVQSSSTGKICNNPHRILDGIDCTLIDALLGDPHCDVFQNETWDLFVERSKAFSNC [SEQ ID NO: 310] | APRGYFKMRTGKSSIMSSDAPIDTCISECITPNGSIPNDKPFQNVNKITYGACPKYVKQNTLKLATGMRNVPEK [SEQ ID NO: 311] |
| H4 (D90302) No Cys | QNYTGNPVICMGHHAVANGTMVKTLADDQVEVVTAQELVESQNLPEL [SEQ ID NO: 186] | VSKCHTDKGSLSTTKPFQNISRIAVGDCPRYVKQGSLKLATGMRNIPEKASR [SEQ ID NO: 235] |
| H4 (D90302) No Cys Δ1 | QNYTGNPVICMGHHAVANGTMVKTLADDQVEVVTAQELVESQNLPEL [SEQ ID NO: 187] | SKCHTDKGSLSTTKPFQNISRIAVGDCPRYVKQGSLKLATGMRNIPEKASR [SEQ ID NO: 236] |

TABLE 1A-continued

Exemplary Influenza A Hemagglutinin Sequences

| HA Subtype (Genbank No.) | HA1 N-terminal Stem Segment | HA1 C-terminal Stem Segment |
|---|---|---|
| H4 (D90302) No Cys Δ3 | QNYTGNPVICMGHHAVANGTMVKTLADDQVEVVTAQELVESQNLPE [SEQ ID NO: 188] | KCHTDKGSLSTTKPFQNISRIAVGDCPRYVKQGSLKLATGMRNIPEKASR [SEQ ID NO: 237] |
| H5 (X07826) No Cys | DQICIGYHANKSTKQVDTIMEKNVTVTHAQDILERTHNGKL [SEQ ID NO: 189] | DTKCQTPVGEINSSMPFHNIHPHTIGECPKYVKSDRLVLATGLRNVPQRKKR [SEQ ID NO: 238] |
| H5 (X07826) No Cys Δ1 | DQICIGYHANKSTKQVDTIMEKNVTVTHAQDILERTHNGKL [SEQ ID NO: 190] | TKCQTPVGEINSSMPFHNIHPHTIGECPKYVKSDRLVLATGLRNVPQRKKR [SEQ ID NO: 239] |
| H5 (X07826) No Cys Δ3 | DQICIGYHANKSTKQVDTIMEKNVTVTHAQDILERTHNGK [SEQ ID NO: 191] | KCQTPVGEINSSMPFHNIHPHTIGECPKYVKSDRLVLATGLRNVPQRKKR [SEQ ID NO: 240] |
| H6 (D90303) No Cys | DKICIGYHANNSTTQIDTILEKNVTVTHSVELLENQKEERF [SEQ ID NO: 192] | DATCQTVAGVLRTNKTFQNVSPLWIGECPKYVKSESLRLATGLRNVPQIETR [SEQ ID NO: 241] |
| H6 (D90303) No Cys Δ1 | DKICIGYHANNSTTQIDTILEKNVTVTHSVELLENQKEERF [SEQ ID NO: 193] | ATCQTVAGVLRTNKTFQNVSPLWIGECPKYVKSESLRLATGLRNVPQIETR [SEQ ID NO: 242] |
| H6 (D90303) No Cys Δ3 | DKICIGYHANNSTTQIDTILEKNVTVTHSVELLENQKEER [SEQ ID NO: 194] | TCQTVAGVLRTNKTFQNVSPLWIGECPKYVKSESLRLATGLRNVPQIETR [SEQ ID NO: 243] |
| H7 (M24457) No Cys | DKICLGHHAVSNGTKVNTLTERGVEVVNATETVERTNIPKI [SEQ ID NO: 195] | EGECYHSGGTITSRLPFQNINSRAVGKCPRYVKQESLLLATGMKNVPEPSKKRKKR [SEQ ID NO: 244] |
| H7 (M24457) No Cys Δ1 | DKICLGHHAVSNGTKVNTLTERGVEVVNATETVERTNIPKI [SEQ ID NO: 196] | GECYHSGGTITSRLPFQNINSRAVGKCPRYVKQESLLLATGMKNVPEPSKKRKKR [SEQ ID NO: 245] |
| H7 (M24457) No Cys Δ3 | DKICLGHHAVSNGTKVNTLTERGVEVVNATETVERTNIPK [SEQ ID NO: 197] | ECYHSGGTITSRLPFQNINSRAVGKCPRYVKQESLLLATGMKNVPEPSKKRKKR [SEQ ID NO: 246] |
| H8 (D90304) No Cys | DRICIGYQSNNSTDTVNTLIEQNVPVTQTMELVETEKHPAY [SEQ ID NO: 198] | NTKCQTYAGAINSSKPFQNASRHYMGECPKYVKKASLRLAVGLRNTPSVEPR [SEQ ID NO: 247] |
| H8 (D90304) No Cys Δ1 | DRICIGYQSNNSTDTVNTLIEQNVPVTQTMELVETEKHPAY [SEQ ID NO: 199] | TKCQTYAGAINSSKPFQNASRHYMGECPKYVKKASLRLAVGLRNTPSVEPR [SEQ ID NO: 248] |
| H8 (D90304) No Cys Δ3 | DRICIGYQSNNSTDTVNTLIEQNVPVTQTMELVETEKHPA [SEQ ID NO: 200] | KCQTYAGAINSSKPFQNASRHYMGECPKYVKKASLRLAVGLRNTPSVEPR [SEQ ID NO: 249] |
| H9 (D90305) No Cys | DKICIGYQSTNSTETVDTLTESNVPVTHTKELLHTEHNGML [SEQ ID NO: 201] | VVQCQTEKGGLNTTLPFHNISKYAFGNCPKYVGVKSLKLPVGLRNVPAVSSR [SEQ ID NO: 250] |
| H9 (D90305) No Cys Δ1 | DKICIGYQSTNSTETVDTLTESNVPVTHTKELLHTEHNGML [SEQ ID NO: 202] | VQCQTEKGGLNTTLPFHNISKYAFGNCPKYVGVKSLKLPVGLRNVPAVSSR [SEQ ID NO: 251] |

TABLE 1A-continued

| Exemplary Influenza A Hemagglutinin Sequences | | |
|---|---|---|
| HA Subtype (Genbank No.) | HA1 N-terminal Stem Segment | HA1 C-terminal Stem Segment |
| H9 (D90305) No Cys Δ3 | DKICIGYQSTNSTETVDT LTESNVPVTHTKELLHTE HNGM [SEQ ID NO: 203] | QCQTEKGGLNTTLPFHNISKYAFGNCP KYVGVKSLKLPVGLRNVPAVSSR [SEQ ID NO: 252] |
| H10 (M21647) No Cys | LDRICLGHHAVANGTIV KTLTNEQEEVTNATETV ESTNLNKL [SEQ ID NO: 204] | ESKCFWRGGSINTKLPFQNLSPRTVGQ CPKYVNQRSLLLATGMRNVPEVVQGR [SEQ ID NO: 253] |
| H10 (M21647) No Cys Δ1 | LDRICLGHHAVANGTIV KTLTNEQEEVTNATETV ESTNLNKL [SEQ ID NO: 205] | SKCFWRGGSINTKLPFQNLSPRTVGQC PKYVNQRSLLLATGMRNVPEVVQGR [SEQ ID NO: 254] |
| H10 (M21647) No Cys Δ3 | LDRICLGHHAVANGTIV KTLTNEQEEVTNATETV ESTNLNK [SEQ ID NO: 206] | KCFWRGGSINTKLPFQNLSPRTVGQCP KYVNQRSLLLATGMRNVPEVVQGR [SEQ ID NO: 255] |
| H11 (D90306) No Cys | DEICIGYLSNNSTDKVDT IIENNVTVTSSVELVETE HTGSF [SEQ ID NO: 207] | STKCQTEIGGINTNKSFHNVHRNTIGD CPKYVNVKSLKLATGPRNVPAIASR [SEQ ID NO: 256] |
| H11 (D90306) No Cys Δ1 | DEICIGYLSNNSTDKVDT IIENNVTVTSSVELVETE HTGSF [SEQ ID NO: 208] | TKCQTEIGGINTNKSFHNVHRNTIGDC PKYVNVKSLKLATGPRNVPAIASR [SEQ ID NO: 257] |
| H11 (D90306) No Cys Δ3 | DEICIGYLSNNSTDKVDT IIENNVTVTSSVELVETE HTGS [SEQ ID NO: 209] | KCQTEIGGINTNKSFHNVHRNTIGDCP KYVNVKSLKLATGPRNVPAIASR [SEQ ID NO: 258] |
| H12 (D90307) No Cys | DKICIGYQTNNSTETVNT LSEQNVPVTQVEELVHR GIDPIL [SEQ ID NO: 210] | VTECQLNEGVMNTSKPFQNTSKHYIG KCPKYIPSGSLKLAIGLRNVPQVQDR [SEQ ID NO: 259] |
| H12 (D90307) No Cys Δ1 | DKICIGYQTNNSTETVNT LSEQNVPVTQVEELVHR GIDPIL [SEQ ID NO: 211] | TECQLNEGVMNTSKPFQNTSKHYIGK CPKYIPSGSLKLAIGLRNVPQVQDR [SEQ ID NO: 260] |
| H12 (D90307) No Cys Δ3 | DKICIGYQTNNSTETVNT LSEQNVPVTQVEELVHR GIDPI [SEQ ID NO: 212] | ECQLNEGVMNTSKPFQNTSKHYIGKC PKYIPSGSLKLAIGLRNVPQVQDR [SEQ ID NO: 261] |
| H13 (D90308) No Cys | DRICVGYLSTNSSERVDT LLENGVPVTSSIDLIETN HTGTY [SEQ ID NO: 213] | NTKCQTSVGGINTNRTFQNIDKNALG DCPKYIKSGQLKLATGLRNVPAISNR [SEQ ID NO: 262] |
| H13 (D90308) No Cys Δ1 | DRICVGYLSTNSSERVDT LLENGVPVTSSIDLIETN HTGTY [SEQ ID NO: 214] | TKCQTSVGGINTNRTFQNIDKNALGD CPKYIKSGQLKLATGLRNVPAISNR [SEQ ID NO: 263] |
| H13 (D90308) No Cys Δ3 | DRICVGYLSTNSSERVDT LLENGVPVTSSIDLIETN HTGT [SEQ ID NO: 215] | KCQTSVGGINTNRTFQNIDKNALGDC PKYIKSGQLKLATGLRNVPAISNR [SEQ ID NO: 264] |
| H14 (M35997) No Cys | QITNGTTGNPIICLGHHA VENGTSVKTLTDNHVEV VSAKELVETNHTDEL [SEQ ID NO: 216] | TSPCLTDKGSIQSDKPFQNVSRIAIGNC PKYVKQGSLMLATGMRNIPGKQAK [SEQ ID NO: 265] |

TABLE 1A-continued

| Exemplary Influenza A Hemagglutinin Sequences | | |
|---|---|---|
| HA Subtype (Genbank No.) | HA1 N-terminal Stem Segment | HA1 C-terminal Stem Segment |
| H14 (M35997) No Cys Δ1 | QITNGTTGNPIICLGHHA VENGTSVKTLTDNHVEV VSAKELVETNHTDEL [SEQ ID NO: 217] | SPCLTDKGSIQSDKPFQNVSRIAIGNCP KYVKQGSLMLATGMRNIPGKQAK [SEQ ID NO: 266] |
| H14 (M35997) No Cys Δ3 | QITNGTTGNPIICLGHHA VENGTSVKTLTDNHVEV VSAKELVETNHTDE [SEQ ID NO: 218] | PCLTDKGSIQSDKPFQNVSRIAIGNCPK YVKQGSLMLATGMRNIPGKQAK [SEQ ID NO: 267] |
| H15 (L43917) No Cys | DKICLGHHAVANGTKV NTLTERGVEVVNATETV EITGIDKV [SEQ ID NO: 219] | EGECFYSGGTINSPLPFQNIDSRAVGK CPRYVKQSSLPLALGMKNVPEKIRTR [SEQ ID NO: 268] |
| H15 (L43917) No Cys Δ1 | DKICLGHHAVANGTKV NTLTERGVEVVNATETV EITGIDKV [SEQ ID NO: 220] | GECFYSGGTINSPLPFQNIDSRAVGKC PRYVKQSSLPLALGMKNVPEKIRTR [SEQ ID NO: 269] |
| H15 (L43917) No Cys Δ3 | DKICLGHHAVANGTKV NTLTERGVEVVNATETV EITGIDK [SEQ ID NO: 221] | ECFYSGGTINSPLPFQNIDSRAVGKCP RYVKQSSLPLALGMKNVPEKIRTR [SEQ ID NO: 270] |
| H16 (EU293865) No Cys | DKICIGYLSNNSSDTVDT LTENGVPVTSSVDLVET NHTGTY [SEQ ID NO: 222] | NTKCQTSLGGINTNKTFQNIERNALGD CPKYIKSGQLKLATGLRNVPSIGER [SEQ ID NO: 271] |
| H16 (EU293865) No Cys Δ1 | DKICIGYLSNNSSDTVDT LTENGVPVTSSVDLVET NHTGTY [SEQ ID NO: 223] | TKCQTSLGGINTNKTFQNIERNALGDC PKYIKSGQLKLATGLRNVPSIGER [SEQ ID NO: 272] |
| H16 (EU293865) No Cys Δ3 | DKICIGYLSNNSSDTVDT LTENGVPVTSSVDLVET NHTGT [SEQ ID NO: 224] | KCQTSLGGINTNKTFQNIERNALGDCP KYIKSGQLKLATGLRNVPSIGER [SEQ ID NO: 273] |

Table 2, below, identifies putative stem domains, luminal domains, transmembrane domains and cytoplasmic domains of HA2 polypeptides.

TABLE 2

| Exemplary Influenza A Hemagglutinin Sequences | | | | |
|---|---|---|---|---|
| HA2 Domain Subtype (Genbank No.) | Stem Domain | Luminal Domain | Transmembrane Domain | Cytoplasmic Domain |
| H1 PR8-H1N1 (EF467821.1) | GLFGAIAGFIEGGWT GMIDGWYGYHHQNE QGSGYAADQKSTQN AINGITNKVNTVIEK MNIQFTAVGKEFNKL EKRMENLNKKVDDG FLDIWTYNAELLVLL ENERTLDFHDSNVKN LYEKVKSQLKNNAK EIGNGCFEFYHKCDN ECMESVRNGTYDYP KYSEESKLNREKVDG VKLES [SEQ ID NO: 82] | MGIYQ [SEQ ID NO: 98] | ILAIYSTVASSL VLLVSLGAISF WMCS [SEQ ID NO: 114] | NGSLQCRICI [SEQ ID NO: 130] |
| H2 (L11136) | GLFGAIAGFIEGGWQ GMIDGWYGYHHSND | MGVYQ [SEQ ID | ILAIYATVAGSL SLAIMIAGISLW | NGSLQCRICI [SEQ ID |

TABLE 2-continued

Exemplary Influenza A Hemagglutinin Sequences

| HA2 Domain Subtype (Genbank No.) | Stem Domain | Luminal Domain | Transmembrane Domain | Cytoplasmic Domain |
|---|---|---|---|---|
| | QGSGYAADKESTQK AIDGITNRVNSVIEK MNTQFEAVGKEFSNL EKRLENLNKKMEDG FLDVWTYNAELLVL MENERTLDFHDSNV KNLYDRVRMQLRDN AKELGNGCFEFYHKC DDECMNSVKNGTYD YPKYEEESKLNRNEI KGVKLSN [SEQ ID NO: 83] | NO: 99] | MCS [SEQ ID NO: 115] | NO: 131] |
| H3 HK68-H3N2 (EF409245) PDB: 1HGJ | GLFGAIAGFIENGWE GMIDGWYGFRHQNS EGTGQAADLKSTQA AIDQINGKLNRVIEKT NEKFHQIEKEFSEVE GRIQDLEKYVEDTKI DLWSYNAELLVALE NQHTIDLTDSEMNKL FEKTRRQLRENAED MGNGCFKIYHKCDN ACIESIRNGTYDHDV YRDEALNNRFQIKGV ELK [SEQ ID NO: 84] | SGYKD [SEQ ID NO: 100] | WILWISFAISCF LLCVVLLGFIM WACQ [SEQ ID NO: 116] | RGNIRCNICI [SEQ ID NO: 132] |
| H4 (D90302) | GLFGAIAGFIENGWQ GLIDGWYGFRHQNA EGTGTAADLKSTQA AIDQINGKLNRLIEKT NDKYHQIEKEFEQVE GRIQDLENYVEDTKI DLWSYNAELLVALE NQHTIDVTDSEMNKL FERVRRQLRENAEDK GNGCFEIFHKCDNNC IESIRNGTYDHDIYRD EAINNRFQIQGVKLT [SEQ ID NO: 85] | QGYKD [SEQ ID NO: 101] | IILWISFSISCFLL VALLLAFILWA CQ [SEQ ID NO: 117] | NGNIRCQICI [SEQ ID NO: 133] |
| H5 (X07826) | GLFGAIAGFIEGGWQ GMVDGWYGYHHSN EQGSGYAADKESTQ KAIDGITNKVNSIIDK MNTRFEAVGKEFNN LERRVENLNKKMED GFLDVWTYNVELLV LMENERTLDFHDSNV NNLYDKVRLQLKDN ARELGNGCFEFYHKC DNECMESVRNGTYD YPQYSEEARLNREEIS GVKLES [SEQ ID NO: 86] | MGVYQ [SEQ ID NO: 102] | ILSIYSTVASSL ALAIMIAGLSF WMCS [SEQ ID NO: 118] | NGSLQCRICI [SEQ ID NO: 134] |
| H6 (D90303) | GLFGAIAGFIEGGWT GMIDGWYGYHHENS QGSGYAADRESTQK AVDGITNKVNSIIDK MNTQFEAVDHEFSNL ERRIDNLNKRMEDGF LDVWTYNAELLVLL ENERTLDLHDANVK NLYERVKSQLRDNA MILGNGCFEFWHKC DDECMESVKNGTYD YPKYQDESKLNRQEI ESVKLES [SEQ ID NO: 87] | LGVYQ [SEQ ID NO: 103] | ILAIYSTVSSSL VLVGLIIAVGL WMCS [SEQ ID NO: 119] | NGSMQCRI CI [SEQ ID NO: 135] |

TABLE 2-continued

Exemplary Influenza A Hemagglutinin Sequences

| HA2 Domain Subtype (Genbank No.) | Stem Domain | Luminal Domain | Transmembrane Domain | Cytoplasmic Domain |
|---|---|---|---|---|
| H7 (M24457) | GLFGAIAGFIENGWE GLVDGWYGFRHQNA QGEGTAADYKSTQS AIDQITGKLNRLIEKT NQQFELIDNEFTEVE KQIGNLINWTKDSITE VWSYNAELIVAMEN QHTIDLADSEMNRLY ERVRKQLRENAEED GTGCFEIFHKCDDDC MASIRNNTYDHSKYR EEAMQNRIQIDPVKLS [SEQ ID NO: 88] | SGYKD [SEQ ID NO: 104] | VILWFSFGASCF LLLAIAMGLVFI CVK [SEQ ID NO: 120] | NGNMRCTI CI [SEQ ID NO: 136] |
| H8 (D90304) | GLFGAIAGFIEGGWS GMIDGWYGFHHSNS EGTGMAADQKSTQE AIDKITNKVNNIVDK MNREFEVVNHEFSEV EKRINMINDKIDDQIE DLWAYNAELLVLLE NQKTLDEHDSNVKN LFDEVKRRLSANAID AGNGCFDILHKCDNE CMETIKNGTYDHKE YEEEAKLERSKINGV KLEE [SEQ ID NO: 89] | NTTYK [SEQ ID NO: 105] | ILSIYSTVAASL CLAILIAGGLIL GMQ [SEQ ID NO: 121] | NGSCRCMF CI [SEQ ID NO: 137] |
| H9 (D90305) | GLFGAIAGFIEGGWP GLVAGWYGFQHSND QGVGMAADKGSTQK AIDKITSKVNNIIDKM NKQYEVIDHEFNELE ARLNMINNKIDDQIQ DIWAYNAELLVLLEN QKTLDEHDANVNNL YNKVKRALGSNAVE DGNGCFELYHKCDD QCMETIRNGTYDRQ KYQEESRLERQKIEG VKLES [SEQ ID NO: 90] | EGTYK [SEQ ID NO: 106] | ILTIYSTVASSL VLAMGFAAFLF WAMS [SEQ ID NO: 122] | NGSCRCNICI [SEQ ID NO: 138] |
| H10 (M21647) | GLFGAIAGFIENGWE GMVDGWYGFRHQN AQGTGQAADYKSTQ AAIDQITGKLNRLIEK TNTEFESIESEFSETEH QIGNVINWTKDSITDI WTYNAELLVAMENQ HTIDMADSEMLNLYE RVRKQLRQNAEEDG KGCFEIYHTCDDSCM ESIRNNTYDHSQYRE EALLNRLNINPVKLS [SEQ ID NO: 91] | SGYKD [SEQ ID NO: 107] | IILWFSFGESCF VLLAVVMGLV FFCLK [SEQ ID NO: 123] | NGNMRCTI CI [SEQ ID NO: 139] |
| H11 (D90306) | GLFGAIAGFIEGGWP GLINGWYGFQHRDE EGTGIAADKESTQKA IDQITSKVNNIVDRM NTNFESVQHEFSEIEE RINQLSKHVDDSVVD IWSYNAQLLVLLENE KTLDLHDSNVRNLHE KVRRMLKDNAKDEG NGCFTFYHKCDNKCI ERVRNGTYDHKEFEE ESKINRQEIEGVKLDSS [SEQ ID NO: 92] | GNVYK [SEQ ID NO: 108] | ILSIYSCIASSLV LAALIMGFMFW ACS [SEQ ID NO: 124] | NGSCRCTICI [SEQ ID NO: 140] |

TABLE 2-continued

Exemplary Influenza A Hemagglutinin Sequences

| HA2 Domain Subtype (Genbank No.) | Stem Domain | Luminal Domain | Transmembrane Domain | Cytoplasmic Domain |
|---|---|---|---|---|
| H12 (D90307) | GLFGAIAGFIEGGWP GLVAGWYGFQHQNA EGTGIAADRDSTQRA IDNMQNKLNNVIDK MNKQFEVVNHEFSE VESRINMINSKIDDQI TDIWAYNAELLVLLE NQKTLDEHDANVRN LHDRVRRVLRENAID TGDGCFEILHKCDNN CMDTIRNGTYNHKE YEEESKIERQKVNGV KLEE [SEQ ID NO: 93] | NSTYK [SEQ ID NO: 109] | ILSIYSSVASSLV LLLMIIGGFIFG CQN [SEQ ID NO: 125] | GNVRCTFCI [SEQ ID NO: 141] |
| H13 (D90308) | GLFGAIAGFIEGGWP GLINGWYGFQHQNE QGTGIAADKESTQKA IDQITTKINNIIDKMN GNYDSIRGEFNQVEK RINMLADRIDDAVTD IWSYNAKLLVLLEND KTLDMHDANVKNLH EQVRRELKDNAIDEG NGCFELLHKCNDSC METIRNGTYDHTEYA EESKLKRQEIDGIKLK SE [SEQ ID NO: 94] | DNVYK [SEQ ID NO: 110] | ALSIYSCIASSV VLVGLILSFIM WACSS [SEQ ID NO: 126] | GNCRFNVCI [SEQ ID NO: 142] |
| H14 (M35997) | GLFGAIAGFIENGWQ GLIDGWYGFRHQNA EGTGTAADLKSTQA AIDQINGKLNRLIEKT NEKYHQIEKEFEQVE GRIQDLEKYVEDTKI DLWSYNAELLVALE NQHTIDVTDSEMNKL FERVRRQLRENAEDQ GNGCFEIFHQCDNNC IESIRNGTYDHNIYRD EAINNRIKINPVTLT [SEQ ID NO: 95] | MGYKD [SEQ ID NO: 111] | IILWISFSMSCF VFVALILGFVL WACQ [SEQ ID NO: 127] | NGNIRCQICI [SEQ ID NO: 143] |
| H15 (L43917) | GLFGAIAGFIENGWE GLIDGWYGFRHQNA QGQGTAADYKSTQA AIDQITGKLNRLIEKT NKQFELIDNEFTEVE QQIGNVINWTRDSLT EIWSYNAELLVAME NQHTIDLADSEMNKL YERVRRQLRENAEED GTGCFEIFHRCDDQC MESIRNNTYNHTEYR QEALQNRIMINPVKLS [SEQ ID NO: 96] | SGYKD [SEQ ID NO: 112] | VILWFSFGASC VMLLAIAMGLI FMCVKN [SEQ ID NO: 128] | GNLRCTICI [SEQ ID NO: 144] |
| H16 (EU293865) | GLFGAIAGFIEGGWP GLINGWYGFQHQNE QGTGIAADKASTQKA INEITTKINNIIEKMNG NYDSIRGEFNQVEKR INMLADRVDDAVTDI WSYNAKLLVLLEND RTLDLHDANVRNLH DQVKRALKSNAIDEG DGCFNLLHKCNDSC METIRNGTYNHEDYR EESQLKRQEIEGIKLK TE [SEQ ID NO: 97] | DNVYK [SEQ ID NO: 113] | VLSIYSCIASSIV LVGLILAFIMW ACS [SEQ ID NO: 129] | NGSCRFNV CI [SEQ ID NO: 145] |

In certain embodiments, the influenza hemagglutinin stem domain polypeptides comprise one or more immunogenic epitopes in the tertiary or quaternary structure of an influenza hemagglutinin polypeptide.

In certain embodiments, the HA1 N-terminal stem segment comprises the amino acid sequence $A_{17}$-$A_{18}$-$(Xaa)_n$-$A_{38}$ (SEQ ID NO:146), wherein $A_{17}$ is Y or H;

$A_{18}$ is H, L, or Q;

$(Xaa)_n$ represents a sequence of 18-20 amino acid residues; and $A_{38}$ is H, S, Q, T or N.

In certain embodiments, the HA1 C-terminal stem segment comprises the amino acid sequence $A_{291}$-$A_{292}$ (SEQ ID NO:147), wherein $A_{291}$ is T, S, N, D, P or K; and $A_{292}$ is L, M, K or R.

In certain embodiments, the HA2 domain comprises the amino acid sequence $A_{18}$-$A_{19}$-$A_{20}$-$A_{21}$ (SEQ ID NO:148), wherein $A_{18}$ is V or I;

$A_{19}$ is D, N or A;

$A_{20}$ is G, and $A_{21}$ is W.

In certain embodiments, the HA2 domain comprises the amino acid sequence $A_{38}$-$A_{39}$-$A_{40}$-$A_{41}$-$A_{42}$-$A_{43}$-$A_{44}$-$A_{45}$-$A_{46}$-$A_{47}$-$A_{48}$-$A_{49}$-$A_{50}$-$A_{51}$-$A_{52}$-$A_{53}$-$A_{54}$-$A_{55}$-$A_{56}$ (SEQ ID NO:149), wherein $A_{38}$ is K, Q, R, L or Y;

$A_{39}$ is any amino acid residue;

$A_{40}$ is any amino acid residue;

$A_{41}$ is T;

$A_{42}$ is Q;

$A_{43}$ is any amino acid residue;

$A_{44}$ is A;

$A_{45}$ is I;

$A_{46}$ is D;

$A_{47}$ is any amino acid residue;

$A_{48}$ is I, V or M;

$A_{49}$ is T, Q or N;

$A_{50}$ is any amino acid residue;

$A_{51}$ is K;

$A_{52}$ is V or L;

$A_{53}$ is N;

$A_{54}$ is any amino acid residue;

$A_{55}$ is V, I or L; and $A_{56}$ is V or I.

In certain embodiments, the influenza stem domain polypeptides comprise two amino acid sequences selected from SEQ ID NOS:146-149. In certain embodiments, the influenza stem domain polypeptides comprise three amino acid sequences selected from SEQ ID NOS:146-149. In certain embodiments, the influenza stem domain polypeptides comprise four amino acid sequences selected from SEQ ID NOS:146-149.

In certain embodiments, the HA1 N-terminal stem segments are based on an influenza B hemagglutinin. In certain embodiments, the HA1 N-terminal stem segment is selected from SEQ ID NOS:154-157, presented in Table 3 below.

In certain embodiments, the HA1 C-terminal stem segments are based on an influenza B hemagglutinin. In certain embodiments, the HA1 C-terminal stem segment is selected from SEQ ID NOS:158-159 and 553-554, presented in Table 3 below.

In certain embodiments, the HA2 stem domains are based on an influenza B hemagglutinin. Exemplary residues for the end of an N-terminal stem segment and the end of a C-terminal stem segment of an influenza B hemagglutinin are indicated in FIG. 2. In certain embodiments, the HA2 stem domain is according to SEQ ID NO:160, presented in Tables 3 and 4 below.

In particular embodiments, the boundaries of the influenza B virus HA1 N-terminal stem segment and influenza B virus HA1 C-terminal segment are defined with respect to six pairs of amino acid residues: $Arg_{50}$ and $Ser_{277}$; $Ala_{66}$ and $Trp_{271}$; $Lys_{80}$ and $Ser_{277}$, $Cys_{94}$ and $Cys_{143}$; $Cys_{178}$ and $Cys_{272}$ and $Cys_{54}$ and $Cys_{272}$. Positions of these six pairs of residues are also highlighted in FIG. 3. The residue numbers are based on the numbering of the B-HA from influenza virus B as described in Protein Data Bank accession No. 3BT6. The amino acid sequence corresponding to the X-ray crystal structure of the B-HA protein in Protein Data Bank accession No. 3BT6 is aligned with representative H1 and H3 amino acid sequence and shown in FIG. 2.

In certain embodiments, an influenza B virus HA1 N-terminal stem segment starts at residue 1 (based on numbering of an influenza B virus HA1 subunit as in PDB file 3BT6) and ends at $Arg_{50}$. In certain embodiments, an influenza B virus HA1 N-terminal stem segment starts at residue 1 and ends at $Ala_{66}$. In some embodiments, an influenza B virus HA1 N-terminal stem segment starts at residue 1 and ends at $Lys_{80}$. In some embodiments, an influenza B virus N-terminal stem segment starts at residue 1 and ends at $Arg_{80}$. In some embodiments, an influenza B virus N-terminal stem segment starts at residue 1 and ends at Cys54. In some embodiments, an influenza B virus N-terminal stem segment starts at residue 1 and ends at $Cys_{94}$. In some embodiments, an influenza B virus N-terminal stem segment starts at residue 1 and ends at $Cys_{178}$.

In some embodiments, an influenza B virus HA1 N-terminal stem segment has an amino acid sequence according to any one of SEQ ID NOS:154-157 and 550-552, as illustrated in TABLE 3. In some embodiments, an influenza B virus HA1 N-terminal stem segment has an amino acid sequence that is at least 70%, 75%, 80%, 85%, 90%, 95%, 96% or 98% identical to any one of the amino acid sequences of any one of SEQ ID NOS:154-157 or 550-552.

In some embodiments, an influenza B virus HA1 N-terminal stem segment has an amino acid sequence that is at least 70%, 75%, 80%, 85%, 90%, 95%, 96% or 98% identical to the amino acid sequence SEQ ID NO:154, which corresponds to residues 1-50 of the influenza B virus HA1.

In some embodiments, an influenza B virus HA1 N-terminal stem segment has an amino acid sequence that is at least 70%, 75%, 80%, 85%, 90%, 95%, 96% or 98% identical to the amino acid sequence SEQ ID NO:155, which corresponds to residues 1-66 of the influenza B virus HA1.

In some embodiments, an influenza B virus HA1 N-terminal stem segment has an amino acid sequence that is at least 70%, 75%, 80%, 85%, 90%, 95%, 96% or 98% identical to the amino acid sequence SEQ ID NO:156, which corresponds to residues 1-80 of the influenza B virus HA1.

In some embodiments, an influenza B virus HA1 N-terminal stem segment has an amino acid sequence that is at least 70%, 75%, 80%, 85%, 90%, 95%, 96% or 98% identical to the amino acid sequence SEQ ID NO:157, which corresponds to residues 1-80 of the influenza B virus HA1 in which the lysine at position 80 is replaced with an arginine.

In some embodiments, an influenza B virus HA1 N-terminal stem segment has an amino acid sequence that is at least 70%, 75%, 80%, 85%, 90%, 95%, 96% or 98% identical to the amino acid sequence SEQ ID NO:550, which corresponds to residues 1-94 of the influenza B virus HA1.

In some embodiments, an influenza B virus HA1 N-terminal stem segment has an amino acid sequence that is at least 70%, 75%, 80%, 85%, 90%, 95%, 96% or 98% identical to the amino acid sequence SEQ ID NO:551, which corresponds to residues 1-178 of the influenza B virus HA1.

In some embodiments, an influenza B virus HA1 N-terminal stem segment has an amino acid sequence that is at least 70%, 75%, 80%, 85%, 90%, 95%, 96% or 98% identical to the amino acid sequence SEQ ID NO:552, which corresponds to residues 1-54 of the influenza B virus HA1.

In some embodiments, an influenza B virus HA1 C-terminal stem segment has an amino acid sequence that starts at $Ser_{277}$, $Trp_{271}$, $Cys_{143}$, $Cys_{272}$ or corresponding residues in other influenza B virus HA subtypes.

In some embodiments, an influenza B virus HA1 C-terminal stem segment has an amino acid sequence according to any one of SEQ ID NOS:158-159 or 553-554, as illustrated in TABLE 3. In some embodiments, an influenza B virus HA1 C-terminal stem segment has an amino acid sequence that is at least 70%, 75%, 80%, 85%, 90%, 95%, 96% or 98% identical to SEQ ID NO:158, which correspond to residues 277-344 of influenza B virus HA1. In some embodiments, an influenza B virus HA1 C-terminal stem segment has an amino acid sequence that is at least 70%, 75%, 80%, 85%, 90%, 95%, 96% or 98% identical to SEQ ID NO:159, which correspond to residues 271-344 of influenza B virus HA1. In some embodiments, an influenza B virus HA1 C-terminal stem segment has an amino acid sequence that is at least 70%, 75%, 80%, 85%, 90%, 95%, 96% or 98% identical to SEQ ID NO:553, which correspond to residues 137-344 of influenza B virus HA1. In some embodiments, an influenza B virus HA1 C-terminal stem segment has an amino acid sequence that is at least 70%, 75%, 80%, 85%, 90%, 95%, 96% or 98% identical to SEQ ID NO:554, which correspond to residues 272-344 of influenza B virus HA1.

In some embodiments, an influenza B virus HA1 C-terminal stem segment starts at residue-276, residue-275, residue-274, residue-273, or residue-272. In other embodiments, an influenza B virus HA1 C-terminal stem segment starts at residue-278, residue-279, residue-280, residue-281, or residue-282.

In certain embodiments, the influenza B virus HA2 domain is in tertiary or quaternary association with the influenza B virus HA1 domain through the influenza B virus HA1 N-terminal segment, the influenza B virus HA1 C-terminal segment, or both.

In some embodiments, the influenza B virus HA1 C-terminal segment and the influenza B virus HA2 subunit are covalently linked. For example, at its C-terminus (e.g., at the ending residue of the second sequence), the influenza B virus HA1 C-terminal segment is covalently linked to the influenza B virus HA2 domain in such embodiments. In some embodiments, the influenza B virus HA1 C-terminal segment and influenza B virus HA2 domain form a continuous polypeptide chain.

In some embodiments, the influenza B virus HA2 domain has the amino acid sequence of SEQ ID NO:160 or 161, as illustrated in TABLE 3 or 4. In some embodiments, the amino acid sequence of the HA2 domain is at least 70%, 75%, 80%, 85%, 90%, 95%, 96% or 98% identical to any one of SEQ ID NOS:160-161.

In certain embodiments, the influenza B stem domain polypeptides comprise a signal peptide. The signal peptide can be any signal peptide deemed suitable to those of skill in the art, including any signal peptide described herein. In certain embodiments, the signal peptide is at least 70%, 75%, 80%, 85%, 90%, 95%, 96% or 98% identical to any of SEQ ID NOS:150-153. In certain embodiments, the signal peptide is according to any of SEQ ID NOS:150-153.

In certain embodiments, the influenza B stem domain polypeptides comprise a luminal domain. The luminal domain can be any luminal domain deemed suitable to those of skill in the art, including any luminal domain described herein. In certain embodiments, the luminal is at least 60% or 80%, identical to SEQ ID NO:162. In certain embodiments, the luminal domain is according to SEQ ID NO:162.

In certain embodiments, the influenza B stem domain polypeptides comprise a transmembrane domain. The transmembrane domain can be any transmembrane domain deemed suitable to those of skill in the art, including any transmembrane domain described herein. In certain embodiments, the transmembrane domain is at least 70%, 75%, 80%, 85%, 90%, 95%, 96% or 98% identical to SEQ ID NO:163. In certain embodiments, the transmembrane domain is according to SEQ ID NO:163.

In certain embodiments, the influenza B stem domain polypeptides comprise a cytoplasmic domain. The cytoplasmic domain can be any cytoplasmic domain deemed suitable to those of skill in the art, including any cytoplasmic domain described herein. In certain embodiments, the cytoplasmic domain is at least 70%, 75%, 80%, 85%, 90%, 95%, 96% or 98% identical to SEQ ID NO:164. In certain embodiments, the cytoplasmic domain is according to SEQ ID NO:164.

TABLE 3

Exemplary Influenza B Hemagglutinin Sequences

| HA construct variants | Signal peptide | HA1 N-terminal Stem Segment | HA1 C-terminal Stem Segment | HA2 Domain |
|---|---|---|---|---|
| Arg50-Ser277 | MKAIIVILMV VTSNA [SEQ ID NO: 150] | DRICTGITSSNS PHVVKTATQG EVNVTGVIPLT TTPTKSHFANL KGTETR [SEQ ID NO: 154] | SKVIKGSLPLI GEADCLHEKY GGLNKSKPYY TGEHAKAIGN CPIWVKTPLKL ANGTKYRPPA KLLKER [SEQ ID NO: 158] | GFFGAIAGFLEGG WEGMIAGWHGY TSHGAHGVAVAA DLKSTQEAINKIT KNLNSLSELEVKN LQRLSGAMDELH NEILELDEKVDDL RADTISSQIELAVL LSNEGIINSEDEHL LALERKLKKMLG PSAVEIGNGCFET KHKCNQTCLDRI AAGTFDAGEFSLP TFDSLNITAASLN |

TABLE 3-continued

Exemplary Influenza B Hemagglutinin Sequences

| HA construct variants | Signal peptide | HA1 N-terminal Stem Segment | HA1 C-terminal Stem Segment | HA2 Domain |
|---|---|---|---|---|
| | | | | DDGLDNHTILLYY STAASSLAVTLMI AIFVVYMVSRDN VSCSICL [SEQ ID NO: 160] |
| Ala66-Trp271 | MKAIIVILMV VTSNA [SEQ ID NO: 151] | DRICTGITSSNS PHVVKTATQG EVNVTGVIPLT TTPTKSHFANL KGTETRGKLC PKCLNCTDLD VA [SEQ ID NO: 155] | WCASGRSKVI KGSLPLIGEAD CLHEKYGGLN KSKPYYTGEH AKAIGNCPIW VKTPLKLANG TKYRPPAKLL KER [SEQ ID NO: 159] | GFFGAIAGFLEGG WEGMIAGWHGY TSHGAHGVAVAA DLKSTQEAINKIT KNLNSLSELEVKN LQRLSGAMDELH NEILELDEKVDDL RADTISSQIELAVL LSNEGIINSEDEHL LALERKLKKMLG PSAVEIGNGCFET KHKCNQTCLDRI AAGTFDAGEFSLP TFDSLNITAASLN DDGLDNHTILLYY STAASSLAVTLMI AIFVVYMVSRDN VSCSICL [SEQ ID NO: 160] |
| Lys80-Ser277 | MKAIIVILMV VTSNA [SEQ ID NO: 152] | DRICTGITSSNS PHVVKTATQG EVNVTGVIPLT TTPTKSHFANL KGTETRGKLC PKCLNCTDLD VALGRPKCTG KIPSAK [SEQ ID NO: 156] | SKVIKGSLPLI GEADCLHEKY GGLNKSKPYY TGEHAKAIGN CPIWVKTPLKL ANGTKYRPPA KLLKER [SEQ ID NO: 158] | GFFGAIAGFLEGG WEGMIAGWHGY TSHGAHGVAVAA DLKSTQEAINKIT KNLNSLSELEVKN LQRLSGAMDELH NEILELDEKVDDL RADTISSQIELAVL LSNEGIINSEDEHL LALERKLKKMLG PSAVEIGNGCFET KHKCNQTCLDRI AAGTFDAGEFSLP TFDSLNITAASLN DDGLDNHTILLYY STAASSLAVTLMI AIFVVYMVSRDN VSCSICL [SEQ ID NO: 160] |
| Arg80-Ser277 | MKAIIVILMV VTSNA [SEQ ID NO: 153] | DRICTGITSSNS PHVVKTATQG EVNVTGVIPLT TTPTKSHFANL KGTETRGKLC PKCLNCTDLD VALGRPKCTG KIPSAR [SEQ ID NO: 157] | SKVIKGSLPLI GEADCLHEKY GGLNKSKPYY TGEHAKAIGN CPIWVKTPLKL ANGTKYRPPA KLLKER [SEQ ID NO: 158] | GFFGAIAGFLEGG WEGMIAGWHGY TSHGAHGVAVAA DLKSTQEAINKIT KNLNSLSELEVKN LQRLSGAMDELH NEILELDEKVDDL RADTISSQIELAVL LSNEGIINSEDEHL LALERKLKKMLG PSAVEIGNGCFET KHKCNQTCLDRI AAGTFDAGEFSLP TFDSLNITAASLN DDGLDNHTILLYY STAASSLAVTLMI AIFVVYMVSRDN VSCSICL [SEQ ID NO: 160] |
| Cys94-Cys143 | MKAIIVILMV VTSNA [SEQ ID NO: 150] | DRICTGITSSNS PHVVKTATQG EVNVTGVIPLT TTPTKSHFANL KGTQTRGKLC PNCLNCTDLD VALGRPKCMG TIPSAKASILHE | CPNVTNGNGF FATMAWAVP KNKTATNPLT VEVPYICTKGE DQITVWGFHS DDETQMVKLY GDSKPQKFTSS ANGVTTHYVS | GFFGAIAGFLEGG WEGMIAGWHGY TSHGAHGVAVAA DLKSTQEAINKIT KNLNSLSELEVKN LQRLSGAMDELH NEILELDEKVDDL RADTISSQIELAVL |

TABLE 3-continued

Exemplary Influenza B Hemagglutinin Sequences

| HA construct variants | Signal peptide | HA1 N-terminal Stem Segment | HA1 C-terminal Stem Segment | HA2 Domain |
|---|---|---|---|---|
| | | VKPVTSGC [SEQ ID NO: 550] | QIGGFPNQAE DEGLPQSGRIV VDYMVQKPG KTGTIAYQRG VLLPQKVWCA SGRSKVIKGSL PLIGEADCLHE KYGGLNKSKP YYTGEHAKAI GNCPIWVKTP LKLANGTKYR PPAKLLK [SEQ ID NO: 553] | LSNEGIINSEDEHL LALERKLKKMLG PSAVEIGNGCFET KHKCNQTCLDRI AAGTFDAGEFSLP TFDSLNITAASLN DDGLDNHTILLYY STAASSLAVTLMI AIFVVYMVSRDN VSCSICL [SEQ ID NO: 160] |
| Cys178-Cys272 | MKAIIVILMV VTSNA [SEQ ID NO: 150] | DRICTGITSSNS PHVVKTATQG EVNVTGVIPLT TTPTKSHFANL KGTQTRGKLC PNCLNCTDLD VALGRPKCMG TIPSAKASILHE VKPVTSGCFPI MHDRTKIRQL PNLLRGYENIR LSARNVTNAE TAPGGPYIVGT SGSCPNVTNG NGFFATMAW AVPKNKTATN PLTVEVPYIC [SEQ ID NO: 551] | CASGRSKVIK GSLPLIGEADC LHEKYGGLNK SKPYYTGEHA KAIGNCPIWV KTPLKLANGT KYRPPAKLLK [SEQ ID NO: 554] | GFFGAIAGFLEGG WEGMIAGWHGY TSHGAHGVAVAA DLKSTQEAINKIT KNLNSLSELEVKN LQRLSGAMDELH NEILELDEKVDDL RADTISSQIELAVL LSNEGIINSEDEHL LALERKLKKMLG PSAVEIGNGCFET KHKCNQTCLDRI AAGTFDAGEFSLP TFDSLNITAASLN DDGLDNHTILLYY STAASSLAVTLMI AIFVVYMVSRDN VSCSICL [SEQ ID NO: 160] |
| Cys54-Cys272 | MKAIIVILMV VTSNA [SEQ ID NO: 150] | DRICTGITSSNS PHVVKTATQG EVNVTGVIPLT TTPTKSHFANL KGTQTRGKLC [SEQ ID NO: 552] | CASGRSKVIK GSLPLIGEADC LHEKYGGLNK SKPYYTGEHA KAIGNCPIWV KTPLKLANGT KYRPPAKLLK [SEQ ID NO: 554] | GFFGAIAGFLEGG WEGMIAGWHGY TSHGAHGVAVAA DLKSTQEAINKIT KNLNSLSELEVKN LQRLSGAMDELH NEILELDEKVDDL RADTISSQIELAVL LSNEGIINSEDEHL LALERKLKKMLG PSAVEIGNGCFET KHKCNQTCLDRI AAGTFDAGEFSLP TFDSLNITAASLN DDGLDNHTILLYY STAASSLAVTLMI AIFVVYMVSRDN VSCSICL [SEQ ID NO: 160] |

Table 4 provides the putative stem domain, luminal domain, transmembrane domain and cytoplasmic domain of HA from influenza B.

TABLE 4

Exemplary Influenza B Hemagglutinin Sequences

| HA2 domain Subtype (Genbank No.) | Stem Domain | Luminal Domain | Transmembrane Domain | Cytoplasmic Domain |
|---|---|---|---|---|
| HA2 (AY096185) | GFFGAIAGFLEG GWEGMIAGWH GYTSHGAHGV | DGLDN [SEQ ID NO: 162] | HTILLYYSTAAS SLAVTLMIAIFV VYMV | SRDNVSCSICL [SEQ ID NO: 164] |

TABLE 4-continued

Exemplary Influenza B Hemagglutinin Sequences

| HA2 domain Subtype (Genbank No.) | Stem Domain | Luminal Domain | Transmembrane Domain | Cytoplasmic Domain |
|---|---|---|---|---|
| | AVAADLKSTQE AINKITKNLNSL SELEVKNLQRL SGAMDELHNEI LELDEKVDDLR ADTISSQIELAV LLSNEGIINSED EHLLALERKLK KMLGPSAVEIG NGCFETKHKCN QTCLDRIAAGT FDAGEFSLPTFD SLNITAASLND [SEQ ID NO: 161] | | [SEQ ID NO: 163] | |

As illustrated in FIGS. 1 and 2, HA1 N-terminal stem segments share sequence identity between influenza A and influenza B and additionally across influenza A subtypes. Similarly, HA1 C-terminal stem segments also share sequence identity between influenza A and influenza B and additionally across influenza A subtypes. Further, HA2 domains also share sequence identity between influenza A and influenza B and additionally across influenza A subtypes.

In some embodiments, the influenza hemagglutinin stem domain polypeptide comprises in the following order: an HA1 N-terminal stem segment, a linker, an HA1 intermediate stem segment, a second linker, an HA1 C-terminal stem segment and an HA2. In some embodiments, the HA1 N-terminal stem segment has an amino acid sequence that is at least 70%, 75%, 80%, 85%, 90%, 95%, 96% or 98% identical to SEQ ID NO:555, as illustrated in Table 5. SEQ ID NO:555 corresponds to residues 1-94 of influenza B virus HA1. In some embodiments, the HA1 C-terminal stem segment has an amino acid sequence that is at least 70%, 75%, 80%, 85%, 90%, 95%, 96% or 98% identical to SEQ ID NO:557, as illustrated in Table 5. SEQ ID NO:557 corresponds to residues 272-344 of influenza B virus HA1. In some embodiments, the HA1 intermediate segment has an amino acid sequence that is at least 70%, 75%, 80%, 85%, 90%, 95%, 96% or 98% identical to SEQ ID NO:556, as illustrated in Table 5. SEQ ID NO:556 corresponds to residues 143-178 of influenza B virus HA1. In some embodiments, the HA2 domain has an amino acid sequence that is at least 70%, 75%, 80%, 85%, 90%, 95%, 96% or 98% identical to SEQ ID NO:160, as described herein. In some embodiments, the first and second linker can be any linker known to those skilled in the art including, but not limited to, linkers described herein.

TABLE 5

Exemplary Influenza B Hemagglutinin Sequences

| HA construct variant | HA1 N-terminal Stem Segment | HA1 Intermediate Segment | HA1 C-terminal Stem Segment | HA2 Domain |
|---|---|---|---|---|
| Cys94-Cys143 Cys178-Cys272 | DRICTGITSSNS PHVVKTATQGE VNVTGVIPLTTT PTKSHFANLKG TQTRGKLCPNC LNCTDLDVALG RPKCMGTIPSA KASILHEVKPV TSGC [SEQ ID NO: 555] | CPNVTNGNGF FATMAWAVP KNKTATNPLT VEVPYIC [SEQ ID NO: 556] | CASGRSKVIKG SLPLIGEADCLH EKYGGLNKSKP YYTGEHAKAIG NCPIWVKTPLK LANGTKYRPPA KLLK [SEQ ID NO: 557] | GFFGAIAGFL EGGWEGMIA GWHGYTSHG AHGVAVAAD LKSTQEAINK ITKNLNSLSE LEVKNLQRLS GAMDELHNE ILELDEKVDD LRADTISSQIE LAVLLSNEGII NSEDEHLLAL ERKLKKMLG PSAVEIGNGC FETKHKCNQ TCLDRIAAGT FDAGEFSLPT FDSLNITAAS LNDDGLDNH TILLYYSTAA SSLAVTLMIA IFVVYMVSR DNVSCSICL [SEQ ID NO: 160] |

In some embodiments, the influenza hemagglutinin stem domain polypeptide is a hybrid polypeptide that comprises or consists essentially of segments and/or domains from a plurality of influenza strains or subtypes. For example, an influenza hemagglutinin stem domain polypeptide might comprise HA1 N-terminal and HA1 C-terminal stem segments from different influenza A virus HA subtypes. In some embodiments, the HA1 N-terminal stem segment is from influenza A virus while the HA1 C-terminal stem segment is from influenza B virus. Similarly, HA2 may also be from influenza A virus while the HA1 N-terminal and/or C-terminal stem segment is from influenza B virus.

It will be understood that any combination of the sequence elements listed in Tables 1-4 or the variants thereof may be used to form the hemagglutinin HA stem domain polypeptides of the present invention.

In an influenza stem domain polypeptide provided herein, a linker covalently connects the HA1 N-terminal stem segment to the HA1 C-terminal stem segment. In certain embodiments, the linker is a direct bond. In certain embodiments, the linker is a peptide that comprises one amino acid residue, two or fewer amino acid residues, three or fewer amino acid residues, four or fewer amino acid residues, five or fewer amino acid residues, ten or fewer amino acid residues, 15 or fewer amino acid residues, 20 or fewer amino acid residues, 30 or fewer amino acid residues, 40 or fewer amino acid residues, or 50 or fewer amino acid residues. In certain embodiments, the linker peptide comprises 50 or more amino acid residues. In certain embodiments the linker substantially lacks a globular head domain. In other words, the linker comprises no more than 10, 9, 8, 7, 6, 5 or 4 contiguous, sequential amino acid residues from the amino acid sequence of an influenza globular head domain. In certain embodiments, the linker is other than Lys-Leu-Asn-Gly-Ser-Gly-Ile-Met-Lys-Thr-Glu-Gly-Thr-Leu-Glu-Asn (SEQ ID NO:542). In certain embodiments, the linker is other than Asn-Asn-Ile-Asp-Thr or Lys-Leu-Asn-Gly-Ser-Gly-Ile-Met-Lys-Thr-Glu-Gly-Thr-Leu-Glu-Asn (SEQ ID NO:543). In certain embodiments, the linker is other than Asn-Asn-Ile-Asp-Thr (SEQ ID NO:546).

In certain embodiments, the linker is covalently connected, at one end, to the C-terminus of the HA1 N-terminal stem segment. The linker peptide is also covalently connected, at the other end, to the N-terminus of the HA1 C-terminal stem segment. In certain embodiments, one of the covalent links is an amide bond. In certain embodiments, both covalent links are amide bonds.

The linker might be any linker deemed suitable by one of skill in the art. In certain embodiments, the linker is selected based on the HA1 N-terminal stem segment and the HA1 C-terminal stem segment. In these embodiments, the linker might be selected with molecular modeling programs such as InsightII and Quanta, both from Accelrys. In certain embodiments, the linker is a structural motif that allows structural alignment of the HA1 N-terminal stem segment and the HA1 C-terminal stem segment that is consistent with the structure of a hemagglutinin stem domain as recognized by those of skill in the art. In certain embodiments, the linker is selected from a library of candidate linkers. In certain embodiments, the library includes three dimensional polypeptide structures in a publicly available database such as the Protein Data Bank (PDB) or the Macromolecular Structure Database at the European Molecular Biology Laboratory (EMBL) or European Bioinformatics Institute (EBI). In certain embodiments, the library includes proprietary three-dimensional polypeptide structures associated with commercial programs such as InsightII and Quanta, both from Accelrys. Additionally, any databases or collections of protein structures or structural elements can be used to select the linker. Exemplary database or collections of protein structural elements include but are not limited to the Structural Classification of Proteins (SCOP, maintained by and available through Cambridge University); the database of protein families (Pfam, maintained by and available through the Wellcome Trust Sanger Institute); the Universal Protein Resource (UniProt, maintained by and available through the UniProt Consortium); the Integrated resource for protein families (InterPro; maintained by and available through EMBL-EBI); the Class Architecture Topology Homologous superfamily (CATH, maintained by and available through Institute of Structural and Molecular Biology at the University College London); and the families of structurally similar proteins (FSSP, maintained by and available through EBI). Any algorithm deemed suitable by one of skill in the art may be used to select the linker, including but not limited by those used by SCOP, CATH and FSSP. Useful examples include but are not limited to Pymol (Delano Scientific LLC), InsightII and Quanta (both from Accelrys), MIDAS (University of California, San Francisco), SwissPDB viewer (Swiss Institute of Bioinformatics), TOPOFIT (Northeastern University), CBSU LOOPP (Cornell University), and SuperPose (University of Alberta, Edmonton).

In certain embodiments, the linker is a direct bond. In certain embodiments, the linker is selected from the group consisting of Gly, Gly-Gly, Gly-Gly-Gly, Gly-Gly-Gly-Gly (SEQ ID NO:560) and Gly-Gly-Gly-Gly-Gly (SEQ ID NO:561). In certain embodiments, the linker is selected from the group consisting of Gly-Pro and Pro-Gly. In certain embodiments, the linker is a 281 turn loop, e.g. having the sequence ITPNGSIPNDKPFQNVNKITYGA (SEQ ID NO:165).

In certain embodiments the linker comprises a glycosylation sequence. In certain embodiments, the linker comprises an amino acid sequence according to Asn-Xaa-Ser/Thr where Xaa is any amino acid other than proline and Ser/Thr is serine or threonine. In certain embodiments, the linker comprises the amino acid sequence Asn-Ala-Ser. In certain embodiments the linker is a glycosylation sequence. In certain embodiments, the linker is an amino acid sequence according to Asn-Xaa-Ser/Thr where Xaa is any amino acid other than proline and Ser/Thr is serine or threonine. In certain embodiments, the linker is the amino acid sequence Asn-Ala-Ser.

In certain embodiments, influenza hemagglutinin stem domain polypeptides are capable of forming a three dimensional structure that is similar to the three dimensional structure of the stem domain of a native influenza hemagglutinin. Structural similarity might be evaluated based on any technique deemed suitable by those of skill in the art. For instance, reaction, e.g. under non-denaturing conditions, of an influenza hemagglutinin stem domain polypeptide with a neutralizing antibody or antiserum that recognizes a native influenza hemagglutinin might indicate structural similarity. Useful neutralizing antibodies or antisera are described in, e.g. Sui, et al., 2009, *Nat. Struct. Mol. Biol.* 16(3):265-273, Ekiert et al., Feb. 26, 2009, *Science* [DOI: 10.1126/science.1171491], and Kashyap et al., 2008, *Proc. Natl. Acad. Sci. USA* 105(16):5986-5991, the contents of which are hereby incorporated by reference in their entireties. In certain embodiments, the antibody or antiserum is an antibody or antiserum that reacts with a non-contiguous epitope (i.e., not contiguous in primary sequence) that is formed by the tertiary or quaternary structure of a hemagglutinin.

In certain embodiments, structural similarity might be assessed by spectroscopic techniques such as circular dichroism, Raman spectroscopy, NMR, 3D NMR and X-ray crystallography. Known influenza hemagglutinin structures determined by X-ray crystallography are described in structural coordinates in Protein Data Bank files including but not limited to 1HGJ (an HA H3N2 strain) and 1RUZ (an HA H1N1 strain).

In certain embodiments, structural similarity is evaluated by RMS deviation between corresponding superimposed portions of two structures. In order to create a meaningful superimposition, in certain embodiments the coordinates of at least 20 corresponding atoms, 25 corresponding atoms, 30 corresponding atoms, 40 corresponding atoms, 50 corresponding atoms, 60 corresponding atoms, 70 corresponding atoms, 80 corresponding atoms, 90 corresponding atoms, 100 corresponding atoms, 120 corresponding atoms, 150 corresponding atoms, 200 corresponding atoms, or 250 corresponding atoms are used to calculate an RMS deviation.

In certain embodiments, the coordinates of all corresponding atoms in amino acid backbones are used to calculate an RMS deviation. In certain embodiments, the coordinates of all corresponding alpha carbon-atoms in the amino acid backbones are used to calculate an RMS deviation. In certain embodiments, the coordinates of all corresponding identical residues, including side chains, are used to calculate an RMS deviation.

In certain embodiments, coordinates of all or a portion of the corresponding atoms in a HA1 N-terminal segment are used to calculate an RMS deviation. In certain embodiments, coordinates of all or a portion of the corresponding atoms in a HA1 C-terminal segment are used to calculate an RMS deviation. In certain embodiments, coordinates of all or a portion of the corresponding atoms in both a HA1 N-terminal segment and a C-terminal segment are used to calculate an RMS deviation. In certain embodiments, coordinates of all or a portion of corresponding atoms in HA2 domains are used to calculate an RMS deviation.

In certain embodiments, the RMS deviation between the structures of a influenza hemagglutinin stem domain polypeptide and corresponding portions of a known influenza A virus hemagglutinin stem domain (e.g., from 1HGJ or 1RUZ) is 5 Å or less, 4 Å or less, 3 Å or less, 2.5 Å or less, 2 Å or less, 1.5 Å or less, 1 Å or less, 0.75 Å or less, 0.5 Å or less, 0.3 Å or less, 0.2 Å or less, or 0.1 Å or less. Commercially available or open source software might be used to perform the structural superimpositions and/or RMS deviation calculations. Useful examples include but are not limited to Pymol (Delano Scientific LLC), InsightII and Quanta (both from Accelrys), MIDAS (University of California, San Francisco), SwissPDB viewer (Swiss Institute of Bioinformatics), TOPOFIT (Northeastern University), CBSU LOOPP (Cornell University), and SuperPose (University of Alberta, Edmonton).

In certain embodiments, any influenza hemagglutinin stem domain polypeptide provided herein can further comprise one or more polypeptide domains deemed suitable to those of skill in the art. Useful polypeptide domains include domains that facilitate purification, folding and cleavage of portions of a polypeptide. For example, a His tag (His-His-His-His-His-His, SEQ ID NO:166), FLAG epitope or other purification tag can facilitate purification of a polypeptide provided herein. A foldon, or trimerization, domain from bacteriophage T4 fibritin can facilitate trimerization of polypeptides provided herein. The foldon domain can have any foldon sequence known to those of skill in the art (see, e.g., Papanikolopoulou et al., 2004, *J. Biol. Chem.* 279(10):8991-8998, the contents of which are hereby incorporated by reference in their entirety. Examples include GSGYIPEAPRDGQAYVRKDGEWVLLSTFL (SEQ ID NO:167). A foldon domain can be useful to facilitate trimerization of soluble polypeptides provided herein. Cleavage sites can be used to facilitate cleavage of a portion of a polypeptide, for example cleavage of a purification tag or foldon domain or both. Useful cleavage sites include a thrombin cleavage site, for example one with the sequence LVPRGSP (SEQ ID NO:168).

In certain embodiments, provided are influenza hemagglutinin stem domain polypeptides comprising an elastase cleavage site. Those of skill in the art will recognize that the trypsin cleavage site at the linkage between HA1 and HA2 can be mutated to an elastase cleavage site by substituting valine for the arginine or lysine at the HA1-HA2 cleavage site in a hemagglutinin sequence (see, e.g., Stech et al., 2005, *Nature Med.* 11(6):683-689). Accordingly, provided herein are influenza hemagglutinin stem domain polypeptides having a valine substitution at the C-terminus of the C-terminal stem segment (i.e., the C-terminus of the HA1 domain). In particular embodiments, provided herein are influenza hemagglutinin stem domain polypeptides comprising any of SEQ ID NOS:50-65 or 158-159 wherein the C-terminal amino acid residue, e.g. arginine or lysine, of SEQ ID NOS:50-65 or 158-159 is substituted with a valine residue.

In certain embodiments, provided herein are influenza hemagglutinin stem domain polypeptides that are predicted to be resistant to protease cleavage at the junction between HA1 and HA2. Those of skill in the art should recognize that the Arg-Gly sequence spanning HA1 and HA2 is a recognition site for trypsin and is typically cleaved for hemagglutinin activiation. Since the stem domain polypeptides described herein need not be activated, provided herein are influenza hemagglutinin stem domain polypeptides that are predicted to be resistant to protease cleavage. In certain embodiments, provided is any influenza hemagglutinin stem domain polypeptide described herein wherein the protease site spanning HA1 and HA2 is mutated to a sequence that is resistant to protease cleavage. In certain embodiments, provided is any influenza hemagglutinin stem domain polypeptide described herein wherein the C-terminal residue of the HA1 C-terminal stem segment is any residue other than Lys or Arg. In certain embodiments, provided is any influenza hemagglutinin stem domain polypeptide described herein wherein the N-terminal residue of the HA2 domain is proline. In certain embodiments, provided is any influenza hemagglutinin stem domain polypeptide described herein wherein the C-terminal residue of the HA1 C-terminal stem segment is Ala and the N-terminal residue of the HA2 domain is also Ala.

In certain embodiments, provided herein are influenza hemagglutinin stem domain polypeptides consisting of an HA1 N-terminal stem segment covalently linked to a linker, in turn covalently linked to an HA1 C-terminal stem segment in binding association with an HA2 stem domain. In certain embodiments, provided herein are influenza hemagglutinin stem domain polypeptides consisting of an HA1 N-terminal stem segment covalently linked to a linker, in turn covalently linked to an HA1 C-terminal stem segment, in turn covalently linked to an HA2 stem domain. In certain embodiments, provided herein are influenza hemagglutinin stem domain polypeptides consisting of a signal peptide covalently linked to an HA1 N-terminal stem segment covalently linked to a linker, in turn covalently linked to an HA1 C-terminal stem segment, in turn covalently linked to an HA2 stem domain.

In certain embodiments, provided herein are influenza hemagglutinin stem domain polypeptides consisting of an HA1 N-terminal stem segment covalently linked to a linker, in turn covalently linked to an HA1 C-terminal stem segment in binding association with an HA2 stem domain that is covalently linked to an HA2 luminal domain. In certain embodiments, provided herein are influenza hemagglutinin stem domain polypeptides consisting of an HA1 N-terminal stem segment covalently linked to a linker, in turn covalently linked to an HA1 C-terminal stem segment, in turn covalently linked to an HA2 stem domain that is covalently linked to an HA2 luminal domain. In certain embodiments, provided herein are influenza hemagglutinin stem domain polypeptides consisting of a signal peptide covalently linked to an HA1 N-terminal stem segment covalently linked to a linker, in turn covalently linked to an HA1 C-terminal stem segment, in turn covalently linked to an HA2 stem domain that is covalently linked to an HA2 luminal domain.

In certain embodiments, provided herein are influenza hemagglutinin stem domain polypeptides consisting of an HA1 N-terminal stem segment covalently linked to a linker, in turn covalently linked to an HA1 C-terminal stem segment in binding association with an HA2 stem domain that is covalently linked to, in sequence, a thrombin cleavage site, a foldon domain and a His tag. In certain embodiments, provided herein are influenza hemagglutinin stem domain polypeptides consisting of an HA1 N-terminal stem segment covalently linked to a linker, in turn covalently linked to an HA1 C-terminal stem segment, in turn covalently linked to an HA2 stem domain that is covalently linked to, in sequence, a thrombin cleavage site, a foldon domain and a His tag. In certain embodiments, provided herein are influenza hemagglutinin stem domain polypeptides consisting of a signal peptide covalently linked to an HA1 N-terminal stem segment covalently linked to a linker, in turn covalently linked to an HA1 C-terminal stem segment, in turn covalently linked to an HA2 stem domain that is covalently linked to, in sequence, a thrombin cleavage site, a foldon domain and a His tag.

In certain embodiments, provided herein are influenza hemagglutinin stem domain polypeptides consisting of an HA1 N-terminal stem segment covalently linked to a linker, in turn covalently linked to an HA1 C-terminal stem segment in binding association with an HA2 stem domain that is covalently linked to an HA2 luminal domain that is covalently linked to, in sequence, a thrombin cleavage site, a foldon domain and a His tag. In certain embodiments, provided herein are influenza hemagglutinin stem domain polypeptides consisting of an HA1 N-terminal stem segment covalently linked to a linker, in turn covalently linked to an HA1 C-terminal stem segment, in turn covalently linked to an HA2 stem domain that is covalently linked to an HA2 luminal domain that is covalently linked to, in sequence, a thrombin cleavage site, a foldon domain and a His tag. In certain embodiments, provided herein are influenza hemagglutinin stem domain polypeptides consisting of a signal peptide covalently linked to an HA1 N-terminal stem segment covalently linked to a linker, in turn covalently linked to an HA1 C-terminal stem segment, in turn covalently linked to an HA2 stem domain that is covalently linked to an HA2 luminal domain that is covalently linked to, in sequence, a thrombin cleavage site, a foldon domain and a His tag.

In certain embodiments, provided herein are influenza hemagglutinin stem domain polypeptides consisting of an HA1 N-terminal stem segment covalently linked to a linker, in turn covalently linked to an HA1 C-terminal stem segment in binding association with an HA2 stem domain that is covalently linked to an HA2 luminal domain that is in turn covalently linked to an HA2 transmembrane domain. In certain embodiments, provided herein are influenza hemagglutinin stem domain polypeptides consisting of an HA1 N-terminal stem segment covalently linked to a linker, in turn covalently linked to an HA1 C-terminal stem segment, in turn covalently linked to an HA2 stem domain that is covalently linked to an HA2 luminal domain that is in turn covalently linked to an HA2 transmembrane domain. In certain embodiments, provided herein are influenza hemagglutinin stem domain polypeptides consisting of a signal peptide covalently linked to an HA1 N-terminal stem segment covalently linked to a linker, in turn covalently linked to an HA1 C-terminal stem segment, in turn covalently linked to an HA2 stem domain that is covalently linked to an HA2 luminal domain that is in turn covalently linked to an HA2 transmembrane domain.

In certain embodiments, provided herein are influenza hemagglutinin stem domain polypeptides consisting of an HA1 N-terminal stem segment covalently linked to a linker, in turn covalently linked to an HA1 C-terminal stem segment in binding association with an HA2 stem domain that is covalently linked to an HA2 luminal domain that is in turn covalently linked to an HA2 transmembrane domain that is in turn covalently linked to an HA2 cytoplasmic domain. In certain embodiments, provided herein are influenza hemagglutinin stem domain polypeptides consisting of an HA1 N-terminal stem segment covalently linked to a linker, in turn covalently linked to an HA1 C-terminal stem segment, in turn covalently linked to an HA2 stem domain that is covalently linked to an HA2 luminal domain that is in turn covalently linked to an HA2 transmembrane domain that is in turn covalently linked to an HA2 cytoplasmic domain. In certain embodiments, provided herein are influenza hemagglutinin stem domain polypeptides consisting of a signal peptide covalently linked to an HA1 N-terminal stem segment covalently linked to a linker, in turn covalently linked to an HA1 C-terminal stem segment, in turn covalently linked to an HA2 stem domain that is covalently linked to an HA2 luminal domain that is in turn covalently linked to an HA2 transmembrane domain that is in turn covalently linked to an HA2 cytoplasmic domain.

In certain embodiments, provided herein is an influenza hemagglutinin polypeptide having a sequence selected from the group consisting of:

```
(SEQ ID NO: 34)-LL-(SEQ ID NO: 50)-
(SEQ ID NO: 66),

(SEQ ID NO: 35)-LL-(SEQ ID NO: 51)-
(SEQ ID NO: 67),

(SEQ ID NO: 36)-LL-(SEQ ID NO: 52)-
(SEQ ID NO: 68),

(SEQ ID NO: 37)-LL-(SEQ ID NO: 53)-
(SEQ ID NO: 69),

(SEQ ID NO: 38)-LL-(SEQ ID NO: 54)-
(SEQ ID NO: 70),

(SEQ ID NO: 39)-LL-(SEQ ID NO: 55)-
(SEQ ID NO: 71),
```

-continued (SEQ ID NO: 40)-LL-(SEQ ID NO: 56)-
(SEQ ID NO: 72), (SEQ ID NO: 41)-LL-(SEQ ID NO: 57)-
(SEQ ID NO: 73), (SEQ ID NO: 42)-LL-(SEQ ID NO: 58)-
(SEQ ID NO: 74), (SEQ ID NO: 43)-LL-(SEQ ID NO: 59)-
(SEQ ID NO: 75), (SEQ ID NO: 44)-LL-(SEQ ID NO: 60)-
(SEQ ID NO: 76), (SEQ ID NO: 45)-LL-(SEQ ID NO: 61)-
(SEQ ID NO: 77), (SEQ ID NO: 46)-LL-(SEQ ID NO: 62)-
(SEQ ID NO: 78), (SEQ ID NO: 47)-LL-(SEQ ID NO: 63)-
(SEQ ID NO: 79), (SEQ ID NO: 48)-LL-(SEQ ID NO: 64)-
(SEQ ID NO: 80),
and (SEQ ID NO: 49)-LL-(SEQ ID NO: 65)-
(SEQ ID NO: 81), wherein each sequence above is linked to the adjacent sequence as described herein and wherein LL is a linker as described herein. In particular, the HA1 C-terminal segments can be covalently or non-covalently linked to the HA2 domains. In certain embodiments, LL is selected from the group consisting of a direct bond, Gly, Gly-Gly, Gly-Gly-Gly, Gly-Gly-Gly-Gly (SEQ ID NO:560), (Gly)n (wherein n indicates any number of Glycine residues so long as there is flexibility in the peptide linker; in certain embodiments, n is 2, 3, 4, 5, 6, or 7 Glycine residues), Gly-Pro, ITPNGSIPNDKPFQNVNKITYGA (SEQ ID NO:165) and Asn-Ala-Ser.

In certain embodiments, provided herein is an influenza hemagglutinin polypeptide having a sequence selected from the group consisting of:

(SEQ ID NO: 34)-LL-(SEQ ID NO: 50)-
(SEQ ID NO: 82), (SEQ ID NO: 35)-LL-(SEQ ID NO: 51)-
(SEQ ID NO: 83),

-continued (SEQ ID NO: 36)-LL-(SEQ ID NO: 52)-
(SEQ ID NO: 84), (SEQ ID NO: 37)-LL-(SEQ ID NO: 53)-
(SEQ ID NO: 85), (SEQ ID NO: 38)-LL-(SEQ ID NO: 54)-
(SEQ ID NO: 86), (SEQ ID NO: 39)-LL-(SEQ ID NO: 55)-
(SEQ ID NO: 87), (SEQ ID NO: 40)-LL-(SEQ ID NO: 56)-
(SEQ ID NO: 88), (SEQ ID NO: 41)-LL-(SEQ ID NO: 57)-
(SEQ ID NO: 89), (SEQ ID NO: 42)-LL-(SEQ ID NO: 58)-
(SEQ ID NO: 90), (SEQ ID NO: 43)-LL-(SEQ ID NO: 59)-
(SEQ ID NO: 91), (SEQ ID NO: 44)-LL-(SEQ ID NO: 60)-
(SEQ ID NO: 92), (SEQ ID NO: 45)-LL-(SEQ ID NO: 61)-
(SEQ ID NO: 93), (SEQ ID NO: 46)-LL-(SEQ ID NO: 62)-
(SEQ ID NO: 94), (SEQ ID NO: 47)-LL-(SEQ ID NO: 63)-
(SEQ ID NO: 95), (SEQ ID NO: 48)-LL-(SEQ ID NO: 64)-
(SEQ ID NO: 96),
and (SEQ ID NO: 49)-LL-(SEQ ID NO: 65)-
(SEQ ID NO: 97), wherein each sequence above is linked to the adjacent sequence as described herein and wherein LL is a linker as described herein. In particular, the HA1 C-terminal segments can be covalently or non-covalently linked to the HA2 domains. In certain embodiments, LL is selected from the group consisting of a direct bond, Gly, Gly-Gly, Gly-Gly-Gly, Gly-Gly-Gly-Gly (SEQ ID NO:560), (Gly)n, Gly-Pro, ITPNGSIPNDKPFQNVNKITYGA (SEQ ID NO:165) and Asn-Ala-Ser.

In certain embodiments, provided herein is an influenza hemagglutinin polypeptide having a sequence selected from the group consisting of:

(SEQ ID NO: 34)-LL-(SEQ ID NO: 50)-(SEQ ID NO: 82)-(SEQ ID NO: 98), (SEQ ID NO: 35)-LL-(SEQ ID NO: 51)-(SEQ ID NO: 83)-(SEQ ID NO: 99), (SEQ ID NO: 36)-LL-(SEQ ID NO: 52)-(SEQ ID NO: 84)-(SEQ ID NO: 100), (SEQ ID NO: 37)-LL-(SEQ ID NO: 53)-(SEQ ID NO: 85)-(SEQ ID NO: 101), (SEQ ID NO: 38)-LL-(SEQ ID NO: 54)-(SEQ ID NO: 86)-(SEQ ID NO: 102), (SEQ ID NO: 39)-LL-(SEQ ID NO: 55)-(SEQ ID NO: 87)-(SEQ ID NO: 103), (SEQ ID NO: 40)-LL-(SEQ ID NO: 56)-(SEQ ID NO: 88)-(SEQ ID NO: 104), (SEQ ID NO: 41)-LL-(SEQ ID NO: 57)-(SEQ ID NO: 89)-(SEQ ID NO: 105), (SEQ ID NO: 42)-LL-(SEQ ID NO: 58)-(SEQ ID NO: 90)-(SEQ ID NO: 106), (SEQ ID NO: 43)-LL-(SEQ ID NO: 59)-(SEQ ID NO: 91)-(SEQ ID NO: 107),

-continued (SEQ ID NO: 44)-LL-(SEQ ID NO: 60)-(SEQ ID NO: 92)-(SEQ ID NO: 108), (SEQ ID NO: 45)-LL-(SEQ ID NO: 61)-(SEQ ID NO: 93)-(SEQ ID NO: 109), (SEQ ID NO: 46)-LL-(SEQ ID NO: 62)-(SEQ ID NO: 94)-(SEQ ID NO: 110), (SEQ ID NO: 47)-LL-(SEQ ID NO: 63)-(SEQ ID NO: 95)-(SEQ ID NO: 111), (SEQ ID NO: 48)-LL-(SEQ ID NO: 64)-(SEQ ID NO: 96)-(SEQ ID NO: 112),
and (SEQ ID NO: 49)-LL-(SEQ ID NO: 65)-(SEQ ID NO: 97)-(SEQ ID NO: 113), wherein each sequence above is linked to the adjacent sequence as described herein and wherein LL is a linker as described herein. In particular, the HA1 C-terminal segments can be covalently or non-covalently linked to the HA2 domains. In certain embodiments, LL is selected from the group consisting of a direct bond, Gly, Gly-Gly, Gly-Gly-Gly, Gly-Gly-Gly-Gly (SEQ ID NO:560), (Gly)n, Gly-Pro, ITPNGSIPNDKPFQNVNKITYGA (SEQ ID NO:165) and Asn-Ala-Ser.

In certain embodiments, provided herein is an influenza hemagglutinin polypeptide having a sequence selected from the group consisting of:

(SEQ ID NO: 34)-LL-(SEQ ID NO: 50)-(SEQ ID NO: 82)-(SEQ ID NO: 168)-(SEQ ID NO: 167)-(SEQ ID NO: 166), (SEQ ID NO: 35)-LL-(SEQ ID NO: 51)-(SEQ ID NO: 83)-(SEQ ID NO: 168)-(SEQ ID NO: 167)-(SEQ ID NO: 166), (SEQ ID NO: 36)-LL-(SEQ ID NO: 52)-(SEQ ID NO: 84)-(SEQ ID NO: 168)-(SEQ ID NO: 167)-(SEQ ID NO: 166), (SEQ ID NO: 37)-LL-(SEQ ID NO: 53)-(SEQ ID NO: 85)-(SEQ ID NO: 168)-(SEQ ID NO: 167)-(SEQ ID NO: 166), (SEQ ID NO: 38)-LL-(SEQ ID NO: 54)-(SEQ ID NO: 86)-(SEQ ID NO: 168)-(SEQ ID NO: 167)-(SEQ ID NO: 166), (SEQ ID NO: 39)-LL-(SEQ ID NO: 55)-(SEQ ID NO: 87)-(SEQ ID NO: 168)-(SEQ ID NO: 167)-(SEQ ID NO: 166), (SEQ ID NO: 40)-LL-(SEQ ID NO: 56)-(SEQ ID NO: 88)-(SEQ ID NO: 168)-(SEQ ID NO: 167)-(SEQ ID NO: 166), (SEQ ID NO: 41)-LL-(SEQ ID NO: 57)-(SEQ ID NO: 89)-(SEQ ID NO: 168)-(SEQ ID NO: 167)-(SEQ ID NO: 166), (SEQ ID NO: 42)-LL-(SEQ ID NO: 58)-(SEQ ID NO: 90)-(SEQ ID NO: 168)-(SEQ ID NO: 167)-(SEQ ID NO: 166), (SEQ ID NO: 43)-LL-(SEQ ID NO: 59)-(SEQ ID NO: 91)-(SEQ ID NO: 168)-(SEQ ID NO: 167)-(SEQ ID NO: 166), (SEQ ID NO: 44)-LL-(SEQ ID NO: 60)-(SEQ ID NO: 92)-(SEQ ID NO: 168)-(SEQ ID NO: 167)-(SEQ ID NO: 166), (SEQ ID NO: 45)-LL-(SEQ ID NO: 61)-(SEQ ID NO: 93)-(SEQ ID NO: 168)-(SEQ ID NO: 167)-(SEQ ID NO: 166), (SEQ ID NO: 46)-LL-(SEQ ID NO: 62)-(SEQ ID NO: 94)-(SEQ ID NO: 168)-(SEQ ID NO: 167)-(SEQ ID NO: 166), (SEQ ID NO: 47)-LL-(SEQ ID NO: 63)-(SEQ ID NO: 95)-(SEQ ID NO: 168)-(SEQ ID NO: 167)-(SEQ ID NO: 166), (SEQ ID NO: 48)-LL-(SEQ ID NO: 64)-(SEQ ID NO: 96)-(SEQ ID NO: 168)-(SEQ ID NO: 167)-(SEQ ID NO: 166),
and (SEQ ID NO: 49)-LL-(SEQ ID NO: 65)-(SEQ ID NO: 97)-(SEQ ID NO: 168)-(SEQ ID

NO: 167)-(SEQ ID NO: 166), wherein each sequence above is linked to the adjacent sequence as described herein and wherein LL is a linker as described herein. In particular, the HA1 C-terminal segments can be covalently or non-covalently linked to the HA2 domains. In certain embodiments, LL is selected from the group consisting of a direct bond, Gly, Gly-Gly, Gly-Gly-Gly, Gly-Gly-Gly-Gly (SEQ ID NO:560), (Gly)n, Gly-Pro, ITPNGSIPNDKPFQNVNKITYGA (SEQ ID NO:165) and Asn-Ala-Ser.

In certain embodiments, provided herein is an influenza hemagglutinin polypeptide having a sequence selected from the group consisting of:

(SEQ ID NO: 34)-LL-(SEQ ID NO: 50)-(SEQ ID NO: 82)-(SEQ ID NO: 98)-(SEQ ID NO: 168)-(SEQ ID NO: 167)-(SEQ ID NO: 166), (SEQ ID NO: 35)-LL-(SEQ ID NO: 51)-(SEQ ID NO: 83)-(SEQ ID NO: 99)-(SEQ ID NO: 168)-(SEQ ID NO: 167)-(SEQ ID NO: 166), (SEQ ID NO: 36)-LL-(SEQ ID NO: 52)-(SEQ ID NO: 84)-(SEQ ID NO: 100)-(SEQ ID NO: 168)-(SEQ ID NO: 167)-(SEQ ID NO: 166), (SEQ ID NO: 37)-LL-(SEQ ID NO: 53)-(SEQ ID NO: 85)-(SEQ ID NO: 101)-(SEQ ID NO: 168)-(SEQ ID NO: 167)-(SEQ ID NO: 166), (SEQ ID NO: 38)-LL-(SEQ ID NO: 54)-(SEQ ID NO: 86)-(SEQ ID NO: 102)-(SEQ ID NO: 168)-(SEQ ID NO: 167)-(SEQ ID NO: 166), (SEQ ID NO: 39)-LL-(SEQ ID NO: 55)-(SEQ ID NO: 87)-(SEQ ID NO: 103)-(SEQ ID NO: 168)-(SEQ ID NO: 167)-(SEQ ID NO: 166), (SEQ ID NO: 40)-LL-(SEQ ID NO: 56)-(SEQ ID NO: 88)-(SEQ ID NO: 104)-(SEQ ID NO: 168)-(SEQ ID NO: 167)-(SEQ ID NO: 166), (SEQ ID NO: 41)-LL-(SEQ ID NO: 57)-(SEQ ID NO: 89)-(SEQ ID NO: 105)-(SEQ ID NO: 168)-(SEQ ID NO: 167)-(SEQ ID NO: 166), (SEQ ID NO: 42)-LL-(SEQ ID NO: 58)-(SEQ ID NO: 90)-(SEQ ID NO: 106)-(SEQ ID NO: 168)-(SEQ ID NO: 167)-(SEQ ID NO: 166), (SEQ ID NO: 43)-LL-(SEQ ID NO: 59)-(SEQ ID NO: 91)-(SEQ ID NO: 107)-(SEQ ID NO: 168)-(SEQ ID NO: 167)-(SEQ ID NO: 166), (SEQ ID NO: 44)-LL-(SEQ ID NO: 60)-(SEQ ID NO: 92)-(SEQ ID NO: 108)-(SEQ ID NO: 168)-(SEQ ID NO: 167)-(SEQ ID NO: 166), (SEQ ID NO: 45)-LL-(SEQ ID NO: 61)-(SEQ ID NO: 93)-(SEQ ID NO: 109)-(SEQ ID NO: 168)-(SEQ ID NO: 167)-(SEQ ID NO: 166), (SEQ ID NO: 46)-LL-(SEQ ID NO: 62)-(SEQ ID NO: 94)-(SEQ ID NO: 110)-(SEQ ID NO: 168)-(SEQ ID NO: 167)-(SEQ ID NO: 166), (SEQ ID NO: 47)-LL-(SEQ ID NO: 63)-(SEQ ID NO: 95)-(SEQ ID NO: 111)-(SEQ ID NO: 168)-(SEQ ID NO: 167)-(SEQ ID NO: 166), (SEQ ID NO: 48)-LL-(SEQ ID NO: 64)-(SEQ ID NO: 96)-(SEQ ID NO: 112)-(SEQ ID NO: 168)-(SEQ ID NO: 167)-(SEQ ID NO: 166),
and (SEQ ID NO: 49)-LL-(SEQ ID NO: 65)-(SEQ ID NO: 97)-(SEQ ID NO: 113)-(SEQ ID NO: 168)-(SEQ ID NO: 167)-(SEQ ID NO: 166), wherein each sequence above is linked to the adjacent sequence as described herein and wherein LL is a linker as described herein. In particular, the HA1 C-terminal segments can be covalently or non-covalently linked to the HA2 domains. In certain embodiments, LL is selected from the group consisting of a direct bond, Gly, Gly-Gly, Gly-Gly-Gly, Gly-Gly-Gly-Gly (SEQ ID NO: 560), (Gly)n, Gly-Pro, ITPNGSIPNDKPFQNVNKITYGA (SEQ ID NO:165) and Asn-Ala-Ser.

In certain embodiments, provided herein is an influenza hemagglutinin polypeptide having a sequence selected from the group consisting of:

(SEQ ID NO: 177)-LL-(SEQ ID NO: 226)-(SEQ ID NO: 66), (SEQ ID NO: 178)-LL-(SEQ ID NO: 227)-(SEQ ID NO: 66), (SEQ ID NO: 179)-LL-(SEQ ID NO: 228)-(SEQ ID NO: 66), (SEQ ID NO: 180)-LL-(SEQ ID NO: 229)-(SEQ ID NO: 67),

-continued (SEQ ID NO: 181)-LL-(SEQ ID NO: 230)-(SEQ ID NO: 67), (SEQ ID NO: 182)-LL-(SEQ ID NO: 231)-(SEQ ID NO: 67), (SEQ ID NO: 183)-LL-(SEQ ID NO: 232)-(SEQ ID NO: 68), (SEQ ID NO: 184)-LL-(SEQ ID NO: 233)-(SEQ ID NO: 68), (SEQ ID NO: 185)-LL-(SEQ ID NO: 234)-(SEQ ID NO: 68), -continued (SEQ ID NO: 186)-LL-(SEQ ID NO: 235)-(SEQ ID NO: 69), (SEQ ID NO: 187)-LL-(SEQ ID NO: 236)-(SEQ ID NO: 69), (SEQ ID NO: 188)-LL-(SEQ ID NO: 237)-(SEQ ID NO: 69), (SEQ ID NO: 189)-LL-(SEQ ID NO: 238)-(SEQ ID NO: 70), (SEQ ID NO: 190)-LL-(SEQ ID NO: 239)-(SEQ ID NO: 70), (SEQ ID NO: 191)-LL-(SEQ ID NO: 240)-(SEQ ID NO: 70), (SEQ ID NO: 192)-LL-(SEQ ID NO: 241)-(SEQ ID NO: 71), (SEQ ID NO: 193)-LL-(SEQ ID NO: 242)-(SEQ ID NO: 71), (SEQ ID NO: 194)-LL-(SEQ ID NO: 243)-(SEQ ID NO: 71), (SEQ ID NO: 195)-LL-(SEQ ID NO: 244)-(SEQ ID NO: 72), (SEQ ID NO: 196)-LL-(SEQ ID NO: 245)-(SEQ ID NO: 72), (SEQ ID NO: 197)-LL-(SEQ ID NO: 246)-(SEQ ID NO: 72), (SEQ ID NO: 198)-LL-(SEQ ID NO: 247)-(SEQ ID NO: 73), (SEQ ID NO: 199)-LL-(SEQ ID NO: 248)-(SEQ ID NO: 73), (SEQ ID NO: 200)-LL-(SEQ ID NO: 249)-(SEQ ID NO: 73), (SEQ ID NO: 201)-LL-(SEQ ID NO: 250)-(SEQ ID NO: 74), (SEQ ID NO: 202)-LL-(SEQ ID NO: 251)-(SEQ ID NO: 74), (SEQ ID NO: 203)-LL-(SEQ ID NO: 252)-(SEQ ID NO: 74), (SEQ ID NO: 204)-LL-(SEQ ID NO: 253)-(SEQ ID NO: 75), (SEQ ID NO: 205)-LL-(SEQ ID NO: 254)-(SEQ ID NO: 75), (SEQ ID NO: 206)-LL-(SEQ ID NO: 255)-(SEQ ID NO: 75), (SEQ ID NO: 207)-LL-(SEQ ID NO: 256)-(SEQ ID NO: 76), (SEQ ID NO: 208)-LL-(SEQ ID NO: 257)-(SEQ ID NO: 76), (SEQ ID NO: 209)-LL-(SEQ ID NO: 258)-(SEQ ID NO: 76), (SEQ ID NO: 210)-LL-(SEQ ID NO: 259)-(SEQ ID NO: 77), (SEQ ID NO: 211)-LL-(SEQ ID NO: 260)-(SEQ ID NO: 77), (SEQ ID NO: 212)-LL-(SEQ ID NO: 261)-(SEQ ID NO: 77), -continued (SEQ ID NO: 213)-LL-(SEQ ID NO: 262)-(SEQ ID NO: 78), (SEQ ID NO: 214)-LL-(SEQ ID NO: 263)-(SEQ ID NO: 78), (SEQ ID NO: 215)-LL-(SEQ ID NO: 264)-(SEQ ID NO: 78), (SEQ ID NO: 216)-LL-(SEQ ID NO: 265)-(SEQ ID NO: 79), (SEQ ID NO: 217)-LL-(SEQ ID NO: 266)-(SEQ ID NO: 79), (SEQ ID NO: 218)-LL-(SEQ ID NO: 267)-(SEQ ID NO: 79), (SEQ ID NO: 219)-LL-(SEQ ID NO: 268)-(SEQ ID NO: 80), (SEQ ID NO: 220)-LL-(SEQ ID NO: 269)-(SEQ ID NO: 80), (SEQ ID NO: 221)-LL-(SEQ ID NO: 270)-(SEQ ID NO: 80), (SEQ ID NO: 222)-LL-(SEQ ID NO: 271)-(SEQ ID NO: 81), (SEQ ID NO: 223)-LL-(SEQ ID NO: 272)-(SEQ ID NO: 81), (SEQ ID NO: 224)-LL-(SEQ ID NO: 273)-(SEQ ID NO: 81), (SEQ ID NO: 312)-LL-(SEQ ID NO: 313)-(SEQ ID NO: 66), (SEQ ID NO: 34)-LL-(SEQ ID NO: 314)-(SEQ ID NO: 66), (SEQ ID NO: 315)-LL-(SEQ ID NO: 316)-(SEQ ID NO: 66), (SEQ ID NO: 308)-LL-(SEQ ID NO: 52)-(SEQ ID NO: 68), (SEQ ID NO: 36)-LL-(SEQ ID NO: 309)-(SEQ ID NO: 68), and (SEQ ID NO: 310)-LL-(SEQ ID NO: 311)-(SEQ ID NO: 68), wherein each sequence above is linked to the adjacent sequence as described herein and wherein LL is a linker as described herein. In particular, the HA1 C-terminal segments can be covalently or non-covalently linked to the HA2 domains. In certain embodiments, LL is selected from the group consisting of a direct bond, Gly, Gly-Gly, Gly-Gly-Gly, Gly-Gly-Gly-Gly (SEQ ID NO: 560), (Gly)n, Gly-Pro, ITPNGSIPNDKPFQNVNKITYGA (SEQ ID NO:165) and Asn-Ala-Ser.

In certain embodiments, provided herein is an influenza hemagglutinin polypeptide having a sequence selected from the group consisting of:

(SEQ ID NO: 154)-LL-(SEQ ID NO: 158)-(SEQ ID NO: 160), (SEQ ID NO: 155)-LL-(SEQ ID NO: 159)-(SEQ ID NO: 160), (SEQ ID NO: 156)-LL-(SEQ ID NO: 158)-(SEQ ID NO: 160),

-continued (SEQ ID NO: 157)-LL-(SEQ ID NO: 158)-(SEQ ID NO: 160), (SEQ ID NO: 550)-LL-(SEQ ID NO: 553)-(SEQ ID NO: 160), (SEQ ID NO: 551)-LL-(SEQ ID NO: 554)-(SEQ ID NO: 160),
and (SEQ ID NO: 552)-LL-(SEQ ID NO: 555)-(SEQ ID NO: 160), wherein each sequence above is linked to the adjacent sequence as described herein and wherein LL is a linker as described herein. In particular, the HA1 C-terminal segments can be covalently or non-covalently linked to the HA2 domains. In certain embodiments, LL is selected from the group consisting of a direct bond, Gly, Gly-Gly, Gly-Gly-Gly, Gly-Gly-Gly-Gly (SEQ ID NO:560), (Gly)n, Gly-Pro, ITPNGSIPNDKPFQNVNKITYGA (SEQ ID NO:165) and Asn-Ala-Ser.

In certain embodiments, provided herein is an influenza hemagglutinin polypeptide having a sequence selected from the group consisting of:

(SEQ ID NO: 154)-LL-(SEQ ID NO: 158)-(SEQ ID NO: 161),

-continued (SEQ ID NO: 155)-LL-(SEQ ID NO: 159)-(SEQ ID NO: 161), (SEQ ID NO: 156)-LL-(SEQ ID NO: 158)-(SEQ ID NO: 161), (SEQ ID NO: 157)-LL-(SEQ ID NO: 158)-(SEQ ID NO: 161), (SEQ ID NO: 550)-LL-(SEQ ID NO: 553)-(SEQ ID NO: 161), -continued (SEQ ID NO: 551)-LL-(SEQ ID NO: 554)-(SEQ ID NO: 161), (SEQ ID NO: 552)-LL-(SEQ ID NO: 555)-(SEQ ID NO: 161),
and (SEQ ID NO: 555)-LL-(SEQ ID NO: 556)-LL-(SeQ ID NO: 557)-(SEQ ID NO: 161), wherein each sequence above is linked to the adjacent sequence as described herein and wherein LL is a linker as described herein. In particular, the HA1 C-terminal segments can be covalently or non-covalently linked to the HA2 domains. In certain embodiments, LL is selected from the group consisting of a direct bond, Gly, Gly-Gly, Gly-Gly-Gly, Gly-Gly-Gly-Gly (SEQ ID NO:560), (Gly)n, Gly-Pro, ITPNGSIPNDKPFQNVNKITYGA (SEQ ID NO:165) and Asn-Ala-Ser.

In certain embodiments, provided herein is an influenza hemagglutinin polypeptide having a sequence selected from the group consisting of:

(SEQ ID NO: 154)-LL-(SEQ ID NO: 158)-(SEQ ID NO: 161)-(SEQ ID NO: 162), (SEQ ID NO: 155)-LL-(SEQ ID NO: 159)-(SEQ ID NO: 161)-(SEQ ID NO: 162), (SEQ ID NO: 156)-LL-(SEQ ID NO: 158)-(SEQ ID NO: 161)-(SEQ ID NO: 162), (SEQ ID NO: 157)-LL-(SEQ ID NO: 158)-(SEQ ID NO: 161)-(SEQ ID NO: 162), (SEQ ID NO: 550)-LL-(SEQ ID NO: 553)-)-(SEQ ID NO: 161)-(SEQ ID NO: 162), (SEQ ID NO: 551)-LL-(SEQ ID NO: 554)-(SEQ ID NO: 161)-(SEQ ID NO: 162), (SEQ ID NO: 552)-LL-(SEQ ID NO: 555)-(SEQ ID NO: 161)-(SEQ ID NO: 162),
and (SEQ ID NO: 555)-LL-(SEQ ID NO: 556)-LL-(SeQ ID NO: 557)-(SEQ ID NO: 161)-(SEQ ID NO: 162), wherein each sequence above is linked to the adjacent sequence as described herein and wherein LL is a linker as described herein. In particular, the HA1 C-terminal segments can be covalently or non-covalently linked to the HA2 domains. In certain embodiments, LL is selected from the group consisting of a direct bond, Gly, Gly-Gly, Gly-Gly-Gly, Gly-Gly-Gly-Gly (SEQ ID NO: 560), (Gly)n, Gly-Pro, ITPNGSIPNDKPFQNVNKITYGA (SEQ ID NO:165) and Asn-Ala-Ser.

In certain embodiments, provided herein is an influenza hemagglutinin polypeptide having a sequence selected from the group consisting of:

(SEQ ID NO: 154)-LL-(SEQ ID NO: 158)-(SEQ ID NO: 161)-(SEQ ID NO: 168)-(SEQ ID NO: 167)-SEQ ID NO: 166), (SEQ ID NO: 155)-LL-(SEQ ID NO: 159)-(SEQ ID NO: 161)-(SEQ ID NO: 168)-(SEQ ID NO: 167)-SEQ ID NO: 166), (SEQ ID NO: 156)-LL-(SEQ ID NO: 158)-(SEQ ID NO: 161)-(SEQ ID NO: 168)-(SEQ

-continued (SEQ ID NO: 167)-SEQ ID NO: 166), (SEQ ID NO: 157)-LL-(SEQ ID NO: 159)-(SEQ ID NO: 161)-(SEQ ID NO: 168)-(SEQ ID NO: 167)-SEQ ID NO: 166), (SEQ ID NO: 550)-LL-(SEQ ID NO: 553)-)-(SEQ ID NO: 161)-(SEQ ID NO: 168)-(SEQ ID NO: 167)-SEQ ID NO: 166), (SEQ ID NO: 551)-LL-(SEQ ID NO: 554)-(SEQ ID NO: 161)-(SEQ ID NO: 168)-(SEQ ID NO: 167)-SEQ ID NO: 166), (SEQ ID NO: 552)-LL-(SEQ ID NO: 555)-(SEQ ID NO: 161)-(SEQ ID NO: 168)-(SEQ ID NO: 167)-SEQ ID NO: 166),
and (SEQ ID NO: 555)-LL-(SEQ ID NO: 556)-LL-(SeQ ID NO: 557)-)-(SEQ ID NO: 161)-(SEQ ID NO: 168)-(SEQ ID NO: 167)-SEQ ID NO: 166), wherein each sequence above is linked to the adjacent sequence as described herein and wherein LL is a linker as described herein. In particular, the HA1 C-terminal segments can be covalently or non-covalently linked to the HA2 domains. In certain embodiments, LL is selected from the group consisting of a direct bond, Gly, Gly-Gly, Gly-Gly-Gly, Gly-Gly-Gly-Gly (SEQ ID NO:560), (Gly)n, Gly-Pro, ITPNGSIPNDKPFQNVNKITYGA (SEQ ID NO:165) and Asn-Ala-Ser.

In certain embodiments, provided herein is an influenza hemagglutinin polypeptide having a sequence selected from the group consisting of:

(SEQ ID NO: 154)-LL-(SEQ ID NO: 158)-(SEQ ID NO: 161)-(SEQ ID NO: 162)-(SEQ ID NO: 168)-(SEQ ID NO: 167)-(SEQ ID NO: 166), (SEQ ID NO: 155)-LL-(SEQ ID NO: 159)-(SEQ ID NO: 161)-(SEQ ID NO: 162)-(SEQ ID NO: 168)-(SEQ ID NO: 167)-(SEQ ID NO: 166), (SEQ ID NO: 156)-LL-(SEQ ID NO: 158)-(SEQ ID NO: 161)-(SEQ ID NO: 162)-(SEQ ID NO: 168)-(SEQ ID NO: 167)-(SEQ ID NO: 166),
and (SEQ ID NO: 157)-LL-(SEQ ID NO: 159)-(SEQ ID NO: 161)-(SEQ ID NO: 162)-(SEQ ID NO: 168)-(SEQ ID NO: 167)-(SEQ ID NO: 166), (SEQ ID NO: 550)-LL-(SEQ ID NO: 553)-)-(SEQ ID NO: 161)-(SEQ ID NO: 162)-(SEQ ID NO: 168)-(SEQ ID NO: 167)-(SEQ ID NO: 166), (SEQ ID NO: 551)-LL-(SEQ ID NO: 554)-(SEQ ID NO: 161)-\(SEQ ID NO: 162)-(SEQ ID NO: 168)-(SEQ ID NO: 167)-(SEQ ID NO: 166), (SEQ ID NO: 552)-LL-(SEQ ID NO: 555)-)-(SEQ ID NO: 161)-(SEQ ID NO: 162)-(SEQ ID NO: 168)-(SEQ ID NO: 167)-(SEQ ID NO: 166),
and (SEQ ID NO: 555)-LL-(SEQ ID NO: 556)-LL-(SEQ ID NO: 557)-(SEQ ID NO: 161)-(SEQ ID NO: 162)-(SEQ ID NO: 168)-(SEQ ID NO: 167)-(SEQ ID NO: 166), wherein each sequence above is linked to the adjacent sequence as described herein and wherein LL is a linker as described herein. In particular, the HA1 C-terminal segments can be covalently or non-covalently linked to the HA2 domains. In certain embodiments, LL is selected from the group consisting of a direct bond, Gly, Gly-Gly, Gly-Gly-Gly, Gly-Gly-Gly-Gly (SEQ ID NO: 560), (Gly)n, Gly-Pro, ITPNGSIPNDKPFQNVNKITYGA (SEQ ID NO:165) and Asn-Ala-Ser.

In certain embodiments, the influenza hemagglutinin polypeptides described herein do not comprise polypeptides having the amino acid sequence of either Thr-Gly-Leu-Arg-Asn (SEQ ID NO:544) or Gly-Ile-Thr-Asn-Lys-Val-Asn-Ser-Val-Ile-Glu-Lys (SEQ ID NO:545). In certain embodiments, the influenza hemagglutinin polypeptides described herein do not comprise polypeptides having the amino acid sequence of Thr-Gly-Leu-Arg-Asn (SEQ ID NO:544) and Gly-Ile-Thr-Asn-Lys-Val-Asn-Ser-Val-Ile-Glu-Lys (SEQ ID NO:545). In certain embodiments, the influenza hemagglutinin polypeptides described herein do not comprise polypeptides having the amino acid sequence of either Thr-Gly-Met-Arg-Asn (SEQ ID NO:547) or Gln-Ile-Asn-Gly-Lys-Leu-Asn-Arg-Leu-Ile-Glu-Lys (SEQ ID NO:548). In certain embodiments, the influenza hemagglutinin polypeptides described herein do not comprise polypeptides having the amino acid sequence of Thr-Gly-Met-Arg-Asn (SEQ ID NO:547) and Gln-Ile-Asn-Gly-Lys-Leu-Asn-Arg-Leu-Ile-Glu-Lys (SEQ ID NO:548). In certain embodiments, the influenza hemagglutinin polypeptides described herein do not comprise polypeptides having the amino acid sequence of either Thr-Gly-Met-Arg-Asn (SEQ ID NO:547) or Gln-Ile-Asn-Gly-Lys-Leu-Asn-Arg-Val-Ile-Glu-Lys (SEQ ID NO:549). In certain embodiments, the influenza hemagglutinin polypeptides described herein do not comprise polypeptides having the amino acid sequence of Thr-Gly-Met-Arg-Asn (SEQ ID NO:547) and Gln-Ile-Asn-Gly-Lys-Leu-Asn-Arg-Val-Ile-Glu-Lys (SEQ ID NO:549).

In certain embodiments, the influenza hemagglutinin polypeptides described herein are not recognized by the antibody C179 (produced by hybridoma FERM BP-4517; clones sold by Takara Bio, Inc. (Otsu, Shiga, Japan)) or by the antibody AI3C (FERM BP-4516).

5.1.1 Influenza Hemagglutinin Short Stem Domain Polypeptides

In certain embodiments, the influenza hemagglutinin stem domain polypeptide is an influenza hemagglutinin short stem domain polypeptide. The typical primary structure of an influenza hemagglutinin short stem domain polypeptide provided herein comprises, in the following order: an HA1 N-terminal stem segment, a linker, an HA1 C-terminal short stem segment and an HA2. The primary sequence can be formed by a single polypeptide, or it can be formed by multiple polypeptides. Typically, a single polypeptide is expressed by any technique deemed suitable by one of skill in the art. In single polypeptide embodiments, the HA1 segments and the HA2 are in tertiary association. As is known to those of skill in the art, a single HA polypeptide can be cleaved, for example by a protease, under appropriate expression conditions to yield two polypeptides in quaternary association. The cleavage is typically between the HA1 C-terminal short stem segment and the HA2. In certain embodiments, provided herein are multiple polypeptides. In multiple polypeptide embodiments, the HA1 segments and HA2 are in quaternary association.

In certain embodiments, an influenza hemagglutinin short stem domain polypeptide provided herein is monomeric. In certain embodiments, an influenza hemagglutinin short stem domain polypeptide provided herein is multimeric. In certain embodiments, an influenza hemagglutinin short stem domain polypeptide provided herein is trimeric. Those of skill in the art will recognize that native influenza hemagglutinin polypeptides are capable of trimerization in vivo and that certain influenza hemagglutinin short stem domain polypeptides provided herein are capable of trimerization. In particular embodiments described below, influenza hemagglutinin short stem domain polypeptides provided herein comprise trimerization domains to facilitate trimerization.

In certain embodiments, an influenza hemagglutinin short stem domain polypeptide comprises a signal peptide. Typically, the signal peptide is cleaved during or after polypeptide expression and translation to yield a mature influenza hemagglutinin short stem domain polypeptide. The signal peptide can be advantageous for expression of the influenza hemagglutinin short stem domain polypeptides. In certain embodiments, also provided herein are mature influenza hemagglutinin short stem domain polypeptides that lack a signal peptide.

Influenza hemagglutinin HA2 typically comprises a stem domain, transmembrane domain and a cytoplasmic domain. In certain embodiments, provided herein are influenza hemagglutinin short stem domain polypeptides that comprise an HA2 stem domain, an HA2 luminal domain, an HA2 transmembrane domain and an HA2 cytoplasmic domain. In certain embodiments, provided herein are influenza hemagglutinin short stem domain polypeptides that comprise an HA2 stem domain, an HA2 luminal domain, and an HA2 transmembrane domain but lack some or all of the typical cytoplasmic domain. In certain embodiments, provided herein are influenza hemagglutinin short stem domain polypeptides that comprise an HA2 stem domain and an HA2 luminal domain but lack both an HA2 transmembrane domain and an HA2 cytoplasmic domain. In certain embodiments, provided herein are influenza hemagglutinin short stem domain polypeptides that comprise an HA2 stem domain but lack an HA2 luminal domain, an HA2 transmembrane domain and an HA2 cytoplasmic domain. In certain embodiments, the influenza hemagglutinin short stem domain polypeptides comprise an HA2 stem domain having at least 70%, 75%, 80%, 85%, 90%, 95%, 96% or 98% amino acid sequence identity to an influenza HA2 stem domain known to those of skill in the art. Exemplary known HA2 stem domains from known influenza A and influenza B hemagglutinins are provided in the tables above.

Also provided herein are influenza hemagglutinin short stem domain polypeptides comprising deleted forms of HA2 stem domains wherein up to 10, 9, 8, 7, 6, 5, 4, 3, 2 or 1 amino acid residues are deleted from either or both termini of the HA2 stem domain. Further provided herein are influenza hemagglutinin short stem domain polypeptides comprising altered forms of HA2 stem domains wherein up to 10, 9, 8, 7, 6, 5, 4, 3, 2 or 1 amino acid residues are conservatively substituted with other amino acids. Further provided are influenza hemagglutinin short stem domain polypeptides comprising deleted and altered HA2 stem domains.

The HA1 N-terminal stem segment can be any HA1 N-terminal stem provided herein. Exemplary known HA1 N-terminal stem segments are provided in the tables below.

The HA1 C-terminal short stem segment can be any HA1 C-terminal short stem segment recognized by one of skill in the art based on the definition provided herein. Typically, an HA1 C-terminal short stem segment corresponds to a polypeptide consisting of the cysteine residue located in sequence at approximately the $305^{th}$ residue of an HA1 (using H3 numbering) through the C-terminal amino acid of the HA1. This cysteine residue, termed $B_q$ herein, is capable of being linked to a cysteine residue $A_p$ in the N-terminal stem segment of HA1. Sequences of 16 representative influenza A hemagglutinins are presented in FIG. 1, and residue $B_q$ is identified in each.

In certain embodiments, the HA1 C-terminal short stem segment does not start at $B_q$ (e.g., $Cys_{305}$ of an HA1 subunit from an H3 hemagglutinin), but at a residue in sequence and structure vicinity to $B_q$. For example, in certain embodiments, the HA1 C-terminal short stem segment starts at $B_{q-1}$, $B_{q-2}$, $B_{q-3}$, or $B_{q-4}$. In other embodiments, the HA1 C-terminal short stem segment starts at $B_{q+1}$, $B_{q+2}$, $B_{q+3}$, $B_{q+4}$ or $B_{q+5}$. The end of an HA1 N-terminal stem segment should be selected in conjunction with the start of the HA1 C-terminal short stem segment and the linker so that the resulting HA1 stem domain is capable of forming a three-dimensional structure similar, as described below, to an influenza hemagglutinin.

In certain embodiments, the influenza hemagglutinin short stem domain polypeptides comprise an HA1 C-terminal short stem segment having at least 70%, 75%, 80%, 85%, 90%, 95%, 96% or 98% amino acid sequence identity to an influenza HA1 C-terminal short stem segment known to those of skill in the art. Exemplary known HA1 C-terminal short stem segments are provided in the tables below.

In certain embodiments, the end of the N-terminal stem segment is $A_{p-1}$, and the start of the C-terminal short stem segment is $B_{q-1}$ In certain embodiments, the end of the N-terminal stem segment is $A_{p-2}$, and the start of the C-terminal short stem segment is $B_{q-2}$. In certain embodiments, the end of the N-terminal stem segment is $A_{p-3}$, and the start of the C-terminal short stem segment is $B_{q-3}$ In certain embodiments, the end of the N-terminal stem segment is $A_{p-4}$, and the start of the C-terminal short stem segment is $B_{q-4}$. In certain embodiments, the end of the N-terminal stem segment is $A_{p-5}$, and the start of the C-terminal short stem segment is $B_{q-5}$.

In certain embodiments, the end of the N-terminal stem segment is $A_{p+1}$, and the start of the C-terminal short stem segment is $B_{q+1}$. In certain embodiments, the end of the N-terminal stem segment is $A_{p+2}$, and the start of the C-terminal short stem segment is $B_{q+2}$ In certain embodiments, the end of the N-terminal stem segment is $A_{p+3}$, and the start of the C-terminal short stem segment is $B_{q+3}$ In certain embodiments, the end of the N-terminal stem segment is $A_{p+4}$, and the start of the C-terminal short stem segment is $B_{q+4.}$ In certain embodiments, the end of the N-terminal stem segment is $A_{p+5}$, and the start of the C-terminal short stem segment is $B_{q+5}$.

In certain embodiments, the end of the N-terminal stem segment is $A_{p-1}$, and the start of the C-terminal short stem segment is $B_{q+1}$. In certain embodiments, the end of the N-terminal stem segment is $A_{p-2}$, and the start of the C-terminal short stem segment is $B_{q+2}$ In certain embodiments, the end of the N-terminal stem segment is $A_{p-3}$, and the start of the C-terminal short stem segment is $B_{q+3}$ In certain embodiments, the end of the N-terminal stem segment is $A_{p-4}$, and the start of the C-terminal short stem segment is $B_{q+4.}$ In certain embodiments, the end of the N-terminal stem segment is $A_{p-5}$, and the start of the C-terminal short stem segment is $B_{q+5}$.

In certain embodiments, the end of the N-terminal stem segment is $A_p$ (i.e., the end of the N-terminal stem segment is Cysteine), and the start of the C-terminal stem segment is $A_q$ (i.e., the start of the C-terminal stem segment is Cysteine) In certain embodiments, the end of the N-terminal stem segment is $A_{p+1}$, and the start of the C-terminal short stem segment is $B_{q-1}$. In certain embodiments, the end of the N-terminal stem segment is $A_{p+2}$, and the start of the C-terminal short stem segment is $B_{q-2}$ In certain embodiments, the end of the N-terminal stem segment is $A_{p+3}$, and the start of the C-terminal short stem segment is $B_{q-3}$ In certain embodiments, the end of the N-terminal stem segment is $A_{p+4}$, and the start of the C-terminal short stem segment is $B_{q-4}$ In certain embodiments, the end of the N-terminal stem segment is $A_{p+5}$, and the start of the C-terminal short stem segment is $B_{q-5}$.

Also provided herein are influenza hemagglutinin short stem domain polypeptides comprising deleted forms of HA1 C-terminal short stem segments wherein up to 10, 9, 8, 7, 6, 5, 4, 3, 2 or 1 amino acid residues are deleted from either or both termini of the HA1 C-terminal short stem segment. In certain embodiments, provided herein are influenza hemagglutinin short stem domain polypeptides that comprise expanded forms of HA1 C-terminal short stem segments wherein 1, 2 or 3 residues are added to the N-terminus of the HA1 C-terminal short stem segments. In particular embodiments, if one residue is added to the C-terminal short stem segment, then one residue is added to the N-terminal stem segment; if two residues are added to the C-terminal short stem segment, then two residues are added to the N-terminal stem segment; if three residues are added to the C-terminal short stem segment, then three residues are added to the N-terminal stem segment. Further provided herein are influenza hemagglutinin short stem domain polypeptides comprising altered forms of HA1 C-terminal short stem segments wherein up to 10, 9, 8, 7, 6, 5, 4, 3, 2 or 1 amino acid residues are conservatively substituted with other amino acids. Further provided are influenza hemagglutinin short stem domain polypeptides comprising deleted and altered HA1 C-terminal short stem segments.

The influenza hemagglutinin short stem domain polypeptides can be based on (i.e. can have sequence identity, as described above) any influenza hemagglutinin known to those of skill or later discovered. In certain embodiments, influenza hemagglutinin short stem domain polypeptides are based on an influenza A hemagglutinin. In certain embodiments, the influenza hemagglutinin short stem domain polypeptides are based on an influenza A hemagglutinin selected from the group consisting of H1, H2, H3, H4, H5, H6, H7, H8, H9, H10, H11, H12, H13, H14, H15 and H16. In certain embodiments, influenza hemagglutinin short stem domain polypeptides are based on an influenza B hemagglutinin, as described in detail below.

The HA1 N-terminal stem segments can be based on (i.e. can have sequence identity, as described above) any HA1 N-terminal stem segments known to those of skill or later discovered. In certain embodiments, the HA1 N-terminal stem segments are based on influenza A HA1 N-terminal stem segments. In certain embodiments, the HA1 N-terminal stem segments are based on an influenza A hemagglutinin selected from the group consisting of H1, H2, H3, H4, H5, H6, H7, H8, H9, H10, H11, H12, H13, H14, H15 and H16. In certain embodiments, the HA1 N-terminal stem segment is selected from SEQ ID NOS:34-49. In certain embodiments, the HA1 N-terminal stem segment is selected from SEQ ID NOS:34-49, each having one amino acid deleted from its C-terminus. In certain embodiments, the HA1 N-terminal stem segment is selected from SEQ ID NOS: 34-49, each having two amino acids deleted from its C-terminus. In certain embodiments, the HA1 N-terminal stem segment is selected from SEQ ID NOS:34-49, each having three amino acids deleted from its C-terminus. In certain embodiments, the HA1 N-terminal stem segment is selected from SEQ ID NOS:34-49, each having four amino acids deleted from its C-terminus. In certain embodiments, the HA1 N-terminal stem segment is selected from SEQ ID NOS:34-49, each having five amino acids deleted from its C-terminus. In certain embodiments, the HA1 N-terminal stem segment is selected from SEQ ID NOS:177-224.

The HA1 C-terminal short stem segments can be based on (i.e. can have sequence identity, as described above) any HA1 C-terminal short stem segments known to those of skill or later discovered. In certain embodiments, the HA1 C-terminal short stem segments are based on influenza A HA1 C-terminal short stem segments. In certain embodiments, the HA1 C-terminal short stem segments are based on an influenza A hemagglutinin selected from the group consisting of H1, H2, H3, H4, H5, H6, H7, H8, H9, H10, H11, H12, H13, H14, H15 and H16. In certain embodiments, the HA1 C-terminal short stem segment is selected from SEQ ID NOS:350-365. In certain embodiments, the HA1 C-terminal short stem segment is selected from SEQ ID NOS:350-365, each having one amino acid deleted from its N-terminus. In certain embodiments, the HA1 C-terminal short stem segment is selected from SEQ ID NOS:350-365, each having two amino acids deleted from its N-terminus. In certain embodiments, the HA1 C-terminal short stem segment is selected from SEQ ID NOS:350-365, each having three amino acids deleted from its N-terminus. In certain embodiments, the HA1 C-terminal short stem segment is selected from SEQ ID NOS:350-365, each having four amino acids deleted from its N-terminus. In certain embodiments, the HA1 C-terminal short stem segment is selected from SEQ ID NOS: 350-365, each having five amino acids deleted from its N-terminus. In certain embodiments, the HA1 C-terminal short stem segment is selected from SEQ ID NOS:366-413.

The HA2 stem domains can be based on (i.e. can have sequence identity, as described above) any HA2 stem domains known to those of skill, later discovered or described herein. In certain embodiments, the HA2 stem domains are based on influenza A HA2 stem domains. In certain embodiments, the HA2 stem domains are based on an influenza A hemagglutinin selected from the group consisting of H1, H2, H3, H4, H5, H6, H7, H8, H9, H10, H11, H12, H13, H14, H15 and H16. In certain embodiments, the HA2 stem domain is selected from SEQ ID NOS:66-97.

In embodiments comprising a signal peptide, the signal peptide can be based on any influenza signal peptide known to those of skill in the art or described herein. In certain embodiments, the signal peptides are based on influenza A signal peptides.

In embodiments comprising a luminal domain, the luminal domain can be based on any influenza luminal domain known to those of skill in the art or described herein.

In embodiments comprising a transmembrane domain, the transmembrane domain can be based on any influenza transmembrane domain known to those of skill in the art or described herein.

In embodiments comprising a cytoplasmic domain, the cytoplasmic domain can be based on any influenza cytoplasmic domain known to those of skill in the art or described herein.

In certain embodiments, one or more of the glycosylation sites in the hemagglutinin short stem domain are altered or deleted such that glycosylation at these sites will not occur during processing and maturation of the polypeptide. Those of skill in the art will recognize that influenza HA typically comprises one or more glycosylation sequences (e.g. Asn-Xaa-Ser/Thr/Cys, wherein Xaa is any amino acid other than Pro). In certain embodiments, one or more amino acid residues in a glycosylation sequence is conservatively substituted with an amino acid residue that disrupts the glycosylation sequence. In certain embodiments, one or more amino acid residues in a glycosylation sequence is substituted with any amino acid residue that disrupts the glycosylation sequence. In certain embodiments, one or more asparagine residues in a glycosylation sequence is substituted with alanine. In a particular embodiment, the asparagine at position 38 of an H3 hemagglutinin is changed to an alanine.

Table 6, below, identifies signal peptides, HA1 N-terminal stem segments, HA1 C-terminal short stem segments and HA2 domains of influenza A hemagglutinin polypeptides. These signal peptides, stem segments and domains are useful in the polypeptides and methods described herein.

TABLE 6

Exemplary Influenza A Hemagglutinin Short Stem Domain Peptide Sequences

| HA Subtype (Genbank No.) | Signal Peptide | HA1 N-terminal Stem Segment | HA1 C-terminal Short Stem Segment | HA2 Domain |
|---|---|---|---|---|
| H1 PR8-H1N1 (EF467821.1) | MKAN LLVLL CALAA ADA [SEQ ID NO: 18] | DTICIGYHANN STDTVDTVLE KNVTVTHSVN LLEDSHNGKLC [SEQ ID NO: 34] | CPKYVRSAKL RMVTGLRNNP SIQSR [SEQ ID NO: 350] | GLFGAIAGFIEGGW TGMIDGWYGYHHQ NEQGSGYAADQKST QNAINGITNKVNTVI EKMNIQFTAVGKEF NKLEKRMENLNKK VDDGFLDIWTYNAE LLVLLENERTLDFH DSNVKNLYEKVKSQ LKNNAKEIGNGCFE FYHKCDNECMESVR NGTYDYPKYSEESK LNREKVDGVKLES MGIYQILAIYSTVAS SLVLLVSLGAISFW MCSNGSLQCRICI [SEQ ID NO: 66] |
| H2 (L11136) | MAIIY LILLFT AVRG [SEQ ID NO: 19] | DQICIGYHSNN STEKVDTILER NVTVTHAQNI LEKTHNGKLC [SEQ ID NO: 35] | CPKYVKSERL VLATGLRNVP QIESR [SEQ ID NO: 351] | GLFGAIAGFIEGGW QGMIDGWYGYHHS NDQGSGYAADKEST QKAIDGITNRVNSVI EKMNTQFEAVGKEF SNLEKRLENLNKKM EDGFLDVWTYNAE LLVLMENERTLDFH DSNVKNLYDRVRM QLRDNAKELGNGCF EFYHKCDDECMNS VKNGTYDYPKYEEE SKLNRNEIKGVKLS NMGVYQILAIYATV AGSLSLAIMIAGISL WMCSNGSLQCRICI [SEQ ID NO: 67] |
| H3 HK68-H3N2 (EF409245) PDB: 1HGJ | MKTII ALSYIF CLALG [SEQ ID NO: 20] | QDLPGNDNST ATLCLGHHAV PNGTLVKTITD DQIEVTNATEL VQSSSTGKIC [SEQ ID NO: 36] | CPKYVKQNTL KLATGMRNVP EKQTR [SEQ ID NO: 352] | GLFGAIAGFIENGW EGMIDGWYGFRHQ NSEGTGQAADLKST QAAIDQINGKLNRVI EKTNEKFHQIEKEFS EVEGRIQDLEKYVE DTKIDLWSYNAELL VALENQHTIDLTDS EMNKLFEKTRRQLR ENAEDMGNGCFKIY |

TABLE 6-continued

Exemplary Influenza A Hemagglutinin Short Stem Domain Peptide Sequences

| HA Subtype (Genbank No.) | Signal Peptide | HA1 N-terminal Stem Segment | HA1 C-terminal Short Stem Segment | HA2 Domain |
|---|---|---|---|---|
| | | | | HKCDNACIESIRNGTYDHDVYRDEALNNRFQIKGVELKSGYKDWILWISFAISCFLLCVVLLGFIMWACQRGNIRCNICI [SEQ ID NO: 68] |
| H4 (D90302) | MLSIVILFLLIAENSS [SEQ ID NO: 21] | QNYTGNPVICMGHHAVANGTMVKTLADDQVEVVTAQELVESQNLPELC [SEQ ID NO: 37] | CPRYVKQGSLKLATGMRNIPEKASR [SEQ ID NO: 353] | GLFGAIAGFIENGWQGLIDGWYGFRHQNAEGTGTAADLKSTQAAIDQINGKLNRLIEKTNDKYHQIEKEFEQVEGRIQDLENYVEDTKIDLWSYNAELLVALENQHTIDVTDSEMNKLFERVRRQLRENAEDKGNGCFEIFHKCDNNCIESIRNGTYDHDIYRDEAINNRFQIQGVKLTQGYKDIILWISFSISCFLLVALLLAFILWACQNGNIRCQICI [SEQ ID NO: 69] |
| H5 (X07826) | MERIVLLLAIVSLVKS [SEQ ID NO: 22] | DQICIGYHANKSTKQVDTIMEKNVTVTHAQDILERTHNGKLC [SEQ ID NO: 38] | CPKYVKSDRLVLATGLRNVPQRKKR [SEQ ID NO: 354] | GLFGAIAGFIEGGWQGMVDGWYGYHHSNEQGSGYAADKESTQKAIDGITNKVNSIIDKMNTRFEAVGKEFNNLERRVENLNKKMEDGFLDVWTYNVELLVLMENERTLDFHDSNVNNLYDKVRLQLKDNARELGNGCFEFYHKCDNECMESVRNGTYDYPQYSEEARLNREEISGVKLESMGVYQILSIYSTVASSLALAIMIAGLSFWMCSNGSLQCRICI [SEQ ID NO: 70] |
| H6 (D90303) | MIAIIVVAILATAGRS [SEQ ID NO: 23] | DKICIGYHANNSTTQIDTILEKNVTVTHSVELLENQKEERFC [SEQ ID NO: 39] | CPKYVKSESLRLATGLRNVPQIETR [SEQ ID NO: 355] | GLFGAIAGFIEGGWTGMIDGWYGYHHENSQGSGYAADRESTQKAVDGITNKVNSIIDKMNTQFEAVDHEFSNLERRIDNLNKRMEDGFLDVWTYNAELLVLLENERTLDLHDANVKNLYERVKSQLRDNAMILGNGCFEFWHKCDDECMESVKNGTYDYPKYQDESKLNRQEIESVKLESLGVYQILAIYSTVSSSLVLVGLIIAVGLWMCSNGSMQCRICI [SEQ ID NO: 71] |
| H7 (M24457) | MNTQILVFALVAVIPTNA [SEQ ID NO: 24] | DKICLGHHAVSNGTKVNTLTERGVEVVNATETVERTNIPKIC [SEQ ID NO: 40] | CPRYVKQESLLLATGMKNVPEPSKKRKKR [SEQ ID NO: 356] | GLFGAIAGFIENGWEGLVDGWYGFRHQNAQGEGTAADYKSTQSAIDQITGKLNRLIEKTNQQFELIDNEFTEVEKQIGNLINWTKDSITEVWSYNAELIVAMENQHTIDLADSEMNRLYERVRKQLRENAEEDGTGCFEIFHKCDDDCMASIRNN |

TABLE 6-continued

Exemplary Influenza A Hemagglutinin Short Stem Domain Peptide Sequences

| HA Subtype (Genbank No.) | Signal Peptide | HA1 N-terminal Stem Segment | HA1 C-terminal Short Stem Segment | HA2 Domain |
|---|---|---|---|---|
| | | | | TYDHSKYREEAMQ NRIQIDPVKLSSGYK DVILWFSFGASCFLL LAIAMGLVFICVKN GNMRCTICI [SEQ ID NO: 72] |
| H8 (D90304) | MEKFI AIATL ASTNAY [SEQ ID NO: 25] | DRICIGYQSNN STDTVNTLIEQ NVPVTQTMEL VETEKHPAYC [SEQ ID NO: 41] | CPKYVKKASL RLAVGLRNTP SVEPR [SEQ ID NO: 357] | GLFGAIAGFIEGGWS GMIDGWYGFHHSN SEGTGMAADQKST QEAIDKITNKVNNIV DKMNREFEVVNHEF SEVEKRINMINDKID DQIEDLWAYNAELL VLLENQKTLDEHDS NVKNLFDEVKRRLS ANAIDAGNGCFDIL HKCDNECMETIKNG TYDHKEYEEEAKLE RSKINGVKLEENTT YKILSIYSTVAASLC LAILIAGGLILGMQN GSCRCMFCI [SEQ ID NO: 73] |
| H9 (D90305) | METK AIIAAL LMVTA ANA [SEQ ID NO: 26] | DKICIGYQSTN STETVDTLTES NVPVTHTKEL LHTEHNGMLC [SEQ ID NO: 42] | CPKYVGVKSL KLPVGLRNVP AVSSR [SEQ ID NO: 358] | GLFGAIAGFIEGGWP GLVAGWYGFQHSN DQGVGMAADKGST QKAIDKITSKVNNII DKMNKQYEVIDHEF NELEARLNMINNKI DDQIQDIWAYNAEL LVLLENQKTLDEHD ANVNNLYNKVKRA LGSNAVEDGNGCFE LYHKCDDQCMETIR NGTYDRQKYQEESR LERQKIEGVKLESEG TYKILTIYSTVASSL VLAMGFAAFLFWA MSNGSCRCNICI [SEQ ID NO: 74] |
| H10 (M21647) | MYKV VVIIAL LGAVKG [SEQ ID NO: 27] | LDRICLGHHA VANGTIVKTL TNEQEEVTNA TETVESTNLN KLC [SEQ ID NO: 43] | CPKYVNQRSL LLATGMRNVP EVVQGR [SEQ ID NO: 359] | GLFGAIAGFIENGW EGMVDGWYGFRHQ NAQGTGQAADYKS TQAAIDQITGKLNRL IEKTNTEFESIESEFS ETEHQIGNVINWTK DSITDIWTYNAELLV AMENQHTIDMADSE MLNLYERVRKQLR QNAEEDGKGCFEIY HTCDDSCMESIRNN TYDHSQYREEALLN RLNINPVKLSSGYK DIILWFSFGESCFVL LAVVMGLVFFCLKN GNMRCTICI [SEQ ID NO: 75] |
| H11 (D90306) | MEKTL LFAAIF LCVKA [SEQ ID NO: 28] | DEICIGYLSNN STDKVDTIIEN NVTVTSSVEL VETEHTGSFC [SEQ ID NO: 44] | CPKYVNVKSL KLATGPRNVP AIASR [SEQ ID NO: 360] | GLFGAIAGFIEGGWP GLINGWYGFQHRDE EGTGIAADKESTQK AIDQITSKVNNIVDR MNTNFESVQHEFSEI EERINQLSKHVDDS VVDIWSYNAQLLVL LENEKTLDLHDSNV RNLHEKVRRMLKD NAKDEGNGCFTFYH KCDNKCIERVRNGT YDHKEFEEESKINR |

TABLE 6-continued

Exemplary Influenza A Hemagglutinin Short Stem Domain Peptide Sequences

| HA Subtype (Genbank No.) | Signal Peptide | HA1 N-terminal Stem Segment | HA1 C-terminal Short Stem Segment | HA2 Domain |
|---|---|---|---|---|
| | | | | QEIEGVKLDSSGNV YKILSIYSCIASSLVL AALIMGFMFWACS NGSCRCTICI [SEQ ID NO: 76] |
| H12 (D90307) | MEKFII LSTVL AASFAY [SEQ ID NO: 29] | DKICIGYQTNN STETVNTLSEQ NVPVTQVEEL VHRGIDPILC [SEQ ID NO: 45] | CPKYIPSGSLK LAIGLRNVPQ VQDR [SEQ ID NO: 361] | GLFGAIAGFIEGGWP GLVAGWYGFQHQN AEGTGIAADRDSTQ RAIDNMQNKLNNVI DKMNKQFEVVNHE FSEVESRINMINSKI DDQITDIWAYNAEL LVLLENQKTLDEHD ANVRNLHDRVRRV LRENAIDTGDGCFEI LHKCDNNCMDTIRN GTYNHKEYEEESKI ERQKVNGVKLEENS TYKILSIYSSVASSL VLLLMIIGGFIFGCQ NGNVRCTFCI [SEQ ID NO: 77] |
| H13 (D90308) | MALN VIATL TLISVC VHA [SEQ ID NO: 30] | DRICVGYLSTN SSERVDTLLEN GVPVTSSIDLIE TNHTGTYC [SEQ ID NO: 46] | CPKYIKSGQL KLATGLRNVP AISNR [SEQ ID NO: 362] | GLFGAIAGFIEGGWP GLINGWYGFQHQNE QGTGIAADKESTQK AIDQITTKINNIIDKM NGNYDSIRGEFNQV EKRINMLADRIDDA VTDIWSYNAKLLVL LENDKTLDMHDAN VKNLHEQVRRELKD NAIDEGNGCFELLH KCNDSCMETIRNGT YDHTEYAEESKLKR QEIDGIKLKSEDNVY KALSIYSCIASSVVL VGLILSFIMWACSSG NCRFNVCI [SEQ ID NO: 78] |
| H14 (M35997) | MIALIL VALAL SHTAYS [SEQ ID NO: 31] | QITNGTTGNPII CLGHHAVENG TSVKTLTDNH VEVVSAKELV ETNHTDELC [SEQ ID NO: 47] | CPKYVKQGSL MLATGMRNIP GKQAK [SEQ ID NO: 363] | GLFGAIAGFIENGW QGLIDGWYGFRHQ NAEGTGTAADLKST QAAIDQINGKLNRLI EKTNEKYHQIEKEF EQVEGRIQDLEKYV EDTKIDLWSYNAEL LVALENQHTIDVTD SEMNKLFERVRRQL RENAEDQGNGCFEI FHQCDNNCIESIRNG TYDHNIYRDEAINN RIKINPVTLTMGYK DIILWISFSMSCFVF VALILGFVLWACQN GNIRCQICI [SEQ ID NO: 79] |
| H15 (L43917) | MNTQI IVILVL GLSMV KS [SEQ ID NO: 32] | DKICLGHHAV ANGTKVNTLT ERGVEVVNAT ETVEITGIDKVC [SEQ ID NO: 48] | CPRYVKQSSL PLALGMKNVP EKIRTR [SEQ ID NO: 364] | GLFGAIAGFIENGW EGLIDGWYGFRHQN AQGQGTAADYKST QAAIDQITGKLNRLI EKTNKQFELIDNEFT EVEQQIGNVINWTR DSLTEIWSYNAELL VAMENQHTIDLADS EMNKLYERVRRQL RENAEEDGTGCFEIF HRCDDQCMESIRNN TYNHTEYRQEALQN RIMINPVKLSSGYKD |

TABLE 6-continued

Exemplary Influenza A Hemagglutinin Short Stem Domain Peptide Sequences

| HA Subtype (Genbank No.) | Signal Peptide | HA1 N-terminal Stem Segment | HA1 C-terminal Short Stem Segment | HA2 Domain |
|---|---|---|---|---|
| | | | | VILWFSFGASCVML LAIAMGLIFMCVKN GNLRCTICI [SEQ ID NO: 80] |
| H16 (EU293865) | MMIK VLYFLI IVLGR YSKA [SEQ ID NO: 33] | DKICIGYLSNN SSDTVDTLTEN GVPVTSSVDL VETNHTGTYC [SEQ ID NO: 49] | CPKYIKSGQL KLATGLRNVP SIGER [SEQ ID NO: 365] | GLFGAIAGFIEGGWP GLINGWYGFQHQNE QGTGIAADKASTQK AINEITTKINNIIEKM NGNYDSIRGEFNQV EKRINMLADRVDDA VTDIWSYNAKLLVL LENDRTLDLHDANV RNLHDQVKRALKS NAIDEGDGCFNLLH KCNDSCMETIRNGT YNHEDYREESQLKR QEIEGIKLKTEDNVY KVLSIYSCIASSIVLV GLILAFIMWACSNG SCRFNVCI [SEQ ID NO: 81] |

Table 6A, below, identifies useful HA1 N-terminal stem segments and HA1 C-terminal short stem segments for the polypeptides and methods described herein.

TABLE 6A

Exemplary Influenza A Hemagglutinin Short Stem Domain Peptide Sequences

| HA Subtype (Genbank No.) | HA1 N-terminal Stem Segment | HA1 C-terminal Stem Segment |
|---|---|---|
| H1 PR8-H1N1 (EF467821.1) No Cys | DTICIGYHANNSTDTVDT VLEKNVTVTHSVNLLED SHNGKL [SEQ ID NO: 177] | PKYVRSAKLRMVTGLRNNPSIQSR [SEQ ID NO: 366] |
| H1 PR8-H1N1 (EF467821.1) No Cys Δ1 | DTICIGYHANNSTDTVDT VLEKNVTVTHSVNLLED SHNGKL [SEQ ID NO: 178] | KYVRSAKLRMVTGLRNNPSIQSR [SEQ ID NO: 367] |
| H1 PR8-H1N1 (EF467821.1) No Cys Δ3 | DTICIGYHANNSTDTVDT VLEKNVTVTHSVNLLED SHNGK [SEQ ID NO: 179] | YVRSAKLRMVTGLRNNPSIQSR [SEQ ID NO: 368] |
| H2 (L11136) No Cys | DQICIGYHSNNSTEKVDT ILERNVTVTHAQNILEKT HNGKL [SEQ ID NO: 180] | PKYVKSERLVLATGLRNVPQIESR [SEQ ID NO: 369] |
| H2 (L11136) No Cys Δ1 | DQICIGYHSNNSTEKVDT ILERNVTVTHAQNILEKT HNGKL [SEQ ID NO: 181] | KYVKSERLVLATGLRNVPQIESR [SEQ ID NO: 370] |
| H2 (L11136) No Cys Δ3 | DQICIGYHSNNSTEKVDT ILERNVTVTHAQNILEKT HNGK [SEQ ID NO: 182] | YVKSERLVLATGLRNVPQIESR [SEQ ID NO: 371] |

TABLE 6A-continued

Exemplary Influenza A Hemagglutinin Short Stem Domain Peptide Sequences

| HA Subtype (Genbank No.) | HA1 N-terminal Stem Segment | HA1 C-terminal Stem Segment |
|---|---|---|
| H3 HK68-H3N2 (EF409245) PDB: 1HGJ No Cys | QDLPGNDNSTATLCLGH HAVPNGTLVKTITDDQIE VTNATELVQSSSTGKI [SEQ ID NO: 183] | PKYVKQNTLKLATGMRNVPEKQTR [SEQ ID NO: 372] |
| H3 HK68-H3N2 (EF409245) PDB: 1HGJ No Cys Δ1 | QDLPGNDNSTATLCLGH HAVPNGTLVKTITDDQIE VTNATELVQSSSTGKI [SEQ ID NO: 184] | KYVKQNTLKLATGMRNVPEKQTR [SEQ ID NO: 373] |
| H3 HK68-H3N2 (EF409245) PDB: 1HGJ No Cys Δ3 | QDLPGNDNSTATLCLGH HAVPNGTLVKTITDDQIE VTNATELVQSSSTGK [SEQ ID NO: 185] | YVKQNTLKLATGMRNVPEKQTR [SEQ ID NO: 374] |
| H4 (D90302) No Cys | QNYTGNPVICMGHHAV ANGTMVKTLADDQVEV VTAQELVESQNLPEL [SEQ ID NO: 186] | PRYVKQGSLKLATGMRNIPEKASR [SEQ ID NO: 375] |
| H4 (D90302) No Cys Δ1 | QNYTGNPVICMGHHAV ANGTMVKTLADDQVEV VTAQELVESQNLPEL [SEQ ID NO: 187] | RYVKQGSLKLATGMRNIPEKASR [SEQ ID NO: 376] |
| H4 (D90302) No Cys Δ3 | QNYTGNPVICMGHHAV ANGTMVKTLADDQVEV VTAQELVESQNLPE [SEQ ID NO: 188] | YVKQGSLKLATGMRNIPEKASR [SEQ ID NO: 377] |
| H5 (X07826) No Cys | DQICIGYHANKSTKQVD TIMEKNVTVTHAQDILE RTHNGKL [SEQ ID NO: 189] | PKYVKSDRLVLATGLRNVPQRKKR [SEQ ID NO: 378] |
| H5 (X07826) No Cys Δ1 | DQICIGYHANKSTKQVD TIMEKNVTVTHAQDILE RTHNGKL [SEQ ID NO: 190] | KYVKSDRLVLATGLRNVPQRKKR [SEQ ID NO: 379] |
| H5 (X07826) No Cys Δ3 | DQICIGYHANKSTKQVD TIMEKNVTVTHAQDILE RTHNGK [SEQ ID NO: 191] | YVKSDRLVLATGLRNVPQRKKR [SEQ ID NO: 380] |
| H6 (D90303) No Cys | DKICIGYHANNSTTQIDT ILEKNVTVTHSVELLENQ KEERF [SEQ ID NO: 192] | PKYVKSESLRLATGLRNVPQIETR [SEQ ID NO: 381] |
| H6 (D90303) No Cys Δ1 | DKICIGYHANNSTTQIDT ILEKNVTVTHSVELLENQ KEERF [SEQ ID NO: 193] | KYVKSESLRLATGLRNVPQIETR [SEQ ID NO: 382] |
| H6 (D90303) No Cys Δ3 | DKICIGYHANNSTTQIDT ILEKNVTVTHSVELLENQ KEER [SEQ ID NO: 194] | YVKSESLRLATGLRNVPQIETR [SEQ ID NO: 383] |
| H7 (M24457) No Cys | DKICLGHHAVSNGTKVN TLTERGVEVVNATETVE RTNIPKI [SEQ ID NO: 195] | PRYVKQESLLLATGMKNVPEPSKKRK KR [SEQ ID NO: 384] |
| H7 (M24457) No Cys Δ1 | DKICLGHHAVSNGTKVN TLTERGVEVVNATETVE RTNIPKI [SEQ ID NO: 196] | RYVKQESLLLATGMKNVPEPSKKRKKR [SEQ ID NO: 385] |

TABLE 6A-continued

| Exemplary Influenza A Hemagglutinin Short Stem Domain Peptide Sequences | | |
|---|---|---|
| HA Subtype (Genbank No.) | HA1 N-terminal Stem Segment | HA1 C-terminal Stem Segment |
| H7 (M24457) No Cys Δ3 | DKICLGHHAVSNGTKVN TLTERGVEVVNATETVE RTNIPK [SEQ ID NO: 197] | YVKQESLLLATGMKNVPEPSKKRKKR [SEQ ID NO: 386] |
| H8 (D90304) No Cys | DRICIGYQSNNSTDTVNT LIEQNVPVTQTMELVET EKHPAY [SEQ ID NO: 198] | PKYVKKASLRLAVGLRNTPSVEPR [SEQ ID NO: 387] |
| H8 (D90304) No Cys Δ1 | DRICIGYQSNNSTDTVNT LIEQNVPVTQTMELVET EKHPAY [SEQ ID NO: 199] | KYVKKASLRLAVGLRNTPSVEPR [SEQ ID NO: 388] |
| H8 (D90304) No Cys Δ3 | DRICIGYQSNNSTDTVNT LIEQNVPVTQTMELVET EKHPA [SEQ ID NO: 200] | YVKKASLRLAVGLRNTPSVEPR [SEQ ID NO: 389] |
| H9 (D90305) No Cys | DKICIGYQSTNSTETVDT LTESNVPVTHTKELLHTE HNGML [SEQ ID NO: 201] | PKYVGVKSLKLPVGLRNVPAVSSR [SEQ ID NO: 390] |
| H9 (D90305) No Cys Δ1 | DKICIGYQSTNSTETVDT LTESNVPVTHTKELLHTE HNGML [SEQ ID NO: 202] | KYVGVKSLKLPVGLRNVPAVSSR [SEQ ID NO: 391] |
| H9 (D90305) No Cys Δ3 | DKICIGYQSTNSTETVDT LTESNVPVTHTKELLHTE HNGM [SEQ ID NO: 203] | YVGVKSLKLPVGLRNVPAVSSR [SEQ ID NO: 392] |
| H10 (M21647) No Cys | LDRICLGHHAVANGTIV KTLTNEQEEVTNATETV ESTNLNKL [SEQ ID NO: 204] | PKYVNQRSLLLATGMRNVPEVVQGR [SEQ ID NO: 393] |
| H10 (M21647) No Cys Δ1 | LDRICLGHHAVANGTIV KTLTNEQEEVTNATETV ESTNLNKL [SEQ ID NO: 205] | KYVNQRSLLLATGMRNVPEVVQGR [SEQ ID NO: 394] |
| H10 (M21647) No Cys Δ3 | LDRICLGHHAVANGTIV KTLTNEQEEVTNATETV ESTNLNK [SEQ ID NO: 206] | YVNQRSLLLATGMRNVPEVVQGR [SEQ ID NO: 395] |
| H11 (D90306) No Cys | DEICIGYLSNNSTDKVDT IIENNVTVTSSVELVETE HTGSF [SEQ ID NO: 207] | PKYVNVKSLKLATGPRNVPAIASR [SEQ ID NO: 396] |
| H11 (D90306) No Cys Δ1 | DEICIGYLSNNSTDKVDT IIENNVTVTSSVELVETE HTGSF [SEQ ID NO: 208] | KYVNVKSLKLATGPRNVPAIASR [SEQ ID NO: 397] |
| H11 (D90306) No Cys Δ3 | DEICIGYLSNNSTDKVDT IIENNVTVTSSVELVETE HTGS [SEQ ID NO: 209] | YVNVKSLKLATGPRNVPAIASR [SEQ ID NO: 398] |
| H12 (D90307) No Cys | DKICIGYQTNNSTETVNT LSEQNVPVTQVEELVHR GIDPIL [SEQ ID NO: 210] | PKYIPSGSLKLAIGLRNVPQVQDR [SEQ ID NO: 399] |
| H12 (D90307) | DKICIGYQTNNSTETVNT LSEQNVPVTQVEELVHR | KYIPSGSLKLAIGLRNVPQVQDR [SEQ ID NO: 400] |

TABLE 6A-continued

Exemplary Influenza A Hemagglutinin Short Stem Domain Peptide Sequences

| HA Subtype (Genbank No.) | HA1 N-terminal Stem Segment | HA1 C-terminal Stem Segment |
|---|---|---|
| No Cys Δ1 | GIDPIL [SEQ ID NO: 211] | |
| H12 (D90307) No Cys Δ3 | DKICIGYQTNNSTETVNT LSEQNVPVTQVEELVHR GIDPI [SEQ ID NO: 212] | YIPSGSLKLAIGLRNVPQVQDR [SEQ ID NO: 401] |
| H13 (D90308) No Cys | DRICVGYLSTNSSERVDT LLENGVPVTSSIDLIETN HTGTY [SEQ ID NO: 213] | PKYIKSGQLKLATGLRNVPAISNR [SEQ ID NO: 402] |
| H13 (D90308) No Cys Δ1 | DRICVGYLSTNSSERVDT LLENGVPVTSSIDLIETN HTGTY [SEQ ID NO: 214] | KYIKSGQLKLATGLRNVPAISNR [SEQ ID NO: 403] |
| H13 (D90308) No Cys Δ3 | DRICVGYLSTNSSERVDT LLENGVPVTSSIDLIETN HTGT [SEQ ID NO: 215] | YIKSGQLKLATGLRNVPAISNR [SEQ ID NO: 404] |
| H14 (M35997) No Cys | QITNGTTGNPIICLGHHA VENGTSVKTLTDNHVEV VSAKELVETNHTDEL [SEQ ID NO: 216] | PKYVKQGSLMLATGMRNIPGKQAK [SEQ ID NO: 405] |
| H14 (M35997) No Cys Δ1 | QITNGTTGNPIICLGHHA VENGTSVKTLTDNHVEV VSAKELVETNHTDEL [SEQ ID NO: 217] | KYVKQGSLMLATGMRNIPGKQAK [SEQ ID NO: 406] |
| H14 (M35997) No Cys Δ3 | QITNGTTGNPIICLGHHA VENGTSVKTLTDNHVEV VSAKELVETNHTDE [SEQ ID NO: 218] | YVKQGSLMLATGMRNIPGKQAK [SEQ ID NO: 407] |
| H15 (L43917) No Cys | DKICLGHHAVANGTKV NTLTERGVEVVNATETV EITGIDKV [SEQ ID NO: 219] | PRYVKQSSLPLALGMKNVPEKIRTR [SEQ ID NO: 408] |
| H15 (L43917) No Cys Δ1 | DKICLGHHAVANGTKV NTLTERGVEVVNATETV EITGIDKV [SEQ ID NO: 220] | RYVKQSSLPLALGMKNVPEKIRTR [SEQ ID NO: 409] |
| H15 (L43917) No Cys Δ3 | DKICLGHHAVANGTKV NTLTERGVEVVNATETV EITGIDK [SEQ ID NO: 221] | YVKQSSLPLALGMKNVPEKIRTR [SEQ ID NO: 410] |
| H16 (EU293865) No Cys | DKICIGYLSNNSSDTVDT LTENGVPVTSSVDLVET NHTGTY [SEQ ID NO: 222] | PKYIKSGQLKLATGLRNVPSIGER [SEQ ID NO: 411] |
| H16 (EU293865) No Cys Δ1 | DKICIGYLSNNSSDTVDT LTENGVPVTSSVDLVET NHTGTY [SEQ ID NO: 223] | KYIKSGQLKLATGLRNVPSIGER [SEQ ID NO: 412] |
| H16 (EU293865) No Cys Δ3 | DKICIGYLSNNSSDTVDT LTENGVPVTSSVDLVET NHTGT [SEQ ID NO: 224] | YIKSGQLKLATGLRNVPSIGER [SEQ ID NO: 413] |

In certain embodiments, the influenza hemagglutinin short stem domain polypeptides comprise one or more immunogenic epitopes in the tertiary or quaternary structure of an influenza hemagglutinin polypeptide.

In certain embodiments, the HA1 N-terminal stem segment comprises the amino acid sequence $A_{17}$-$A_{18}$-$(Xaa)_n$-$A_{38}$ (SEQ ID NO:146), wherein $A_{17}$ is Y or H;

$A_{18}$ is H, L, or Q;

$(Xaa)_n$ represents a sequence of 18-20 amino acid residues; and $A_{38}$ is H, S, Q, T or N.

In certain embodiments, the HA2 domain comprises the amino acid sequence $A_{18}$-$A_{19}$-$A_{20}$-$A_{21}$ (SEQ ID NO:148), wherein $A_{18}$ is V or I;

$A_{19}$ is D, N or A;

$A_{20}$ is G, and $A_{21}$ is W.

In certain embodiments, the HA2 domain comprises the amino acid sequence $A_{38}$-$A_{39}$-$A_{40}$-$A_{41}$-$A_{42}$-$A_{43}$-$A_{44}$-$A_{45}$-$A_{46}$-$A_{47}$-$A_{48}$-$A_{49}$-$A_{50}$-$A_{51}$-$A_{52}$-$A_{53}$-$A_{54}$-$A_{55}$-$A_{56}$ (SEQ ID NO:149), wherein $A_{38}$ is K, Q, R, L or Y;

$A_{39}$ is any amino acid residue;

$A_{40}$ is any amino acid residue;

$A_{41}$ is T;

$A_{42}$ is Q;

$A_{43}$ is any amino acid residue;

$A_{44}$ is A;

$A_{45}$ is I;

$A_{46}$ is D;

$A_{47}$ is any amino acid residue;

$A_{48}$ is I, V or M;

$A_{49}$ is T, Q or N;

$A_{50}$ is any amino acid residue;

$A_{51}$ is K;

$A_{52}$ is V or L;

$A_{53}$ is N;

$A_{54}$ is any amino acid residue;

$A_{55}$ is V, I or L; and $A_{56}$ is V or I.

As illustrated in FIGS. 1 and 2, HA1 N-terminal stem segments share sequence identity between influenza A and influenza B and additionally across influenza A subtypes. Similarly, HA1 C-terminal short stem segments also share sequence identity between influenza A and influenza B and additionally across influenza A subtypes. Further, HA2 domains also share sequence identity between influenza A and influenza B and additionally across influenza A subtypes.

In some embodiments, the influenza hemagglutinin short stem domain polypeptide is a hybrid polypeptide that comprises or consists essentially of segments and/or domains from a plurality of influenza strains or subtypes. For example, an influenza hemagglutinin short stem domain polypeptide can comprise HA1 N-terminal and HA1 C-terminal short stem segments from different influenza A virus HA subtypes. In some embodiments, the HA1 N-terminal stem segment is from influenza B virus while the HA1 C-terminal short stem segment is from influenza A virus. Similarly, HA2 and the HA1 C-terminal short stem segment may also be from influenza A virus while the HA1 N-terminal is from influenza B virus.

It will be understood that any combination of the sequence elements listed in Tables 2, 4, 5 and sequences listed under the "Signal peptide," "HA1 N-terminal stem segment," and "HA2 Domain" columns of Table 3 or the variants thereof may be used to form the hemagglutinin HA stem domain polypeptides of the present invention.

In an influenza hemagglutinin short stem domain polypeptide provided herein, a linker covalently connects the HA1 N-terminal stem segment to the HA1 C-terminal short stem segment. The linker can be any linker deemed suitable by one of skill in the art including, but not limited to, those linkers described herein.

In certain embodiments, influenza hemagglutinin short stem domain polypeptides are capable of forming a three dimensional structure that is similar to the three dimensional structure of the stem domain of a native influenza hemagglutinin. Structural similarity can be evaluated based on any technique deemed suitable by those of skill in the art including, but not limited to, those techniques described herein.

In certain embodiments, any influenza hemagglutinin short stem domain polypeptide provided herein can further comprise one or more polypeptide domains deemed suitable to those of skill in the art. Useful polypeptide domains include domains that facilitate purification, folding and cleavage of portions of a polypeptide. For example, a His tag (His-His-His-His-His-His, SEQ ID NO:166), FLAG epitope or other purification tag can facilitate purification of a polypeptide provided herein. A foldon, or trimerization, domain from bacteriophage T4 fibritin can facilitate trimerization of polypeptides provided herein. The foldon domain can have any foldon sequence known to those of skill in the art (see, e.g., Papanikolopoulou et al., 2004, 1 Biol. Chem. 279(10):8991-8998, the contents of which are hereby incorporated by reference in their entirety. Examples include GSGYIPEAPRDGQAYVRKDGEWVLLSTFL (SEQ ID NO:167). A foldon domain can be useful to facilitate trimerization of soluble polypeptides provided herein. Cleavage sites can be used to facilitate cleavage of a portion of a polypeptide, for example cleavage of a purification tag or foldon domain or both. Useful cleavage sites include a thrombin cleavage site, for example one with the sequence LVPRGSP (SEQ ID NO:168).

In certain embodiments, provided are influenza hemagglutinin short stem domain polypeptides comprising an elastase cleavage site as described herein. In particular embodiments, provided herein are influenza hemagglutinin short stem domain polypeptides comprising any of SEQ ID NOS:350-365 wherein the C-terminal amino acid residue, e.g. arginine or lysine, of SEQ ID NOS:350-365 is substituted with a valine residue.

In certain embodiments, provided herein are influenza hemagglutinin stem short domain polypeptides that are predicted to be resistant to protease cleavage at the junction between HA1 and HA2. In certain embodiments, provided is any influenza hemagglutinin short stem domain polypeptide described herein wherein the protease site spanning HA1 and HA2 is mutated to a sequence that is resistant to protease cleavage. In certain embodiments, provided is any influenza hemagglutinin short stem domain polypeptide described herein wherein the C-terminal residue of the HA1 C-terminal short stem segment is any residue other than Lys or Arg. In certain embodiments, provided is any influenza hemagglutinin short stem domain polypeptide described herein wherein the N-terminal residue of the HA2 domain is proline. In certain embodiments, provided is any influenza hemagglutinin short stem domain polypeptide described herein wherein the C-terminal residue of the HA1 C-terminal short stem segment is Ala and the N-terminal residue of the HA2 domain is also Ala.

In certain embodiments, provided herein are influenza hemagglutinin short stem domain polypeptides consisting of an HA1 N-terminal stem segment covalently linked to a linker, in turn covalently linked to an HA1 C-terminal short stem segment in binding association with an HA2 stem domain. In certain embodiments, provided herein are influenza hemagglutinin short stem domain polypeptides consisting of an HA1 N-terminal stem segment covalently linked to a linker, in turn covalently linked to an HA1 C-terminal short stem segment, in turn covalently linked to an HA2 stem domain. In certain embodiments, provided herein are influenza hemagglutinin short stem domain polypeptides consisting of a signal peptide covalently linked to an HA1 N-terminal stem segment covalently linked to a linker, in turn covalently linked to an HA1 C-terminal short stem segment, in turn covalently linked to an HA2 stem domain.

In certain embodiments, provided herein are influenza hemagglutinin short stem domain polypeptides consisting of an HA1 N-terminal stem segment covalently linked to a linker, in turn covalently linked to an HA1 C-terminal short stem segment in binding association with an HA2 stem domain that is covalently linked to an HA2 luminal domain. In certain embodiments, provided herein are influenza hemagglutinin short stem domain polypeptides consisting of an HA1 N-terminal stem segment covalently linked to a linker, in turn covalently linked to an HA1 C-terminal short stem segment, in turn covalently linked to an HA2 stem domain that is covalently linked to an HA2 luminal domain. In certain embodiments, provided herein are influenza hemagglutinin short stem domain polypeptides consisting of a signal peptide covalently linked to an HA1 N-terminal stem segment covalently linked to a linker, in turn covalently linked to an HA1 C-terminal short stem segment, in turn covalently linked to an HA2 stem domain that is covalently linked to an HA2 luminal domain.

In certain embodiments, provided herein are influenza hemagglutinin short stem domain polypeptides consisting of an HA1 N-terminal stem segment covalently linked to a linker, in turn covalently linked to an HA1 C-terminal short stem segment in binding association with an HA2 stem domain that is covalently linked to, in sequence, a thrombin cleavage site, a foldon domain and a His tag. In certain embodiments, provided herein are influenza hemagglutinin short stem domain polypeptides consisting of an HA1 N-terminal stem segment covalently linked to a linker, in turn covalently linked to an HA1 C-terminal short stem segment, in turn covalently linked to an HA2 stem domain that is covalently linked to, in sequence, a thrombin cleavage site, a foldon domain and a His tag. In certain embodiments, provided herein are influenza hemagglutinin short stem domain polypeptides consisting of a signal peptide covalently linked to an HA1 N-terminal stem segment covalently linked to a linker, in turn covalently linked to an HA1 C-terminal short stem segment, in turn covalently linked to an HA2 stem domain that is covalently linked to, in sequence, a thrombin cleavage site, a foldon domain and a His tag.

In certain embodiments, provided herein are influenza hemagglutinin short stem domain polypeptides consisting of an HA1 N-terminal stem segment covalently linked to a linker, in turn covalently linked to an HA1 C-terminal short stem segment in binding association with an HA2 stem domain that is covalently linked to an HA2 luminal domain that is covalently linked to, in sequence, a thrombin cleavage site, a foldon domain and a His tag. In certain embodiments, provided herein are influenza hemagglutinin short stem domain polypeptides consisting of an HA1 N-terminal stem segment covalently linked to a linker, in turn covalently linked to an HA1 C-terminal short stem segment, in turn covalently linked to an HA2 stem domain that is covalently linked to an HA2 luminal domain that is covalently linked to, in sequence, a thrombin cleavage site, a foldon domain and a His tag. In certain embodiments, provided herein are influenza hemagglutinin short stem domain polypeptides consisting of a signal peptide covalently linked to an HA1 N-terminal stem segment covalently linked to a linker, in turn covalently linked to an HA1 C-terminal short stem segment, in turn covalently linked to an HA2 stem domain that is covalently linked to an HA2 luminal domain that is covalently linked to, in sequence, a thrombin cleavage site, a foldon domain and a His tag.

In certain embodiments, provided herein are influenza hemagglutinin short stem domain polypeptides consisting of an HA1 N-terminal stem segment covalently linked to a linker, in turn covalently linked to an HA1 C-terminal short stem segment in binding association with an HA2 stem domain that is covalently linked to an HA2 luminal domain that is in turn covalently linked to an HA2 transmembrane domain. In certain embodiments, provided herein are influenza hemagglutinin short stem domain polypeptides consisting of an HA1 N-terminal stem segment covalently linked to a linker, in turn covalently linked to an HA1 C-terminal short stem segment, in turn covalently linked to an HA2 stem domain that is covalently linked to an HA2 luminal domain that is in turn covalently linked to an HA2 transmembrane domain. In certain embodiments, provided herein are influenza hemagglutinin short stem domain polypeptides consisting of a signal peptide covalently linked to an HA1 N-terminal stem segment covalently linked to a linker, in turn covalently linked to an HA1 C-terminal short stem segment, in turn covalently linked to an HA2 stem domain that is covalently linked to an HA2 luminal domain that is in turn covalently linked to an HA2 transmembrane domain.

In certain embodiments, provided herein are influenza hemagglutinin short stem domain polypeptides consisting of an HA1 N-terminal stem segment covalently linked to a linker, in turn covalently linked to an HA1 C-terminal short stem segment in binding association with an HA2 stem domain that is covalently linked to an HA2 luminal domain that is in turn covalently linked to an HA2 transmembrane domain that is in turn covalently linked to an HA2 cytoplasmic domain. In certain embodiments, provided herein are influenza hemagglutinin short stem domain polypeptides consisting of an HA1 N-terminal stem segment covalently linked to a linker, in turn covalently linked to an HA1 C-terminal short stem segment, in turn covalently linked to an HA2 stem domain that is covalently linked to an HA2 luminal domain that is in turn covalently linked to an HA2 transmembrane domain that is in turn covalently linked to an HA2 cytoplasmic domain. In certain embodiments, provided herein are influenza hemagglutinin short stem domain polypeptides consisting of a signal peptide covalently linked to an HA1 N-terminal stem segment covalently linked to a linker, in turn covalently linked to an HA1 C-terminal short stem segment, in turn covalently linked to an HA2 stem domain that is covalently linked to an HA2 luminal domain that is in turn covalently linked to an HA2 transmembrane domain that is in turn covalently linked to an HA2 cytoplasmic domain.

In certain embodiments, provided herein is an influenza hemagglutinin short stem polypeptide having a sequence selected from the group consisting of:

(SEQ ID NO: 34)-LL-(SEQ ID NO: 350)-(SEQ ID NO: 66), (SEQ ID NO: 35)-LL-(SEQ ID NO: 351)-(SEQ ID NO: 67), (SEQ ID NO: 36)-LL-(SEQ ID NO: 352)-(SEQ ID NO: 68), (SEQ ID NO: 37)-LL-(SEQ ID NO: 353)-(SEQ ID NO: 69), (SEQ ID NO: 38)-LL-(SEQ ID NO: 354)-(SEQ ID NO: 70), (SEQ ID NO: 39)-LL-(SEQ ID NO: 355)-(SEQ ID NO: 71), (SEQ ID NO: 40)-LL-(SEQ ID NO: 356)-(SEQ ID NO: 72), (SEQ ID NO: 41)-LL-(SEQ ID NO: 357)-(SEQ ID NO: 73), (SEQ ID NO: 42)-LL-(SEQ ID NO: 358)-(SEQ ID NO: 74), (SEQ ID NO: 43)-LL-(SEQ ID NO: 359)-(SEQ ID NO: 75), (SEQ ID NO: 44)-LL-(SEQ ID NO: 360)-(SEQ ID NO: 76), (SEQ ID NO: 45)-LL-(SEQ ID NO: 361)-(SEQ ID NO: 77), (SEQ ID NO: 46)-LL-(SEQ ID NO: 362)-(SEQ ID NO: 78), (SEQ ID NO: 47)-LL-(SEQ ID NO: 363)-(SEQ ID NO: 79), (SEQ ID NO: 48)-LL-(SEQ ID NO: 364)-(SEQ ID NO: 80),
and (SEQ ID NO: 49)-LL-(SEQ ID NO: 365)-(SEQ ID NO: 81), wherein each sequence above is linked to the adjacent sequence as described herein and wherein LL is a linker as described herein. In particular, the HA1 C-terminal segments can be covalently or non-covalently linked to the HA2 domains. In certain embodiments, LL is selected from the group consisting of a direct bond, Gly, Gly-Gly, Gly-Gly-Gly, Gly-Gly-Gly-Gly (SEQ ID NO: 560), (Gly)n (wherein n is any number of Glycine residues so long as there is flexibility in the peptide linker; in certain embodiments, n is 2, 3, 4, 5, 6, or 7 Glycine residues), Gly-Pro, ITPNGSIPNDKPFQNVNKITYGA (SEQ ID NO:165) and Asn-Ala-Ser.

In certain embodiments, provided herein is an influenza hemagglutinin short stem polypeptide having a sequence selected from the group consisting of:

(SEQ ID NO: 34)-LL-(SEQ ID NO: 350)-(SEQ ID NO: 82), (SEQ ID NO: 35)-LL-(SEQ ID NO: 351)-(SEQ ID NO: 83), (SEQ ID NO: 36)-LL-(SEQ ID NO: 352)-(SEQ ID NO: 84), (SEQ ID NO: 37)-LL-(SEQ ID NO: 353)-(SEQ ID NO: 85), (SEQ ID NO: 38)-LL-(SEQ ID NO: 354)-(SEQ ID NO: 86), (SEQ ID NO: 39)-LL-(SEQ ID NO: 355)-(SEQ ID NO: 87), (SEQ ID NO: 40)-LL-(SEQ ID NO: 356)-(SEQ ID NO: 88), (SEQ ID NO: 41)-LL-(SEQ ID NO: 357)-(SEQ ID NO: 89), (SEQ ID NO: 42)-LL-(SEQ ID NO: 358)-(SEQ ID NO: 90), (SEQ ID NO: 43)-LL-(SEQ ID NO: 359)-(SEQ ID NO: 91), (SEQ ID NO: 44)-LL-(SEQ ID NO: 360)-(SEQ ID NO: 92), (SEQ ID NO: 45)-LL-(SEQ ID NO: 361)-(SEQ ID NO: 93), (SEQ ID NO: 46)-LL-(SEQ ID NO: 362)-(SEQ ID NO: 94), (SEQ ID NO: 47)-LL-(SEQ ID NO: 363)-(SEQ ID NO: 95), (SEQ ID NO: 48)-LL-(SEQ ID NO: 364)-(SEQ ID NO: 96),
and (SEQ ID NO: 49)-LL-(SEQ ID NO: 365)-(SEQ ID NO: 97), wherein each sequence above is linked to the adjacent sequence as described herein and wherein LL is a linker as described herein. In particular, the HA1 C-terminal segments can be covalently or non-covalently linked to the HA2 domains. In certain embodiments, LL is selected from the group consisting of a direct bond, Gly, Gly-Gly, Gly-Gly-Gly, Gly-Gly-Gly-Gly (SEQ ID NO: 560), (Gly)n, Gly-Pro, ITPNGSIPNDKPFQNVNKITYGA (SEQ ID NO:165) and Asn-Ala-Ser.

In certain embodiments, provided herein is an influenza hemagglutinin short stem polypeptide having a sequence selected from the group consisting of:

(SEQ ID NO: 34)-LL-(SEQ ID NO: 350)-(SEQ ID NO: 82)-(SEQ ID NO: 98), (SEQ ID NO: 35)-LL-(SEQ ID NO: 351)-(SEQ ID NO: 83)-(SEQ ID NO: 99), (SEQ ID NO: 36)-LL-(SEQ ID NO: 352)-(SEQ ID NO: 84)-(SEQ ID NO: 100), (SEQ ID NO: 37)-LL-(SEQ ID NO: 353)-(SEQ ID NO: 85)-(SEQ ID NO: 101), (SEQ ID NO: 38)-LL-(SEQ ID NO: 354)-(SEQ ID NO: 86)-(SEQ ID NO: 102), (SEQ ID NO: 39)-LL-(SEQ ID NO: 355)-(SEQ ID NO: 87)-(SEQ ID NO: 103),

-continued (SEQ ID NO: 40)-LL-(SEQ ID NO: 356)-(SEQ ID NO: 88)-(SEQ ID NO: 104), (SEQ ID NO: 41)-LL-(SEQ ID NO: 357)-(SEQ ID NO: 89)-(SEQ ID NO: 105), (SEQ ID NO: 42)-LL-(SEQ ID NO: 358)-(SEQ ID NO: 90)-(SEQ ID NO: 106), (SEQ ID NO: 43)-LL-(SEQ ID NO: 359)-(SEQ ID NO: 91)-(SEQ ID NO: 107), (SEQ ID NO: 44)-LL-(SEQ ID NO: 360)-(SEQ ID NO: 92)-(SEQ ID NO: 108), (SEQ ID NO: 45)-LL-(SEQ ID NO: 361)-(SEQ ID NO: 93)-(SEQ ID NO: 109), (SEQ ID NO: 46)-LL-(SEQ ID NO: 362)-(SEQ ID NO: 94)-(SEQ ID NO: 110), (SEQ ID NO: 47)-LL-(SEQ ID NO: 363)-(SEQ ID NO: 95)-(SEQ ID NO: 111), (SEQ ID NO: 48)-LL-(SEQ ID NO: 364)-(SEQ ID NO: 96)-(SEQ ID NO: 112),
and (SEQ ID NO: 49)-LL-(SEQ ID NO: 365)-(SEQ ID NO: 97)-(SEQ ID NO: 113), wherein each sequence above is linked to the adjacent sequence as described herein and wherein LL is a linker as described herein. In particular, the HA1 C-terminal short stem segments can be covalently or non-covalently linked to the HA2 domains. In certain embodiments, LL is selected from the group consisting of a direct bond, Gly, Gly-Gly, Gly-Gly-Gly, Gly-Gly-Gly-Gly (SEQ ID NO: 560), (Gly)n, Gly-Pro, ITPNGSIPNDKPFQNVNKITYGA (SEQ ID NO:165) and Asn-Ala-Ser.

In certain embodiments, provided herein is an influenza hemagglutinin short stem polypeptide having a sequence selected from the group consisting of:

(SEQ ID NO: 34)-LL-(SEQ ID NO: 350)-(SEQ ID NO: 82)-(SEQ ID NO: 168)-(SEQ ID NO: 167)-(SEQ ID NO: 166), (SEQ ID NO: 35)-LL-(SEQ ID NO: 351)-(SEQ ID NO: 83)-(SEQ ID NO: 168)-(SEQ ID NO: 167)-(SEQ ID NO: 166), (SEQ ID NO: 36)-LL-(SEQ ID NO: 352)-(SEQ ID NO: 84)-(SEQ ID NO: 168)-(SEQ ID NO: 167)-(SEQ ID NO: 166), (SEQ ID NO: 37)-LL-(SEQ ID NO: 353)-(SEQ ID NO: 85)-(SEQ ID NO: 168)-(SEQ ID NO: 167)-(SEQ ID NO: 166), (SEQ ID NO: 38)-LL-(SEQ ID NO: 354)-(SEQ ID NO: 86)-(SEQ ID NO: 168)-(SEQ ID NO: 167)-(SEQ ID NO: 166), (SEQ ID NO: 39)-LL-(SEQ ID NO: 355)-(SEQ ID NO: 87)-(SEQ ID NO: 168)-(SEQ ID NO: 167)-(SEQ ID NO: 166), (SEQ ID NO: 40)-LL-(SEQ ID NO: 356)-(SEQ ID NO: 88)-(SEQ ID NO: 168)-(SEQ ID NO: 167)-(SEQ ID NO: 166), (SEQ ID NO: 41)-LL-(SEQ ID NO: 357)-(SEQ ID NO: 89)-(SEQ ID NO: 168)-(SEQ ID NO: 167)-(SEQ ID NO: 166), (SEQ ID NO: 42)-LL-(SEQ ID NO: 358)-(SEQ ID NO: 90)-(SEQ ID NO: 168)-(SEQ ID NO: 167)-(SEQ ID NO: 166), (SEQ ID NO: 43)-LL-(SEQ ID NO: 359)-(SEQ ID NO: 91)-(SEQ ID NO: 168)-(SEQ ID NO: 167)-(SEQ ID NO: 166), (SEQ ID NO: 44)-LL-(SEQ ID NO: 360)-(SEQ ID NO: 92)-(SEQ ID NO: 168)-(SEQ ID NO: 167)-(SEQ ID NO: 166), (SEQ ID NO: 45)-LL-(SEQ ID NO: 361)-(SEQ ID NO: 93)-(SEQ ID NO: 168)-(SEQ ID NO: 167)-(SEQ ID NO: 166), (SEQ ID NO: 46)-LL-(SEQ ID NO: 362)-(SEQ ID NO: 94)-(SEQ ID NO: 168)-(SEQ ID NO: 167)-(SEQ ID NO: 166), (SEQ ID NO: 47)-LL-(SEQ ID NO: 363)-(SEQ ID NO: 95)-(SEQ ID NO: 168)-(SEQ ID NO: 167)-(SEQ ID NO: 166), (SEQ ID NO: 48)-LL-(SEQ ID NO: 364)-(SEQ ID NO: 96)-(SEQ ID NO: 168)-(SEQ ID NO: 167)-(SEQ ID NO: 166),
and (SEQ ID NO: 49)-LL-(SEQ ID NO: 365)-(SEQ ID NO: 97)-(SEQ ID NO: 168)-(SEQ ID NO: 167)-(SEQ ID NO: 166), wherein each sequence above is linked to the adjacent sequence as described herein and wherein LL is a linker as described herein. In particular, the HA1 C-terminal short stem segments can be covalently or non-covalently linked to the HA2 domains. In certain embodiments, LL is selected from the group consisting of a direct bond, Gly, Gly-Gly, Gly-Gly-Gly, Gly-Gly-Gly-Gly (SEQ ID NO: 560), (Gly)n, Gly-Pro, ITPNGSIPNDKPFQNVNKITYGA (SEQ ID NO:165) and Asn-Ala-Ser.

In certain embodiments, provided herein is an influenza hemagglutinin short stem polypeptide having a sequence selected from the group consisting of:

(SEQ ID NO: 177)-LL-(SEQ ID NO: 366)-(SEQ ID NO: 66), (SEQ ID NO: 178)-LL-(SEQ ID NO: 367)-(SEQ ID NO: 66), (SEQ ID NO: 179)-LL-(SEQ ID NO: 368)-(SEQ ID NO: 66), (SEQ ID NO: 180)-LL-(SEQ ID NO: 369)-(SEQ ID NO: 67), (SEQ ID NO: 34)-LL-(SEQ ID NO: 350)-(SEQ ID NO: 82)-(SEQ ID NO: 98)-(SEQ ID NO: 168)-(SEQ ID NO: 167)-(SEQ ID NO: 166), (SEQ ID NO: 35)-LL-(SEQ ID NO: 351)-(SEQ ID NO: 83)-(SEQ ID NO: 99)-(SEQ ID NO: 168)-(SEQ ID NO: 167)-(SEQ ID NO: 166), (SEQ ID NO: 36)-LL-(SEQ ID NO: 352)-(SEQ ID NO: 84)-(SEQ ID NO: 100)-(SEQ ID NO: 168)-(SEQ ID NO: 167)-(SEQ ID NO: 166), (SEQ ID NO: 37)-LL-(SEQ ID NO: 353)-(SEQ ID NO: 85)-(SEQ ID NO: 101)-(SEQ ID NO: 168)-(SEQ ID NO: 167)-(SEQ ID NO: 166), (SEQ ID NO: 38)-LL-(SEQ ID NO: 354)-(SEQ ID NO: 86)-(SEQ ID NO: 102)-(SEQ ID NO: 168)-(SEQ ID NO: 167)-(SEQ ID NO: 166), (SEQ ID NO: 39)-LL-(SEQ ID NO: 355)-(SEQ ID NO: 87)-(SEQ ID NO: 103)-(SEQ ID NO: 168)-(SEQ ID NO: 167)-(SEQ ID NO: 166), (SEQ ID NO: 40)-LL-(SEQ ID NO: 356)-(SEQ ID NO: 88)-(SEQ ID NO: 104)-(SEQ ID NO: 168)-(SEQ ID NO: 167)-(SEQ ID NO: 166), (SEQ ID NO: 41)-LL-(SEQ ID NO: 357)-(SEQ ID NO: 89)-(SEQ ID NO: 105)-(SEQ ID NO: 168)-(SEQ ID NO: 167)-(SEQ ID NO: 166), (SEQ ID NO: 42)-LL-(SEQ ID NO: 358)-(SEQ ID NO: 90)-(SEQ ID NO: 106)-(SEQ ID NO: 168)-(SEQ ID NO: 167)-(SEQ ID NO: 166), (SEQ ID NO: 43)-LL-(SEQ ID NO: 359)-(SEQ ID NO: 91)-(SEQ ID NO: 107)-(SEQ ID NO: 168)-(SEQ ID NO: 167)-(SEQ ID NO: 166), (SEQ ID NO: 44)-LL-(SEQ ID NO: 360)-(SEQ ID NO: 92)-(SEQ ID NO: 108)-(SEQ ID NO: 168)-(SEQ ID NO: 167)-(SEQ ID NO: 166), (SEQ ID NO: 45)-LL-(SEQ ID NO: 361)-(SEQ ID NO: 93)-(SEQ ID NO: 109)-(SEQ ID NO: 168)-(SEQ ID NO: 167)-(SEQ ID NO: 166), (SEQ ID NO: 46)-LL-(SEQ ID NO: 362)-(SEQ ID NO: 94)-(SEQ ID NO: 110)-(SEQ ID NO: 168)-(SEQ ID NO: 167)-(SEQ ID NO: 166), (SEQ ID NO: 47)-LL-(SEQ ID NO: 363)-(SEQ ID NO: 95)-(SEQ ID NO: 111)-(SEQ ID NO: 168)-(SEQ ID NO: 167)-(SEQ ID NO: 166), (SEQ ID NO: 48)-LL-(SEQ ID NO: 364)-(SEQ ID NO: 96)-(SEQ ID NO: 112)-(SEQ ID NO: 168)-(SEQ ID NO: 167)-(SEQ ID NO: 166),
and (SEQ ID NO: 49)-LL-(SEQ ID NO: 365)-(SEQ ID NO: 97)-(SEQ ID NO: 113)-(SEQ ID NO: 168)-(SEQ ID NO: 167)-(SEQ ID NO: 166), wherein each sequence above is linked to the adjacent sequence as described herein and wherein LL is a linker as described herein. In particular, the HA1 C-terminal short stem segments can be covalently or non-covalently linked to the HA2 domains. In certain embodiments, LL is selected from the group consisting of a direct bond, Gly, Gly-Gly, Gly-Gly-Gly, Gly-Gly-Gly-Gly (SEQ ID NO: 560), Gly, (Gly)n, Gly-Pro, ITPNGSIPNDKPFQNVNKITYGA (SEQ ID NO:165) and Asn-Ala-Ser.

In certain embodiments, provided herein is an influenza hemagglutinin short stem polypeptide having a sequence selected from the group consisting of:

-continued (SEQ ID NO: 181)-LL-(SEQ ID NO: 370)-(SEQ ID NO: 67), (SEQ ID NO: 182)-LL-(SEQ ID NO: 371)-(SEQ ID NO: 67), (SEQ ID NO: 183)-LL-(SEQ ID NO: 372)-(SEQ ID NO: 68), (SEQ ID NO: 184)-LL-(SEQ ID NO: 373)-(SEQ ID NO: 68), (SEQ ID NO: 185)-LL-(SEQ ID NO: 374)-(SEQ ID NO: 68), -continued (SEQ ID NO: 186)-LL-(SEQ ID NO: 375)-(SEQ ID NO: 69), (SEQ ID NO: 187)-LL-(SEQ ID NO: 376)-(SEQ ID NO: 69), (SEQ ID NO: 188)-LL-(SEQ ID NO: 377)-(SEQ ID NO: 69), (SEQ ID NO: 189)-LL-(SEQ ID NO: 378)-(SEQ ID NO: 70), (SEQ ID NO: 190)-LL-(SEQ ID NO: 379)-(SEQ ID NO: 70), (SEQ ID NO: 191)-LL-(SEQ ID NO: 380)-(SEQ ID NO: 70), (SEQ ID NO: 192)-LL-(SEQ ID NO: 381)-(SEQ ID NO: 71), (SEQ ID NO: 193)-LL-(SEQ ID NO: 382)-(SEQ ID NO: 71), (SEQ ID NO: 194)-LL-(SEQ ID NO: 383)-(SEQ ID NO: 71), (SEQ ID NO: 195)-LL-(SEQ ID NO: 384)-(SEQ ID NO: 72), (SEQ ID NO: 196)-LL-(SEQ ID NO: 385)-(SEQ ID NO: 72), (SEQ ID NO: 197)-LL-(SEQ ID NO: 386)-(SEQ ID NO: 72), (SEQ ID NO: 198)-LL-(SEQ ID NO: 387)-(SEQ ID NO: 73), (SEQ ID NO: 199)-LL-(SEQ ID NO: 388)-(SEQ ID NO: 73), (SEQ ID NO: 200)-LL-(SEQ ID NO: 389)-(SEQ ID NO: 73), (SEQ ID NO: 201)-LL-(SEQ ID NO: 390)-(SEQ ID NO: 74), (SEQ ID NO: 202)-LL-(SEQ ID NO: 391)-(SEQ ID NO: 74), (SEQ ID NO: 203)-LL-(SEQ ID NO: 392)-(SEQ ID NO: 74), (SEQ ID NO: 204)-LL-(SEQ ID NO: 393)-(SEQ ID NO: 75), (SEQ ID NO: 205)-LL-(SEQ ID NO: 394)-(SEQ ID NO: 75), (SEQ ID NO: 206)-LL-(SEQ ID NO: 395)-(SEQ ID NO: 75), (SEQ ID NO: 207)-LL-(SEQ ID NO: 396)-(SEQ ID NO: 76), (SEQ ID NO: 208)-LL-(SEQ ID NO: 397)-(SEQ ID NO: 76), (SEQ ID NO: 209)-LL-(SEQ ID NO: 398)-(SEQ ID NO: 76), (SEQ ID NO: 210)-LL-(SEQ ID NO: 399)-(SEQ ID NO: 77), (SEQ ID NO: 211)-LL-(SEQ ID NO: 400)-(SEQ ID NO: 77), (SEQ ID NO: 212)-LL-(SEQ ID NO: 401)-(SEQ ID NO: 77), -continued (SEQ ID NO: 213)-LL-(SEQ ID NO: 402)-(SEQ ID NO: 78), (SEQ ID NO: 214)-LL-(SEQ ID NO: 403)-(SEQ ID NO: 78), (SEQ ID NO: 215)-LL-(SEQ ID NO: 404)-(SEQ ID NO: 78), (SEQ ID NO: 216)-LL-(SEQ ID NO: 405)-(SEQ ID NO: 79), (SEQ ID NO: 217)-LL-(SEQ ID NO: 406)-(SEQ ID NO: 79), (SEQ ID NO: 218)-LL-(SEQ ID NO: 407)-(SEQ ID NO: 79), (SEQ ID NO: 219)-LL-(SEQ ID NO: 408)-(SEQ ID NO: 80), (SEQ ID NO: 220)-LL-(SEQ ID NO: 409)-(SEQ ID NO: 80), (SEQ ID NO: 221)-LL-(SEQ ID NO: 410)-(SEQ ID NO: 80), (SEQ ID NO: 222)-LL-(SEQ ID NO: 411)-(SEQ ID NO: 81), (SEQ ID NO: 223)-LL-(SEQ ID NO: 412)-(SEQ ID NO: 81),
and (SEQ ID NO: 224)-LL-(SEQ ID NO: 413)-(SEQ ID NO: 81), and wherein each sequence above is linked to the adjacent sequence as described herein and wherein LL is a linker as described herein. In particular, the HA1 C-terminal short stem segments can be covalently or non-covalently linked to the HA2 domains. In certain embodiments, LL is selected from the group consisting of a direct bond, Gly, Gly-Gly, Gly-Gly-Gly, Gly-Gly-Gly-Gly (SEQ ID NO: 560), (Gly)n, Gly-Pro, ITPNGSIPNDKPFQNVNKITYGA (SEQ ID NO:165) and Asn-Ala-Ser.

5.1.2 Influenza Hemagglutinin Long Stem Domain Polypeptides

In certain embodiments, the influenza hemagglutinin stem domain polypeptide is an influenza hemagglutinin long stem domain polypeptide. The typical primary structure of an influenza hemagglutinin long stem domain polypeptide provided herein comprises, in the following order: an HA1 N-terminal long stem segment, a linker, an HA1 C-terminal long stem segment and an HA2. The primary sequence can be formed by a single polypeptide, or it can be formed by multiple polypeptides. Typically, a single polypeptide is expressed by any technique deemed suitable by one of skill in the art. In single polypeptide embodiments, the HA1 segments and the HA2 are in tertiary association. As is known to those of skill in the art, a single HA polypeptide can be cleaved, for example by a protease, under appropriate expression conditions to yield two polypeptides in quaternary association. The cleavage is typically between the HA1 C-terminal short stem segment and the HA2. In certain embodiments, provided herein are multiple polypeptides. In multiple polypeptide embodiments, the HA1 segments and HA2 are in quaternary association.

In certain embodiments, an influenza hemagglutinin long stem domain polypeptide provided herein is monomeric. In certain embodiments, an influenza hemagglutinin long stem domain polypeptide provided herein is multimeric. In certain embodiments, an influenza hemagglutinin long stem domain polypeptide provided herein is trimeric. Those of skill in the art will recognize that native influenza hemagglutinin long stem domain polypeptides are capable of trimerization in vivo and that certain influenza hemagglutinin long stem domain polypeptides provided herein are capable of trimerization. In particular embodiments described below, influenza hemagglutinin long stem domain polypeptides provided herein comprise trimerization domains to facilitate trimerization.

In certain embodiments, an influenza hemagglutinin long stem domain polypeptide comprises a signal peptide. In certain embodiments, also provided herein are mature influenza hemagglutinin long stem domain polypeptides that lack a signal peptide.

In certain embodiments, provided herein are influenza hemagglutinin long stem domain polypeptides that comprise an HA2 stem domain, an HA2 luminal domain, an HA2 transmembrane domain and an HA2 cytoplasmic domain. In certain embodiments, provided herein are influenza hemagglutinin long stem domain polypeptides that comprise an HA2 stem domain, an HA2 luminal domain, and an HA2 transmembrane domain but lack some or all of the typical cytoplasmic domain. In certain embodiments, provided herein are influenza hemagglutinin long stem domain polypeptides that comprise an HA2 stem domain and an HA2 luminal domain but lack both an HA2 transmembrane domain and an HA2 cytoplasmic domain. In certain embodiments, provided herein are influenza hemagglutinin long stem domain polypeptides that comprise an HA2 stem domain but lack an HA2 luminal domain, an HA2 transmembrane domain and an HA2 cytoplasmic domain. In certain embodiments, the influenza hemagglutinin long stem domain polypeptides comprise an HA2 stem domain having at least 70%, 75%, 80%, 85%, 90%, 95%, 96% or 98% amino acid sequence identity to an influenza HA2 stem domain known to those of skill in the art. Exemplary known HA2 stem domains from known influenza A hemagglutinins are provided in the tables below.

Also provided herein are influenza hemagglutinin long stem domain polypeptides comprising deleted forms of HA2 stem domains wherein up to 10, 9, 8, 7, 6, 5, 4, 3, 2 or 1 amino acid residues are deleted from either or both termini of the HA2 stem domain. Further provided herein are influenza hemagglutinin long stem domain polypeptides comprising altered forms of HA2 stem domains wherein up to 10, 9, 8, 7, 6, 5, 4, 3, 2 or 1 amino acid residues are conservatively substituted with other amino acids. Further provided are influenza hemagglutinin long stem domain polypeptides comprising deleted and altered HA2 stem domains.

The HA1 N-terminal long stem segment can be any HA1 N-terminal long stem segment recognized by one of skill in the art based on the definition provided herein. Typically, an HA1 N-terminal long stem segment corresponds to a polypeptide consisting of the N-terminal amino acid of a mature HA1 (i.e. an HA1 lacking a signal peptide) through the cysteine residue located in sequence at approximately the $97^{th}$ residue of the HA1 (using H3 numbering). This cystine residue, termed $C_p$ herein, is generally capable of being linked to a cysteine residue $C_q$ in the C-terminal long stem segment of HA1. Sequences of 16 representative influenza A hemagglutinins are presented in FIG. 1, and residue $C_p$ is identified in each.

In certain embodiments, the HA1 N-terminal long stem segment does not end exactly at $C_p$ (e.g., $Cys_{97}$ of an HA1 subunit from an H3 hemagglutinin), but at a residue in sequence and structure vicinity to $C_p$. For example, in certain embodiments, the HA1 N-terminal long stem segment ends at $C_{p-1}$, $C_{p-2}$, $C_{p-3}$, or $C_{p-4}$. In other embodiments, the HA1 N-terminal long stem segment ends at $C_{p+i}$, $C_{p+2}$, $C_{p+3}$, $C_{p+4}$ or $C_{p+5}$. The end of an HA1 N-terminal long stem segment should be selected in conjunction with the end of the HA1 C-terminal long stem segment and the linker so that the resulting linked HA1 stem domain is capable of forming a three-dimensional structure similar, as described below, to an influenza hemagglutinin stem domain.

In certain embodiments, the influenza hemagglutinin long stem domain polypeptides comprise an HA1 N-terminal long stem segment having at least 70%, 75%, 80%, 85%, 90%, 95%, 96% or 98% amino acid sequence identity to an influenza HA1 N-terminal long stem segment known to those of skill in the art. Exemplary known HA1 N-terminal long stem segments are provided in the tables below.

Also provided herein are influenza hemagglutinin long stem domain polypeptides comprising deleted forms of HA1 N-terminal long stem segments wherein up to 10, 9, 8, 7, 6, 5, 4, 3, 2 or 1 amino acid residues are deleted from either or both termini of the HA1 N-terminal long stem segment. In certain embodiments, provided herein are influenza hemagglutinin long stem domain polypeptides that comprise expanded forms of HA1 N-terminal long stem segments wherein 1, 2 or 3 residues are added to the C-terminus of the HA1 N-terminal long stem segments; these added residues can be derived from the amino acid sequence of a globular head domain adjacent to an HA1 N-terminal long stem segment. Further provided herein are influenza hemagglutinin long stem domain polypeptides comprising altered forms of HA1 N-terminal long stem segments wherein up to 10, 9, 8, 7, 6, 5, 4, 3, 2 or 1 amino acid residues are conservatively substituted with other amino acids. Further provided are influenza hemagglutinin long stem domain polypeptides comprising deleted and altered HA1 N-terminal long stem segments.

The HA1 C-terminal long stem segment can be any HA1 C-terminal long stem segment recognized by one of skill in the art based on the definition provided herein. Typically, an HA1 C-terminal long stem segment corresponds to a polypeptide consisting of the alanine residue located in sequence at approximately the $253^{rd}$ residue of an HA1 (using H3 numbering) through the C-terminal amino acid of the HA1. This alanine residue, termed $C_q$ herein, is generally capable of being linked to a cysteine residue $C_p$ in the N-terminal long stem segment of HA1. Sequences of 16 representative influenza A hemagglutinins are presented in FIG. 1, and residue $C_q$ is identified in each.

In certain embodiments, the HA1 C-terminal long stem segment does not start at $C_q$ (e.g., $Ala_{253}$ of an HA1 subunit from an H3 hemagglutinin), but at a residue in sequence and structure vicinity to $C_q$. For example, in certain embodiments, the HA1 C-terminal long stem segment starts at $C_{q-1}$, $C_{q-2}$, $C_{q-3}$, or $C_{q-4}$. In other embodiments, the HA1 C-terminal long stem segment starts at $C_{q+1}$, $C_{q+2}$, $C_{q+3}$, $C_{q+4}$ or $C_{q+5}$. The end of an HA1 N-terminal long stem segment should be selected in conjunction with the start of the HA1 C-terminal long stem segment and the linker so that the resulting HA1 stem domain is capable of forming a three-dimensional structure similar, as described below, to an influenza hemagglutinin.

In certain embodiments, the influenza hemagglutinin long stem domain polypeptides comprise an HA1 C-terminal long stem segment having at least 70%, 75%, 80%, 85%, 90%, 95%, 96% or 98% amino acid sequence identity to an influenza HA1 C-terminal long stem segment known to those of skill in the art. Exemplary known HA1 C-terminal long stem segments are provided in the tables below.

In certain embodiments, the end of the N-terminal long stem segment is $C_{p-1}$, and the start of the C-terminal long stem segment is $C_{q-1}$. In certain embodiments, the end of the N-terminal long stem segment is $A_{p-2}$, and the start of the C-terminal long stem segment is $C_{q-2}$ In certain embodiments, the end of the N-terminal long stem segment is $C_{p-3}$, and the start of the C-terminal long stem segment is $C_{q-3}$ In certain embodiments, the end of the N-terminal long stem segment is $C_{p-4}$, and the start of the C-terminal long stem segment is $C_{q-4}$ In certain embodiments, the end of the N-terminal long stem segment is $C_{p-5}$, and the start of the C-terminal long stem segment is $C_{q-5}$.

In certain embodiments, the end of the N-terminal long stem segment is $C_{p+1}$, and the start of the C-terminal long stem segment is $C_{q+1}$ In certain embodiments, the end of the N-terminal long stem segment is $C_{p+2}$, and the start of the C-terminal long stem segment is $C_{q+2}$ In certain embodiments, the end of the N-terminal long stem segment is $C_{p+3}$, and the start of the C-terminal long stem segment is $C_{q+3}$ In certain embodiments, the end of the N-terminal long stem segment is $C_{p+4}$, and the start of the C-terminal long stem segment is $C_{q+4}$ In certain embodiments, the end of the N-terminal long stem segment is $C_{p+5}$, and the start of the C-terminal long stem segment is $C_{q+5}$.

In certain embodiments, the end of the N-terminal long stem segment is $C_{p-1}$, and the start of the C-terminal long stem segment is $C_{q+1}$ In certain embodiments, the end of the N-terminal long stem segment is $C_{p-2}$, and the start of the C-terminal long stem segment is $C_{q+2}$ In certain embodiments, the end of the N-terminal long stem segment is $C_{p-3}$, and the start of the C-terminal long stem segment is $C_{q+3}$. In certain embodiments, the end of the N-terminal long stem segment is $C_{p-4}$, and the start of the C-terminal long stem segment is $C_{q+4}$ In certain embodiments, the end of the N-terminal long stem segment is $C_{p-5}$, and the start of the C-terminal long stem segment is $C_{q+5}$.

In certain embodiments, the end of the N-terminal long stem segment is $C_{p+1}$, and the start of the C-terminal long stem segment is $C_{q-1}$. In certain embodiments, the end of the N-terminal long stem segment is $C_{p+2}$, and the start of the C-terminal long stem segment is $C_{q-2}$ In certain embodiments, the end of the N-terminal long stem segment is $C_{p+3}$, and the start of the C-terminal long stem segment is $C_{q-3}$ In certain embodiments, the end of the N-terminal long stem segment is $C_{p+4}$, and the start of the C-terminal long stem segment is $C_{q-4}$ In certain embodiments, the end of the N-terminal long stem segment is $C_{p+5}$, and the start of the C-terminal long stem segment is $C_{q-5}$.

Also provided herein are influenza hemagglutinin long stem domain polypeptides comprising deleted forms of HA1 C-terminal long stem segments wherein up to 10, 9, 8, 7, 6, 5, 4, 3, 2 or 1 amino acid residues are deleted from either or both termini of the HA1 C-terminal long stem segment. In certain embodiments, provided herein are influenza hemagglutinin long stem domain polypeptides that comprise expanded forms of HA1 C-terminal long stem segments wherein 1, 2 or 3 residues are added to the N-terminus of the HA1 C-terminal long stem segments; these added residues can be derived from the amino acid sequence of a globular head domain adjacent to an HA1 C-terminal long stem segment. In particular embodiments, if one residue is added to the C-terminal long stem segment, then one residue is added to the N-terminal long stem segment; if two residues are added to the C-terminal long stem segment, then two residues are added to the N-terminal long stem segment; if three residues are added to the C-terminal long stem segment, then three residues are added to the N-terminal long stem segment. Further provided herein are influenza hemagglutinin long stem domain polypeptides comprising altered forms of HA1 C-terminal long stem segments wherein up to 10, 9, 8, 7, 6, 5, 4, 3, 2 or 1 amino acid residues are conservatively substituted with other amino acids. Further provided are influenza hemagglutinin long stem domain polypeptides comprising deleted and altered HA1 C-terminal long stem segments.

The influenza hemagglutinin long stem domain polypeptides can be based on (i.e. can have sequence identity, as described above) any influenza hemagglutinin known to those of skill or later discovered. In certain embodiments, influenza hemagglutinin long stem domain polypeptides are based on an influenza A hemagglutinin. In certain embodiments, the influenza hemagglutinin long stem domain polypeptides are based on an influenza A hemagglutinin selected from the group consisting of H1, H2, H3, H4, H5, H6, H7, H8, H9, H10, H11, H12, H13, H14, H15 and H16. In certain embodiments, influenza hemagglutinin long stem domain polypeptides are based on an influenza B hemagglutinin, as described in detail below.

The HA1 N-terminal long stem segments can be based on (i.e. can have sequence identity, as described above) any HA1 N-terminal long stem segments known to those of skill or later discovered. In certain embodiments, the HA1 N-terminal long stem segments are based on influenza A HA1 N-terminal long stem segments. In certain embodiments, the HA1 N-terminal long stem segments are based on an influenza A hemagglutinin selected from the group consisting of H1, H2, H3, H4, H5, H6, H7, H8, H9, H10, H11, H12, H13, H14, H15 and H16. In certain embodiments, the HA1 N-terminal long stem segment is selected from SEQ ID NOS:414-429. In certain embodiments, the HA1 N-terminal long stem segment is selected from SEQ ID NOS:414-429, each having one amino acid deleted from its C-terminus. In certain embodiments, the HA1 N-terminal long stem segment is selected from SEQ ID NOS:414-429, each having two amino acids deleted from its C-terminus. In certain embodiments, the HA1 N-terminal long stem segment is selected from SEQ ID NOS:414-429, each having three amino acids deleted from its C-terminus. In certain embodiments, the HA1 N-terminal long stem segment is selected from SEQ ID NOS:414-429, each having four amino acids deleted from its C-terminus. In certain embodiments, the HA1 N-terminal long stem segment is selected from SEQ ID NOS:414-429, each having five amino acids deleted from its C-terminus. In certain embodiments, the HA1 N-terminal long stem segment is selected from SEQ ID NOS:446-493.

The HA1 C-terminal long stem segments can be based on (i.e. can have sequence identity, as described above) any HA1 C-terminal long stem segments known to those of skill or later discovered. In certain embodiments, the HA1 C-terminal long stem segments are based on influenza A HA1 C-terminal long stem segments. In certain embodiments, the HA1 C-terminal long stem segments are based on an influenza A hemagglutinin selected from the group consisting of H1, H2, H3, H4, H5, H6, H7, H8, H9, H10, H11, H12, H13, H14, H15 and H16. In certain embodiments, the HA1 C-terminal long stem segment is selected from SEQ ID NOS:430-445. In certain embodiments, the HA1 C-terminal long stem segment is selected from SEQ ID NOS: 430-445, each having one amino acid deleted from its N-terminus. In certain embodiments, the HA1 C-terminal long stem segment is selected from SEQ ID NOS: 430-445, each having two amino acids deleted from its N-terminus. In certain embodiments, the HA1 C-terminal long stem segment is selected from SEQ ID NOS: 430-445, each having three amino acids deleted from its N-terminus. In certain embodiments, the HA1 C-terminal long stem segment is selected from SEQ ID NOS: 430-445, each having four amino acids deleted from its N-terminus. In certain embodiments, the HA1 C-terminal long stem segment is selected from SEQ ID NOS: 430-445, each having five amino acids deleted from its N-terminus. In certain embodiments, the HA1 C-terminal long stem segment is selected from SEQ ID NOS:494-541.

The HA2 stem domains can be based on (i.e. can have sequence identity, as described above) any HA2 stem domains known to those of skill, later discovered, or described herein. In certain embodiments, the HA2 stem domains are based on influenza A HA2 stem domains. In certain embodiments, the HA2 stem domains are based on an influenza A hemagglutinin selected from the group consisting of H1, H2, H3, H4, H5, H6, H7, H8, H9, H10, H11, H12, H13, H14, H15 and H16. In certain embodiments, the HA2 stem domain is selected from SEQ ID NOS:66-97.

In embodiments comprising a signal peptide, the signal peptide can be based on any influenza signal peptide known to those of skill in the art or described herein. In certain embodiments, the signal peptide is selected from SEQ ID NOS:18-33.

In embodiments comprising a luminal domain, the luminal domain can be based on any influenza luminal domain known to those of skill in the art or described herein. In certain embodiments, the luminal domain is selected from SEQ ID NOS:98-113.

In embodiments comprising a transmembrane domain, the transmembrane domain can be based on any influenza transmembrane domain known to those of skill in the art or described herein. In certain embodiments, the transmembrane domain is selected from SEQ ID NOS:114-129.

In embodiments comprising a cytoplasmic domain, the cytoplasmic domain can be based on any influenza cytoplasmic domain known to those of skill in the art or described herein. In certain embodiments, the cytoplasmic domain is selected from SEQ ID NOS:130-145.

In certain embodiments, one or more of the glycosylation sites in the hemagglutinin stem domain are altered or deleted such that glycosylation at these sites will not occur during processing and maturation of the polypeptide. Those of skill in the art will recognize that influenza HA typically comprises one or more glycosylation sequences (e.g. Asn-Xaa-Ser/Thr/Cys, wherein Xaa is any amino acid other than Pro). In certain embodiments, one or more amino acid residues in a glycosylation sequence is conservatively substituted with an amino acid residue that disrupts the glycosylation sequence. In certain embodiments, one or more amino acid residues in a glycosylation sequence is substituted with any amino acid residue that disrupts the glycosylation sequence. In certain embodiments, one or more asparagine residues in a glycosylation sequence is substituted with alanine. In a particular embodiment, the asparagine at position 38 of an H3 hemagglutinin is changed to an alanine.

Table 7, below, identifies signal peptides, HA1 N-terminal long stem segments, HA1 C-terminal long stem segments and HA2 domains of influenza A hemagglutinin polypeptides. These signal peptides, stem segments and domains are useful in the polypeptides and methods described herein.

TABLE 7

Exemplary Influenza A Hemagglutinin Long Stem Domain Peptide Sequences

| HA Subtype (Genbank No.) | Signal Peptide | HA1 N-terminal Long Stem Segment | HA1 C-terminal Long Stem Segment | HA2 Domain |
|---|---|---|---|---|
| H1 PR8-H1N1 (EF467821.1) | MKAN LLVLL CALAA ADA [SEQ ID NO: 18] | DTICIGYHANN STDTVDTVLE KNVTVTHSVN LLEDSHNGKL CRLKGIAPLQL GKCNIAGWLL GNPECDPLLPV RSWSYIVETPN SENGIC [SEQ ID NO: 414] | APMYAFALSR GFGSGIITSNA SMHECNTKCQ TPLGAINSSLP YQNIHPVTIGE CPKYVRSAKL RMVTGLRNNP SIQSR [SEQ ID NO: 430] | GLFGAIAGFIEGGW TGMIDGWYGYHHQ NEQGSGYAADQKST QNAINGITNKVNTVI EKMNIQFTAVGKEF NKLEKRMENLNKK VDDGFLDIWTYNAE LLVLLENERTLDFH DSNVKNLYEKVKSQ LKNNAKEIGNGCFE FYHKCDNECMESVR NGTYDYPKYSEESK LNREKVDGVKLES MGIYQILAIYSTVAS SLVLLVSLGAISFW MCSNGSLQCRICI [SEQ ID NO: 66] |
| H2 (L11136) | MAIIY LILLFT AVRG [SEQ ID NO: 19] | DQICIGYHSNN STEKVDTILER NVTVTHAQNI LEKTHNGKLC KLNGIPPLELG DCSIAGWLLG NPECDRLLTVP EWSYIMEKEN PRNGLC [SEQ ID NO: 415] | APEYGFRISKR GSSGIMKTEGT LEN CETKCQTPLG AINTTLPFHNV HPLTIGECPKY VKSERLVLAT GLRNVPQIESR [SEQ ID NO: 431] | GLFGAIAGFIEGGW QGMIDGWYGYHHS NDQGSGYAADKEST QKAIDGITNRVNSVI EKMNTQFEAVGKEF SNLEKRLENLNKKM EDGFLDVWTYNAE LLVLMENERTLDFH DSNVKNLYDRVRM QLRDNAKELGNGCF EFYHKCDDECMNS VKNGTYDYPKYEEE SKLNRNEIKGVKLS NMGVYQILAIYATV |

TABLE 7-continued

Exemplary Influenza A Hemagglutinin Long Stem Domain Peptide Sequences

| HA Subtype (Genbank No.) | Signal Peptide | HA1 N-terminal Long Stem Segment | HA1 C-terminal Long Stem Segment | HA2 Domain |
|---|---|---|---|---|
| | | | | AGSLSLAIMIAGISL WMCSNGSLQCRICI [SEQ ID NO: 67] |
| H3 HK68-H3N2 (EF409245) PDB: 1HGJ | MKTII ALSYIF CLALG [SEQ ID NO: 20] | QDLPGNDNST ATLCLGHHAV PNGTLVKTITD DQIEVTNATEL VQSSSTGKICN NPHRILDGIDC TLIDALLGDPH CDVFQNETWD LFVERSKAFSNC [SEQ ID NO: 416] | APRGYFKMRT GKSSIMSSDAP IDTCISECITPN GSIPNDKPFQN VNKITYGACP KYVKQNTLKL ATGMRNVPEK QTR [SEQ ID NO: 432] | GLFGAIAGFIENGW EGMIDGWYGFRHQ NSEGTGQAADLKST QAAIDQINGKLNRVI EKTNEKFHQIEKEFS EVEGRIQDLEKYVE DTKIDLWSYNAELL VALENQHTIDLTDS EMNKLFEKTRRQLR ENAEDMGNGCFKIY HKCDNACIESIRNGT YDHDVYRDEALNN RFQIKGVELKSGYK DWILWISFAISCFLL CVVLLGFIMWACQR GNIRCNICI [SEQ ID NO: 68] |
| H4 (D90302) | MLSIVI LFLLIA ENSS [SEQ ID NO: 21] | QNYTGNPVIC MGHHAVANG TMVKTLADDQ VEVVTAQELV ESQNLPELCPS PLRLVDGQTC DIINGALGSPG CDHLNGAEW DVFIERPNAVD TC [SEQ ID NO: 417] | APRGHYKLNN QKKSTILNTAI PIGSCVSKCHT DKGSLSTTKPF QNISRIAVGDC PRYVKQGSLK LATGMRNIPE KASR [SEQ ID NO: 433] | GLFGAIAGFIENGW QGLIDGWYGFRHQ NAEGTGTAADLKST QAAIDQINGKLNRLI EKTNDKYHQIEKEF EQVEGRIQDLENYV EDTKIDLWSYNAEL LVALENQHTIDVTD SEMNKLFERVRRQL RENAEDKGNGCFEI FHKCDNNCIESIRNG TYDHDIYRDEAINN RFQIQGVKLTQGYK DIILWISFSISCFLLV ALLLAFILWACQNG NIRCQICI [SEQ ID NO: 69] |
| H5 (X07826) | MERIV LLLAI VSLVKS [SEQ ID NO: 22] | DQICIGYHAN KSTKQVDTIM EKNVTVTHAQ DILERTHNGKL CSLNGVKPLIL RDCSVAGWLL GNPMCDEFLN LPEWLYIVEK DNPINSLC [SEQ ID NO: 418] | APRYAYKIVK KGDSAIMKSG LAYGNCDTKC QTPVGEINSSM PFHNIHPHTIG ECPKYVKSDR LVLATGLRNV PQRKKR [SEQ ID NO: 434] | GLFGAIAGFIEGGW QGMVDGWYGYHH SNEQGSGYAADKES TQKAIDGITNKVNSI IDKMNTRFEAVGKE FNNLERRVENLNKK MEDGFLDVWTYNV ELLVLMENERTLDF HDSNVNNLYDKVR LQLKDNARELGNGC FEFYHKCDNECMES VRNGTYDYPQYSEE ARLNREEISGVKLES MGVYQILSIYSTVAS SLALAIMIAGLSFW MCSNGSLQCRICI [SEQ ID NO: 70] |
| H6 (D90303) | MIAIIV VAILA TAGRS [SEQ ID NO: 23] | DKICIGYHAN NSTTQIDTILE KNVTVTHSVE LLENQKEERF CKILKKAPLDL KGCTIEGWILG NPQCDLLLGD QSWSYIVERPT AQNGIC [SEQ ID NO: 419] | APWYAFRFVS TSNKGAVFKS NLPIENCDATC QTVAGVLRTN KTFQNVSPLWI GECPKYVKSE SLRLATGLRN VPQIETR [SEQ ID NO: 435] | GLFGAIAGFIEGGW TGMIDGWYGYHHE NSQGSGYAADREST QKAVDGITNKVNSII DKMNTQFEAVDHE FSNLERRIDNLNKR MEDGFLDVWTYNA ELLVLLENERTLDL HDANVKNLYERVK SQLRDNAMILGNGC FEFWHKCDDECMES VKNGTYDYPKYQD ESKLNRQEIESVKLE SLGVYQILAIYSTVS SSLVLVGLIIAVGLW |

TABLE 7-continued

Exemplary Influenza A Hemagglutinin Long Stem Domain Peptide Sequences

| HA Subtype (Genbank No.) | Signal Peptide | HA1 N-terminal Long Stem Segment | HA1 C-terminal Long Stem Segment | HA2 Domain |
|---|---|---|---|---|
| | | | | MCSNGSMQCRICI [SEQ ID NO: 71] |
| H7 (M24457) | MNTQILVFALVAVIPTNA [SEQ ID NO: 24] | DKICLGHHAVSNGTKVNTLTERGVEVVNATETVERTNIPKICSKGKRTTDLGQCGLLGTITGPPQCDQFLEFSADLIIERREGNDVC [SEQ ID NO: 420] | APNRASFLRGKSMGIQSDVQVDANCEGECYHSGGTITSRLPFQNINSRAVGKCPRYVKQESLLLATGMKNVPEPSKKRKKR [SEQ ID NO: 436] | GLFGAIAGFIENGWEGLVDGWYGFRHQNAQGEGTAADYKSTQSAIDQITGKLNRLIEKTNQQFELIDNEFTEVEKQIGNLINWTKDSITEVWSYNAELIVAMENQHTIDLADSEMNRLYERVRKQLRENAEEDGTGCFEIFHKCDDDCMASIRNNTYDHSKYREEAMQNRIQIDPVKLSSGYKDVILWFSFGASCFLLLAIAMGLVFICVKNGNMRCTICI [SEQ ID NO: 72] |
| H8 (D90304) | MEKFIAIATLASTNAY [SEQ ID NO: 25] | DRICIGYQSNNSTDTVNTLIEQNVPVTQTMELVETEKHPAYCNTDLGAPLELRDCKIEAVIYGNPKCDIHLKDQGWSYIVERPSAPEGMC [SEQ ID NO: 421] | APEFGYLLKGESYGRIIQNEDIPIGNCNTKCQTYAGAINSSKPFQNASRHYMGECPKYVKKASLRLAVGLRNTPSVEPR [SEQ ID NO: 437] | GLFGAIAGFIEGGWSGMIDGWYGFHHSNSEGTGMAADQKSTQEAIDKITNKVNNIVDKMNREFEVVNHEFSEVEKRINMINDKIDDQIEDLWAYNAELLVLLENQKTLDEHDSNVKNLFDEVKRRLSANAIDAGNGCFDILHKCDNECMETIKNGTYDHKEYEEEAKLERSKINGVKLEENTTYKILSIYSTVAASLCLAILIAGGLILGMQNGSCRCMFCI [SEQ ID NO: 73] |
| H9 (D90305) | METKAIIAALMVTAANA [SEQ ID NO: 26] | DKICIGYQSTNSTETVDTLTESNVPVTHTKELLHTEHNGMLCATDLGHPLILDTCTIEGLIYGNPSCDILLGGKEWSYIVERSSAVNGMC [SEQ ID NO: 422] | APWYGHVLTGESHGRILKTDLNNGNCVVQCQTEKGGLNTTLPFHNISKYAFGNCPKYVGVKSLKLPVGLRNVPAVSSR [SEQ ID NO: 438] | GLFGAIAGFIEGGWPGLVAGWYGFQHSNDQGVGMAADKGSTQKAIDKITSKVNNIIDKMNKQYEVIDHEFNELEARLNMINNKIDDQIQDIWAYNAELLVLLENQKTLDEHDANVNNLYNKVKRALGSNAVEDGNGCFELYHKCDDQCMETIRNGTYDRQKYQEESRLERQKIEGVKLESEGTYKILTIYSTVASSLVLAMGFAAFLFWAMSNGSCRCNICI [SEQ ID NO: 74] |
| H10 (M21647) | MYKVVVIIALLGAVKG [SEQ ID NO: 27] | LDRICLGHHAVANGTIVKTLTNEQEEVTNATETVESTNLNKLCMKGRSYKDLGNCHPVGMLIGTPVCDPHLTGTWDTLIERENAIAHC [SEQ ID NO: 423] | APSRVSKLTGRDLGIQSEALIDNSCESKCFWRGGSINTKLPFQNLSPRTVGQCPKYVNQRSLLLATGMRNVPEVVQGR [SEQ ID NO: 439] | GLFGAIAGFIENGWEGMVDGWYGFRHQNAQGTGQAADYKSTQAAIDQITGKLNRLIEKTNTEFESIESEFSETEHQIGNVINWTKDSITDIWTYNAELLVAMENQHTIDMADSEMLNLYERVRKQLRQNAEEDGKGCFEIYHTCDDSCMESIRNNTYDHSQYREEALLNRLNINPVKLSSGYK |

TABLE 7-continued

Exemplary Influenza A Hemagglutinin Long Stem Domain Peptide Sequences

| HA Subtype (Genbank No.) | Signal Peptide | HA1 N-terminal Long Stem Segment | HA1 C-terminal Long Stem Segment | HA2 Domain |
|---|---|---|---|---|
| | | | | DIILWFSFGESCFVL LAVVMGLVFFCLKN GNMRCTICI [SEQ ID NO: 75] |
| H11 (D90306) | MEKTL LFAAIF LCVKA [SEQ ID NO: 28] | DEICIGYLSNN STDKVDTIIEN NVTVTSSVEL VETEHTGSFCS INGKQPISLGD CSFAGWILGN PMCDELIGKTS WSYIVEKPNPT NGIC [SEQ ID NO: 424] | APRYAFEIVSV GNGKLFRSEL NIESCSTKCQT EIGGINTNKSF HNVHRNTIGD CPKYVNVKSL KLATGPRNVP AIASR [SEQ ID NO: 440] | GLFGAIAGFIEGGWP GLINGWYGFQHRDE EGTGIAADKESTQK AIDQITSKVNNIVDR MNTNFESVQHEFSEI EERINQLSKHVDDS VVDIWSYNAQLLVL LENEKTLDLHDSNV RNLHEKVRRMLKD NAKDEGNGCFTFYH KCDNKCIERVRNGT YDHKEFEEESKINR QEIEGVKLDSSGNV YKILSIYSCIASSLVL AALIMGFMFWACS NGSCRCTICI [SEQ ID NO: 76] |
| H12 (D90307) | MEKFII LSTVL AASFAY [SEQ ID NO: 29] | DKICIGYQTNN STETVNTLSEQ NVPVTQVEEL VHRGIDPILCG TELGSPLVLDD CSLEGLILGNP KCDLYLNGRE WSYIVERPKE MEGVC [SEQ ID NO: 425] | APEYGHLITG KSHGRILKNN LPMGQCVTEC QLNEGVMNTS KPFQNTSKHYI GKCPKYIPSGS LKLAIGLRNVP QVQDR [SEQ ID NO: 441] | GLFGAIAGFIEGGWP GLVAGWYGFQHQN AEGTGIAADRDSTQ RAIDNMQNKLNNVI DKMNKQFEVVNHE FSEVESRINMINSKI DDQITDIWAYNAEL LVLLENQKTLDEHD ANVRNLHDRVRRV LRENAIDTGDGCFEI LHKCDNNCMDTIRN GTYNHKEYEEESKI ERQKVNGVKLEENS TYKILSIYSSVASSL VLLLMIIGGFIFGCQ NGNVRCTFCI [SEQ ID NO: 77] |
| H13 (D90308) | MALN VIATL TLISVC VHA [SEQ ID NO: 30] | DRICVGYLSTN SSERVDTLLEN GVPVTSSIDLIE TNHTGTYCSL NGVSPVHLGD CSFEGWIVGN PACTSNFGIRE WSYLIEDPAAP HGLC [SEQ ID NO: 426] | APRYGYIIEEY GKGRIFQSRIR MSRCNTKCQT SVGGINTNRTF QNIDKNALGD CPKYIKSGQLK LATGLRNVPAI SNR [SEQ ID NO: 442] | GLFGAIAGFIEGGWP GLINGWYGFQHQNE QGTGIAADKESTQK AIDQITTKINNIIDKM NGNYDSIRGEFNQV EKRINMLADRIDDA VTDIWSYNAKLLVL LENDKTLDMHDAN VKNLHEQVRRELKD NAIDEGNGCFELLH KCNDSCMETIRNGT YDHTEYAEESKLKR QEIDGIKLKSEDNVY KALSIYSCIASSVVL VGLILSFIMWACSSG NCRFNVCI [SEQ ID NO: 78] |
| H14 (M35997) | MIALIL VALAL SHTAYS [SEQ ID NO: 31] | QITNGTTGNPII CLGHHAVENG TSVKTLTDNH VEVVSAKELV ETNHTDELCPS PLKLVDGQDC HLINGALGSPG CDRLQDTTWD VFIERPTAVDTC [SEQ ID NO: 427] | APRGHYKISKS TKSTVLKSDK RIGSCTSPCLT DKGSIQSDKPF QNVSRIAIGNC PKYVKQGSLM LATGMRNIPG KQAK [SEQ ID NO: 443] | GLFGAIAGFIENGW QGLIDGWYGFRHQ NAEGTGTAADLKST QAAIDQINGKLNRLI EKTNEKYHQIEKEF EQVEGRIQDLEKYV EDTKIDLWSYNAEL LVALENQHTIDVTD SEMNKLFERVRRQL RENAEDQGNGCFEI FHQCDNNCIESIRNG TYDHNIYRDEAINN RIKINPVTLTMGYK DIILWISFSMSCFVF |

TABLE 7-continued

Exemplary Influenza A Hemagglutinin Long Stem Domain Peptide Sequences

| HA Subtype (Genbank No.) | Signal Peptide | HA1 N-terminal Long Stem Segment | HA1 C-terminal Long Stem Segment | HA2 Domain |
|---|---|---|---|---|
| | | | | VALILGFVLWACQN GNIRCQICI [SEQ ID NO: 79] |
| H15 (L43917) | MNTQI IVILVL GLSMV KS [SEQ ID NO: 32] | DKICLGHHAV ANGTKVNTLT ERGVEVVNAT ETVEITGIDKV CTKGKKAVDL GSCGILGTIIGP PQCDLHLEFK ADLIIERRNSS DIC [SEQ ID NO: 428] | APDRATFLRS NAPSGIEYNG KSLGIQSDAQI DESCEGECFYS GGTINSPLPFQ NIDSRAVGKC PRYVKQSSLPL ALGMKNVPEK IRTR [SEQ ID NO: 444] | GLFGAIAGFIENGW EGLIDGWYGFRHQN AQGQGTAADYKST QAAIDQITGKLNRLI EKTNKQFELIDNEFT EVEQQIGNVINWTR DSLTEIWSYNAELL VAMENQHTIDLADS EMNKLYERVRRQL RENAEEDGTGCFEIF HRCDDQCMESIRNN TYNHTEYRQEALQN RIMINPVKLSSGYKD VILWFSFGASCVML LAIAMGLIFMCVKN GNLRCTICI [SEQ ID NO: 80] |
| H16 (EU293865) | MMIK VLYFLI IVLGR YSKA [SEQ ID NO: 33] | DKICIGYLSNN SSDTVDTLTEN GVPVTSSVDL VETNHTGTYC SLNGISPIHLG DCSFEGWIVG NPSCATNINIR EWSYLIEDPN APNKFC [SEQ ID NO: 429] | APRYGYIIEKY GTGRIFQSGVR MARCNTKCQT SLGGINTNKTF QNIERNALGD CPKYIKSGQLK LATGLRNVPSI GER [SEQ ID NO: 445] | GLFGAIAGFIEGGWP GLINGWYGFQHQNE QGTGIAADKASTQK AINEITTKINNIIEKM NGNYDSIRGEFNQV EKRINMLADRVDDA VTDIWSYNAKLLVL LENDRTLDLHDANV RNLHDQVKRALKS NAIDEGDGCFNLLH KCNDSCMETIRNGT YNHEDYREESQLKR QEIEGIKLKTEDNVY KVLSIYSCIASSIVLV GLILAFIMWACSNG SCRFNVCI [SEQ ID NO: 81] |

Table 7A, below, identifies useful HA1 N-terminal long stem segments and HA1 C-terminal long stem segments for the polypeptides and methods described herein.

TABLE 7A

Exemplary Influenza A Hemagglutinin Long Stem Domain Sequences

| HA Subtype (Genbank No.) | HA1 N-terminal Long Stem Segment | HA1 C-terminal Long Stem Segment |
|---|---|---|
| H1 PR8-H1N1 (EF467821.1) No Cys, Ala | DTICIGYHANNSTDTVDT VLEKNVTVTHSVNLLED SHNGKLCRLKGIAPLQL GKCNIAGWLLGNPECDP LLPVRSWSYIVETPNSEN GI [SEQ ID NO: 446] | PMYAFALSRGFGSGIITSNASMHECNT KCQTPLGAINSSLPYQNIHPVTIGECPK YVRSAKLRMVTGLRNNPSIQSR [SEQ ID NO: 494] |
| H1 PR8-H1N1 (EF467821.1) No Cys, Ala Δ1 | DTICIGYHANNSTDTVDT VLEKNVTVTHSVNLLED SHNGKLCRLKGIAPLQL GKCNIAGWLLGNPECDP LLPVRSWSYIVETPNSEN GI [SEQ ID NO: 447] | MYAFALSRGFGSGIITSNASMHECNTK CQTPLGAINSSLPYQNIHPVTIGECPKY VRSAKLRMVTGLRNNPSIQSR [SEQ ID NO: 495] |
| H1 PR8-H1N1 | DTICIGYHANNSTDTVDT VLEKNVTVTHSVNLLED | YAFALSRGFGSGIITSNASMHECNTKC QTPLGAINSSLPYQNIHPVTIGECPKYV |

TABLE 7A-continued

Exemplary Influenza A Hemagglutinin Long Stem Domain Sequences

| HA Subtype (Genbank No.) | HA1 N-terminal Long Stem Segment | HA1 C-terminal Long Stem Segment |
|---|---|---|
| (EF467821.1) No Cys, Ala Δ3 | SHNGKLCRLKGIAPLQL GKCNIAGWLLGNPECDP LLPVRSWSYIVETPNSENG [SEQ ID NO: 448] | RSAKLRMVTGLRNNPSIQSR [SEQ ID NO: 496] |
| H2 (L11136) No Cys, Ala | DQICIGYHSNNSTEKVDT ILERNVTVTHAQNILEKT HNGKLCKLNGIPPLELG DCSIAGWLLGNPECDRL LTVPEWSYIMEKENPRN GL [SEQ ID NO: 449] | PEYGFRISKRGSSGIMKTEGTLENCET KCQTPLGAINTTLPFHNVHPLTIGECP KYVKSERLVLATGLRNVPQIESR [SEQ ID NO: 497] |
| H2 (L11136) No Cys, Ala Δ1 | DQICIGYHSNNSTEKVDT ILERNVTVTHAQNILEKT HNGKLCKLNGIPPLELG DCSIAGWLLGNPECDRL LTVPEWSYIMEKENPRN GL [SEQ ID NO: 450] | EYGFRISKRGSSGIMKTEGTLENCETK CQTPLGAINTTLPFHNVHPLTIGECPK YVKSERLVLATGLRNVPQIESR [SEQ ID NO: 498] |
| H2 (L11136) No Cys, Ala Δ3 | DQICIGYHSNNSTEKVDT ILERNVTVTHAQNILEKT HNGKLCKLNGIPPLELG DCSIAGWLLGNPECDRL LTVPEWSYIMEKENPRNG [SEQ ID NO: 451] | YGFRISKRGSSGIMKTEGTLENCETKC QTPLGAINTTLPFHNVHPLTIGECPKY VKSERLVLATGLRNVPQIESR [SEQ ID NO: 499] |
| H3 HK68-H3N2 (EF409245) PDB: 1HGJ No Cys, Ala | QDLPGNDNSTATLCLGH HAVPNGTLVKTITDDQIE VTNATELVQSSSTGKICN NPHRILDGIDCTLIDALL GDPHCDVFQNETWDLF VERSKAFSN [SEQ ID NO: 452] | PRGYFKMRTGKSSIMSSDAPIDTCISEC ITPNGSIPNDKPFQNVNKITYGACPKY VKQNTLKLATGMRNVPEKQTR [SEQ ID NO: 500] |
| H3 HK68-H3N2 (EF409245) PDB: 1HGJ No Cys, Ala Δ1 | QDLPGNDNSTATLCLGH HAVPNGTLVKTITDDQIE VTNATELVQSSSTGKICN NPHRILDGIDCTLIDALL GDPHCDVFQNETWDLF VERSKAFSN [SEQ ID NO: 453] | RGYFKMRTGKSSIMSSDAPIDTCISECI TPNGSIPNDKPFQNVNKITYGACPKYV KQNTLKLATGMRNVPEKQTR [SEQ ID NO: 501] |
| H3 HK68-H3N2 (EF409245) PDB: 1HGJ No Cys, Ala Δ3 | QDLPGNDNSTATLCLGH HAVPNGTLVKTITDDQIE VTNATELVQSSSTGKICN NPHRILDGIDCTLIDALL GDPHCDVFQNETWDLF VERSKAFS [SEQ ID NO: 454] | GYFKMRTGKSSIMSSDAPIDTCISECIT PNGSIPNDKPFQNVNKITYGACPKYVK QNTLKLATGMRNVPEKQTR [SEQ ID NO: 502] |
| H4 (D90302) No Cys, Ala | QNYTGNPVICMGHHAV ANGTMVKTLADDQVEV VTAQELVESQNLPELCPS PLRLVDGQTCDIINGALG SPGCDHLNGAEWDVFIE RPNAVDT [SEQ ID NO: 455] | PRGHYKLNNQKKSTILNTAIPIGSCVS KCHTDKGSLSTTKPFQNISRIAVGDCP RYVKQGSLKLATGMRNIPEKASR [SEQ ID NO: 503] |
| H4 (D90302) No Cys, Ala Δ1 | QNYTGNPVICMGHHAV ANGTMVKTLADDQVEV VTAQELVESQNLPELCPS PLRLVDGQTCDIINGALG SPGCDHLNGAEWDVFIE RPNAVDT [SEQ ID NO: 456] | RGHYKLNNQKKSTILNTAIPIGSCVSK CHTDKGSLSTTKPFQNISRIAVGDCPR YVKQGSLKLATGMRNIPEKASR [SEQ ID NO: 504] |

TABLE 7A-continued

Exemplary Influenza A Hemagglutinin Long Stem Domain Sequences

| HA Subtype (Genbank No.) | HA1 N-terminal Long Stem Segment | HA1 C-terminal Long Stem Segment |
|---|---|---|
| H4 (D90302) No Cys, Ala Δ3 | QNYTGNPVICMGHHAV ANGTMVKTLADDQVEV VTAQELVESQNLPELCPS PLRLVDGQTCDIINGALG SPGCDHLNGAEWDVFIE RPNAVD [SEQ ID NO: 457] | GHYKLNNQKKSTILNTAIPIGSCVSKC HTDKGSLSTTKPFQNISRIAVGDCPRY VKQGSLKLATGMRNIPEKASR [SEQ ID NO: 505] |
| H5 (X07826) No Cys, Ala | DQICIGYHANKSTKQVD TIMEKNVTVTHAQDILE RTHNGKLCSLNGVKPLI LRDCSVAGWLLGNPMC DEFLNLPEWLYIVEKDN PINSL [SEQ ID NO: 458] | PRYAYKIVKKGDSAIMKSGLAYGNCD TKCQTPVGEINSSMPFHNIHPHTIGECP KYVKSDRLVLATGLRNVPQRKKR [SEQ ID NO: 506] |
| H5 (X07826) No Cys, Ala Δ1 | DQICIGYHANKSTKQVD TIMEKNVTVTHAQDILE RTHNGKLCSLNGVKPLI LRDCSVAGWLLGNPMC DEFLNLPEWLYIVEKDN PINSL [SEQ ID NO: 459] | RYAYKIVKKGDSAIMKSGLAYGNCDT KCQTPVGEINSSMPFHNIHPHTIGECPK YVKSDRLVLATGLRNVPQRKKR [SEQ ID NO: 507] |
| H5 (X07826) No Cys, Ala Δ3 | DQICIGYHANKSTKQVD TIMEKNVTVTHAQDILE RTHNGKLCSLNGVKPLI LRDCSVAGWLLGNPMC DEFLNLPEWLYIVEKDN PINS [SEQ ID NO: 460] | YAYKIVKKGDSAIMKSGLAYGNCDTK CQTPVGEINSSMPFHNIHPHTIGECPKY VKSDRLVLATGLRNVPQRKKR [SEQ ID NO: 508] |
| H6 (D90303) No Cys, Ala | DKICIGYHANNSTTQIDT ILEKNVTVTHSVELLENQ KEERFCKILKKAPLDLK GCTIEGWILGNPQCDLLL GDQSWSYIVERPTAQNGI [SEQ ID NO: 461] | PWYAFRFVSTSNKGAVFKSNLPIENC DATCQTVAGVLRTNKTFQNVSPLWIG ECPKYVKSESLRLATGLRNVPQIETR [SEQ ID NO: 509] |
| H6 (D90303) No Cys, Ala Δ1 | DKICIGYHANNSTTQIDT ILEKNVTVTHSVELLENQ KEERFCKILKKAPLDLK GCTIEGWILGNPQCDLLL GDQSWSYIVERPTAQNGI [SEQ ID NO: 462] | WYAFRFVSTSNKGAVFKSNLPIENCD ATCQTVAGVLRTNKTFQNVSPLWIGE CPKYVKSESLRLATGLRNVPQIETR [SEQ ID NO: 510] |
| H6 (D90303) No Cys, Ala Δ3 | DKICIGYHANNSTTQIDT ILEKNVTVTHSVELLENQ KEERFCKILKKAPLDLK GCTIEGWILGNPQCDLLL GDQSWSYIVERPTAQNG [SEQ ID NO: 463] | YAFRFVSTSNKGAVFKSNLPIENCDAT CQTVAGVLRTNKTFQNVSPLWIGECP KYVKSESLRLATGLRNVPQIETR [SEQ ID NO: 511] |
| H7 (M24457) No Cys, Ala | DKICLGHHAVSNGTKVN TLTERGVEVVNATETVE RTNIPKICSKGKRTTDLG QCGLLGTITGPPQCDQFL EFSADLIIERREGNDV [SEQ ID NO: 464] | PNRASFLRGKSMGIQSDVQVDANCEG ECYHSGGTITSRLPFQNINSRAVGKCP RYVKQESLLLATGMKNVPEPSKKRKKR [SEQ ID NO: 512] |
| H7 (M24457) No Cys, Ala Δ1 | DKICLGHHAVSNGTKVN TLTERGVEVVNATETVE RTNIPKICSKGKRTTDLG QCGLLGTITGPPQCDQFL EFSADLIIERREGNDV [SEQ ID NO: 465] | NRASFLRGKSMGIQSDVQVDANCEGE CYHSGGTITSRLPFQNINSRAVGKCPR YVKQESLLLATGMKNVPEPSKKRKKR [SEQ ID NO: 513] |
| H7 (M24457) No Cys, Ala Δ3 | DKICLGHHAVSNGTKVN TLTERGVEVVNATETVE RTNIPKICSKGKRTTDLG QCGLLGTITGPPQCDQFL EFSADLIIERREGND [SEQ ID NO: 466] | RASFLRGKSMGIQSDVQVDANCEGEC YHSGGTITSRLPFQNINSRAVGKCPRY VKQESLLLATGMKNVPEPSKKRKKR [SEQ ID NO: 514] |

TABLE 7A-continued

Exemplary Influenza A Hemagglutinin Long Stem Domain Sequences

| HA Subtype (Genbank No.) | HA1 N-terminal Long Stem Segment | HA1 C-terminal Long Stem Segment |
|---|---|---|
| H8 (D90304) No Cys, Ala | DRICIGYQSNNSTDTVNT LIEQNVPVTQTMELVET EKHPAYCNTDLGAPLEL RDCKIEAVIYGNPKCDIH LKDQGWSYIVERPSAPE GM [SEQ ID NO: 467] | PEFGYLLKGESYGRIIQNEDIPIGNCNT KCQTYAGAINSSKPFQNASRHYMGEC PKYVKKASLRLAVGLRNTPSVEPR [SEQ ID NO: 515] |
| H8 (D90304) No Cys, Ala Δ1 | DRICIGYQSNNSTDTVNT LIEQNVPVTQTMELVET EKHPAYCNTDLGAPLEL RDCKIEAVIYGNPKCDIH LKDQGWSYIVERPSAPE GM [SEQ ID NO: 468] | EFGYLLKGESYGRIIQNEDIPIGNCNTK CQTYAGAINSSKPFQNASRHYMGECP KYVKKASLRLAVGLRNTPSVEPR [SEQ ID NO: 516] |
| H8 (D90304) No Cys, Ala Δ3 | DRICIGYQSNNSTDTVNT LIEQNVPVTQTMELVET EKHPAYCNTDLGAPLEL RDCKIEAVIYGNPKCDIH LKDQGWSYIVERPSAPEG [SEQ ID NO: 469] | FGYLLKGESYGRIIQNEDIPIGNCNTKC QTYAGAINSSKPFQNASRHYMGECPK YVKKASLRLAVGLRNTPSVEPR [SEQ ID NO: 517] |
| H9 (D90305) No Cys, Ala | DKICIGYQSTNSTETVDT LTESNVPVTHTKELLHTE HNGMLCATDLGHPLILD TCTIEGLIYGNPSCDILLG GKEWSYIVERSSAVNGM [SEQ ID NO: 470] | PWYGHVLTGESHGRILKTDLNNGNCV VQCQTEKGGLNTTLPFHNISKYAFGN CPKYVGVKSLKLPVGLRNVPAVSSR [SEQ ID NO: 518] |
| H9 (D90305) No Cys, Ala Δ1 | DKICIGYQSTNSTETVDT LTESNVPVTHTKELLHTE HNGMLCATDLGHPLILD TCTIEGLIYGNPSCDILLG GKEWSYIVERSSAVNGM [SEQ ID NO: 471] | WYGHVLTGESHGRILKTDLNNGNCV VQCQTEKGGLNTTLPFHNISKYAFGN CPKYVGVKSLKLPVGLRNVPAVSSR [SEQ ID NO: 519] |
| H9 (D90305) No Cys, Ala Δ3 | DKICIGYQSTNSTETVDT LTESNVPVTHTKELLHTE HNGMLCATDLGHPLILD TCTIEGLIYGNPSCDILLG GKEWSYIVERSSAVNG [SEQ ID NO: 472] | YGHVLTGESHGRILKTDLNNGNCVVQ CQTEKGGLNTTLPFHNISKYAFGNCPK YVGVKSLKLPVGLRNVPAVSSR [SEQ ID NO: 520] |
| H10 (M21647) No Cys, Ala | LDRICLGHHAVANGTIV KTLTNEQEEVTNATETV ESTNLNKLCMKGRSYKD LGNCHPVGMLIGTPVCD PHLTGTWDTLIERENAIAH [SEQ ID NO: 473] | PSRVSKLTGRDLGIQSEALIDNSCESK CFWRGGSINTKLPFQNLSPRTVGQCPK YVNQRSLLLATGMRNVPEVVQGR [SEQ ID NO: 521] |
| H10 (M21647) No Cys, Ala Δ1 | LDRICLGHHAVANGTIV KTLTNEQEEVTNATETV ESTNLNKLCMKGRSYKD LGNCHPVGMLIGTPVCD PHLTGTWDTLIERENAIAH [SEQ ID NO: 474] | SRVSKLTGRDLGIQSEALIDNSCESKC FWRGGSINTKLPFQNLSPRTVGQCPKY VNQRSLLLATGMRNVPEVVQGR [SEQ ID NO: 522] |
| H10 (M21647) No Cys, Ala Δ3 | LDRICLGHHAVANGTIV KTLTNEQEEVTNATETV ESTNLNKLCMKGRSYKD LGNCHPVGMLIGTPVCD PHLTGTWDTLIERENAIA [SEQ ID NO: 475] | RVSKLTGRDLGIQSEALIDNSCESKCF WRGGSINTKLPFQNLSPRTVGQCPKY VNQRSLLLATGMRNVPEVVQGR [SEQ ID NO: 523] |
| H11 (D90306) No Cys, Ala | DEICIGYLSNNSTDKVDT IIENNVTVTSSVELVETE HTGSFCSINGKQPISLGD CSFAGWILGNPMCDELI GKTSWSYIVEKPNPTNGI [SEQ ID NO: 476] | PRYAFEIVSVGNGKLFRSELNIESCSTK CQTEIGGINTNKSFHNVHRNTIGDCPK YVNVKSLKLATGPRNVPAIASR [SEQ ID NO: 524] |

TABLE 7A-continued

Exemplary Influenza A Hemagglutinin Long Stem Domain Sequences

| HA Subtype (Genbank No.) | HA1 N-terminal Long Stem Segment | HA1 C-terminal Long Stem Segment |
|---|---|---|
| H11<br>(D90306)<br>No Cys, Ala<br>Δ1 | DEICIGYLSNNSTDKVDT<br>IIENNVTVTSSVELVETE<br>HTGSFCSINGKQPISLGD<br>CSFAGWILGNPMCDELI<br>GKTSWSYIVEKPNPTNGI<br>[SEQ ID NO: 477] | RYAFEIVSVGNGKLFRSELNIESCSTKC<br>QTEIGGINTNKSFHNVHRNTIGDCPKY<br>VNVKSLKLATGPRNVPAIASR<br>[SEQ ID NO: 525] |
| H11<br>(D90306)<br>No Cys, Ala<br>Δ3 | DEICIGYLSNNSTDKVDT<br>IIENNVTVTSSVELVETE<br>HTGSFCSINGKQPISLGD<br>CSFAGWILGNPMCDELI<br>GKTSWSYIVEKPNPTNG<br>[SEQ ID NO: 478] | YAFEIVSVGNGKLFRSELNIESCSTKC<br>QTEIGGINTNKSFHNVHRNTIGDCPKY<br>VNVKSLKLATGPRNVPAIASR<br>[SEQ ID NO: 526] |
| H12<br>(D90307)<br>No Cys, Ala | DKICIGYQTNNSTETVNT<br>LSEQNVPVTQVEELVHR<br>GIDPILCGTELGSPLVLD<br>DCSLEGLILGNPKCDLYL<br>NGREWSYIVERPKEMEGV<br>[SEQ ID NO: 479] | PEYGHLITGKSHGRILKNNLPMGQCV<br>TECQLNEGVMNTSKPFQNTSKHYIGK<br>CPKYIPSGSLKLAIGLRNVPQVQDR<br>[SEQ ID NO: 527] |
| H12<br>(D90307)<br>No Cys, Ala<br>Δ1 | DKICIGYQTNNSTETVNT<br>LSEQNVPVTQVEELVHR<br>GIDPILCGTELGSPLVLD<br>DCSLEGLILGNPKCDLYL<br>NGREWSYIVERPKEMEGV<br>[SEQ ID NO: 480] | EYGHLITGKSHGRILKNNLPMGQCVT<br>ECQLNEGVMNTSKPFQNTSKHYIGKC<br>PKYIPSGSLKLAIGLRNVPQVQDR<br>[SEQ ID NO: 528] |
| H12<br>(D90307)<br>No Cys, Ala<br>Δ3 | DKICIGYQTNNSTETVNT<br>LSEQNVPVTQVEELVHR<br>GIDPILCGTELGSPLVLD<br>DCSLEGLILGNPKCDLYL<br>NGREWSYIVERPKEMEG<br>[SEQ ID NO: 481] | YGHLITGKSHGRILKNNLPMGQCVTE<br>CQLNEGVMNTSKPFQNTSKHYIGKCP<br>KYIPSGSLKLAIGLRNVPQVQDR<br>[SEQ ID NO: 529] |
| H13<br>(D90308)<br>No Cys, Ala | DRICVGYLSTNSSERVDT<br>LLENGVPVTSSIDLIETN<br>HTGTYCSLNGVSPVHLG<br>DCSFEGWIVGNPACTSN<br>FGIREWSYLIEDPAAPHGL<br>[SEQ ID NO: 482] | PRYGYIIEEYGKGRIFQSRIRMSRCNTK<br>CQTSVGGINTNRTFQNIDKNALGDCP<br>KYIKSGQLKLATGLRNVPAISNR<br>[SEQ ID NO: 530] |
| H13<br>(D90308)<br>No Cys, Ala<br>Δ1 | DRICVGYLSTNSSERVDT<br>LLENGVPVTSSIDLIETN<br>HTGTYCSLNGVSPVHLG<br>DCSFEGWIVGNPACTSN<br>FGIREWSYLIEDPAAPHGL<br>[SEQ ID NO: 483] | RYGYIIEEYGKGRIFQSRIRMSRCNTK<br>CQTSVGGINTNRTFQNIDKNALGDCP<br>KYIKSGQLKLATGLRNVPAISNR<br>[SEQ ID NO: 531] |
| H13<br>(D90308)<br>No Cys, Ala<br>Δ3 | DRICVGYLSTNSSERVDT<br>LLENGVPVTSSIDLIETN<br>HTGTYCSLNGVSPVHLG<br>DCSFEGWIVGNPACTSN<br>FGIREWSYLIEDPAAPHG<br>[SEQ ID NO: 484] | YGYIIEEYGKGRIFQSRIRMSRCNTKC<br>QTSVGGINTNRTFQNIDKNALGDCPK<br>YIKSGQLKLATGLRNVPAISNR<br>[SEQ ID NO: 532] |
| H14<br>(M35997)<br>No Cys, Ala | QITNGTTGNPIICLGHHA<br>VENGTSVKTLTDNHVEV<br>VSAKELVETNHTDELCP<br>SPLKLVDGQDCHLINGA<br>LGSPGCDRLQDTTWDVF<br>IERPTAVDT<br>[SEQ ID NO: 485] | PRGHYKISKSTKSTVLKSDKRIGSCTSP<br>CLTDKGSIQSDKPFQNVSRIAIGNCPK<br>YVKQGSLMLATGMRNIPGKQAK<br>[SEQ ID NO: 533] |
| H14<br>(M35997)<br>No Cys, Ala<br>Δ1 | QITNGTTGNPIICLGHHA<br>VENGTSVKTLTDNHVEV<br>VSAKELVETNHTDELCP<br>SPLKLVDGQDCHLINGA<br>LGSPGCDRLQDTTWDVF<br>IERPTAVDT<br>[SEQ ID NO: 486] | RGHYKISKSTKSTVLKSDKRIGSCTSP<br>CLTDKGSIQSDKPFQNVSRIAIGNCPK<br>YVKQGSLMLATGMRNIPGKQAK<br>[SEQ ID NO: 534] |

TABLE 7A-continued

Exemplary Influenza A Hemagglutinin Long Stem Domain Sequences

| HA Subtype (Genbank No.) | HA1 N-terminal Long Stem Segment | HA1 C-terminal Long Stem Segment |
|---|---|---|
| H14 (M35997) No Cys, Ala Δ3 | QITNGTTGNPIICLGHHA VENGTSVKTLTDNHVEV VSAKELVETNHTDELCP SPLKLVDGQDCHLINGA LGSPGCDRLQDTTWDVF IERPTAVD [SEQ ID NO: 487] | GHYKISKSTKSTVLKSDKRIGSCTSPC LTDKGSIQSDKPFQNVSRIAIGNCPKY VKQGSLMLATGMRNIPGKQAK [SEQ ID NO: 535] |
| H15 (L43917) No Cys, Ala | DKICLGHHAVANGTKV NTLTERGVEVVNATETV EITGIDKVCTKGKKAVD LGSCGILGTIIGPPQCDLH LEFKADLIIERRNSSDI [SEQ ID NO: 488] | PDRATFLRSNAPSGIEYNGKSLGIQSD AQIDESCEGECFYSGGTINSPLPFQNID SRAVGKCPRYVKQSSLPLALGMKNVP EKIRTR [SEQ ID NO: 536] |
| H15 (L43917) No Cys, Ala Δ1 | DKICLGHHAVANGTKV NTLTERGVEVVNATETV EITGIDKVCTKGKKAVD LGSCGILGTIIGPPQCDLH LEFKADLIIERRNSSDI [SEQ ID NO: 489] | DRATFLRSNAPSGIEYNGKSLGIQSDA QIDESCEGECFYSGGTINSPLPFQNIDS RAVGKCPRYVKQSSLPLALGMKNVPE KIRTR [SEQ ID NO: 537] |
| H15 (L43917) No Cys, Ala Δ3 | DKICLGHHAVANGTKV NTLTERGVEVVNATETV EITGIDKVCTKGKKAVD LGSCGILGTIIGPPQCDLH LEFKADLIIERRNSSD [SEQ ID NO: 490] | RATFLRSNAPSGIEYNGKSLGIQSDAQI DESCEGECFYSGGTINSPLPFQNIDSRA VGKCPRYVKQSSLPLALGMKNVPEKI RTR [SEQ ID NO: 538] |
| H16 (EU293865) No Cys, Ala | DKICIGYLSNNSSDTVDT LTENGVPVTSSVDLVET NHTGTYCSLNGISPIHLG DCSFEGWIVGNPSCATNI NIREWSYLIEDPNAPNKF [SEQ ID NO: 491] | PRYGYIIEKYGTGRIFQSGVRMARCNT KCQTSLGGINTNKTFQNIERNALGDCP KYIKSGQLKLATGLRNVPSIGER [SEQ ID NO: 539] |
| H16 (EU293865) No Cys, Ala Δ1 | DKICIGYLSNNSSDTVDT LTENGVPVTSSVDLVET NHTGTYCSLNGISPIHLG DCSFEGWIVGNPSCATNI NIREWSYLIEDPNAPNKF [SEQ ID NO: 492] | RYGYIIEKYGTGRIFQSGVRMARCNT KCQTSLGGINTNKTFQNIERNALGDCP KYIKSGQLKLATGLRNVPSIGER [SEQ ID NO: 540] |
| H16 (EU293865) No Cys, Ala Δ3 | DKICIGYLSNNSSDTVDT LTENGVPVTSSVDLVET NHTGTYCSLNGISPIHLG DCSFEGWIVGNPSCATNI NIREWSYLIEDPNAPNK [SEQ ID NO: 493] | YGYIIEKYGTGRIFQSGVRMARCNTK CQTSLGGINTNKTFQNIERNALGDCPK YIKSGQLKLATGLRNVPSIGER [SEQ ID NO: 541] |

In certain embodiments, the influenza hemagglutinin long stem domain polypeptides comprise one or more immunogenic epitopes in the tertiary or quaternary structure of an influenza hemagglutinin long stem domain polypeptide.

In certain embodiments, the HA1 N-terminal long stem segment comprises the amino acid sequence $A_{17}$-$A_{18}$-(Xaa)$_n$-$A_{38}$ (SEQ ID NO:146), wherein $A_{17}$ is Y or H;

$A_{18}$ is H, L, or Q;

(Xaa)$_n$ represents a sequence of 18-20 amino acid residues; and $A_{38}$ is H, S, Q, T or N.

In certain embodiments, the HA1 C-terminal long stem segment comprises the amino acid sequence $A_{291}$-$A_{292}$ (SEQ ID NO:147), wherein $A_{291}$ is T, S, N, D, P or K; and $A_{292}$ is L, M, K or R.

In certain embodiments, the HA2 domain comprises the amino acid sequence $A_{18}$-$A_{19}$-$A_{20}$-$A_{21}$ (SEQ ID NO:148), wherein $A_{18}$ is V or I;

$A_{19}$ is D, N or A;

$A_{20}$ is G, and $A_{21}$ is W.

In certain embodiments, the HA2 domain comprises the amino acid sequence $A_{38}$-$A_{39}$-$A_{40}$-$A_{41}$-$A_{42}$-$A_{43}$-$A_{44}$-$A_{45}$-$A_{46}$-$A_{47}$-$A_{48}$-$A_{49}$-$A_{50}$-$A_{51}$-$A_{52}$-$A_{53}$-$A_{54}$-$A_{55}$-$A_{56}$ (SEQ ID NO:149), wherein $A_{38}$ is K, Q, R, L or Y;

$A_{39}$ is any amino acid residue;

$A_{40}$ is any amino acid residue;

$A_{41}$ is T;

$A_{42}$ is Q;

$A_{43}$ is any amino acid residue;

$A_{44}$ is A;

$A_{45}$ is I;
$A_{46}$ is D;
$A_{47}$ is any amino acid residue;
$A_{48}$ is I, V or M;
$A_{49}$ is T, Q or N;
$A_{50}$ is any amino acid residue;
$A_{51}$ is K;
$A_{52}$ is V or L;
$A_{53}$ is N;
$A_{54}$ is any amino acid residue;
$A_{55}$ is V, I or L; and
$A_{56}$ is V or I.

In certain embodiments, the influenza stem domain polypeptides comprise two amino acid sequences selected from SEQ ID NOS:146-149. In certain embodiments, the influenza stem domain polypeptides comprise three amino acid sequences selected from SEQ ID NOS:146-149. In certain embodiments, the influenza stem domain polypeptides comprise four amino acid sequences selected from SEQ ID NOS:146-149.

As illustrated in FIGS. 1 and 2, HA1 N-terminal long stem segments share sequence identity between influenza A and influenza B and additionally across influenza A subtypes. Similarly, HA1 C-terminal long stem segments also share sequence identity between influenza A and influenza B and additionally across influenza A subtypes. Further, HA2 domains also share sequence identity between influenza A and influenza B and additionally across influenza A subtypes.

In some embodiments, the influenza hemagglutinin long stem domain polypeptide is a hybrid polypeptide that comprises or consists essentially of segments and/or domains from a plurality of influenza strains or subtypes. For example, an influenza hemagglutinin long stem domain polypeptide can comprise HA1 N-terminal and HA1 C-terminal long stem segments from different influenza A virus HA subtypes. In some embodiments, the HA1 N-terminal long stem segment is from influenza A virus while the HA1 C-terminal long stem segment is from influenza B virus. Similarly, HA2 may also be from influenza A virus while the HA1 N-terminal and/or C-terminal long stem segment is from influenza B virus.

It will be understood that any combination of the sequence elements listed in Tables 2-4, 6, 6a or the variants thereof may be used to form the hemagglutinin HA long stem domain polypeptides of the present invention.

In an influenza stem domain polypeptide provided herein, a linker covalently connects the HA1 N-terminal long stem segment to the HA1 C-terminal long stem segment. The linker can be any linked deemed suitable by one of skill in the art including, but not limited to, those linkers described herein.

In certain embodiments, influenza hemagglutinin long stem domain polypeptides are capable of forming a three dimensional structure that is similar to the three dimensional structure of the stem domain of a native influenza hemagglutinin. Structural similarity can be evaluated based on any technique deemed suitable by those of skill in the art including, but not limited to, those techniques described herein.

In certain embodiments, any influenza hemagglutinin long stem domain polypeptide provided herein can further comprise one or more polypeptide domains deemed suitable to those of skill in the art. Useful polypeptide domains include domains that facilitate purification, folding and cleavage of portions of a polypeptide. For example, a His tag (His-His-His-His-His-His, SEQ ID NO:166), FLAG epitope or other purification tag can facilitate purification of a polypeptide provided herein. A foldon, or trimerization, domain from bacteriophage T4 fibritin can facilitate trimerization of polypeptides provided herein. The foldon domain can have any foldon sequence known to those of skill in the art (see, e.g., Papanikolopoulou et al., 2004, *J. Biol. Chem.* 279(10):8991-8998, the contents of which are hereby incorporated by reference in their entirety. Examples include GSGYIPEAPRDGQAYVRKDGEWVLLSTFL (SEQ ID NO:167). A foldon domain can be useful to facilitate trimerization of soluble polypeptides provided herein. Cleavage sites can be used to facilitate cleavage of a portion of a polypeptide, for example cleavage of a purification tag or foldon domain or both. Useful cleavage sites include a thrombin cleavage site, for example one with the sequence LVPRGSP (SEQ ID NO:168).

In certain embodiments, provided are influenza hemagglutinin long stem domain polypeptides comprising an elastase cleavage site as described herein. In particular embodiments, provided herein are influenza hemagglutinin long stem domain polypeptides comprising any of SEQ ID NOS:430-445 wherein the C-terminal amino acid residue, e.g. arginine or lysine, of SEQ ID NOS:430-445 is substituted with a valine residue.

In certain embodiments, provided herein are influenza hemagglutinin long stem domain polypeptides that are predicted to be resistant to protease cleavage at the junction between HA1 and HA2. Those of skill in the art should recognize that the Arg-Gly sequence spanning HA1 and HA2 is a recognition site for trypsin and is typically cleaved for hemagglutinin activiation. Since the stem domain polypeptides described herein need not be activated, provided herein are influenza hemagglutinin long stem domain polypeptides that are predicted to be resistant to protease cleavage. In certain embodiments, provided is any influenza hemagglutinin long stem domain polypeptide described herein wherein the protease site spanning HA1 and HA2 is mutated to a sequence that is resistant to protease cleavage. In certain embodiments, provided is any influenza hemagglutinin long stem domain polypeptide described herein wherein the C-terminal residue of the HA1 C-terminal long stem segment is any residue other than Lys or Arg. In certain embodiments, provided is any influenza hemagglutinin long stem domain polypeptide described herein wherein the N-terminal residue of the HA2 domain is proline. In certain embodiments, provided is any influenza hemagglutinin long stem domain polypeptide described herein wherein the C-terminal residue of the HA1 C-terminal long stem segment is Ala and the N-terminal residue of the HA2 domain is also Ala. In certain embodiments, provided is any influenza hemagglutinin long stem domain polypeptide described herein wherein the N-terminal residue of the HA2 domain is any residue other than glycine.

In certain embodiments, provided herein are influenza hemagglutinin long stem domain polypeptides consisting of an HA1 N-terminal long stem segment covalently linked to a linker, in turn covalently linked to an HA1 C-terminal long stem segment in binding association with an HA2 stem domain. In certain embodiments, provided herein are influenza hemagglutinin long stem domain polypeptides consisting of an HA1 N-terminal long stem segment covalently linked to a linker, in turn covalently linked to an HA1 C-terminal long stem segment, in turn covalently linked to an HA2 stem domain. In certain embodiments, provided herein are influenza hemagglutinin long stem domain polypeptides consisting of a signal peptide covalently linked to an HA1 N-terminal long stem segment covalently linked to a linker, in turn covalently linked to an HA1 C-terminal long stem segment, in turn covalently linked to an HA2 stem domain.

In certain embodiments, provided herein are influenza hemagglutinin long stem domain polypeptides consisting of an HA1 N-terminal long stem segment covalently linked to a linker, in turn covalently linked to an HA1 C-terminal long stem segment in binding association with an HA2 stem domain that is covalently linked to an HA2 luminal domain. In certain embodiments, provided herein are influenza hemagglutinin long stem domain polypeptides consisting of an HA1 N-terminal long stem segment covalently linked to a linker, in turn covalently linked to an HA1 C-terminal long stem segment, in turn covalently linked to an HA2 stem domain that is covalently linked to an HA2 luminal domain. In certain embodiments, provided herein are influenza hemagglutinin long stem domain polypeptides consisting of a signal peptide covalently linked to an HA1 N-terminal long stem segment covalently linked to a linker, in turn covalently linked to an HA1 C-terminal long stem segment, in turn covalently linked to an HA2 stem domain that is covalently linked to an HA2 luminal domain.

In certain embodiments, provided herein are influenza hemagglutinin long stem domain polypeptides consisting of an HA1 N-terminal long stem segment covalently linked to a linker, in turn covalently linked to an HA1 C-terminal long stem segment in binding association with an HA2 stem domain that is covalently linked to, in sequence, a thrombin cleavage site, a foldon domain and a His tag. In certain embodiments, provided herein are influenza hemagglutinin long stem domain polypeptides consisting of an HA1 N-terminal long stem segment covalently linked to a linker, in turn covalently linked to an HA1 C-terminal long stem segment, in turn covalently linked to an HA2 stem domain that is covalently linked to, in sequence, a thrombin cleavage site, a foldon domain and a His tag. In certain embodiments, provided herein are influenza hemagglutinin long stem domain polypeptides consisting of a signal peptide covalently linked to an HA1 N-terminal long stem segment covalently linked to a linker, in turn covalently linked to an HA1 C-terminal long stem segment, in turn covalently linked to an HA2 stem domain that is covalently linked to, in sequence, a thrombin cleavage site, a foldon domain and a His tag.

In certain embodiments, provided herein are influenza hemagglutinin long stem domain polypeptides consisting of an HA1 N-terminal long stem segment covalently linked to a linker, in turn covalently linked to an HA1 C-terminal long stem segment in binding association with an HA2 stem domain that is covalently linked to an HA2 luminal domain that is covalently linked to, in sequence, a thrombin cleavage site, a foldon domain and a His tag. In certain embodiments, provided herein are influenza hemagglutinin long stem domain polypeptides consisting of an HA1 N-terminal long stem segment covalently linked to a linker, in turn covalently linked to an HA1 C-terminal long stem segment, in turn covalently linked to an HA2 stem domain that is covalently linked to an HA2 luminal domain that is covalently linked to, in sequence, a thrombin cleavage site, a foldon domain and a His tag. In certain embodiments, provided herein are influenza hemagglutinin long stem domain polypeptides consisting of a signal peptide covalently linked to an HA1 N-terminal long stem segment covalently linked to a linker, in turn covalently linked to an HA1 C-terminal long stem segment, in turn covalently linked to an HA2 stem domain that is covalently linked to an HA2 luminal domain that is covalently linked to, in sequence, a thrombin cleavage site, a foldon domain and a His tag.

In certain embodiments, provided herein are influenza hemagglutinin long stem domain polypeptides consisting of an HA1 N-terminal long stem segment covalently linked to a linker, in turn covalently linked to an HA1 C-terminal long stem segment in binding association with an HA2 stem domain that is covalently linked to an HA2 luminal domain that is in turn covalently linked to an HA2 transmembrane domain. In certain embodiments, provided herein are influenza hemagglutinin long stem domain polypeptides consisting of an HA1 N-terminal long stem segment covalently linked to a linker, in turn covalently linked to an HA1 C-terminal long stem segment, in turn covalently linked to an HA2 stem domain that is covalently linked to an HA2 luminal domain that is in turn covalently linked to an HA2 transmembrane domain. In certain embodiments, provided herein are influenza hemagglutinin long stem domain polypeptides consisting of a signal peptide covalently linked to an HA1 N-terminal long stem segment covalently linked to a linker, in turn covalently linked to an HA1 C-terminal long stem segment, in turn covalently linked to an HA2 stem domain that is covalently linked to an HA2 luminal domain that is in turn covalently linked to an HA2 transmembrane domain.

In certain embodiments, provided herein are influenza hemagglutinin long stem domain polypeptides consisting of an HA1 N-terminal long stem segment covalently linked to a linker, in turn covalently linked to an HA1 C-terminal long stem segment in binding association with an HA2 stem domain that is covalently linked to an HA2 luminal domain that is in turn covalently linked to an HA2 transmembrane domain that is in turn covalently linked to an HA2 cytoplasmic domain. In certain embodiments, provided herein are influenza hemagglutinin long stem domain polypeptides consisting of an HA1 N-terminal long stem segment covalently linked to a linker, in turn covalently linked to an HA1 C-terminal long stem segment, in turn covalently linked to an HA2 stem domain that is covalently linked to an HA2 luminal domain that is in turn covalently linked to an HA2 transmembrane domain that is in turn covalently linked to an HA2 cytoplasmic domain. In certain embodiments, provided herein are influenza hemagglutinin long stem domain polypeptides consisting of a signal peptide covalently linked to an HA1 N-terminal long stem segment covalently linked to a linker, in turn covalently linked to an HA1 C-terminal long stem segment, in turn covalently linked to an HA2 stem domain that is covalently linked to an HA2 luminal domain that is in turn covalently linked to an HA2 transmembrane domain that is in turn covalently linked to an HA2 cytoplasmic domain.

In certain embodiments, provided herein is an influenza hemagglutinin long stem domain polypeptide having a sequence selected from the group consisting of:

```
(SEQ ID NO: 414)-LL-(SEQ ID NO: 430)-
(SEQ ID NO: 66),

(SEQ ID NO: 415)-LL-(SEQ ID NO: 431)-
(SEQ ID NO: 67),

(SEQ ID NO: 416)-LL-(SEQ ID NO: 432)-
(SEQ ID NO: 68),

(SEQ ID NO: 417)-LL-(SEQ ID NO: 433)-
(SEQ ID NO: 69),
```

-continued (SEQ ID NO: 418)-LL-(SEQ ID NO: 434)-(SEQ ID NO: 70), (SEQ ID NO: 419)-LL-(SEQ ID NO: 435)-(SEQ ID NO: 71), (SEQ ID NO: 420)-LL-(SEQ ID NO: 436)-(SEQ ID NO: 72), (SEQ ID NO: 421)-LL-(SEQ ID NO: 437)-(SEQ ID NO: 73), (SEQ ID NO: 422)-LL-(SEQ ID NO: 438)-(SEQ ID NO: 74), (SEQ ID NO: 423)-LL-(SEQ ID NO: 439)-(SEQ ID NO: 75), (SEQ ID NO: 424)-LL-(SEQ ID NO: 440)-(SEQ ID NO: 76), (SEQ ID NO: 425)-LL-(SEQ ID NO: 441)-(SEQ ID NO: 77), (SEQ ID NO: 426)-LL-(SEQ ID NO: 442)-(SEQ ID NO: 78), (SEQ ID NO: 427)-LL-(SEQ ID NO: 443)-(SEQ ID NO: 79), (SEQ ID NO: 428)-LL-(SEQ ID NO: 444)-(SEQ ID NO: 80),
and (SEQ ID NO: 429)-LL-(SEQ ID NO: 445)-(SEQ ID NO: 81), wherein each sequence above is linked to the adjacent sequence as described herein and wherein LL is a linker as described herein. In particular, the HA1 C-terminal long stem segments can be covalently or non-covalently linked to the HA2 domains. In certain embodiments, LL is selected from the group consisting of a direct bond, Gly, Gly-Gly, Gly-Gly-Gly, Gly-Gly-Gly-Gly (SEQ ID NO: 560), (Gly)n (wherein n is any number of Glycine residues so long as there is flexibility in the peptide linker; in certain embodiments, n is 2, 3, 4, 5, 6, or 7 Glycine residues), Gly-Pro, ITPNGSIPNDKPFQNVNKITYGA (SEQ ID NO:165) and Asn-Ala-Ser.

In certain embodiments, provided herein is an influenza hemagglutinin long stem domain polypeptide having a sequence selected from the group consisting of:

(SEQ ID NO: 414)-LL-(SEQ ID NO: 430)-(SEQ ID NO: 82), (SEQ ID NO: 415)-LL-(SEQ ID NO: 431)-(SEQ ID NO: 83), (SEQ ID NO: 416)-LL-(SEQ ID NO: 432)-(SEQ ID NO: 84), (SEQ ID NO: 417)-LL-(SEQ ID NO: 433)-(SEQ ID NO: 85), (SEQ ID NO: 418)-LL-(SEQ ID NO: 434)-(SEQ ID NO: 86), (SEQ ID NO: 419)-LL-(SEQ ID NO: 435)-(SEQ ID NO: 87), (SEQ ID NO: 420)-LL-(SEQ ID NO: 436)-(SEQ ID NO: 88), (SEQ ID NO: 421)-LL-(SEQ ID NO: 437)-(SEQ ID NO: 89),

-continued (SEQ ID NO: 422)-LL-(SEQ ID NO: 438)-(SEQ ID NO: 90), (SEQ ID NO: 423)-LL-(SEQ ID NO: 439)-(SEQ ID NO: 91), (SEQ ID NO: 424)-LL-(SEQ ID NO: 440)-(SEQ ID NO: 92), (SEQ ID NO: 425)-LL-(SEQ ID NO: 441)-(SEQ ID NO: 93), (SEQ ID NO: 426)-LL-(SEQ ID NO: 442)-(SEQ ID NO: 94), (SEQ ID NO: 427)-LL-(SEQ ID NO: 443)-(SEQ ID NO: 95), (SEQ ID NO: 428)-LL-(SEQ ID NO: 444)-(SEQ ID NO: 96),
and (SEQ ID NO: 429)-LL-(SEQ ID NO: 445)-(SEQ ID NO: 97), wherein each sequence above is linked to the adjacent sequence as described herein and wherein LL is a linker as described herein. In particular, the HA1 C-terminal long stem segments can be covalently or non-covalently linked to the HA2 domains. In certain embodiments, LL is selected from the group consisting of a direct bond, Gly, Gly-Gly, Gly-Gly-Gly, Gly-Gly-Gly-Gly (SEQ ID NO: 560), (Gly)n, Gly-Pro, ITPNGSIPNDKPFQNVNKITYGA (SEQ ID NO:165) and Asn-Ala-Ser.

In certain embodiments, provided herein is an influenza hemagglutinin long stem domain polypeptide having a sequence selected from the group consisting of:

(SEQ ID NO: 414)-LL-(SEQ ID NO: 430)-(SEQ ID NO: 82)-(SEQ ID NO: 98), (SEQ ID NO: 415)-LL-(SEQ ID NO: 431)-(SEQ ID NO: 83)-(SEQ ID NO: 99), (SEQ ID NO: 416)-LL-(SEQ ID NO: 432)-(SEQ ID NO: 84)-(SEQ ID NO: 100), (SEQ ID NO: 417)-LL-(SEQ ID NO: 433)-(SEQ ID NO: 85)-(SEQ ID NO: 101), (SEQ ID NO: 418)-LL-(SEQ ID NO: 434)-(SEQ ID NO: 86)-(SEQ ID NO: 102), (SEQ ID NO: 419)-LL-(SEQ ID NO: 435)-(SEQ ID NO: 87)-(SEQ ID NO: 103), (SEQ ID NO: 420)-LL-(SEQ ID NO: 436)-(SEQ ID NO: 88)-(SEQ ID NO: 104), (SEQ ID NO: 421)-LL-(SEQ ID NO: 437)-(SEQ ID NO: 89)-(SEQ ID NO: 105), (SEQ ID NO: 422)-LL-(SEQ ID NO: 438)-(SEQ ID NO: 90)-(SEQ ID NO: 106), (SEQ ID NO: 423)-LL-(SEQ ID NO: 439)-(SEQ ID NO: 91)-(SEQ ID NO: 107), (SEQ ID NO: 424)-LL-(SEQ ID NO: 440)-(SEQ ID NO: 92)-(SEQ ID NO: 108), (SEQ ID NO: 425)-LL-(SEQ ID NO: 441)-(SEQ ID NO: 93)-(SEQ ID NO: 109), (SEQ ID NO: 426)-LL-(SEQ ID NO: 442)-(SEQ ID NO: 94)-(SEQ ID NO: 110),

-continued (SEQ ID NO: 427)-LL-(SEQ ID NO: 443)-
(SEQ ID NO: 95)-(SEQ ID NO: 111), (SEQ ID NO: 428)-LL-(SEQ ID NO: 444)-
(SEQ ID NO: 96)-(SEQ ID NO: 112),
and (SEQ ID NO: 429)-LL-(SEQ ID NO: 445)-
(SEQ ID NO: 97)-(SEQ ID NO: 113), wherein each sequence above is linked to the adjacent sequence as described herein and wherein LL is a linker as described herein. In particular, the HA1 C-terminal long stem segments can be covalently or non-covalently linked to the HA2 domains. In certain embodiments, LL is selected from the group consisting of a direct bond, Gly, Gly-Gly, Gly-Gly-Gly, Gly-Gly-Gly-Gly (SEQ ID NO: 560), (Gly)n, Gly-Pro, ITPNGSIPNDKPFQNVNKITYGA (SEQ ID NO:165) and Asn-Ala-Ser.

In certain embodiments, provided herein is an influenza hemagglutinin long stem domain polypeptide having a sequence selected from the group consisting of:

(SEQ ID NO: 414)-LL-(SEQ ID NO: 430)-
(SEQ ID NO: 82)-(SEQ ID NO: 168)-
(SEQ ID NO: 167)-(SEQ ID NO: 166), (SEQ ID NO: 415)-LL-(SEQ ID NO: 431)-
(SEQ ID NO: 83)-(SEQ ID NO: 168)-
(SEQ ID NO: 167)-(SEQ ID NO: 166), (SEQ ID NO: 416)-LL-(SEQ ID NO: 432)-
(SEQ ID NO: 84)-(SEQ ID NO: 168)-
(SEQ ID NO: 167)-(SEQ ID NO: 166), (SEQ ID NO: 417)-LL-(SEQ ID NO: 433)-
(SEQ ID NO: 85)-(SEQ ID NO: 168)-
(SEQ ID NO: 167)-(SEQ ID NO: 166), (SEQ ID NO: 418)-LL-(SEQ ID NO: 434)-
(SEQ ID NO: 86)-(SEQ ID NO: 168)-
(SEQ ID NO: 167)-(SEQ ID NO: 166), (SEQ ID NO: 419)-LL-(SEQ ID NO: 435)-
(SEQ ID NO: 87)-(SEQ ID NO: 168)-
(SEQ ID NO: 167)-(SEQ ID NO: 166), (SEQ ID NO: 420)-LL-(SEQ ID NO: 436)-
(SEQ ID NO: 88)-(SEQ ID NO: 168)-
(SEQ ID NO: 167)-(SEQ ID NO: 166), (SEQ ID NO: 421)-LL-(SEQ ID NO: 437)-
(SEQ ID NO: 89)-(SEQ ID NO: 168)-
(SEQ ID NO: 167)-(SEQ ID NO: 166), (SEQ ID NO: 422)-LL-(SEQ ID NO: 438)-
(SEQ ID NO: 90)-(SEQ ID NO: 168)-
(SEQ ID NO: 167)-(SEQ ID NO: 166), (SEQ ID NO: 423)-LL-(SEQ ID NO: 439)-
(SEQ ID NO: 91)-(SEQ ID NO: 168)-
(SEQ ID NO: 167)-(SEQ ID NO: 166), (SEQ ID NO: 424)-LL-(SEQ ID NO: 440)-
(SEQ ID NO: 92)-(SEQ ID NO: 168)-
(SEQ ID NO: 167)-(SEQ ID NO: 166), (SEQ ID NO: 425)-LL-(SEQ ID NO: 441)-
(SEQ ID NO: 93)-(SEQ ID NO: 168)-
(SEQ ID NO: 167)-(SEQ ID NO: 166), (SEQ ID NO: 426)-LL-(SEQ ID NO: 442)-
(SEQ ID NO: 94)-(SEQ ID NO: 168)-
(SEQ ID NO: 167)-(SEQ ID NO: 166),

-continued (SEQ ID NO: 427)-LL-(SEQ ID NO: 443)-
(SEQ ID NO: 95)-(SEQ ID NO: 168)-
(SEQ ID NO: 167)-(SEQ ID NO: 166), (SEQ ID NO: 428)-LL-(SEQ ID NO: 444)-
(SEQ ID NO: 96)-(SEQ ID NO: 168)-
(SEQ ID NO: 167)-(SEQ ID NO: 166),
and (SEQ ID NO: 429)-LL-(SEQ ID NO: 445)-
(SEQ ID NO: 97)-(SEQ ID NO: 168)-
(SEQ ID NO: 167)-(SEQ ID NO: 166), wherein each sequence above is linked to the adjacent sequence as described herein and wherein LL is a linker as described herein. In particular, the HA1 C-terminal long stem segments can be covalently or non-covalently linked to the HA2 domains. In certain embodiments, LL is selected from the group consisting of a direct bond, Gly, Gly-Gly, Gly-Gly-Gly, Gly-Gly-Gly-Gly (SEQ ID NO:560), (Gly)n, Gly-Pro, ITPNGSIPNDKPFQNVNKITYGA (SEQ ID NO:165) and Asn-Ala-Ser.

In certain embodiments, provided herein is an influenza hemagglutinin long stem domain polypeptide having a sequence selected from the group consisting of:

(SEQ ID NO: 414)-LL-(SEQ ID NO: 430)-
(SEQ ID NO: 82)-(SEQ ID NO: 98)-
(SEQ ID NO: 168)-(SEQ ID NO: 167)-
(SEQ ID NO: 166), (SEQ ID NO: 415)-LL-(SEQ ID NO: 431)-
(SEQ ID NO: 83)-(SEQ ID NO: 99)-
(SEQ ID NO: 168)-(SEQ ID NO: 167)-
(SEQ ID NO: 166), (SEQ ID NO: 416)-LL-(SEQ ID NO: 432)-
(SEQ ID NO: 84)-(SEQ ID NO: 100)-
(SEQ ID NO: 168)-(SEQ ID NO: 167)-
(SEQ ID NO: 166), (SEQ ID NO: 417)-LL-(SEQ ID NO: 433)-
(SEQ ID NO: 85)-(SEQ ID NO: 101)-
(SEQ ID NO: 168)-(SEQ ID NO: 167)-
(SEQ ID NO: 166), (SEQ ID NO: 418)-LL-(SEQ ID NO: 434)-
(SEQ ID NO: 86)-(SEQ ID NO: 102)-
(SEQ ID NO: 168)-(SEQ ID NO: 167)-
(SEQ ID NO: 166), (SEQ ID NO: 419)-LL-(SEQ ID NO: 435)-
(SEQ ID NO: 87)-(SEQ ID NO: 103)-
(SEQ ID NO: 168)-(SEQ ID NO: 167)-
(SEQ ID NO: 166), (SEQ ID NO: 420)-LL-(SEQ ID NO: 436)-
(SEQ ID NO: 88)-(SEQ ID NO: 104)-
(SEQ ID NO: 168)-(SEQ ID NO: 167)-
(SEQ ID NO: 166), (SEQ ID NO: 421)-LL-(SEQ ID NO: 437)-
(SEQ ID NO: 89)-(SEQ ID NO: 105)-
(SEQ ID NO: 168)-(SEQ ID NO: 167)-
(SEQ ID NO: 166), (SEQ ID NO: 422)-LL-(SEQ ID NO: 438)-
(SEQ ID NO: 90)-(SEQ ID NO: 106)-
(SEQ ID NO: 168)-(SEQ ID NO: 167)-
(SEQ ID NO: 166), (SEQ ID NO: 423)-LL-(SEQ ID NO: 439)-
(SEQ ID NO: 91)-(SEQ ID NO: 107)-
(SEQ ID NO: 168)-(SEQ ID NO: 167)-
(SEQ ID NO: 166),

-continued (SEQ ID NO: 424)-LL-(SEQ ID NO: 440)-
(SEQ ID NO: 92)-(SEQ ID NO: 108)-
(SEQ ID NO: 168)-(SEQ ID NO: 167)-
(SEQ ID NO: 166), (SEQ ID NO: 425)-LL-(SEQ ID NO: 441)-
(SEQ ID NO: 93)-(SEQ ID NO: 109)-
(SEQ ID NO: 168)-(SEQ ID NO: 167)-
(SEQ ID NO: 166), (SEQ ID NO: 426)-LL-(SEQ ID NO: 442)-
(SEQ ID NO: 94)-(SEQ ID NO: 110)-
(SEQ ID NO: 168)-(SEQ ID NO: 167)-
(SEQ ID NO: 166), (SEQ ID NO: 427)-LL-(SEQ ID NO: 443)-
(SEQ ID NO: 95)-(SEQ ID NO: 111)-
(SEQ ID NO: 168)-(SEQ ID NO: 167)-
(SEQ ID NO: 166), (SEQ ID NO: 428)-LL-(SEQ ID NO: 444)-
(SEQ ID NO: 96)-(SEQ ID NO: 112)-
(SEQ ID NO: 168)-(SEQ ID NO: 167)-
(SEQ ID NO: 166),
and (SEQ ID NO: 429)-LL-(SEQ ID NO: 445)-
(SEQ ID NO: 97)-(SEQ ID NO: 113)-
(SEQ ID NO: 168)-(SEQ ID NO: 167)-
(SEQ ID NO: 166), wherein each sequence above is linked to the adjacent sequence as described herein and wherein LL is a linker as described herein. In particular, the HA1 C-terminal long stem segments can be covalently or non-covalently linked to the HA2 domains. In certain embodiments, LL is selected from the group consisting of a direct bond, Gly, Gly-Gly, Gly-Gly-Gly, Gly-Gly-Gly-Gly (SEQ ID NO: 560), (Gly)n, Gly-Pro, ITPNGSIPNDKPFQNVNKITYGA (SEQ ID NO:165) and Asn-Ala-Ser.

In certain embodiments, provided herein is an influenza hemagglutinin long stem domain polypeptide having a sequence selected from the group consisting of:

(SEQ ID NO: 446)-LL-(SEQ ID NO: 494)-
(SEQ ID NO: 66), (SEQ ID NO: 447)-LL-(SEQ ID NO: 495)-
(SEQ ID NO: 66), (SEQ ID NO: 448)-LL-(SEQ ID NO: 496)-
(SEQ ID NO: 66), (SEQ ID NO: 449)-LL-(SEQ ID NO: 497)-
(SEQ ID NO: 67), (SEQ ID NO: 450)-LL-(SEQ ID NO: 498)-
(SEQ ID NO: 67), (SEQ ID NO: 451)-LL-(SEQ ID NO: 499)-
(SEQ ID NO: 67), (SEQ ID NO: 452)-LL-(SEQ ID NO: 500)-
(SEQ ID NO: 68), (SEQ ID NO: 453)-LL-(SEQ ID NO: 501)-
(SEQ ID NO: 68), (SEQ ID NO: 454)-LL-(SEQ ID NO: 502)-
(SEQ ID NO: 68), (SEQ ID NO: 455)-LL-(SEQ ID NO: 503)-
(SEQ ID NO: 69), (SEQ ID NO: 456)-LL-(SEQ ID NO: 504)-
(SEQ ID NO: 69),

-continued (SEQ ID NO: 457)-LL-(SEQ ID NO: 505)-
(SEQ ID NO: 69), (SEQ ID NO: 458)-LL-(SEQ ID NO: 506)-
(SEQ ID NO: 70), (SEQ ID NO: 459)-LL-(SEQ ID NO: 507)-
(SEQ ID NO: 70), (SEQ ID NO: 460)-LL-(SEQ ID NO: 508)-
(SEQ ID NO: 70), (SEQ ID NO: 461)-LL-(SEQ ID NO: 509)-
(SEQ ID NO: 71), (SEQ ID NO: 462)-LL-(SEQ ID NO: 510)-
(SEQ ID NO: 71), (SEQ ID NO: 463)-LL-(SEQ ID NO: 511)-
(SEQ ID NO: 71), (SEQ ID NO: 464)-LL-(SEQ ID NO: 512)-
(SEQ ID NO: 72), (SEQ ID NO: 465)-LL-(SEQ ID NO: 513)-
(SEQ ID NO: 72), (SEQ ID NO: 466)-LL-(SEQ ID NO: 514)-
(SEQ ID NO: 72), (SEQ ID NO: 467)-LL-(SEQ ID NO: 515)-
(SEQ ID NO: 73), (SEQ ID NO: 468)-LL-(SEQ ID NO: 516)-
(SEQ ID NO: 73), (SEQ ID NO: 469)-LL-(SEQ ID NO: 517)-
(SEQ ID NO: 73), (SEQ ID NO: 470)-LL-(SEQ ID NO: 518)-
(SEQ ID NO: 74), (SEQ ID NO: 471)-LL-(SEQ ID NO: 519)-
(SEQ ID NO: 74), (SEQ ID NO: 472)-LL-(SEQ ID NO: 520)-
(SEQ ID NO: 74), (SEQ ID NO: 473)-LL-(SEQ ID NO: 521)-
(SEQ ID NO: 75), (SEQ ID NO: 474)-LL-(SEQ ID NO: 522)-
(SEQ ID NO: 75), (SEQ ID NO: 475)-LL-(SEQ ID NO: 523)-
(SEQ ID NO: 75), (SEQ ID NO: 476)-LL-(SEQ ID NO: 524)-
(SEQ ID NO: 76), (SEQ ID NO: 477)-LL-(SEQ ID NO: 525)-
(SEQ ID NO: 76), (SEQ ID NO: 478)-LL-(SEQ ID NO: 526)-
(SEQ ID NO: 76), (SEQ ID NO: 479)-LL-(SEQ ID NO: 527)-
(SEQ ID NO: 77), (SEQ ID NO: 480)-LL-(SEQ ID NO: 528)-
(SEQ ID NO: 77), (SEQ ID NO: 481)-LL-(SEQ ID NO: 529)-
(SEQ ID NO: 77), (SEQ ID NO: 482)-LL-(SEQ ID NO: 530)-
(SEQ ID NO: 78), (SEQ ID NO: 483)-LL-(SEQ ID NO: 531)-
(SEQ ID NO: 78), -continued

```
(SEQ ID NO: 484)-LL-(SEQ ID NO: 532)-
(SEQ ID NO: 78),

(SEQ ID NO: 485)-LL-(SEQ ID NO: 533)-
(SEQ ID NO: 79),

(SEQ ID NO: 486)-LL-(SEQ ID NO: 534)-
(SEQ ID NO: 79),

(SEQ ID NO: 487)-LL-(SEQ ID NO: 535)-
(SEQ ID NO: 79),

(SEQ ID NO: 488)-LL-(SEQ ID NO: 536)-
(SEQ ID NO: 80),

(SEQ ID NO: 489)-LL-(SEQ ID NO: 537)-
(SEQ ID NO: 80),

(SEQ ID NO: 490)-LL-(SEQ ID NO: 538)-
(SEQ ID NO: 80),

(SEQ ID NO: 491)-LL-(SEQ ID NO: 539)-
(SEQ ID NO: 81),

(SEQ ID NO: 492)-LL-(SEQ ID NO: 540)-
(SEQ ID NO: 81),
and

(SEQ ID NO: 493)-LL-(SEQ ID NO: 541)-
(SEQ ID NO: 81),
```

wherein each sequence above is linked to the adjacent sequence as described herein and wherein LL is a linker as described herein. In particular, the HA1 C-terminal long stem segments can be covalently or non-covalently linked to the HA2 domains. In certain embodiments, LL is selected from the group consisting of a direct bond, Gly, Gly-Gly, Gly-Gly-Gly, Gly-Gly-Gly-Gly (SEQ ID NO: 560), (Gly)n, Gly-Pro, ITPNGSIPNDKPFQNVNKITYGA (SEQ ID NO:165) and Asn-Ala-Ser.

5.2 Nucleic Acids Encoding Influenza Hemagglutinin Stem Domain Polypeptides

Provided herein are nucleic acids that encode an influenza hemagglutinin stem domain polypeptide. In a specific embodiment, provided herein is a nucleic acid that encodes an influenza virus hemagglutinin stem domain polypeptide. In another specific embodiment, provided herein is a nucleic acid that encodes an influenza virus hemagglutinin short stem domain polypeptide. In another specific embodiment, provided herein is a nucleic acid that encodes an influenza virus hemagglutinin long stem domain polypeptide. Due to the degeneracy of the genetic code, any nucleic acid that encodes an influenza hemagglutinin stem domain polypeptide described herein (including influenza virus hemagglutinin short stem domain polypeptides and influenza virus hemagglutinin long stem domain polypeptides) is encompassed herein. In certain embodiments, nucleic acids corresponding to naturally occurring influenza virus nucleic acids encoding an HA1 N-terminal stem segment, an HA1 C-terminal stem segment, HA2 domain, luminal domain, transmembrane domain, and/or cytoplasmic domain are used to produce an influenza hemagglutinin stem domain polypeptide.

Also provided herein are nucleic acids capable of hybridizing to a nucleic acid encoding an influenza hemagglutinin stem domain polypeptide (including influenza virus hemagglutinin short stem domain polypeptides and influenza virus hemagglutinin long stem domain polypeptides). In certain embodiments, provided herein are nucleic acids capable of hybridizing to a fragment of a nucleic acid encoding an influenza hemagglutinin stem domain polypeptide. In other embodiments, provided herein are nucleic acids capable of hybridizing to the full length of a nucleic acid encoding an influenza hemagglutinin stem domain polypeptide. General parameters for hybridization conditions for nucleic acids are described in Sambrook et al., Molecular Cloning—A Laboratory Manual (2nd Ed.), Vols. 1-3, Cold Spring Harbor Laboratory, Cold Spring Harbor, N.Y. (1989), and in Ausubel et al., Current Protocols in Molecular Biology, vol. 2, Current Protocols Publishing, New York (1994). Hybridization may be performed under high stringency conditions, medium stringency conditions, or low stringency conditions. Those of skill in the art will understand that low, medium and high stringency conditions are contingent upon multiple factors all of which interact and are also dependent upon the nucleic acids in question. For example, high stringency conditions may include temperatures within 5° C. melting temperature of the nucleic acid(s), a low salt concentration (e.g., less than 250 mM), and a high co-solvent concentration (e.g., 1-20% of co-solvent, e.g., DMSO). Low stringency conditions, on the other hand, may include temperatures greater than 10° C. below the melting temperature of the nucleic acid(s), a high salt concentration (e.g., greater than 1000 mM) and the absence of co-solvents.

In some embodiments, a nucleic acid encoding an influenza virus hemagglutinin stem domain polypeptide is isolated. In certain embodiments, an "isolated" nucleic acid refers to a nucleic acid molecule which is separated from other nucleic acid molecules which are present in the natural source of the nucleic acid. In other words, the isolated nucleic acid can comprise heterologous nucleic acids that are not associated with it in nature. In other embodiments, an "isolated" nucleic acid, such as a cDNA molecule, can be substantially free of other cellular material, or culture medium when produced by recombinant techniques, or substantially free of chemical precursors or other chemicals when chemically synthesized. The term "substantially free of cellular material" includes preparations of nucleic acid in which the nucleic acid is separated from cellular components of the cells from which it is isolated or recombinantly produced. Thus, nucleic acid that is substantially free of cellular material includes preparations of nucleic acid having less than about 30%, 20%, 10%, or 5% (by dry weight) of other nucleic acids. The term "substantially free of culture medium" includes preparations of nucleic acid in which the culture medium represents less than about 50%, 20%, 10%, or 5% of the volume of the preparation. The term "substantially free of chemical precursors or other chemicals" includes preparations in which the nucleic acid is separated from chemical precursors or other chemicals which are involved in the synthesis of the nucleic acid. In specific embodiments, such preparations of the nucleic acid have less than about 50%, 30%, 20%, 10%, 5% (by dry weight) of chemical precursors or compounds other than the nucleic acid of interest.

In addition, provided herein are nucleic acids encoding the individual components of an influenza hemagglutinin stem domain polypeptide. In specific embodiments, nucleic acids encoding an HA1 N-terminal stem segment, an HA1 C-terminal stem segment and/or HA2 domain are provided. Nucleic acids encoding components of an influenza hemagglutinin stem domain polypeptide may be assembled using standard molecular biology techniques known to the one of skill in the art.

5.3 Expression of Influenza Hemagglutinin Stem Domain Polypeptides

Provided herein are vectors, including expression vectors, containing a nucleic acid encoding an influenza hemagglutinin stem domain polypeptide. In a specific embodiment, the vector is an expression vector that is capable of directing the expression of a nucleic acid encoding an influenza hemagglutinin stem domain polypeptide. Non-limiting examples of expression vectors include, but are not limited to, plasmids and viral vectors, such as replication defective retroviruses, adenoviruses, adeno-associated viruses and baculoviruses.

In some embodiments, provided herein are expression vectors encoding components of an influenza hemagglutinin stem domain polypeptide (e.g., HA1 N-terminal stem segment, an HA1 C-terminal stem segment and/or an HA2). Such vectors may be used to express the components in one or more host cells and the components may be isolated and conjugated together with a linker using techniques known to one of skill in the art.

An expression vector comprises a nucleic acid encoding an influenza hemagglutinin stem domain polypeptide in a form suitable for expression of the nucleic acid in a host cell. In a specific embodiment, an expression vector includes one or more regulatory sequences, selected on the basis of the host cells to be used for expression, which is operably linked to the nucleic acid to be expressed. Within an expression vector, "operably linked" is intended to mean that a nucleic acid of interest is linked to the regulatory sequence(s) in a manner which allows for expression of the nucleic acid (e.g., in an in vitro transcription/translation system or in a host cell when the vector is introduced into the host cell). Regulatory sequences include promoters, enhancers and other expression control elements (e.g., polyadenylation signals). Regulatory sequences include those which direct constitutive expression of a nucleic acid in many types of host cells, those which direct expression of the nucleic acid only in certain host cells (e.g., tissue-specific regulatory sequences), and those which direct the expression of the nucleic acid upon stimulation with a particular agent (e.g., inducible regulatory sequences). It will be appreciated by those skilled in the art that the design of the expression vector can depend on such factors as the choice of the host cell to be transformed, the level of expression of protein desired, etc. The term "host cell" is intended to include a particular subject cell transformed or transfected with a nucleic acid and the progeny or potential progeny of such a cell. Progeny of such a cell may not be identical to the parent cell transformed or transfected with the nucleic acid due to mutations or environmental influences that may occur in succeeding generations or integration of the nucleic acid into the host cell genome.

Expression vectors can be designed for expression of an influenza hemagglutinin stem domain polypeptide using prokaryotic (e g., *E. coli*) or eukaryotic cells (e.g., insect cells (using baculovirus expression vectors, see, e.g., Treanor et al., 2007, JAMA, 297(14):1577-1582 incorporated by reference herein in its entirety), yeast cells, plant cells, algae or mammalian cells). Examples of mammalian host cells include, but are not limited to, Crucell Per.C6 cells, Vero cells, CHO cells, VERY cells, BHK cells, HeLa cells, COS cells, MDCK cells, 293 cells, 3T3 cells or WI38 cells. In certain embodiments, the hosts cells are myeloma cells, e.g., NS0 cells, 45.6 TG1.7 cells, AF-2 clone 9B5 cells, AF-2 clone 9B5 cells, J558L cells, MOPC 315 cells, MPC-11 cells, NCI-H929 cells, NP cells, NS0/1 cells, P3 NS1 Ag4 cells, P3/NS1/1-Ag4-1 cells, P3U1 cells, P3X63Ag8 cells, P3X63Ag8.653 cells, P3X63Ag8U.1 cells, RPMI 8226 cells, Sp20-Ag14 cells, U266B1 cells, X63AG8.653 cells, Y3.Ag.1.2.3 cells, and YO cells. Non-limiting examples of insect cells include Sf9, Sf21, *Trichoplusia ni, Spodoptera frugiperda* and *Bombyx mori*. In a particular embodiment, a mammalian cell culture system (e.g. Chinese hamster ovary or baby hamster kidney cells) is used for expression of an influenza hemagglutinin stem domain polypeptide. In another embodiment, a plant cell culture sytem is used for expression of an influenza hemagglutinin stem domain polypeptide. See, e.g., U.S. Pat. Nos. 7,504,560; 6,770,799; 6,551,820; 6,136,320; 6,034,298; 5,914,935; 5,612,487; and 5,484,719, and U.S. patent application publication Nos. 2009/0208477, 2009/0082548, 2009/0053762, 2008/0038232, 2007/0275014 and 2006/0204487 for plant cells and methods for the production of proteins utilizing plant cell culture systems.

An expression vector can be introduced into host cells via conventional transformation or transfection techniques. Such techniques include, but are not limited to, calcium phosphate or calcium chloride co-precipitation, DEAE-dextran-mediated transfection, lipofection, and electroporation. Suitable methods for transforming or transfecting host cells can be found in Sambrook et al., 1989, Molecular Cloning—A Laboratory Manual, 2nd Edition, Cold Spring Harbor Press, New York, and other laboratory manuals. In certain embodiments, a host cell is transiently transfected with an expression vector containing a nucleic acid encoding an influenza hemagglutinin stem domain polypeptide. In other embodiments, a host cell is stably transfected with an expression vector containing a nucleic acid encoding an influenza hemagglutinin stem domain polypeptide.

For stable transfection of mammalian cells, it is known that, depending upon the expression vector and transfection technique used, only a small fraction of cells may integrate the foreign DNA into their genome. In order to identify and select these integrants, a nucleic acid that encodes a selectable marker (e.g., for resistance to antibiotics) is generally introduced into the host cells along with the nucleic acid of interest. Examples of selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

As an alternative to recombinant expression of an influenza hemagglutinin stem domain polypeptide using a host cell, an expression vector containing a nucleic acid encoding an influenza hemagglutinin stem domain polypeptide can be transcribed and translated in vitro using, e.g., T7 promoter regulatory sequences and T7 polymerase. In a specific embodiment, a coupled transcription/translation system, such as Promega TNT®, or a cell lysate or cell extract comprising the components necessary for transcription and translation may be used to produce an influenza hemagglutinin stem domain polypeptide.

Once an influenza hemagglutinin stem domain polypeptide has been produced, it may be isolated or purified by any method known in the art for isolation or purification of a protein, for example, by chromatography (e.g., ion exchange, affinity, particularly by affinity for the specific antigen, by Protein A, and sizing column chromatography), centrifugation, differential solubility, or by any other standard technique for the isolation or purification of proteins. In certain embodiments, an influenza hemagglutinin stem domain polypeptide may be conjugated to heterologous proteins, e.g., a major histocompatibility complex (MHC) with or without heat shock proteins (e.g., Hsp10, Hsp20, Hsp30, Hsp40, Hsp60, Hsp70, Hsp90, or Hsp100). In certain embodiments, an influenza hemagglutinin stem domain polypeptide may be conjugated to immunomodulatory molecules, such as proteins which would target the influenza hemagglutinin stem domain polypeptide to immune cells such as B cells (e.g., C3d) or T cells. In certain embodiments, an influenza hemagglutinin stem domain polypeptide may be conjugated to proteins which stimulate the innate immune system such as interferon type 1, alpha, beta, or gamma interferon, colony stimulating factors such as granulocyte-macrophage colony-stimulating factor (GM-CSF), interleukin (IL)-1, IL-2, IL-4, IL-5, IL-6, IL-7, IL-12, IL-15, IL-18, IL-21, IL-23, tumor necrosis factor (TNF)-β, TNFα, B7.1, B7.2, 4-1BB, CD40 ligand (CD40L), and drug-inducible CD40 (iCD40).

Accordingly, provided herein are methods for producing an influenza hemagglutinin stem domain polypeptide. In one embodiment, the method comprises culturing a host cell containing a nucleic acid encoding the polypeptide in a suitable medium such that the polypeptide is produced. In some embodiments, the method further comprises isolating the polypeptide from the medium or the host cell.

5.4 Influenza Virus Vectors

In one aspect, provided herein are influenza viruses containing an influenza hemagglutinin stem domain polypeptide. In a specific embodiment, the influenza hemagglutinin stem domain polypeptide is incorporated into the virions of the influenza virus. The influenza viruses may be conjugated to moieties that target the viruses to particular cell types, such as immune cells. In some embodiments, the virions of the influenza virus have incorporated into them or express a heterologous polypeptide in addition to an influenza hemagglutinin stem domain polypeptide. The heterologous polypeptide may be a polypeptide that has immunopotentiating activity, or that targets the influenza virus to a particular cell type, such as an antibody that binds to an antigen on a specific cell type or a ligand that binds a specific receptor on a specific cell type.

Influenza viruses containing an influenza hemagglutinin stem domain polypeptide may be produced by supplying in trans the influenza hemagglutinin stem domain polypeptide during production of virions using techniques known to one skilled in the art, such as reverse genetics and helper-free plasmid rescue. Alternatively, the replication of a parental influenza virus comprising a genome engineered to express an influenza hemagglutinin stem domain polypeptide in cells susceptible to infection with the virus wherein hemagglutinin function is provided in trans will produce progeny influenza viruses containing the influenza hemagglutinin stem domain polypeptide.

In another aspect, provided herein are influenza viruses comprising a genome engineered to express an influenza hemagglutinin stem domain polypeptide. In a specific embodiment, the genome of a parental influenza virus is engineered to encode an influenza hemagglutinin stem domain polypeptide, which is expressed by progeny influenza virus. In another specific embodiment, the genome of a parental influenza virus is engineered to encode an influenza hemagglutinin stem domain polypeptide, which is expressed and incorporated into the virions of progeny influenza virus. Thus, the progeny influenza virus resulting from the replication of the parental influenza virus contain an influenza hemagglutinin stem domain polypeptide. The virions of the parental influenza virus may have incorporated into them an influenza virus hemagglutinin polypeptide that is from the same or a different type, subtype or strain of influenza virus. Alternatively, the virions of the parental influenza virus may have incorporated into them a moiety that is capable of functionally replacing one or more of the activities of influenza virus hemagglutinin polypeptide (e.g., the receptor binding and/or fusogenic activities of influenza virus hemagglutinin). In certain embodiments, one or more of the activities of the influenza virus hemagglutinin polypeptide is provided by a fusion protein comprising (i) an ectodomain of a polypeptide heterologous to influenza virus fused to (ii) a transmembrane domain, or a transmembrane domain and a cytoplasmic domain of an influenza virus hemagglutinin polypeptide. In a specific embodiment, the virions of the parental influenza virus may have incorporated into them a fusion protein comprising (i) an ectodomain of a receptor binding/fusogenic polypeptide of an infectious agent other than influenza virus fused to (ii) a transmembrane domain, or a transmembrane domain and a cytoplasmic domain of an influenza virus hemagglutinin. For a description of fusion proteins that provide one or more activities of an influenza virus hemagglutinin polypeptide and methods for the production of influenza viruses engineered to express such fusion proteins, see, e.g., International patent application Publication No. WO 2007/064802, published Jun. 7, 2007, which is incorporated herein by reference in its entirety.

In some embodiments, the virions of the parental influenza virus have incorporated into them a heterologous polypeptide. In certain embodiments, the genome of a parental influenza virus is engineered to encode a heterologous polypeptide and an influenza virus hemagglutinin stem domain polypeptide, which are expressed by progeny influenza virus. In specific embodiments, the influenza hemagglutinin stem domain polypeptide, the heterologous polypeptide or both are incorporated into virions of the progeny influenza virus.

The heterologous polypeptide may be a polypeptide that targets the influenza virus to a particular cell type, such as an antibody that recognizes an antigen on a specific cell type or a ligand that binds a specific receptor on a specific cell type. In some embodiments, the targeting polypeptide replaces the target cell recognition function of the virus. In a specific embodiment, the heterologous polypeptide targets the influenza virus to the same cell types that influenza virus infects in nature. In other specific embodiments, the heterologous polypeptide targets the progeny influenza virus to immune cells, such as B cells, T cells, macrophages or dendritic cells. In some embodiments, the heterologous polypeptide recognizes and binds to cell-specific markers of antigen presenting cells, such as dendritic cells (e.g., such as CD44). In one embodiment, the heterologous polypeptide is DC-SIGN which targets the virus to dendritic cells. In another embodiment, the heterologous polypeptide is an antibody (e.g., a single-chain antibody) that targets the virus to an immune cell, which may be fused with a transmembrane domain from another polypeptide so that it is incorporated into the influenza virus virion. In some embodiments, the antibody is a CD20 antibody, a CD34 antibody, or an antibody against DEC-205. Techniques for engineering viruses to express polypeptides with targeting functions are known in the art. See, e.g., Yang et al., 2006, PNAS 103: 11479-11484 and United States patent application Publication No. 20080019998, published Jan. 24, 2008, and No. 20070020238, published Jan. 25, 2007, the contents of each of which are incorporated herein in their entirety.

In another embodiment, the heterologous polypeptide is a viral attachment protein. Non-limiting examples of viruses whose attachment protein(s) can be used in this aspect are viruses selected from the group of: Lassa fever virus, Hepatitis B virus, Rabies virus, Newcastle disease virus (NDV), a retrovirus such as human immunodeficiency virus, tick-borne encephalitis virus, vaccinia virus, herpesvirus, poliovirus, alphaviruses such as Semliki Forest virus, Ross River virus, and Aura virus (which comprise surface glycoproteins such as E1, E2, and E3), Borna disease virus, Hantaan virus, foamyvirus, and SARS-CoV virus.

In one embodiment, a flavivirus surface glycoprotein may be used, such as Dengue virus (DV) E protein. In some embodiments, a Sindbis virus glycoprotein from the alphavirus family is used (K. S. Wang, R. J. Kuhn, E. G. Strauss, S. Ou, J. H. Strauss, J. Virol. 66, 4992 (1992)). In certain embodiments, the heterologous polypeptide is derived from an NDV HN or F protein; a human immunodeficiency virus (HIV) gp160 (or a product thereof, such as gp41 or gp120); a hepatitis B virus surface antigen (HBsAg); a glycoprotein of herpesvirus (e.g., gD, gE); or VP1 of poliovirus.

In another embodiment, the heterologous polypeptide is derived from any non-viral targeting system known in the art. In certain embodiments, a protein of a nonviral pathogen such as an intracellular bacteria or protozoa is used. In some embodiments, the bacterial polypeptide is provided by, e.g., *Chlamydia, Rikettsia, Coxelia, Listeria, Brucella*, or *Legionella*. In some embodiments, protozoan polypeptide is provided by, e.g., Plasmodia species, *Leishmania* spp., *Toxoplasma gondii*, or *Trypanosoma cruzi*. Other exemplary targeting systems are described in Waehler et al., 2007, "Engineering targeted viral vectors for gene therapy," Nature Reviews Genetics 8: 573-587, which is incorporated herein in its entirety.

In certain embodiments, the heterologous polypeptide expressed by an influenza virus has immunopotentiating (immune stimulating) activity. Non-limiting examples of immunopotentiating polypeptides include, but are not limited to, stimulation molecules, cytokines, chemokines, antibodies and other agents such as Flt-3 ligands. Specific examples of polypeptides with immunopotentiating activity include: interferon type 1, alpha, beta, or gamma interferon, colony stimulating factors such as granulocyte-macrophage colony-stimulating factor (GM-CSF), interleukin (IL)-1, IL-2, IL-4, IL-5, IL-6, IL-7, IL-12, IL-15, IL-18, IL-21, IL-23, tumor necrosis factor (TNF)-β, TNFα, B7.1, B7.2, 4-1BB, CD40 ligand (CD40L), and drug-inducible CD40 (iCD40) (see, e.g., Hanks, B. A., et al. 2005. Nat Med 11:130-137, which is incorporated herein by reference in its entirety.)

Since the genome of influenza A and B viruses consist of eight (8) single-stranded, negative sense segments (influenza C viruses consist of seven (7) single-stranded, negative sense segments), the genome of a parental influenza virus may be engineered to express an influenza hemagglutinin stem domain polypeptide (and any other polypeptide, such as a heterologous polypeptide) using a recombinant segment and techniques known to one skilled in the art, such a reverse genetics and helper-free plasmid rescue. In one embodiment, the recombinant segment comprises a nucleic acid encoding the influenza hemagglutinin stem domain polypeptide as well as the 3' and 5' incorporation signals which are required for proper replication, transcription and packaging of the vRNAs (Fujii et al., 2003, Proc. Natl. Acad. Sci. USA 100:2002-2007; Zheng, et al., 1996, Virology 217:242-251, both of which are incorporated by reference herein in their entireties). In a specific embodiment, the recombinant segment uses the 3' and 5' noncoding and/or nontranslated sequences of segments of influenza viruses that are from a different or the same type, subtype or strain as the parental influenza virus. In some embodiments, the recombinant segment comprises the 3' noncoding region of an influenza virus hemagglutinin polypeptide, the untranslated regions of an influenza virus hemagglutinin polypeptide, and the 5' non-coding region of an influenza virus hemagglutinin polypeptide. In specific embodiments, the recombinant segment comprises the 3' and 5' noncoding and/or nontranslated sequences of the HA segment of an influenza virus that is the same type, subtype or strain as the influenza virus type, subtype or strain as the HA1 N-terminal stem segment, the HA1 C-terminal stem segment and/or the HA2 of an influenza hemagglutinin stem domain polypeptide. In certain embodiments, the recombinant segment encoding the influenza hemagglutinin stem domain polypeptide may replace the HA segment of a parental influenza virus. In some embodiments, the recombinant segment encoding the influenza hemagglutinin stem domain polypeptide may replace the NS1 gene of the parental influenza virus. In some embodiments, the recombinant segment encoding the influenza hemagglutinin stem domain polypeptide may replace the NA gene of the parental influenza virus. Exemplary influenza virus strains that can be used to express the influenza hemagglutinin stem domain polypeptides include Ann Arbor/1/50, A/Puerto Rico/8/34, A/South Dakota/6/2007, A/Uruguay/716/2007, and B/Brisbane/60/2008.

In some embodiments, the genome of a parental influenza virus may be engineered to express an influenza hemagglutinin stem domain polypeptide using a recombinant segment that is bicistronic. Bicistronic techniques allow the engineering of coding sequences of multiple proteins into a single mRNA through the use of internal ribosome entry site (IRES) sequences. IRES sequences direct the internal recruitment of ribosomes to the RNA molecule and allow downstream translation in a cap independent manner. Briefly, a coding region of one protein is inserted into the open reading frame (ORF) of a second protein. The insertion is flanked by an IRES and any untranslated signal sequences necessary for proper expression and/or function. The insertion must not disrupt the ORF, polyadenylation or transcriptional promoters of the second protein (see, e.g., Garcia-Sastre et al., 1994, J. Virol. 68:6254-6261 and Garcia-Sastre et al., 1994 Dev. Biol. Stand. 82:237-246, each of which is hereby incorporated by reference in its entirety). See also, e.g., U.S. Pat. No. 6,887,699, U.S. Pat. No. 6,001,634, U.S. Pat. No. 5,854,037 and U.S. Pat. No. 5,820,871, each of which is incorporated herein by reference in its entirety. Any IRES known in the art or described herein may be used in accordance with the invention (e.g., the IRES of BiP gene, nucleotides 372 to 592 of GenBank database entry HUMGRP78; or the IRES of encephalomyocarditis virus (EMCV), nucleotides 1430-2115 of GenBank database entry CQ867238.). Thus, in certain embodiments, a parental influenza virus is engineered to contain a bicistronic RNA segment that expresses the influenza hemagglutinin stem domain polypeptide and another polypeptide, such as gene expressed by the parental influenza virus. In some embodiments, the parental influenza virus gene is the HA gene. In some embodiments, the parental influenza virus gene is the NA gene. In some embodiments, the parental influenza virus gene is the NS1 gene.

Techniques known to one skilled in the art may be used to produce an influenza virus containing an influenza hemagglutinin stem domain polypeptide and an influenza virus comprising a genome engineered to express an influenza hemagglutinin stem domain polypeptide. For example, reverse genetics techniques may be used to generate such an influenza virus. Briefly, reverse genetics techniques generally involve the preparation of synthetic recombinant viral RNAs that contain the non-coding regions of the negative-strand, viral RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. A more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in European Patent Publication EP 0702085A1, published Feb. 20, 1996; in U.S. patent application Ser. No. 09/152,845; in International Patent Publications PCT WO 97/12032 published Apr. 3, 1997; WO 96/34625 published Nov. 7, 1996; in European Patent Publication EP A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 475A1 published Jun. 25, 1997, each of which is incorporated by reference herein in its entirety.

Alternatively, helper-free plasmid technology may be used to produce an influenza virus containing an influenza hemagglutinin stem domain polypeptide and an influenza virus comprising a genome engineered to express an influenza hemagglutinin stem domain polypeptide. Briefly, full length cDNAs of viral segments are amplified using PCR with primers that include unique restriction sites, which allow the insertion of the PCR product into the plasmid vector (Flandorfer et al., 2003, J. Virol. 77:9116-9123; Nakaya et al., 2001, J. Virol. 75:11868-11873; both of which are incorporated herein by reference in their entireties). The plasmid vector is designed so that an exact negative (vRNA sense) transcript is expressed. For example, the plasmid vector may be designed to position the PCR product between a truncated human RNA polymerase I promoter and a hepatitis delta virus ribozyme sequence such that an exact negative (vRNA sense) transcript is produced from the polymerase I promoter. Separate plasmid vectors comprising each viral segment as well as expression vectors comprising necessary viral proteins may be transfected into cells leading to production of recombinant viral particles. In another example, plasmid vectors from which both the viral genomic RNA and mRNA encoding the necessary viral proteins are expressed may be used. For a detailed description of helper-free plasmid technology see, e.g., International Publication No. WO 01/04333; U.S. Pat. Nos. 6,951,754, 7,384,774, 6,649,372, and 7,312,064; Fodor et al., 1999, J. Virol. 73:9679-9682; Quinlivan et al., 2005, J. Virol. 79:8431-8439; Hoffmann et al., 2000, Proc. Natl. Acad. Sci. USA 97:6108-6113; and Neumann et al., 1999, Proc. Natl. Acad. Sci. USA 96:9345-9350, which are incorporated herein by reference in their entireties.

The influenza viruses described herein may be propagated in any substrate that allows the virus to grow to titers that permit their use in accordance with the methods described herein. In one embodiment, the substrate allows the viruses to grow to titers comparable to those determined for the corresponding wild-type viruses. In certain embodiments, the substrate is one which is biologically relevant to the influenza virus or to the virus from which the HA function is derived. In a specific embodiment, an attenuated influenza virus by virtue of, e.g., a mutation in the NS1 gene, may be propagated in an IFN-deficient substrate. For example, a suitable IFN-deficient substrate may be one that is defective in its ability to produce or respond to interferon, or is one which An IFN-deficient substrate may be used for the growth of any number of viruses which may require interferon-deficient growth environment. See, for example, U.S. Pat. No. 6,573,079, issued Jun. 3, 2003, U.S. Pat. No. 6,852,522, issued Feb. 8, 2005, and U.S. Pat. No. 7,494,808, issued Feb. 24, 2009, the entire contents of each of which is incorporated herein by reference in its entirety.

The influenza viruses described herein may be isolated and purified by any method known to those of skill in the art. In one embodiment, the virus is removed from cell culture and separated from cellular components, typically by well known clarification procedures, e.g., such as gradient centrifugation and column chromatography, and may be further purified as desired using procedures well known to those skilled in the art, e.g., plaque assays.

In certain embodiments, the influenza viruses, or influenza virus polypeptides, genes or genome segments for use as described herein are obtained or derived from an influenza A virus. In certain embodiments, the influenza viruses, or influenza virus polypeptides, genes or genome segments for use as described herein are obtained or derived from a single influenza A virus subtype or strain. In other embodiments, the influenza viruses, or influenza virus polypeptides, genes or genome segments for use as described herein are obtained or derived from two or more influenza A virus subtypes or strains.

In some embodiments, the influenza viruses, or influenza virus polypeptides, genes or genome segments for use as described herein are obtained or derived from an influenza B virus. In certain embodiments, the influenza viruses, or influenza virus polypeptides, genes or genome segments for use as described herein are obtained or derived from a single influenza B virus subtype or strain. In other embodiments, the influenza viruses, or influenza virus polypeptides, genes or genome segments for use as described herein are obtained or derived from two or more influenza B virus subtypes or strains. In other embodiments, the influenza viruses, or influenza virus polypeptides, genes or genome segments for use as described herein are obtained or derived from a combination of influenza A and influenza B virus subtypes or strains.

In some embodiments, the influenza viruses, or influenza virus polypeptides, genes or genome segments for use as described herein are obtained or derived from an influenza C virus. In certain embodiments, the influenza viruses, or influenza virus polypeptides, genes or genome segments for use as described herein are obtained or derived from a single influenza C virus subtype or strain. In other embodiments, the influenza viruses, or influenza virus polypeptides, genes or genome segments for use as described herein are obtained or derived from two or more influenza C virus subtypes or strains. In other embodiments, the influenza viruses, or influenza virus polypeptides, genes or genome segments for use as described herein are obtained or derived from a combination of influenza C virus and influenza A virus and/or influenza B virus subtypes or strains.

Non-limiting examples of influenza A viruses include subtype H10N4, subtype H10N5, subtype H10N7, subtype H10N8, subtype H10N9, subtype H11N1, subtype H11N13, subtype H11N2, subtype H11N4, subtype H11N6, subtype H11N8, subtype H11N9, subtype H12N1, subtype H12N4, subtype H12N5, subtype H12N8, subtype H13N2, subtype H13N3, subtype H13N6, subtype H13N7, subtype H14N5, subtype H14N6, subtype H15N8, subtype H15N9, subtype H16N3, subtype H1N1, subtype H1N2, subtype H1N3, subtype H1N6, subtype H1N9, subtype H2N1, subtype H2N2, subtype H2N3, subtype H2N5, subtype H2N7, subtype H2N8, subtype H2N9, subtype H3N1, subtype H3N2, subtype H3N3, subtype H3N4, subtype H3N5, subtype H3N6, subtype H3N8, subtype H3N9, subtype H4N1, subtype H4N2, subtype H4N3, subtype H4N4, subtype H4N5, subtype H4N6, subtype H4N8, subtype H4N9, subtype H5N1, subtype H5N2, subtype H5N3, subtype H5N4, subtype H5N6, subtype H5N7, subtype H5N8, subtype H5N9, subtype H6N1, subtype H6N2, subtype H6N3, subtype H6N4, subtype H6N5, subtype H6N6, subtype H6N7, subtype H6N8, subtype H6N9, subtype H7N1, subtype H7N2, subtype H7N3, subtype H7N4, subtype H7N5, subtype H7N7, subtype H7N8, subtype H7N9, subtype H8N4, subtype H8N5, subtype H9N1, subtype H9N2, subtype H9N3, subtype H9N5, subtype H9N6, subtype H9N7, subtype H9N8, and subtype H9N9.

Specific examples of strains of influenza A virus include, but are not limited to: A/sw/Iowa/15/30 (H1N1); A/WSN/33 (H1N1); A/eq/Prague/1/56 (H7N7); A/PR/8/34; A/mallard/Potsdam/178-4/83 (H2N2); A/herring gull/DE/712/88 (H16N3); A/sw/Hong Kong/168/1993 (H1N1); A/mallard/Alberta/211/98 (H1N1); A/shorebird/Delaware/168/06 (H16N3); A/sw/Netherlands/25/80 (H1N1); A/sw/Germany/2/81 (H1N1); A/sw/Hannover/1/81 (H1N1); A/sw/Potsdam/1/81 (H1N1); A/sw/Potsdam/15/81 (H1N1); A/sw/Potsdam/268/81 (H1N1); A/sw/Finistere/2899/82 (H1N1); A/sw/Potsdam/35/82 (H3N2); A/sw/Cote d'Armor/3633/84 (H3N2); A/sw/Gent/1/84 (H3N2); A/sw/Netherlands/12/85 (H1N1); A/sw/Karrenzien/2/87 (H3N2); A/sw/Schwerin/103/89 (H1N1); A/turkey/Germany/3/91 (H1N1); A/sw/Germany/8533/91 (H1N1); A/sw/Belgium/220/92 (H3N2); A/sw/Gent/V230/92 (H1N1); A/sw/Leipzig/145/92 (H3N2); A/sw/Re220/92 hp (H3N2); A/sw/Bakum/909/93 (H3N2); A/sw/Schleswig-Holstein/1/93 (H1N1); A/sw/Scotland/419440/94 (H1N2); A/sw/Bakum/5/95 (H1N1); A/sw/Best/5C/96 (H1N1); A/sw/England/17394/96 (H1N2); A/sw/Jena/5/96 (H3N2); A/sw/Oedenrode/7C/96 (H3N2); A/sw/Lohne/1/97 (H3N2); A/sw/Cote d'Armor/790/97 (H1N2); A/sw/Bakum/1362/98 (H3N2); A/sw/Italy/1521/98 (H1N2); A/sw/Italy/1553-2/98 (H3N2); A/sw/Italy/1566/98 (H1N1); A/sw/Italy/1589/98 (H1N1); A/sw/Bakum/8602/99 (H3N2); A/sw/Cotes d'Armor/604/99 (H1N2); A/sw/Cote d'Armor/1482/99 (H1N1); A/sw/Gent/7625/99 (H1N2); A/Hong Kong/1774/99 (H3N2); A/sw/Hong Kong/5190/99 (H3N2); A/sw/Hong Kong/5200/99 (H3N2); A/sw/Hong Kong/5212/99 (H3N2); A/sw/Ille et Villaine/1455/99 (H1N1); A/sw/Italy/1654-1/99 (H1N2); A/sw/Italy/2034/99 (H1N1); A/sw/Italy/2064/99 (H1N2); A/sw/Berlin/1578/00 (H3N2); A/sw/Bakum/1832/00 (H1N2); A/sw/Bakum/1833/00 (H1N2); A/sw/Cote d'Armor/800/00 (H1N2); A/sw/Hong Kong/7982/00 (H3N2); A/sw/Italy/1081/00 (H1N2); A/sw/Belzig/2/01 (H1N1); A/sw/Belzig/54/01 (H3N2); A/sw/Hong Kong/9296/01 (H3N2); A/sw/Hong Kong/9745/01 (H3N2); A/sw/Spain/33601/01 (H3N2); A/sw/Hong Kong/1144/02 (H3N2); A/sw/Hong Kong/1197/02 (H3N2); A/sw/Spain/39139/02 (H3N2); A/sw/Spain/42386/02 (H3N2); A/Switzerland/8808/2002 (H1N1); A/sw/Bakum/1769/03 (H3N2); A/sw/Bissendorf/IDT1864/03 (H3N2); A/sw/Ehren/IDT2570/03 (H1N2); A/sw/Gescher/IDT2702/03 (H1N2); A/sw/Haselünne/2617/03 hp (H1N1); A/sw/Löningen/IDT2530/03 (H1N2); A/sw/IVD/IDT2674/03 (H1N2); A/swNordkirchen/IDT1993/03 (H3N2); A/sw/Nordwalde/IDT2197/03 (H1N2); A/swNorden/IDT2308/03 (H1N2); A/sw/Spain/50047/03 (H1N1); A/sw/Spain/51915/03 (H1N1); A/sw/Vechta/2623/03 (H1N1); A/sw/Visbek/IDT2869/03 (H1N2); A/sw/Waltersdorf/IDT2527/03 (H1N2); A/sw/Damme/IDT2890/04 (H3N2); A/sw/Geldern/IDT2888/04 (H1N1); A/sw/Granstedt/IDT3475/04 (H1N2); A/sw/Greven/IDT2889/04 (H1N1); A/sw/Gudensberg/IDT2930/04 (H1N2); A/sw/Gudensberg/IDT2931/04 (H1N2); A/sw/Lohne/IDT3357/04 (H3N2); A/sw/Nortrup/IDT3685/04 (H1N2); A/sw/Seesen/IDT3055/04 (H3N2); A/sw/Spain/53207/04 (H1N1); A/sw/Spain/54008/04 (H3N2); A/sw/Stolzenau/IDT3296/04 (H1N2); A/sw/Wedel/IDT2965/04 (H1N1); A/sw/Bad Griesbach/IDT4191/05 (H3N2); A/sw/Cloppenburg/IDT4777/05 (H1N2); A/sw/Dotlingen/IDT3780/05 (H1N2); A/sw/Dotlingen/IDT4735/05 (H1N2); A/sw/Egglham/IDT5250/05 (H3N2); A/sw/Harkenblek/IDT4097/05 (H3N2); A/sw/Hertzen/IDT4317/05 (H3N2); A/sw/Krogel/IDT4192/05 (H1N1); A/sw/Laer/IDT3893/05 (H1N1); A/sw/Laer/IDT4126/05 (H3N2); A/sw/Merzen/IDT4114/05 (H3N2); A/sw/Muesleringen-S./IDT4263/05 (H3N2); A/sw/O sterhofen/IDT4004/05 (H3N2); A/sw/Sprenge/IDT3805/05 (H1N2); A/sw/Stadtlohn/IDT3853/05 (H1N2); A/sw/Voglarn/IDT4096/05 (H1N1); A/sw/Wohlerst/IDT4093/05 (H1N1); A/sw/Bad Griesbach/IDT5604/06 (H1N1); A/sw/Herzlake/IDT5335/06 (H3N2); A/sw/Herzlake/IDT5336/06 (H3N2); A/sw/Herzlake/IDT5337/06 (H3N2); and A/wild boar/Germany/R169/2006 (H3N2).

Other specific examples of strains of influenza A virus include, but are not limited to: A/Toronto/3141/2009 (H1N1); A/Regensburg/D6/2009 (H1N1); A/Bayern/62/2009 (H1N1); A/Bayern/62/2009 (H1N1); A/Bradenburg/19/2009 (H1N1); A/Bradenburg/20/2009 (H1N1); A/Distrito Federal/2611/2009 (H1N1); A/Mato Grosso/2329/2009 (H1N1); A/Sao Paulo/1454/2009 (H1N1); A/Sao Paulo/2233/2009 (H1N1); A/Stockholm/37/2009 (H1N1); A/Stockholm/41/2009 (H1N1); A/Stockholm/45/2009 (H1N1); A/swine/Alberta/OTH-33-1/2009 (H1N1); A/swine/Alberta/OTH-33-14/2009 (H1N1); A/swine/Alberta/OTH-33-2/2009 (H1N1); A/swine/Alberta/OTH-33-21/2009 (H1N1); A/swine/Alberta/OTH-33-22/2009 (H1N1); A/swine/Alberta/OTH-33-23/2009 (H1N1); A/swine/Alberta/OTH-33-24/2009 (H1N1); A/swine/Alberta/OTH-33-25/2009 (H1N1); A/swine/Alberta/OTH-33-3/2009 (H1N1); A/swine/Alberta/OTH-33-7/2009 (H1N1); A/Beijing/502/2009 (H1N1); A/Firenze/10/2009 (H1N1); A/Hong Kong/2369/2009 (H1N1); A/Italy/85/2009 (H1N1); A/Santo Domingo/572N/2009 (H1N1); A/Catalonia/385/2009 (H1N1); A/Catalonia/386/2009 (H1N1); A/Catalonia/387/2009 (H1N1); A/Catalonia/390/2009 (H1N1); A/Catalonia/394/2009 (H1N1); A/Catalonia/397/2009 (H1N1); A/Catalonia/398/2009 (H1N1); A/Catalonia/399/2009 (H1N1); A/Sao Paulo/2303/2009 (H1N1); A/Akita/1/2009 (H1N1); A/Castro/JXP/2009 (H1N1); A/Fukushima/1/2009 (H1N1); A/Israel/276/2009 (H1N1); A/Israel/277/2009 (H1N1); A/Israel/70/2009 (H1N1); A/Iwate/1/2009 (H1N1); A/Iwate/2/2009 (H1N1); A/Kagoshima/1/2009 (H1N1); A/Osaka/180/2009 (H1N1); A/Puerto Montt/Bio87/2009 (H1 N1); A/Sao Paulo/2303/2009 (H1N1); A/Sapporo/1/2009 (H1N1); A/Stockholm/30/2009 (H1N1); A/Stockholm/31/2009 (H1N1); A/Stockholm/32/2009 (H1N1); A/Stockholm/33/2009 (H1N1); A/Stockholm/34/2009 (H1N1); A/Stockholm/35/2009 (H1N1); A/Stockholm/36/2009 (H1N1); A/Stockholm/38/2009 (H1N1); A/Stockholm/39/2009 (H1N1); A/Stockholm/40/2009 (H1N1;) A/Stockholm/42/2009 (H1N1); A/Stockholm/43/2009 (H1N1); A/Stockholm/44/2009 (H1N1); A/Utsunomiya/2/2009 (H1N1); A/WRAIR/0573N/2009 (H1N1); and A/Zhejiang/DTID-ZJU01/2009 (H1N1).

Non-limiting examples of influenza B viruses include strain Aichi/5/88, strain Akita/27/2001, strain Akita/5/2001, strain Alaska/16/2000, strain Alaska/1777/2005, strain Argentina/69/2001, strain Arizona/146/2005, strain Arizona/148/2005, strain Bangkok/163/90, strain Bangkok/34/99, strain Bangkok/460/03, strain Bangkok/54/99, strain Barcelona/215/03, strain Beijing/15/84, strain Beijing/184/93, strain Beijing/243/97, strain Beijing/43/75, strain Beijing/5/76, strain Beijing/76/98, strain Belgium/WV106/2002, strain Belgium/WV107/2002, strain Belgium/WV109/2002, strain Belgium/WV114/2002, strain Belgium/WV122/2002, strain Bonn/43, strain Brazil/952/2001, strain Bucharest/795/03, strain Buenos Aires/161/00), strain Buenos Aires/9/95, strain Buenos Aires/SW16/97, strain Buenos Aires/VL518/99, strain Canada/464/2001, strain Canada/464/2002, strain Chaco/366/00, strain Chaco/R113/00, strain Cheju/303/03, strain Chiba/447/98, strain Chongqing/3/2000, strain clinical isolate SA1 Thailand/2002, strain clinical isolate SA10 Thailand/2002, strain clinical isolate SA100 Philippines/2002, strain clinical isolate SA101 Philippines/2002, strain clinical isolate SA110 Philippines/2002), strain clinical isolate SA112 Philippines/2002, strain clinical isolate SA113 Philippines/2002, strain clinical isolate SA114 Philippines/2002, strain clinical isolate SA2 Thailand/2002, strain clinical isolate SA20 Thailand/2002, strain clinical isolate SA38 Philippines/2002, strain clinical isolate SA39 Thailand/2002, strain clinical isolate SA99 Philippines/2002, strain CNIC/27/2001, strain Colorado/2597/2004, strain Cordoba/VA418/99, strain Czechoslovakia/16/89, strain Czechoslovakia/69/90, strain Daeku/10/97, strain Daeku/45/97, strain Daeku/47/97, strain Daeku/9/97, strain B/Du/4/78, strain B/Durban/39/98, strain Durban/43/98, strain Durban/44/98, strain B/Durban/52/98, strain Durban/55/98, strain Durban/56/98, strain England/1716/2005, strain England/2054/2005), strain England/23/04, strain Finland/154/2002, strain Finland/159/2002, strain Finland/160/2002, strain Finland/161/2002, strain Finland/162/03, strain Finland/162/2002, strain Finland/162/91, strain Finland/164/2003, strain Finland/172/91, strain Finland/173/2003, strain Finland/176/2003, strain Finland/184/91, strain Finland/188/2003, strain Finland/190/2003, strain Finland/220/2003, strain Finland/WV5/2002, strain Fujian/36/82, strain Geneva/5079/03, strain Genoa/11/02, strain Genoa/2/02, strain Genoa/21/02, strain Genova/54/02, strain Genova/55/02, strain Guangdong/05/94, strain Guangdong/08/93, strain Guangdong/5/94, strain Guangdong/55/89, strain Guangdong/8/93, strain Guangzhou/7/97, strain Guangzhou/86/92, strain Guangzhou/87/92, strain Gyeonggi/592/2005, strain Hannover/2/90, strain Harbin/07/94, strain Hawaii/10/2001, strain Hawaii/1990/2004, strain Hawaii/38/2001, strain Hawaii/9/2001, strain Hebei/19/94, strain Hebei/3/94), strain Henan/22/97, strain Hiroshima/23/2001, strain Hong Kong/110/99, strain Hong Kong/1115/2002, strain Hong Kong/112/2001, strain Hong Kong/123/2001, strain Hong Kong/1351/2002, strain Hong Kong/1434/2002, strain Hong Kong/147/99, strain Hong Kong/156/99, strain Hong Kong/157/99, strain Hong Kong/22/2001, strain Hong Kong/22/89, strain Hong Kong/336/2001, strain Hong Kong/666/2001, strain Hong Kong/9/89, strain Houston/1/91, strain Houston/1/96, strain Houston/2/96, strain Hunan/4/72, strain Ibaraki/2/85, strain ncheon/297/2005, strain India/3/89, strain India/77276/2001, strain Israel/95/03, strain Israel/WV187/2002, strain Japan/1224/2005, strain Jiangsu/10/03, strain Johannesburg/1/99, strain Johannesburg/96/01, strain Kadoma/1076/99, strain Kadoma/122/99, strain Kagoshima/15/94, strain Kansas/22992/99, strain Khazkov/224/91, strain Kobe/1/2002, strain, strain Kouchi/193/99, strain Lazio/1/02, strain Lee/40, strain Leningrad/129/91, strain Lissabon/2/90), strain Los Angeles/1/02, strain Lusaka/270/99, strain Lyon/1271/96, strain Malaysia/83077/2001, strain Maputo/1/99, strain Mar del Plata/595/99, strain Maryland/1/01, strain Memphis/1/01, strain Memphis/12/97-MA, strain Michigan/22572/99, strain Mie/1/93, strain Milano/1/01, strain Minsk/318/90, strain Moscow/3/03, strain Nagoya/20/99, strain Nanchang/1/00, strain Nashville/107/93, strain Nashville/45/91, strain Nebraska/2/01, strain Netherland/801/90, strain Netherlands/429/98, strain New York/1/2002, strain NIB/48/90, strain Ningxia/45/83, strain Norway/1/84, strain Oman/16299/2001, strain Osaka/1059/97, strain Osaka/983/97-V2, strain Oslo/1329/2002, strain Oslo/1846/2002, strain Panama/45/90, strain Paris/329/90, strain Parma/23/02, strain Perth/211/2001, strain Peru/1364/2004, strain Philippines/5072/2001, strain Pusan/270/99, strain Quebec/173/98, strain Quebec/465/98, strain Quebec/7/01, strain Roma/1/03, strain Saga/S172/99, strain Seoul/13/95, strain Seoul/37/91, strain Shangdong/7/97, strain Shanghai/361/2002), strain Shiga/T30/98, strain Sichuan/379/99, strain Singapore/222/79, strain Spain/WV27/2002, strain Stockholm/10/90, strain Switzerland/5441/90, strain Taiwan/0409/00, strain Taiwan/0722/02, strain Taiwan/97271/2001, strain Tehran/80/02, strain Tokyo/6/98, strain Trieste/28/02, strain Ulan Ude/4/02, strain United Kingdom/34304/99, strain USSR/100/83, strain Victoria/103/89, strain Vienna/1/99, strain Wuhan/356/2000, strain WV194/2002, strain Xuanwu/23/82, strain Yamagata/1311/2003, strain Yamagata/K500/2001, strain Alaska/12/96, strain GA/86, strain NAGASAKI/1/87, strain Tokyo/942/96, and strain Rochester/02/2001.

Non-limiting examples of influenza C viruses include strain Aichi/1/81, strain Ann Arbor/1/50, strain Aomori/74, strain California/78, strain England/83, strain Greece/79, strain Hiroshima/246/2000, strain Hiroshima/252/2000, strain Hyogo/1/83, strain Johannesburg/66, strain Kanagawa/1/76, strain Kyoto/1/79, strain Mississippi/80, strain Miyagi/1/97, strain Miyagi/5/2000, strain Miyagi/9/96, strain Nara/2/85, strain NewJersey/76, strain pig/Beijing/115/81, strain Saitama/3/2000), strain Shizuoka/79, strain Yamagata/2/98, strain Yamagata/6/2000, strain Yamagata/9/96, strain BERLIN/1/85, strain ENGLAND/892/8, strain GREAT LAKES/1167/54, strain JJ/50, strain PIG/BEIJING/10/81, strain PIG/BEIJING/439/82), strain TAYLOR/1233/47, and strain C/YAMAGATA/10/81.

In certain embodiments, the influenza viruses provided herein have an attenuated phenotype. In specific embodiments, the attenuated influenza virus is based on influenza A virus. In other embodiments, the attenuated influenza virus is based on influenza B virus. In yet other embodiments, the attenuated influenza virus is based on influenza C virus. In other embodiments, the attenuated influenza virus may comprise genes or genome segments from one or more strains or subtypes of influenza A, influenza B, and/or influenza C virus. In some embodiments, the attenuated backbone virus comprises genes from an influenza A virus and an influenza B virus.

In specific embodiments, attenuation of influenza virus is desired such that the virus remains, at least partially, infectious and can replicate in vivo, but only generate low titers resulting in subclinical levels of infection that are non-pathogenic. Such attenuated viruses are especially suited for embodiments described herein wherein the virus or an immunogenic composition thereof is administered to a subject to induce an immune response. Attenuation of the influenza virus can be accomplished according to any method known in the art, such as, e.g., selecting viral mutants generated by chemical mutagenesis, mutation of the genome by genetic engineering, selecting reassortant viruses that contain segments with attenuated function, or selecting for conditional virus mutants (e.g., cold-adapted viruses).

Alternatively, naturally occurring attenuated influenza viruses may be used as influenza virus backbones for the influenza virus vectors.

In one embodiment, an influenza virus may be attenuated, at least in part, by virtue of substituting the HA gene of the parental influenza virus with an influenza hemagglutinin stem domain polypeptide described herein. In some embodiments, an influenza virus may be attenuated, at least in part, by engineering the influenza virus to express a mutated NS1 gene that impairs the ability of the virus to antagonize the cellular interferon (IFN) response. Examples of the types of mutations that can be introduced into the influenza virus NS1 gene include deletions, substitutions, insertions and combinations thereof. One or more mutations can be introduced anywhere throughout the NS1 gene (e.g., the N-terminus, the C-terminus or somewhere in between) and/or the regulatory element of the NS1 gene. In one embodiment, an attenuated influenza virus comprises a genome having a mutation in an influenza virus NS1 gene resulting in a deletion consisting of 5, preferably 10, 15, 20, 25, 30, 35, 40, 45, 50, 55, 60, 65, 75, 80, 85, 90, 95, 99, 100, 105, 110, 115, 120, 125, 126, 130, 135, 140, 145, 150, 155, 160, 165, 170 or 175 amino acid residues from the C-terminus of NS1, or a deletion of between 5-170, 25-170, 50-170, 100-170, 100-160, or 105-160 amino acid residues from the C-terminus. In another embodiment, an attenuated influenza virus comprises a genome having a mutation in an influenza virus NS1 gene such that it encodes an NS1 protein of amino acid residues 1-130, amino acid residues 1-126, amino acid residues 1-120, amino acid residues 1-115, amino acid residues 1-110, amino acid residues 1-100, amino acid residues 1-99, amino acid residues 1-95, amino acid residues 1-85, amino acid residues 1-83, amino acid residues 1-80, amino acid residues 1-75, amino acid residues 1-73, amino acid residues 1-70, amino acid residues 1-65, or amino acid residues 1-60, wherein the N-terminus amino acid is number 1. For examples of NS1 mutations and influenza viruses comprising a mutated NS1, see, e.g., U.S. Pat. Nos. 6,468,544 and 6,669,943; and Li et al., 1999, J. Infect. Dis. 179:1132-1138, each of which is incorporated by reference herein in its entirety.

5.5 Non-Influenza Virus Vectors

In one aspect, provided herein are non-influenza viruses containing an influenza hemagglutinin stem domain polypeptide. In a specific embodiment, the influenza hemagglutinin stem domain polypeptide is incorporated into the virions of the non-influenza virus. The non-influenza viruses may be conjugated to moieties that target the viruses to particular cell types, such as immune cells. In some embodiments, the virions of the non-influenza virus have incorporated into them or express a heterologous polypeptide in addition to an influenza hemagglutinin stem domain polypeptide. The heterologous polypeptide may be a polypeptide that has immunopotentiating activity, or that targets the non-influenza virus to a particular cell type, such as an antibody that recognizes an antigen on a specific cell type or a ligand that binds a specific receptor on a specific cell type. See Section 5.4 supra for examples of such heterologous polypeptides.

Non-influenza viruses containing an influenza hemagglutinin stem domain polypeptide may be produced by supplying in trans the influenza hemagglutinin stem domain polypeptide during production of virions using techniques known to one skilled in the art. Alternatively, the replication of a parental non-influenza virus comprising a genome engineered to express an influenza hemagglutinin stem domain polypeptide in cells susceptible to infection with the virus wherein hemagglutinin function is provided in trans will produce progeny viruses containing the influenza hemagglutinin stem domain polypeptide.

Any virus type, subtype or strain including, but not limited to, naturally occurring strains, variants or mutants, mutagenized viruses, reassortants and/or genetically modified viruses may be used as a non-influenza virus vector. In a specific embodiment, the parental non-influenza virus is not a naturally occurring virus. In another specific embodiment, the parental non-influenza virus is a genetically engineered virus. In certain embodiments, an enveloped virus is preferred for the expression of a membrane bound influenza hemagglutinin stem domain polypeptide described herein.

In an exemplary embodiment, the non-influenza virus vector is a Newcastle disease virus (NDV). In another embodiment, the non-influenza virus vector is a vaccinia virus. In other exemplary, non-limiting, embodiments, the non-influenza virus vector is adenovirus, adeno-associated virus (AAV), hepatitis B virus, retrovirus (such as, e.g., a gammaretrovirus such as Mouse Stem Cell Virus (MSCV) genome or Murine Leukemia Virus (MLV), e.g., Moloney murine leukemia virus, oncoretrovirus, or lentivirus), an alphavirus (e.g., Venezuelan equine encephalitis virus), a rhabdovirus, such as vesicular stomatitis virus or papillomaviruses, poxvirus (such as, e.g., vaccinia virus, a MVA-T7 vector, or fowlpox), metapneumovirus, measles virus, herpesvirus, such as herpes simplex virus, or foamyvirus. See, e.g., Lawrie and Tumin, 1993, Cur. Opin. Genet. Develop. 3, 102-109 (retroviral vectors); Bett et al., 1993, J. Virol. 67, 5911 (adenoviral vectors); Zhou et al., 1994, J. Exp. Med. 179, 1867 (adeno-associated virus vectors); Dubensky et al., 1996, J. Virol. 70, 508-519 (viral vectors from the pox family including vaccinia virus and the avian pox viruses and viral vectors from the alpha virus genus such as those derived from Sindbis and Semliki Forest Viruses); U.S. Pat. No. 5,643,576 (Venezuelan equine encephalitis virus); WO 96/34625 (VSV); Ohe et al., 1995, Human Gene Therapy 6, 325-333; Woo et al., WO 94/12629; Xiao & Brandsma, 1996, Nucleic Acids. Res. 24, 2630-2622 (papillomaviruses); and Bukreyev and Collins, 2008, Curr Opin Mol Ther. 10:46-55 (NDV), each of which is incorporated by reference herein in its entirety.

In a specific embodiment, the non-influenza virus vector is NDV. Any NDV type, subtype or strain may serve as the backbone that is engineered to express an influenza hemagglutinin stem domain polypeptide, including, but not limited to, naturally-occurring strains, variants or mutants, mutagenized viruses, reassortants and/or genetically engineered viruses. In a specific embodiment, the NDV that serves as the backbone for genetic engineering is a naturally-occurring strain. In certain embodiments, the NDV that serves as the backbone for genetic engineering is a lytic strain. In other embodiments, the NDV that serves as the backbone for genetic engineering is a non-lytic strain. In certain embodiments, the NDV that serves as the backbone for genetic engineering is lentogenic strain. In some embodiments, the NDV that serves as the backbone for genetic engineering is a mesogenic strain. In other embodiments, the NDV that serves as the backbone for genetic engineering is a velogenic strain. Specific examples of NDV strains include, but are not limited to, the 73-T strain, Ulster strain, MTH-68 strain, Italien strain, Hickman strain, PV701 strain, Hitchner B1 strain, La Sota strain, YG97 strain, MET95 strain, and F48E9 strain. In a specific embodiment, the NDV that serves as the backbone for genetic engineering is the Hitchner B1 strain. In another specific embodiment, the NDV that serves as the backbone for genetic engineering is the La Sota strain.

In one embodiment, the NDV used as the backbone for a non-influenza virus vector is engineered to express a modified F protein in which the cleavage site of the F protein is replaced with one containing one or two extra arginine residues, allowing the mutant cleavage site to be activated by ubiquitously expressed proteases of the furin family. Specific examples of NDVs that express such a modified F protein include, but are not limited to, rNDV/F2aa and rNDV/F3aa. For a description of mutations introduced into a NDV F protein to produce a modified F protein with a mutated cleavage site, see, e.g., Park et al. (2006) "Engineered viral vaccine constructs with dual specificity: Avian influenza and Newcastle disease." PNAS USA 103: 8203-2808, which is incorporated herein by reference in its entirety.

In one embodiment, the non-influenza virus vector is a poxvirus. A poxvirus vector may be based on any member of the poxviridae, in particular, a vaccinia virus or an avipox virus (e.g., such as canarypox, fowlpox, etc.) that provides suitable sequences for vaccine vectors. In a specific embodiment, the poxviral vector is a vaccinia virus vector. Suitable vaccinia viruses include, but are not limited to, the Copenhagen (VC-2) strain (Goebel, et al., Virol 179: 247-266, 1990; Johnson, et al., Virol. 196: 381-401, 1993), modified Copenhagen strain (NYVAC) (U.S. Pat. No. 6,265,189), the WYETH strain and the modified Ankara (MVA) strain (Antoine, et al., Virol. 244: 365-396, 1998). Other suitable poxviruses include fowlpox strains such as ALVAC and TROVAC vectors that provide desirable properties and are highly attenuated (see, e.g., U.S. Pat. No. 6,265,189; Tartaglia et al., In AIDS Research Reviews, Koff, et al., eds., Vol. 3, Marcel Dekker, N.Y., 1993; and Tartaglia et al., 1990, Reviews in Immunology 10: 13-30, 1990).

Methods of engineering non-influenza viruses to express an influenza hemagglutinin stem domain polypeptide are well known in the art, as are methods for attenuating, propagating, and isolating and purifying such viruses. For such techniques with respect to NDV vectors, see, e.g., International Publication No. WO 01/04333; U.S. Pat. Nos. 7,442,379, 6,146,642, 6,649,372, 6,544,785 and 7,384,774; Swayne et al. (2003). Avian Dis. 47:1047-1050; and Swayne et al. (2001). J. Virol. 11868-11873, each of which is incorporated by reference in its entirety. For such techniques with respect to poxviruses, see, e.g., Piccini, et al., Methods of Enzymology 153: 545-563, 1987; International Publication No. WO 96/11279; U.S. Pat. No. 4,769,330; U.S. Pat. No. 4,722,848; U.S. Pat. No. 4,769,330; U.S. Pat. No. 4,603,112; U.S. Pat. No. 5,110,587; U.S. Pat. No. 5,174,993; EP 83 286; EP 206 920; Mayr et al., Infection 3: 6-14, 1975; and Sutter and Moss, Proc. Natl. Acad. Sci. USA 89: 10847-10851, 1992. In certain embodiments, the non-influenza virus is attenuated.

Exemplary considerations for the selection of a non-influenza virus vector, particularly for use in compositions for administration to a subject, are safety, low toxicity, stability, cell type specificity, and immunogenicity, particularly, antigenicity of the influenza hemagglutinin stem domain polypeptide expressed by the non-influenza virus vector.

5.6 Viral-Like Particles and Virosomes

Influenza hemagglutinin stem domain polypeptides can be incorporated into viral-like particle (VLP) vectors. VLPs generally comprise a viral polypeptide(s) typically derived from a structural protein(s) of a virus. In some embodiments, the VLPs are not capable of replicating. In certain embodiments, the VLPs may lack the complete genome of a virus or comprise a portion of the genome of a virus. In some embodiments, the VLPs are not capable of infecting a cell. In some embodiments, the VLPs express on their surface one or more of viral (e.g., virus surface glycoprotein) or non-viral (e.g., antibody or protein) targeting moieties known to one skilled in the art or described herein. In some embodiments, the VLPs comprise an influenza hemagglutinin stem domain polpeptide and a viral structural protein, such as HIV gag. In a specific embodiment, the VLPs comprise an influenza hemagglutinin stem domain polypeptide and an HIV gag polypeptide, such as described in Example 2 in Section 6.2 below.

Methods for producing and characterizing recombinantly produced VLPs have been described based on several viruses, including influenza virus (Bright et al. (2007) Vaccine. 25:3871), human papilloma virus type 1 (Hagnesee et al. (1991) J. Virol. 67:315), human papilloma virus type 16 (Kirnbauer et al. Proc. Natl. Acad. Sci. (1992)89:12180), HIV-1 (Haffer et al., (1990) J. Virol. 64:2653), and hepatitis A (Winokur (1991) 65:5029), each of which is incorporated herein in its entirety. Methods for expressing VLPs that contain NDV proteins are provided by Pantua et al. (2006) J. Virol. 80:11062-11073, and in United States patent application Publication No. 20090068221, published Mar. 12, 2009, each of which is incorporated in its entirety herein.

In a specific embodiment, an influenza hemagglutinin stem domain polypeptide may be incorporated into a virosome. A virosome containing an influenza hemagglutinin stem domain polypeptide may be produced using techniques known to those skilled in the art. For example, a virosome may be produced by disrupting a purified virus, extracting the genome, and reassembling particles with the viral proteins (e.g., an influenza hemagglutinin stem domain polypeptide) and lipids to form lipid particles containing viral proteins.

5.7 Bacterial Vectors

In a specific embodiment, bacteria may be engineered to express an influenza hemagglutinin stem domain polypeptide described herein. Suitable bacteria for expression of an influenza virus hemagglutinin stem domain include, but are not limited to, *Listeria, Salmonella, Shigella* sp., *Mycobacterium tuberculosis, E. coli, Neisseria meningitides, Brucella abortus, Brucella melitensis, Borrelia burgdorferi*, and *Francisella tularensis*. In a specific embodiment, the bacteria engineered to express an influenza hemagglutinin stem domain polypeptide are attenuated. Techniques for the production of bacteria engineered to express a heterologous polypeptide are known in the art and can be applied to the expression of an influenza hemagglutinin stem domain polypeptide. See, e.g., United States Patent Application Publication No. 20080248066, published Oct. 9, 2008, and United States Patent Application Publication No. 20070207171, published Sep. 6, 2007, each of which are incorporated by reference herein in their entirety.

5.8 Plant and Algae Vectors

In certain embodiments, plants (e.g., plants of the genus *Nicotiana*) may be engineered to express an influenza hemagglutinin stem domain polypeptide described herein. In specific embodiments, plants are engineered to express an influenza hemagglutinin stem domain polypeptide described herein via an agroinfiltration procedure using methods known in the art. For example, nucleic acids encoding a gene of interest, e.g., a gene encoding influenza hemagglutinin stem domain polypeptide described herein, are introduced into a strain of *Agrobacterium*. Subsequently the strain is grown in a liquid culture and the resulting bacteria are washed and suspended into a buffer solution. The plants are then exposed (e.g., via injection or submersion) to the

*Agrobacterium* that comprises the nucleic acids encoding an influenza hemagglutinin stem domain polypeptide described herein such that the *Agrobacterium* transforms the gene of interest to a portion of the plant cells. The influenza hemagglutinin stem domain polypeptide is then transiently expressed by the plant and can isolated using methods known in the art and described herein. (For specific examples see Shoji et al., 2008, Vaccine, 26(23):2930-2934; and D'Aoust et al., 2008, J. Plant Biotechnology, 6(9):930-940). In a specific embodiment, the plant is a tobacco plant (i.e., *Nicotiana tabacum*). In another specific embodiment, the plant is a relative of the tobacco plant (e.g., *Nicotiana benthamiana*).

In other embodiments, algae (e.g., *Chlamydomonas reinhardtii*) may be engineered to express an influenza hemagglutinin stem domain polypeptide described herein (see, e.g., Rasala et al., 2010, Plant Biotechnology Journal (Published online Mar. 7, 2010)).

5.9 Generation of Antibodies Against Influenza Hemagglutinin Stem Domain Polypeptide The influenza hemagglutinin stem domain polypeptides, nucleic acids encoding such polypeptides, or vectors comprising such nucleic acids or polypeptides described herein may be used to elicit neutralizing antibodies against influenza, for example, against the stalk region of influenza virus hemagglutinin polypeptide. In a specific embodiment, the influenza hemagglutinin stem domain polypeptides, nucleic acids encoding such polypeptides, or vectors comprising such nucleic acids or polypeptides described herein may be administered to a non-human subject (e.g., a mouse, rabbit, rat, guinea pig, etc.) to induce an immune response that includes the production of antibodies which may be isolated using techniques known to one of skill in the art (e.g., immunoaffinity chromatography, centrifugation, precipitation, etc.).

Alternatively, influenza hemagglutinin stem domain polypeptides described herein may be used to screen for antibodies from antibody libraries. For example, an isolated influenza hemagglutinin stem domain polypeptide may be immobilized to a solid support (e.g., a silica gel, a resin, a derivatized plastic film, a glass bead, cotton, a plastic bead, a polystyrene bead, an alumina gel, or a polysaccharide, a magnetic bead), and screened for binding to antibodies. As an alternative, the antibodies may be immobilized to a solid support and screened for binding to the isolated influenza hemagglutinin stem domain polypeptide. Any screening assay, such as a panning assay, ELISA, surface plasmon resonance, or other antibody screening assay known in the art may be used to screen for antibodies that bind to the influenza hemagglutinin stem domain. The antibody library screened may be a commercially available antibody library, an in vitro generated library, or a library obtained by identifying and cloning or isolating antibodies from an individual infected with influenza. In particular embodiments, the antibody library is generated from a survivor of an influenza virus outbreak. Antibody libraries may be generated in accordance with methods known in the art. In a particular embodiment, the antibody library is generated by cloning the antibodies and using them in phage display libraries or a phagemid display library.

Antibodies identified in the methods described herein may be tested for neutralizing activity and lack of autoreactivity using the biological assays known in the art or described herein. In one embodiment, an antibody isolated from a non-human animal or an antibody library neutralizes a hemagglutinin polypeptide from more than one influenza subtype. In some embodiments, an antibody elicited or identified using an influenza hemagglutinin stem domain polypeptide, a nucleic acid encoding such a polypeptide, or a vector encoding such a nucleic acid or polypeptide neutralizes an influenza H3 virus. In some embodiments, an antibody elicited or identified using an influenza hemagglutinin stem domain polypeptide, a nucleic acid encoding such a polypeptide, or a vector comprising such a nucleic acid or polypeptide neutralizes 1, 2, 3, 4, 5, 6, 7, 8, 9, 10, 11, 12, 13, 14, 15, or 16 or more subtypes or strains of influenza virus. In one embodiment, the neutralizing antibody neutralizes one or more influenza A viruses and one or more influenza B viruses. In particular embodiments, the neutralizing antibody is not, or does not bind the same epitope as CR6261, CR6325, CR6329, CR6307, CR6323, 2A, D7, D8, F10, G17, H40, A66, D80, E88, E90, H98, C179 (produced by hybridoma FERM BP-4517; clones sold by Takara Bio, Inc. (Otsu, Shiga, Japan)), AI3C (FERM BP-4516) or any other antibody described in Ekiert D C et al. (2009) Antibody Recognition of a Highly Conserved Influenza Virus Epitope. Science (published in Science Express Feb. 26, 2009); Kashyap et al. (2008) Combinatorial antibody libraries from survivors of the Turkish H5N1 avian influenza outbreak reveal virus neutralization strategies. Proc Natl Acad Sci USA 105: 5986-5991; Sui et al. (2009) Structural and functional bases for broad-spectrum neutralization of avian and human influenza A viruses. Nat Struct Mol Biol 16: 265-273; U.S. Pat. Nos. 5,589,174, 5,631,350, 6,337,070, and 6,720,409; International Application No. PCT/US2007/068983 published as International Publication No. WO 2007/134237; International Application No. PCT/US2008/075998 published as International Publication No. WO 2009/036157; International Application No. PCT/EP2007/059356 published as International Publication No. WO 2008/028946; and International Application No. PCT/US2008/085876 published as International Publication No. WO 2009/079259. In other embodiments, the neutralizing antibody is not an antibody described in Wang et al. (2010) "Broadly Protective Monoclonal Antibodies against H3 Influenza Viruses following Sequential Immunization with Different Hemagglutinins," PLOS Pathogens 6(2):1-9. In particular embodiments, the neutralizing antibody does not use the Ig VH1-69 segment. In some embodiments, the interaction of the neutralizing antibody with the antigen is not mediated exclusively by the heavy chain.

Antibodies identified or elicited using an influenza hemagglutinin stem domain polypeptide, a nucleic acid encoding such a polypeptide, or a vector comprising such a nucleic acid or polypeptide include immunoglobulin molecules and immunologically active portions of immunoglobulin molecules, i.e., molecules that contain an antigen binding site that specifically binds to a hemagglutinin polypeptide. The immunoglobulin molecules may be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass of immunoglobulin molecule. Antibodies include, but are not limited to, monoclonal antibodies, multispecific antibodies, human antibodies, humanized antibodies, chimeric antibodies, single-chain Fvs (scFv), single chain antibodies, Fab fragments, F(ab') fragments, disulfide-linked Fvs (sdFv), and anti-idiotypic (anti-Id) antibodies (including, e.g., anti-Id antibodies to antibodies elicited or identified using a method described herein), and epitope-binding fragments of any of the above.

Antibodies elicited or identified using an influenza hemagglutinin stem domain polypeptide, nucleic acids encoding such a polypeptide or a vector comprising such a nucleic acid or polypeptide may be used in diagnostic immunoassays, passive immunotherapy, and generation of antiidiotypic antibodies. The antibodies before being used in passive immunotherapy may be modified, e.g., the antibodies may be chimerized or humanized. See, e.g., U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741, each of which is incorporated herein by reference in its entirety, for reviews on the generation of chimeric and humanized antibodies. In addition, the ability of the antibodies to neutralize hemagglutinin polypeptides and the specificity of the antibodies for the polypeptides may be tested prior to using the antibodies in passive immunotherapy. See Section 5.11 infra for a discussion regarding use of neutralizing antibodies for the prevention or treatment of disease caused by influenza virus infection.

Antibodies elicited or identified using an influenza hemagglutinin stem domain polypeptide, a nucleic acid encoding such a polypeptide, or a vector comprising such a nucleic acid or polypeptide may be used to monitor the efficacy of a therapy and/or disease progression. Any immunoassay system known in the art may be used for this purpose including, but not limited to, competitive and non-competitive assay systems using techniques such as radioimmunoassays, ELISA (enzyme linked immunosorbent assays), "sandwich" immunoassays, precipitin reactions, gel diffusion precipitin reactions, immunodiffusion assays, agglutination assays, complement fixation assays, immunoradiometric assays, fluorescent immunoassays, protein A immunoassays and immunoelectrophoresis assays, to name but a few.

Antibodies elicited or identified using an influenza hemagglutinin stem domain polypeptide, a nucleic acid encoding such a polypeptide, or a vector comprising such a nucleic acid or polypeptide may be used in the production of antiidiotypic antibody. The antiidiotypic antibody can then in turn be used for immunization, in order to produce a subpopulation of antibodies that bind a particular antigen of influenza, e.g., a neutralizing epitope of a hemagglutinin polypeptide (Jerne, 1974, Ann. Immunol. (Paris) 125c:373; Jerne et al., 1982, EMBO J. 1:234, incorporated herein by reference in its entirety).

5.10 Stimulation of Cells with Influenza Hemagglutinin Stem Domain Polypeptide

In another aspect, provided herein are methods for stimulating cells ex vivo with an influenza hemagglutinin stem domain polypeptide described herein. Such cells, e.g., dendritic cells, may be used in vitro to generate antibodies against the influenza hemagglutinin stem domain polypeptide or may themselves be administered to a subject by, e.g., an adoptive transfer technique known in the art. See, e.g., United States patent application Publication No. 20080019998, published Jan. 24, 2008, which is incorporated herein by reference in its entirety, for a description of adoptive transfer techniques. In certain embodiments, when cells that have been stimulated ex vivo with an influenza hemagglutinin stem domain polypeptide described herein are administered to a subject, the cells are not mammalian cells (e.g., CB-1 cells).

In one non-limiting example, a vector, e.g., an influenza virus vector, engineered to express an influenza hemagglutinin stem domain polypeptide described herein can be used to generate dendritic cells (DCs) that express the influenza hemagglutinin stem domain polypeptide and display immunostimulatory properties directed against an influenza virus hemagglutinin polypeptide. Such DCs may be used to expand memory T cells and are potent stimulators of T cells, including influenza hemagglutinin stem domain polypeptide-specific cytotoxic T lymphocyte clones. See Strobel et al., 2000, Human Gene Therapy 11:2207-2218, which is incorporated herein by reference in its entirety.

An influenza hemagglutinin stem domain polypeptide described herein may be delivered to a target cell in any way that allows the polypeptide to contact the target cell, e.g., a DC, and deliver the polypeptide to the target cell. In certain embodiments, the influenza hemagglutinin stem domain polypeptide is delivered to a subject, as described herein. In some such embodiments, cells contacted with the polypeptide may be isolated and propagated.

In certain embodiments, an influenza hemagglutinin stem domain polypeptide is delivered to a target cell in vitro. Techniques known to one of skill in the art may be used to deliver the polypeptide to target cells. For example, target cells may be contacted with the polypeptide in a tissue culture plate, tube or other container. The polypeptide may be suspended in media and added to the wells of a culture plate, tube or other container. The media containing the polypeptide may be added prior to plating of the cells or after the cells have been plated. The target cells are preferably incubated with the polypeptide for a sufficient amount of time to allow the polypeptide to contact the cells. In certain embodiments, the cells are incubated with the polypeptide for about 1 hour or more, about 5 hours or more, about 10 hours or more, about 12 hours or more, about 16 hours or more, about 24, hours or more, about 48 hours or more, about 1 hour to about 12 hours, about 3 hours to about 6 hours, about 6 hours to about 12 hours, about 12 hours to about 24 hours, or about 24 hours to about 48 hours. In certain embodiments, wherein the influenza hemagglutinin stem domain polypeptide is in a virus, the contacting of the target cells comprises infecting the cells with the virus.

The target cells may be from any species, including, e.g., humans, mice, rats, rabbits and guinea pigs. In some embodiments, target cells are DCs obtained from a healthy subject or a subject in need of treatment. In certain embodiments, target cells are DCs obtained from a subject in whom it is desired to stimulate an immune response to the polypeptide. Methods of obtaining cells from a subject are well known in the art.

5.11 Compositions

The nucleic acids, vectors, polypeptides, bacteria, antibodies, or cells described herein (sometimes referred to herein as "active compounds") may be incorporated into compositions. In a specific embodiment, the compositions are pharmaceutical compositions, such as immunogenic compositions (e.g., vaccine formulations). The pharmaceutical compositions provided herein can be in any form that allows for the composition to be administered to a subject. In a specific embodiment, the pharmaceutical compositions are suitable for veterinary and/or human administration. The compositions may be used in methods of preventing or treating an influenza virus disease.

In one embodiment, a pharmaceutical composition comprises an influenza hemagglutinin stem domain polypeptide, in an admixture with a pharmaceutically acceptable carrier. In another embodiment, a pharmaceutical composition comprises a nucleic acid encoding an influenza hemagglutinin stem domain polypeptide described herein, in an admixture with a pharmaceutically acceptable carrier. In another embodiment, a pharmaceutical composition comprises an expression vector comprising a nucleic acid encoding an influenza hemagglutinin stem domain polypeptide, in an admixture with a pharmaceutically acceptable carrier. In another embodiment, a pharmaceutical composition comprises an influenza virus or non-influenza virus containing an influenza hemagglutinin stem domain polypeptide, in an admixture with a pharmaceutically acceptable carrier. In another embodiment, a pharmaceutical composition comprises an influenza virus or non-influenza virus having a genome engineered to express an influenza hemagglutinin stem domain polypeptide, in admixture with a pharmaceutically acceptable carrier. In another embodiment, a pharmaceutical composition comprises a viral-like particle or virosome containing an influenza hemagglutinin stem domain polypeptide, in an admixture with a pharmaceutically acceptable carrier. In another embodiment, a pharmaceutical composition comprises a bacteria expressing or engineered to express an influenza hemagglutinin stem domain polypeptide, in an admixture with a pharmaceutically acceptable carrier. In another embodiment, a pharmaceutical composition comprises cells stimulated with an influenza hemagglutinin stem domain polypeptide, in an admixture with a pharmaceutically acceptable carrier.

In some embodiments, a pharmaceutical composition may comprise one or more other therapies in addition to an active compound.

As used herein, the term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should suit the mode of administration.

In a specific embodiment, pharmaceutical compositions are formulated to be suitable for the intended route of administration to a subject. For example, the pharmaceutical composition may be formulated to be suitable for parenteral, oral, intradermal, transdermal, colorectal, intraperitoneal, and rectal administration. In a specific embodiment, the pharmaceutical composition may be formulated for intravenous, oral, intraperitoneal, intranasal, intratracheal, subcutaneous, intramuscular, topical, intradermal, transdermal or pulmonary administration.

In certain embodiments, biodegradable polymers, such as ethylene vinyl acetate, polyanhydrides, polyethylene glycol (PEGylation), polymethyl methacrylate polymers, polylactides, poly(lactide-co-glycolides), polyglycolic acid, collagen, polyorthoesters, and polylactic acid, may be used as carriers. In some embodiments, the active compounds are prepared with carriers that increase the protection of the compound against rapid elimination from the body, such as a controlled release formulation, including implants and microencapsulated delivery systems. Methods for preparation of such formulations will be apparent to those skilled in the art. Liposomes or micelles can also be used as pharmaceutically acceptable carriers. These can be prepared according to methods known to those skilled in the art, for example, as described in U.S. Pat. No. 4,522,811. In certain embodiments, the pharmaceutical compositions comprise one or more adjuvants.

In specific embodiments, immunogenic compositions described herein are monovalent formulations. In other embodiments, immunogenic compositions described herein are multivalent formulations. In one example, a multivalent formulation comprises one or more vectors expressing an influenza hemagglutinin stem domain polypeptide derived from an influenza A virus hemagglutinin polypeptide and one or more vectors expressing an influenza hemagglutinin stem domain polypeptide derived from an influenza B virus hemagglutinin polypeptide. In another example, a multivalent formulation comprises a vector expressing an influenza hemagglutinin stem domain polypeptide derived from an influenza A virus H3 antigen and a vector expressing an influenza hemagglutinin stem domain polypeptide derived from an influenza A virus H1 antigen. In another example, a multivalent formulation comprises a vector expressing an influenza hemagglutinin stem domain polypeptide derived from an influenza A virus H3 antigen, a vector expressing an influenza hemagglutinin stem domain polypeptide derived from an influenza A virus H1 antigen, and a vector expressing an influenza hemagglutinin stem domain polypeptide derived from an influenza B virus HA antigen. In certain embodiments, a multivalent formulation may comprise one or more different influenza hemagglutinin stem domain polypeptides expressed using a single vector.

In certain embodiments, the pharmaceutical compositions described herein additionally comprise a preservative, e.g., the mercury derivative thimerosal. In a specific embodiment, the pharmaceutical compositions described herein comprises 0.001% to 0.01% thimerosal. In other embodiments, the pharmaceutical compositions described herein do not comprise a preservative. In a specific embodiment, thimerosal is used during the manufacture of a pharmaceutical composition described herein and the thimerosal is removed via purification steps following production of the pharmaceutical composition, i.e., the pharmaceutical composition contains trace amounts of thimerosal (<0.3 μg of mercury per dose after purification; such pharmaceutical compositions are considered thimerosal-free products).

In certain embodiments, the pharmaceutical compositions described herein additionally comprise egg protein (e.g., ovalbumin or other egg proteins). The amount of egg protein in the pharmaceutical compositions described herein may range from about 0.0005 to about 1.2. μg of egg protein to 1 ml of pharmaceutical composition. In other embodiments, the pharmaceutical compositions described herein do not comprise egg protein.

In certain embodiments, the pharmaceutical compositions described herein additionally comprise one or more antimicrobial agents (e.g., antibiotics) including, but not limited to gentamicin, neomycin, polymyxin (e.g., polymyxin B), and kanamycin, streptomycin. In other embodiments, the pharmaceutical compositions described herein do not comprise any antibiotics.

In certain embodiments, the pharmaceutical compositions described herein additionally comprise one or more components used to inactivate a virus, e.g., formalin or formaldehyde or a detergent such as sodium deoxycholate, octoxynol 9 (Triton X-100), and octoxynol 10. In other embodiments, the pharmaceutical compositions described herein do not comprise any components used to inactivate a virus.

In certain embodiments, the pharmaceutical compositions described herein additionally comprise gelatin. In other embodiments, the pharmaceutical compositions described herein do not comprise gelatin.

In certain embodiments, the pharmaceutical compositions described herein additionally comprise one or more buffers, e.g., phosphate buffer and sucrose phosphate glutamate buffer. In other embodiments, the pharmaceutical compositions described herein do not comprise buffers.

In certain embodiments, the pharmaceutical compositions described herein additionally comprise one or more salts, e.g., sodium chloride, calcium chloride, sodium phosphate, monosodium glutamate, and aluminum salts (e.g., aluminum hydroxide, aluminum phosphate, alum (potassium aluminum sulfate), or a mixture of such aluminum salts). In other embodiments, the pharmaceutical compositions described herein do not comprise salts.

In specific embodiments, the the pharmaceutical compositions described herein are low-additive influenza virus vaccines, i.e., the pharmaceutical compositions do not comprise one or more additives commonly found in influenza virus vaccines. Low-additive influenza vaccines have been described (see, e.g., International Aplication No. PCT/M2008/002238 published as International Publication No. WO 09/001217 which is herein incorporated by reference in its entirety).

The pharmaceutical compositions described herein can be included in a container, pack, or dispenser together with instructions for administration.

The pharmaceutical compositions described herein can be stored before use, e.g., the pharmaceutical compositions can be stored frozen (e.g., at about −20° C. or at about −70° C.); stored in refrigerated conditions (e.g., at about 4° C.); or stored at room temperature (see International Aplication No. PCT/M2007/001149 published as International Publication No. WO 07/110776, which is herein incorporated by reference in its entirety, for methods of storing compositions comprising influenza vaccines without refrigeration).

In certain embodiments, when the active compound in a pharmaceutical composition described herein is a cell engineered to express an influenza hemagglutinin stem domain polypeptide, the cells in the pharmaceutical composition are not mammalian cells (e.g., CB-1 cells).

5.11.1 Subunit Vaccines

In a specific embodiment, provided herein are subunit vaccines comprising an influenza hemagglutinin stem domain polypeptide described herein. In some embodiments, a subunit vaccine comprises an influenza hemagglutinin stem domain polypeptide and one or more surface glycoproteins (e.g., influenza virus neuraminidase), other targeting moieties or adjuvants. In specific embodiments, a subunit vaccine comprises a single influenza hemagglutinin stem domain polypeptide. In other embodiments, a subunit vaccine comprises two, three, four or more influenza hemagglutinin stem domain polypeptides. In specific embodiments, the influenza hemagglutinin stem domain polypeptide(s) used in a subunit vaccine is not membrane-bound, i.e., it is soluble.

In certain embodiments, provided herein are subunit vaccines comprising about 10 μg to about 60 μg of one or more influenza hemagglutinin stem domain polypeptides described herein, about 0.001% to 0.01% thimerosal, about 0.1 μg to about 1.0 μg chicken egg protein, about 1.0 μg to about 5.0 μg polymyxin, about 1.0 μg to about 5.0 μg neomycin, about 0.1 μg to about 0.5 μg betapropiolactone, and about 0.001 to about 0.05% w/v of nonylphenol ethoxylate per dose.

In a specific embodiment, a subunit vaccine provided herein comprises or consists of a 0.5 ml dose that comprises 45 μg of influenza hemagglutinin stem domain polypeptide (s) provided herein, ≤1.0 μg of mercury (from thimerosal), ≤1.0 μg chicken egg protein (i.e., ovalbumin), ≤3.75 μg polymyxin, and ≤2.5 μg neomycin. In some embodiments, a subunit vaccine provided herein additionally comprises or consists of not more than 0.5 μg betapropiolactone, and not more than 0.015% w/v of nonylphenol ethoxylate per dose. In some embodiments, the 0.5 ml dose subunit vaccine is packaged in a pre-filled syringe.

In a specific embodiment, a subunit vaccine provided herein consists of a 5.0 ml multidose vial (0.5 ml per dose) that comprises 45 μg of influenza hemagglutinin stem domain polypeptide(s) provided herein, 25.0 μg of mercury (from thimerosal), ≤1.0 μg chicken egg protein (i.e., ovalbumin), ≤3.75 μg polymyxin, and ≤2.5 neomycin. In some embodiments, a subunit vaccine provided herein additionally comprises or consists of not more than 0.5 μg betapropiolactone, and not more than 0.015% w/v of nonylphenol ethoxylate per dose.

In a specific embodiment, the subunit vaccine is prepared using influenza virus that was propagated in embryonated chicken eggs (i.e., the components of the subunit vaccine (e.g., a hemagglutinin stem domain polypeptide) are isolated from virus that was propagated in embryonated chicken eggs). In another specific embodiment, the subunit vaccine is prepared using influenza virus that was not propagated in embryonated chicken eggs (i.e., the components of the subunit vaccine (e.g., a hemagglutinin stem domain polypeptide) are isolated from virus that was not propagated in embryonated chicken eggs). In another specific embodiment, the subunit vaccine is prepared using influenza virus that was propagated in mammalian cells, e.g., immortalized human cells (see, e.g., International Application No. PCT/EP2006/067566 published as International Publication No. WO 07/045674 which is herein incorporated by reference in its entirety) or canine kidney cells such as MDCK cells (see, e.g., International Application No. PCT/IB2007/003536 published as International Publication No. WO 08/032219 which is herein incorporated by reference in its entirety) (i.e., the components of the subunit vaccine (e.g., a hemagglutinin stem domain polypeptide) are isolated from virus that was propagated in mammalian cells). In another specific embodiment, the hemagglutinin stem domain polypeptide(s) in a subunit vaccine are prepared using an expression vector, e.g., a viral vector, plant vector or a bacterial vector (i.e., the hemagglutinin stem domain polypeptide(s) in the subunit vaccine are obtained/isolated from an expression vector).

5.11.2 Live Virus Vaccines

In one embodiment, provided herein are immunogenic compositions (e.g., vaccines) comprising live virus containing an influenza hemagglutinin stem domain polypeptide. In another embodiment, provided herein are immunogenic compositions (e.g., vaccines) comprising live virus that is engineered to encode an influenza hemagglutinin stem domain polypeptide, which is expressed by progeny virus produced in the subjects administered the compositions. In specific embodiments, the influenza hemagglutinin stem domain polypeptide is membrane-bound. In other specific embodiments, the influenza virus hemagglutinin stem domain polypeptide is not membrane-bound, i.e., soluble. In particular embodiments, the live virus is an influenza virus, such as described in Section 5.4, supra. In other embodiments, the live virus is a non-influenza virus, such as described in Section 5.5, supra. In some embodiments, the live virus is attenuated. In some embodiments, an immunogenic composition comprises two, three, four or more live viruses containing or engineered to express two, three, four or more different influenza hemagglutinin stem domain polypeptides.

In certain embodiments, provided herein are immunogenic compositions (e.g., vaccines) comprising about $10^5$ to about $10^{10}$ fluorescent focus units (FFU) of live attenuated influenza virus containing one or more influenza hemagglutinin stem domain polypeptides described herein, about 0.1 to about 0.5 mg monosodium glutamate, about 1.0 to about 5.0 mg hydrolyzed procine gelatin, about 1.0 to about 5.0 mg arginine, about 10 to about 15 mg sucrose, about 1.0 to about 5.0 mg dibasic potassium phosphate, about 0.5 to about 2.0 mg monobasic potassium phosphate, and about 0.001 to about 0.05 μg/ml gentamicin sulfate per dose. In some embodiments, the immunogenic compositions (e.g., vaccines) are packaged as pre-filled sprayers containing single 0.2 ml doses.

In a specific embodiment, provided herein are immunogenic compositions (e.g., vaccines) comprising $10^{6.5}$ to $10^{7.5}$ FFU of live attenuated influenza virus containing one or more influenza hemagglutinin stem domain polypeptides described herein, 0.188 mg monosodium glutamate, 2.0 mg hydrolyzed procine gelatin, 2.42 mg arginine, 13.68 mg sucrose, 2.26 mg dibasic potassium phosphate, 0.96 mg monobasic potassium phosphate, and <0.015 μg/ml gentamicin sulfate per dose. In some embodiments, the immunogenic compositions (e.g., vaccines) are packaged as pre-filled sprayers containing single 0.2 ml doses.

In a specific embodiment, the live virus that contains an influenza hemagglutinin stem domain polypeptide is propagated in embryonated chicken eggs before its use in an immunogenic composition described herein. In another specific embodiment, the live virus that contains an influenza hemagglutinin stem domain polypeptide is not propagated in embryonated chicken eggs before its use in an immunogenic composition described herein. In another specific embodiment, the live virus that contains an influenza hemagglutinin stem domain polypeptide is propagated in mammalian cells, e.g., immortalized human cells (see, e.g., International Application No. PCT/EP2006/067566 published as International Publication No. WO 07/045674 which is herein incorporated by reference in its entirety) or canine kidney cells such as MDCK cells (see, e.g., International Application No. PCT/IB2007/003536 published as International Publication No. WO 08/032219 which is herein incorporated by reference in its entirety) before its use in an immunogenic composition described herein.

An immunogenic composition comprising a live virus for administration to a subject may be preferred because multiplication of the virus in the subject may lead to a prolonged stimulus of similar kind and magnitude to that occurring in natural infections, and therefore, confer substantial, long lasting immunity.

5.11.3 Inactivated Virus Vaccines

In one embodiment, provided herein are immunogenic compositions (e.g., vaccines) comprising an inactivated virus containing an influenza hemagglutinin stem domain polypeptide. In specific embodiments, the influenza hemagglutinin stem domain polypeptide is membrane-bound. In particular embodiments, the inactivated virus is an influenza virus, such as described in Section 5.4, supra. In other embodiments, the inactivated virus is a non-influenza virus, such as described in Section 5.5, supra. In some embodiments, an immunogenic composition comprises two, three, four or more inactivated viruses containing two, three, four or more different influenza hemagglutinin stem domain polypeptides. In certain embodiments, the inactivated virus immunogenic compositions comprise one or more adjuvants.

Techniques known to one of skill in the art may be used to inactivate viruses containing an influenza hemagglutinin stem domain polypeptide. Common methods use formalin, heat, or detergent for inactivation. See, e.g., U.S. Pat. No. 6,635,246, which is herein incorporated by reference in its entirety. Other methods include those described in U.S. Pat. Nos. 5,891,705; 5,106,619 and 4,693,981, which are incorporated herein by reference in their entireties.

In certain embodiments, provided herein are immunogenic compositions (e.g., vaccines) comprising inactivated influenza virus such that each dose of the immunogenic composition comprises about 15 to about 60 μg of influenza hemagglutinin stem domain polypeptide described herein, about 1.0 to about 5.0 mg sodium chloride, about 20 to about 100 μg monobasic sodium phosphate, about 100 to about 500 μg dibasic sodium phosphate, about 5 to about 30 μg monobasic potassium phosphate, about 5 to about 30 μg potassium chloride, and about 0.5 to about 3.0 μg calcium chloride. In some embodiments, the immunogenic compositions (e.g., vaccines) are packaged as single 0.25 ml or single 0.5 ml doses. In other embodiments, the immunogenic compositions (e.g., vaccines) are packaged as multi-dose formulations.

In certain embodiments, provided herein are immunogenic compositions (e.g., vaccines) comprising inactivated influenza virus such that each dose of the immunogenic composition comprises about 15 to about 60 μg of influenza hemagglutinin stem domain polypeptide described herein, about 0.001% to 0.01% thimerosal, about 1.0 to about 5.0 mg sodium chloride, about 20 to about 100 μg monobasic sodium phosphate, about 100 to about 500 μg dibasic sodium phosphate, about 5 to about 30 μg monobasic potassium phosphate, about 5 to about 30 μg potassium chloride, and about 0.5 to about 3.0 μg calcium chloride per dose. In some embodiments, the immunogenic compositions (e.g., vaccines) are packaged as single 0.25 ml or single 0.5 ml doses. In other embodiments, the immunogenic compositions (e.g., vaccines) are packaged as multi-dose formulations.

In a specific embodiment, immunogenic compositions (e.g., vaccines) provided herein are packaged as single 0.25 ml doses and comprise 22.5 μg of influenza hemagglutinin stem domain polypeptide described herein, 2.05 mg sodium chloride, 40 μg monobasic sodium phosphate, 150 μg dibasic sodium phosphate, 10 μg monobasic potassium phosphate, 10 μg potassium chloride, and 0.75 μg calcium chloride per dose.

In a specific embodiment, immunogenic compositions (e.g., vaccines) provided herein are packaged as single 0.5 ml doses and comprise 45 μg of influenza hemagglutinin stem domain polypeptide described herein, 4.1 mg sodium chloride, 80 μg monobasic sodium phosphate, 300 μg dibasic sodium phosphate, 20 μg monobasic potassium phosphate, 20 μg potassium chloride, and 1.5 μg calcium chloride per dose.

In a specific embodiment, immunogenic compositions (e.g., vaccines) are packaged as multi-dose formulations comprising or consisting of 5.0 ml of vaccine (0.5 ml per dose) and comprise 24.5 μg of mercury (from thimerosal), 45 μg of influenza hemagglutinin stem domain polypeptide described herein, 4.1 mg sodium chloride, 80 monobasic sodium phosphate, 300 μg dibasic sodium phosphate, 20 μg monobasic potassium phosphate, 20 μg potassium chloride, and 1.5 μg calcium chloride per dose.

In a specific embodiment, the inactivated virus that contains an influenza hemagglutinin stem domain polypeptide was propagated in embryonated chicken eggs before its inactivation and subsequent use in an immunogenic composition described herein. In another specific embodiment, the inactivated virus that contains an influenza hemagglutinin stem domain polypeptide was not propagated in embryonated chicken eggs before its inactivation and subsequent use in an immunogenic composition described herein. In another specific embodiment, the inactivated virus that contains an influenza hemagglutinin stem domain polypeptide was propagated in mammalian cells, e.g., immortalized human cells (see, e.g., International Application No. PCT/EP2006/067566 published as International Publication No. WO 07/045674 which is herein incorporated by reference in its entirety) or canine kidney cells such as MDCK cells (see, e.g., International Application No. PCT/IB2007/003536 published as International Publication No. WO 08/032219 which is herein incorporated by reference in its entirety) before its inactivation and subsequent use in an immunogenic composition described herein.

5.11.4 Split Virus Vaccines

In one embodiment, an immunogenic composition comprising an influenza hemagglutinin stem domain polypeptide is a split virus vaccine. In some embodiments, split virus vaccine contains two, three, four or more different influenza hemagglutinin stem domain polypeptides. In certain embodiments, the influenza hemagglutinin stem domain polypeptide is/was membrane-bound. In certain embodiments, the split virus vaccines comprise one or more adjuvants.

Techniques for producing split virus vaccines are known to those skilled in the art. By way of non-limiting example, an influenza virus split vaccine may be prepared using inactivated particles disrupted with detergents. One example of a split virus vaccine that can be adapted for use in accordance with the methods described herein is the Fluzone®, Influenza Virus Vaccine (Zonal Purified, Subvirion) for intramuscular use, which is formulated as a sterile suspension prepared from influenza viruses propagated in embryonated chicken eggs. The virus-containing fluids are harvested and inactivated with formaldehyde. Influenza virus is concentrated and purified in a linear sucrose density gradient solution using a continuous flow centrifuge. The virus is then chemically disrupted using a nonionic surfactant, octoxinol-9, (Triton® X-100-A registered trademark of Union Carbide, Co.) producing a "split virus." The split virus is then further purified by chemical means and suspended in sodium phosphate-buffered isotonic sodium chloride solution.

In certain embodiments, provided herein are split virus vaccines comprising about 10 μg to about 60 μg of one or more influenza hemagglutinin stem domain polypeptides described herein, about 0.01 to about 1.0 mg octoxynol-10 (TRITON X-100®, about 0.5 to 0.5 mg α-tocopheryl hydrogen succinate, about 0.1 to 1.0 mg polysorbate 80 (Tween 80), about 0.001 to about 0.003 μg hydrocortisone, about 0.05 to about 0.3 μg gentamcin sulfate, about 0.5 to about 2.0 mchicken egg protein (ovalbumin), about 25 to 75 μg formaldehyde, and about 25 to 75 μg sodium deoxycholate.

In a specific embodiment, a split virus vaccine provided herein comprises or consists of a 0.5 ml dose that comprises 45 μg of influenza hemagglutinin stem domain polypeptide (s) provided herein, ≤0.085 mg octoxynol-10 (TRITON X-100®, ≤0.1 mg α-tocopheryl hydrogen succinate, ≤0.415 mg polysorbate 80 (Tween 80), ≤0.0016 μg hydrocortisone, ≤0.15 μg gentamcin sulfate, ≤1.0 chicken egg protein (ovalbumin), ≤50 μg formaldehyde, and ≤50 μg sodium deoxycholate. In some embodiments, the 0.5 ml dose subunit vaccine is packaged in a pre-filled syringe.

In a specific embodiment, the split virus vaccine is prepared using influenza virus that was propagated in embryonated chicken eggs. In another specific embodiment, the split virus vaccine is prepared using influenza virus that was not propagated in embryonated chicken eggs. In another specific embodiment, the split virus vaccine is prepared using influenza virus that was propagated in mammalian cells, e.g., immortalized human cells (see, e.g., PCT/EP2006/067566 published as WO 07/045674 which is herein incorporated by reference in its entirety) or canine kidney cells such as MDCK cells (see, e.g., PCT/IB2007/003536 published as WO 08/032219 which is herein incorporated by reference in its entirety).

5.11.5 Adjuvants

In certain embodiments, the compositions described herein comprise, or are administered in combination with, an adjuvant. The adjuvant for administration in combination with a composition described herein may be administered before, concommitantly with, or after administration of said composition. In some embodiments, the term "adjuvant" refers to a compound that when administered in conjunction with or as part of a composition described herein augments, enhances and/or boosts the immune response to an influenza hemagglutinin stem domain polypeptide, but when the compound is administered alone does not generate an immune response to the polypeptide. In some embodiments, the adjuvant generates an immune response to the polypeptide and does not produce an allergy or other adverse reaction. Adjuvants can enhance an immune response by several mechanisms including, e.g., lymphocyte recruitment, stimulation of B and/or T cells, and stimulation of macrophages.

In certain embodiments, an adjuvant augments the intrinsic response to the influenza hemagglutinin stem domain polypeptide without causing conformational changes in the polypeptide that affect the qualitative form of the response. Specific examples of adjuvants include, but are not limited to, aluminum salts (alum) (such as aluminum hydroxide, aluminum phosphate, and aluminum sulfate), 3 De-O-acylated monophosphoryl lipid A (MPL) (see GB 2220211), MF59 (Novartis), AS03 (GlaxoSmithKline), AS04 (GlaxoSmithKline), polysorbate 80 (Tween 80; ICL Americas, Inc.), imidazopyridine compounds (see International Application No. PCT/US2007/064857, published as International Publication No. WO2007/109812), imidazoquinoxaline compounds (see International Application No. PCT/US2007/064858, published as International Publication No. WO2007/109813) and saponins, such as QS21 (see Kensil et al., in Vaccine Design: The Subunit and Adjuvant Approach (eds. Powell & Newman, Plenum Press, N Y, 1995); U.S. Pat. No. 5,057,540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al., N. Engl. J. Med. 336, 86-91 (1997)). Another adjuvant is CpG (Bioworld Today, Nov. 15, 1998). Such adjuvants can be used with or without other specific immunostimulating agents such as MPL or 3-DMP, QS21, polymeric or monomeric amino acids such as polyglutamic acid or polylysine, or other immunopotentiating agents described in Section 5.4, supra. It should be understood that different formulations of influenza hemagglutinin stem domain polypeptide may comprise different adjuvants or may comprise the same adjuvant.

5.12 Prophylactic and Therapeutic Uses

In one aspect, provided herein are methods for inducing an immune response in a subject utilizing an active compound, i.e., an influenza hemagglutinin stem domain polypeptide described herein, a nucleic acid encoding such a polypeptide, a vector (e.g., a viral vector, or a bacteria)

containing or expressing such a polypeptide, or cells stimulated with such a polypeptide. In a specific embodiment, a method for inducing an immune response to an influenza virus hemagglutinin polypeptide in a subject comprises administering to a subject in need thereof an effective amount of an influenza virus hemagglutinin stem domain polypeptide or an immunogenic composition thereof. In another embodiment, a method for inducing an immune response to an influenza virus hemagglutinin polypeptide in a subject comprises administering to a subject in need thereof an effective amount of a nucleic acid encoding an influenza hemagglutinin stem domain polypeptide or an immunogenic composition thereof. In another embodiment, a method for inducing an immune response to an influenza virus hemagglutinin polypeptide in a subject comprises administering to a subject in need thereof an effective amount of a viral vector containing or expressing an influenza hemagglutinin stem domain polypeptide or an immunogenic composition thereof. In yet another embodiment, a method for inducing an immune response to an influenza virus hemagglutinin polypeptide in a subject comprises administering to a subject in need thereof an effective amount of cells stimulated with an influenza hemagglutinin stem domain polypeptide or a pharmaceutical composition thereof. In certain embodiments, an influenza hemagglutinin stem domain polypeptide used in the method is a purified influenza hemagglutinin stem domain polypeptide derived from a mammalian cell, a plant cell, or an insect cell.

In a specific embodiment, a method for inducing an immune response to an influenza virus hemagglutinin polypeptide in a subject comprises administering to a subject in need thereof a subunit vaccine described herein. In another embodiment, a method for inducing an immune response to an influenza virus hemagglutinin polypeptide in a subject comprises administering to a subject in need thereof a live virus vaccine described herein. In particular embodiments, the live virus vaccine comprises an attenuated virus. In another embodiment, a method for inducing an immune response to an influenza virus hemagglutinin polypeptide in a subject comprises administering to a subject in need thereof an inactivated virus vaccine described herein. In another embodiment, a method for inducing an immune response to an influenza virus hemagglutinin polypeptide in a subject comprises administering to a subject in need thereof a split virus vaccine described herein. In another embodiment, a method for inducing an immune response to an influenza virus hemagglutinin polypeptide in a subject comprises administering to a subject in need thereof a viral-like particle vaccine described herein. In another embodiment, a method for inducing an immune response to an influenza hemagglutinin polypeptide comprises administering to a subject in need thereof a virosome described herein. In another embodiment, a method for inducing an immune response to an influenza hemagglutinin polypeptide comprises administering to a subject in need thereof a bacteria expressing or engineered to express an influenza hemagglutinin stem domain polypeptide or a composition thereof. In certain embodiments, an influenza hemagglutinin stem domain polypeptide used in the method is a purified influenza hemagglutinin stem domain polypeptide derived from a mammalian cell, a plant cell, or an insect cell.

In some embodiments, the immune response induced by an active compound or a composition described herein is effective to prevent and/or treat an influenza virus infection caused by any subtype or strain of influenza virus. In certain embodiments, the immune response induced by an active compound or a composition described herein is effective to prevent and/or treat an influenza virus infection caused by a subtype of influenza virus that belongs to one HA group (e.g., Group 1, which comprises H1, H2, H5, H6, H8, H9, H11, H12, H13, and H16) and not the other HA group (e.g., Group 2, which comprises H3, H4, H7, H10, H14, and H15). For example, the immune response induced may be effective to prevent and/or treat an influenza virus infection caused by an influenza virus that belongs to the HA group consisting of H11, H13, H16, H9, H8, H12, H6, H1, H5 and H2. Alternatively, the immune response induced may be effective to prevent and/or treat an influenza virus infection caused by an influenza virus that belongs to the HA group consisting of H3, H4, H14, H10, H15 and H7. In some embodiments, the immune response induced by an active compound or a composition described herein is effective to prevent and/or treat an influenza virus infection caused by one, two, three, four or five subtypes of influenza virus. In certain embodiments, the immune response induced by an active compound or a composition described herein is effective to prevent and/or treat an influenza virus infection caused by six, seven, eight, nine, ten, eleven, twelve, thirteen, fourteen or fifteen subtypes of influenza virus. In some embodiments, the immune response induced by an active compound or a composition described herein is effective to prevent and/or treat an influenza virus infection caused by one or more variants within the same subtype of influenza virus.

In some embodiments, the immune response induced by an active compound or a composition described herein is effective to prevent and/or treat an influenza virus infection caused by both H1N1 and H2N2 subtypes. In other embodiments, the immune response induced by an active compound or a composition described herein is not effective to prevent and/or treat an influenza virus infection caused by both H1N1 and H2N2 subtypes. In some embodiments, the immune response induced by an active compound or a composition described herein is effective to prevent and/or treat an influenza virus infection caused by H1N1, H2N2, and H3N2 subtypes. In some embodiments, the immune response induced by an active compound or a composition described herein is effective to prevent and/or treat an influenza virus infection caused by H3N2 subtypes. In other embodiments, the immune response induced by an active compound or a composition described herein is not effective to prevent and/or treat an influenza virus infection caused by H3N2 subtypes.

In some embodiments, the immune response induced by an active compound or a composition described herein is effective to prevent and/or treat an influenza virus disease caused by any subtype or strain of influenza virus. In certain embodiments, the immune response induced by an active compound or a composition described herein is effective to prevent and/or treat an influenza virus disease caused by a subtype of influenza virus that belongs to one HA group and not the other HA group. For example, the immune response induced may be effective to prevent and/or treat an influenza virus disease caused by an influenza virus that belongs to the HA group consisting of H11, H13, H16, H9, H8, H12, H6, H1, H5 and H2. Alternatively, the immune response induced may be effective to prevent and/or treat an influenza virus disease caused by an influenza virus that belongs to the HA group consisting of H3, H4, H14, H10, H15 and H7. In some embodiments, the immune response induced by an active compound or a composition described herein is effective to prevent and/or treat an influenza virus disease caused by any of one, two, three, four or five subtypes of influenza virus. In certain embodiments, the immune response induced by an active compound or a composition described herein is effective to prevent and/or treat an influenza virus disease caused by any of six, seven, eight, nine, ten, eleven, twelve, thirteen, fourteen or fifteen subtypes of influenza virus. In some embodiments, the immune response induced by an active compound or a composition described herein is effective to prevent and/or treat an influenza virus disease caused by one or more variants within the same subtype of influenza virus.

In some embodiments, the immune response induced by an active compound or a composition described herein is effective to reduce symptoms resulting from an influenza virus disease/infection. Symptoms of influenza virus disease/infection include, but are not limited to, body aches (especially joints and throat), fever, nausea, headaches, irritated eyes, fatigue, sore throat, reddened eyes or skin, and abdominal pain.

In some embodiments, the immune response induced by an active compound or a composition described herein is effective to reduce the hospitalization of a subject suffering from an influenza virus disease/infection. In some embodiments, the immune response induced by an active compound or a composition described herein is effective to reduce the duration of hospitalization of a subject suffering from an influenza virus disease/infection.

In another aspect, provided herein are methods for preventing and/or treating an influenza virus infection in a subject utilizing an active compound (e.g., an influenza hemagglutinin stem domain polypeptide described herein, a nucleic acid encoding such a polypeptide, a vector containing or expressing such a polypeptide, or cells stimulated with such a polypeptide) or a composition described herein. In one embodiment, a method for preventing or treating an influenza virus infection in a subject comprises administering to a subject in need thereof an influenza hemagglutinin stem domain polypeptide, a nucleic acid encoding such a polypeptide, a vector containing or expressing such a polypeptide, or a composition of any one of the foregoing. In a specific embodiment, a method for preventing or treating an influenza virus infection in a subject comprises administering to a subject in need thereof a subunit vaccine, a live virus vaccine, an inactivated virus vaccine, a split virus vaccine or a viral-like particle vaccine.

In another aspect, provided herein are methods for preventing and/or treating an influenza virus disease in a subject utilizing an influenza hemagglutinin stem domain polypeptide described herein, a nucleic acid encoding such a polypeptide, a vector containing or expressing such a polypeptide, or cells stimulated with such a polypeptide. In a specific embodiment, a method for preventing or treating an influenza virus disease in a subject comprises administering to a subject in need thereof an effective amount of an influenza hemagglutinin stem domain polypeptide or an immunogenic composition thereof. In another embodiment, a method for preventing or treating an influenza virus disease in a subject comprises administering to a subject in need thereof an effective amount of a nucleic acid encoding an influenza hemagglutinin stem domain polypeptide or an immunogenic composition thereof. In another embodiment, a method for preventing or treating an influenza virus disease in a subject comprises administering to a subject in need thereof an effective amount of a viral vector containing or expressing an influenza hemagglutinin stem domain polypeptide or an immunogenic composition thereof. In yet another embodiment, a method for preventing or treating an influenza virus disease in a subject comprises administering to a subject in need thereof an effective amount of cells stimulated with an influenza hemagglutinin stem domain polypeptide or a pharmaceutical composition thereof.

In a specific embodiment, a method for preventing or treating an influenza virus disease in a subject comprises administering to a subject in need thereof a subunit vaccine described herein. In another embodiment, a method for preventing or treating an influenza virus disease in a subject comprises administering to a subject in need thereof a live virus vaccine described herein. In particular embodiments, the live virus vaccine comprises an attenuated virus. In another embodiment, a method for preventing or treating an influenza virus disease in a subject comprises administering to a subject in need thereof an inactivated virus vaccine described herein. In another embodiment, a method for preventing or treating an influenza virus disease in a subject comprises administering to a subject in need thereof a split virus vaccine described herein. In another embodiment, a method for preventing or treating an influenza virus disease comprises administering to a subject in need thereof a viral-like particle vaccine described herein. In another embodiment, a method for preventing or treating an influenza virus disease in a subject, comprising administering to a subject in need thereof a virosome described herein. In another embodiment, a method for preventing or treating an influenza virus disease in a subject comprising administering to a subject in need thereof a bacteria expressing or engineered to express an influenza hemagglutinin stem domain polypeptide or a composition thereof.

In another aspect, provided herein are methods of preventing and/or treating an influenza virus disease in a subject by administering neutralizing antibodies described herein. In a specific embodiment, a method for preventing or treating an influenza virus disease in a subject comprises administering to a subject in need thereof an effective amount of a neutralizing antibody described herein, or a pharmaceutical composition thereof. In particular embodiments, the neutralizing antibody is a monoclonal antibody. In certain embodiments, the neutralizing antibody is not CR6261, CR6325, CR6329, CR6307, CR6323, 2A, D7, D8, F10, G17, H40, A66, D80, E88, E90, H98, C179 (FERM BP-4517), AI3C (FERM BP-4516) or any other antibody described in Ekiert D C et al. (2009) Antibody Recognition of a Highly Conserved Influenza Virus Epitope. Science (published in Science Express Feb. 26, 2009); Kashyap et al. (2008) Combinatorial antibody libraries from survivors of the Turkish H5N1 avian influenza outbreak reveal virus neutralization strategies. Proc Natl Acad Sci USA 105: 5986-5991; Sui et al. (2009) Structural and functional bases for broad-spectrum neutralization of avian and human influenza A viruses. Nat Struct Mol Biol 16: 265-273; U.S. Pat. Nos. 5,589,174, 5,631,350, 6,337,070, and 6,720,409; International Application No. PCT/US2007/068983 published as International Publication No. WO 2007/134237; International Application No. PCT/US2008/075998 published as International Publication No. WO 2009/036157; International Application No. PCT/EP2007/059356 published as International Publication No. WO 2008/028946; and International Application No. PCT/US2008/085876 published as International Publication No. WO 2009/079259. In other embodiments, the neutralizing antibody is not an antibody described in Wang et al. (2010) "Broadly Protective Monoclonal Antibodies against H3 Influenza Viruses following Sequential Immunization with Different Hemagglutinins," PLOS Pathogens 6(2):1-9.

In certain embodiments, the methods for preventing or treating an influenza virus disease or infection in a subject (e.g., a human or non-human animal) provided herein result in a reduction in the replication of the influenza virus in the subject as measured by in vivo and in vitro assays known to those of skill in the art and described herein. In some embodiments, the replication of the influenza virus is reduced by approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs.

5.12.1 Combination Therapies

In various embodiments, an influenza hemagglutinin stem domain polypeptide described herein, a nucleic acid encoding such a polypeptide, a vector (e.g., a viral vector or a bacteria) containing or expressing such a polypeptide, cells stimulated with such a polypeptide, or a neutralizing antibody may be administered to a subject in combination with one or more other therapies (e.g., antiviral, antibacterial, or immunomodulatory therapies). In some embodiments, a pharmaceutical composition (e.g., an immunogenic composition) described herein may be administered to a subject in combination with one or more therapies. The one or more other therapies may be beneficial in the treatment or prevention of an influenza virus disease or may ameliorate a symptom or condition associated with an influenza virus disease. In some embodiments, the one or more other therapies are pain relievers, anti-fever medications, or therapies that alleviate or assist with breathing. In certain embodiments, the therapies are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In specific embodiments, two or more therapies are administered within the same patent visit.

Any anti-viral agents well-known to one of skill in the art may used in combination with an active compound or pharmaceutical composition described herein. Non-limiting examples of anti-viral agents include proteins, polypeptides, peptides, fusion proteins antibodies, nucleic acid molecules, organic molecules, inorganic molecules, and small molecules that inhibit and/or reduce the attachment of a virus to its receptor, the internalization of a virus into a cell, the replication of a virus, or release of virus from a cell. In particular, anti-viral agents include, but are not limited to, nucleoside analogs (e.g., zidovudine, acyclovir, gangcyclovir, vidarabine, idoxuridine, trifluridine, and ribavirin), foscarnet, amantadine, peramivir, rimantadine, saquinavir, indinavir, ritonavir, alpha-interferons and other interferons, AZT, zanamivir (Relenza®), and oseltamivir (Tamiflu®). Other anti-viral agents include influenza virus vaccines, e.g., Fluarix® (GlaxoSmithKline), FluMist® (MedImmune Vaccines), Fluvirin® (Chiron Corporation), Flulaval® (GlaxoSmithKline), Afluria® (CSL Biotherapies Inc.), Agriflu® (Novartis) or Fluzone® (Aventis Pasteur).

In specific embodiments, the anti-viral agent is an immunomodulatory agent that is specific for a viral antigen. In particular embodiments, the viral antigen is an influenza virus polypeptide other than a hemagglutinin polypeptide. In other embodiments, the viral antigen is an influenza virus hemagglutinin polypeptide.

Any anti-bacterial agents known to one of skill in the art may used in combination with an active compound or pharmaceutical composition described herein. Non-limiting examples of anti-bacterial agents include Amikacin, Amoxicillin, Amoxicillin-clavulanic acid, Amphothericin-B, Ampicillin, Ampicllin-sulbactam, Apramycin, Azithromycin, Aztreonam, Bacitracin, Benzylpenicillin, Caspofungin, Cefaclor, Cefadroxil, Cefalexin, Cefalothin, Cefazolin, Cefdinir, Cefepime, Cefixime, Cefmenoxime, Cefoperazone, Cefoperazone-sulbactam, Cefotaxime, Cefoxitin, Cefpirome, Cefpodoxime, Cefpodoxime-clavulanic acid, Cefpodoxime-sulbactam, Cefprozil, Cefquinome, Ceftazidime, Ceftibutin, Ceftiofur, Ceftobiprole, Ceftriaxon, Cefuroxime, Chloramphenicole, Florfenicole, Ciprofloxacin, Clarithromycin, Clinafloxacin, Clindamycin, Cloxacillin, Colistin, Cotrimoxazol (Trimthoprim/sulphamethoxazole), Dalbavancin, Dalfopristin/Quinopristin, Daptomycin, Dibekacin, Dicloxacillin, Doripenem, Doxycycline, Enrofloxacin, Ertapenem, Erythromycin, Flucloxacillin, Fluconazol, Flucytosin, Fosfomycin, Fusidic acid, Garenoxacin, Gatifloxacin, Gemifloxacin, Gentamicin, Imipenem, Itraconazole, Kanamycin, Ketoconazole, Levofloxacin, Lincomycin, Linezolid, Loracarbef, Mecillnam (amdinocillin), Meropenem, Metronidazole, Meziocillin, Mezlocillin-sulbactam, Minocycline, Moxifloxacin, Mupirocin, Nalidixic acid, Neomycin, Netilmicin, Nitrofurantoin, Norfloxacin, Ofloxacin, Oxacillin, Pefloxacin, Penicillin V, Piperacillin, Piperacillin-sulbactam, Piperacillin-tazobactam, Rifampicin, Roxythromycin, Sparfloxacin, Spectinomycin, Spiramycin, Streptomycin, Sulbactam, Sulfamethoxazole, Teicoplanin, Telavancin, Telithromycin, Temocillin, Tetracyklin, Ticarcillin, Ticarcillin-clavulanic acid, Tigecycline, Tobramycin, Trimethoprim, Trovafloxacin, Tylosin, Vancomycin, Virginiamycin, and Voriconazole.

In some embodiments, a combination therapy comprises active immunization with an influenza hemagglutinin stem domain polypeptide, or one or more vectors described in Sections 5.2-5.7 and passive immunization with one or more neutralizing antibodies described in Section 5.9. In some embodiments, a combination therapy comprises immunization with one or more vectors described in Sections 5.2-5.7 and administration of cells (e.g., by adoptive transfer) described in Section 5.9.

In some embodiments, a combination therapy comprises administration of two or more different vectors described in Sections 5.2-5.7. In one example, one or more vectors expressing an influenza hemagglutinin stem domain polypeptide derived from an influenza A virus hemagglutinin polypeptide and one or more vectors expressing an influenza hemagglutinin stem domain polypeptide derived from an influenza B virus hemagglutinin polypeptide are administered in combination. In some embodiments, a combination therapy comprises administration of a vector expressing an influenza hemagglutinin stem domain polypeptide derived from an influenza A virus H3 antigen and a vector expressing an influenza hemagglutinin stem domain polypeptide derived from an influenza A virus H1 antigen. In some embodiments, the combination therapy comprises administration of a vector expressing an influenza hemagglutinin stem domain polypeptide derived from an influenza A virus H3 antigen, a vector expressing an influenza hemagglutinin stem domain polypeptide derived from an influenza A virus H1 antigen, and a vector expressing an influenza hemagglutinin stem domain polypeptide derived from an influenza B virus hemagglutinin polypeptide.

In some embodiments, a combination therapy comprises active immunization with an active compound that induces an immune response to one, two, three, or more HA subtypes in one HA group (e.g., Group 1) in combination with an active compound that induces an immune response to one, two, three, or more HA subtypes in the other HA group (e.g., Group 2).

In some embodiments, a combination therapy comprises active immunization with two or more influenza hemagglutinin stem domain polypeptides described in Sections 5.1.1-5.1.2. In some embodiments, a combination therapy comprises active immunization with two or more influenza hemagglutinin stem domain polypeptides described in Section 5.1.

5.12.2 Patient Populations

In certain embodiments, an active compound or composition described herein may be administered to a naïve subject, i.e., a subject that does not have a disease caused by influenza virus infection or has not been and is not currently infected with an influenza virus infection. In one embodiment, an active compound or composition described herein is administered to a naïve subject that is at risk of acquiring an influenza virus infection. In one embodiment, an active compound or composition described herein is administered to a subject that does not have a disease caused by the specific influenza virus, or has not been and is not infected with the specific influenza virus to which the influenza hemagglutinin stem domain polypeptide induces an immune response. An active compound or composition described herein may also be administered to a subject that is and/or has been infected with the influenza virus or another type, subtype or strain of the influenza virus to which the influenza hemagglutinin stem domain polypeptide induces an immune response.

In certain embodiments, an active compound or composition described herein is administered to a patient who has been diagnosed with an influenza virus infection. In some embodiments, an active compound or composition described herein is administered to a patient infected with an influenza virus before symptoms manifest or symptoms become severe (e.g., before the patient requires hospitalization). In some embodiments, an active compound or composition described herein is administered to a patient that is infected with or has been diagnosed with a different type of influenza virus than that of the influenza virus from which the HA stem domain polypeptide of the active compound or composition was derived.

In certain embodiments, an active compound or composition described herein is administered to a patient that may be or is infected with an influenza virus that belongs to the same HA group as that of the influenza hemagglutinin stem domain polypeptide. In certain embodiments, an active compound or composition described herein is administered to a patient that may be or is infected with an influenza virus of the same subtype as that of the influenza hemagglutinin stem domain polypeptide.

In some embodiments, a subject to be administered an active compound or composition described herein is an animal. In certain embodiments, the animal is a bird. In certain embodiments, the animal is a canine. In certain embodiments, the animal is a feline. In certain embodiments, the animal is a horse. In certain embodiments, the animal is a cow. In certain embodiments, the animal is a mammal, e.g., a horse, swine, mouse, or primate, preferably a human.

In certain embodiments, a subject to be administered an active compound or composition described herein is a human adult. In certain embodiments, a subject to be administered an active compound or composition described herein is a human adult more than 50 years old. In certain embodiments, a subject to be administered an active compound or composition described herein is an elderly human subject.

In certain embodiments, a subject to be administered an active compound or composition described herein is a human child. In certain embodiments, a subject to be administered an active compound or composition described herein is a human infant. In certain embodiments, a subject to whom an active compound or composition described herein is administered is not an infant of less than 6 months old. In a specific embodiment, a subject to be administered an active compound or composition described herein is 2 years old or younger.

In specific embodiments, a subject to be administered an active compound or composition described herein is any infant or child more than 6 months of age and any adult over 50 years of age. In other embodiments, the subject is an individual who is pregnant. In another embodiment, the subject is an individual who may or will be pregnant during the influenza season (e.g., November to April). In specific embodiments, a subject to be administered an active compound or composition described herein is a woman who has given birth 1, 2, 3, 4, 5, 6, 7, or 8 weeks earlier.

In some embodiments, the human subject to be administered an active compound or composition described herein is any individual at increased risk of influenza virus infection or disease resulting from influenza virus infection (e.g., an immunocompromised or immunodeficient individual). In some embodiments, the human subject to be administered an active compound or composition described herein is any individual in close contact with an individual with increased risk of influenza virus infection or disease resulting from influenza virus infection (e.g., immunocompromised or immunosuppressed individuals).

In some embodiments, the human subject to be administered an active compound or composition described herein is an individual affected by any condition that increases susceptibility to influenza virus infection or complications or disease resulting from influenza virus infection. In other embodiments, an active compound or composition described herein is administered to a subject in which an influenza virus infection has the potential to increase complications of another condition that the individual is affected by, or for which they are at risk. In particular embodiments, such conditions that increase susceptibility to influenza virus complications or for which influenza virus increases complications associated with the condition are, e.g., conditions that affect the lung, such as cystic fibrosis, emphysema, asthma, or bacterial infections (e.g., infections caused by *Haemophilus influenzae, Streptococcus pneumoniae, Legionella pneumophila*, and *Chlamydia trachomatus*); cardiovascular disease (e.g., congenital heart disease, congestive heart failure, and coronary artery disease); endocrine disorders (e.g., diabetes), neurological and neuron-developmental conditions (e.g., disorders of the brain, the spinal cord, the peripheral nerve, and muscle (such as cerebral palsy, epilepsy (seizure disorders), stroke, intellectual disability (e.g, mental retardation), muscular dystrophy, and spinal cord injury)).

In some embodiments, the human subject to be administered an active compound or composition described herein is an individual that resides in a group home, such as a nursing home. In some embodiments, the human subject to be administered an active compound or composition described herein works in, or spends a significant amount of time in, a group home, e.g., a nursing home. In some embodiments, the human subject to be administered an active compound or composition described herein is a health care worker (e.g., a doctor or nurse). In some embodiments, the human subject to be administered an active compound or composition described herein is a smoker. In a specific embodiment, the human subject to be administered an active compound or composition described herein is immunocompromised or immunosuppressed.

In addition, subjects at increased risk of developing complications from influenza who may be administered an active compound or composition described herein include: any individual who can transmit influenza viruses to those at high risk for complications, such as, e.g., members of households with high-risk individuals, including households that will include infants younger than 6 months, individuals coming into contact with infants less than 6 months of age, or individuals who will come into contact with individuals who live in nursing homes or other long-term care facilities; individuals with long-term disorders of the lungs, heart, or circulation; individuals with metabolic diseases (e.g., diabetes); individuals with kidney disorders; individuals with blood disorders (including anemia or sickle cell disease); individuals with weakened immune systems (including immunosuppression caused by medications, malignancies such as cancer, organ transplant, or HIV infection); children who receive long-term aspirin therapy (and therefore have a higher chance of developing Reye syndrome if infected with influenza).

In other embodiments, subjects for administration of an active compound or composition described herein include healthy individuals six months of age or older, who: plan to travel to foreign countries and areas where flu outbreaks may be occurring, such, e.g., as the tropics and the Southern Hemisphere from April through September; travel as a part of large organized tourist groups that may include persons from areas of the world where influenza viruses are circulating; attend school or college and reside in dormitories, or reside in institutional settings; or wish to reduce their risk of becoming ill with influenza.

In some embodiments, a subject for whom administration of an active compound or composition described herein is contraindicated include any individual for whom influenza vaccination is contraindicated, such as: infants younger than six months of age; and individuals who have had an anaphylactic reaction (allergic reactions that cause difficulty breathing, which is often followed by shock) to eggs, egg products, or other components used in the production of the immunogenic formulation. In certain embodiments, when administration of an active compound or composition described herein is contraindicated due to one or more components used in the production of the immunogenic formulation (e.g., due to the presence of egg or egg products), the active compound or composition may be produced in a manner that does not include the component that causes the administration of an active compound or composition to be contraindicated (e.g., the active compound or composition may be produced without the use of eggs or egg products).

In some embodiments, it may be advisable not to administer a live virus vaccine to one or more of the following patient populations: elderly humans; infants younger than 6 months old; pregnant individuals; infants under the age of 1 years old; children under the age of 2 years old; children under the age of 3 years old; children under the age of 4 years old; children under the age of 5 years old; adults under the age of 20 years old; adults under the age of 25 years old; adults under the age of 30 years old; adults under the age of 35 years old; adults under the age of 40 years old; adults under the age of 45 years old; adults under the age of 50 years old; elderly humans over the age of 70 years old; elderly humans over the age of 75 years old; elderly humans over the age of 80 years old; elderly humans over the age of 85 years old; elderly humans over the age of 90 years old; elderly humans over the age of 95 years old; children and adolescents (2-17 years of age) receiving aspirin or aspirin-containing medications, because of the complications associated with aspirin and wild-type influenza virus infections in this age group; individuals with a history of asthma or other reactive airway diseases; individuals with chronic underlying medical conditions that may predispose them to severe influenza infections; individuals with a history of Guillain-Barre syndrome; individuals with acute serious illness with fever; or individuals who are moderately or severely ill. For such individuals, administration of inactivated virus vaccines, split virus vaccines, subunit vaccines, virosomes, viral-like particles or the non-viral vectors described herein may be preferred. In certain embodiments, subjects preferably administered a live virus vaccine may include healthy children and adolescents, ages 2-17 years, and healthy adults, ages 18-49.

In certain embodiments, an immunogenic formulation comprising a live virus vector is not given concurrently with other live-virus vaccines.

5.13 Modes of Administration 5.13.1 Routes of Delivery

An active compound or composition described herein may be delivered to a subject by a variety of routes. These include, but are not limited to, intranasal, intratracheal, oral, intradermal, intramuscular, intraperitoneal, transdermal, intravenous, conjunctival and subcutaneous routes. In some embodiments, a composition is formulated for topical administration, for example, for application to the skin. In specific embodiments, the route of administration is nasal, e.g., as part of a nasal spray. In certain embodiments, a composition is formulated for intramuscular administration. In some embodiments, a composition is formulated for subcutaneous administration. In certain embodiments, a composition is not formulated for administration by injection. In specific embodiments for live virus vaccines, the vaccine is formulated for administration by a route other than injection.

In cases where the antigen is a viral vector, a virus-like particle vector, or a bacterial vector, for example, it may be preferable to introduce an immunogenic composition via the natural route of infection of the backbone virus or bacteria from which the vector was derived. Alternatively, it may be preferable to introduce an influenza hemagglutinin stem domain polypeptide via the natural route of infection of the influenza virus from which polypeptide is derived. The ability of an antigen, particularly a viral vector, to induce a vigorous secretory and cellular immune response can be used advantageously. For example, infection of the respiratory tract by a viral vector may induce a strong secretory immune response, for example in the urogenital system, with concomitant protection against an influenza virus. In addition, in a preferred embodiment it may be desirable to introduce the pharmaceutical compositions into the lungs by any suitable route. Pulmonary administration can also be employed, e.g., by use of an inhaler or nebulizer, and formulation with an aerosolizing agent for use as a spray.

In a specific embodiment, a subunit vaccine is administered intramuscularly. In another embodiment, a live influenza virus or live NDV vaccine is administered intranasally. In another embodiment, an inactivated influenza virus vaccine, or a split influenza virus vaccine is administered intramuscularly. In another embodiment, an inactivated NDV virus vaccine or a split NDV virus vaccine is administered intramuscularly. In another embodiment, a viral-like particle or composition thereof is administered intramuscularly.

In some embodiments, cells stimulated with an influenza hemagglutinin stem domain polypeptide in vitro may be introduced (or re-introduced) into a subject using techniques known to one of skill in the art. In some embodiments, the cells can be introduced into the dermis, under the dermis, or into the peripheral blood stream. In some embodiments, the cells introduced into a subject are preferably cells derived from that subject, to avoid an adverse immune response. In other embodiments, cells also can be used that are derived from a donor host having a similar immune background. Other cells also can be used, including those designed to avoid an adverse immunogenic response.

5.13.2 Dosage and Frequency of Administration

The amount of an active compound or composition which will be effective in the treatment and/or prevention of an influenza virus infection or an influenza virus disease will depend on the nature of the disease, and can be determined by standard clinical techniques.

The precise dose to be employed in the formulation will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight, health), whether the patient is human or an animal, other medications administered, and whether treatment is prophylactic or therapeutic. Usually, the patient is a human but nonhuman mammals including transgenic mammals can also be treated. Treatment dosages are optimally titrated to optimize safety and efficacy.

In certain embodiments, an in vitro assay is employed to help identify optimal dosage ranges. Effective doses may be extrapolated from dose response curves derived from in vitro or animal model test systems.

Exemplary doses for nucleic acids encoding influenza hemagglutinin stem domain polypeptides range from about 10 ng to 1 g, 100 ng to 100 mg, 1 μg to 10 mg, or 30-300 μg nucleic acid, e.g., DNA, per patient.

In certain embodiments, exemplary doses for influenza hemagglutinin stem domain polypeptides (e.g., as provided in split virus vaccines and subunit vaccines) range from about 5 μg to 100 mg, 15 μg to 50 mg, 15 μg to 25 mg, 15 μg to 10 mg, 15 μg to 5 mg, 15 μg to 1 mg, 15 μg to 100 μg, 15 μg to 75 μg, 5 μg to 50 μg, 10 μg to 15 μg to 45 μg, 20 μg to 40 μg, or 25 to 35 μg per kilogram of the patient. In other embodiments, exemplary doses for influenza hemagglutinin stem domain polypeptides range from about 1 μg to 50 mg, 5 μg to 50 mg, 1 μg to 100 mg, 5 μg to 100 mg, 15 μg to 50 mg, 15 μg to 25 mg, 15 μg to 10 mg, 15 μg to 5 mg, 15 μg to 1 mg, 15 μg to 100 μg, 15 μg to 75 μg, 5 μg to 50 μg, 10 μg to 50 μg, 15 μg to 45 μg, 20 μg to 40 μg, or 25 to 35 μg of influenza hemagglutinin stem domain polypeptides per dose.

Doses for infectious viral vectors may vary from 10-100, or more, virions per dose. In some embodiments, suitable dosages of a virus vector are $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $1\times10^9$, $5\times10^9$, $1\times10^{10}$, $5\times10^{10}$, $1\times10^{11}$, $5\times10^{11}$ or $10^{12}$ pfu, and can be administered to a subject once, twice, three or more times with intervals as often as needed.

In certain embodiments, exemplary doses for VLPs range from about 0.01 μg to about 100 mg, about 0.1 μg to about 100 mg, about 5 μg to about 100 mg, about 15 μg to about 50 mg, about 15 μg to about 25 mg, about 15 μg to about 10 mg, about 15 μg to about 5 mg, about 15 μg to about 1 mg, about 15 μg to about 100 μg, about 15 μg to about 75 μg, about 5 μg to about 50 μg, about 10 μg to about 50 μg, about 15 μg to about 45 μg, about 20 μg to about 40 μg, or about 25 to about 35 μg per kilogram of the patient. In other embodiments, exemplary doses for influenza hemagglutinin stem domain polypeptides range from about 1 μg to about 50 mg, about 5 μg to about 50 mg, about 1 μg to about 100 mg, about 5 μg to about 100 mg, about 15 μg to about 50 mg, about 15 μg to about 25 mg, about 15 μg to about 10 mg, about 15 μg to about 5 mg, about 15 μg to about 1 mg, about 15 μg to about 100 about 15 μg to about 75 about 5 μg to about 50 about 10 μg to about 50 about 15 μg to about 45 about 20 μg to about 40 μg, or about 25 to about 35 μg of influenza hemagglutinin stem domain polypeptides per dose, and can be administered to a subject once, twice, three or more times with intervals as often as needed.

In one embodiment, an inactivated vaccine is formulated such that it contains about 5 μg to about 50 μg, about 10 μg to about 50 μg, about about 15 μg to about 100 μg, about 15 μg to about 75 μg, about 15 μg to about 50 μg, about 15 μg to about 30 μg, about 20 μg to about 50 μg, about 25 μg to about 40 μg, about 25 μg to about 35 μg of an influenza hemagglutinin stem domain polypeptide. Such a vaccine may contain a combination of one or more different influenza hemagglutinin stem domain polypeptides, for example, one or more influenza hemagglutinin stem domain polypeptides from an influenza A virus and one or more influenza hemagglutinin stem domain polypeptides from an influenza B virus. In some embodiments, influenza hemagglutinin stem domain polypeptides derived from, e.g., A/H1N1, A/H3N2, and B hemagglutinin polypeptides are included in a trivalent inactivated vaccine (TIV), formulated such that a 0.5-mL dose contains 15 μg each of influenza hemagglutinin stem domain polypeptide. In one embodiment, a live attenuated influenza vaccine (LAIV) is formulated such that a 0.2-mL dose contains $10^{6.5-7.5}$ fluorescent focal units of live attenuated influenza viruses from three strains expressing at least one influenza hemagglutinin stem domain polypeptide.

In certain embodiments, an active compound or composition is administered to a subject once as a single dose. In certain embodiments, an active compound or composition is administered to a subject as a single dose followed by a second dose 3 to 6 weeks later. In accordance with these embodiments, booster inoculations may be administered to the subject at 6 to 12 month intervals following the second inoculation. In certain embodiments, the booster inoculations may utilize a different active compound or composition. In some embodiments, the administration of the same active compound or composition may be repeated and the administrations may be separated by at least 1 day, 2 days, 3 days, 5 days, 10 days, 15 days, 30 days, 45 days, 2 months, 75 days, 3 months, or at least 6 months. In certain embodiments, an active compound or composition is administered to a subject as a single dose once per year.

In specific embodiments for administration to children, two doses of an active compound or composition, given at least one month apart, are administered to a child. In specific embodiments for administration to adults, a single dose is given. In another embodiment, two doses of an active compound or composition, given at least one month apart, are administered to an adult. In another embodiment, a young child (six months to nine years old) may be administered an active compound or composition for the first time in two doses given one month apart. In a particular embodiment, a child who received only one dose in their first year of vaccination should receive two doses in the following year. In some embodiments, two doses administered 4 weeks apart are preferred for children 2-8 years of age who are administered an influenza vaccine, e.g., an immunogenic formulation described herein, for the first time. In certain embodiments, for children 6-35 months of age, a half dose (0.25 ml) may be preferred, in contrast to 0.5 ml which may be preferred for subjects over three years of age.

In particular embodiments, an active compound or composition is administered to a subject in the fall or winter, i.e., prior to or during the influenza season in each hemisphere. In one embodiment, children are administered their first dose early in the season, e.g., late September or early October, so that the second dose can be given prior to the peak of the influenza season.

For passive immunization with an antibody, the dosage ranges from about 0.0001 to 100 mg/kg, and more usually 0.01 to 5 mg/kg, of the patient body weight. For example, dosages can be 1 mg/kg body weight or 10 mg/kg body weight or within the range of 1-10 mg/kg or in other words, 70 mg or 700 mg or within the range of 70-700 mg, respectively, for a 70 kg patient. An exemplary treatment regime entails administration once per every two weeks or once a month or once every 3 to 6 months for a period of one year or over several years, or over several year-intervals. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of antibody to the influenza hemagglutinin stem domain polypeptide in the patient.

5.14 Biological Assays 5.14.1 Assays for Testing Activity of Influenza Hemagglutinin Stem Domain Polypeptide Assays for testing the expression of a influenza hemagglutinin stem domain polypeptide in a vector disclosed herein may be conducted using any assay known in the art. For example, an assay for incorporation into a viral vector comprises growing the virus as described in this section or Sections 5.4 or 5.5, purifying the viral particles by centrifugation through a sucrose cushion, and subsequent analysis for influenza hemagglutinin stem domain polypeptide expression by an immunoassay, such as Western blotting, using methods well known in the art.

In one embodiment, an influenza hemagglutinin stem domain polypeptide disclosed herein is assayed for proper folding and functionality by testing its ability to bind specifically to a neutralizing antibody directed to an influenza virus hemagglutinin polypeptide, such as the stalk region of the polypeptide, using any assay for antibody-antigen interaction known in the art. Neutralizing antibodies for use in such assays include, for example, the neutralizing antibodies described in Ekiert et al., 2009, *Science Express,* 26 Feb. 2009; Kashyap et al., 2008, *Proc Natl Acad Sci USA* 105: 5986-5991; Sui et al. 2009, *Nature Structural and Molecular Biology,* 16:265-273; Wang et al., 2010, *PLOS Pathogens* 6(2):1-9; U.S. Pat. Nos. 5,589,174, 5,631,350, 6,337,070, and 6,720,409; International Application No. PCT/US2007/068983 published as International Publication No. WO 2007/134237; International Application No. PCT/US2008/075998 published as International Publication No. WO 2009/036157; International Application No. PCT/EP2007/059356 published as International Publication No. WO 2008/028946; and International Application No. PCT/US2008/085876 published as International Publication No. WO 2009/079259. These antibodies include CR6261, CR6325, CR6329, CR6307, CR6323, 2A, D7, D8, F10, G17, H40, A66, D80, E88, E90, H98, C179 (FERM BP-4517), AI3C (FERM BP-4516), among others.

In another embodiment, an influenza hemagglutinin stem domain polypeptide disclosed herein is assayed for proper folding by determination of the structure or conformation of the influenza hemagglutinin stem domain polypeptide using any method known in the art such as, e.g., NMR, X-ray crystallographic methods, or secondary structure prediction methods, e.g., circular dichroism.

5.14.2 Assays for Testing Activity of Antibodies Generated Using Influenza Hemagglutinin Stem Domain Polypeptide Antibodies described herein may be characterized in a variety of ways known to one of skill in the art (e.g. ELISA, Surface Plasmon resonance display (BIAcore), Western blot, immunofluorescence, immunostaining and/or microneutralization assays). In some embodiments, antibodies are assayed for the ability to specifically bind to an influenza virus hemagglutinin polypeptide, or a vector comprising said polypeptide. Such an assay may be performed in solution (e.g., Houghten, 1992, Bio/Techniques 13:412 421), on beads (Lam, 1991, Nature 354:82 84), on chips (Fodor, 1993, Nature 364:555 556), on bacteria (U.S. Pat. No. 5,223,409), on spores (U.S. Pat. Nos. 5,571,698; 5,403,484; and 5,223,409), on plasmids (Cull et al., 1992, Proc. Natl. Acad. Sci. USA 89:1865 1869) or on phage (Scott and Smith, 1990, Science 249:386 390; Cwirla et al., 1990, Proc. Natl. Acad. Sci. USA 87:6378 6382; and Felici, 1991, J. Mol. Biol. 222:301 310) (each of these references is incorporated herein in its entirety by reference).

Specific binding of an antibody to the influenza virus hemagglutinin polypeptide and cross-reactivity with other antigens can be assessed by any method known in the art. Immunoassays which can be used to analyze specific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds., 1994, Current Protocols in Molecular Biology, Vol. 1, John Wiley & Sons, Inc., New York, which is incorporated by reference herein in its entirety).

The binding affinity of an antibody to an influenza virus hemagglutinin polypeptide and the off-rate of an antibody-antigen interaction can be determined by competitive binding assays. One example of a competitive binding assay is a radioimmunoassay comprising the incubation of labeled antigen (e.g., $^{3}H$ or $^{125}I$) with the antibody of interest in the presence of increasing amounts of unlabeled antigen, and the detection of the antibody bound to the labeled antigen. The affinity of the antibody for an influenza virus hemagglutinin polypeptide and the binding off-rates can be determined from the data by Scatchard plot analysis. Competition with a second antibody can also be determined using radioimmunoassays. In this case, an influenza virus hemagglutinin polypeptide is incubated with the test antibody conjugated to a labeled compound (e.g., $^{3}H$ or $^{125}I$) in the presence of increasing amounts of an unlabeled second antibody.

In certain embodiments, antibody binding affinity and rate constants are measured using the KinExA 3000 System (Sapidyne Instruments, Boise, Id.). In some embodiments, surface plasmon resonance (e.g., BIAcore kinetic) analysis is used to determine the binding on and off rates of the antibodies to an influenza virus hemagglutinin polypeptide. BIAcore kinetic analysis comprises analyzing the binding and dissociation of influenza virus hemagglutinin polypeptide from chips with immobilized antibodies to an influenza virus hemagglutinin polypeptide on their surface. A typical BIAcore kinetic study involves the injection of 250 μL of an antibody reagent (mAb, Fab) at varying concentration in HBS buffer containing 0.005% Tween-20 over a sensor chip surface, onto which has been immobilized the influenza virus hemagglutinin polypeptide. The flow rate is maintained constant at 75 μL/min. Dissociation data is collected for 15 min or longer as necessary. Following each injection/dissociation cycle, the bound antibody is removed from the influenza virus hemagglutinin polypeptide surface using brief, 1 min pulses of dilute acid, typically 10-100 mM HCl, though other regenerants are employed as the circumstances warrant. More specifically, for measurement of the rates of association, $k_{on}$, and dissociation, $k_{off}$, the polypeptide is directly immobilized onto the sensor chip surface through the use of standard amine coupling chemistries, namely the EDC/NHS method (EDC=N-diethylaminopropyl)-carbodiimide). Briefly, a 5-100 nM solution of the polypeptide in 10 mM NaOAc, pH 4 or pH 5 is prepared and passed over the EDC/NHS-activated surface until approximately 30-50 RU's worth of polypeptide are immobilized. Following this, the unreacted active esters are "capped" off with an injection of 1M Et-$NH_2$. A blank surface, containing no polypeptide, is prepared under identical immobilization conditions for reference purposes. Once an appropriate surface has been prepared, a suitable dilution series of each one of the antibody reagents is prepared in HBS/Tween-20, and passed over both the polypeptide and reference cell surfaces, which are connected in series. The range of antibody concentrations that are prepared varies, depending on what the equilibrium binding constant, $K_D$, is estimated to be. As described above, the bound antibody is removed after each injection/dissociation cycle using an appropriate regenerant.

The neutralizing activity of an antibody can be determined utilizing any assay known to one skilled in the art. Antibodies described herein can be assayed for their ability to inhibit the binding of an influenza virus, or any other composition comprising influenza virus hemagglutinin polypeptide (e.g., a VLP, liposome, or detergent extract), to its host cell receptor (i.e., sialic acid) using techniques known to those of skill in the art. For example, cells expressing influenza virus receptors can be contacted with a composition comprising influenza virus hemagglutinin polypeptide in the presence or absence of the antibody and the ability of the antibody to inhibit the antigen's binding can measured by, for example, flow cytometry or a scintillation assay. The composition comprising an influenza virus hemagglutinin polypeptide or the antibody can be labeled with a detectable compound such as a radioactive label (e.g., $^{32}P$, $^{35}S$, and $^{125}I$) or a fluorescent label (e.g., fluorescein isothiocyanate, rhodamine, phycoerythrin, phycocyanin, allophycocyanin, o-phthaldehyde and fluorescamine) to enable detection of an interaction between the composition comprising an influenza virus hemagglutinin polypeptide and a cell receptor. Alternatively, the ability of antibodies to inhibit an influenza virus hemagglutinin polypeptide from binding to its receptor can be determined in cell-free assays. For example, a composition comprising an influenza virus hemagglutinin polypeptide can be contacted with an antibody and the ability of the antibody to inhibit the composition comprising an influenza virus hemagglutinin polypeptide from binding to a cell receptor can be determined. In a specific embodiment, the antibody is immobilized on a solid support and the composition comprising an influenza virus hemagglutinin polypeptide is labeled with a detectable compound. Alternatively, a composition comprising an influenza virus hemagglutinin polypeptide is immobilized on a solid support and the antibody is labeled with a detectable compound. In certain embodiments, the ability of an antibody to inhibit an influenza virus hemagglutinin polypeptide from binding to a cell receptor is determined by assessing the percentage of binding inhibition of the antibody relative to a control (e.g., an antibody known to inhibit the influenza virus hemagglutinin polypeptide from binding to the cell receptor).

In other embodiments, an antibody suitable for use in the methods described herein does not inhibit influenza virus receptor binding, yet is still found to be neutralizing in an assay described herein. In some embodiments, an antibody suitable for use in accordance with the methods described herein reduces or inhibits virus-host membrane fusion in an assay known in the art or described herein.

In one embodiment, virus-host membrane fusion is assayed in an in vitro assay using an influenza virus containing a reporter and a host cell capable of being infected with the virus. An antibody inhibits fusion if reporter activity is inhibited or reduced compared to a negative control (e.g., reporter activity in the presence of a control antibody or in the absence of antibody).

In one embodiment, virus-host membrane fusion is detected using a model system of cell fusion. In an exemplary cell fusion assay, cells (e.g., HeLa cells) are transfected with a plasmid encoding an influenza hemagglutinin polypeptide and contacted and exposed to a buffer that allows the hemagglutinin polypeptide fusion function (e.g., pH 5.0 buffer) in the presence of an antibody. An antibody is neutralizing if it reduces or inhibits syncytia formation compared to a negative control (e.g., syncytia formation in the presence of a control antibody or in the absence of antibody).

In other embodiments, virus-host membrane fusion is assayed using an in vitro liposome-based assay. In an exemplary assay, the host cell receptor is reconstituted into liposomes containing one half of a reporter. Influenza hemagglutinin polypeptide is reconstituted into another set of liposomes containing another half of a reporter. When the two liposome populations are mixed together, fusion is detected by reconstitution of the reporter, for example, an enzymatic reaction that can be detected colorimetrically. The antibody inhibits fusion if reporter activity is reduced or inhibited compared to reporter activity in an assay conducted in the absence of antibody or in the presence of a control antibody. In certain embodiments, the ability of an antibody to inhibit fusion is determined by assessing the percentage of fusion in the presence of the antibody relative to the percentage of fusion in the presence a control.

5.14.3 Assays for Testing Activity of Stimulated Cells

Cells stimulated in accordance with the methods described herein may be analyzed, for example, for integration, transcription and/or expression of the polynucleotide or gene(s) of interest, the number of copies of the gene integrated, and the location of the integration. Such analysis may be carried out at any time and may be carried out by any methods known in the art. In other embodiments, successful stimulation of the target cell with an influenza hemagglutinin stem domain polypeptide described herein is determined by detecting production of neutralizing antibodies against the influenza hemagglutinin stem domain polypeptide using methods known in the art or described herein.

In certain embodiments, subjects in which the stimulated cells, e.g., DCs, are administered can be analyzed for location of the cells, expression of a vector-delivered polynucleotide or gene encoding the influenza hemagglutinin stem domain polypeptide, stimulation of an immune response (e.g., production of neutralizing antibodies against the influenza hemagglutinin stem domain polypeptide), and/or monitored for symptoms associated with influenza virus infection or a disease associated therewith by any methods known in the art or described herein.

Reporter assays can be used to determine the specificity of the targeting of the influenza hemagglutinin stem domain polypeptide. For example, a mixed population of bone marrow cells can be obtained from a subject and cultured in vitro. The influenza hemagglutinin stem domain polypeptide can be administered to the mixed population of bone marrow cells, and expression of a reporter gene associated with the influenza hemagglutinin stem domain polypeptide can be assayed in the cultured cells. In some embodiments, at least about 50%, more preferably at least about 60%, 70%, 80% or 90%, still more preferably at least about 95% of stimulated cells in the mixed cell population are dendritic cells.

5.14.4 Antiviral Activity Assays

Antibodies described herein or compositions thereof can be assessed in vitro for antiviral activity. In one embodiment, the antibodies or compositions thereof are tested in vitro for their effect on growth of an influenza virus. Growth of influenza virus can be assessed by any method known in the art or described herein (e.g. in cell culture). In a specific embodiment, cells are infected at a MOI of 0.0005 and 0.001, 0.001 and 0.01, 0.01 and 0.1, 0.1 and 1, or 1 and 10, or a MOI of 0.0005, 0.001, 0.005, 0.01, 0.05, 0.1, 0.5, 1, 5 or 10 and incubated with serum free media supplemented. Viral titers are determined in the supernatant by hemagglutinin plaques or any other viral assay described herein. Cells in which viral titers can be assessed include, but are not limited to, EFK-2 cells, Vero cells, MDCK cells, primary human umbilical vein endothelial cells (HUVEC), H292 human epithelial cell line and HeLa cells. In vitro assays include those that measure altered viral replication (as determined, e.g., by plaque formation) or the production of viral proteins (as determined, e.g., by Western blot analysis) or viral RNAs (as determined, e.g., by RT-PCR or northern blot analysis) in cultured cells in vitro using methods which are well known in the art or described herein.

In one non-limiting example, a monolayer of the target mammalian cell line is infected with different amounts (e.g., multiplicity of 3 plaque forming units (pfu) or 5 pfu) of virus (e.g., influenza) and subsequently cultured in the presence or absence of various dilutions of antibodies (e.g., 0.1 μg/ml, 1 μg/ml, 5 μg/ml, or 10 μg/ml). Infected cultures are harvested 48 hours or 72 hours post infection and titered by standard plaque assays known in the art on the appropriate target cell line (e.g., Vero cells).

In a non-limiting example of a hemagglutination assay, cells are contacted with an antibody and are concurrently or subsequently infected with the virus (e.g., at an MOI of 1) and the virus is incubated under conditions to permit virus replication (e.g., 20-24 hours). The antibodies are preferably present throughout the course of infection. Viral replication and release of viral particles is then determined by hemagglutination assays using 0.5% chicken red blood cells. See, e.g., Kashyap et al., PNAS USA 105: 5986-5991. In some embodiments, a compound is considered an inhibitor of viral replication if it reduces viral replication by at least 2 wells of HA, which equals approximately a 75% reduction in viral titer. In specific embodiments, an inhibitor reduces viral titer in this assay by 50% or more, by 55% or more, by 60% or more, by 65% or more, by 70% or more, by 75% or more, by 80% or more, by 85% or more, by 90% or more, or by 95% or more. In other specific embodiments an inhibitor results in a reduction of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs in influenza virus titer in the subject. The log-reduction in Influenza virus titer may be as compared to a negative control, as compared to another treatment, or as compared to the titer in the patient prior to antibody administration.

5.14.5 Cytotoxicity Assays

Many assays well-known in the art can be used to assess viability of cells (infected or uninfected) or cell lines following exposure to an active compound or a composition thereof and, thus, determine the cytotoxicity of the compound or composition. For example, cell proliferation can be assayed by measuring Bromodeoxyuridine (BrdU) incorporation (See, e.g., Hoshino et al., 1986, Int. J. Cancer 38, 369; Campana et al., 1988, J. Immunol. Meth. 107:79), (3H) thymidine incorporation (See, e.g., Chen, J., 1996, Oncogene 13:1395-403; Jeoung, J., 1995, J. Biol. Chem. 270: 18367 73), by direct cell count, or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription. Cell viability can be assessed by using trypan-blue staining or other cell death or viability markers known in the art. In a specific embodiment, the level of cellular ATP is measured to determined cell viability.

In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes may include enlargement, granularity, cells with ragged edges, a filmy appearance, rounding, detachment from the surface of the well, or other changes. These changes are given a designation of T (100% toxic), PVH (partially toxic—very heavy—80%), PH (partially toxic—heavy—60%), P (partially toxic—40%), Ps (partially toxic—slight—20%), or 0 (no toxicity—0%), conforming to the degree of cytotoxicity seen. A 50% cell inhibitory (cytotoxic) concentration ($IC_{50}$) is determined by regression analysis of these data.

In a specific embodiment, the cells used in the cytotoxicity assay are animal cells, including primary cells and cell lines. In some embodiments, the cells are human cells. In certain embodiments, cytotoxicity is assessed in one or more of the following cell lines: U937, a human monocyte cell line; primary peripheral blood mononuclear cells (PBMC); Huh7, a human hepatoblastoma cell line; 293T, a human embryonic kidney cell line; and THP-1, monocytic cells. In certain embodiments, cytotoxicity is assessed in one or more of the following cell lines: MDCK, MEF, Huh 7.5, Detroit, or human tracheobronchial epithelial (HTBE) cells.

Active compounds or compositions thereof can be tested for in vivo toxicity in animal models. For example, animal models, described herein and/or others known in the art, used to test the activities of active compounds can also be used to determine the in vivo toxicity of these compounds. For example, animals are administered a range of concentrations of active compounds. Subsequently, the animals are monitored over time for lethality, weight loss or failure to gain weight, and/or levels of serum markers that may be indicative of tissue damage (e.g., creatine phosphokinase level as an indicator of general tissue damage, level of glutamic oxalic acid transaminase or pyruvic acid transaminase as indicators for possible liver damage). These in vivo assays may also be adapted to test the toxicity of various administration mode and/or regimen in addition to dosages.

The toxicity and/or efficacy of an active compound can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. An active compound that exhibits large therapeutic indices is preferred. While an active compound that exhibits toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of an active compound for use in humans. The dosage of such agents lies preferably within a range of circulating concentrations that include the $ED_{50}$ with little or no toxicity. The dosage may vary within this range depending upon the dosage form employed and the route of administration utilized. For any active compound used in a method described herein, the effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high-performance liquid chromatography. Additional information concerning dosage determination is provided herein.

Further, any assays known to those skilled in the art can be used to evaluate the prophylactic and/or therapeutic utility of the active compounds and compositions described herein, for example, by measuring viral infection or a condition or symptoms associated therewith.

5.14.6 In Vivo Antiviral Activity

Active compounds and compositions thereof are preferably assayed in vivo for the desired therapeutic or prophylactic activity prior to use in humans. For example, in vivo assays can be used to determine whether it is preferable to administer an active compound or composition thereof and/or another therapy. For example, to assess the use of an active compound or composition thereof to prevent an influenza virus disease, the composition can be administered before the animal is infected with influenza virus. Alternatively, or in addition, an active compound or composition thereof can be administered to the animal at the same time that the animal is infected with influenza virus. To assess the use of an active compound or composition thereof to treat an influenza virus infection or disease associated therewith, the compound or composition may be administered after infecting the animal with influenza virus. In a specific embodiment, an active compound or composition thereof is administered to the animal more than one time.

Active compounds and compositions thereof can be tested for antiviral activity in animal model systems including, but are not limited to, rats, mice, chicken, cows, monkeys, pigs, goats, sheep, dogs, rabbits, guinea pigs, etc. In a specific embodiment, active compounds and compositions thereof are tested in a mouse model system. Such model systems are widely used and well-known to the skilled artisan. In a specific embodiment, active compounds and compositions thereof are tested in a mouse model system. Non-limiting examples of animal models for influenza virus are provided in this section.

In general, animals are infected with influenza virus and concurrently or subsequently treated with an active compound or composition thereof, or placebo. Alternatively, animals are treated with an active compound or composition thereof or placebo and subsequently infected with influenza virus. Samples obtained from these animals (e.g., serum, urine, sputum, semen, saliva, plasma, or tissue sample) can be tested for viral replication via well known methods in the art, e.g., those that measure altered viral titers (as determined, e.g., by plaque formation), the production of viral proteins (as determined, e.g., by Western blot, ELISA, or flow cytometry analysis) or the production of viral nucleic acids (as determined, e.g., by RT-PCR or northern blot analysis). For quantitation of virus in tissue samples, tissue samples are homogenized in phosphate-buffered saline (PBS), and dilutions of clarified homogenates are adsorbed for 1 hour at 37° C. onto monolayers of cells (e.g., Vero, CEF or MDCK cells). In other assays, histopathologic evaluations are performed after infection, preferably evaluations of the organ(s) the virus is known to target for infection. Virus immunohistochemistry can be performed using a viral-specific monoclonal antibody.

The effect of an active compound or composition thereof on the virulence of a virus can also be determined using in vivo assays in which the titer of the virus in an infected subject administered an active compound or composition thereof, the length of survival of an infected subject administered an active compound or composition thereof, the immune response in an infected subject administered an active compound or composition thereof, the number, duration and/or severity of the symptoms in an infected subject administered an active compound or composition thereof, and/or the time period before onset of one or more symptoms in an infected subject administered an active compound or composition thereof, is assessed. Techniques known to one of skill in the art can be used to measure such effects. In certain embodiments, an active compound or composition thereof results in a 0.5 fold, 1 fold, 2 fold, 4 fold, 6 fold, 8 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titer of influenza virus relative to an untreated subject. In some embodiments, an active compound or composition thereof results in a reduction in titer of influenza virus relative to an untreated subject of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs.

Influenza virus animal models, such as ferret, mouse, guinea pig, squirrel monkey, macaque, and chicken, developed for use to test antiviral agents against influenza virus have been described. See, e.g., Sidwell et al., Antiviral Res., 2000, 48:1-16; Lowen A. C. et al. PNAS., 2006, 103: 9988-92; and McCauley et al., Antiviral Res., 1995, 27:179-186 and Rimmelzwann et al., Avian Diseases, 2003, 47:931-933. For mouse models of influenza, non-limiting examples of parameters that can be used to assay antiviral activity of active compounds administered to the influenza-infected mice include pneumonia-associated death, serum al-acid glycoprotein increase, animal weight, lung virus assayed by hemagglutinin, lung virus assayed by plaque assays, and histopathological change in the lung. Statistical analysis is carried out to calculate significance (e.g., a P value of 0.05 or less).

In other assays, histopathologic evaluations are performed after infection of an animal model subject. Nasal turbinates and trachea may be examined for epithelial changes and subepithelial inflammation. The lungs may be examined for bronchiolar epithelial changes and peribronchiolar inflammation in large, medium, and small or terminal bronchioles. The alveoli are also evaluated for inflammatory changes. The medium bronchioles are graded on a scale of 0 to 3+ as follows: 0 (normal: lined by medium to tall columnar epithelial cells with ciliated apical borders and basal pseudostratified nuclei; minimal inflammation); 1+(epithelial layer columnar and even in outline with only slightly increased proliferation; cilia still visible on many cells); 2+(prominent changes in the epithelial layer ranging from attenuation to marked proliferation; cells disorganized and layer outline irregular at the luminal border); 3+(epithelial layer markedly disrupted and disorganized with necrotic cells visible in the lumen; some bronchioles attenuated and others in marked reactive proliferation).

The trachea is graded on a scale of 0 to 2.5+ as follows: 0 (normal: Lined by medium to tall columnar epithelial cells with ciliated apical border, nuclei basal and pseudostratified. Cytoplasm evident between apical border and nucleus. Occasional small focus with squamous cells); 1+(focal squamous metaplasia of the epithelial layer); 2+(diffuse squamous metaplasia of much of the epithelial layer, cilia may be evident focally); 2.5+(diffuse squamous metaplasia with very few cilia evident).

Virus immunohistochemistry is performed using a viral-specific monoclonal antibody (e.g. NP-, N- or HN-specific monoclonal antibodies). Staining is graded 0 to 3+ as follows: 0 (no infected cells); 0.5+ (few infected cells); 1+ (few infected cells, as widely separated individual cells); 1.5+ (few infected cells, as widely separated singles and in small clusters); 2+ (moderate numbers of infected cells, usually affecting clusters of adjacent cells in portions of the epithelial layer lining bronchioles, or in small sublobular foci in alveoli); 3+ (numerous infected cells, affecting most of the epithelial layer in bronchioles, or widespread in large sublobular foci in alveoli).

In one example, the ability to induce lung lesions and cause infection in an animal model of virus infection is compared using wild-type virus and mock virus. Lung lesions can be assessed as a percentage of lung lobes that are healthy by visual inspection. Animals are euthanized 5 days p.i. by intravenous administration of pentobarbital, and their lungs are removed in toto. The percentage of the surface of each pulmonary lobe that is affected by macroscopic lesions is estimated visually. The percentages are averaged to obtain a mean value for the 7 pulmonary lobes of each animal. In other assays, nasal swabs can be tested to determine virus burden or titer. Nasal swabs can be taken during necropsy to determine viral burden post-infection.

In one embodiment, virus is quantified in tissue samples. For example, tissue samples are homogenized in phosphate-buffered saline (PBS), and dilutions of clarified homogenates adsorbed for 1 h at 37° C. onto monolayers of cells (e.g., MDCK cells). Infected monolayers are then overlaid with a solution of minimal essential medium containing 0.1% bovine serum albumin (BSA), 0.01% DEAE-dextran, 0.1% $NaHCO_3$, and 1% agar. Plates are incubated 2 to 3 days until plaques could be visualized. Tissue culture infectious dose (TCID) assays to titrate virus from PR8-infected samples are carried out as follows. Confluent monolayers of cells (e.g., MDCK cells) in 96-well plates are incubated with log dilutions of clarified tissue homogenates in media. Two to three days after inoculation, 0.05-ml aliquots from each well are assessed for viral growth by hemagglutination assay (HA assay).

5.14.6.1.1 Assays in Humans

In one embodiment, an active compound or composition thereof that modulates replication an influenza virus are assessed in infected human subjects. In accordance with this embodiment, an active compound or composition thereof is administered to the human subject, and the effect of the active compound or composition on viral replication is determined by, e.g., analyzing the level of the virus or viral nucleic acids in a biological sample (e.g., serum or plasma). An active compound or composition thereof that alters virus replication can be identified by comparing the level of virus replication in a subject or group of subjects treated with a control to that in a subject or group of subjects treated with an active compound or composition thereof. Alternatively, alterations in viral replication can be identified by comparing the level of the virus replication in a subject or group of subjects before and after the administration of an active compound or composition thereof. Techniques known to those of skill in the art can be used to obtain the biological sample and analyze the mRNA or protein expression.

In another embodiment, the effect of an active compound or composition thereof on the severity of one or more symptoms associated with an influenza virus infection/ disease are assessed in an infected subject. In accordance with this embodiment, an active compound or composition thereof or a control is administered to a human subject suffering from influenza virus infection and the effect of the active compound or composition on one or more symptoms of the virus infection is determined. An active compound or composition thereof that reduces one or more symptoms can be identified by comparing the subjects treated with a control to the subjects treated with the active compound or composition. In another embodiment, an active compound or composition thereof is administered to a healthy human subject and monitored for efficacy as a vaccine (e.g., the subject is monitored for the onset of symptoms of influenza virus infection; the ability of influenza virus to infect the subject; and/or a reduction in/absence of one or more symptoms associated with influenza virus infection). Techniques known to physicians familiar with infectious diseases can be used to determine whether an active compound or composition thereof reduces one or more symptoms associated with the influenza virus disease.

5.15 Kits

Provided herein is a pharmaceutical pack or kit comprising one or more containers filled with one or more of the ingredients of the pharmaceutical compositions described herein, such as one or more active compounds provided herein. Optionally associated with such container(s) can be a notice in the form prescribed by a governmental agency regulating the manufacture, use or sale of pharmaceuticals or biological products, which notice reflects approval by the agency of manufacture, use or sale for human administration.

The kits encompassed herein can be used in the above methods. In one embodiment, a kit comprises an active compound described herein, preferably one or more influenza hemagglutinin stem domain polypeptides, in one or more containers. In certain embodiments, a kit comprises a vaccine described herein, e.g., a split virus vaccine, a subunit vaccine, an inactivated influenza virus vaccine, or a live influenza virus vaccine.

6. EXAMPLES

6.1 Example 1: Influenza Hemagglutinin Stem Domain Polypeptides

TABLE 8

Summary of Constructs

| Name | HA1 N-terminal Stem Segment | Linker | HA1 C-terminal Stem Segment | HA2 Domain |
|---|---|---|---|---|
| PR8-2G | SEQ ID NO: 34 | Gly-Gly | SEQ ID NO: 50 | SEQ ID NO: 66 |
| PR8-4G | SEQ ID NO: 34 | Gly-Gly-Gly-Gly (SEQ ID NO: 560) | SEQ ID NO: 50 | SEQ ID NO: 66 |
| PR8-PG | SEQ ID NO: 34 | Pro-Gly | SEQ ID NO: 50 | SEQ ID NO: 66 |
| PR8-No Cys-1G | SEQ ID NO: 177 | Gly | SEQ ID NO: 226 | SEQ ID NO: 66 |
| PR8-No Cys 2G | SEQ ID NO: 177 | Gly-Gly | SEQ ID NO: 226 | SEQ ID NO: 66 |
| PR8-No Cys 3G | SEQ ID NO: 177 | Gly-Gly-Gly | SEQ ID NO: 226 | SEQ ID NO: 66 |
| PR8-No Cys | SEQ ID NO: 177 | direct bond | SEQ ID NO: 226 | SEQ ID NO: 66 |
| PR8-No Cys Δ1 | SEQ ID NO: 178 | direct bond | SEQ ID NO: 227 | SEQ ID NO: 66 |
| PR8-No Cys Δ3 | SEQ ID NO: 179 | direct bond | SEQ ID NO: 228 | SEQ ID NO: 66 |
| PR8-No Cys NAS | SEQ ID NO: 177 | Asn-Ala-Ser | SEQ ID NO: 226 | SEQ ID NO: 66 |
| PR8-CON-A | SEQ ID NO: 312 | Gly-Gly-Gly-Gly (SEQ ID NO: 560) | SEQ ID NO: 313 | SEQ ID NO: 66 |
| PR8-CON-B | SEQ ID NO: 34 | Gly-Gly | SEQ ID NO: 314 | SEQ ID NO: 66 |
| PR8-CON-C | SEQ ID NO: 315 | Gly-Gly | SEQ ID NO: 316 | SEQ ID NO: 66 |
| HK68-2G | SEQ ID NO: 36 | Gly-Gly | SEQ ID NO: 52 | SEQ ID NO: 68 |
| HK68-4G | SEQ ID NO: 36 | Gly-Gly-Gly-Gly (SEQ ID NO: 560) | SEQ ID NO: 52 | SEQ ID NO: 68 |
| HK68-PG | SEQ ID NO: 36 | Pro-Gly | SEQ ID NO: 52 | SEQ ID NO: 68 |
| HK68-No Cys | SEQ ID NO: 183 | direct bond | SEQ ID NO: 232 | SEQ ID NO: 68 |
| HK68-No Cys Δ1 | SEQ ID NO: 184 | direct bond | SEQ ID NO: 233 | SEQ ID NO: 68 |
| HK68-No Cys Δ3 | SEQ ID NO: 185 | direct bond | SEQ ID NO: 234 | SEQ ID NO: 68 |
| HK68-No Cys NAS | SEQ ID NO: 183 | Asn-Ala-Ser | SEQ ID NO: 232 | SEQ ID NO: 68 |
| HK68-CON-A | SEQ ID NO: 308 | Gly-Gly-Gly-Gly (SEQ ID NO: 560) | SEQ ID NO: 52 | SEQ ID NO: 68 |
| HK68-CON-B | SEQ ID NO: 36 | Gly-Gly | SEQ ID NO: 309 | SEQ ID NO: 68 |
| HK68-CON-C | SEQ ID NO: 310 | Gly-Gly-Gly-Gly (SEQ ID NO: 560) | SEQ ID NO: 311 | SEQ ID NO: 68 |

The instant example provides useful polypeptides in Table 8 that can be prepared according to the methods described herein.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A polypeptide comprising:

(A) (a) (i) an influenza hemagglutinin HA1 domain that comprises an HA1 N-terminal stem segment, or a deleted form of said HA1 N-terminal stem segment, wherein up to 7, 6, 5, 4, 3, 2, or 1 amino acid residues are deleted, covalently linked to (ii) a linker of 1 to 50 heterologous residues that is in turn covalently linked to (iii) an HA1 C-terminal short stem segment, or a deleted form of said HA1 C-terminal short stem segment, wherein up to 7, 6, 5, 4, 3, 2, or 1 amino acid residues are deleted;

said HA1 domain being in tertiary association with (b) an influenza hemagglutinin HA2 domain, wherein the amino acid sequence of the HA2 domain is at least 70%, 75%, 80%, 85%, 90%, 95%, 96% or 98% identical to the amino acid sequence of an HA2 from an H1, H2, H3, H4, H5, H6, H7, H8, H9, H10, H11, H12, H13, H14, H15 or H16 influenza A, wherein the HA1 N-terminal stem segment consists of amino acid residues $HA1_{N\text{-}term}$ through $A_p$ of the HA1 domain, wherein $HA1_{N\text{-}term}$ is the N-terminal amino acid of a mature HA0 protein lacking a signal peptide, and wherein $A_p$ is Cys that corresponds to amino acid position 52 of an HA1 domain using H3 numbering; and wherein the HA1 C-terminal short stem segment consists of amino acid residues $B_q$ through $HA1_{C\text{-}term}$ of an HA1 domain, wherein $B_q$ is Cys that corresponds to amino acid position 305 of an HA1 domain using H3 numbering, and wherein $HA1_{C\text{-}term}$ is the C-terminal amino acid of the HA1 domain; or (B) (a) (i) an influenza hemagglutinin HA1 domain that comprises a deleted form of an HA1 N-terminal stem segment, wherein up to 7, 6, 5, 4, 3, 2, or 1 amino acid residues are deleted, covalently linked to (ii) a linker of 1 to 50 heterologous residues that is in turn covalently linked to (iii) a sequence having at least 70%, 75%, 80%, 85%, 90%, 95%, 96% or 98% amino acid sequence identity to an HA1 C-terminal short stem segment from an H1, H2, H3, H4, H5, H6, H7, H8, H9, H10, H11, H12, H13, H14, H15 or H16 influenza A;

said HA1 domain being in tertiary association with (b) an influenza hemagglutinin HA2 domain, wherein the amino acid sequence of the HA2 domain is at least 70%, 75%, 80%, 85%, 90%, 95%, 96% or 98% identical to the amino acid sequence of an HA2 from an H1, H2, H3, H4, H5, H6, H7, H8, H9, H10, H11, H12, H13, H14, H15 or H16 influenza A, wherein the HA1 N-terminal stem segment consists of amino acid residues $HA1_{N\text{-}term}$ through $A_p$ of the HA1 domain, wherein $HA1_{N\text{-}term}$ is the N-terminal amino acid of a mature HA0 protein lacking a signal peptide, and wherein $A_p$ is Cys that corresponds to amino acid position 52 of an HA1 domain using H3 numbering; and wherein the HA1 C-terminal short stem segment consists of amino acid residues $B_q$ through $HA1_{C\text{-}term}$ of an HA1 domain, wherein $B_q$ is Cys that corresponds to amino acid position 305 of an HA1 domain using H3 numbering, and wherein $HA1_{C\text{-}term}$ is the C-terminal amino acid of the HA1 domain.

2. The polypeptide of claim 1, which is soluble.

3. The polypeptide of claim 1, wherein the HA1 C-terminal short stem segment is covalently linked to the HA2 domain.

4. The polypeptide of claim 1, wherein the polypeptide selectively binds neutralizing antiserum capable of binding an influenza hemagglutinin.

5. The polypeptide of claim 1, wherein:

(a) said linker is of 1 to 40, 1 to 30 residues, 1 to 20 residues, 1 to 10 residues, 1 to 5 residues, 1 to 4 residues, 1 to 3 residues, 1 to 2 residues or 1 residue; or (b) said linker is selected from the group consisting of GG, PG, GGG, GGGG (SEQ ID NO:560), GGGGG (SEQ ID NO 561), ITPNGSIPNDKPFQNVNKITYGA (SEQ ID NO:165), and NAS.

6. The polypeptide of claim 1, wherein:

(a) the HA1 N-terminal stem segment comprises the amino acid sequence A17-A18-$(Xaa)_n$-$A_{38}$ (SEQ ID NO:146), wherein $A_{17}$ is Y or H;

$A_{18}$ is H, L, or Q;

$(Xaa)_n$ represents a sequence of 18-20 amino acid residues; and $A_{38}$ is H, S, Q, T or N;

(b) the HA2 domain comprises the amino acid sequence $A_{18}$-$A_{19}$-$A_{20}$-$A_{21}$ (SEQ ID NO:148), wherein $A_{18}$ is V or I;

$A_{19}$ is D, N or A;

$A_{20}$ is G, and $A_{21}$ is W;

(c) the HA2 domain comprises the amino acid sequence $A_{38}$-$A_{39}$-$A_{40}$-$A_{41}$-$A_{42}$-$A_{43}$-$A_{44}$-$A_{45}$-$A_{46}$-$A_{47}$-$A_{48}$-$A_{49}$-$A_{50}$-$A_{51}$-$A_{52}$-$A_{53}$-$A_{54}$-$A_{55}$-$A_{56}$ (SEQ ID NO:149), wherein $A_{38}$ is K, Q, R, L or Y;

$A_{39}$ is any amino acid residue;

$A_{40}$ is any amino acid residue;

$A_{41}$ is T;

$A_{42}$ is Q;

$A_{43}$ is any amino acid residue;

$A_{44}$ is A;

$A_{45}$ is I;

$A_{46}$ is D;

$A_{47}$ is any amino acid residue;

$A_{48}$ is I, V or M;

$A_{49}$ is T, Q or N;

$A_{50}$ is any amino acid residue;

$A_{51}$ is K;

$A_{52}$ is V or L;

$A_{53}$ is N;

$A_{54}$ is any amino acid residue;

$A_{55}$ is V, I or L; and $A_{56}$ is V or I.

7. A nucleic acid encoding the polypeptide of claim 1.

8. An isolated host cell expressing the nucleic acid of claim 7.

9. A virus comprising a genome engineered to express the nucleic acid of claim 7.

10. A virus comprising the polypeptide of claim 1.

11. The virus of claim 9, wherein the virus is:

a Newcastle disease virus (NDV), a vaccinia virus, an adenovirus, an adeno-associated virus (AAV), or a retrovirus;

(ii) influenza A virus or influenza B virus; or (iii) inactivated or split.

12. The virus of claim 10, wherein the virus is:

(i) a Newcastle disease virus (NDV), a vaccinia virus, an adenovirus, an adeno-associated virus (AAV), or a retrovirus;

(ii) influenza A virus or influenza B virus; or (iii) inactivated or split.

13. A viral-like particle comprising the polypeptide of claim 1.

14. An immunogenic composition comprising the polypeptide of claim 1.

15. An immunogenic composition comprising the virus of claim 9.

16. An immunogenic composition comprising the virus of claim 10.

17. An immunogenic composition comprising the viral-like particle of claim 13.

18. A method for immunizing a subject against influenza virus or preventing an influenza virus disease in a subject, comprising administering to the subject the immunogenic composition of claim 14.

19. A method for immunizing a subject against influenza virus or preventing an influenza virus disease in a subject, comprising administering to the subject the immunogenic composition of claim 15.

20. A method for immunizing a subject against influenza virus or preventing an influenza virus disease in a subject, comprising administering to the subject the immunogenic composition of claim 16.

21. A method for immunizing a subject against influenza virus or preventing an influenza virus disease in a subject, comprising administering to the subject the immunogenic composition of claim 17.

22. A method for treating an influenza virus infection or influenza virus disease in a subject, comprising administering to the subject the immunogenic composition of claim 14.

23. A method for treating an influenza virus infection or influenza virus disease in a subject, comprising administering to the subject the immunogenic composition of claim 15.

24. A method for treating an influenza virus infection or influenza virus disease in a subject, comprising administering to the subject the immunogenic composition of claim 16.

25. A method for treating an influenza virus infection or influenza virus disease in a subject, comprising administering to the subject the immunogenic composition of claim 17.

26. The method of claim 18, wherein the subject is a human.

27. The method of claim 22, wherein the subject is a human.

* * * * *

SEQUENCE LISTING

<160> NUMBER OF SEQ ID NOS: 561

<210> SEQ ID NO 1
<211> LENGTH: 565
<212> TYPE: PRT
<213> ORGANISM: Influenza virus A
<220> FEATURE:
<223> OTHER INFORMATION: influenza virus A hemagglutinin subtype H1

<400> SEQUENCE: 1

```
Met Lys Ala Asn Leu Leu Val Leu Leu Cys Ala Leu Ala Ala Ala Asp
 1               5                  10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Leu Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Asn Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
```

```
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 2
<211> LENGTH: 562
<212> TYPE: PRT
<213> ORGANISM: Influenza virus A
<220> FEATURE:
<223> OTHER INFORMATION: influenza virus A hemagglutinin subtype H2

<400> SEQUENCE: 2

Met Ala Ile Ile Tyr Leu Ile Leu Leu Phe Thr Ala Val Arg Gly Asp
 1               5                  10                  15

Gln Ile Cys Ile Gly Tyr His Ser Asn Asn Ser Thr Glu Lys Val Asp
            20                  25                  30

Thr Ile Leu Glu Arg Asn Val Thr Val Thr His Ala Gln Asn Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Thr Val Pro Glu Trp Ser Tyr Ile Met Glu
                85                  90                  95

Lys Glu Asn Pro Arg Asn Gly Leu Cys Tyr Pro Gly Ser Phe Asn Asp
            100                 105                 110

Tyr Glu Glu Leu Lys His Leu Leu Ser Ser Val Thr His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
```

-continued

```
145                 150                 155                 160

Met Val Trp Leu Thr Lys Lys Gly Ser Asn Tyr Pro Ile Ala Lys Gly
                165                 170                 175

Ser Tyr Asn Asn Thr Ser Gly Glu Gln Met Leu Ile Ile Trp Gly Val
            180                 185                 190

His His Pro Asn Asp Glu Thr Glu Gln Arg Thr Leu Tyr Gln Asn Val
        195                 200                 205

Gly Thr Tyr Val Ser Ile Gly Thr Ser Thr Leu Asn Lys Arg Ser Ile
    210                 215                 220

Pro Val Ile Ala Thr Arg Pro Lys Val Asn Gly Gln Gly Gly Arg Met
225                 230                 235                 240

Glu Phe Ser Trp Thr Ile Leu Asp Ile Trp Asp Thr Ile Asn Phe Glu
                245                 250                 255

Ser Thr Gly Asn Leu Ile Ala Pro Glu Tyr Gly Phe Arg Ile Ser Lys
            260                 265                 270

Arg Gly Ser Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320

Lys Ser Glu Arg Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Ile Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380

Ile Asp Gly Ile Thr Asn Arg Val Asn Ser Val Ile Glu Lys Met Asn
385                 390                 395                 400

Thr Gln Phe Glu Ala Val Gly Lys Glu Phe Ser Asn Leu Glu Lys Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Arg Val Arg Met
    450                 455                 460

Gln Leu Arg Asp Asn Ala Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Glu Ser Lys Leu Asn Arg Asn Glu
            500                 505                 510

Ile Lys Gly Val Lys Leu Ser Asn Met Gly Val Tyr Gln Ile Leu Ala
        515                 520                 525

Ile Tyr Ala Thr Val Ala Gly Ser Leu Ser Leu Ala Ile Met Ile Ala
    530                 535                 540

Gly Ile Ser Leu Trp Met Cys Ser Asn Gly Ser Leu Gln Cys Arg Ile
545                 550                 555                 560

Cys Ile
```

<210> SEQ ID NO 3
<211> LENGTH: 566
<212> TYPE: PRT
<213> ORGANISM: Influenza virus A
<220> FEATURE:
<223> OTHER INFORMATION: influenza virus A hemagglutinin subtype H3

<400> SEQUENCE: 3

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Thr
    50                  55                  60

Gly Lys Ile Cys Asn Asn Pro His Arg Ile Leu Asp Gly Ile Asp Cys
65                  70                  75                  80

Thr Leu Ile Asp Ala Leu Leu Gly Asp Pro His Cys Asp Val Phe Gln
                85                  90                  95

Asn Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Thr Glu Gly Phe Thr Trp Thr
    130                 135                 140

Gly Val Thr Gln Asn Gly Gly Ser Asn Ala Cys Lys Arg Gly Pro Gly
145                 150                 155                 160

Asn Gly Phe Phe Ser Arg Leu Asn Trp Leu Thr Lys Ser Gly Ser Thr
                165                 170                 175

Tyr Pro Val Leu Asn Val Thr Met Pro Asn Asn Asp Asn Phe Asp Lys
            180                 185                 190

Leu Tyr Ile Trp Gly Val His His Pro Ser Thr Asn Gln Glu Gln Thr
        195                 200                 205

Ser Leu Tyr Val Gln Glu Ser Gly Arg Val Thr Val Ser Thr Arg Arg
    210                 215                 220

Ser Gln Gln Ser Ile Ile Pro Asn Ile Gly Ser Arg Pro Trp Val Arg
225                 230                 235                 240

Gly Gln Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
            260                 265                 270

Tyr Phe Lys Met Arg Thr Gly Lys Ser Ser Ile Met Ser Ser Asp Ala
        275                 280                 285

Pro Ile Asp Thr Cys Ile Ser Glu Cys Ile Thr Pro Asn Gly Ser Ile
    290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Ile Asp Gly Trp Tyr Gly
        355                 360                 365
```

```
Phe Arg His Gln Asn Ser Glu Gly Thr Gly Gln Ala Ala Asp Leu Lys
    370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Arg Gly Asn Ile
545                 550                 555                 560

Arg Cys Asn Ile Cys Ile
                565


<210> SEQ ID NO 4
<211> LENGTH: 564
<212> TYPE: PRT
<213> ORGANISM: Influenza virus A
<220> FEATURE:
<223> OTHER INFORMATION: influenza virus A hemagglutinin subtype H4

<400> SEQUENCE: 4

Met Leu Ser Ile Val Ile Leu Phe Leu Leu Ile Ala Glu Asn Ser Ser
 1               5                  10                  15

Gln Asn Tyr Thr Gly Asn Pro Val Ile Cys Met Gly His His Ala Val
            20                  25                  30

Ala Asn Gly Thr Met Val Lys Thr Leu Ala Asp Asp Gln Val Glu Val
        35                  40                  45

Val Thr Ala Gln Glu Leu Val Glu Ser Gln Asn Leu Pro Glu Leu Cys
    50                  55                  60

Pro Ser Pro Leu Arg Leu Val Asp Gly Gln Thr Cys Asp Ile Ile Asn
65                  70                  75                  80

Gly Ala Leu Gly Ser Pro Gly Cys Asp His Leu Asn Gly Ala Glu Trp
                85                  90                  95

Asp Val Phe Ile Glu Arg Pro Asn Ala Val Asp Thr Cys Tyr Pro Phe
            100                 105                 110

Asp Val Pro Glu Tyr Gln Ser Leu Arg Ser Ile Leu Ala Asn Asn Gly
        115                 120                 125

Lys Phe Glu Phe Ile Ala Glu Glu Phe Gln Trp Asn Thr Val Lys Gln
    130                 135                 140

Asn Gly Lys Ser Gly Ala Cys Lys Arg Ala Asn Val Asp Asp Phe Phe
145                 150                 155                 160
```

-continued

```
Asn Arg Leu Asn Trp Leu Val Lys Ser Asp Gly Asn Ala Tyr Pro Leu
                165                 170                 175

Gln Asn Leu Thr Lys Ile Asn Asn Gly Asp Tyr Ala Arg Leu Tyr Ile
            180                 185                 190

Trp Gly Val His His Pro Ser Thr Ser Thr Glu Gln Thr Asn Leu Tyr
        195                 200                 205

Lys Asn Asn Pro Gly Arg Val Thr Val Ser Thr Lys Thr Ser Gln Thr
    210                 215                 220

Ser Val Val Pro Asp Ile Gly Ser Arg Pro Leu Val Arg Gly Gln Ser
225                 230                 235                 240

Gly Arg Val Ser Phe Tyr Trp Thr Ile Val Glu Pro Gly Asp Leu Ile
                245                 250                 255

Val Phe Asn Thr Ile Gly Asn Leu Ile Ala Pro Arg Gly His Tyr Lys
            260                 265                 270

Leu Asn Asn Gln Lys Lys Ser Thr Ile Leu Asn Thr Ala Ile Pro Ile
        275                 280                 285

Gly Ser Cys Val Ser Lys Cys His Thr Asp Lys Gly Ser Leu Ser Thr
    290                 295                 300

Thr Lys Pro Phe Gln Asn Ile Ser Arg Ile Ala Val Gly Asp Cys Pro
305                 310                 315                 320

Arg Tyr Val Lys Gln Gly Ser Leu Lys Leu Ala Thr Gly Met Arg Asn
                325                 330                 335

Ile Pro Glu Lys Ala Ser Arg Gly Leu Phe Gly Ala Ile Ala Gly Phe
            340                 345                 350

Ile Glu Asn Gly Trp Gln Gly Leu Ile Asp Gly Trp Tyr Gly Phe Arg
        355                 360                 365

His Gln Asn Ala Glu Gly Thr Gly Thr Ala Ala Asp Leu Lys Ser Thr
    370                 375                 380

Gln Ala Ala Ile Asp Gln Ile Asn Gly Lys Leu Asn Arg Leu Ile Glu
385                 390                 395                 400

Lys Thr Asn Asp Lys Tyr His Gln Ile Glu Lys Glu Phe Glu Gln Val
                405                 410                 415

Glu Gly Arg Ile Gln Asp Leu Glu Asn Tyr Val Glu Asp Thr Lys Ile
            420                 425                 430

Asp Leu Trp Ser Tyr Asn Ala Glu Leu Leu Val Ala Leu Glu Asn Gln
        435                 440                 445

His Thr Ile Asp Val Thr Asp Ser Glu Met Asn Lys Leu Phe Glu Arg
    450                 455                 460

Val Arg Arg Gln Leu Arg Glu Asn Ala Glu Asp Lys Gly Asn Gly Cys
465                 470                 475                 480

Phe Glu Ile Phe His Lys Cys Asp Asn Asn Cys Ile Glu Ser Ile Arg
                485                 490                 495

Asn Gly Thr Tyr Asp His Asp Ile Tyr Arg Asp Glu Ala Ile Asn Asn
            500                 505                 510

Arg Phe Gln Ile Gln Gly Val Lys Leu Thr Gln Gly Tyr Lys Asp Ile
        515                 520                 525

Ile Leu Trp Ile Ser Phe Ser Ile Ser Cys Phe Leu Leu Val Ala Leu
    530                 535                 540

Leu Leu Ala Phe Ile Leu Trp Ala Cys Gln Asn Gly Asn Ile Arg Cys
545                 550                 555                 560

Gln Ile Cys Ile
```

<210> SEQ ID NO 5

<211> LENGTH: 564
<212> TYPE: PRT
<213> ORGANISM: Influenza virus A
<220> FEATURE:
<223> OTHER INFORMATION: influenza virus A hemagglutinin subtype H5

<400> SEQUENCE: 5

```
Met Glu Arg Ile Val Leu Leu Leu Ala Ile Val Ser Leu Val Lys Ser
 1               5                  10                  15

Asp Gln Ile Cys Ile Gly Tyr His Ala Asn Lys Ser Thr Lys Gln Val
            20                  25                  30

Asp Thr Ile Met Glu Lys Asn Val Thr Val Thr His Ala Gln Asp Ile
        35                  40                  45

Leu Glu Arg Thr His Asn Gly Lys Leu Cys Ser Leu Asn Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Leu Asn Leu Pro Glu Trp Leu Tyr Ile Val
                85                  90                  95

Glu Lys Asp Asn Pro Ile Asn Ser Leu Cys Tyr Pro Gly Asp Phe Asn
            100                 105                 110

Asp Tyr Glu Glu Leu Lys Tyr Leu Leu Ser Ser Thr Asn His Phe Glu
        115                 120                 125

Lys Ile Arg Ile Ile Pro Arg Ser Ser Trp Ser Asn His Asp Ala Ser
    130                 135                 140

Ser Gly Val Ser Ser Ala Cys Pro Tyr Ile Gly Arg Ser Ser Phe Leu
145                 150                 155                 160

Arg Asn Val Val Trp Leu Ile Lys Lys Asn Asn Thr Tyr Pro Thr Ile
                165                 170                 175

Lys Arg Ser Tyr Asn Asn Thr Asn Gln Glu Asp Leu Leu Ile Leu Trp
            180                 185                 190

Gly Ile His His Pro Asn Asp Ala Ala Glu Gln Thr Lys Leu Tyr Gln
        195                 200                 205

Asn Pro Thr Thr Tyr Val Ser Val Gly Thr Ser Thr Leu Asn Gln Arg
    210                 215                 220

Ser Ile Pro Glu Ile Ala Thr Arg Pro Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Arg Tyr Ala Tyr Lys Ile
            260                 265                 270

Val Lys Lys Gly Asp Ser Ala Ile Met Lys Ser Gly Leu Ala Tyr Gly
        275                 280                 285

Asn Cys Asp Thr Lys Cys Gln Thr Pro Val Gly Glu Ile Asn Ser Ser
    290                 295                 300

Met Pro Phe His Asn Ile His Pro His Thr Ile Gly Glu Cys Pro Lys
305                 310                 315                 320

Tyr Val Lys Ser Asp Arg Leu Val Leu Ala Thr Gly Leu Arg Asn Val
                325                 330                 335

Pro Gln Arg Lys Lys Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380
```

-continued

```
Lys Ala Ile Asp Gly Ile Thr Asn Lys Val Asn Ser Ile Ile Asp Lys
385                 390                 395                 400

Met Asn Thr Arg Phe Glu Ala Val Gly Lys Glu Phe Asn Asn Leu Glu
                405                 410                 415

Arg Arg Val Glu Asn Leu Asn Lys Lys Met Glu Asp Gly Phe Leu Asp
            420                 425                 430

Val Trp Thr Tyr Asn Val Glu Leu Leu Val Leu Met Glu Asn Glu Arg
        435                 440                 445

Thr Leu Asp Phe His Asp Ser Asn Val Asn Asn Leu Tyr Asp Lys Val
    450                 455                 460

Arg Leu Gln Leu Lys Asp Asn Ala Arg Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ala Arg Leu Asn Arg
            500                 505                 510

Glu Glu Ile Ser Gly Val Lys Leu Glu Ser Met Gly Val Tyr Gln Ile
        515                 520                 525

Leu Ser Ile Tyr Ser Thr Val Ala Ser Ser Leu Ala Leu Ala Ile Met
    530                 535                 540

Ile Ala Gly Leu Ser Phe Trp Met Cys Ser Asn Gly Ser Leu Gln Cys
545                 550                 555                 560

Arg Ile Cys Ile


<210> SEQ ID NO 6
<211> LENGTH: 566
<212> TYPE: PRT
<213> ORGANISM: Influenza virus A
<220> FEATURE:
<223> OTHER INFORMATION: influenza virus A hemagglutinin subtype H6

<400> SEQUENCE: 6

Met Ile Ala Ile Ile Val Val Ala Ile Leu Ala Thr Ala Gly Arg Ser
 1               5                  10                  15

Asp Lys Ile Cys Ile Gly Tyr His Ala Asn Asn Ser Thr Thr Gln Ile
            20                  25                  30

Asp Thr Ile Leu Glu Lys Asn Val Thr Val Thr His Ser Val Glu Leu
        35                  40                  45

Leu Glu Asn Gln Lys Glu Glu Arg Phe Cys Lys Ile Leu Lys Lys Ala
    50                  55                  60

Pro Leu Asp Leu Lys Gly Cys Thr Ile Glu Gly Trp Ile Leu Gly Asn
65                  70                  75                  80

Pro Gln Cys Asp Leu Leu Leu Gly Asp Gln Ser Trp Ser Tyr Ile Val
                85                  90                  95

Glu Arg Pro Thr Ala Gln Asn Gly Ile Cys Tyr Pro Gly Val Leu Asn
            100                 105                 110

Glu Val Glu Glu Leu Lys Ala Leu Ile Gly Ser Gly Glu Arg Val Glu
        115                 120                 125

Arg Phe Glu Met Phe Pro Lys Ser Thr Trp Thr Gly Val Asp Thr Ser
    130                 135                 140

Ser Gly Val Thr Arg Ala Cys Pro Tyr Asn Ser Gly Ser Ser Phe Tyr
145                 150                 155                 160

Arg Asn Leu Leu Trp Ile Ile Lys Thr Lys Ser Ala Ala Tyr Ser Val
                165                 170                 175
```

-continued

```
Ile Lys Gly Ala Tyr Asn Asn Thr Gly Asn Gln Pro Ile Leu Tyr Phe
            180                 185                 190

Trp Gly Val His His Pro Pro Asp Thr Asn Glu Gln Asn Thr Leu Tyr
        195                 200                 205

Gly Ser Gly Asp Arg Tyr Val Arg Met Gly Thr Glu Ser Met Asn Phe
    210                 215                 220

Ala Lys Ser Pro Glu Ile Ala Ala Arg Pro Ala Val Asn Gly Gln Arg
225                 230                 235                 240

Gly Arg Ile Asp Tyr Tyr Trp Ser Ile Leu Lys Pro Gly Glu Thr Leu
                245                 250                 255

Asn Val Glu Ser Asn Gly Asn Leu Ile Ala Pro Trp Tyr Ala Phe Arg
            260                 265                 270

Phe Val Ser Thr Ser Asn Lys Gly Ala Val Phe Lys Ser Asn Leu Pro
        275                 280                 285

Ile Glu Asn Cys Asp Ala Thr Cys Gln Thr Val Ala Gly Val Leu Arg
    290                 295                 300

Thr Asn Lys Thr Phe Gln Asn Val Ser Pro Leu Trp Ile Gly Glu Cys
305                 310                 315                 320

Pro Lys Tyr Val Lys Ser Glu Ser Leu Arg Leu Ala Thr Gly Leu Arg
                325                 330                 335

Asn Val Pro Gln Ile Glu Thr Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Glu Asn Ser Gln Gly Ser Gly Tyr Ala Ala Asp Arg Glu Ser
    370                 375                 380

Thr Gln Lys Ala Val Asp Gly Ile Thr Asn Lys Val Asn Ser Ile Ile
385                 390                 395                 400

Asp Lys Met Asn Thr Gln Phe Glu Ala Val Asp His Glu Phe Ser Asn
                405                 410                 415

Leu Glu Arg Arg Ile Asp Asn Leu Asn Lys Arg Met Glu Asp Gly Phe
            420                 425                 430

Leu Asp Val Trp Thr Tyr Asn Ala Glu Leu Leu Val Leu Leu Glu Asn
        435                 440                 445

Glu Arg Thr Leu Asp Leu His Asp Ala Asn Val Lys Asn Leu Tyr Glu
    450                 455                 460

Arg Val Lys Ser Gln Leu Arg Asp Asn Ala Met Ile Leu Gly Asn Gly
465                 470                 475                 480

Cys Phe Glu Phe Trp His Lys Cys Asp Asp Glu Cys Met Glu Ser Val
                485                 490                 495

Lys Asn Gly Thr Tyr Asp Tyr Pro Lys Tyr Gln Asp Glu Ser Lys Leu
            500                 505                 510

Asn Arg Gln Glu Ile Glu Ser Val Lys Leu Glu Ser Leu Gly Val Tyr
        515                 520                 525

Gln Ile Leu Ala Ile Tyr Ser Thr Val Ser Ser Ser Leu Val Leu Val
    530                 535                 540

Gly Leu Ile Ile Ala Val Gly Leu Trp Met Cys Ser Asn Gly Ser Met
545                 550                 555                 560

Gln Cys Arg Ile Cys Ile
                565
```

<210> SEQ ID NO 7
<211> LENGTH: 563
<212> TYPE: PRT

```
<213> ORGANISM: Influenza virus A
<220> FEATURE:
<223> OTHER INFORMATION: influenza virus A hemagglutinin subtype H7

<400> SEQUENCE: 7

Met Asn Thr Gln Ile Leu Val Phe Ala Leu Val Ala Val Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Thr Asn Ile Pro Lys Ile Cys Ser Lys Gly Lys
    50                  55                  60

Arg Thr Thr Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Asn Asp Val Cys Tyr Pro Gly Lys Phe Val Asn
            100                 105                 110

Glu Glu Ala Leu Arg Gln Ile Leu Arg Gly Ser Gly Gly Ile Asp Lys
        115                 120                 125

Glu Thr Met Gly Phe Thr Tyr Ser Gly Ile Arg Thr Asn Gly Thr Thr
    130                 135                 140

Ser Ala Cys Arg Arg Ser Gly Ser Ser Phe Tyr Ala Glu Met Glu Trp
145                 150                 155                 160

Leu Leu Ser Asn Thr Asp Asn Ala Ser Phe Pro Gln Met Thr Lys Ser
                165                 170                 175

Tyr Lys Asn Thr Arg Arg Glu Ser Ala Leu Ile Val Trp Gly Ile His
            180                 185                 190

His Ser Gly Ser Thr Thr Glu Gln Thr Lys Leu Tyr Gly Ser Gly Asn
        195                 200                 205

Lys Leu Ile Thr Val Gly Ser Ser Lys Tyr His Gln Ser Phe Val Pro
    210                 215                 220

Ser Pro Gly Thr Arg Pro Gln Ile Asn Gly Gln Ser Gly Arg Ile Asp
225                 230                 235                 240

Phe His Trp Leu Ile Leu Asp Pro Asn Asp Thr Val Thr Phe Ser Phe
                245                 250                 255

Asn Gly Ala Phe Ile Ala Pro Asn Arg Ala Ser Phe Leu Arg Gly Lys
            260                 265                 270

Ser Met Gly Ile Gln Ser Asp Val Gln Val Asp Ala Asn Cys Glu Gly
        275                 280                 285

Glu Cys Tyr His Ser Gly Gly Thr Ile Thr Ser Arg Leu Pro Phe Gln
    290                 295                 300

Asn Ile Asn Ser Arg Ala Val Gly Lys Cys Pro Arg Tyr Val Lys Gln
305                 310                 315                 320

Glu Ser Leu Leu Leu Ala Thr Gly Met Lys Asn Val Pro Glu Pro Ser
                325                 330                 335

Lys Lys Arg Lys Lys Arg Gly Leu Phe Gly Ala Ile Ala Gly Phe Ile
            340                 345                 350

Glu Asn Gly Trp Glu Gly Leu Val Asp Gly Trp Tyr Gly Phe Arg His
        355                 360                 365

Gln Asn Ala Gln Gly Glu Gly Thr Ala Ala Asp Tyr Lys Ser Thr Gln
    370                 375                 380

Ser Ala Ile Asp Gln Ile Thr Gly Lys Leu Asn Arg Leu Ile Glu Lys
```

```
385                 390                 395                 400

Thr Asn Gln Gln Phe Glu Leu Ile Asp Asn Glu Phe Thr Glu Val Glu
                405                 410                 415

Lys Gln Ile Gly Asn Leu Ile Asn Trp Thr Lys Asp Ser Ile Thr Glu
            420                 425                 430

Val Trp Ser Tyr Asn Ala Glu Leu Ile Val Ala Met Glu Asn Gln His
        435                 440                 445

Thr Ile Asp Leu Ala Asp Ser Glu Met Asn Arg Leu Tyr Glu Arg Val
    450                 455                 460

Arg Lys Gln Leu Arg Glu Asn Ala Glu Glu Asp Gly Thr Gly Cys Phe
465                 470                 475                 480

Glu Ile Phe His Lys Cys Asp Asp Asp Cys Met Ala Ser Ile Arg Asn
                485                 490                 495

Asn Thr Tyr Asp His Ser Lys Tyr Arg Glu Glu Ala Met Gln Asn Arg
            500                 505                 510

Ile Gln Ile Asp Pro Val Lys Leu Ser Ser Gly Tyr Lys Asp Val Ile
        515                 520                 525

Leu Trp Phe Ser Phe Gly Ala Ser Cys Phe Leu Leu Leu Ala Ile Ala
    530                 535                 540

Met Gly Leu Val Phe Ile Cys Val Lys Asn Gly Asn Met Arg Cys Thr
545                 550                 555                 560

Ile Cys Ile


<210> SEQ ID NO 8
<211> LENGTH: 565
<212> TYPE: PRT
<213> ORGANISM: Influenza virus A
<220> FEATURE:
<223> OTHER INFORMATION: influenza virus A hemagglutinin subtype H8

<400> SEQUENCE: 8

Met Glu Lys Phe Ile Ala Ile Ala Thr Leu Ala Ser Thr Asn Ala Tyr
 1               5                  10                  15

Asp Arg Ile Cys Ile Gly Tyr Gln Ser Asn Asn Ser Thr Asp Thr Val
            20                  25                  30

Asn Thr Leu Ile Glu Gln Asn Val Pro Val Thr Gln Thr Met Glu Leu
        35                  40                  45

Val Glu Thr Glu Lys His Pro Ala Tyr Cys Asn Thr Asp Leu Gly Ala
    50                  55                  60

Pro Leu Glu Leu Arg Asp Cys Lys Ile Glu Ala Val Ile Tyr Gly Asn
65                  70                  75                  80

Pro Lys Cys Asp Ile His Leu Lys Asp Gln Gly Trp Ser Tyr Ile Val
                85                  90                  95

Glu Arg Pro Ser Ala Pro Glu Gly Met Cys Tyr Pro Gly Ser Val Glu
            100                 105                 110

Asn Leu Glu Glu Leu Arg Phe Val Phe Ser Ser Ala Ala Ser Tyr Lys
        115                 120                 125

Arg Ile Arg Leu Phe Asp Tyr Ser Arg Trp Asn Val Thr Arg Ser Gly
    130                 135                 140

Thr Ser Lys Ala Cys Asn Ala Ser Thr Gly Gly Gln Ser Phe Tyr Arg
145                 150                 155                 160

Ser Ile Asn Trp Leu Thr Lys Lys Glu Pro Asp Thr Tyr Asp Phe Asn
                165                 170                 175

Glu Gly Ala Tyr Val Asn Asn Glu Asp Gly Asp Ile Ile Phe Leu Trp
            180                 185                 190
```

-continued

```
Gly Ile His His Pro Pro Asp Thr Lys Glu Gln Thr Thr Leu Tyr Lys
        195                 200                 205

Asn Ala Asn Thr Leu Ser Ser Val Thr Thr Asn Thr Ile Asn Arg Ser
    210                 215                 220

Phe Gln Pro Asn Ile Gly Pro Arg Pro Leu Val Arg Gly Gln Gln Gly
225                 230                 235                 240

Arg Met Asp Tyr Tyr Trp Gly Ile Leu Lys Arg Gly Glu Thr Leu Lys
                245                 250                 255

Ile Arg Thr Asn Gly Asn Leu Ile Ala Pro Glu Phe Gly Tyr Leu Leu
            260                 265                 270

Lys Gly Glu Ser Tyr Gly Arg Ile Ile Gln Asn Glu Asp Ile Pro Ile
        275                 280                 285

Gly Asn Cys Asn Thr Lys Cys Gln Thr Tyr Ala Gly Ala Ile Asn Ser
    290                 295                 300

Ser Lys Pro Phe Gln Asn Ala Ser Arg His Tyr Met Gly Glu Cys Pro
305                 310                 315                 320

Lys Tyr Val Lys Lys Ala Ser Leu Arg Leu Ala Val Gly Leu Arg Asn
                325                 330                 335

Thr Pro Ser Val Glu Pro Arg Gly Leu Phe Gly Ala Ile Ala Gly Phe
            340                 345                 350

Ile Glu Gly Gly Trp Ser Gly Met Ile Asp Gly Trp Tyr Gly Phe His
        355                 360                 365

His Ser Asn Ser Glu Gly Thr Gly Met Ala Ala Asp Gln Lys Ser Thr
    370                 375                 380

Gln Glu Ala Ile Asp Lys Ile Thr Asn Lys Val Asn Asn Ile Val Asp
385                 390                 395                 400

Lys Met Asn Arg Glu Phe Glu Val Val Asn His Glu Phe Ser Glu Val
                405                 410                 415

Glu Lys Arg Ile Asn Met Ile Asn Asp Lys Ile Asp Asp Gln Ile Glu
            420                 425                 430

Asp Leu Trp Ala Tyr Asn Ala Glu Leu Leu Val Leu Leu Glu Asn Gln
        435                 440                 445

Lys Thr Leu Asp Glu His Asp Ser Asn Val Lys Asn Leu Phe Asp Glu
    450                 455                 460

Val Lys Arg Arg Leu Ser Ala Asn Ala Ile Asp Ala Gly Asn Gly Cys
465                 470                 475                 480

Phe Asp Ile Leu His Lys Cys Asp Asn Glu Cys Met Glu Thr Ile Lys
                485                 490                 495

Asn Gly Thr Tyr Asp His Lys Glu Tyr Glu Glu Glu Ala Lys Leu Glu
            500                 505                 510

Arg Ser Lys Ile Asn Gly Val Lys Leu Glu Glu Asn Thr Thr Tyr Lys
        515                 520                 525

Ile Leu Ser Ile Tyr Ser Thr Val Ala Ala Ser Leu Cys Leu Ala Ile
    530                 535                 540

Leu Ile Ala Gly Gly Leu Ile Leu Gly Met Gln Asn Gly Ser Cys Arg
545                 550                 555                 560

Cys Met Phe Cys Ile
                565
```

<210> SEQ ID NO 9
<211> LENGTH: 560
<212> TYPE: PRT
<213> ORGANISM: Influenza virus A
<220> FEATURE:

<223> OTHER INFORMATION: influenza virus A hemagglutinin subtype H9

<400> SEQUENCE: 9

```
Met Glu Thr Lys Ala Ile Ile Ala Ala Leu Leu Met Val Thr Ala Ala
 1               5                  10                  15

Asn Ala Asp Lys Ile Cys Ile Gly Tyr Gln Ser Thr Asn Ser Thr Glu
            20                  25                  30

Thr Val Asp Thr Leu Thr Glu Ser Asn Val Pro Val Thr His Thr Lys
        35                  40                  45

Glu Leu Leu His Thr Glu His Asn Gly Met Leu Cys Ala Thr Asp Leu
    50                  55                  60

Gly His Pro Leu Ile Leu Asp Thr Cys Thr Ile Glu Gly Leu Ile Tyr
65                  70                  75                  80

Gly Asn Pro Ser Cys Asp Ile Leu Leu Gly Gly Lys Glu Trp Ser Tyr
                85                  90                  95

Ile Val Glu Arg Ser Ser Ala Val Asn Gly Met Cys Tyr Pro Gly Asn
            100                 105                 110

Val Glu Asn Leu Glu Glu Leu Arg Ser Leu Phe Ser Ser Ala Lys Ser
        115                 120                 125

Tyr Lys Arg Ile Gln Ile Phe Pro Asp Lys Thr Trp Asn Val Thr Tyr
    130                 135                 140

Ser Gly Thr Ser Arg Ala Cys Ser Asn Ser Phe Tyr Arg Ser Met Arg
145                 150                 155                 160

Trp Leu Thr His Lys Ser Asn Ser Tyr Pro Phe Gln Asn Ala His Tyr
                165                 170                 175

Thr Asn Asn Glu Arg Glu Asn Ile Leu Phe Met Trp Gly Ile His His
            180                 185                 190

Pro Pro Thr Asp Thr Glu Gln Thr Asp Leu Tyr Lys Asn Ala Asp Thr
        195                 200                 205

Thr Thr Ser Val Thr Thr Glu Asp Ile Asn Arg Thr Phe Lys Pro Val
    210                 215                 220

Ile Gly Pro Arg Pro Leu Val Asn Gly Gln Gln Gly Arg Ile Asp Tyr
225                 230                 235                 240

Tyr Trp Ser Val Leu Lys Pro Gly Gln Thr Leu Arg Ile Arg Ser Asn
                245                 250                 255

Gly Asn Leu Ile Ala Pro Trp Tyr Gly His Val Leu Thr Gly Glu Ser
            260                 265                 270

His Gly Arg Ile Leu Lys Thr Asp Leu Asn Asn Gly Asn Cys Val Val
        275                 280                 285

Gln Cys Gln Thr Glu Lys Gly Gly Leu Asn Thr Thr Leu Pro Phe His
    290                 295                 300

Asn Ile Ser Lys Tyr Ala Phe Gly Asn Cys Pro Lys Tyr Val Gly Val
305                 310                 315                 320

Lys Ser Leu Lys Leu Pro Val Gly Leu Arg Asn Val Pro Ala Val Ser
                325                 330                 335

Ser Arg Gly Leu Phe Gly Ala Ile Ala Gly Phe Ile Glu Gly Gly Trp
            340                 345                 350

Pro Gly Leu Val Ala Gly Trp Tyr Gly Phe Gln His Ser Asn Asp Gln
        355                 360                 365

Gly Val Gly Met Ala Ala Asp Lys Gly Ser Thr Gln Lys Ala Ile Asp
    370                 375                 380

Lys Ile Thr Ser Lys Val Asn Asn Ile Ile Asp Lys Met Asn Lys Gln
385                 390                 395                 400
```

-continued

```
Tyr Glu Val Ile Asp His Glu Phe Asn Glu Leu Glu Ala Arg Leu Asn
                405                 410                 415

Met Ile Asn Asn Lys Ile Asp Asp Gln Ile Gln Asp Ile Trp Ala Tyr
            420                 425                 430

Asn Ala Glu Leu Leu Val Leu Leu Glu Asn Gln Lys Thr Leu Asp Glu
        435                 440                 445

His Asp Ala Asn Val Asn Asn Leu Tyr Asn Lys Val Lys Arg Ala Leu
    450                 455                 460

Gly Ser Asn Ala Val Glu Asp Gly Asn Gly Cys Phe Glu Leu Tyr His
465                 470                 475                 480

Lys Cys Asp Asp Gln Cys Met Glu Thr Ile Arg Asn Gly Thr Tyr Asp
                485                 490                 495

Arg Gln Lys Tyr Gln Glu Glu Ser Arg Leu Glu Arg Gln Lys Ile Glu
            500                 505                 510

Gly Val Lys Leu Glu Ser Glu Gly Thr Tyr Lys Ile Leu Thr Ile Tyr
        515                 520                 525

Ser Thr Val Ala Ser Ser Leu Val Leu Ala Met Gly Phe Ala Ala Phe
    530                 535                 540

Leu Phe Trp Ala Met Ser Asn Gly Ser Cys Arg Cys Asn Ile Cys Ile
545                 550                 555                 560


<210> SEQ ID NO 10
<211> LENGTH: 561
<212> TYPE: PRT
<213> ORGANISM: Influenza virus A
<220> FEATURE:
<223> OTHER INFORMATION: influenza virus A hemagglutinin subtype H10

<400> SEQUENCE: 10

Met Tyr Lys Val Val Val Ile Ile Ala Leu Leu Gly Ala Val Lys Gly
 1               5                  10                  15

Leu Asp Arg Ile Cys Leu Gly His His Ala Val Ala Asn Gly Thr Ile
            20                  25                  30

Val Lys Thr Leu Thr Asn Glu Gln Glu Glu Val Thr Asn Ala Thr Glu
        35                  40                  45

Thr Val Glu Ser Thr Asn Leu Asn Lys Leu Cys Met Lys Gly Arg Ser
    50                  55                  60

Tyr Lys Asp Leu Gly Asn Cys His Pro Val Gly Met Leu Ile Gly Thr
65                  70                  75                  80

Pro Val Cys Asp Pro His Leu Thr Gly Thr Trp Asp Thr Leu Ile Glu
                85                  90                  95

Arg Glu Asn Ala Ile Ala His Cys Tyr Pro Gly Ala Thr Ile Asn Glu
            100                 105                 110

Glu Ala Leu Arg Gln Lys Ile Met Glu Ser Gly Gly Ile Ser Lys Met
        115                 120                 125

Ser Thr Gly Phe Thr Tyr Gly Ser Ser Ile Thr Ser Ala Gly Thr Thr
    130                 135                 140

Lys Ala Cys Met Arg Asn Gly Gly Asp Ser Phe Tyr Ala Glu Leu Lys
145                 150                 155                 160

Trp Leu Val Ser Lys Thr Lys Gly Gln Asn Phe Pro Gln Thr Thr Asn
                165                 170                 175

Thr Tyr Arg Asn Thr Asp Thr Ala Glu His Leu Ile Ile Trp Gly Ile
            180                 185                 190

His His Pro Ser Ser Thr Gln Glu Lys Asn Asp Leu Tyr Gly Thr Gln
        195                 200                 205
```

-continued

```
Ser Leu Ser Ile Ser Val Glu Ser Ser Thr Tyr Gln Asn Asn Phe Val
    210                 215                 220

Pro Val Val Gly Ala Arg Pro Gln Val Asn Gly Gln Ser Gly Arg Ile
225                 230                 235                 240

Asp Phe His Trp Thr Leu Val Gln Pro Gly Asp Asn Ile Thr Phe Ser
                245                 250                 255

Asp Asn Gly Gly Leu Ile Ala Pro Ser Arg Val Ser Lys Leu Thr Gly
            260                 265                 270

Arg Asp Leu Gly Ile Gln Ser Glu Ala Leu Ile Asp Asn Ser Cys Glu
        275                 280                 285

Ser Lys Cys Phe Trp Arg Gly Gly Ser Ile Asn Thr Lys Leu Pro Phe
    290                 295                 300

Gln Asn Leu Ser Pro Arg Thr Val Gly Gln Cys Pro Lys Tyr Val Asn
305                 310                 315                 320

Gln Arg Ser Leu Leu Leu Ala Thr Gly Met Arg Asn Val Pro Glu Val
                325                 330                 335

Val Gln Gly Arg Gly Leu Phe Gly Ala Ile Ala Gly Phe Ile Glu Asn
            340                 345                 350

Gly Trp Glu Gly Met Val Asp Gly Trp Tyr Gly Phe Arg His Gln Asn
        355                 360                 365

Ala Gln Gly Thr Gly Gln Ala Ala Asp Tyr Lys Ser Thr Gln Ala Ala
    370                 375                 380

Ile Asp Gln Ile Thr Gly Lys Leu Asn Arg Leu Ile Glu Lys Thr Asn
385                 390                 395                 400

Thr Glu Phe Glu Ser Ile Glu Ser Glu Phe Ser Glu Thr Glu His Gln
                405                 410                 415

Ile Gly Asn Val Ile Asn Trp Thr Lys Asp Ser Ile Thr Asp Ile Trp
            420                 425                 430

Thr Tyr Asn Ala Glu Leu Leu Val Ala Met Glu Asn Gln His Thr Ile
        435                 440                 445

Asp Met Ala Asp Ser Glu Met Leu Asn Leu Tyr Glu Arg Val Arg Lys
    450                 455                 460

Gln Leu Arg Gln Asn Ala Glu Glu Asp Gly Lys Gly Cys Phe Glu Ile
465                 470                 475                 480

Tyr His Thr Cys Asp Asp Ser Cys Met Glu Ser Ile Arg Asn Asn Thr
                485                 490                 495

Tyr Asp His Ser Gln Tyr Arg Glu Glu Ala Leu Leu Asn Arg Leu Asn
            500                 505                 510

Ile Asn Pro Val Lys Leu Ser Ser Gly Tyr Lys Asp Ile Ile Leu Trp
        515                 520                 525

Phe Ser Phe Gly Glu Ser Cys Phe Val Leu Leu Ala Val Val Met Gly
    530                 535                 540

Leu Val Phe Phe Cys Leu Lys Asn Gly Asn Met Arg Cys Thr Ile Cys
545                 550                 555                 560

Ile


<210> SEQ ID NO 11
<211> LENGTH: 565
<212> TYPE: PRT
<213> ORGANISM: Influenza virus A
<220> FEATURE:
<223> OTHER INFORMATION: influenza virus A hemagglutinin subtype H11

<400> SEQUENCE: 11

Met Glu Lys Thr Leu Leu Phe Ala Ala Ile Phe Leu Cys Val Lys Ala
```

-continued

```
1               5                   10                  15

Asp Glu Ile Cys Ile Gly Tyr Leu Ser Asn Asn Ser Thr Asp Lys Val
            20                  25                  30

Asp Thr Ile Ile Glu Asn Asn Val Thr Val Thr Ser Ser Val Glu Leu
        35                  40                  45

Val Glu Thr Glu His Thr Gly Ser Phe Cys Ser Ile Asn Gly Lys Gln
    50                  55                  60

Pro Ile Ser Leu Gly Asp Cys Ser Phe Ala Gly Trp Ile Leu Gly Asn
65                  70                  75                  80

Pro Met Cys Asp Glu Leu Ile Gly Lys Thr Ser Trp Ser Tyr Ile Val
                85                  90                  95

Glu Lys Pro Asn Pro Thr Asn Gly Ile Cys Tyr Pro Gly Thr Leu Glu
            100                 105                 110

Ser Glu Glu Glu Leu Arg Leu Lys Phe Ser Gly Val Leu Glu Phe Asn
        115                 120                 125

Lys Phe Glu Val Phe Thr Ser Asn Gly Trp Gly Ala Val Asn Ser Gly
    130                 135                 140

Val Gly Val Thr Ala Ala Cys Lys Phe Gly Gly Ser Asn Ser Phe Phe
145                 150                 155                 160

Arg Asn Met Val Trp Leu Ile His Gln Ser Gly Thr Tyr Pro Val Ile
                165                 170                 175

Lys Arg Thr Phe Asn Asn Thr Lys Gly Arg Asp Val Leu Ile Val Trp
            180                 185                 190

Gly Ile His His Pro Ala Thr Leu Thr Glu His Gln Asp Leu Tyr Lys
        195                 200                 205

Lys Asp Ser Ser Tyr Val Ala Val Gly Ser Glu Thr Tyr Asn Arg Arg
    210                 215                 220

Phe Thr Pro Glu Ile Asn Thr Arg Pro Arg Val Asn Gly Gln Ala Gly
225                 230                 235                 240

Arg Met Thr Phe Tyr Trp Lys Ile Val Lys Pro Gly Glu Ser Ile Thr
                245                 250                 255

Phe Glu Ser Asn Gly Ala Phe Leu Ala Pro Arg Tyr Ala Phe Glu Ile
            260                 265                 270

Val Ser Val Gly Asn Gly Lys Leu Phe Arg Ser Glu Leu Asn Ile Glu
        275                 280                 285

Ser Cys Ser Thr Lys Cys Gln Thr Glu Ile Gly Gly Ile Asn Thr Asn
    290                 295                 300

Lys Ser Phe His Asn Val His Arg Asn Thr Ile Gly Asp Cys Pro Lys
305                 310                 315                 320

Tyr Val Asn Val Lys Ser Leu Lys Leu Ala Thr Gly Pro Arg Asn Val
                325                 330                 335

Pro Ala Ile Ala Ser Arg Gly Leu Phe Gly Ala Ile Ala Gly Phe Ile
            340                 345                 350

Glu Gly Gly Trp Pro Gly Leu Ile Asn Gly Trp Tyr Gly Phe Gln His
        355                 360                 365

Arg Asp Glu Glu Gly Thr Gly Ile Ala Ala Asp Lys Glu Ser Thr Gln
    370                 375                 380

Lys Ala Ile Asp Gln Ile Thr Ser Lys Val Asn Asn Ile Val Asp Arg
385                 390                 395                 400

Met Asn Thr Asn Phe Glu Ser Val Gln His Glu Phe Ser Glu Ile Glu
                405                 410                 415

Glu Arg Ile Asn Gln Leu Ser Lys His Val Asp Asp Ser Val Val Asp
            420                 425                 430
```

```
Ile Trp Ser Tyr Asn Ala Gln Leu Leu Val Leu Leu Glu Asn Glu Lys
        435                 440                 445

Thr Leu Asp Leu His Asp Ser Asn Val Arg Asn Leu His Glu Lys Val
    450                 455                 460

Arg Arg Met Leu Lys Asp Asn Ala Lys Asp Glu Gly Asn Gly Cys Phe
465                 470                 475                 480

Thr Phe Tyr His Lys Cys Asp Asn Lys Cys Ile Glu Arg Val Arg Asn
                485                 490                 495

Gly Thr Tyr Asp His Lys Glu Phe Glu Glu Glu Ser Lys Ile Asn Arg
            500                 505                 510

Gln Glu Ile Glu Gly Val Lys Leu Asp Ser Ser Gly Asn Val Tyr Lys
        515                 520                 525

Ile Leu Ser Ile Tyr Ser Cys Ile Ala Ser Ser Leu Val Leu Ala Ala
    530                 535                 540

Leu Ile Met Gly Phe Met Phe Trp Ala Cys Ser Asn Gly Ser Cys Arg
545                 550                 555                 560

Cys Thr Ile Cys Ile
                565


<210> SEQ ID NO 12
<211> LENGTH: 564
<212> TYPE: PRT
<213> ORGANISM: Influenza virus A
<220> FEATURE:
<223> OTHER INFORMATION: influenza virus A hemagglutinin subtype H12

<400> SEQUENCE: 12

Met Glu Lys Phe Ile Ile Leu Ser Thr Val Leu Ala Ala Ser Phe Ala
 1               5                  10                  15

Tyr Asp Lys Ile Cys Ile Gly Tyr Gln Thr Asn Asn Ser Thr Glu Thr
            20                  25                  30

Val Asn Thr Leu Ser Glu Gln Asn Val Pro Val Thr Gln Val Glu Glu
        35                  40                  45

Leu Val His Arg Gly Ile Asp Pro Ile Leu Cys Gly Thr Glu Leu Gly
    50                  55                  60

Ser Pro Leu Val Leu Asp Asp Cys Ser Leu Glu Gly Leu Ile Leu Gly
65                  70                  75                  80

Asn Pro Lys Cys Asp Leu Tyr Leu Asn Gly Arg Glu Trp Ser Tyr Ile
                85                  90                  95

Val Glu Arg Pro Lys Glu Met Glu Gly Val Cys Tyr Pro Gly Ser Ile
            100                 105                 110

Glu Asn Gln Glu Glu Leu Arg Ser Leu Phe Ser Ser Ile Lys Lys Tyr
        115                 120                 125

Glu Arg Val Lys Met Phe Asp Phe Thr Lys Trp Asn Val Thr Tyr Thr
    130                 135                 140

Gly Thr Ser Lys Ala Cys Asn Asn Thr Ser Asn Gln Gly Ser Phe Tyr
145                 150                 155                 160

Arg Ser Met Arg Trp Leu Thr Leu Lys Ser Gly Gln Phe Pro Val Gln
                165                 170                 175

Thr Asp Glu Tyr Lys Asn Thr Arg Asp Ser Asp Ile Val Phe Thr Trp
            180                 185                 190

Ala Ile His His Pro Pro Thr Ser Asp Glu Gln Val Lys Leu Tyr Lys
        195                 200                 205

Asn Pro Asp Thr Leu Ser Ser Val Thr Thr Val Glu Ile Asn Arg Ser
    210                 215                 220
```

-continued

```
Phe Lys Pro Asn Ile Gly Pro Arg Pro Leu Val Arg Gly Gln Gln Gly
225                 230                 235                 240

Arg Met Asp Tyr Tyr Trp Ala Val Leu Lys Pro Gly Gln Thr Val Lys
                245                 250                 255

Ile Gln Thr Asn Gly Asn Leu Ile Ala Pro Glu Tyr Gly His Leu Ile
            260                 265                 270

Thr Gly Lys Ser His Gly Arg Ile Leu Lys Asn Asn Leu Pro Met Gly
        275                 280                 285

Gln Cys Val Thr Glu Cys Gln Leu Asn Glu Gly Val Met Asn Thr Ser
    290                 295                 300

Lys Pro Phe Gln Asn Thr Ser Lys His Tyr Ile Gly Lys Cys Pro Lys
305                 310                 315                 320

Tyr Ile Pro Ser Gly Ser Leu Lys Leu Ala Ile Gly Leu Arg Asn Val
                325                 330                 335

Pro Gln Val Gln Asp Arg Gly Leu Phe Gly Ala Ile Ala Gly Phe Ile
            340                 345                 350

Glu Gly Gly Trp Pro Gly Leu Val Ala Gly Trp Tyr Gly Phe Gln His
        355                 360                 365

Gln Asn Ala Glu Gly Thr Gly Ile Ala Ala Asp Arg Asp Ser Thr Gln
    370                 375                 380

Arg Ala Ile Asp Asn Met Gln Asn Lys Leu Asn Asn Val Ile Asp Lys
385                 390                 395                 400

Met Asn Lys Gln Phe Glu Val Val Asn His Glu Phe Ser Glu Val Glu
                405                 410                 415

Ser Arg Ile Asn Met Ile Asn Ser Lys Ile Asp Asp Gln Ile Thr Asp
            420                 425                 430

Ile Trp Ala Tyr Asn Ala Glu Leu Leu Val Leu Leu Glu Asn Gln Lys
        435                 440                 445

Thr Leu Asp Glu His Asp Ala Asn Val Arg Asn Leu His Asp Arg Val
    450                 455                 460

Arg Arg Val Leu Arg Glu Asn Ala Ile Asp Thr Gly Asp Gly Cys Phe
465                 470                 475                 480

Glu Ile Leu His Lys Cys Asp Asn Asn Cys Met Asp Thr Ile Arg Asn
                485                 490                 495

Gly Thr Tyr Asn His Lys Glu Tyr Glu Glu Glu Ser Lys Ile Glu Arg
            500                 505                 510

Gln Lys Val Asn Gly Val Lys Leu Glu Glu Asn Ser Thr Tyr Lys Ile
        515                 520                 525

Leu Ser Ile Tyr Ser Ser Val Ala Ser Ser Leu Val Leu Leu Leu Met
    530                 535                 540

Ile Ile Gly Gly Phe Ile Phe Gly Cys Gln Asn Gly Asn Val Arg Cys
545                 550                 555                 560

Thr Phe Cys Ile
```

<210> SEQ ID NO 13
<211> LENGTH: 566
<212> TYPE: PRT
<213> ORGANISM: Influenza virus A
<220> FEATURE:
<223> OTHER INFORMATION: influenza virus A hemagglutinin subtype H13

<400> SEQUENCE: 13

```
Met Ala Leu Asn Val Ile Ala Thr Leu Thr Leu Ile Ser Val Cys Val
 1               5                  10                  15
```

-continued

```
His Ala Asp Arg Ile Cys Val Gly Tyr Leu Ser Thr Asn Ser Ser Glu
            20                  25                  30

Arg Val Asp Thr Leu Leu Glu Asn Gly Val Pro Val Thr Ser Ser Ile
        35                  40                  45

Asp Leu Ile Glu Thr Asn His Thr Gly Thr Tyr Cys Ser Leu Asn Gly
    50                  55                  60

Val Ser Pro Val His Leu Gly Asp Cys Ser Phe Glu Gly Trp Ile Val
65                  70                  75                  80

Gly Asn Pro Ala Cys Thr Ser Asn Phe Gly Ile Arg Glu Trp Ser Tyr
                85                  90                  95

Leu Ile Glu Asp Pro Ala Ala Pro His Gly Leu Cys Tyr Pro Gly Glu
            100                 105                 110

Leu Asn Asn Asn Gly Glu Leu Arg His Leu Phe Ser Gly Ile Arg Ser
        115                 120                 125

Phe Ser Arg Thr Glu Leu Ile Pro Pro Thr Ser Trp Gly Glu Val Leu
    130                 135                 140

Asp Gly Thr Thr Ser Ala Cys Arg Asp Asn Thr Gly Thr Asn Ser Phe
145                 150                 155                 160

Tyr Arg Asn Leu Val Trp Phe Ile Lys Lys Asn Thr Arg Tyr Pro Val
                165                 170                 175

Ile Ser Lys Thr Tyr Asn Asn Thr Thr Gly Arg Asp Val Leu Val Leu
            180                 185                 190

Trp Gly Ile His His Pro Val Ser Val Asp Glu Thr Lys Thr Leu Tyr
        195                 200                 205

Val Asn Ser Asp Pro Tyr Thr Leu Val Ser Thr Lys Ser Trp Ser Glu
    210                 215                 220

Lys Tyr Lys Leu Glu Thr Gly Val Arg Pro Gly Tyr Asn Gly Gln Arg
225                 230                 235                 240

Ser Trp Met Lys Ile Tyr Trp Ser Leu Ile His Pro Gly Glu Met Ile
                245                 250                 255

Thr Phe Glu Ser Asn Gly Gly Phe Leu Ala Pro Arg Tyr Gly Tyr Ile
            260                 265                 270

Ile Glu Glu Tyr Gly Lys Gly Arg Ile Phe Gln Ser Arg Ile Arg Met
        275                 280                 285

Ser Arg Cys Asn Thr Lys Cys Gln Thr Ser Val Gly Gly Ile Asn Thr
    290                 295                 300

Asn Arg Thr Phe Gln Asn Ile Asp Lys Asn Ala Leu Gly Asp Cys Pro
305                 310                 315                 320

Lys Tyr Ile Lys Ser Gly Gln Leu Lys Leu Ala Thr Gly Leu Arg Asn
                325                 330                 335

Val Pro Ala Ile Ser Asn Arg Gly Leu Phe Gly Ala Ile Ala Gly Phe
            340                 345                 350

Ile Glu Gly Gly Trp Pro Gly Leu Ile Asn Gly Trp Tyr Gly Phe Gln
        355                 360                 365

His Gln Asn Glu Gln Gly Thr Gly Ile Ala Ala Asp Lys Glu Ser Thr
    370                 375                 380

Gln Lys Ala Ile Asp Gln Ile Thr Thr Lys Ile Asn Asn Ile Ile Asp
385                 390                 395                 400

Lys Met Asn Gly Asn Tyr Asp Ser Ile Arg Gly Glu Phe Asn Gln Val
                405                 410                 415

Glu Lys Arg Ile Asn Met Leu Ala Asp Arg Ile Asp Asp Ala Val Thr
            420                 425                 430

Asp Ile Trp Ser Tyr Asn Ala Lys Leu Leu Val Leu Leu Glu Asn Asp
```

```
        435                 440                 445

Lys Thr Leu Asp Met His Asp Ala Asn Val Lys Asn Leu His Glu Gln
    450                 455                 460

Val Arg Arg Glu Leu Lys Asp Asn Ala Ile Asp Glu Gly Asn Gly Cys
465                 470                 475                 480

Phe Glu Leu Leu His Lys Cys Asn Asp Ser Cys Met Glu Thr Ile Arg
                485                 490                 495

Asn Gly Thr Tyr Asp His Thr Glu Tyr Ala Glu Glu Ser Lys Leu Lys
            500                 505                 510

Arg Gln Glu Ile Asp Gly Ile Lys Leu Lys Ser Glu Asp Asn Val Tyr
        515                 520                 525

Lys Ala Leu Ser Ile Tyr Ser Cys Ile Ala Ser Ser Val Val Leu Val
    530                 535                 540

Gly Leu Ile Leu Ser Phe Ile Met Trp Ala Cys Ser Ser Gly Asn Cys
545                 550                 555                 560

Arg Phe Asn Val Cys Ile
                565


<210> SEQ ID NO 14
<211> LENGTH: 568
<212> TYPE: PRT
<213> ORGANISM: Influenza virus A
<220> FEATURE:
<223> OTHER INFORMATION: influenza virus A hemagglutinin subtype H14

<400> SEQUENCE: 14

Met Ile Ala Leu Ile Leu Val Ala Leu Ala Leu Ser His Thr Ala Tyr
 1               5                  10                  15

Ser Gln Ile Thr Asn Gly Thr Thr Gly Asn Pro Ile Ile Cys Leu Gly
            20                  25                  30

His His Ala Val Glu Asn Gly Thr Ser Val Lys Thr Leu Thr Asp Asn
        35                  40                  45

His Val Glu Val Val Ser Ala Lys Glu Leu Val Glu Thr Asn His Thr
    50                  55                  60

Asp Glu Leu Cys Pro Ser Pro Leu Lys Leu Val Asp Gly Gln Asp Cys
65                  70                  75                  80

His Leu Ile Asn Gly Ala Leu Gly Ser Pro Gly Cys Asp Arg Leu Gln
                85                  90                  95

Asp Thr Thr Trp Asp Val Phe Ile Glu Arg Pro Thr Ala Val Asp Thr
            100                 105                 110

Cys Tyr Pro Phe Asp Val Pro Asp Tyr Gln Ser Leu Arg Ser Ile Leu
        115                 120                 125

Ala Ser Ser Gly Ser Leu Glu Phe Ile Ala Glu Gln Phe Thr Trp Asn
    130                 135                 140

Gly Val Lys Val Asp Gly Ser Ser Ser Ala Cys Leu Arg Gly Gly Arg
145                 150                 155                 160

Asn Ser Phe Phe Ser Arg Leu Asn Trp Leu Thr Lys Ala Thr Asn Gly
                165                 170                 175

Asn Tyr Gly Pro Ile Asn Val Thr Lys Glu Asn Thr Gly Ser Tyr Val
            180                 185                 190

Arg Leu Tyr Leu Trp Gly Val His His Pro Ser Ser Asp Asn Glu Gln
        195                 200                 205

Thr Asp Leu Tyr Lys Val Ala Thr Gly Arg Val Thr Val Ser Thr Arg
    210                 215                 220

Ser Asp Gln Ile Ser Ile Val Pro Asn Ile Gly Ser Arg Pro Arg Val
```

-continued

```
225                 230                 235                 240

Arg Asn Gln Ser Gly Arg Ile Ser Ile Tyr Trp Thr Leu Val Asn Pro
                245                 250                 255

Gly Asp Ser Ile Ile Phe Asn Ser Ile Gly Asn Leu Ile Ala Pro Arg
            260                 265                 270

Gly His Tyr Lys Ile Ser Lys Ser Thr Lys Ser Thr Val Leu Lys Ser
        275                 280                 285

Asp Lys Arg Ile Gly Ser Cys Thr Ser Pro Cys Leu Thr Asp Lys Gly
    290                 295                 300

Ser Ile Gln Ser Asp Lys Pro Phe Gln Asn Val Ser Arg Ile Ala Ile
305                 310                 315                 320

Gly Asn Cys Pro Lys Tyr Val Lys Gln Gly Ser Leu Met Leu Ala Thr
                325                 330                 335

Gly Met Arg Asn Ile Pro Gly Lys Gln Ala Lys Gly Leu Phe Gly Ala
            340                 345                 350

Ile Ala Gly Phe Ile Glu Asn Gly Trp Gln Gly Leu Ile Asp Gly Trp
        355                 360                 365

Tyr Gly Phe Arg His Gln Asn Ala Glu Gly Thr Gly Thr Ala Ala Asp
    370                 375                 380

Leu Lys Ser Thr Gln Ala Ala Ile Asp Gln Ile Asn Gly Lys Leu Asn
385                 390                 395                 400

Arg Leu Ile Glu Lys Thr Asn Glu Lys Tyr His Gln Ile Glu Lys Glu
                405                 410                 415

Phe Glu Gln Val Glu Gly Arg Ile Gln Asp Leu Glu Lys Tyr Val Glu
            420                 425                 430

Asp Thr Lys Ile Asp Leu Trp Ser Tyr Asn Ala Glu Leu Leu Val Ala
        435                 440                 445

Leu Glu Asn Gln His Thr Ile Asp Val Thr Asp Ser Glu Met Asn Lys
    450                 455                 460

Leu Phe Glu Arg Val Arg Arg Gln Leu Arg Glu Asn Ala Glu Asp Gln
465                 470                 475                 480

Gly Asn Gly Cys Phe Glu Ile Phe His Gln Cys Asp Asn Asn Cys Ile
                485                 490                 495

Glu Ser Ile Arg Asn Gly Thr Tyr Asp His Asn Ile Tyr Arg Asp Glu
            500                 505                 510

Ala Ile Asn Asn Arg Ile Lys Ile Asn Pro Val Thr Leu Thr Met Gly
        515                 520                 525

Tyr Lys Asp Ile Ile Leu Trp Ile Ser Phe Ser Met Ser Cys Phe Val
    530                 535                 540

Phe Val Ala Leu Ile Leu Gly Phe Val Leu Trp Ala Cys Gln Asn Gly
545                 550                 555                 560

Asn Ile Arg Cys Gln Ile Cys Ile
                565


<210> SEQ ID NO 15
<211> LENGTH: 570
<212> TYPE: PRT
<213> ORGANISM: Influenza virus A
<220> FEATURE:
<223> OTHER INFORMATION: influenza virus A hemagglutinin subtype H15

<400> SEQUENCE: 15

Met Asn Thr Gln Ile Ile Val Ile Leu Val Leu Gly Leu Ser Met Val
 1               5                  10                  15

Lys Ser Asp Lys Ile Cys Leu Gly His His Ala Val Ala Asn Gly Thr
```

-continued

```
            20                  25                  30

Lys Val Asn Thr Leu Thr Glu Arg Gly Val Glu Val Val Asn Ala Thr
        35                  40                  45

Glu Thr Val Glu Ile Thr Gly Ile Asp Lys Val Cys Thr Lys Gly Lys
    50                  55                  60

Lys Ala Val Asp Leu Gly Ser Cys Gly Ile Leu Gly Thr Ile Ile Gly
65                  70                  75                  80

Pro Pro Gln Cys Asp Leu His Leu Glu Phe Lys Ala Asp Leu Ile Ile
                85                  90                  95

Glu Arg Arg Asn Ser Ser Asp Ile Cys Tyr Pro Gly Arg Phe Thr Asn
            100                 105                 110

Glu Glu Ala Leu Arg Gln Ile Ile Arg Glu Ser Gly Gly Ile Asp Lys
        115                 120                 125

Glu Ser Met Gly Phe Arg Tyr Ser Gly Ile Arg Thr Asp Gly Ala Thr
    130                 135                 140

Ser Ala Cys Lys Arg Thr Val Ser Ser Phe Tyr Ser Glu Met Lys Trp
145                 150                 155                 160

Leu Ser Ser Ser Met Asn Asn Gln Val Phe Pro Gln Leu Asn Gln Thr
                165                 170                 175

Tyr Arg Asn Thr Arg Lys Glu Pro Ala Leu Ile Val Trp Gly Val His
            180                 185                 190

His Ser Ser Ser Leu Asp Glu Gln Asn Lys Leu Tyr Gly Thr Gly Asn
        195                 200                 205

Lys Leu Ile Thr Val Gly Ser Ser Lys Tyr Gln Gln Ser Phe Ser Pro
    210                 215                 220

Ser Pro Gly Ala Arg Pro Lys Val Asn Gly Gln Ala Gly Arg Ile Asp
225                 230                 235                 240

Phe His Trp Met Leu Leu Asp Pro Gly Asp Thr Val Thr Phe Thr Phe
                245                 250                 255

Asn Gly Ala Phe Ile Ala Pro Asp Arg Ala Thr Phe Leu Arg Ser Asn
            260                 265                 270

Ala Pro Ser Gly Ile Glu Tyr Asn Gly Lys Ser Leu Gly Ile Gln Ser
        275                 280                 285

Asp Ala Gln Ile Asp Glu Ser Cys Glu Gly Glu Cys Phe Tyr Ser Gly
    290                 295                 300

Gly Thr Ile Asn Ser Pro Leu Pro Phe Gln Asn Ile Asp Ser Arg Ala
305                 310                 315                 320

Val Gly Lys Cys Pro Arg Tyr Val Lys Gln Ser Ser Leu Pro Leu Ala
                325                 330                 335

Leu Gly Met Lys Asn Val Pro Glu Lys Ile Arg Thr Arg Gly Leu Phe
            340                 345                 350

Gly Ala Ile Ala Gly Phe Ile Glu Asn Gly Trp Glu Gly Leu Ile Asp
        355                 360                 365

Gly Trp Tyr Gly Phe Arg His Gln Asn Ala Gln Gly Gln Gly Thr Ala
    370                 375                 380

Ala Asp Tyr Lys Ser Thr Gln Ala Ala Ile Asp Gln Ile Thr Gly Lys
385                 390                 395                 400

Leu Asn Arg Leu Ile Glu Lys Thr Asn Lys Gln Phe Glu Leu Ile Asp
                405                 410                 415

Asn Glu Phe Thr Glu Val Glu Gln Gln Ile Gly Asn Val Ile Asn Trp
            420                 425                 430

Thr Arg Asp Ser Leu Thr Glu Ile Trp Ser Tyr Asn Ala Glu Leu Leu
        435                 440                 445
```

Val Ala Met Glu Asn Gln His Thr Ile Asp Leu Ala Asp Ser Glu Met
    450                 455                 460

Asn Lys Leu Tyr Glu Arg Val Arg Arg Gln Leu Arg Glu Asn Ala Glu
465                 470                 475                 480

Glu Asp Gly Thr Gly Cys Phe Glu Ile Phe His Arg Cys Asp Asp Gln
                485                 490                 495

Cys Met Glu Ser Ile Arg Asn Asn Thr Tyr Asn His Thr Glu Tyr Arg
            500                 505                 510

Gln Glu Ala Leu Gln Asn Arg Ile Met Ile Asn Pro Val Lys Leu Ser
        515                 520                 525

Ser Gly Tyr Lys Asp Val Ile Leu Trp Phe Ser Phe Gly Ala Ser Cys
    530                 535                 540

Val Met Leu Leu Ala Ile Ala Met Gly Leu Ile Phe Met Cys Val Lys
545                 550                 555                 560

Asn Gly Asn Leu Arg Cys Thr Ile Cys Ile
                565                 570

<210> SEQ ID NO 16
<211> LENGTH: 565
<212> TYPE: PRT
<213> ORGANISM: Influenza virus A
<220> FEATURE:
<223> OTHER INFORMATION: influenza virus A hemagglutinin subtype H16

<400> SEQUENCE: 16

Met Met Ile Lys Val Leu Tyr Phe Leu Ile Ile Val Leu Gly Arg Tyr
1               5                   10                  15

Ser Lys Ala Asp Lys Ile Cys Ile Gly Tyr Leu Ser Asn Asn Ser Ser
            20                  25                  30

Asp Thr Val Asp Thr Leu Thr Glu Asn Gly Val Pro Val Thr Ser Ser
        35                  40                  45

Val Asp Leu Val Glu Thr Asn His Thr Gly Thr Tyr Cys Ser Leu Asn
    50                  55                  60

Gly Ile Ser Pro Ile His Leu Gly Asp Cys Ser Phe Glu Gly Trp Ile
65                  70                  75                  80

Val Gly Asn Pro Ser Cys Ala Thr Asn Ile Asn Ile Arg Glu Trp Ser
                85                  90                  95

Tyr Leu Ile Glu Asp Pro Asn Ala Pro Asn Lys Phe Cys Tyr Pro Gly
            100                 105                 110

Glu Leu Asp Asn Asn Gly Glu Leu Arg His Leu Phe Ser Gly Val Asn
        115                 120                 125

Ser Phe Ser Arg Thr Glu Leu Ile Asn Pro Ser Lys Trp Gly Asn Val
    130                 135                 140

Leu Asp Gly Val Thr Ala Ser Cys Leu Asp Arg Gly Ala Ser Ser Phe
145                 150                 155                 160

Tyr Arg Asn Leu Val Trp Ile Val Lys Lys Asp Glu Lys Tyr Pro Val
                165                 170                 175

Ile Lys Gly Asp Tyr Asn Asn Thr Thr Gly Arg Asp Val Leu Val Leu
            180                 185                 190

Trp Gly Ile His His Pro Asp Thr Glu Thr Thr Ala Thr Asn Leu Tyr
        195                 200                 205

Val Asn Lys Asn Pro Tyr Thr Leu Val Ser Thr Lys Glu Trp Ser Lys
    210                 215                 220

Arg Tyr Glu Leu Glu Ile Gly Thr Arg Ile Gly Asp Gly Gln Arg Ser
225                 230                 235                 240

-continued

```
Trp Met Lys Leu Tyr Trp His Leu Met His Pro Gly Glu Arg Ile Met
                245                 250                 255

Phe Glu Ser Asn Gly Gly Leu Ile Ala Pro Arg Tyr Gly Tyr Ile Ile
            260                 265                 270

Glu Lys Tyr Gly Thr Gly Arg Ile Phe Gln Ser Gly Val Arg Met Ala
        275                 280                 285

Arg Cys Asn Thr Lys Cys Gln Thr Ser Leu Gly Gly Ile Asn Thr Asn
    290                 295                 300

Lys Thr Phe Gln Asn Ile Glu Arg Asn Ala Leu Gly Asp Cys Pro Lys
305                 310                 315                 320

Tyr Ile Lys Ser Gly Gln Leu Lys Leu Ala Thr Gly Leu Arg Asn Val
                325                 330                 335

Pro Ser Ile Gly Glu Arg Gly Leu Phe Gly Ala Ile Ala Gly Phe Ile
            340                 345                 350

Glu Gly Gly Trp Pro Gly Leu Ile Asn Gly Trp Tyr Gly Phe Gln His
        355                 360                 365

Gln Asn Glu Gln Gly Thr Gly Ile Ala Ala Asp Lys Ala Ser Thr Gln
    370                 375                 380

Lys Ala Ile Asn Glu Ile Thr Thr Lys Ile Asn Asn Ile Ile Glu Lys
385                 390                 395                 400

Met Asn Gly Asn Tyr Asp Ser Ile Arg Gly Glu Phe Asn Gln Val Glu
                405                 410                 415

Lys Arg Ile Asn Met Leu Ala Asp Arg Val Asp Asp Ala Val Thr Asp
            420                 425                 430

Ile Trp Ser Tyr Asn Ala Lys Leu Leu Val Leu Leu Glu Asn Asp Arg
        435                 440                 445

Thr Leu Asp Leu His Asp Ala Asn Val Arg Asn Leu His Asp Gln Val
    450                 455                 460

Lys Arg Ala Leu Lys Ser Asn Ala Ile Asp Glu Gly Asp Gly Cys Phe
465                 470                 475                 480

Asn Leu Leu His Lys Cys Asn Asp Ser Cys Met Glu Thr Ile Arg Asn
                485                 490                 495

Gly Thr Tyr Asn His Glu Asp Tyr Arg Glu Glu Ser Gln Leu Lys Arg
            500                 505                 510

Gln Glu Ile Glu Gly Ile Lys Leu Lys Thr Glu Asp Asn Val Tyr Lys
        515                 520                 525

Val Leu Ser Ile Tyr Ser Cys Ile Ala Ser Ser Ile Val Leu Val Gly
    530                 535                 540

Leu Ile Leu Ala Phe Ile Met Trp Ala Cys Ser Asn Gly Ser Cys Arg
545                 550                 555                 560

Phe Asn Val Cys Ile
                565
```

<210> SEQ ID NO 17
<211> LENGTH: 342
<212> TYPE: PRT
<213> ORGANISM: Influenza virus B
<220> FEATURE:
<223> OTHER INFORMATION: influenza B virus hemagglutinin (in Fig. 3)

<400> SEQUENCE: 17

```
Asp Arg Ile Cys Thr Gly Ile Thr Ser Ser Asn Ser Pro His Val Val
 1               5                  10                  15

Lys Thr Ala Thr Gln Gly Glu Val Asn Val Thr Gly Val Ile Pro Leu
            20                  25                  30
```

Thr Thr Thr Pro Thr Lys Ser His Phe Ala Asn Leu Lys Gly Thr Gln
35 40 45

Thr Arg Gly Lys Leu Cys Pro Asn Cys Leu Asn Cys Thr Asp Leu Asp
50 55 60

Val Ala Leu Gly Arg Pro Lys Cys Met Gly Thr Ile Pro Ser Ala Lys
65 70 75 80

Ala Ser Ile Leu His Glu Val Lys Pro Val Thr Ser Gly Cys Phe Pro
85 90 95

Ile Met His Asp Arg Thr Lys Ile Arg Gln Leu Pro Asn Leu Leu Arg
100 105 110

Gly Tyr Glu Asn Ile Arg Leu Ser Ala Arg Asn Val Thr Asn Ala Glu
115 120 125

Thr Ala Pro Gly Gly Pro Tyr Ile Val Gly Thr Ser Gly Ser Cys Pro
130 135 140

Asn Val Thr Asn Gly Asn Gly Phe Phe Ala Thr Met Ala Trp Ala Val
145 150 155 160

Pro Lys Asn Lys Thr Ala Thr Asn Pro Leu Thr Val Glu Val Pro Tyr
165 170 175

Ile Cys Thr Lys Gly Glu Asp Gln Ile Thr Val Trp Gly Phe His Ser
180 185 190

Asp Asp Glu Thr Gln Met Val Lys Leu Tyr Gly Asp Ser Lys Pro Gln
195 200 205

Lys Phe Thr Ser Ser Ala Asn Gly Val Thr Thr His Tyr Val Ser Gln
210 215 220

Ile Gly Gly Phe Pro Asn Gln Ala Glu Asp Glu Gly Leu Pro Gln Ser
225 230 235 240

Gly Arg Ile Val Val Asp Tyr Met Val Gln Lys Pro Gly Lys Thr Gly
245 250 255

Thr Ile Ala Tyr Gln Arg Gly Val Leu Leu Pro Gln Lys Val Trp Cys
260 265 270

Ala Ser Gly Arg Ser Lys Val Ile Lys Gly Ser Leu Pro Leu Ile Gly
275 280 285

Glu Ala Asp Cys Leu His Glu Lys Tyr Gly Gly Leu Asn Lys Ser Lys
290 295 300

Pro Tyr Tyr Thr Gly Glu His Ala Lys Ala Ile Gly Asn Cys Pro Ile
305 310 315 320

Trp Val Lys Thr Pro Leu Lys Leu Ala Asn Gly Thr Lys Tyr Arg Pro
325 330 335

Pro Ala Lys Leu Leu Lys
340

<210> SEQ ID NO 18
<211> LENGTH: 17
<212> TYPE: PRT
<213> ORGANISM: Influenza virus A
<220> FEATURE:
<223> OTHER INFORMATION: influenza A HA subtype H1 signal peptides

<400> SEQUENCE: 18

Met Lys Ala Asn Leu Leu Val Leu Leu Cys Ala Leu Ala Ala Ala Asp
1 5 10 15

Ala

<210> SEQ ID NO 19
<211> LENGTH: 15

<212> TYPE: PRT
<213> ORGANISM: Influenza virus A
<220> FEATURE:
<223> OTHER INFORMATION: influenza A HA subtype H2 signal peptides

<400> SEQUENCE: 19

Met Ala Ile Ile Tyr Leu Ile Leu Leu Phe Thr Ala Val Arg Gly
1 5 10 15

<210> SEQ ID NO 20
<211> LENGTH: 16
<212> TYPE: PRT
<213> ORGANISM: Influenza virus A
<220> FEATURE:
<223> OTHER INFORMATION: influenza A HA subtype H3 signal peptides

<400> SEQUENCE: 20

Met Lys Thr Ile Ile Ala Leu Ser Tyr Ile Phe Cys Leu Ala Leu Gly
1 5 10 15

<210> SEQ ID NO 21
<211> LENGTH: 16
<212> TYPE: PRT
<213> ORGANISM: Influenza virus A
<220> FEATURE:
<223> OTHER INFORMATION: influenza A HA subtype H4 signal peptides

<400> SEQUENCE: 21

Met Leu Ser Ile Val Ile Leu Phe Leu Leu Ile Ala Glu Asn Ser Ser
1 5 10 15

<210> SEQ ID NO 22
<211> LENGTH: 16
<212> TYPE: PRT
<213> ORGANISM: Influenza virus A
<220> FEATURE:
<223> OTHER INFORMATION: influenza A HA subtype H5 signal peptides

<400> SEQUENCE: 22

Met Glu Arg Ile Val Leu Leu Leu Ala Ile Val Ser Leu Val Lys Ser
1 5 10 15

<210> SEQ ID NO 23
<211> LENGTH: 16
<212> TYPE: PRT
<213> ORGANISM: Influenza virus A
<220> FEATURE:
<223> OTHER INFORMATION: influenza A HA subtype H6 signal peptides

<400> SEQUENCE: 23

Met Ile Ala Ile Ile Val Val Ala Ile Leu Ala Thr Ala Gly Arg Ser
1 5 10 15

<210> SEQ ID NO 24
<211> LENGTH: 18
<212> TYPE: PRT
<213> ORGANISM: Influenza virus A
<220> FEATURE:
<223> OTHER INFORMATION: influenza A HA subtype H7 signal peptides

<400> SEQUENCE: 24

Met Asn Thr Gln Ile Leu Val Phe Ala Leu Val Ala Val Ile Pro Thr
1 5 10 15

Asn Ala

<210> SEQ ID NO 25

<211> LENGTH: 16
<212> TYPE: PRT
<213> ORGANISM: Influenza virus A
<220> FEATURE:
<223> OTHER INFORMATION: influenza A HA subtype H8 signal peptides

<400> SEQUENCE: 25

Met Glu Lys Phe Ile Ala Ile Ala Thr Leu Ala Ser Thr Asn Ala Tyr
1 5 10 15

<210> SEQ ID NO 26
<211> LENGTH: 18
<212> TYPE: PRT
<213> ORGANISM: Influenza virus A
<220> FEATURE:
<223> OTHER INFORMATION: influenza A HA subtype H9 signal peptides

<400> SEQUENCE: 26

Met Glu Thr Lys Ala Ile Ile Ala Ala Leu Leu Met Val Thr Ala Ala
1 5 10 15

Asn Ala

<210> SEQ ID NO 27
<211> LENGTH: 16
<212> TYPE: PRT
<213> ORGANISM: Influenza virus A
<220> FEATURE:
<223> OTHER INFORMATION: influenza A HA subtype H10 signal peptides

<400> SEQUENCE: 27

Met Tyr Lys Val Val Val Ile Ile Ala Leu Leu Gly Ala Val Lys Gly
1 5 10 15

<210> SEQ ID NO 28
<211> LENGTH: 16
<212> TYPE: PRT
<213> ORGANISM: Influenza virus A
<220> FEATURE:
<223> OTHER INFORMATION: influenza A HA subtype H11 signal peptides

<400> SEQUENCE: 28

Met Glu Lys Thr Leu Leu Phe Ala Ala Ile Phe Leu Cys Val Lys Ala
1 5 10 15

<210> SEQ ID NO 29
<211> LENGTH: 17
<212> TYPE: PRT
<213> ORGANISM: Influenza virus A
<220> FEATURE:
<223> OTHER INFORMATION: influenza A HA subtype H12 signal peptides

<400> SEQUENCE: 29

Met Glu Lys Phe Ile Ile Leu Ser Thr Val Leu Ala Ala Ser Phe Ala
1 5 10 15

Tyr

<210> SEQ ID NO 30
<211> LENGTH: 18
<212> TYPE: PRT
<213> ORGANISM: Influenza virus A
<220> FEATURE:
<223> OTHER INFORMATION: influenza A HA subtype H13 signal peptides

<400> SEQUENCE: 30

Met Ala Leu Asn Val Ile Ala Thr Leu Thr Leu Ile Ser Val Cys Val
1 5 10 15

His Ala

<210> SEQ ID NO 31
<211> LENGTH: 17
<212> TYPE: PRT
<213> ORGANISM: Influenza virus A
<220> FEATURE:
<223> OTHER INFORMATION: influenza A HA subtype H14 signal peptides

<400> SEQUENCE: 31

Met Ile Ala Leu Ile Leu Val Ala Leu Ala Leu Ser His Thr Ala Tyr
1 5 10 15

Ser

<210> SEQ ID NO 32
<211> LENGTH: 18
<212> TYPE: PRT
<213> ORGANISM: Influenza virus A
<220> FEATURE:
<223> OTHER INFORMATION: influenza A HA subtype H15 signal peptides

<400> SEQUENCE: 32

Met Asn Thr Gln Ile Ile Val Ile Leu Val Leu Gly Leu Ser Met Val
1 5 10 15

Lys Ser

<210> SEQ ID NO 33
<211> LENGTH: 19
<212> TYPE: PRT
<213> ORGANISM: Influenza virus A
<220> FEATURE:
<223> OTHER INFORMATION: influenza A HA subtype H16 signal peptides

<400> SEQUENCE: 33

Met Met Ile Lys Val Leu Tyr Phe Leu Ile Ile Val Leu Gly Arg Tyr
1 5 10 15

Ser Lys Ala

<210> SEQ ID NO 34
<211> LENGTH: 42
<212> TYPE: PRT
<213> ORGANISM: Influenza virus A
<220> FEATURE:
<223> OTHER INFORMATION: influenza A HA subtype H1 N-terminal stem segment

<400> SEQUENCE: 34

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asp Ser His Asn Gly Lys Leu Cys
35 40

<210> SEQ ID NO 35
<211> LENGTH: 42
<212> TYPE: PRT
<213> ORGANISM: Influenza virus A
<220> FEATURE:
<223> OTHER INFORMATION: influenza A HA subtype H2 N-terminal stem segment

<400> SEQUENCE: 35

-continued

```
Asp Gln Ile Cys Ile Gly Tyr His Ser Asn Asn Ser Thr Glu Lys Val
 1               5                  10                  15

Asp Thr Ile Leu Glu Arg Asn Val Thr Val Thr His Ala Gln Asn Ile
            20                  25                  30

Leu Glu Lys Thr His Asn Gly Lys Leu Cys
        35                  40


<210> SEQ ID NO 36
<211> LENGTH: 52
<212> TYPE: PRT
<213> ORGANISM: Influenza virus A
<220> FEATURE:
<223> OTHER INFORMATION: influenza A HA subtype H3 N-terminal stem
      segment

<400> SEQUENCE: 36

Gln Asp Leu Pro Gly Asn Asp Asn Ser Thr Ala Thr Leu Cys Leu Gly
 1               5                  10                  15

His His Ala Val Pro Asn Gly Thr Leu Val Lys Thr Ile Thr Asp Asp
            20                  25                  30

Gln Ile Glu Val Thr Asn Ala Thr Glu Leu Val Gln Ser Ser Ser Thr
        35                  40                  45

Gly Lys Ile Cys
    50


<210> SEQ ID NO 37
<211> LENGTH: 48
<212> TYPE: PRT
<213> ORGANISM: Influenza virus A
<220> FEATURE:
<223> OTHER INFORMATION: influenza A HA subtype H4 N-terminal stem
      segment

<400> SEQUENCE: 37

Gln Asn Tyr Thr Gly Asn Pro Val Ile Cys Met Gly His His Ala Val
 1               5                  10                  15

Ala Asn Gly Thr Met Val Lys Thr Leu Ala Asp Asp Gln Val Glu Val
            20                  25                  30

Val Thr Ala Gln Glu Leu Val Glu Ser Gln Asn Leu Pro Glu Leu Cys
        35                  40                  45


<210> SEQ ID NO 38
<211> LENGTH: 42
<212> TYPE: PRT
<213> ORGANISM: Influenza virus A
<220> FEATURE:
<223> OTHER INFORMATION: influenza A HA subtype H5 N-terminal stem
      segment

<400> SEQUENCE: 38

Asp Gln Ile Cys Ile Gly Tyr His Ala Asn Lys Ser Thr Lys Gln Val
 1               5                  10                  15

Asp Thr Ile Met Glu Lys Asn Val Thr Val Thr His Ala Gln Asp Ile
            20                  25                  30

Leu Glu Arg Thr His Asn Gly Lys Leu Cys
        35                  40


<210> SEQ ID NO 39
<211> LENGTH: 42
<212> TYPE: PRT
<213> ORGANISM: Influenza virus A
<220> FEATURE:
<223> OTHER INFORMATION: influenza A HA subtype H6 N-terminal stem
```

segment

<400> SEQUENCE: 39

```
Asp Lys Ile Cys Ile Gly Tyr His Ala Asn Asn Ser Thr Thr Gln Ile
 1               5                  10                  15

Asp Thr Ile Leu Glu Lys Asn Val Thr Val Thr His Ser Val Glu Leu
            20                  25                  30

Leu Glu Asn Gln Lys Glu Glu Arg Phe Cys
        35                  40
```

<210> SEQ ID NO 40
<211> LENGTH: 42
<212> TYPE: PRT
<213> ORGANISM: Influenza virus A
<220> FEATURE:
<223> OTHER INFORMATION: influenza A HA subtype H7 N-terminal stem segment

<400> SEQUENCE: 40

```
Asp Lys Ile Cys Leu Gly His His Ala Val Ser Asn Gly Thr Lys Val
 1               5                  10                  15

Asn Thr Leu Thr Glu Arg Gly Val Glu Val Val Asn Ala Thr Glu Thr
            20                  25                  30

Val Glu Arg Thr Asn Ile Pro Lys Ile Cys
        35                  40
```

<210> SEQ ID NO 41
<211> LENGTH: 42
<212> TYPE: PRT
<213> ORGANISM: Influenza virus A
<220> FEATURE:
<223> OTHER INFORMATION: influenza A HA subtype H8 N-terminal stem segment

<400> SEQUENCE: 41

```
Asp Arg Ile Cys Ile Gly Tyr Gln Ser Asn Asn Ser Thr Asp Thr Val
 1               5                  10                  15

Asn Thr Leu Ile Glu Gln Asn Val Pro Val Thr Gln Thr Met Glu Leu
            20                  25                  30

Val Glu Thr Glu Lys His Pro Ala Tyr Cys
        35                  40
```

<210> SEQ ID NO 42
<211> LENGTH: 42
<212> TYPE: PRT
<213> ORGANISM: Influenza virus A
<220> FEATURE:
<223> OTHER INFORMATION: influenza A HA subtype H9 N-terminal stem segment

<400> SEQUENCE: 42

```
Asp Lys Ile Cys Ile Gly Tyr Gln Ser Thr Asn Ser Thr Glu Thr Val
 1               5                  10                  15

Asp Thr Leu Thr Glu Ser Asn Val Pro Val Thr His Thr Lys Glu Leu
            20                  25                  30

Leu His Thr Glu His Asn Gly Met Leu Cys
        35                  40
```

<210> SEQ ID NO 43
<211> LENGTH: 43
<212> TYPE: PRT
<213> ORGANISM: Influenza virus A
<220> FEATURE:

<223> OTHER INFORMATION: influenza A HA subtype H10 N-terminal stem
      segment

<400> SEQUENCE: 43

Leu Asp Arg Ile Cys Leu Gly His His Ala Val Ala Asn Gly Thr Ile
 1               5                  10                  15

Val Lys Thr Leu Thr Asn Glu Gln Glu Glu Val Thr Asn Ala Thr Glu
            20                  25                  30

Thr Val Glu Ser Thr Asn Leu Asn Lys Leu Cys
        35                  40

<210> SEQ ID NO 44
<211> LENGTH: 42
<212> TYPE: PRT
<213> ORGANISM: Influenza virus A
<220> FEATURE:
<223> OTHER INFORMATION: influenza A HA subtype H11 N-terminal stem
      segment

<400> SEQUENCE: 44

Asp Glu Ile Cys Ile Gly Tyr Leu Ser Asn Asn Ser Thr Asp Lys Val
 1               5                  10                  15

Asp Thr Ile Ile Glu Asn Asn Val Thr Val Thr Ser Ser Val Glu Leu
            20                  25                  30

Val Glu Thr Glu His Thr Gly Ser Phe Cys
        35                  40

<210> SEQ ID NO 45
<211> LENGTH: 42
<212> TYPE: PRT
<213> ORGANISM: Influenza virus A
<220> FEATURE:
<223> OTHER INFORMATION: influenza A HA subtype H12 N-terminal stem
      segment

<400> SEQUENCE: 45

Asp Lys Ile Cys Ile Gly Tyr Gln Thr Asn Asn Ser Thr Glu Thr Val
 1               5                  10                  15

Asn Thr Leu Ser Glu Gln Asn Val Pro Val Thr Gln Val Glu Glu Leu
            20                  25                  30

Val His Arg Gly Ile Asp Pro Ile Leu Cys
        35                  40

<210> SEQ ID NO 46
<211> LENGTH: 42
<212> TYPE: PRT
<213> ORGANISM: Influenza virus A
<220> FEATURE:
<223> OTHER INFORMATION: influenza A HA subtype H13 N-terminal stem
      segment

<400> SEQUENCE: 46

Asp Arg Ile Cys Val Gly Tyr Leu Ser Thr Asn Ser Ser Glu Arg Val
 1               5                  10                  15

Asp Thr Leu Leu Glu Asn Gly Val Pro Val Thr Ser Ser Ile Asp Leu
            20                  25                  30

Ile Glu Thr Asn His Thr Gly Thr Tyr Cys
        35                  40

<210> SEQ ID NO 47
<211> LENGTH: 51
<212> TYPE: PRT
<213> ORGANISM: Influenza virus A

```
<220> FEATURE:
<223> OTHER INFORMATION: influenza A HA subtype H14 N-terminal stem
      segment

<400> SEQUENCE: 47

Gln Ile Thr Asn Gly Thr Thr Gly Asn Pro Ile Ile Cys Leu Gly His
 1               5                  10                  15

His Ala Val Glu Asn Gly Thr Ser Val Lys Thr Leu Thr Asp Asn His
            20                  25                  30

Val Glu Val Val Ser Ala Lys Glu Leu Val Glu Thr Asn His Thr Asp
        35                  40                  45

Glu Leu Cys
    50


<210> SEQ ID NO 48
<211> LENGTH: 42
<212> TYPE: PRT
<213> ORGANISM: Influenza virus A
<220> FEATURE:
<223> OTHER INFORMATION: influenza A HA subtype H15 N-terminal stem
      segment

<400> SEQUENCE: 48

Asp Lys Ile Cys Leu Gly His His Ala Val Ala Asn Gly Thr Lys Val
 1               5                  10                  15

Asn Thr Leu Thr Glu Arg Gly Val Glu Val Val Asn Ala Thr Glu Thr
            20                  25                  30

Val Glu Ile Thr Gly Ile Asp Lys Val Cys
        35                  40


<210> SEQ ID NO 49
<211> LENGTH: 42
<212> TYPE: PRT
<213> ORGANISM: Influenza virus A
<220> FEATURE:
<223> OTHER INFORMATION: influenza A HA subtype H16 N-terminal stem
      segment

<400> SEQUENCE: 49

Asp Lys Ile Cys Ile Gly Tyr Leu Ser Asn Asn Ser Ser Asp Thr Val
 1               5                  10                  15

Asp Thr Leu Thr Glu Asn Gly Val Pro Val Thr Ser Ser Val Asp Leu
            20                  25                  30

Val Glu Thr Asn His Thr Gly Thr Tyr Cys
        35                  40


<210> SEQ ID NO 50
<211> LENGTH: 53
<212> TYPE: PRT
<213> ORGANISM: Influenza virus A
<220> FEATURE:
<223> OTHER INFORMATION: influenza A HA subtype H1 C-terminal stem
      segment

<400> SEQUENCE: 50

Cys Asn Thr Lys Cys Gln Thr Pro Leu Gly Ala Ile Asn Ser Ser Leu
 1               5                  10                  15

Pro Tyr Gln Asn Ile His Pro Val Thr Ile Gly Glu Cys Pro Lys Tyr
            20                  25                  30

Val Arg Ser Ala Lys Leu Arg Met Val Thr Gly Leu Arg Asn Asn Pro
        35                  40                  45

Ser Ile Gln Ser Arg
```

50

<210> SEQ ID NO 51
<211> LENGTH: 53
<212> TYPE: PRT
<213> ORGANISM: Influenza virus A
<220> FEATURE:
<223> OTHER INFORMATION: influenza A HA subtype H2 C-terminal stem segment

<400> SEQUENCE: 51

Cys Glu Thr Lys Cys Gln Thr Pro Leu Gly Ala Ile Asn Thr Thr Leu
1 5 10 15

Pro Phe His Asn Val His Pro Leu Thr Ile Gly Glu Cys Pro Lys Tyr
20 25 30

Val Lys Ser Glu Arg Leu Val Leu Ala Thr Gly Leu Arg Asn Val Pro
35 40 45

Gln Ile Glu Ser Arg
50

<210> SEQ ID NO 52
<211> LENGTH: 53
<212> TYPE: PRT
<213> ORGANISM: Influenza virus A
<220> FEATURE:
<223> OTHER INFORMATION: influenza A HA subtype H3 C-terminal stem segment

<400> SEQUENCE: 52

Cys Ile Ser Glu Cys Ile Thr Pro Asn Gly Ser Ile Pro Asn Asp Lys
1 5 10 15

Pro Phe Gln Asn Val Asn Lys Ile Thr Tyr Gly Ala Cys Pro Lys Tyr
20 25 30

Val Lys Gln Asn Thr Leu Lys Leu Ala Thr Gly Met Arg Asn Val Pro
35 40 45

Glu Lys Gln Thr Arg
50

<210> SEQ ID NO 53
<211> LENGTH: 53
<212> TYPE: PRT
<213> ORGANISM: Influenza virus A
<220> FEATURE:
<223> OTHER INFORMATION: influenza A HA subtype H4 C-terminal stem segment

<400> SEQUENCE: 53

Cys Val Ser Lys Cys His Thr Asp Lys Gly Ser Leu Ser Thr Thr Lys
1 5 10 15

Pro Phe Gln Asn Ile Ser Arg Ile Ala Val Gly Asp Cys Pro Arg Tyr
20 25 30

Val Lys Gln Gly Ser Leu Lys Leu Ala Thr Gly Met Arg Asn Ile Pro
35 40 45

Glu Lys Ala Ser Arg
50

<210> SEQ ID NO 54
<211> LENGTH: 53
<212> TYPE: PRT
<213> ORGANISM: Influenza virus A
<220> FEATURE:
<223> OTHER INFORMATION: influenza A HA subtype H5 C-terminal stem segment

<400> SEQUENCE: 54

Cys Asp Thr Lys Cys Gln Thr Pro Val Gly Glu Ile Asn Ser Ser Met
1 5 10 15

Pro Phe His Asn Ile His Pro His Thr Ile Gly Glu Cys Pro Lys Tyr
20 25 30

Val Lys Ser Asp Arg Leu Val Leu Ala Thr Gly Leu Arg Asn Val Pro
35 40 45

Gln Arg Lys Lys Arg
50

<210> SEQ ID NO 55
<211> LENGTH: 53
<212> TYPE: PRT
<213> ORGANISM: Influenza virus A
<220> FEATURE:
<223> OTHER INFORMATION: influenza A HA subtype H6 C-terminal stem segment

<400> SEQUENCE: 55

Cys Asp Ala Thr Cys Gln Thr Val Ala Gly Val Leu Arg Thr Asn Lys
1 5 10 15

Thr Phe Gln Asn Val Ser Pro Leu Trp Ile Gly Glu Cys Pro Lys Tyr
20 25 30

Val Lys Ser Glu Ser Leu Arg Leu Ala Thr Gly Leu Arg Asn Val Pro
35 40 45

Gln Ile Glu Thr Arg
50

<210> SEQ ID NO 56
<211> LENGTH: 57
<212> TYPE: PRT
<213> ORGANISM: Influenza virus A
<220> FEATURE:
<223> OTHER INFORMATION: influenza A HA subtype H7 C-terminal stem segment

<400> SEQUENCE: 56

Cys Glu Gly Glu Cys Tyr His Ser Gly Gly Thr Ile Thr Ser Arg Leu
1 5 10 15

Pro Phe Gln Asn Ile Asn Ser Arg Ala Val Gly Lys Cys Pro Arg Tyr
20 25 30

Val Lys Gln Glu Ser Leu Leu Leu Ala Thr Gly Met Lys Asn Val Pro
35 40 45

Glu Pro Ser Lys Lys Arg Lys Lys Arg
50 55

<210> SEQ ID NO 57
<211> LENGTH: 53
<212> TYPE: PRT
<213> ORGANISM: Influenza virus A
<220> FEATURE:
<223> OTHER INFORMATION: influenza A HA subtype H8 C-terminal stem segment

<400> SEQUENCE: 57

Cys Asn Thr Lys Cys Gln Thr Tyr Ala Gly Ala Ile Asn Ser Ser Lys
1 5 10 15

Pro Phe Gln Asn Ala Ser Arg His Tyr Met Gly Glu Cys Pro Lys Tyr
20 25 30

Val Lys Lys Ala Ser Leu Arg Leu Ala Val Gly Leu Arg Asn Thr Pro 35 40 45

Ser Val Glu Pro Arg
50

<210> SEQ ID NO 58
<211> LENGTH: 53
<212> TYPE: PRT
<213> ORGANISM: Influenza virus A
<220> FEATURE:
<223> OTHER INFORMATION: influenza A HA subtype H9 C-terminal stem segment

<400> SEQUENCE: 58

Cys Val Val Gln Cys Gln Thr Glu Lys Gly Gly Leu Asn Thr Thr Leu
1 5 10 15

Pro Phe His Asn Ile Ser Lys Tyr Ala Phe Gly Asn Cys Pro Lys Tyr
20 25 30

Val Gly Val Lys Ser Leu Lys Leu Pro Val Gly Leu Arg Asn Val Pro
35 40 45

Ala Val Ser Ser Arg
50

<210> SEQ ID NO 59
<211> LENGTH: 54
<212> TYPE: PRT
<213> ORGANISM: Influenza virus A
<220> FEATURE:
<223> OTHER INFORMATION: influenza A HA subtype H10 C-terminal stem segment

<400> SEQUENCE: 59

Cys Glu Ser Lys Cys Phe Trp Arg Gly Gly Ser Ile Asn Thr Lys Leu
1 5 10 15

Pro Phe Gln Asn Leu Ser Pro Arg Thr Val Gly Gln Cys Pro Lys Tyr
20 25 30

Val Asn Gln Arg Ser Leu Leu Leu Ala Thr Gly Met Arg Asn Val Pro
35 40 45

Glu Val Val Gln Gly Arg
50

<210> SEQ ID NO 60
<211> LENGTH: 53
<212> TYPE: PRT
<213> ORGANISM: Influenza virus A
<220> FEATURE:
<223> OTHER INFORMATION: influenza A HA subtype H11 C-terminal stem segment

<400> SEQUENCE: 60

Cys Ser Thr Lys Cys Gln Thr Glu Ile Gly Gly Ile Asn Thr Asn Lys
1 5 10 15

Ser Phe His Asn Val His Arg Asn Thr Ile Gly Asp Cys Pro Lys Tyr
20 25 30

Val Asn Val Lys Ser Leu Lys Leu Ala Thr Gly Pro Arg Asn Val Pro
35 40 45

Ala Ile Ala Ser Arg
50

<210> SEQ ID NO 61
<211> LENGTH: 53
<212> TYPE: PRT
<213> ORGANISM: Influenza virus A

```
<220> FEATURE:
<223> OTHER INFORMATION: influenza A HA subtype H12 C-terminal stem
      segment

<400> SEQUENCE: 61

Cys Val Thr Glu Cys Gln Leu Asn Glu Gly Val Met Asn Thr Ser Lys
1               5                   10                  15

Pro Phe Gln Asn Thr Ser Lys His Tyr Ile Gly Lys Cys Pro Lys Tyr
            20                  25                  30

Ile Pro Ser Gly Ser Leu Lys Leu Ala Ile Gly Leu Arg Asn Val Pro
        35                  40                  45

Gln Val Gln Asp Arg
    50


<210> SEQ ID NO 62
<211> LENGTH: 53
<212> TYPE: PRT
<213> ORGANISM: Influenza virus A
<220> FEATURE:
<223> OTHER INFORMATION: influenza A HA subtype H13 C-terminal stem
      segment

<400> SEQUENCE: 62

Cys Asn Thr Lys Cys Gln Thr Ser Val Gly Gly Ile Asn Thr Asn Arg
1               5                   10                  15

Thr Phe Gln Asn Ile Asp Lys Asn Ala Leu Gly Asp Cys Pro Lys Tyr
            20                  25                  30

Ile Lys Ser Gly Gln Leu Lys Leu Ala Thr Gly Leu Arg Asn Val Pro
        35                  40                  45

Ala Ile Ser Asn Arg
    50


<210> SEQ ID NO 63
<211> LENGTH: 53
<212> TYPE: PRT
<213> ORGANISM: Influenza virus A
<220> FEATURE:
<223> OTHER INFORMATION: influenza A HA subtype H14 C-terminal stem
      segment

<400> SEQUENCE: 63

Cys Thr Ser Pro Cys Leu Thr Asp Lys Gly Ser Ile Gln Ser Asp Lys
1               5                   10                  15

Pro Phe Gln Asn Val Ser Arg Ile Ala Ile Gly Asn Cys Pro Lys Tyr
            20                  25                  30

Val Lys Gln Gly Ser Leu Met Leu Ala Thr Gly Met Arg Asn Ile Pro
        35                  40                  45

Gly Lys Gln Ala Lys
    50


<210> SEQ ID NO 64
<211> LENGTH: 54
<212> TYPE: PRT
<213> ORGANISM: Influenza virus A
<220> FEATURE:
<223> OTHER INFORMATION: influenza A HA subtype H15 C-terminal stem
      segment

<400> SEQUENCE: 64

Cys Glu Gly Glu Cys Phe Tyr Ser Gly Gly Thr Ile Asn Ser Pro Leu
1               5                   10                  15

Pro Phe Gln Asn Ile Asp Ser Arg Ala Val Gly Lys Cys Pro Arg Tyr
```

-continued

```
            20                  25                  30

Val Lys Gln Ser Ser Leu Pro Leu Ala Leu Gly Met Lys Asn Val Pro
        35                  40                  45

Glu Lys Ile Arg Thr Arg
    50


<210> SEQ ID NO 65
<211> LENGTH: 53
<212> TYPE: PRT
<213> ORGANISM: Influenza virus A
<220> FEATURE:
<223> OTHER INFORMATION: influenza A HA subtype H16 C-terminal stem
      segment

<400> SEQUENCE: 65

Cys Asn Thr Lys Cys Gln Thr Ser Leu Gly Gly Ile Asn Thr Asn Lys
 1               5                  10                  15

Thr Phe Gln Asn Ile Glu Arg Asn Ala Leu Gly Asp Cys Pro Lys Tyr
            20                  25                  30

Ile Lys Ser Gly Gln Leu Lys Leu Ala Thr Gly Leu Arg Asn Val Pro
        35                  40                  45

Ser Ile Gly Glu Arg
    50


<210> SEQ ID NO 66
<211> LENGTH: 222
<212> TYPE: PRT
<213> ORGANISM: Influenza virus A
<220> FEATURE:
<223> OTHER INFORMATION: influenza A HA subtype H1 HA2 domain

<400> SEQUENCE: 66

Gly Leu Phe Gly Ala Ile Ala Gly Phe Ile Glu Gly Gly Trp Thr Gly
 1               5                  10                  15

Met Ile Asp Gly Trp Tyr Gly Tyr His His Gln Asn Glu Gln Gly Ser
            20                  25                  30

Gly Tyr Ala Ala Asp Gln Lys Ser Thr Gln Asn Ala Ile Asn Gly Ile
        35                  40                  45

Thr Asn Lys Val Asn Thr Val Ile Glu Lys Met Asn Ile Gln Phe Thr
    50                  55                  60

Ala Val Gly Lys Glu Phe Asn Lys Leu Glu Lys Arg Met Glu Asn Leu
65                  70                  75                  80

Asn Lys Lys Val Asp Asp Gly Phe Leu Asp Ile Trp Thr Tyr Asn Ala
                85                  90                  95

Glu Leu Leu Val Leu Leu Glu Asn Glu Arg Thr Leu Asp Phe His Asp
            100                 105                 110

Ser Asn Val Lys Asn Leu Tyr Glu Lys Val Lys Ser Gln Leu Lys Asn
        115                 120                 125

Asn Ala Lys Glu Ile Gly Asn Gly Cys Phe Glu Phe Tyr His Lys Cys
    130                 135                 140

Asp Asn Glu Cys Met Glu Ser Val Arg Asn Gly Thr Tyr Asp Tyr Pro
145                 150                 155                 160

Lys Tyr Ser Glu Glu Ser Lys Leu Asn Arg Glu Lys Val Asp Gly Val
                165                 170                 175

Lys Leu Glu Ser Met Gly Ile Tyr Gln Ile Leu Ala Ile Tyr Ser Thr
            180                 185                 190

Val Ala Ser Ser Leu Val Leu Leu Val Ser Leu Gly Ala Ile Ser Phe
        195                 200                 205
```

Trp Met Cys Ser Asn Gly Ser Leu Gln Cys Arg Ile Cys Ile
    210                 215                 220

<210> SEQ ID NO 67
<211> LENGTH: 222
<212> TYPE: PRT
<213> ORGANISM: Influenza virus A
<220> FEATURE:
<223> OTHER INFORMATION: influenza A HA subtype H2 HA2 domain

<400> SEQUENCE: 67

Gly Leu Phe Gly Ala Ile Ala Gly Phe Ile Glu Gly Gly Trp Gln Gly
1               5                   10                  15

Met Ile Asp Gly Trp Tyr Gly Tyr His His Ser Asn Asp Gln Gly Ser
            20                  25                  30

Gly Tyr Ala Ala Asp Lys Glu Ser Thr Gln Lys Ala Ile Asp Gly Ile
        35                  40                  45

Thr Asn Arg Val Asn Ser Val Ile Glu Lys Met Asn Thr Gln Phe Glu
    50                  55                  60

Ala Val Gly Lys Glu Phe Ser Asn Leu Glu Lys Arg Leu Glu Asn Leu
65                  70                  75                  80

Asn Lys Lys Met Glu Asp Gly Phe Leu Asp Val Trp Thr Tyr Asn Ala
                85                  90                  95

Glu Leu Leu Val Leu Met Glu Asn Glu Arg Thr Leu Asp Phe His Asp
            100                 105                 110

Ser Asn Val Lys Asn Leu Tyr Asp Arg Val Arg Met Gln Leu Arg Asp
        115                 120                 125

Asn Ala Lys Glu Leu Gly Asn Gly Cys Phe Glu Phe Tyr His Lys Cys
    130                 135                 140

Asp Asp Glu Cys Met Asn Ser Val Lys Asn Gly Thr Tyr Asp Tyr Pro
145                 150                 155                 160

Lys Tyr Glu Glu Glu Ser Lys Leu Asn Arg Asn Glu Ile Lys Gly Val
                165                 170                 175

Lys Leu Ser Asn Met Gly Val Tyr Gln Ile Leu Ala Ile Tyr Ala Thr
            180                 185                 190

Val Ala Gly Ser Leu Ser Leu Ala Ile Met Ile Ala Gly Ile Ser Leu
        195                 200                 205

Trp Met Cys Ser Asn Gly Ser Leu Gln Cys Arg Ile Cys Ile
    210                 215                 220

<210> SEQ ID NO 68
<211> LENGTH: 221
<212> TYPE: PRT
<213> ORGANISM: Influenza virus A
<220> FEATURE:
<223> OTHER INFORMATION: influenza A HA subtype H3 HA2 domain

<400> SEQUENCE: 68

Gly Leu Phe Gly Ala Ile Ala Gly Phe Ile Glu Asn Gly Trp Glu Gly
1               5                   10                  15

Met Ile Asp Gly Trp Tyr Gly Phe Arg His Gln Asn Ser Glu Gly Thr
            20                  25                  30

Gly Gln Ala Ala Asp Leu Lys Ser Thr Gln Ala Ala Ile Asp Gln Ile
        35                  40                  45

Asn Gly Lys Leu Asn Arg Val Ile Glu Lys Thr Asn Glu Lys Phe His
    50                  55                  60

Gln Ile Glu Lys Glu Phe Ser Glu Val Glu Gly Arg Ile Gln Asp Leu

-continued

```
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Leu Thr Asp
            100                 105                 110

Ser Glu Met Asn Lys Leu Phe Glu Lys Thr Arg Arg Gln Leu Arg Glu
        115                 120                 125

Asn Ala Glu Asp Met Gly Asn Gly Cys Phe Lys Ile Tyr His Lys Cys
    130                 135                 140

Asp Asn Ala Cys Ile Glu Ser Ile Arg Asn Gly Thr Tyr Asp His Asp
145                 150                 155                 160

Val Tyr Arg Asp Glu Ala Leu Asn Asn Arg Phe Gln Ile Lys Gly Val
                165                 170                 175

Glu Leu Lys Ser Gly Tyr Lys Asp Trp Ile Leu Trp Ile Ser Phe Ala
            180                 185                 190

Ile Ser Cys Phe Leu Leu Cys Val Val Leu Leu Gly Phe Ile Met Trp
        195                 200                 205

Ala Cys Gln Arg Gly Asn Ile Arg Cys Asn Ile Cys Ile
    210                 215                 220


<210> SEQ ID NO 69
<211> LENGTH: 221
<212> TYPE: PRT
<213> ORGANISM: Influenza virus A
<220> FEATURE:
<223> OTHER INFORMATION: influenza A HA subtype H4 HA2 domain

<400> SEQUENCE: 69

Gly Leu Phe Gly Ala Ile Ala Gly Phe Ile Glu Asn Gly Trp Gln Gly
 1               5                  10                  15

Leu Ile Asp Gly Trp Tyr Gly Phe Arg His Gln Asn Ala Glu Gly Thr
            20                  25                  30

Gly Thr Ala Ala Asp Leu Lys Ser Thr Gln Ala Ala Ile Asp Gln Ile
        35                  40                  45

Asn Gly Lys Leu Asn Arg Leu Ile Glu Lys Thr Asn Asp Lys Tyr His
    50                  55                  60

Gln Ile Glu Lys Glu Phe Glu Gln Val Glu Gly Arg Ile Gln Asp Leu
65                  70                  75                  80

Glu Asn Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Val Thr Asp
            100                 105                 110

Ser Glu Met Asn Lys Leu Phe Glu Arg Val Arg Arg Gln Leu Arg Glu
        115                 120                 125

Asn Ala Glu Asp Lys Gly Asn Gly Cys Phe Glu Ile Phe His Lys Cys
    130                 135                 140

Asp Asn Asn Cys Ile Glu Ser Ile Arg Asn Gly Thr Tyr Asp His Asp
145                 150                 155                 160

Ile Tyr Arg Asp Glu Ala Ile Asn Asn Arg Phe Gln Ile Gln Gly Val
                165                 170                 175

Lys Leu Thr Gln Gly Tyr Lys Asp Ile Ile Leu Trp Ile Ser Phe Ser
            180                 185                 190

Ile Ser Cys Phe Leu Leu Val Ala Leu Leu Leu Ala Phe Ile Leu Trp
        195                 200                 205

Ala Cys Gln Asn Gly Asn Ile Arg Cys Gln Ile Cys Ile
```

```
    210                 215                 220


<210> SEQ ID NO 70
<211> LENGTH: 222
<212> TYPE: PRT
<213> ORGANISM: Influenza virus A
<220> FEATURE:
<223> OTHER INFORMATION: influenza A HA subtype H5 HA2 domain

<400> SEQUENCE: 70

Gly Leu Phe Gly Ala Ile Ala Gly Phe Ile Glu Gly Gly Trp Gln Gly
 1               5                  10                  15

Met Val Asp Gly Trp Tyr Gly Tyr His His Ser Asn Glu Gln Gly Ser
            20                  25                  30

Gly Tyr Ala Ala Asp Lys Glu Ser Thr Gln Lys Ala Ile Asp Gly Ile
        35                  40                  45

Thr Asn Lys Val Asn Ser Ile Ile Asp Lys Met Asn Thr Arg Phe Glu
    50                  55                  60

Ala Val Gly Lys Glu Phe Asn Asn Leu Glu Arg Arg Val Glu Asn Leu
65                  70                  75                  80

Asn Lys Lys Met Glu Asp Gly Phe Leu Asp Val Trp Thr Tyr Asn Val
                85                  90                  95

Glu Leu Leu Val Leu Met Glu Asn Glu Arg Thr Leu Asp Phe His Asp
            100                 105                 110

Ser Asn Val Asn Asn Leu Tyr Asp Lys Val Arg Leu Gln Leu Lys Asp
        115                 120                 125

Asn Ala Arg Glu Leu Gly Asn Gly Cys Phe Glu Phe Tyr His Lys Cys
    130                 135                 140

Asp Asn Glu Cys Met Glu Ser Val Arg Asn Gly Thr Tyr Asp Tyr Pro
145                 150                 155                 160

Gln Tyr Ser Glu Glu Ala Arg Leu Asn Arg Glu Glu Ile Ser Gly Val
                165                 170                 175

Lys Leu Glu Ser Met Gly Val Tyr Gln Ile Leu Ser Ile Tyr Ser Thr
            180                 185                 190

Val Ala Ser Ser Leu Ala Leu Ala Ile Met Ile Ala Gly Leu Ser Phe
        195                 200                 205

Trp Met Cys Ser Asn Gly Ser Leu Gln Cys Arg Ile Cys Ile
    210                 215                 220


<210> SEQ ID NO 71
<211> LENGTH: 222
<212> TYPE: PRT
<213> ORGANISM: Influenza virus A
<220> FEATURE:
<223> OTHER INFORMATION: influenza A HA subtype H6 HA2 domain

<400> SEQUENCE: 71

Gly Leu Phe Gly Ala Ile Ala Gly Phe Ile Glu Gly Gly Trp Thr Gly
 1               5                  10                  15

Met Ile Asp Gly Trp Tyr Gly Tyr His His Glu Asn Ser Gln Gly Ser
            20                  25                  30

Gly Tyr Ala Ala Asp Arg Glu Ser Thr Gln Lys Ala Val Asp Gly Ile
        35                  40                  45

Thr Asn Lys Val Asn Ser Ile Ile Asp Lys Met Asn Thr Gln Phe Glu
    50                  55                  60

Ala Val Asp His Glu Phe Ser Asn Leu Glu Arg Arg Ile Asp Asn Leu
65                  70                  75                  80
```

```
Asn Lys Arg Met Glu Asp Gly Phe Leu Asp Val Trp Thr Tyr Asn Ala
                85                  90                  95

Glu Leu Leu Val Leu Leu Glu Asn Glu Arg Thr Leu Asp Leu His Asp
            100                 105                 110

Ala Asn Val Lys Asn Leu Tyr Glu Arg Val Lys Ser Gln Leu Arg Asp
        115                 120                 125

Asn Ala Met Ile Leu Gly Asn Gly Cys Phe Glu Phe Trp His Lys Cys
    130                 135                 140

Asp Asp Glu Cys Met Glu Ser Val Lys Asn Gly Thr Tyr Asp Tyr Pro
145                 150                 155                 160

Lys Tyr Gln Asp Glu Ser Lys Leu Asn Arg Gln Glu Ile Glu Ser Val
                165                 170                 175

Lys Leu Glu Ser Leu Gly Val Tyr Gln Ile Leu Ala Ile Tyr Ser Thr
            180                 185                 190

Val Ser Ser Ser Leu Val Leu Val Gly Leu Ile Ile Ala Val Gly Leu
        195                 200                 205

Trp Met Cys Ser Asn Gly Ser Met Gln Cys Arg Ile Cys Ile
    210                 215                 220


<210> SEQ ID NO 72
<211> LENGTH: 221
<212> TYPE: PRT
<213> ORGANISM: Influenza virus A
<220> FEATURE:
<223> OTHER INFORMATION: influenza A HA subtype H7 HA2 domain

<400> SEQUENCE: 72

Gly Leu Phe Gly Ala Ile Ala Gly Phe Ile Glu Asn Gly Trp Glu Gly
 1               5                  10                  15

Leu Val Asp Gly Trp Tyr Gly Phe Arg His Gln Asn Ala Gln Gly Glu
            20                  25                  30

Gly Thr Ala Ala Asp Tyr Lys Ser Thr Gln Ser Ala Ile Asp Gln Ile
        35                  40                  45

Thr Gly Lys Leu Asn Arg Leu Ile Glu Lys Thr Asn Gln Gln Phe Glu
    50                  55                  60

Leu Ile Asp Asn Glu Phe Thr Glu Val Glu Lys Gln Ile Gly Asn Leu
65                  70                  75                  80

Ile Asn Trp Thr Lys Asp Ser Ile Thr Glu Val Trp Ser Tyr Asn Ala
                85                  90                  95

Glu Leu Ile Val Ala Met Glu Asn Gln His Thr Ile Asp Leu Ala Asp
            100                 105                 110

Ser Glu Met Asn Arg Leu Tyr Glu Arg Val Arg Lys Gln Leu Arg Glu
        115                 120                 125

Asn Ala Glu Glu Asp Gly Thr Gly Cys Phe Glu Ile Phe His Lys Cys
    130                 135                 140

Asp Asp Asp Cys Met Ala Ser Ile Arg Asn Asn Thr Tyr Asp His Ser
145                 150                 155                 160

Lys Tyr Arg Glu Glu Ala Met Gln Asn Arg Ile Gln Ile Asp Pro Val
                165                 170                 175

Lys Leu Ser Ser Gly Tyr Lys Asp Val Ile Leu Trp Phe Ser Phe Gly
            180                 185                 190

Ala Ser Cys Phe Leu Leu Leu Ala Ile Ala Met Gly Leu Val Phe Ile
        195                 200                 205

Cys Val Lys Asn Gly Asn Met Arg Cys Thr Ile Cys Ile
    210                 215                 220
```

<210> SEQ ID NO 73
<211> LENGTH: 222
<212> TYPE: PRT
<213> ORGANISM: Influenza virus A
<220> FEATURE:
<223> OTHER INFORMATION: influenza A HA subtype H8 HA2 domain

<400> SEQUENCE: 73

```
Gly Leu Phe Gly Ala Ile Ala Gly Phe Ile Glu Gly Gly Trp Ser Gly
 1               5                  10                  15

Met Ile Asp Gly Trp Tyr Gly Phe His His Ser Asn Ser Glu Gly Thr
            20                  25                  30

Gly Met Ala Ala Asp Gln Lys Ser Thr Gln Glu Ala Ile Asp Lys Ile
        35                  40                  45

Thr Asn Lys Val Asn Asn Ile Val Asp Lys Met Asn Arg Glu Phe Glu
    50                  55                  60

Val Val Asn His Glu Phe Ser Glu Val Glu Lys Arg Ile Asn Met Ile
65                  70                  75                  80

Asn Asp Lys Ile Asp Asp Gln Ile Glu Asp Leu Trp Ala Tyr Asn Ala
                85                  90                  95

Glu Leu Leu Val Leu Leu Glu Asn Gln Lys Thr Leu Asp Glu His Asp
            100                 105                 110

Ser Asn Val Lys Asn Leu Phe Asp Glu Val Lys Arg Arg Leu Ser Ala
        115                 120                 125

Asn Ala Ile Asp Ala Gly Asn Gly Cys Phe Asp Ile Leu His Lys Cys
    130                 135                 140

Asp Asn Glu Cys Met Glu Thr Ile Lys Asn Gly Thr Tyr Asp His Lys
145                 150                 155                 160

Glu Tyr Glu Glu Glu Ala Lys Leu Glu Arg Ser Lys Ile Asn Gly Val
                165                 170                 175

Lys Leu Glu Glu Asn Thr Thr Tyr Lys Ile Leu Ser Ile Tyr Ser Thr
            180                 185                 190

Val Ala Ala Ser Leu Cys Leu Ala Ile Leu Ile Ala Gly Gly Leu Ile
        195                 200                 205

Leu Gly Met Gln Asn Gly Ser Cys Arg Cys Met Phe Cys Ile
    210                 215                 220
```

<210> SEQ ID NO 74
<211> LENGTH: 222
<212> TYPE: PRT
<213> ORGANISM: Influenza virus A
<220> FEATURE:
<223> OTHER INFORMATION: influenza A HA subtype H9 HA2 domain

<400> SEQUENCE: 74

```
Gly Leu Phe Gly Ala Ile Ala Gly Phe Ile Glu Gly Gly Trp Pro Gly
 1               5                  10                  15

Leu Val Ala Gly Trp Tyr Gly Phe Gln His Ser Asn Asp Gln Gly Val
            20                  25                  30

Gly Met Ala Ala Asp Lys Gly Ser Thr Gln Lys Ala Ile Asp Lys Ile
        35                  40                  45

Thr Ser Lys Val Asn Asn Ile Ile Asp Lys Met Asn Lys Gln Tyr Glu
    50                  55                  60

Val Ile Asp His Glu Phe Asn Glu Leu Glu Ala Arg Leu Asn Met Ile
65                  70                  75                  80

Asn Asn Lys Ile Asp Asp Gln Ile Gln Asp Ile Trp Ala Tyr Asn Ala
                85                  90                  95
```

```
Glu Leu Leu Val Leu Leu Glu Asn Gln Lys Thr Leu Asp Glu His Asp
            100                 105                 110

Ala Asn Val Asn Asn Leu Tyr Asn Lys Val Lys Arg Ala Leu Gly Ser
        115                 120                 125

Asn Ala Val Glu Asp Gly Asn Gly Cys Phe Glu Leu Tyr His Lys Cys
    130                 135                 140

Asp Asp Gln Cys Met Glu Thr Ile Arg Asn Gly Thr Tyr Asp Arg Gln
145                 150                 155                 160

Lys Tyr Gln Glu Glu Ser Arg Leu Glu Arg Gln Lys Ile Glu Gly Val
                165                 170                 175

Lys Leu Glu Ser Glu Gly Thr Tyr Lys Ile Leu Thr Ile Tyr Ser Thr
            180                 185                 190

Val Ala Ser Ser Leu Val Leu Ala Met Gly Phe Ala Ala Phe Leu Phe
        195                 200                 205

Trp Ala Met Ser Asn Gly Ser Cys Arg Cys Asn Ile Cys Ile
    210                 215                 220


<210> SEQ ID NO 75
<211> LENGTH: 221
<212> TYPE: PRT
<213> ORGANISM: Influenza virus A
<220> FEATURE:
<223> OTHER INFORMATION: influenza A HA subtype H10 HA2 domain

<400> SEQUENCE: 75

Gly Leu Phe Gly Ala Ile Ala Gly Phe Ile Glu Asn Gly Trp Glu Gly
1               5                   10                  15

Met Val Asp Gly Trp Tyr Gly Phe Arg His Gln Asn Ala Gln Gly Thr
            20                  25                  30

Gly Gln Ala Ala Asp Tyr Lys Ser Thr Gln Ala Ala Ile Asp Gln Ile
        35                  40                  45

Thr Gly Lys Leu Asn Arg Leu Ile Glu Lys Thr Asn Thr Glu Phe Glu
    50                  55                  60

Ser Ile Glu Ser Glu Phe Ser Glu Thr Glu His Gln Ile Gly Asn Val
65                  70                  75                  80

Ile Asn Trp Thr Lys Asp Ser Ile Thr Asp Ile Trp Thr Tyr Asn Ala
                85                  90                  95

Glu Leu Leu Val Ala Met Glu Asn Gln His Thr Ile Asp Met Ala Asp
            100                 105                 110

Ser Glu Met Leu Asn Leu Tyr Glu Arg Val Arg Lys Gln Leu Arg Gln
        115                 120                 125

Asn Ala Glu Glu Asp Gly Lys Gly Cys Phe Glu Ile Tyr His Thr Cys
    130                 135                 140

Asp Asp Ser Cys Met Glu Ser Ile Arg Asn Asn Thr Tyr Asp His Ser
145                 150                 155                 160

Gln Tyr Arg Glu Glu Ala Leu Leu Asn Arg Leu Asn Ile Asn Pro Val
                165                 170                 175

Lys Leu Ser Ser Gly Tyr Lys Asp Ile Ile Leu Trp Phe Ser Phe Gly
            180                 185                 190

Glu Ser Cys Phe Val Leu Leu Ala Val Val Met Gly Leu Val Phe Phe
        195                 200                 205

Cys Leu Lys Asn Gly Asn Met Arg Cys Thr Ile Cys Ile
    210                 215                 220


<210> SEQ ID NO 76
```

```
<211> LENGTH: 223
<212> TYPE: PRT
<213> ORGANISM: Influenza virus A
<220> FEATURE:
<223> OTHER INFORMATION: influenza A HA subtype H11 HA2 domain

<400> SEQUENCE: 76

Gly Leu Phe Gly Ala Ile Ala Gly Phe Ile Glu Gly Gly Trp Pro Gly
 1               5                  10                  15

Leu Ile Asn Gly Trp Tyr Gly Phe Gln His Arg Asp Glu Glu Gly Thr
            20                  25                  30

Gly Ile Ala Ala Asp Lys Glu Ser Thr Gln Lys Ala Ile Asp Gln Ile
        35                  40                  45

Thr Ser Lys Val Asn Asn Ile Val Asp Arg Met Asn Thr Asn Phe Glu
    50                  55                  60

Ser Val Gln His Glu Phe Ser Glu Ile Glu Glu Arg Ile Asn Gln Leu
65                  70                  75                  80

Ser Lys His Val Asp Asp Ser Val Val Asp Ile Trp Ser Tyr Asn Ala
                85                  90                  95

Gln Leu Leu Val Leu Leu Glu Asn Glu Lys Thr Leu Asp Leu His Asp
            100                 105                 110

Ser Asn Val Arg Asn Leu His Glu Lys Val Arg Arg Met Leu Lys Asp
        115                 120                 125

Asn Ala Lys Asp Glu Gly Asn Gly Cys Phe Thr Phe Tyr His Lys Cys
    130                 135                 140

Asp Asn Lys Cys Ile Glu Arg Val Arg Asn Gly Thr Tyr Asp His Lys
145                 150                 155                 160

Glu Phe Glu Glu Glu Ser Lys Ile Asn Arg Gln Glu Ile Glu Gly Val
                165                 170                 175

Lys Leu Asp Ser Ser Gly Asn Val Tyr Lys Ile Leu Ser Ile Tyr Ser
            180                 185                 190

Cys Ile Ala Ser Ser Leu Val Leu Ala Ala Leu Ile Met Gly Phe Met
        195                 200                 205

Phe Trp Ala Cys Ser Asn Gly Ser Cys Arg Cys Thr Ile Cys Ile
    210                 215                 220


<210> SEQ ID NO 77
<211> LENGTH: 222
<212> TYPE: PRT
<213> ORGANISM: Influenza virus A
<220> FEATURE:
<223> OTHER INFORMATION: influenza A HA subtype H12 HA2 domain

<400> SEQUENCE: 77

Gly Leu Phe Gly Ala Ile Ala Gly Phe Ile Glu Gly Gly Trp Pro Gly
 1               5                  10                  15

Leu Val Ala Gly Trp Tyr Gly Phe Gln His Gln Asn Ala Glu Gly Thr
            20                  25                  30

Gly Ile Ala Ala Asp Arg Asp Ser Thr Gln Arg Ala Ile Asp Asn Met
        35                  40                  45

Gln Asn Lys Leu Asn Asn Val Ile Asp Lys Met Asn Lys Gln Phe Glu
    50                  55                  60

Val Val Asn His Glu Phe Ser Glu Val Glu Ser Arg Ile Asn Met Ile
65                  70                  75                  80

Asn Ser Lys Ile Asp Asp Gln Ile Thr Asp Ile Trp Ala Tyr Asn Ala
                85                  90                  95

Glu Leu Leu Val Leu Leu Glu Asn Gln Lys Thr Leu Asp Glu His Asp
```

```
            100                 105                 110

Ala Asn Val Arg Asn Leu His Asp Arg Val Arg Arg Val Leu Arg Glu
        115                 120                 125

Asn Ala Ile Asp Thr Gly Asp Gly Cys Phe Glu Ile Leu His Lys Cys
    130                 135                 140

Asp Asn Asn Cys Met Asp Thr Ile Arg Asn Gly Thr Tyr Asn His Lys
145                 150                 155                 160

Glu Tyr Glu Glu Glu Ser Lys Ile Glu Arg Gln Lys Val Asn Gly Val
                165                 170                 175

Lys Leu Glu Glu Asn Ser Thr Tyr Lys Ile Leu Ser Ile Tyr Ser Ser
            180                 185                 190

Val Ala Ser Ser Leu Val Leu Leu Leu Met Ile Ile Gly Gly Phe Ile
        195                 200                 205

Phe Gly Cys Gln Asn Gly Asn Val Arg Cys Thr Phe Cys Ile
    210                 215                 220


<210> SEQ ID NO 78
<211> LENGTH: 223
<212> TYPE: PRT
<213> ORGANISM: Influenza virus A
<220> FEATURE:
<223> OTHER INFORMATION: influenza A HA subtype H13 HA2 domain

<400> SEQUENCE: 78

Gly Leu Phe Gly Ala Ile Ala Gly Phe Ile Glu Gly Gly Trp Pro Gly
 1               5                  10                  15

Leu Ile Asn Gly Trp Tyr Gly Phe Gln His Gln Asn Glu Gln Gly Thr
            20                  25                  30

Gly Ile Ala Ala Asp Lys Glu Ser Thr Gln Lys Ala Ile Asp Gln Ile
        35                  40                  45

Thr Thr Lys Ile Asn Asn Ile Ile Asp Lys Met Asn Gly Asn Tyr Asp
    50                  55                  60

Ser Ile Arg Gly Glu Phe Asn Gln Val Glu Lys Arg Ile Asn Met Leu
65                  70                  75                  80

Ala Asp Arg Ile Asp Asp Ala Val Thr Asp Ile Trp Ser Tyr Asn Ala
                85                  90                  95

Lys Leu Leu Val Leu Leu Glu Asn Asp Lys Thr Leu Asp Met His Asp
            100                 105                 110

Ala Asn Val Lys Asn Leu His Glu Gln Val Arg Arg Glu Leu Lys Asp
        115                 120                 125

Asn Ala Ile Asp Glu Gly Asn Gly Cys Phe Glu Leu Leu His Lys Cys
    130                 135                 140

Asn Asp Ser Cys Met Glu Thr Ile Arg Asn Gly Thr Tyr Asp His Thr
145                 150                 155                 160

Glu Tyr Ala Glu Glu Ser Lys Leu Lys Arg Gln Glu Ile Asp Gly Ile
                165                 170                 175

Lys Leu Lys Ser Glu Asp Asn Val Tyr Lys Ala Leu Ser Ile Tyr Ser
            180                 185                 190

Cys Ile Ala Ser Ser Val Val Leu Val Gly Leu Ile Leu Ser Phe Ile
        195                 200                 205

Met Trp Ala Cys Ser Ser Gly Asn Cys Arg Phe Asn Val Cys Ile
    210                 215                 220


<210> SEQ ID NO 79
<211> LENGTH: 221
<212> TYPE: PRT
```

```
<213> ORGANISM: Influenza virus A
<220> FEATURE:
<223> OTHER INFORMATION: influenza A HA subtype H14 HA2 domain

<400> SEQUENCE: 79

Gly Leu Phe Gly Ala Ile Ala Gly Phe Ile Glu Asn Gly Trp Gln Gly
 1               5                  10                  15

Leu Ile Asp Gly Trp Tyr Gly Phe Arg His Gln Asn Ala Glu Gly Thr
            20                  25                  30

Gly Thr Ala Ala Asp Leu Lys Ser Thr Gln Ala Ala Ile Asp Gln Ile
        35                  40                  45

Asn Gly Lys Leu Asn Arg Leu Ile Glu Lys Thr Asn Glu Lys Tyr His
    50                  55                  60

Gln Ile Glu Lys Glu Phe Glu Gln Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Val Thr Asp
            100                 105                 110

Ser Glu Met Asn Lys Leu Phe Glu Arg Val Arg Arg Gln Leu Arg Glu
        115                 120                 125

Asn Ala Glu Asp Gln Gly Asn Gly Cys Phe Glu Ile Phe His Gln Cys
    130                 135                 140

Asp Asn Asn Cys Ile Glu Ser Ile Arg Asn Gly Thr Tyr Asp His Asn
145                 150                 155                 160

Ile Tyr Arg Asp Glu Ala Ile Asn Asn Arg Ile Lys Ile Asn Pro Val
                165                 170                 175

Thr Leu Thr Met Gly Tyr Lys Asp Ile Ile Leu Trp Ile Ser Phe Ser
            180                 185                 190

Met Ser Cys Phe Val Phe Val Ala Leu Ile Leu Gly Phe Val Leu Trp
        195                 200                 205

Ala Cys Gln Asn Gly Asn Ile Arg Cys Gln Ile Cys Ile
    210                 215                 220


<210> SEQ ID NO 80
<211> LENGTH: 221
<212> TYPE: PRT
<213> ORGANISM: Influenza virus A
<220> FEATURE:
<223> OTHER INFORMATION: influenza A HA subtype H15 HA2 domain

<400> SEQUENCE: 80

Gly Leu Phe Gly Ala Ile Ala Gly Phe Ile Glu Asn Gly Trp Glu Gly
 1               5                  10                  15

Leu Ile Asp Gly Trp Tyr Gly Phe Arg His Gln Asn Ala Gln Gly Gln
            20                  25                  30

Gly Thr Ala Ala Asp Tyr Lys Ser Thr Gln Ala Ala Ile Asp Gln Ile
        35                  40                  45

Thr Gly Lys Leu Asn Arg Leu Ile Glu Lys Thr Asn Lys Gln Phe Glu
    50                  55                  60

Leu Ile Asp Asn Glu Phe Thr Glu Val Glu Gln Gln Ile Gly Asn Val
65                  70                  75                  80

Ile Asn Trp Thr Arg Asp Ser Leu Thr Glu Ile Trp Ser Tyr Asn Ala
                85                  90                  95

Glu Leu Leu Val Ala Met Glu Asn Gln His Thr Ile Asp Leu Ala Asp
            100                 105                 110
```

```
Ser Glu Met Asn Lys Leu Tyr Glu Arg Val Arg Arg Gln Leu Arg Glu
        115                 120                 125

Asn Ala Glu Glu Asp Gly Thr Gly Cys Phe Glu Ile Phe His Arg Cys
    130                 135                 140

Asp Asp Gln Cys Met Glu Ser Ile Arg Asn Asn Thr Tyr Asn His Thr
145                 150                 155                 160

Glu Tyr Arg Gln Glu Ala Leu Gln Asn Arg Ile Met Ile Asn Pro Val
                165                 170                 175

Lys Leu Ser Ser Gly Tyr Lys Asp Val Ile Leu Trp Phe Ser Phe Gly
            180                 185                 190

Ala Ser Cys Val Met Leu Leu Ala Ile Ala Met Gly Leu Ile Phe Met
        195                 200                 205

Cys Val Lys Asn Gly Asn Leu Arg Cys Thr Ile Cys Ile
    210                 215                 220


<210> SEQ ID NO 81
<211> LENGTH: 223
<212> TYPE: PRT
<213> ORGANISM: Influenza virus A
<220> FEATURE:
<223> OTHER INFORMATION: influenza A HA subtype H16 HA2 domain

<400> SEQUENCE: 81

Gly Leu Phe Gly Ala Ile Ala Gly Phe Ile Glu Gly Gly Trp Pro Gly
 1               5                  10                  15

Leu Ile Asn Gly Trp Tyr Gly Phe Gln His Gln Asn Glu Gln Gly Thr
            20                  25                  30

Gly Ile Ala Ala Asp Lys Ala Ser Thr Gln Lys Ala Ile Asn Glu Ile
        35                  40                  45

Thr Thr Lys Ile Asn Asn Ile Ile Glu Lys Met Asn Gly Asn Tyr Asp
    50                  55                  60

Ser Ile Arg Gly Glu Phe Asn Gln Val Glu Lys Arg Ile Asn Met Leu
65                  70                  75                  80

Ala Asp Arg Val Asp Asp Ala Val Thr Asp Ile Trp Ser Tyr Asn Ala
                85                  90                  95

Lys Leu Leu Val Leu Leu Glu Asn Asp Arg Thr Leu Asp Leu His Asp
            100                 105                 110

Ala Asn Val Arg Asn Leu His Asp Gln Val Lys Arg Ala Leu Lys Ser
        115                 120                 125

Asn Ala Ile Asp Glu Gly Asp Gly Cys Phe Asn Leu Leu His Lys Cys
    130                 135                 140

Asn Asp Ser Cys Met Glu Thr Ile Arg Asn Gly Thr Tyr Asn His Glu
145                 150                 155                 160

Asp Tyr Arg Glu Glu Ser Gln Leu Lys Arg Gln Glu Ile Glu Gly Ile
                165                 170                 175

Lys Leu Lys Thr Glu Asp Asn Val Tyr Lys Val Leu Ser Ile Tyr Ser
            180                 185                 190

Cys Ile Ala Ser Ser Ile Val Leu Val Gly Leu Ile Leu Ala Phe Ile
        195                 200                 205

Met Trp Ala Cys Ser Asn Gly Ser Cys Arg Phe Asn Val Cys Ile
    210                 215                 220


<210> SEQ ID NO 82
<211> LENGTH: 180
<212> TYPE: PRT
<213> ORGANISM: Influenza virus A
<220> FEATURE:
```

<223> OTHER INFORMATION: influenza A HA2 domain subtype H1 stem domain

<400> SEQUENCE: 82

Gly Leu Phe Gly Ala Ile Ala Gly Phe Ile Glu Gly Gly Trp Thr Gly
1 5 10 15

Met Ile Asp Gly Trp Tyr Gly Tyr His His Gln Asn Glu Gln Gly Ser
20 25 30

Gly Tyr Ala Ala Asp Gln Lys Ser Thr Gln Asn Ala Ile Asn Gly Ile
35 40 45

Thr Asn Lys Val Asn Thr Val Ile Glu Lys Met Asn Ile Gln Phe Thr
50 55 60

Ala Val Gly Lys Glu Phe Asn Lys Leu Glu Lys Arg Met Glu Asn Leu
65 70 75 80

Asn Lys Lys Val Asp Asp Gly Phe Leu Asp Ile Trp Thr Tyr Asn Ala
85 90 95

Glu Leu Leu Val Leu Leu Glu Asn Glu Arg Thr Leu Asp Phe His Asp
100 105 110

Ser Asn Val Lys Asn Leu Tyr Glu Lys Val Lys Ser Gln Leu Lys Asn
115 120 125

Asn Ala Lys Glu Ile Gly Asn Gly Cys Phe Glu Phe Tyr His Lys Cys
130 135 140

Asp Asn Glu Cys Met Glu Ser Val Arg Asn Gly Thr Tyr Asp Tyr Pro
145 150 155 160

Lys Tyr Ser Glu Glu Ser Lys Leu Asn Arg Glu Lys Val Asp Gly Val
165 170 175

Lys Leu Glu Ser
180

<2 10> SEQ ID NO 83
<211> LENGTH: 180
<212> TYPE: PRT
<21 3> ORGANISM: Influenza virus A
<220> FEATURE:
<223> OTHER INFORMATION: influenza A HA2 domain subtype H2 stem domain

<400> SEQUENCE: 83

Gly Leu Phe Gly Ala Ile Ala Gly Phe Ile Glu Gly Gly Trp Gln Gly
1 5 10 15

Met Ile Asp Gly Trp Tyr Gly Tyr His His Ser Asn Asp Gln Gly Ser
20 25 30

Gly Tyr Ala Ala Asp Lys Glu Ser Thr Gln Lys Ala Ile Asp Gly Ile
35 40 45

Thr Asn Arg Val Asn Ser Val Ile Glu Lys Met Asn Thr Gln Phe Glu
50 55 60

Ala Val Gly Lys Glu Phe Ser Asn Leu Glu Lys Arg Leu Glu Asn Leu
65 70 75 80

Asn Lys Lys Met Glu Asp Gly Phe Leu Asp Val Trp Thr Tyr Asn Ala
85 90 95

Glu Leu Leu Val Leu Met Glu Asn Glu Arg Thr Leu Asp Phe His Asp
100 105 110

Ser Asn Val Lys Asn Leu Tyr Asp Arg Val Arg Met Gln Leu Arg Asp
115 120 125

Asn Ala Lys Glu Leu Gly Asn Gly Cys Phe Glu Phe Tyr His Lys Cys
130 135 140

Asp Asp Glu Cys Met Asn Ser Val Lys Asn Gly Thr Tyr Asp Tyr Pro
145 150 155 160

```
Lys Tyr Glu Glu Glu Ser Lys Leu Asn Arg Asn Glu Ile Lys Gly Val
                165                 170                 175

Lys Leu Ser Asn
            180


<210> SEQ ID NO 84
<211> LENGTH: 179
<212> TYPE: PRT
<213> ORGANISM: Influenza virus A
<220> FEATURE:
<223> OTHER INFORMATION: influenza A HA2 domain subtype H3 stem domain

<400> SEQUENCE: 84

Gly Leu Phe Gly Ala Ile Ala Gly Phe Ile Glu Asn Gly Trp Glu Gly
1               5                   10                  15

Met Ile Asp Gly Trp Tyr Gly Phe Arg His Gln Asn Ser Glu Gly Thr
            20                  25                  30

Gly Gln Ala Ala Asp Leu Lys Ser Thr Gln Ala Ala Ile Asp Gln Ile
        35                  40                  45

Asn Gly Lys Leu Asn Arg Val Ile Glu Lys Thr Asn Glu Lys Phe His
    50                  55                  60

Gln Ile Glu Lys Glu Phe Ser Glu Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Leu Thr Asp
            100                 105                 110

Ser Glu Met Asn Lys Leu Phe Glu Lys Thr Arg Arg Gln Leu Arg Glu
        115                 120                 125

Asn Ala Glu Asp Met Gly Asn Gly Cys Phe Lys Ile Tyr His Lys Cys
    130                 135                 140

Asp Asn Ala Cys Ile Glu Ser Ile Arg Asn Gly Thr Tyr Asp His Asp
145                 150                 155                 160

Val Tyr Arg Asp Glu Ala Leu Asn Asn Arg Phe Gln Ile Lys Gly Val
                165                 170                 175

Glu Leu Lys


<210> SEQ ID NO 85
<211> LENGTH: 179
<212> TYPE: PRT
<213> ORGANISM: Influenza virus A
<220> FEATURE:
<223> OTHER INFORMATION: influenza A HA2 domain subtype H4 stem domain

<400> SEQUENCE: 85

Gly Leu Phe Gly Ala Ile Ala Gly Phe Ile Glu Asn Gly Trp Gln Gly
1               5                   10                  15

Leu Ile Asp Gly Trp Tyr Gly Phe Arg His Gln Asn Ala Glu Gly Thr
            20                  25                  30

Gly Thr Ala Ala Asp Leu Lys Ser Thr Gln Ala Ala Ile Asp Gln Ile
        35                  40                  45

Asn Gly Lys Leu Asn Arg Leu Ile Glu Lys Thr Asn Asp Lys Tyr His
    50                  55                  60

Gln Ile Glu Lys Glu Phe Glu Gln Val Glu Gly Arg Ile Gln Asp Leu
65                  70                  75                  80

Glu Asn Tyr Val Glu Asp Thr Lys Ile Asp Leu Trp Ser Tyr Asn Ala
                85                  90                  95
```

```
Glu Leu Leu Val Ala Leu Glu Asn Gln His Thr Ile Asp Val Thr Asp
            100                 105                 110

Ser Glu Met Asn Lys Leu Phe Glu Arg Val Arg Arg Gln Leu Arg Glu
        115                 120                 125

Asn Ala Glu Asp Lys Gly Asn Gly Cys Phe Glu Ile Phe His Lys Cys
    130                 135                 140

Asp Asn Asn Cys Ile Glu Ser Ile Arg Asn Gly Thr Tyr Asp His Asp
145                 150                 155                 160

Ile Tyr Arg Asp Glu Ala Ile Asn Asn Arg Phe Gln Ile Gln Gly Val
                165                 170                 175

Lys Leu Thr


<210> SEQ ID NO 86
<211> LENGTH: 180
<212> TYPE: PRT
<213> ORGANISM: Influenza virus A
<220> FEATURE:
<223> OTHER INFORMATION: influenza A HA2 domain subtype H5 stem domain

<400> SEQUENCE: 86

Gly Leu Phe Gly Ala Ile Ala Gly Phe Ile Glu Gly Gly Trp Gln Gly
 1               5                  10                  15

Met Val Asp Gly Trp Tyr Gly Tyr His His Ser Asn Glu Gln Gly Ser
            20                  25                  30

Gly Tyr Ala Ala Asp Lys Glu Ser Thr Gln Lys Ala Ile Asp Gly Ile
        35                  40                  45

Thr Asn Lys Val Asn Ser Ile Ile Asp Lys Met Asn Thr Arg Phe Glu
    50                  55                  60

Ala Val Gly Lys Glu Phe Asn Asn Leu Glu Arg Arg Val Glu Asn Leu
65                  70                  75                  80

Asn Lys Lys Met Glu Asp Gly Phe Leu Asp Val Trp Thr Tyr Asn Val
                85                  90                  95

Glu Leu Leu Val Leu Met Glu Asn Glu Arg Thr Leu Asp Phe His Asp
            100                 105                 110

Ser Asn Val Asn Asn Leu Tyr Asp Lys Val Arg Leu Gln Leu Lys Asp
        115                 120                 125

Asn Ala Arg Glu Leu Gly Asn Gly Cys Phe Glu Phe Tyr His Lys Cys
    130                 135                 140

Asp Asn Glu Cys Met Glu Ser Val Arg Asn Gly Thr Tyr Asp Tyr Pro
145                 150                 155                 160

Gln Tyr Ser Glu Glu Ala Arg Leu Asn Arg Glu Glu Ile Ser Gly Val
                165                 170                 175

Lys Leu Glu Ser
            180


<210> SEQ ID NO 87
<211> LENGTH: 180
<212> TYPE: PRT
<213> ORGANISM: Influenza virus A
<220> FEATURE:
<223> OTHER INFORMATION: influenza A HA2 domain subtype H6 stem domain

<400> SEQUENCE: 87

Gly Leu Phe Gly Ala Ile Ala Gly Phe Ile Glu Gly Gly Trp Thr Gly
 1               5                  10                  15

Met Ile Asp Gly Trp Tyr Gly Tyr His His Glu Asn Ser Gln Gly Ser
            20                  25                  30
```

```
Gly Tyr Ala Ala Asp Arg Glu Ser Thr Gln Lys Ala Val Asp Gly Ile
        35                  40                  45

Thr Asn Lys Val Asn Ser Ile Ile Asp Lys Met Asn Thr Gln Phe Glu
    50                  55                  60

Ala Val Asp His Glu Phe Ser Asn Leu Glu Arg Arg Ile Asp Asn Leu
65                  70                  75                  80

Asn Lys Arg Met Glu Asp Gly Phe Leu Asp Val Trp Thr Tyr Asn Ala
                85                  90                  95

Glu Leu Leu Val Leu Leu Glu Asn Glu Arg Thr Leu Asp Leu His Asp
            100                 105                 110

Ala Asn Val Lys Asn Leu Tyr Glu Arg Val Lys Ser Gln Leu Arg Asp
        115                 120                 125

Asn Ala Met Ile Leu Gly Asn Gly Cys Phe Glu Phe Trp His Lys Cys
    130                 135                 140

Asp Asp Glu Cys Met Glu Ser Val Lys Asn Gly Thr Tyr Asp Tyr Pro
145                 150                 155                 160

Lys Tyr Gln Asp Glu Ser Lys Leu Asn Arg Gln Glu Ile Glu Ser Val
                165                 170                 175

Lys Leu Glu Ser
            180


<210> SEQ ID NO 88
<211> LENGTH: 179
<212> TYPE: PRT
<213> ORGANISM: Influenza virus A
<220> FEATURE:
<223> OTHER INFORMATION: influenza A HA2 domain subtype H7 stem domain

<400> SEQUENCE: 88

Gly Leu Phe Gly Ala Ile Ala Gly Phe Ile Glu Asn Gly Trp Glu Gly
 1               5                  10                  15

Leu Val Asp Gly Trp Tyr Gly Phe Arg His Gln Asn Ala Gln Gly Glu
            20                  25                  30

Gly Thr Ala Ala Asp Tyr Lys Ser Thr Gln Ser Ala Ile Asp Gln Ile
        35                  40                  45

Thr Gly Lys Leu Asn Arg Leu Ile Glu Lys Thr Asn Gln Gln Phe Glu
    50                  55                  60

Leu Ile Asp Asn Glu Phe Thr Glu Val Glu Lys Gln Ile Gly Asn Leu
65                  70                  75                  80

Ile Asn Trp Thr Lys Asp Ser Ile Thr Glu Val Trp Ser Tyr Asn Ala
                85                  90                  95

Glu Leu Ile Val Ala Met Glu Asn Gln His Thr Ile Asp Leu Ala Asp
            100                 105                 110

Ser Glu Met Asn Arg Leu Tyr Glu Arg Val Arg Lys Gln Leu Arg Glu
        115                 120                 125

Asn Ala Glu Glu Asp Gly Thr Gly Cys Phe Glu Ile Phe His Lys Cys
    130                 135                 140

Asp Asp Asp Cys Met Ala Ser Ile Arg Asn Asn Thr Tyr Asp His Ser
145                 150                 155                 160

Lys Tyr Arg Glu Glu Ala Met Gln Asn Arg Ile Gln Ile Asp Pro Val
                165                 170                 175

Lys Leu Ser


<210> SEQ ID NO 89
<211> LENGTH: 180
```

<212> TYPE: PRT
<213> ORGANISM: Influenza virus A
<220> FEATURE:
<223> OTHER INFORMATION: influenza A HA2 domain subtype H8 stem domain

<400> SEQUENCE: 89

Gly Leu Phe Gly Ala Ile Ala Gly Phe Ile Glu Gly Gly Trp Ser Gly
1               5                   10                  15

Met Ile Asp Gly Trp Tyr Gly Phe His His Ser Asn Ser Glu Gly Thr
            20                  25                  30

Gly Met Ala Ala Asp Gln Lys Ser Thr Gln Glu Ala Ile Asp Lys Ile
        35                  40                  45

Thr Asn Lys Val Asn Asn Ile Val Asp Lys Met Asn Arg Glu Phe Glu
    50                  55                  60

Val Val Asn His Glu Phe Ser Glu Val Glu Lys Arg Ile Asn Met Ile
65                  70                  75                  80

Asn Asp Lys Ile Asp Asp Gln Ile Glu Asp Leu Trp Ala Tyr Asn Ala
                85                  90                  95

Glu Leu Leu Val Leu Leu Glu Asn Gln Lys Thr Leu Asp Glu His Asp
            100                 105                 110

Ser Asn Val Lys Asn Leu Phe Asp Glu Val Lys Arg Arg Leu Ser Ala
        115                 120                 125

Asn Ala Ile Asp Ala Gly Asn Gly Cys Phe Asp Ile Leu His Lys Cys
    130                 135                 140

Asp Asn Glu Cys Met Glu Thr Ile Lys Asn Gly Thr Tyr Asp His Lys
145                 150                 155                 160

Glu Tyr Glu Glu Glu Ala Lys Leu Glu Arg Ser Lys Ile Asn Gly Val
                165                 170                 175

Lys Leu Glu Glu
            180

<210> SEQ ID NO 90
<211> LENGTH: 180
<212> TYPE: PRT
<213> ORGANISM: Influenza virus A
<220> FEATURE:
<223> OTHER INFORMATION: influenza A HA2 domain subtype H9 stem domain

<400> SEQUENCE: 90

Gly Leu Phe Gly Ala Ile Ala Gly Phe Ile Glu Gly Gly Trp Pro Gly
1               5                   10                  15

Leu Val Ala Gly Trp Tyr Gly Phe Gln His Ser Asn Asp Gln Gly Val
            20                  25                  30

Gly Met Ala Ala Asp Lys Gly Ser Thr Gln Lys Ala Ile Asp Lys Ile
        35                  40                  45

Thr Ser Lys Val Asn Asn Ile Ile Asp Lys Met Asn Lys Gln Tyr Glu
    50                  55                  60

Val Ile Asp His Glu Phe Asn Glu Leu Glu Ala Arg Leu Asn Met Ile
65                  70                  75                  80

Asn Asn Lys Ile Asp Asp Gln Ile Gln Asp Ile Trp Ala Tyr Asn Ala
                85                  90                  95

Glu Leu Leu Val Leu Leu Glu Asn Gln Lys Thr Leu Asp Glu His Asp
            100                 105                 110

Ala Asn Val Asn Asn Leu Tyr Asn Lys Val Lys Arg Ala Leu Gly Ser
        115                 120                 125

Asn Ala Val Glu Asp Gly Asn Gly Cys Phe Glu Leu Tyr His Lys Cys
    130                 135                 140

```
Asp Asp Gln Cys Met Glu Thr Ile Arg Asn Gly Thr Tyr Asp Arg Gln
145                 150                 155                 160

Lys Tyr Gln Glu Glu Ser Arg Leu Glu Arg Gln Lys Ile Glu Gly Val
                165                 170                 175

Lys Leu Glu Ser
            180


<210> SEQ ID NO 91
<211> LENGTH: 179
<212> TYPE: PRT
<213> ORGANISM: Influenza virus A
<220> FEATURE:
<223> OTHER INFORMATION: influenza A HA2 domain subtype H10 stem domain

<400> SEQUENCE: 91

Gly Leu Phe Gly Ala Ile Ala Gly Phe Ile Glu Asn Gly Trp Glu Gly
 1               5                  10                  15

Met Val Asp Gly Trp Tyr Gly Phe Arg His Gln Asn Ala Gln Gly Thr
            20                  25                  30

Gly Gln Ala Ala Asp Tyr Lys Ser Thr Gln Ala Ala Ile Asp Gln Ile
        35                  40                  45

Thr Gly Lys Leu Asn Arg Leu Ile Glu Lys Thr Asn Thr Glu Phe Glu
    50                  55                  60

Ser Ile Glu Ser Glu Phe Ser Glu Thr Glu His Gln Ile Gly Asn Val
65                  70                  75                  80

Ile Asn Trp Thr Lys Asp Ser Ile Thr Asp Ile Trp Thr Tyr Asn Ala
                85                  90                  95

Glu Leu Leu Val Ala Met Glu Asn Gln His Thr Ile Asp Met Ala Asp
            100                 105                 110

Ser Glu Met Leu Asn Leu Tyr Glu Arg Val Arg Lys Gln Leu Arg Gln
        115                 120                 125

Asn Ala Glu Glu Asp Gly Lys Gly Cys Phe Glu Ile Tyr His Thr Cys
    130                 135                 140

Asp Asp Ser Cys Met Glu Ser Ile Arg Asn Asn Thr Tyr Asp His Ser
145                 150                 155                 160

Gln Tyr Arg Glu Glu Ala Leu Leu Asn Arg Leu Asn Ile Asn Pro Val
                165                 170                 175

Lys Leu Ser


<210> SEQ ID NO 92
<211> LENGTH: 181
<212> TYPE: PRT
<213> ORGANISM: Influenza virus A
<220> FEATURE:
<223> OTHER INFORMATION: influenza A HA2 domain subtype H11 stem domain

<400> SEQUENCE: 92

Gly Leu Phe Gly Ala Ile Ala Gly Phe Ile Glu Gly Gly Trp Pro Gly
 1               5                  10                  15

Leu Ile Asn Gly Trp Tyr Gly Phe Gln His Arg Asp Glu Glu Gly Thr
            20                  25                  30

Gly Ile Ala Ala Asp Lys Glu Ser Thr Gln Lys Ala Ile Asp Gln Ile
        35                  40                  45

Thr Ser Lys Val Asn Asn Ile Val Asp Arg Met Asn Thr Asn Phe Glu
    50                  55                  60

Ser Val Gln His Glu Phe Ser Glu Ile Glu Glu Arg Ile Asn Gln Leu
65                  70                  75                  80
```

Ser Lys His Val Asp Asp Ser Val Val Asp Ile Trp Ser Tyr Asn Ala
85 90 95

Gln Leu Leu Val Leu Leu Glu Asn Glu Lys Thr Leu Asp Leu His Asp
100 105 110

Ser Asn Val Arg Asn Leu His Glu Lys Val Arg Arg Met Leu Lys Asp
115 120 125

Asn Ala Lys Asp Glu Gly Asn Gly Cys Phe Thr Phe Tyr His Lys Cys
130 135 140

Asp Asn Lys Cys Ile Glu Arg Val Arg Asn Gly Thr Tyr Asp His Lys
145 150 155 160

Glu Phe Glu Glu Glu Ser Lys Ile Asn Arg Gln Glu Ile Glu Gly Val
165 170 175

Lys Leu Asp Ser Ser
180

<210> SEQ ID NO 93
<211> LENGTH: 180
<212> TYPE: PRT
<213> ORGANISM: Influenza virus A
<220> FEATURE:
<223> OTHER INFORMATION: influenza A HA2 domain subtype H12 stem domain

<400> SEQUENCE: 93

Gly Leu Phe Gly Ala Ile Ala Gly Phe Ile Glu Gly Gly Trp Pro Gly
1 5 10 15

Leu Val Ala Gly Trp Tyr Gly Phe Gln His Gln Asn Ala Glu Gly Thr
20 25 30

Gly Ile Ala Ala Asp Arg Asp Ser Thr Gln Arg Ala Ile Asp Asn Met
35 40 45

Gln Asn Lys Leu Asn Asn Val Ile Asp Lys Met Asn Lys Gln Phe Glu
50 55 60

Val Val Asn His Glu Phe Ser Glu Val Glu Ser Arg Ile Asn Met Ile
65 70 75 80

Asn Ser Lys Ile Asp Asp Gln Ile Thr Asp Ile Trp Ala Tyr Asn Ala
85 90 95

Glu Leu Leu Val Leu Leu Glu Asn Gln Lys Thr Leu Asp Glu His Asp
100 105 110

Ala Asn Val Arg Asn Leu His Asp Arg Val Arg Arg Val Leu Arg Glu
115 120 125

Asn Ala Ile Asp Thr Gly Asp Gly Cys Phe Glu Ile Leu His Lys Cys
130 135 140

Asp Asn Asn Cys Met Asp Thr Ile Arg Asn Gly Thr Tyr Asn His Lys
145 150 155 160

Glu Tyr Glu Glu Glu Ser Lys Ile Glu Arg Gln Lys Val Asn Gly Val
165 170 175

Lys Leu Glu Glu
180

<210> SEQ ID NO 94
<211> LENGTH: 181
<212> TYPE: PRT
<213> ORGANISM: Influenza virus A
<220> FEATURE:
<223> OTHER INFORMATION: influenza A HA2 domain subtype H13 stem domain

<400> SEQUENCE: 94

Gly Leu Phe Gly Ala Ile Ala Gly Phe Ile Glu Gly Gly Trp Pro Gly

-continued

```
 1               5                   10                  15

Leu Ile Asn Gly Trp Tyr Gly Phe Gln His Gln Asn Glu Gln Gly Thr
            20                  25                  30

Gly Ile Ala Ala Asp Lys Glu Ser Thr Gln Lys Ala Ile Asp Gln Ile
        35                  40                  45

Thr Thr Lys Ile Asn Asn Ile Ile Asp Lys Met Asn Gly Asn Tyr Asp
    50                  55                  60

Ser Ile Arg Gly Glu Phe Asn Gln Val Glu Lys Arg Ile Asn Met Leu
65                  70                  75                  80

Ala Asp Arg Ile Asp Asp Ala Val Thr Asp Ile Trp Ser Tyr Asn Ala
                85                  90                  95

Lys Leu Leu Val Leu Leu Glu Asn Asp Lys Thr Leu Asp Met His Asp
            100                 105                 110

Ala Asn Val Lys Asn Leu His Glu Gln Val Arg Arg Glu Leu Lys Asp
        115                 120                 125

Asn Ala Ile Asp Glu Gly Asn Gly Cys Phe Glu Leu Leu His Lys Cys
    130                 135                 140

Asn Asp Ser Cys Met Glu Thr Ile Arg Asn Gly Thr Tyr Asp His Thr
145                 150                 155                 160

Glu Tyr Ala Glu Glu Ser Lys Leu Lys Arg Gln Glu Ile Asp Gly Ile
                165                 170                 175

Lys Leu Lys Ser Glu
            180


<210> SEQ ID NO 95
<211> LENGTH: 179
<212> TYPE: PRT
<213> ORGANISM: Influenza virus A
<220> FEATURE:
<223> OTHER INFORMATION: influenza A HA2 domain subtype H14 stem domain

<400> SEQUENCE: 95

Gly Leu Phe Gly Ala Ile Ala Gly Phe Ile Glu Asn Gly Trp Gln Gly
 1               5                   10                  15

Leu Ile Asp Gly Trp Tyr Gly Phe Arg His Gln Asn Ala Glu Gly Thr
            20                  25                  30

Gly Thr Ala Ala Asp Leu Lys Ser Thr Gln Ala Ala Ile Asp Gln Ile
        35                  40                  45

Asn Gly Lys Leu Asn Arg Leu Ile Glu Lys Thr Asn Glu Lys Tyr His
    50                  55                  60

Gln Ile Glu Lys Glu Phe Glu Gln Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Val Thr Asp
            100                 105                 110

Ser Glu Met Asn Lys Leu Phe Glu Arg Val Arg Arg Gln Leu Arg Glu
        115                 120                 125

Asn Ala Glu Asp Gln Gly Asn Gly Cys Phe Glu Ile Phe His Gln Cys
    130                 135                 140

Asp Asn Asn Cys Ile Glu Ser Ile Arg Asn Gly Thr Tyr Asp His Asn
145                 150                 155                 160

Ile Tyr Arg Asp Glu Ala Ile Asn Asn Arg Ile Lys Ile Asn Pro Val
                165                 170                 175

Thr Leu Thr
```

<210> SEQ ID NO 96
<211> LENGTH: 179
<212> TYPE: PRT
<213> ORGANISM: Influenza virus A
<220> FEATURE:
<223> OTHER INFORMATION: influenza A HA2 domain subtype H15 stem domain

<400> SEQUENCE: 96

Gly Leu Phe Gly Ala Ile Ala Gly Phe Ile Glu Asn Gly Trp Glu Gly
1 5 10 15

Leu Ile Asp Gly Trp Tyr Gly Phe Arg His Gln Asn Ala Gln Gly Gln
20 25 30

Gly Thr Ala Ala Asp Tyr Lys Ser Thr Gln Ala Ala Ile Asp Gln Ile
35 40 45

Thr Gly Lys Leu Asn Arg Leu Ile Glu Lys Thr Asn Lys Gln Phe Glu
50 55 60

Leu Ile Asp Asn Glu Phe Thr Glu Val Glu Gln Gln Ile Gly Asn Val
65 70 75 80

Ile Asn Trp Thr Arg Asp Ser Leu Thr Glu Ile Trp Ser Tyr Asn Ala
85 90 95

Glu Leu Leu Val Ala Met Glu Asn Gln His Thr Ile Asp Leu Ala Asp
100 105 110

Ser Glu Met Asn Lys Leu Tyr Glu Arg Val Arg Arg Gln Leu Arg Glu
115 120 125

Asn Ala Glu Glu Asp Gly Thr Gly Cys Phe Glu Ile Phe His Arg Cys
130 135 140

Asp Asp Gln Cys Met Glu Ser Ile Arg Asn Asn Thr Tyr Asn His Thr
145 150 155 160

Glu Tyr Arg Gln Glu Ala Leu Gln Asn Arg Ile Met Ile Asn Pro Val
165 170 175

Lys Leu Ser

<210> SEQ ID NO 97
<211> LENGTH: 181
<212> TYPE: PRT
<213> ORGANISM: Influenza virus A
<220> FEATURE:
<223> OTHER INFORMATION: influenza A HA2 domain subtype H16 stem domain

<400> SEQUENCE: 97

Gly Leu Phe Gly Ala Ile Ala Gly Phe Ile Glu Gly Gly Trp Pro Gly
1 5 10 15

Leu Ile Asn Gly Trp Tyr Gly Phe Gln His Gln Asn Glu Gln Gly Thr
20 25 30

Gly Ile Ala Ala Asp Lys Ala Ser Thr Gln Lys Ala Ile Asn Glu Ile
35 40 45

Thr Thr Lys Ile Asn Asn Ile Ile Glu Lys Met Asn Gly Asn Tyr Asp
50 55 60

Ser Ile Arg Gly Glu Phe Asn Gln Val Glu Lys Arg Ile Asn Met Leu
65 70 75 80

Ala Asp Arg Val Asp Asp Ala Val Thr Asp Ile Trp Ser Tyr Asn Ala
85 90 95

Lys Leu Leu Val Leu Leu Glu Asn Asp Arg Thr Leu Asp Leu His Asp
100 105 110

Ala Asn Val Arg Asn Leu His Asp Gln Val Lys Arg Ala Leu Lys Ser
115 120 125

```
Asn Ala Ile Asp Glu Gly Asp Gly Cys Phe Asn Leu Leu His Lys Cys
    130                 135                 140

Asn Asp Ser Cys Met Glu Thr Ile Arg Asn Gly Thr Tyr Asn His Glu
145                 150                 155                 160

Asp Tyr Arg Glu Glu Ser Gln Leu Lys Arg Gln Glu Ile Glu Gly Ile
                165                 170                 175

Lys Leu Lys Thr Glu
            180


<210> SEQ ID NO 98
<211> LENGTH: 5
<212> TYPE: PRT
<213> ORGANISM: Influenza virus A
<220> FEATURE:
<223> OTHER INFORMATION: influenza A HA2 domain subtype H1 Luminal
      domain

<400> SEQUENCE: 98

Met Gly Ile Tyr Gln
 1               5


<210> SEQ ID NO 99
<211> LENGTH: 5
<212> TYPE: PRT
<213> ORGANISM: Influenza virus A
<220> FEATURE:
<223> OTHER INFORMATION: influenza A HA2 domain subtype H2 Luminal
      domain

<400> SEQUENCE: 99

Met Gly Val Tyr Gln
 1               5


<210> SEQ ID NO 100
<211> LENGTH: 5
<212> TYPE: PRT
<213> ORGANISM: Influenza virus A
<220> FEATURE:
<223> OTHER INFORMATION: influenza A HA2 domain subtype H3 Luminal
      domain

<400> SEQUENCE: 100

Ser Gly Tyr Lys Asp
 1               5


<210> SEQ ID NO 101
<211> LENGTH: 5
<212> TYPE: PRT
<213> ORGANISM: Influenza virus A
<220> FEATURE:
<223> OTHER INFORMATION: influenza A HA2 domain subtype H4 Luminal
      domain

<400> SEQUENCE: 101

Gln Gly Tyr Lys Asp
 1               5


<210> SEQ ID NO 102
<211> LENGTH: 5
<212> TYPE: PRT
<213> ORGANISM: Influenza virus A
<220> FEATURE:
<223> OTHER INFORMATION: influenza A HA2 domain subtype H5 Luminal
      domain

<400> SEQUENCE: 102
```

```
Met Gly Val Tyr Gln
 1              5


<210> SEQ ID NO 103
<211> LENGTH: 5
<212> TYPE: PRT
<213> ORGANISM: Influenza virus A
<220> FEATURE:
<223> OTHER INFORMATION: influenza A HA2 domain subtype H6 Luminal
      domain

<400> SEQUENCE: 103

Leu Gly Val Tyr Gln
 1              5


<210> SEQ ID NO 104
<211> LENGTH: 5
<212> TYPE: PRT
<213> ORGANISM: Influenza virus A
<220> FEATURE:
<223> OTHER INFORMATION: influenza A HA2 domain subtype H7 Luminal
      domain

<400> SEQUENCE: 104

Ser Gly Tyr Lys Asp
 1              5


<210> SEQ ID NO 105
<211> LENGTH: 5
<212> TYPE: PRT
<213> ORGANISM: Influenza virus A
<220> FEATURE:
<223> OTHER INFORMATION: influenza A HA2 domain subtype H8 Luminal
      domain

<400> SEQUENCE: 105

Asn Thr Thr Tyr Lys
 1              5


<210> SEQ ID NO 106
<211> LENGTH: 5
<212> TYPE: PRT
<213> ORGANISM: Influenza virus A
<220> FEATURE:
<223> OTHER INFORMATION: influenza A HA2 domain subtype H9 Luminal
      domain

<400> SEQUENCE: 106

Glu Gly Thr Tyr Lys
 1              5


<210> SEQ ID NO 107
<211> LENGTH: 5
<212> TYPE: PRT
<213> ORGANISM: Influenza virus A
<220> FEATURE:
<223> OTHER INFORMATION: influenza A HA2 domain subtype H10 Luminal
      domain

<400> SEQUENCE: 107

Ser Gly Tyr Lys Asp
 1              5


<210> SEQ ID NO 108
<211> LENGTH: 5
<212> TYPE: PRT
<213> ORGANISM: Influenza virus A
```

```
<220> FEATURE:
<223> OTHER INFORMATION: influenza A HA2 domain subtype H11 Luminal
      domain

<400> SEQUENCE: 108

Gly Asn Val Tyr Lys
 1              5


<210> SEQ ID NO 109
<211> LENGTH: 5
<212> TYPE: PRT
<213> ORGANISM: Influenza virus A
<220> FEATURE:
<223> OTHER INFORMATION: influenza A HA2 domain subtype H12 Luminal
      domain

<400> SEQUENCE: 109

Asn Ser Thr Tyr Lys
 1              5


<210> SEQ ID NO 110
<211> LENGTH: 5
<212> TYPE: PRT
<213> ORGANISM: Influenza virus A
<220> FEATURE:
<223> OTHER INFORMATION: influenza A HA2 domain subtype H13 Luminal
      domain

<400> SEQUENCE: 110

Asp Asn Val Tyr Lys
 1              5


<210> SEQ ID NO 111
<211> LENGTH: 5
<212> TYPE: PRT
<213> ORGANISM: Influenza virus A
<220> FEATURE:
<223> OTHER INFORMATION: influenza A HA2 domain subtype H14 Luminal
      domain

<400> SEQUENCE: 111

Met Gly Tyr Lys Asp
 1              5


<210> SEQ ID NO 112
<211> LENGTH: 5
<212> TYPE: PRT
<213> ORGANISM: Influenza virus A
<220> FEATURE:
<223> OTHER INFORMATION: influenza A HA2 domain subtype H15 Luminal
      domain

<400> SEQUENCE: 112

Ser Gly Tyr Lys Asp
 1              5


<210> SEQ ID NO 113
<211> LENGTH: 5
<212> TYPE: PRT
<213> ORGANISM: Influenza virus A
<220> FEATURE:
<223> OTHER INFORMATION: influenza A HA2 domain subtype H16 Luminal
      domain

<400> SEQUENCE: 113

Asp Asn Val Tyr Lys
 1              5
```

<210> SEQ ID NO 114
<211> LENGTH: 27
<212> TYPE: PRT
<213> ORGANISM: Influenza virus A
<220> FEATURE:
<223> OTHER INFORMATION: influenza A HA2 domain subtype H1 transmembrane domain

<400> SEQUENCE: 114

```
Ile Leu Ala Ile Tyr Ser Thr Val Ala Ser Ser Leu Val Leu Leu Val
 1               5                  10                  15

Ser Leu Gly Ala Ile Ser Phe Trp Met Cys Ser
            20                  25
```

<210> SEQ ID NO 115
<211> LENGTH: 27
<212> TYPE: PRT
<213> ORGANISM: Influenza virus A
<220> FEATURE:
<223> OTHER INFORMATION: influenza A HA2 domain subtype H2 transmembrane domain

<400> SEQUENCE: 115

```
Ile Leu Ala Ile Tyr Ala Thr Val Ala Gly Ser Leu Ser Leu Ala Ile
 1               5                  10                  15

Met Ile Ala Gly Ile Ser Leu Trp Met Cys Ser
            20                  25
```

<210> SEQ ID NO 116
<211> LENGTH: 27
<212> TYPE: PRT
<213> ORGANISM: Influenza virus A
<220> FEATURE:
<223> OTHER INFORMATION: influenza A HA2 domain subtype H3 transmembrane domain

<400> SEQUENCE: 116

```
Trp Ile Leu Trp Ile Ser Phe Ala Ile Ser Cys Phe Leu Leu Cys Val
 1               5                  10                  15

Val Leu Leu Gly Phe Ile Met Trp Ala Cys Gln
            20                  25
```

<210> SEQ ID NO 117
<211> LENGTH: 27
<212> TYPE: PRT
<213> ORGANISM: Influenza virus A
<220> FEATURE:
<223> OTHER INFORMATION: influenza A HA2 domain subtype H4 transmembrane domain

<400> SEQUENCE: 117

```
Ile Ile Leu Trp Ile Ser Phe Ser Ile Ser Cys Phe Leu Leu Val Ala
 1               5                  10                  15

Leu Leu Leu Ala Phe Ile Leu Trp Ala Cys Gln
            20                  25
```

<210> SEQ ID NO 118
<211> LENGTH: 27
<212> TYPE: PRT
<213> ORGANISM: Influenza virus A
<220> FEATURE:
<223> OTHER INFORMATION: influenza A HA2 domain subtype H5 transmembrane domain

<400> SEQUENCE: 118

```
Ile Leu Ser Ile Tyr Ser Thr Val Ala Ser Ser Leu Ala Leu Ala Ile
 1               5                  10                  15

Met Ile Ala Gly Leu Ser Phe Trp Met Cys Ser
            20                  25


<210> SEQ ID NO 119
<211> LENGTH: 27
<212> TYPE: PRT
<213> ORGANISM: Influenza virus A
<220> FEATURE:
<223> OTHER INFORMATION: influenza A HA2 domain subtype H6 transmembrane
      domain

<400> SEQUENCE: 119

Ile Leu Ala Ile Tyr Ser Thr Val Ser Ser Ser Leu Val Leu Val Gly
 1               5                  10                  15

Leu Ile Ile Ala Val Gly Leu Trp Met Cys Ser
            20                  25


<210> SEQ ID NO 120
<211> LENGTH: 27
<212> TYPE: PRT
<213> ORGANISM: Influenza virus A
<220> FEATURE:
<223> OTHER INFORMATION: influenza A HA2 domain subtype H7 transmembrane
      domain

<400> SEQUENCE: 120

Val Ile Leu Trp Phe Ser Phe Gly Ala Ser Cys Phe Leu Leu Leu Ala
 1               5                  10                  15

Ile Ala Met Gly Leu Val Phe Ile Cys Val Lys
            20                  25


<210> SEQ ID NO 121
<211> LENGTH: 27
<212> TYPE: PRT
<213> ORGANISM: Influenza virus A
<220> FEATURE:
<223> OTHER INFORMATION: influenza A HA2 domain subtype H8 transmembrane
      domain

<400> SEQUENCE: 121

Ile Leu Ser Ile Tyr Ser Thr Val Ala Ala Ser Leu Cys Leu Ala Ile
 1               5                  10                  15

Leu Ile Ala Gly Gly Leu Ile Leu Gly Met Gln
            20                  25


<210> SEQ ID NO 122
<211> LENGTH: 27
<212> TYPE: PRT
<213> ORGANISM: Influenza virus A
<220> FEATURE:
<223> OTHER INFORMATION: influenza A HA2 domain subtype H9 transmembrane
      domain

<400> SEQUENCE: 122

Ile Leu Thr Ile Tyr Ser Thr Val Ala Ser Ser Leu Val Leu Ala Met
 1               5                  10                  15

Gly Phe Ala Ala Phe Leu Phe Trp Ala Met Ser
            20                  25


<210> SEQ ID NO 123
<211> LENGTH: 27
<212> TYPE: PRT
<213> ORGANISM: Influenza virus A
```

<220> FEATURE:
<223> OTHER INFORMATION: influenza A HA2 domain subtype H10
      transmembrane domain

<400> SEQUENCE: 123

Ile Ile Leu Trp Phe Ser Phe Gly Glu Ser Cys Phe Val Leu Leu Ala
 1               5                  10                  15

Val Val Met Gly Leu Val Phe Phe Cys Leu Lys
            20                  25

<210> SEQ ID NO 124
<211> LENGTH: 27
<212> TYPE: PRT
<213> ORGANISM: Influenza virus A
<220> FEATURE:
<223> OTHER INFORMATION: influenza A HA2 domain subtype H11
      transmembrane domain

<400> SEQUENCE: 124

Ile Leu Ser Ile Tyr Ser Cys Ile Ala Ser Ser Leu Val Leu Ala Ala
 1               5                  10                  15

Leu Ile Met Gly Phe Met Phe Trp Ala Cys Ser
            20                  25

<210> SEQ ID NO 125
<211> LENGTH: 28
<212> TYPE: PRT
<213> ORGANISM: Influenza virus A
<220> FEATURE:
<223> OTHER INFORMATION: influenza A HA2 domain subtype H12
      transmembrane domain

<400> SEQUENCE: 125

Ile Leu Ser Ile Tyr Ser Ser Val Ala Ser Ser Leu Val Leu Leu Leu
 1               5                  10                  15

Met Ile Ile Gly Gly Phe Ile Phe Gly Cys Gln Asn
            20                  25

<210> SEQ ID NO 126
<211> LENGTH: 28
<212> TYPE: PRT
<213> ORGANISM: Influenza virus A
<220> FEATURE:
<223> OTHER INFORMATION: influenza A HA2 domain subtype H13
      transmembrane domain

<400> SEQUENCE: 126

Ala Leu Ser Ile Tyr Ser Cys Ile Ala Ser Ser Val Val Leu Val Gly
 1               5                  10                  15

Leu Ile Leu Ser Phe Ile Met Trp Ala Cys Ser Ser
            20                  25

<210> SEQ ID NO 127
<211> LENGTH: 27
<212> TYPE: PRT
<213> ORGANISM: Influenza virus A
<220> FEATURE:
<223> OTHER INFORMATION: influenza A HA2 domain subtype H14
      transmembrane domain

<400> SEQUENCE: 127

Ile Ile Leu Trp Ile Ser Phe Ser Met Ser Cys Phe Val Phe Val Ala
 1               5                  10                  15

Leu Ile Leu Gly Phe Val Leu Trp Ala Cys Gln
            20                  25

<210> SEQ ID NO 128
<211> LENGTH: 28
<212> TYPE: PRT
<213> ORGANISM: Influenza virus A
<220> FEATURE:
<223> OTHER INFORMATION: influenza A HA2 domain subtype H15 transmembrane domain

<400> SEQUENCE: 128

Val Ile Leu Trp Phe Ser Phe Gly Ala Ser Cys Val Met Leu Leu Ala
1 5 10 15

Ile Ala Met Gly Leu Ile Phe Met Cys Val Lys Asn
20 25

<210> SEQ ID NO 129
<211> LENGTH: 27
<212> TYPE: PRT
<213> ORGANISM: Influenza virus A
<220> FEATURE:
<223> OTHER INFORMATION: influenza A HA2 domain subtype H16 transmembrane domain

<400> SEQUENCE: 129

Val Leu Ser Ile Tyr Ser Cys Ile Ala Ser Ser Ile Val Leu Val Gly
1 5 10 15

Leu Ile Leu Ala Phe Ile Met Trp Ala Cys Ser
20 25

<210> SEQ ID NO 130
<211> LENGTH: 10
<212> TYPE: PRT
<213> ORGANISM: Influenza virus A
<220> FEATURE:
<223> OTHER INFORMATION: influenza A HA2 domain subtype H1 cytoplasmic domain

<400> SEQUENCE: 130

Asn Gly Ser Leu Gln Cys Arg Ile Cys Ile
1 5 10

<210> SEQ ID NO 131
<211> LENGTH: 10
<212> TYPE: PRT
<213> ORGANISM: Influenza virus A
<220> FEATURE:
<223> OTHER INFORMATION: influenza A HA2 domain subtype H2 cytoplasmic domain

<400> SEQUENCE: 131

Asn Gly Ser Leu Gln Cys Arg Ile Cys Ile
1 5 10

<210> SEQ ID NO 132
<211> LENGTH: 10
<212> TYPE: PRT
<213> ORGANISM: Influenza virus A
<220> FEATURE:
<223> OTHER INFORMATION: influenza A HA2 domain subtype H3 cytoplasmic domain

<400> SEQUENCE: 132

Arg Gly Asn Ile Arg Cys Asn Ile Cys Ile
1 5 10

<210> SEQ ID NO 133

<211> LENGTH: 10
<212> TYPE: PRT
<213> ORGANISM: Influenza virus A
<220> FEATURE:
<223> OTHER INFORMATION: influenza A HA2 domain subtype H4 cytoplasmic domain

<400> SEQUENCE: 133

Asn Gly Asn Ile Arg Cys Gln Ile Cys Ile
1 5 10

<210> SEQ ID NO 134
<211> LENGTH: 10
<212> TYPE: PRT
<213> ORGANISM: Influenza virus A
<220> FEATURE:
<223> OTHER INFORMATION: influenza A HA2 domain subtype H5 cytoplasmic domain

<400> SEQUENCE: 134

Asn Gly Ser Leu Gln Cys Arg Ile Cys Ile
1 5 10

<210> SEQ ID NO 135
<211> LENGTH: 10
<212> TYPE: PRT
<213> ORGANISM: Influenza virus A
<220> FEATURE:
<223> OTHER INFORMATION: influenza A HA2 domain subtype H6 cytoplasmic domain

<400> SEQUENCE: 135

Asn Gly Ser Met Gln Cys Arg Ile Cys Ile
1 5 10

<210> SEQ ID NO 136
<211> LENGTH: 10
<212> TYPE: PRT
<213> ORGANISM: Influenza virus A
<220> FEATURE:
<223> OTHER INFORMATION: influenza A HA2 domain subtype H7 cytoplasmic domain

<400> SEQUENCE: 136

Asn Gly Asn Met Arg Cys Thr Ile Cys Ile
1 5 10

<210> SEQ ID NO 137
<211> LENGTH: 10
<212> TYPE: PRT
<213> ORGANISM: Influenza virus A
<220> FEATURE:
<223> OTHER INFORMATION: influenza A HA2 domain subtype H8 cytoplasmic domain

<400> SEQUENCE: 137

Asn Gly Ser Cys Arg Cys Met Phe Cys Ile
1 5 10

<210> SEQ ID NO 138
<211> LENGTH: 10
<212> TYPE: PRT
<213> ORGANISM: Influenza virus A
<220> FEATURE:
<223> OTHER INFORMATION: influenza A HA2 domain subtype H9 cytoplasmic domain

<400> SEQUENCE: 138

Asn Gly Ser Cys Arg Cys Asn Ile Cys Ile
 1               5                   10

<210> SEQ ID NO 139
<211> LENGTH: 10
<212> TYPE: PRT
<213> ORGANISM: Influenza virus A
<220> FEATURE:
<223> OTHER INFORMATION: influenza A HA2 domain subtype H10 cytoplasmic domain

<400> SEQUENCE: 139

Asn Gly Asn Met Arg Cys Thr Ile Cys Ile
 1               5                   10

<210> SEQ ID NO 140
<211> LENGTH: 10
<212> TYPE: PRT
<213> ORGANISM: Influenza virus A
<220> FEATURE:
<223> OTHER INFORMATION: influenza A HA2 domain subtype H11 cytoplasmic domain

<400> SEQUENCE: 140

Asn Gly Ser Cys Arg Cys Thr Ile Cys Ile
 1               5                   10

<210> SEQ ID NO 141
<211> LENGTH: 9
<212> TYPE: PRT
<213> ORGANISM: Influenza virus A
<220> FEATURE:
<223> OTHER INFORMATION: influenza A HA2 domain subtype H12 cytoplasmic domain

<400> SEQUENCE: 141

Gly Asn Val Arg Cys Thr Phe Cys Ile
 1               5

<210> SEQ ID NO 142
<211> LENGTH: 9
<212> TYPE: PRT
<213> ORGANISM: Influenza virus A
<220> FEATURE:
<223> OTHER INFORMATION: influenza A HA2 domain subtype H13 cytoplasmic domain

<400> SEQUENCE: 142

Gly Asn Cys Arg Phe Asn Val Cys Ile
 1               5

<210> SEQ ID NO 143
<211> LENGTH: 10
<212> TYPE: PRT
<213> ORGANISM: Influenza virus A
<220> FEATURE:
<223> OTHER INFORMATION: influenza A HA2 domain subtype H14 cytoplasmic domain

<400> SEQUENCE: 143

Asn Gly Asn Ile Arg Cys Gln Ile Cys Ile
 1               5                   10

<210> SEQ ID NO 144
<211> LENGTH: 9
<212> TYPE: PRT
<213> ORGANISM: Influenza virus A
<220> FEATURE:

<223> OTHER INFORMATION: influenza A HA2 domain subtype H15 cytoplasmic
      domain

<400> SEQUENCE: 144

Gly Asn Leu Arg Cys Thr Ile Cys Ile
 1               5

<210> SEQ ID NO 145
<211> LENGTH: 10
<212> TYPE: PRT
<213> ORGANISM: Influenza virus A
<220> FEATURE:
<223> OTHER INFORMATION: influenza A HA2 domain subtype H16 cytoplasmic
      domain

<400> SEQUENCE: 145

Asn Gly Ser Cys Arg Phe Asn Val Cys Ile
 1               5                   10

<210> SEQ ID NO 146
<211> LENGTH: 23
<212> TYPE: PRT
<213> ORGANISM: Artificial Sequence
<220> FEATURE:
<223> OTHER INFORMATION: sequence of HA1 N-terminal stem segment
<220> FEATURE:
<221> NAME/KEY: VARIANT
<222> LOCATION: 1
<223> OTHER INFORMATION: Xaa = Tyr or His
<220> FEATURE:
<221> NAME/KEY: VARIANT
<222> LOCATION: 2
<223> OTHER INFORMATION: Xaa = His, Leu or Gln
<220> FEATURE:
<221> NAME/KEY: VARIANT
<222> LOCATION: 3.....20
<223> OTHER INFORMATION: Xaa = any amino acid
<220> FEATURE:
<221> NAME/KEY: VARIANT
<222> LOCATION: 21
<223> OTHER INFORMATION: Xaa = any amino acid or absent
<220> FEATURE:
<221> NAME/KEY: VARIANT
<222> LOCATION: 22
<223> OTHER INFORMATION: Xaa = any amino acid or absent
<220> FEATURE:
<221> NAME/KEY: VARIANT
<222> LOCATION: 23
<223> OTHER INFORMATION: Xaa = His, Ser, Gln, Thr or Asn

<400> SEQUENCE: 146

Xaa Xaa Xaa Xaa Xaa Xaa Xaa Xaa Xaa Xaa Xaa Xaa Xaa Xaa Xaa Xaa
 1               5                   10                  15

Xaa Xaa Xaa Xaa Xaa Xaa Xaa
            20

<210> SEQ ID NO 147
<211> LENGTH: 2
<212> TYPE: PRT
<213> ORGANISM: Artificial Sequence
<220> FEATURE:
<223> OTHER INFORMATION: sequence of HA1 c-terminal stem segment
<220> FEATURE:
<221> NAME/KEY: VARIANT
<222> LOCATION: 1
<223> OTHER INFORMATION: Xaa = Thr, Ser, Asn, Asp, Pro or Lys
<220> FEATURE:
<221> NAME/KEY: VARIANT
<222> LOCATION: 2
<223> OTHER INFORMATION: Xaa = Leu, Met, Lys or Arg

<400> SEQUENCE: 147

Xaa Xaa
 1

<210> SEQ ID NO 148
<211> LENGTH: 4
<212> TYPE: PRT
<213> ORGANISM: Artificial Sequence
<220> FEATURE:
<223> OTHER INFORMATION: sequence of HA2 domain
<220> FEATURE:
<221> NAME/KEY: VARIANT
<222> LOCATION: 1
<223> OTHER INFORMATION: Xaa = Val or Ile
<220> FEATURE:
<221> NAME/KEY: VARIANT
<222> LOCATION: 2
<223> OTHER INFORMATION: Xaa = Asp, Asn or Ala

<400> SEQUENCE: 148

Xaa Xaa Gly Trp
 1

<210> SEQ ID NO 149
<211> LENGTH: 19
<212> TYPE: PRT
<213> ORGANISM: Artificial Sequence
<220> FEATURE:
<223> OTHER INFORMATION: sequence of HA2 domain
<220> FEATURE:
<221> NAME/KEY: VARIANT
<222> LOCATION: 1
<223> OTHER INFORMATION: Xaa = Lys, Gln, Arg, Leu or Tyr
<220> FEATURE:
<221> NAME/KEY: VARIANT
<222> LOCATION: 2, 3, 6, 10, 13, 17
<223> OTHER INFORMATION: Xaa = any amino acid
<220> FEATURE:
<221> NAME/KEY: VARIANT
<222> LOCATION: 11
<223> OTHER INFORMATION: Xaa = Ile, Val or Met
<220> FEATURE:
<221> NAME/KEY: VARIANT
<222> LOCATION: 12
<223> OTHER INFORMATION: Xaa = Thr, Gln or Asn
<220> FEATURE:
<221> NAME/KEY: VARIANT
<222> LOCATION: 15
<223> OTHER INFORMATION: Xaa = Val or Leu
<220> FEATURE:
<221> NAME/KEY: VARIANT
<222> LOCATION: 18
<223> OTHER INFORMATION: Xaa = Val, Ile or Leu
<220> FEATURE:
<221> NAME/KEY: VARIANT
<222> LOCATION: 19
<223> OTHER INFORMATION: Xaa = Val or Ile

<400> SEQUENCE: 149

Xaa Xaa Xaa Thr Gln Xaa Ala Ile Asp Xaa Xaa Xaa Xaa Lys Xaa Asn
 1               5                   10                  15

Xaa Xaa Xaa

<210> SEQ ID NO 150
<211> LENGTH: 15
<212> TYPE: PRT
<213> ORGANISM: Influenza virus B
<220> FEATURE:
<223> OTHER INFORMATION: Signal peptide of Influenza B HA construct
      variant Arg50-Ser277

<400> SEQUENCE: 150

Met Lys Ala Ile Ile Val Ile Leu Met Val Val Thr Ser Asn Ala
1 5 10 15

<210> SEQ ID NO 151
<211> LENGTH: 15
<212> TYPE: PRT
<213> ORGANISM: Influenza virus B
<220> FEATURE:
<223> OTHER INFORMATION: Signal peptide of Influenza B HA construct variant Ala66-Trp271

<400> SEQUENCE: 151

Met Lys Ala Ile Ile Val Ile Leu Met Val Val Thr Ser Asn Ala
1 5 10 15

<210> SEQ ID NO 152
<211> LENGTH: 15
<212> TYPE: PRT
<213> ORGANISM: Influenza virus B
<220> FEATURE:
<223> OTHER INFORMATION: Signal peptide of Influenza B HA construct variant Lys80-Ser277

<400> SEQUENCE: 152

Met Lys Ala Ile Ile Val Ile Leu Met Val Val Thr Ser Asn Ala
1 5 10 15

<210> SEQ ID NO 153
<211> LENGTH: 15
<212> TYPE: PRT
<213> ORGANISM: Influenza virus B
<220> FEATURE:
<223> OTHER INFORMATION: Signal peptide of Influenza B HA construct variant Arg80-Ser277

<400> SEQUENCE: 153

Met Lys Ala Ile Ile Val Ile Leu Met Val Val Thr Ser Asn Ala
1 5 10 15

<210> SEQ ID NO 154
<211> LENGTH: 50
<212> TYPE: PRT
<213> ORGANISM: Influenza virus B
<220> FEATURE:
<223> OTHER INFORMATION: HA1 N-terminal Stem Segment of Influenza B HA construct variant Arg50-Ser277

<400> SEQUENCE: 154

Asp Arg Ile Cys Thr Gly Ile Thr Ser Ser Asn Ser Pro His Val Val
1 5 10 15

Lys Thr Ala Thr Gln Gly Glu Val Asn Val Thr Gly Val Ile Pro Leu
20 25 30

Thr Thr Thr Pro Thr Lys Ser His Phe Ala Asn Leu Lys Gly Thr Glu
35 40 45

Thr Arg
50

<210> SEQ ID NO 155
<211> LENGTH: 66
<212> TYPE: PRT
<213> ORGANISM: Influenza virus B
<220> FEATURE:
<223> OTHER INFORMATION: HA1 N-terminal Stem Segment of Influenza B HA construct variant Ala66-Trp271

<400> SEQUENCE: 155

```
Asp Arg Ile Cys Thr Gly Ile Thr Ser Ser Asn Ser Pro His Val Val
 1               5                  10                  15

Lys Thr Ala Thr Gln Gly Glu Val Asn Val Thr Gly Val Ile Pro Leu
            20                  25                  30

Thr Thr Thr Pro Thr Lys Ser His Phe Ala Asn Leu Lys Gly Thr Glu
        35                  40                  45

Thr Arg Gly Lys Leu Cys Pro Lys Cys Leu Asn Cys Thr Asp Leu Asp
    50                  55                  60

Val Ala
65


<210> SEQ ID NO 156
<211> LENGTH: 80
<212> TYPE: PRT
<213> ORGANISM: Influenza virus B
<220> FEATURE:
<223> OTHER INFORMATION: HA1 N-terminal Stem Segment of Influenza B HA
      construct variant Lys80-Ser277

<400> SEQUENCE: 156

Asp Arg Ile Cys Thr Gly Ile Thr Ser Ser Asn Ser Pro His Val Val
 1               5                  10                  15

Lys Thr Ala Thr Gln Gly Glu Val Asn Val Thr Gly Val Ile Pro Leu
            20                  25                  30

Thr Thr Thr Pro Thr Lys Ser His Phe Ala Asn Leu Lys Gly Thr Glu
        35                  40                  45

Thr Arg Gly Lys Leu Cys Pro Lys Cys Leu Asn Cys Thr Asp Leu Asp
    50                  55                  60

Val Ala Leu Gly Arg Pro Lys Cys Thr Gly Lys Ile Pro Ser Ala Lys
65                  70                  75                  80


<210> SEQ ID NO 157
<211> LENGTH: 80
<212> TYPE: PRT
<213> ORGANISM: Influenza virus B
<220> FEATURE:
<223> OTHER INFORMATION: HA1 N-terminal Stem Segment of Influenza B HA
      construct variant Arg80-Ser277

<400> SEQUENCE: 157

Asp Arg Ile Cys Thr Gly Ile Thr Ser Ser Asn Ser Pro His Val Val
 1               5                  10                  15

Lys Thr Ala Thr Gln Gly Glu Val Asn Val Thr Gly Val Ile Pro Leu
            20                  25                  30

Thr Thr Thr Pro Thr Lys Ser His Phe Ala Asn Leu Lys Gly Thr Glu
        35                  40                  45

Thr Arg Gly Lys Leu Cys Pro Lys Cys Leu Asn Cys Thr Asp Leu Asp
    50                  55                  60

Val Ala Leu Gly Arg Pro Lys Cys Thr Gly Lys Ile Pro Ser Ala Arg
65                  70                  75                  80


<210> SEQ ID NO 158
<211> LENGTH: 68
<212> TYPE: PRT
<213> ORGANISM: Influenza virus B
<220> FEATURE:
<223> OTHER INFORMATION: HA1 C-terminal Stem Segment of Influenza B HA
      construct variant Arg50-Ser277

<400> SEQUENCE: 158

Ser Lys Val Ile Lys Gly Ser Leu Pro Leu Ile Gly Glu Ala Asp Cys
```

```
 1               5                   10                  15

Leu His Glu Lys Tyr Gly Gly Leu Asn Lys Ser Lys Pro Tyr Tyr Thr
            20                  25                  30

Gly Glu His Ala Lys Ala Ile Gly Asn Cys Pro Ile Trp Val Lys Thr
        35                  40                  45

Pro Leu Lys Leu Ala Asn Gly Thr Lys Tyr Arg Pro Pro Ala Lys Leu
    50                  55                  60

Leu Lys Glu Arg
65
```

<210> SEQ ID NO 159
<211> LENGTH: 74
<212> TYPE: PRT
<213> ORGANISM: Influenza virus B
<220> FEATURE:
<223> OTHER INFORMATION: HA1 C-terminal Stem Segment of Influenza B HA construct variant Ala66-Trp271

<400> SEQUENCE: 159

```
Trp Cys Ala Ser Gly Arg Ser Lys Val Ile Lys Gly Ser Leu Pro Leu
 1               5                   10                  15

Ile Gly Glu Ala Asp Cys Leu His Glu Lys Tyr Gly Gly Leu Asn Lys
            20                  25                  30

Ser Lys Pro Tyr Tyr Thr Gly Glu His Ala Lys Ala Ile Gly Asn Cys
        35                  40                  45

Pro Ile Trp Val Lys Thr Pro Leu Lys Leu Ala Asn Gly Thr Lys Tyr
    50                  55                  60

Arg Pro Pro Ala Lys Leu Leu Lys Glu Arg
65                  70
```

<210> SEQ ID NO 160
<211> LENGTH: 223
<212> TYPE: PRT
<213> ORGANISM: Influenza virus B
<220> FEATURE:
<223> OTHER INFORMATION: HA2 Domain of Influenza B HA construct variant Arg50-Ser277 and other variants listed in Table 3

<400> SEQUENCE: 160

```
Gly Phe Phe Gly Ala Ile Ala Gly Phe Leu Glu Gly Gly Trp Glu Gly
 1               5                   10                  15

Met Ile Ala Gly Trp His Gly Tyr Thr Ser His Gly Ala His Gly Val
            20                  25                  30

Ala Val Ala Ala Asp Leu Lys Ser Thr Gln Glu Ala Ile Asn Lys Ile
        35                  40                  45

Thr Lys Asn Leu Asn Ser Leu Ser Glu Leu Glu Val Lys Asn Leu Gln
    50                  55                  60

Arg Leu Ser Gly Ala Met Asp Glu Leu His Asn Glu Ile Leu Glu Leu
65                  70                  75                  80

Asp Glu Lys Val Asp Asp Leu Arg Ala Asp Thr Ile Ser Ser Gln Ile
                85                  90                  95

Glu Leu Ala Val Leu Leu Ser Asn Glu Gly Ile Ile Asn Ser Glu Asp
            100                 105                 110

Glu His Leu Leu Ala Leu Glu Arg Lys Leu Lys Lys Met Leu Gly Pro
        115                 120                 125

Ser Ala Val Glu Ile Gly Asn Gly Cys Phe Glu Thr Lys His Lys Cys
    130                 135                 140

Asn Gln Thr Cys Leu Asp Arg Ile Ala Ala Gly Thr Phe Asp Ala Gly
```

```
145                 150                 155                 160

Glu Phe Ser Leu Pro Thr Phe Asp Ser Leu Asn Ile Thr Ala Ala Ser
                165                 170                 175

Leu Asn Asp Asp Gly Leu Asp Asn His Thr Ile Leu Leu Tyr Tyr Ser
            180                 185                 190

Thr Ala Ala Ser Ser Leu Ala Val Thr Leu Met Ile Ala Ile Phe Val
        195                 200                 205

Val Tyr Met Val Ser Arg Asp Asn Val Ser Cys Ser Ile Cys Leu
    210                 215                 220


<210> SEQ ID NO 161
<211> LENGTH: 179
<212> TYPE: PRT
<213> ORGANISM: Influenza virus B
<220> FEATURE:
<223> OTHER INFORMATION: Stem domain of Influenza B HA2 domain subtype
      HA2

<400> SEQUENCE: 161

Gly Phe Phe Gly Ala Ile Ala Gly Phe Leu Glu Gly Gly Trp Glu Gly
 1               5                  10                  15

Met Ile Ala Gly Trp His Gly Tyr Thr Ser His Gly Ala His Gly Val
            20                  25                  30

Ala Val Ala Ala Asp Leu Lys Ser Thr Gln Glu Ala Ile Asn Lys Ile
        35                  40                  45

Thr Lys Asn Leu Asn Ser Leu Ser Glu Leu Glu Val Lys Asn Leu Gln
    50                  55                  60

Arg Leu Ser Gly Ala Met Asp Glu Leu His Asn Glu Ile Leu Glu Leu
65                  70                  75                  80

Asp Glu Lys Val Asp Asp Leu Arg Ala Asp Thr Ile Ser Ser Gln Ile
                85                  90                  95

Glu Leu Ala Val Leu Leu Ser Asn Glu Gly Ile Ile Asn Ser Glu Asp
            100                 105                 110

Glu His Leu Leu Ala Leu Glu Arg Lys Leu Lys Lys Met Leu Gly Pro
        115                 120                 125

Ser Ala Val Glu Ile Gly Asn Gly Cys Phe Glu Thr Lys His Lys Cys
    130                 135                 140

Asn Gln Thr Cys Leu Asp Arg Ile Ala Ala Gly Thr Phe Asp Ala Gly
145                 150                 155                 160

Glu Phe Ser Leu Pro Thr Phe Asp Ser Leu Asn Ile Thr Ala Ala Ser
                165                 170                 175

Leu Asn Asp


<210> SEQ ID NO 162
<211> LENGTH: 5
<212> TYPE: PRT
<213> ORGANISM: Influenza virus B
<220> FEATURE:
<223> OTHER INFORMATION: luminal domain of Influenza B HA2 domain
      subtype HA2

<400> SEQUENCE: 162

Asp Gly Leu Asp Asn
 1               5


<210> SEQ ID NO 163
<211> LENGTH: 28
<212> TYPE: PRT
<213> ORGANISM: Influenza virus B
```

```
<220> FEATURE:
<223> OTHER INFORMATION: transmembrane domain of Influenza B HA2 domain
      subtype HA2

<400> SEQUENCE: 163

His Thr Ile Leu Leu Tyr Tyr Ser Thr Ala Ala Ser Ser Leu Ala Val
 1               5                  10                  15

Thr Leu Met Ile Ala Ile Phe Val Val Tyr Met Val
            20                  25


<210> SEQ ID NO 164
<211> LENGTH: 11
<212> TYPE: PRT
<213> ORGANISM: Influenza virus B
<220> FEATURE:
<223> OTHER INFORMATION: cytoplasmic domain of Influenza B HA2 domain
      subtype HA2

<400> SEQUENCE: 164

Ser Arg Asp Asn Val Ser Cys Ser Ile Cys Leu
 1               5                  10


<210> SEQ ID NO 165
<211> LENGTH: 23
<212> TYPE: PRT
<213> ORGANISM: Artificial Sequence
<220> FEATURE:
<223> OTHER INFORMATION: turn loop linker sequence

<400> SEQUENCE: 165

Ile Thr Pro Asn Gly Ser Ile Pro Asn Asp Lys Pro Phe Gln Asn Val
 1               5                  10                  15

Asn Lys Ile Thr Tyr Gly Ala
            20


<210> SEQ ID NO 166
<211> LENGTH: 6
<212> TYPE: PRT
<213> ORGANISM: Artificial Sequence
<220> FEATURE:
<223> OTHER INFORMATION: His tag

<400> SEQUENCE: 166

His His His His His His
 1               5


<210> SEQ ID NO 167
<211> LENGTH: 29
<212> TYPE: PRT
<213> ORGANISM: Artificial Sequence
<220> FEATURE:
<223> OTHER INFORMATION: example of a foldon domain

<400> SEQUENCE: 167

Gly Ser Gly Tyr Ile Pro Glu Ala Pro Arg Asp Gly Gln Ala Tyr Val
 1               5                  10                  15

Arg Lys Asp Gly Glu Trp Val Leu Leu Ser Thr Phe Leu
            20                  25


<210> SEQ ID NO 168
<211> LENGTH: 7
<212> TYPE: PRT
<213> ORGANISM: Artificial Sequence
<220> FEATURE:
<223> OTHER INFORMATION: thrombin cleavage site
```

<400> SEQUENCE: 168

Leu Val Pro Arg Gly Ser Pro
1 5

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177
<211> LENGTH: 41
<212> TYPE: PRT
<213> ORGANISM: Influenza virus A
<220> FEATURE:
<223> OTHER INFORMATION: N-terminal stem segment of Influenza A HA subtype H1(no Cys) Short Stem Domain sequence

<400> SEQUENCE: 177

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asp Ser His Asn Gly Lys Leu 35 40

<210> SEQ ID NO 178
<211> LENGTH: 41
<212> TYPE: PRT
<213> ORGANISM: Influenza virus A
<220> FEATURE:
<223> OTHER INFORMATION: N-terminal stem segment of Influenza A HA subtype H1(no Cys-delta 1) Short Stem Domain sequence

<400> SEQUENCE: 178

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asp Ser His Asn Gly Lys Leu
35 40

<210> SEQ ID NO 179
<211> LENGTH: 40
<212> TYPE: PRT
<213> ORGANISM: Influenza virus A
<220> FEATURE:
<223> OTHER INFORMATION: N-terminal stem segment of Influenza A HA subtype H1(no Cys-delta 3) Short Stem Domain sequence

<400> SEQUENCE: 179

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asp Ser His Asn Gly Lys
35 40

<210> SEQ ID NO 180
<211> LENGTH: 41
<212> TYPE: PRT
<213> ORGANISM: Influenza virus A
<220> FEATURE:
<223> OTHER INFORMATION: N-terminal stem segment of Influenza A HA subtype H2(no Cys) Short Stem Domain sequence

<400> SEQUENCE: 180

Asp Gln Ile Cys Ile Gly Tyr His Ser Asn Asn Ser Thr Glu Lys Val
1 5 10 15

Asp Thr Ile Leu Glu Arg Asn Val Thr Val Thr His Ala Gln Asn Ile
20 25 30

Leu Glu Lys Thr His Asn Gly Lys Leu
35 40

<210> SEQ ID NO 181
<211> LENGTH: 41
<212> TYPE: PRT
<213> ORGANISM: Influenza virus A
<220> FEATURE:
<223> OTHER INFORMATION: N-terminal stem segment of Influenza A HA subtype H2(no Cys-delta 1) Short Stem Domain sequence

<400> SEQUENCE: 181

Asp Gln Ile Cys Ile Gly Tyr His Ser Asn Asn Ser Thr Glu Lys Val
1 5 10 15

Asp Thr Ile Leu Glu Arg Asn Val Thr Val Thr His Ala Gln Asn Ile
20 25 30

-continued

Leu Glu Lys Thr His Asn Gly Lys Leu
35 40

<210> SEQ ID NO 182
<211> LENGTH: 40
<212> TYPE: PRT
<213> ORGANISM: Influenza virus A
<220> FEATURE:
<223> OTHER INFORMATION: N-terminal stem segment of Influenza A HA subtype H2(no Cys-delta 3) Short Stem Domain sequence

<400> SEQUENCE: 182

Asp Gln Ile Cys Ile Gly Tyr His Ser Asn Asn Ser Thr Glu Lys Val
1 5 10 15

Asp Thr Ile Leu Glu Arg Asn Val Thr Val Thr His Ala Gln Asn Ile
20 25 30

Leu Glu Lys Thr His Asn Gly Lys
35 40

<210> SEQ ID NO 183
<211> LENGTH: 51
<212> TYPE: PRT
<213> ORGANISM: Influenza virus A
<220> FEATURE:
<223> OTHER INFORMATION: N-terminal stem segment of Influenza A HA subtype H3(no Cys) Short Stem Domain sequence

<400> SEQUENCE: 183

Gln Asp Leu Pro Gly Asn Asp Asn Ser Thr Ala Thr Leu Cys Leu Gly
1 5 10 15

His His Ala Val Pro Asn Gly Thr Leu Val Lys Thr Ile Thr Asp Asp
20 25 30

Gln Ile Glu Val Thr Asn Ala Thr Glu Leu Val Gln Ser Ser Ser Thr
35 40 45

Gly Lys Ile
50

<210> SEQ ID NO 184
<211> LENGTH: 51
<212> TYPE: PRT
<213> ORGANISM: Influenza virus A
<220> FEATURE:
<223> OTHER INFORMATION: N-terminal stem segment of Influenza A HA subtype H3(no Cys-delta 1) Short Stem Domain sequence

<400> SEQUENCE: 184

Gln Asp Leu Pro Gly Asn Asp Asn Ser Thr Ala Thr Leu Cys Leu Gly
1 5 10 15

His His Ala Val Pro Asn Gly Thr Leu Val Lys Thr Ile Thr Asp Asp
20 25 30

Gln Ile Glu Val Thr Asn Ala Thr Glu Leu Val Gln Ser Ser Ser Thr
35 40 45

Gly Lys Ile
50

<210> SEQ ID NO 185
<211> LENGTH: 50
<212> TYPE: PRT
<213> ORGANISM: Influenza virus A
<220> FEATURE:
<223> OTHER INFORMATION: N-terminal stem segment of Influenza A HA subtype H3(no Cys-delta 3) Short Stem Domain sequence

<400> SEQUENCE: 185

Gln Asp Leu Pro Gly Asn Asp Asn Ser Thr Ala Thr Leu Cys Leu Gly
1 5 10 15

His His Ala Val Pro Asn Gly Thr Leu Val Lys Thr Ile Thr Asp Asp
20 25 30

Gln Ile Glu Val Thr Asn Ala Thr Glu Leu Val Gln Ser Ser Ser Thr
35 40 45

Gly Lys
50

<210> SEQ ID NO 186
<211> LENGTH: 47
<212> TYPE: PRT
<213> ORGANISM: Influenza virus A
<220> FEATURE:
<223> OTHER INFORMATION: N-terminal stem segment of Influenza A HA subtype H4(no Cys) Short Stem Domain sequence

<400> SEQUENCE: 186

Gln Asn Tyr Thr Gly Asn Pro Val Ile Cys Met Gly His His Ala Val
1 5 10 15

Ala Asn Gly Thr Met Val Lys Thr Leu Ala Asp Asp Gln Val Glu Val
20 25 30

Val Thr Ala Gln Glu Leu Val Glu Ser Gln Asn Leu Pro Glu Leu
35 40 45

<210> SEQ ID NO 187
<211> LENGTH: 47
<212> TYPE: PRT
<213> ORGANISM: Influenza virus A
<220> FEATURE:
<223> OTHER INFORMATION: N-terminal stem segment of Influenza A HA subtype H4(no Cys-delta 1) Short Stem Domain sequence

<400> SEQUENCE: 187

Gln Asn Tyr Thr Gly Asn Pro Val Ile Cys Met Gly His His Ala Val
1 5 10 15

Ala Asn Gly Thr Met Val Lys Thr Leu Ala Asp Asp Gln Val Glu Val
20 25 30

Val Thr Ala Gln Glu Leu Val Glu Ser Gln Asn Leu Pro Glu Leu
35 40 45

<210> SEQ ID NO 188
<211> LENGTH: 46
<212> TYPE: PRT
<213> ORGANISM: Influenza virus A
<220> FEATURE:
<223> OTHER INFORMATION: N-terminal stem segment of Influenza A HA subtype H4(no Cys-delta 3) Short Stem Domain sequence

<400> SEQUENCE: 188

Gln Asn Tyr Thr Gly Asn Pro Val Ile Cys Met Gly His His Ala Val
1 5 10 15

Ala Asn Gly Thr Met Val Lys Thr Leu Ala Asp Asp Gln Val Glu Val
20 25 30

Val Thr Ala Gln Glu Leu Val Glu Ser Gln Asn Leu Pro Glu
35 40 45

<210> SEQ ID NO 189
<211> LENGTH: 41
<212> TYPE: PRT
<213> ORGANISM: Influenza virus A
<220> FEATURE:

<223> OTHER INFORMATION: N-terminal stem segment of Influenza A HA
subtype H5(no Cys) Short Stem Domain sequence

<400> SEQUENCE: 189

```
Asp Gln Ile Cys Ile Gly Tyr His Ala Asn Lys Ser Thr Lys Gln Val
 1               5                  10                  15

Asp Thr Ile Met Glu Lys Asn Val Thr Val Thr His Ala Gln Asp Ile
            20                  25                  30

Leu Glu Arg Thr His Asn Gly Lys Leu
        35                  40
```

<210> SEQ ID NO 190
<211> LENGTH: 41
<212> TYPE: PRT
<213> ORGANISM: Influenza virus A
<220> FEATURE:
<223> OTHER INFORMATION: N-terminal stem segment of Influenza A HA
subtype H5(no Cys-delta 1) Short Stem Domain sequence

<400> SEQUENCE: 190

```
Asp Gln Ile Cys Ile Gly Tyr His Ala Asn Lys Ser Thr Lys Gln Val
 1               5                  10                  15

Asp Thr Ile Met Glu Lys Asn Val Thr Val Thr His Ala Gln Asp Ile
            20                  25                  30

Leu Glu Arg Thr His Asn Gly Lys Leu
        35                  40
```

<210> SEQ ID NO 191
<211> LENGTH: 40
<212> TYPE: PRT
<213> ORGANISM: Influenza virus A
<220> FEATURE:
<223> OTHER INFORMATION: N-terminal stem segment of Influenza A HA
subtype H5(no Cys-delta 3) Short Stem Domain sequence

<400> SEQUENCE: 191

```
Asp Gln Ile Cys Ile Gly Tyr His Ala Asn Lys Ser Thr Lys Gln Val
 1               5                  10                  15

Asp Thr Ile Met Glu Lys Asn Val Thr Val Thr His Ala Gln Asp Ile
            20                  25                  30

Leu Glu Arg Thr His Asn Gly Lys
        35                  40
```

<210> SEQ ID NO 192
<211> LENGTH: 41
<212> TYPE: PRT
<213> ORGANISM: Influenza virus A
<220> FEATURE:
<223> OTHER INFORMATION: N-terminal stem segment of Influenza A HA
subtype H6(no Cys) Short Stem Domain sequence

<400> SEQUENCE: 192

```
Asp Lys Ile Cys Ile Gly Tyr His Ala Asn Asn Ser Thr Thr Gln Ile
 1               5                  10                  15

Asp Thr Ile Leu Glu Lys Asn Val Thr Val Thr His Ser Val Glu Leu
            20                  25                  30

Leu Glu Asn Gln Lys Glu Glu Arg Phe
        35                  40
```

<210> SEQ ID NO 193
<211> LENGTH: 41
<212> TYPE: PRT
<213> ORGANISM: Influenza virus A
<220> FEATURE:
<223> OTHER INFORMATION: N-terminal stem segment of Influenza A HA subtype H6(no Cys-delta 1) Short Stem Domain sequence

<400> SEQUENCE: 193

```
Asp Lys Ile Cys Ile Gly Tyr His Ala Asn Asn Ser Thr Thr Gln Ile
 1               5                  10                  15

Asp Thr Ile Leu Glu Lys Asn Val Thr Val Thr His Ser Val Glu Leu
            20                  25                  30

Leu Glu Asn Gln Lys Glu Glu Arg Phe
        35                  40
```

<210> SEQ ID NO 194
<211> LENGTH: 40
<212> TYPE: PRT
<213> ORGANISM: Influenza virus A
<220> FEATURE:
<223> OTHER INFORMATION: N-terminal stem segment of Influenza A HA subtype H6(no Cys-delta 3) Short Stem Domain sequence

<400> SEQUENCE: 194

```
Asp Lys Ile Cys Ile Gly Tyr His Ala Asn Asn Ser Thr Thr Gln Ile
 1               5                  10                  15

Asp Thr Ile Leu Glu Lys Asn Val Thr Val Thr His Ser Val Glu Leu
            20                  25                  30

Leu Glu Asn Gln Lys Glu Glu Arg
        35                  40
```

<210> SEQ ID NO 195
<211> LENGTH: 41
<212> TYPE: PRT
<213> ORGANISM: Influenza virus A
<220> FEATURE:
<223> OTHER INFORMATION: N-terminal stem segment of Influenza A HA subtype H7(no Cys) Short Stem Domain sequence

<400> SEQUENCE: 195

```
Asp Lys Ile Cys Leu Gly His His Ala Val Ser Asn Gly Thr Lys Val
 1               5                  10                  15

Asn Thr Leu Thr Glu Arg Gly Val Glu Val Val Asn Ala Thr Glu Thr
            20                  25                  30

Val Glu Arg Thr Asn Ile Pro Lys Ile
        35                  40
```

<210> SEQ ID NO 196
<211> LENGTH: 41
<212> TYPE: PRT
<213> ORGANISM: Influenza virus A
<220> FEATURE:
<223> OTHER INFORMATION: N-terminal stem segment of Influenza A HA subtype H7(no Cys-delta 1) Short Stem Domain sequence

<400> SEQUENCE: 196

```
Asp Lys Ile Cys Leu Gly His His Ala Val Ser Asn Gly Thr Lys Val
 1               5                  10                  15

Asn Thr Leu Thr Glu Arg Gly Val Glu Val Val Asn Ala Thr Glu Thr
            20                  25                  30

Val Glu Arg Thr Asn Ile Pro Lys Ile
        35                  40
```

<210> SEQ ID NO 197
<211> LENGTH: 40
<212> TYPE: PRT

<213> ORGANISM: Influenza virus A
<220> FEATURE:
<223> OTHER INFORMATION: N-terminal stem segment of Influenza A HA subtype H7(no Cys-delta 3) Short Stem Domain sequence

<400> SEQUENCE: 197

```
Asp Lys Ile Cys Leu Gly His His Ala Val Ser Asn Gly Thr Lys Val
 1               5                  10                  15

Asn Thr Leu Thr Glu Arg Gly Val Glu Val Val Asn Ala Thr Glu Thr
            20                  25                  30

Val Glu Arg Thr Asn Ile Pro Lys
        35                  40
```

<210> SEQ ID NO 198
<211> LENGTH: 41
<212> TYPE: PRT
<213> ORGANISM: Influenza virus A
<220> FEATURE:
<223> OTHER INFORMATION: N-terminal stem segment of Influenza A HA subtype H8(no Cys) Short Stem Domain sequence

<400> SEQUENCE: 198

```
Asp Arg Ile Cys Ile Gly Tyr Gln Ser Asn Asn Ser Thr Asp Thr Val
 1               5                  10                  15

Asn Thr Leu Ile Glu Gln Asn Val Pro Val Thr Gln Thr Met Glu Leu
            20                  25                  30

Val Glu Thr Glu Lys His Pro Ala Tyr
        35                  40
```

<210> SEQ ID NO 199
<211> LENGTH: 41
<212> TYPE: PRT
<213> ORGANISM: Influenza virus A
<220> FEATURE:
<223> OTHER INFORMATION: N-terminal stem segment of Influenza A HA subtype H8(no Cys-delta 1) Short Stem Domain sequence

<400> SEQUENCE: 199

```
Asp Arg Ile Cys Ile Gly Tyr Gln Ser Asn Asn Ser Thr Asp Thr Val
 1               5                  10                  15

Asn Thr Leu Ile Glu Gln Asn Val Pro Val Thr Gln Thr Met Glu Leu
            20                  25                  30

Val Glu Thr Glu Lys His Pro Ala Tyr
        35                  40
```

<210> SEQ ID NO 200
<211> LENGTH: 40
<212> TYPE: PRT
<213> ORGANISM: Influenza virus A
<220> FEATURE:
<223> OTHER INFORMATION: N-terminal stem segment of Influenza A HA subtype H8(no Cys-delta 3) Short Stem Domain sequence

<400> SEQUENCE: 200

```
Asp Arg Ile Cys Ile Gly Tyr Gln Ser Asn Asn Ser Thr Asp Thr Val
 1               5                  10                  15

Asn Thr Leu Ile Glu Gln Asn Val Pro Val Thr Gln Thr Met Glu Leu
            20                  25                  30

Val Glu Thr Glu Lys His Pro Ala
        35                  40
```

<210> SEQ ID NO 201
<211> LENGTH: 41

```
<212> TYPE: PRT
<213> ORGANISM: Influenza virus A
<220> FEATURE:
<223> OTHER INFORMATION: N-terminal stem segment of Influenza A
      HA subtype H9(no Cys) Short Stem Domain sequence

<400> SEQUENCE: 201

Asp Lys Ile Cys Ile Gly Tyr Gln Ser Thr Asn Ser Thr Glu Thr Val
1               5                   10                  15

Asp Thr Leu Thr Glu Ser Asn Val Pro Val Thr His Thr Lys Glu Leu
            20                  25                  30

Leu His Thr Glu His Asn Gly Met Leu
        35                  40


<210> SEQ ID NO 202
<211> LENGTH: 41
<212> TYPE: PRT
<213> ORGANISM: Influenza virus A
<220> FEATURE:
<223> OTHER INFORMATION: N-terminal stem segment of Influenza A HA
      subtype H9(no Cys-delta 1) Short Stem Domain sequence

<400> SEQUENCE: 202

Asp Lys Ile Cys Ile Gly Tyr Gln Ser Thr Asn Ser Thr Glu Thr Val
1               5                   10                  15

Asp Thr Leu Thr Glu Ser Asn Val Pro Val Thr His Thr Lys Glu Leu
            20                  25                  30

Leu His Thr Glu His Asn Gly Met Leu
        35                  40


<210> SEQ ID NO 203
<211> LENGTH: 40
<212> TYPE: PRT
<213> ORGANISM: Influenza virus A
<220> FEATURE:
<223> OTHER INFORMATION: N-terminal stem segment of Influenza A HA
      subtype H9(no Cys-delta 3) Short Stem Domain sequence

<400> SEQUENCE: 203

Asp Lys Ile Cys Ile Gly Tyr Gln Ser Thr Asn Ser Thr Glu Thr Val
1               5                   10                  15

Asp Thr Leu Thr Glu Ser Asn Val Pro Val Thr His Thr Lys Glu Leu
            20                  25                  30

Leu His Thr Glu His Asn Gly Met
        35                  40


<210> SEQ ID NO 204
<211> LENGTH: 42
<212> TYPE: PRT
<213> ORGANISM: Influenza virus A
<220> FEATURE:
<223> OTHER INFORMATION: N-terminal stem segment of Influenza A
      HA subtype H10(no Cys) Short Stem Domain sequence

<400> SEQUENCE: 204

Leu Asp Arg Ile Cys Leu Gly His His Ala Val Ala Asn Gly Thr Ile
1               5                   10                  15

Val Lys Thr Leu Thr Asn Glu Gln Glu Glu Val Thr Asn Ala Thr Glu
            20                  25                  30

Thr Val Glu Ser Thr Asn Leu Asn Lys Leu
        35                  40


<210> SEQ ID NO 205
```

```
<211> LENGTH: 42
<212> TYPE: PRT
<213> ORGANISM: Influenza virus A
<220> FEATURE:
<223> OTHER INFORMATION: N-terminal stem segment of Influenza A HA
      subtype H10(no Cys-delta 1) Short Stem Domain sequence

<400> SEQUENCE: 205

Leu Asp Arg Ile Cys Leu Gly His His Ala Val Ala Asn Gly Thr Ile
 1               5                  10                  15

Val Lys Thr Leu Thr Asn Glu Gln Glu Glu Val Thr Asn Ala Thr Glu
            20                  25                  30

Thr Val Glu Ser Thr Asn Leu Asn Lys Leu
        35                  40


<210> SEQ ID NO 206
<211> LENGTH: 41
<212> TYPE: PRT
<213> ORGANISM: Influenza virus A
<220> FEATURE:
<223> OTHER INFORMATION: N-terminal stem segment of Influenza A HA
      subtype H10(no Cys-delta 3) Short Stem Domain sequence

<400> SEQUENCE: 206

Leu Asp Arg Ile Cys Leu Gly His His Ala Val Ala Asn Gly Thr Ile
 1               5                  10                  15

Val Lys Thr Leu Thr Asn Glu Gln Glu Glu Val Thr Asn Ala Thr Glu
            20                  25                  30

Thr Val Glu Ser Thr Asn Leu Asn Lys
        35                  40


<210> SEQ ID NO 207
<211> LENGTH: 41
<212> TYPE: PRT
<213> ORGANISM: Influenza virus A
<220> FEATURE:
<223> OTHER INFORMATION: N-terminal stem segment of Influenza A
      HA subtype H11(no Cys) Short Stem Domain sequence

<400> SEQUENCE: 207

Asp Glu Ile Cys Ile Gly Tyr Leu Ser Asn Asn Ser Thr Asp Lys Val
 1               5                  10                  15

Asp Thr Ile Ile Glu Asn Asn Val Thr Val Thr Ser Ser Val Glu Leu
            20                  25                  30

Val Glu Thr Glu His Thr Gly Ser Phe
        35                  40


<210> SEQ ID NO 208
<211> LENGTH: 41
<212> TYPE: PRT
<213> ORGANISM: Influenza virus A
<220> FEATURE:
<223> OTHER INFORMATION: N-terminal stem segment of Influenza A HA
      subtype H11(no Cys-delta 1) Short Stem Domain sequence

<400> SEQUENCE: 208

Asp Glu Ile Cys Ile Gly Tyr Leu Ser Asn Asn Ser Thr Asp Lys Val
 1               5                  10                  15

Asp Thr Ile Ile Glu Asn Asn Val Thr Val Thr Ser Ser Val Glu Leu
            20                  25                  30

Val Glu Thr Glu His Thr Gly Ser Phe
        35                  40
```

```
<210> SEQ ID NO 209
<211> LENGTH: 40
<212> TYPE: PRT
<213> ORGANISM: Influenza virus A
<220> FEATURE:
<223> OTHER INFORMATION: N-terminal stem segment of Influenza A HA
      subtype H11(no Cys-delta 3) Short Stem Domain sequence

<400> SEQUENCE: 209

Asp Glu Ile Cys Ile Gly Tyr Leu Ser Asn Asn Ser Thr Asp Lys Val
 1               5                  10                  15

Asp Thr Ile Ile Glu Asn Asn Val Thr Val Thr Ser Ser Val Glu Leu
            20                  25                  30

Val Glu Thr Glu His Thr Gly Ser
        35                  40


<210> SEQ ID NO 210
<211> LENGTH: 41
<212> TYPE: PRT
<213> ORGANISM: Influenza virus A
<220> FEATURE:
<223> OTHER INFORMATION: N-terminal stem segment of Influenza A
      HA subtype H12(no Cys) Short Stem Domain sequence

<400> SEQUENCE: 210

Asp Lys Ile Cys Ile Gly Tyr Gln Thr Asn Asn Ser Thr Glu Thr Val
 1               5                  10                  15

Asn Thr Leu Ser Glu Gln Asn Val Pro Val Thr Gln Val Glu Glu Leu
            20                  25                  30

Val His Arg Gly Ile Asp Pro Ile Leu
        35                  40


<210> SEQ ID NO 211
<211> LENGTH: 41
<212> TYPE: PRT
<213> ORGANISM: Influenza virus A
<220> FEATURE:
<223> OTHER INFORMATION: N-terminal stem segment of Influenza A HA
      subtype H12(no Cys-delta 1) Short Stem Domain sequence

<400> SEQUENCE: 211

Asp Lys Ile Cys Ile Gly Tyr Gln Thr Asn Asn Ser Thr Glu Thr Val
 1               5                  10                  15

Asn Thr Leu Ser Glu Gln Asn Val Pro Val Thr Gln Val Glu Glu Leu
            20                  25                  30

Val His Arg Gly Ile Asp Pro Ile Leu
        35                  40


<210> SEQ ID NO 212
<211> LENGTH: 40
<212> TYPE: PRT
<213> ORGANISM: Influenza virus A
<220> FEATURE:
<223> OTHER INFORMATION: N-terminal stem segment of Influenza A HA
      subtype H12(no Cys-delta 3) Short Stem Domain sequence

<400> SEQUENCE: 212

Asp Lys Ile Cys Ile Gly Tyr Gln Thr Asn Asn Ser Thr Glu Thr Val
 1               5                  10                  15

Asn Thr Leu Ser Glu Gln Asn Val Pro Val Thr Gln Val Glu Glu Leu
            20                  25                  30

Val His Arg Gly Ile Asp Pro Ile
        35                  40
```

<210> SEQ ID NO 213
<211> LENGTH: 41
<212> TYPE: PRT
<213> ORGANISM: Influenza virus A
<220> FEATURE:
<223> OTHER INFORMATION: N-terminal stem segment of Influenza A HA subtype H13(no Cys) Short Stem Domain sequence

<400> SEQUENCE: 213

```
Asp Arg Ile Cys Val Gly Tyr Leu Ser Thr Asn Ser Ser Glu Arg Val
 1               5                  10                  15

Asp Thr Leu Leu Glu Asn Gly Val Pro Val Thr Ser Ser Ile Asp Leu
            20                  25                  30

Ile Glu Thr Asn His Thr Gly Thr Tyr
        35                  40
```

<210> SEQ ID NO 214
<211> LENGTH: 41
<212> TYPE: PRT
<213> ORGANISM: Influenza virus A
<220> FEATURE:
<223> OTHER INFORMATION: N-terminal stem segment of Influenza A HA subtype H13(no Cys-delta 1) Short Stem Domain sequence

<400> SEQUENCE: 214

```
Asp Arg Ile Cys Val Gly Tyr Leu Ser Thr Asn Ser Ser Glu Arg Val
 1               5                  10                  15

Asp Thr Leu Leu Glu Asn Gly Val Pro Val Thr Ser Ser Ile Asp Leu
            20                  25                  30

Ile Glu Thr Asn His Thr Gly Thr Tyr
        35                  40
```

<210> SEQ ID NO 215
<211> LENGTH: 40
<212> TYPE: PRT
<213> ORGANISM: Influenza virus A
<220> FEATURE:
<223> OTHER INFORMATION: N-terminal stem segment of Influenza A HA subtype H13(no Cys-delta 3) Short Stem Domain sequence

<400> SEQUENCE: 215

```
Asp Arg Ile Cys Val Gly Tyr Leu Ser Thr Asn Ser Ser Glu Arg Val
 1               5                  10                  15

Asp Thr Leu Leu Glu Asn Gly Val Pro Val Thr Ser Ser Ile Asp Leu
            20                  25                  30

Ile Glu Thr Asn His Thr Gly Thr
        35                  40
```

<210> SEQ ID NO 216
<211> LENGTH: 50
<212> TYPE: PRT
<213> ORGANISM: Influenza virus A
<220> FEATURE:
<223> OTHER INFORMATION: N-terminal stem segment of Influenza A HA subtype H14(no Cys) Short Stem Domain sequence

<400> SEQUENCE: 216

```
Gln Ile Thr Asn Gly Thr Thr Gly Asn Pro Ile Ile Cys Leu Gly His
 1               5                  10                  15

His Ala Val Glu Asn Gly Thr Ser Val Lys Thr Leu Thr Asp Asn His
            20                  25                  30

Val Glu Val Val Ser Ala Lys Glu Leu Val Glu Thr Asn His Thr Asp
        35                  40                  45
```

```
Glu Leu
    50


<210> SEQ ID NO 217
<211> LENGTH: 50
<212> TYPE: PRT
<213> ORGANISM: Influenza virus A
<220> FEATURE:
<223> OTHER INFORMATION: N-terminal stem segment of Influenza A HA
      subtype H14(no Cys-delta 1) Short Stem Domain sequence

<400> SEQUENCE: 217

Gln Ile Thr Asn Gly Thr Thr Gly Asn Pro Ile Ile Cys Leu Gly His
 1               5                  10                  15

His Ala Val Glu Asn Gly Thr Ser Val Lys Thr Leu Thr Asp Asn His
            20                  25                  30

Val Glu Val Val Ser Ala Lys Glu Leu Val Glu Thr Asn His Thr Asp
        35                  40                  45

Glu Leu
    50


<210> SEQ ID NO 218
<211> LENGTH: 49
<212> TYPE: PRT
<213> ORGANISM: Influenza virus A
<220> FEATURE:
<223> OTHER INFORMATION: N-terminal stem segment of Influenza A HA
      subtype H14(no Cys-delta 3) Short Stem Domain sequence

<400> SEQUENCE: 218

Gln Ile Thr Asn Gly Thr Thr Gly Asn Pro Ile Ile Cys Leu Gly His
 1               5                  10                  15

His Ala Val Glu Asn Gly Thr Ser Val Lys Thr Leu Thr Asp Asn His
            20                  25                  30

Val Glu Val Val Ser Ala Lys Glu Leu Val Glu Thr Asn His Thr Asp
        35                  40                  45

Glu


<210> SEQ ID NO 219
<211> LENGTH: 41
<212> TYPE: PRT
<213> ORGANISM: Influenza virus A
<220> FEATURE:
<223> OTHER INFORMATION: N-terminal stem segment of Influenza A
      HA subtype H15(no Cys) Short Stem Domain sequence

<400> SEQUENCE: 219

Asp Lys Ile Cys Leu Gly His His Ala Val Ala Asn Gly Thr Lys Val
 1               5                  10                  15

Asn Thr Leu Thr Glu Arg Gly Val Glu Val Val Asn Ala Thr Glu Thr
            20                  25                  30

Val Glu Ile Thr Gly Ile Asp Lys Val
        35                  40


<210> SEQ ID NO 220
<211> LENGTH: 41
<212> TYPE: PRT
<213> ORGANISM: Influenza virus A
<220> FEATURE:
<223> OTHER INFORMATION: N-terminal stem segment of Influenza A HA
      subtype H15(no Cys-delta 1) Short Stem Domain sequence

<400> SEQUENCE: 220
```

```
Asp Lys Ile Cys Leu Gly His His Ala Val Ala Asn Gly Thr Lys Val
1               5                   10                  15

Asn Thr Leu Thr Glu Arg Gly Val Glu Val Val Asn Ala Thr Glu Thr
            20                  25                  30

Val Glu Ile Thr Gly Ile Asp Lys Val
        35                  40


<210> SEQ ID NO 221
<211> LENGTH: 40
<212> TYPE: PRT
<213> ORGANISM: Influenza virus A
<220> FEATURE:
<223> OTHER INFORMATION: N-terminal stem segment of Influenza A HA
      subtype H15(no Cys-delta 3) Short Stem Domain sequence

<400> SEQUENCE: 221

Asp Lys Ile Cys Leu Gly His His Ala Val Ala Asn Gly Thr Lys Val
1               5                   10                  15

Asn Thr Leu Thr Glu Arg Gly Val Glu Val Val Asn Ala Thr Glu Thr
            20                  25                  30

Val Glu Ile Thr Gly Ile Asp Lys
        35                  40


<210> SEQ ID NO 222
<211> LENGTH: 41
<212> TYPE: PRT
<213> ORGANISM: Influenza virus A
<220> FEATURE:
<223> OTHER INFORMATION: N-terminal stem segment of Influenza A
      HA subtype H16(no Cys) Short Stem Domain sequence

<400> SEQUENCE: 222

Asp Lys Ile Cys Ile Gly Tyr Leu Ser Asn Asn Ser Ser Asp Thr Val
1               5                   10                  15

Asp Thr Leu Thr Glu Asn Gly Val Pro Val Thr Ser Ser Val Asp Leu
            20                  25                  30

Val Glu Thr Asn His Thr Gly Thr Tyr
        35                  40


<210> SEQ ID NO 223
<211> LENGTH: 41
<212> TYPE: PRT
<213> ORGANISM: Influenza virus A
<220> FEATURE:
<223> OTHER INFORMATION: N-terminal stem segment of Influenza A HA
      subtype H16(no Cys-delta 1) Short Stem Domain sequence

<400> SEQUENCE: 223

Asp Lys Ile Cys Ile Gly Tyr Leu Ser Asn Asn Ser Ser Asp Thr Val
1               5                   10                  15

Asp Thr Leu Thr Glu Asn Gly Val Pro Val Thr Ser Ser Val Asp Leu
            20                  25                  30

Val Glu Thr Asn His Thr Gly Thr Tyr
        35                  40


<210> SEQ ID NO 224
<211> LENGTH: 40
<212> TYPE: PRT
<213> ORGANISM: Influenza virus A
<220> FEATURE:
<223> OTHER INFORMATION: N-terminal stem segment of Influenza A HA
      subtype H16(no Cys-delta 3) Short Stem Domain sequence
```

<400> SEQUENCE: 224

Asp Lys Ile Cys Ile Gly Tyr Leu Ser Asn Asn Ser Ser Asp Thr Val
1 5 10 15

Asp Thr Leu Thr Glu Asn Gly Val Pro Val Thr Ser Ser Val Asp Leu
20 25 30

Val Glu Thr Asn His Thr Gly Thr
35 40

<210> SEQ ID NO 225

<400> SEQUENCE: 225

000

<210> SEQ ID NO 226
<211> LENGTH: 52
<212> TYPE: PRT
<213> ORGANISM: Influenza virus A
<220> FEATURE:
<223> OTHER INFORMATION: C-terminal stem segment of Influenza A HA subtype H1(no Cys)

<400> SEQUENCE: 226

Asn Thr Lys Cys Gln Thr Pro Leu Gly Ala Ile Asn Ser Ser Leu Pro
1 5 10 15

Tyr Gln Asn Ile His Pro Val Thr Ile Gly Glu Cys Pro Lys Tyr Val
20 25 30

Arg Ser Ala Lys Leu Arg Met Val Thr Gly Leu Arg Asn Asn Pro Ser
35 40 45

Ile Gln Ser Arg
50

<210> SEQ ID NO 227
<211> LENGTH: 51
<212> TYPE: PRT
<213> ORGANISM: Influenza virus A
<220> FEATURE:
<223> OTHER INFORMATION: C-terminal stem segment of Influenza A HA subtype H1(no Cys-delta 1)

<400> SEQUENCE: 227

Thr Lys Cys Gln Thr Pro Leu Gly Ala Ile Asn Ser Ser Leu Pro Tyr
1 5 10 15

Gln Asn Ile His Pro Val Thr Ile Gly Glu Cys Pro Lys Tyr Val Arg
20 25 30

Ser Ala Lys Leu Arg Met Val Thr Gly Leu Arg Asn Asn Pro Ser Ile
35 40 45

Gln Ser Arg
50

<210> SEQ ID NO 228
<211> LENGTH: 50
<212> TYPE: PRT
<213> ORGANISM: Influenza virus A
<220> FEATURE:
<223> OTHER INFORMATION: C-terminal stem segment of Influenza A HA subtype H1(no Cys-delta 3)

<400> SEQUENCE: 228

Lys Cys Gln Thr Pro Leu Gly Ala Ile Asn Ser Ser Leu Pro Tyr Gln
1 5 10 15

Asn Ile His Pro Val Thr Ile Gly Glu Cys Pro Lys Tyr Val Arg Ser

```
            20                  25                  30

Ala Lys Leu Arg Met Val Thr Gly Leu Arg Asn Asn Pro Ser Ile Gln
        35                  40                  45

Ser Arg
    50


<210> SEQ ID NO 229
<211> LENGTH: 52
<212> TYPE: PRT
<213> ORGANISM: Influenza virus A
<220> FEATURE:
<223> OTHER INFORMATION: C-terminal stem segment of Influenza A HA
      subtype H2(no Cys)

<400> SEQUENCE: 229

Glu Thr Lys Cys Gln Thr Pro Leu Gly Ala Ile Asn Thr Thr Leu Pro
 1               5                  10                  15

Phe His Asn Val His Pro Leu Thr Ile Gly Glu Cys Pro Lys Tyr Val
            20                  25                  30

Lys Ser Glu Arg Leu Val Leu Ala Thr Gly Leu Arg Asn Val Pro Gln
        35                  40                  45

Ile Glu Ser Arg
    50


<210> SEQ ID NO 230
<211> LENGTH: 51
<212> TYPE: PRT
<213> ORGANISM: Influenza virus A
<220> FEATURE:
<223> OTHER INFORMATION: C-terminal stem segment of Influenza A HA
      subtype H2(no Cys-delta 1)

<400> SEQUENCE: 230

Thr Lys Cys Gln Thr Pro Leu Gly Ala Ile Asn Thr Thr Leu Pro Phe
 1               5                  10                  15

His Asn Val His Pro Leu Thr Ile Gly Glu Cys Pro Lys Tyr Val Lys
            20                  25                  30

Ser Glu Arg Leu Val Leu Ala Thr Gly Leu Arg Asn Val Pro Gln Ile
        35                  40                  45

Glu Ser Arg
    50


<210> SEQ ID NO 231
<211> LENGTH: 50
<212> TYPE: PRT
<213> ORGANISM: Influenza virus A
<220> FEATURE:
<223> OTHER INFORMATION: C-terminal stem segment of Influenza A HA
      subtype H2(no Cys-delta 3)

<400> SEQUENCE: 231

Lys Cys Gln Thr Pro Leu Gly Ala Ile Asn Thr Thr Leu Pro Phe His
 1               5                  10                  15

Asn Val His Pro Leu Thr Ile Gly Glu Cys Pro Lys Tyr Val Lys Ser
            20                  25                  30

Glu Arg Leu Val Leu Ala Thr Gly Leu Arg Asn Val Pro Gln Ile Glu
        35                  40                  45

Ser Arg
    50


<210> SEQ ID NO 232
```

<211> LENGTH: 52
<212> TYPE: PRT
<213> ORGANISM: Influenza virus A
<220> FEATURE:
<223> OTHER INFORMATION: C-terminal stem segment of Influenza A HA subtype H3(no Cys)

<400> SEQUENCE: 232

Ile Ser Glu Cys Ile Thr Pro Asn Gly Ser Ile Pro Asn Asp Lys Pro
1 5 10 15

Phe Gln Asn Val Asn Lys Ile Thr Tyr Gly Ala Cys Pro Lys Tyr Val
20 25 30

Lys Gln Asn Thr Leu Lys Leu Ala Thr Gly Met Arg Asn Val Pro Glu
35 40 45

Lys Gln Thr Arg
50

<210> SEQ ID NO 233
<211> LENGTH: 51
<212> TYPE: PRT
<213> ORGANISM: Influenza virus A
<220> FEATURE:
<223> OTHER INFORMATION: C-terminal stem segment of Influenza A HA subtype H3(no Cys-delta 1)

<400> SEQUENCE: 233

Ser Glu Cys Ile Thr Pro Asn Gly Ser Ile Pro Asn Asp Lys Pro Phe
1 5 10 15

Gln Asn Val Asn Lys Ile Thr Tyr Gly Ala Cys Pro Lys Tyr Val Lys
20 25 30

Gln Asn Thr Leu Lys Leu Ala Thr Gly Met Arg Asn Val Pro Glu Lys
35 40 45

Gln Thr Arg
50

<210> SEQ ID NO 234
<211> LENGTH: 50
<212> TYPE: PRT
<213> ORGANISM: Influenza virus A
<220> FEATURE:
<223> OTHER INFORMATION: C-terminal stem segment of Influenza A HA subtype H3(no Cys-delta 3)

<400> SEQUENCE: 234

Glu Cys Ile Thr Pro Asn Gly Ser Ile Pro Asn Asp Lys Pro Phe Gln
1 5 10 15

Asn Val Asn Lys Ile Thr Tyr Gly Ala Cys Pro Lys Tyr Val Lys Gln
20 25 30

Asn Thr Leu Lys Leu Ala Thr Gly Met Arg Asn Val Pro Glu Lys Gln
35 40 45

Thr Arg
50

<210> SEQ ID NO 235
<211> LENGTH: 52
<212> TYPE: PRT
<213> ORGANISM: Influenza virus A
<220> FEATURE:
<223> OTHER INFORMATION: C-terminal stem segment of Influenza A HA subtype H4(no Cys)

<400> SEQUENCE: 235

Val Ser Lys Cys His Thr Asp Lys Gly Ser Leu Ser Thr Thr Lys Pro

```
 1               5                   10                  15

Phe Gln Asn Ile Ser Arg Ile Ala Val Gly Asp Cys Pro Arg Tyr Val
            20                  25                  30

Lys Gln Gly Ser Leu Lys Leu Ala Thr Gly Met Arg Asn Ile Pro Glu
        35                  40                  45

Lys Ala Ser Arg
    50


<210> SEQ ID NO 236
<211> LENGTH: 51
<212> TYPE: PRT
<213> ORGANISM: Influenza virus A
<220> FEATURE:
<223> OTHER INFORMATION: C-terminal stem segment of Influenza A HA
      subtype H4(no Cys-delta 1)

<400> SEQUENCE: 236

Ser Lys Cys His Thr Asp Lys Gly Ser Leu Ser Thr Thr Lys Pro Phe
 1               5                   10                  15

Gln Asn Ile Ser Arg Ile Ala Val Gly Asp Cys Pro Arg Tyr Val Lys
            20                  25                  30

Gln Gly Ser Leu Lys Leu Ala Thr Gly Met Arg Asn Ile Pro Glu Lys
        35                  40                  45

Ala Ser Arg
    50


<210> SEQ ID NO 237
<211> LENGTH: 50
<212> TYPE: PRT
<213> ORGANISM: Influenza virus A
<220> FEATURE:
<223> OTHER INFORMATION: C-terminal stem segment of Influenza A HA
      subtype H4(no Cys-delta 3)

<400> SEQUENCE: 237

Lys Cys His Thr Asp Lys Gly Ser Leu Ser Thr Thr Lys Pro Phe Gln
 1               5                   10                  15

Asn Ile Ser Arg Ile Ala Val Gly Asp Cys Pro Arg Tyr Val Lys Gln
            20                  25                  30

Gly Ser Leu Lys Leu Ala Thr Gly Met Arg Asn Ile Pro Glu Lys Ala
        35                  40                  45

Ser Arg
    50


<210> SEQ ID NO 238
<211> LENGTH: 52
<212> TYPE: PRT
<213> ORGANISM: Influenza virus A
<220> FEATURE:
<223> OTHER INFORMATION: C-terminal stem segment of Influenza A
      HA subtype H5(no Cys)

<400> SEQUENCE: 238

Asp Thr Lys Cys Gln Thr Pro Val Gly Glu Ile Asn Ser Ser Met Pro
 1               5                   10                  15

Phe His Asn Ile His Pro His Thr Ile Gly Glu Cys Pro Lys Tyr Val
            20                  25                  30

Lys Ser Asp Arg Leu Val Leu Ala Thr Gly Leu Arg Asn Val Pro Gln
        35                  40                  45

Arg Lys Lys Arg
    50
```

<210> SEQ ID NO 239
<211> LENGTH: 51
<212> TYPE: PRT
<213> ORGANISM: Influenza virus A
<220> FEATURE:
<223> OTHER INFORMATION: C-terminal stem segment of Influenza A HA
subtype H5(no Cys-delta 1)

<400> SEQUENCE: 239

```
Thr Lys Cys Gln Thr Pro Val Gly Glu Ile Asn Ser Ser Met Pro Phe
 1               5                  10                  15

His Asn Ile His Pro His Thr Ile Gly Glu Cys Pro Lys Tyr Val Lys
            20                  25                  30

Ser Asp Arg Leu Val Leu Ala Thr Gly Leu Arg Asn Val Pro Gln Arg
        35                  40                  45

Lys Lys Arg
    50
```

<210> SEQ ID NO 240
<211> LENGTH: 50
<212> TYPE: PRT
<213> ORGANISM: Influenza virus A
<220> FEATURE:
<223> OTHER INFORMATION: C-terminal stem segment of Influenza A HA
subtype H5(no Cys-delta 3)

<400> SEQUENCE: 240

```
Lys Cys Gln Thr Pro Val Gly Glu Ile Asn Ser Ser Met Pro Phe His
 1               5                  10                  15

Asn Ile His Pro His Thr Ile Gly Glu Cys Pro Lys Tyr Val Lys Ser
            20                  25                  30

Asp Arg Leu Val Leu Ala Thr Gly Leu Arg Asn Val Pro Gln Arg Lys
        35                  40                  45

Lys Arg
    50
```

<210> SEQ ID NO 241
<211> LENGTH: 52
<212> TYPE: PRT
<213> ORGANISM: Influenza virus A
<220> FEATURE:
<223> OTHER INFORMATION: C-terminal stem segment of Influenza A
HA subtype H6(no Cys)

<400> SEQUENCE: 241

```
Asp Ala Thr Cys Gln Thr Val Ala Gly Val Leu Arg Thr Asn Lys Thr
 1               5                  10                  15

Phe Gln Asn Val Ser Pro Leu Trp Ile Gly Glu Cys Pro Lys Tyr Val
            20                  25                  30

Lys Ser Glu Ser Leu Arg Leu Ala Thr Gly Leu Arg Asn Val Pro Gln
        35                  40                  45

Ile Glu Thr Arg
    50
```

<210> SEQ ID NO 242
<211> LENGTH: 51
<212> TYPE: PRT
<213> ORGANISM: Influenza virus A
<220> FEATURE:
<223> OTHER INFORMATION: C-terminal stem segment of Influenza A HA
subtype H6(no Cys-delta 1)

<400> SEQUENCE: 242

Ala Thr Cys Gln Thr Val Ala Gly Val Leu Arg Thr Asn Lys Thr Phe
1 5 10 15

Gln Asn Val Ser Pro Leu Trp Ile Gly Glu Cys Pro Lys Tyr Val Lys
20 25 30

Ser Glu Ser Leu Arg Leu Ala Thr Gly Leu Arg Asn Val Pro Gln Ile
35 40 45

Glu Thr Arg
50

<210> SEQ ID NO 243
<211> LENGTH: 50
<212> TYPE: PRT
<213> ORGANISM: Influenza virus A
<220> FEATURE:
<223> OTHER INFORMATION: C-terminal stem segment of Influenza A HA subtype H6(no Cys-delta 3)

<400> SEQUENCE: 243

Thr Cys Gln Thr Val Ala Gly Val Leu Arg Thr Asn Lys Thr Phe Gln
1 5 10 15

Asn Val Ser Pro Leu Trp Ile Gly Glu Cys Pro Lys Tyr Val Lys Ser
20 25 30

Glu Ser Leu Arg Leu Ala Thr Gly Leu Arg Asn Val Pro Gln Ile Glu
35 40 45

Thr Arg
50

<210> SEQ ID NO 244
<211> LENGTH: 56
<212> TYPE: PRT
<213> ORGANISM: Influenza virus A
<220> FEATURE:
<223> OTHER INFORMATION: C-terminal stem segment of Influenza A HA subtype H7(no Cys)

<400> SEQUENCE: 244

Glu Gly Glu Cys Tyr His Ser Gly Gly Thr Ile Thr Ser Arg Leu Pro
1 5 10 15

Phe Gln Asn Ile Asn Ser Arg Ala Val Gly Lys Cys Pro Arg Tyr Val
20 25 30

Lys Gln Glu Ser Leu Leu Leu Ala Thr Gly Met Lys Asn Val Pro Glu
35 40 45

Pro Ser Lys Lys Arg Lys Lys Arg
50 55

<210> SEQ ID NO 245
<211> LENGTH: 55
<212> TYPE: PRT
<213> ORGANISM: Influenza virus A
<220> FEATURE:
<223> OTHER INFORMATION: C-terminal stem segment of Influenza A HA subtype H7(no Cys-delta 1)

<400> SEQUENCE: 245

Gly Glu Cys Tyr His Ser Gly Gly Thr Ile Thr Ser Arg Leu Pro Phe
1 5 10 15

Gln Asn Ile Asn Ser Arg Ala Val Gly Lys Cys Pro Arg Tyr Val Lys
20 25 30

Gln Glu Ser Leu Leu Leu Ala Thr Gly Met Lys Asn Val Pro Glu Pro
35 40 45

```
Ser Lys Lys Arg Lys Lys Arg
    50                  55


<210> SEQ ID NO 246
<211> LENGTH: 54
<212> TYPE: PRT
<213> ORGANISM: Influenza virus A
<220> FEATURE:
<223> OTHER INFORMATION: C-terminal stem segment of Influenza A HA
      subtype H7(no Cys-delta 3)

<400> SEQUENCE: 246

Glu Cys Tyr His Ser Gly Gly Thr Ile Thr Ser Arg Leu Pro Phe Gln
 1               5                  10                  15

Asn Ile Asn Ser Arg Ala Val Gly Lys Cys Pro Arg Tyr Val Lys Gln
            20                  25                  30

Glu Ser Leu Leu Leu Ala Thr Gly Met Lys Asn Val Pro Glu Pro Ser
        35                  40                  45

Lys Lys Arg Lys Lys Arg
    50


<210> SEQ ID NO 247
<211> LENGTH: 52
<212> TYPE: PRT
<213> ORGANISM: Influenza virus A
<220> FEATURE:
<223> OTHER INFORMATION: C-terminal stem segment of Influenza A
      HA subtype H8(no Cys)

<400> SEQUENCE: 247

Asn Thr Lys Cys Gln Thr Tyr Ala Gly Ala Ile Asn Ser Ser Lys Pro
 1               5                  10                  15

Phe Gln Asn Ala Ser Arg His Tyr Met Gly Glu Cys Pro Lys Tyr Val
            20                  25                  30

Lys Lys Ala Ser Leu Arg Leu Ala Val Gly Leu Arg Asn Thr Pro Ser
        35                  40                  45

Val Glu Pro Arg
    50


<210> SEQ ID NO 248
<211> LENGTH: 51
<212> TYPE: PRT
<213> ORGANISM: Influenza virus A
<220> FEATURE:
<223> OTHER INFORMATION: C-terminal stem segment of Influenza A HA
      subtype H8(no Cys-delta 1)

<400> SEQUENCE: 248

Thr Lys Cys Gln Thr Tyr Ala Gly Ala Ile Asn Ser Ser Lys Pro Phe
 1               5                  10                  15

Gln Asn Ala Ser Arg His Tyr Met Gly Glu Cys Pro Lys Tyr Val Lys
            20                  25                  30

Lys Ala Ser Leu Arg Leu Ala Val Gly Leu Arg Asn Thr Pro Ser Val
        35                  40                  45

Glu Pro Arg
    50


<210> SEQ ID NO 249
<211> LENGTH: 50
<212> TYPE: PRT
<213> ORGANISM: Influenza virus A
<220> FEATURE:
```

<223> OTHER INFORMATION: C-terminal stem segment of Influenza A HA subtype H8(no Cys-delta 3)

<400> SEQUENCE: 249

Lys Cys Gln Thr Tyr Ala Gly Ala Ile Asn Ser Ser Lys Pro Phe Gln
1 5 10 15

Asn Ala Ser Arg His Tyr Met Gly Glu Cys Pro Lys Tyr Val Lys Lys
20 25 30

Ala Ser Leu Arg Leu Ala Val Gly Leu Arg Asn Thr Pro Ser Val Glu
35 40 45

Pro Arg
50

<210> SEQ ID NO 250
<211> LENGTH: 52
<212> TYPE: PRT
<213> ORGANISM: Influenza virus A
<220> FEATURE:
<223> OTHER INFORMATION: C-terminal stem segment of Influenza A HA subtype H9(no Cys)

<400> SEQUENCE: 250

Val Val Gln Cys Gln Thr Glu Lys Gly Gly Leu Asn Thr Thr Leu Pro
1 5 10 15

Phe His Asn Ile Ser Lys Tyr Ala Phe Gly Asn Cys Pro Lys Tyr Val
20 25 30

Gly Val Lys Ser Leu Lys Leu Pro Val Gly Leu Arg Asn Val Pro Ala
35 40 45

Val Ser Ser Arg
50

<210> SEQ ID NO 251
<211> LENGTH: 51
<212> TYPE: PRT
<213> ORGANISM: Influenza virus A
<220> FEATURE:
<223> OTHER INFORMATION: C-terminal stem segment of Influenza A HA subtype H9(no Cys-delta 1)

<400> SEQUENCE: 251

Val Gln Cys Gln Thr Glu Lys Gly Gly Leu Asn Thr Thr Leu Pro Phe
1 5 10 15

His Asn Ile Ser Lys Tyr Ala Phe Gly Asn Cys Pro Lys Tyr Val Gly
20 25 30

Val Lys Ser Leu Lys Leu Pro Val Gly Leu Arg Asn Val Pro Ala Val
35 40 45

Ser Ser Arg
50

<210> SEQ ID NO 252
<211> LENGTH: 50
<212> TYPE: PRT
<213> ORGANISM: Influenza virus A
<220> FEATURE:
<223> OTHER INFORMATION: C-terminal stem segment of Influenza A HA subtype H9(no Cys-delta 3)

<400> SEQUENCE: 252

Gln Cys Gln Thr Glu Lys Gly Gly Leu Asn Thr Thr Leu Pro Phe His
1 5 10 15

Asn Ile Ser Lys Tyr Ala Phe Gly Asn Cys Pro Lys Tyr Val Gly Val
20 25 30

```
Lys Ser Leu Lys Leu Pro Val Gly Leu Arg Asn Val Pro Ala Val Ser
        35                  40                  45

Ser Arg
    50


<210> SEQ ID NO 253
<211> LENGTH: 53
<212> TYPE: PRT
<213> ORGANISM: Influenza virus A
<220> FEATURE:
<223> OTHER INFORMATION: C-terminal stem segment of Influenza A
      HA subtype H10(no Cys)

<400> SEQUENCE: 253

Glu Ser Lys Cys Phe Trp Arg Gly Gly Ser Ile Asn Thr Lys Leu Pro
 1               5                  10                  15

Phe Gln Asn Leu Ser Pro Arg Thr Val Gly Gln Cys Pro Lys Tyr Val
            20                  25                  30

Asn Gln Arg Ser Leu Leu Leu Ala Thr Gly Met Arg Asn Val Pro Glu
        35                  40                  45

Val Val Gln Gly Arg
    50


<210> SEQ ID NO 254
<211> LENGTH: 52
<212> TYPE: PRT
<213> ORGANISM: Influenza virus A
<220> FEATURE:
<223> OTHER INFORMATION: C-terminal stem segment of Influenza A HA
      subtype H10(no Cys-delta 1)

<400> SEQUENCE: 254

Ser Lys Cys Phe Trp Arg Gly Gly Ser Ile Asn Thr Lys Leu Pro Phe
 1               5                  10                  15

Gln Asn Leu Ser Pro Arg Thr Val Gly Gln Cys Pro Lys Tyr Val Asn
            20                  25                  30

Gln Arg Ser Leu Leu Leu Ala Thr Gly Met Arg Asn Val Pro Glu Val
        35                  40                  45

Val Gln Gly Arg
    50


<210> SEQ ID NO 255
<211> LENGTH: 51
<212> TYPE: PRT
<213> ORGANISM: Influenza virus A
<220> FEATURE:
<223> OTHER INFORMATION: C-terminal stem segment of Influenza A HA
      subtype H10(no Cys-delta 3)

<400> SEQUENCE: 255

Lys Cys Phe Trp Arg Gly Gly Ser Ile Asn Thr Lys Leu Pro Phe Gln
 1               5                  10                  15

Asn Leu Ser Pro Arg Thr Val Gly Gln Cys Pro Lys Tyr Val Asn Gln
            20                  25                  30

Arg Ser Leu Leu Leu Ala Thr Gly Met Arg Asn Val Pro Glu Val Val
        35                  40                  45

Gln Gly Arg
    50


<210> SEQ ID NO 256
<211> LENGTH: 52
```

<212> TYPE: PRT
<213> ORGANISM: Influenza virus A
<220> FEATURE:
<223> OTHER INFORMATION: C-terminal stem segment of Influenza A HA subtype H11(no Cys)

<400> SEQUENCE: 256

Ser Thr Lys Cys Gln Thr Glu Ile Gly Gly Ile Asn Thr Asn Lys Ser
1 5 10 15

Phe His Asn Val His Arg Asn Thr Ile Gly Asp Cys Pro Lys Tyr Val
20 25 30

Asn Val Lys Ser Leu Lys Leu Ala Thr Gly Pro Arg Asn Val Pro Ala
35 40 45

Ile Ala Ser Arg
50

<210> SEQ ID NO 257
<211> LENGTH: 51
<212> TYPE: PRT
<213> ORGANISM: Influenza virus A
<220> FEATURE:
<223> OTHER INFORMATION: C-terminal stem segment of Influenza A HA subtype H11(no Cys-delta 1)

<400> SEQUENCE: 257

Thr Lys Cys Gln Thr Glu Ile Gly Gly Ile Asn Thr Asn Lys Ser Phe
1 5 10 15

His Asn Val His Arg Asn Thr Ile Gly Asp Cys Pro Lys Tyr Val Asn
20 25 30

Val Lys Ser Leu Lys Leu Ala Thr Gly Pro Arg Asn Val Pro Ala Ile
35 40 45

Ala Ser Arg
50

<210> SEQ ID NO 258
<211> LENGTH: 50
<212> TYPE: PRT
<213> ORGANISM: Influenza virus A
<220> FEATURE:
<223> OTHER INFORMATION: C-terminal stem segment of Influenza A HA subtype H11(no Cys-delta 3)

<400> SEQUENCE: 258

Lys Cys Gln Thr Glu Ile Gly Gly Ile Asn Thr Asn Lys Ser Phe His
1 5 10 15

Asn Val His Arg Asn Thr Ile Gly Asp Cys Pro Lys Tyr Val Asn Val
20 25 30

Lys Ser Leu Lys Leu Ala Thr Gly Pro Arg Asn Val Pro Ala Ile Ala
35 40 45

Ser Arg
50

<210> SEQ ID NO 259
<211> LENGTH: 52
<212> TYPE: PRT
<213> ORGANISM: Influenza virus A
<220> FEATURE:
<223> OTHER INFORMATION: C-terminal stem segment of Influenza A HA subtype H12(no Cys)

<400> SEQUENCE: 259

Val Thr Glu Cys Gln Leu Asn Glu Gly Val Met Asn Thr Ser Lys Pro
1 5 10 15

-continued

Phe Gln Asn Thr Ser Lys His Tyr Ile Gly Lys Cys Pro Lys Tyr Ile
20 25 30

Pro Ser Gly Ser Leu Lys Leu Ala Ile Gly Leu Arg Asn Val Pro Gln
35 40 45

Val Gln Asp Arg
50

<210> SEQ ID NO 260
<211> LENGTH: 51
<212> TYPE: PRT
<213> ORGANISM: Influenza virus A
<220> FEATURE:
<223> OTHER INFORMATION: C-terminal stem segment of Influenza A HA subtype H12(no Cys-delta 1)

<400> SEQUENCE: 260

Thr Glu Cys Gln Leu Asn Glu Gly Val Met Asn Thr Ser Lys Pro Phe
1 5 10 15

Gln Asn Thr Ser Lys His Tyr Ile Gly Lys Cys Pro Lys Tyr Ile Pro
20 25 30

Ser Gly Ser Leu Lys Leu Ala Ile Gly Leu Arg Asn Val Pro Gln Val
35 40 45

Gln Asp Arg
50

<210> SEQ ID NO 261
<211> LENGTH: 50
<212> TYPE: PRT
<213> ORGANISM: Influenza virus A
<220> FEATURE:
<223> OTHER INFORMATION: C-terminal stem segment of Influenza A HA subtype H12(no Cys-delta 3)

<400> SEQUENCE: 261

Glu Cys Gln Leu Asn Glu Gly Val Met Asn Thr Ser Lys Pro Phe Gln
1 5 10 15

Asn Thr Ser Lys His Tyr Ile Gly Lys Cys Pro Lys Tyr Ile Pro Ser
20 25 30

Gly Ser Leu Lys Leu Ala Ile Gly Leu Arg Asn Val Pro Gln Val Gln
35 40 45

Asp Arg
50

<210> SEQ ID NO 262
<211> LENGTH: 52
<212> TYPE: PRT
<213> ORGANISM: Influenza virus A
<220> FEATURE:
<223> OTHER INFORMATION: C-terminal stem segment of Influenza A HA subtype H13(no Cys)

<400> SEQUENCE: 262

Asn Thr Lys Cys Gln Thr Ser Val Gly Gly Ile Asn Thr Asn Arg Thr
1 5 10 15

Phe Gln Asn Ile Asp Lys Asn Ala Leu Gly Asp Cys Pro Lys Tyr Ile
20 25 30

Lys Ser Gly Gln Leu Lys Leu Ala Thr Gly Leu Arg Asn Val Pro Ala
35 40 45

Ile Ser Asn Arg
50

<210> SEQ ID NO 263
<211> LENGTH: 51
<212> TYPE: PRT
<213> ORGANISM: Influenza virus A
<220> FEATURE:
<223> OTHER INFORMATION: C-terminal stem segment of Influenza A HA subtype H13(no Cys-delta 1)

<400> SEQUENCE: 263

```
Thr Lys Cys Gln Thr Ser Val Gly Gly Ile Asn Thr Asn Arg Thr Phe
 1               5                  10                  15

Gln Asn Ile Asp Lys Asn Ala Leu Gly Asp Cys Pro Lys Tyr Ile Lys
            20                  25                  30

Ser Gly Gln Leu Lys Leu Ala Thr Gly Leu Arg Asn Val Pro Ala Ile
        35                  40                  45

Ser Asn Arg
    50
```

<210> SEQ ID NO 264
<211> LENGTH: 50
<212> TYPE: PRT
<213> ORGANISM: Influenza virus A
<220> FEATURE:
<223> OTHER INFORMATION: C-terminal stem segment of Influenza A HA subtype H13(no Cys-delta 3)

<400> SEQUENCE: 264

```
Lys Cys Gln Thr Ser Val Gly Gly Ile Asn Thr Asn Arg Thr Phe Gln
 1               5                  10                  15

Asn Ile Asp Lys Asn Ala Leu Gly Asp Cys Pro Lys Tyr Ile Lys Ser
            20                  25                  30

Gly Gln Leu Lys Leu Ala Thr Gly Leu Arg Asn Val Pro Ala Ile Ser
        35                  40                  45

Asn Arg
    50
```

<210> SEQ ID NO 265
<211> LENGTH: 52
<212> TYPE: PRT
<213> ORGANISM: Influenza virus A
<220> FEATURE:
<223> OTHER INFORMATION: C-terminal stem segment of Influenza A HA subtype H14(no Cys)

<400> SEQUENCE: 265

```
Thr Ser Pro Cys Leu Thr Asp Lys Gly Ser Ile Gln Ser Asp Lys Pro
 1               5                  10                  15

Phe Gln Asn Val Ser Arg Ile Ala Ile Gly Asn Cys Pro Lys Tyr Val
            20                  25                  30

Lys Gln Gly Ser Leu Met Leu Ala Thr Gly Met Arg Asn Ile Pro Gly
        35                  40                  45

Lys Gln Ala Lys
    50
```

<210> SEQ ID NO 266
<211> LENGTH: 51
<212> TYPE: PRT
<213> ORGANISM: Influenza virus A
<220> FEATURE:
<223> OTHER INFORMATION: C-terminal stem segment of Influenza A HA subtype H14(no Cys-delta 1)

<400> SEQUENCE: 266

Ser Pro Cys Leu Thr Asp Lys Gly Ser Ile Gln Ser Asp Lys Pro Phe
1 5 10 15

Gln Asn Val Ser Arg Ile Ala Ile Gly Asn Cys Pro Lys Tyr Val Lys
20 25 30

Gln Gly Ser Leu Met Leu Ala Thr Gly Met Arg Asn Ile Pro Gly Lys
35 40 45

Gln Ala Lys
50

<210> SEQ ID NO 267
<211> LENGTH: 50
<212> TYPE: PRT
<213> ORGANISM: Influenza virus A
<220> FEATURE:
<223> OTHER INFORMATION: C-terminal stem segment of Influenza A HA subtype H14(no Cys-delta 3)

<400> SEQUENCE: 267

Pro Cys Leu Thr Asp Lys Gly Ser Ile Gln Ser Asp Lys Pro Phe Gln
1 5 10 15

Asn Val Ser Arg Ile Ala Ile Gly Asn Cys Pro Lys Tyr Val Lys Gln
20 25 30

Gly Ser Leu Met Leu Ala Thr Gly Met Arg Asn Ile Pro Gly Lys Gln
35 40 45

Ala Lys
50

<210> SEQ ID NO 268
<211> LENGTH: 53
<212> TYPE: PRT
<213> ORGANISM: Influenza virus A
<220> FEATURE:
<223> OTHER INFORMATION: C-terminal stem segment of Influenza A HA subtype H15(no Cys)

<400> SEQUENCE: 268

Glu Gly Glu Cys Phe Tyr Ser Gly Gly Thr Ile Asn Ser Pro Leu Pro
1 5 10 15

Phe Gln Asn Ile Asp Ser Arg Ala Val Gly Lys Cys Pro Arg Tyr Val
20 25 30

Lys Gln Ser Ser Leu Pro Leu Ala Leu Gly Met Lys Asn Val Pro Glu
35 40 45

Lys Ile Arg Thr Arg
50

<210> SEQ ID NO 269
<211> LENGTH: 52
<212> TYPE: PRT
<213> ORGANISM: Influenza virus A
<220> FEATURE:
<223> OTHER INFORMATION: C-terminal stem segment of Influenza A HA subtype H15(no Cys-delta 1)

<400> SEQUENCE: 269

Gly Glu Cys Phe Tyr Ser Gly Gly Thr Ile Asn Ser Pro Leu Pro Phe
1 5 10 15

Gln Asn Ile Asp Ser Arg Ala Val Gly Lys Cys Pro Arg Tyr Val Lys
20 25 30

Gln Ser Ser Leu Pro Leu Ala Leu Gly Met Lys Asn Val Pro Glu Lys
35 40 45

Ile Arg Thr Arg
    50

<210> SEQ ID NO 270
<211> LENGTH: 51
<212> TYPE: PRT
<213> ORGANISM: Influenza virus A
<220> FEATURE:
<223> OTHER INFORMATION: C-terminal stem segment of Influenza A HA subtype H15(no Cys-delta 3)

<400> SEQUENCE: 270

Glu Cys Phe Tyr Ser Gly Gly Thr Ile Asn Ser Pro Leu Pro Phe Gln
 1               5                  10                  15

Asn Ile Asp Ser Arg Ala Val Gly Lys Cys Pro Arg Tyr Val Lys Gln
            20                  25                  30

Ser Ser Leu Pro Leu Ala Leu Gly Met Lys Asn Val Pro Glu Lys Ile
        35                  40                  45

Arg Thr Arg
    50

<210> SEQ ID NO 271
<211> LENGTH: 52
<212> TYPE: PRT
<213> ORGANISM: Influenza virus A
<220> FEATURE:
<223> OTHER INFORMATION: C-terminal stem segment of Influenza A HA subtype H16(no Cys)

<400> SEQUENCE: 271

Asn Thr Lys Cys Gln Thr Ser Leu Gly Gly Ile Asn Thr Asn Lys Thr
 1               5                  10                  15

Phe Gln Asn Ile Glu Arg Asn Ala Leu Gly Asp Cys Pro Lys Tyr Ile
            20                  25                  30

Lys Ser Gly Gln Leu Lys Leu Ala Thr Gly Leu Arg Asn Val Pro Ser
        35                  40                  45

Ile Gly Glu Arg
    50

<210> SEQ ID NO 272
<211> LENGTH: 51
<212> TYPE: PRT
<213> ORGANISM: Influenza virus A
<220> FEATURE:
<223> OTHER INFORMATION: C-terminal stem segment of Influenza A HA subtype H16(no Cys-delta 1)

<400> SEQUENCE: 272

Thr Lys Cys Gln Thr Ser Leu Gly Gly Ile Asn Thr Asn Lys Thr Phe
 1               5                  10                  15

Gln Asn Ile Glu Arg Asn Ala Leu Gly Asp Cys Pro Lys Tyr Ile Lys
            20                  25                  30

Ser Gly Gln Leu Lys Leu Ala Thr Gly Leu Arg Asn Val Pro Ser Ile
        35                  40                  45

Gly Glu Arg
    50

<210> SEQ ID NO 273
<211> LENGTH: 50
<212> TYPE: PRT
<213> ORGANISM: Influenza virus A
<220> FEATURE:
<223> OTHER INFORMATION: C-terminal stem segment of Influenza A HA subtype H16(no Cys-delta 3)

<400> SEQUENCE: 273

```
Lys Cys Gln Thr Ser Leu Gly Gly Ile Asn Thr Asn Lys Thr Phe Gln
 1               5                  10                  15

Asn Ile Glu Arg Asn Ala Leu Gly Asp Cys Pro Lys Tyr Ile Lys Ser
            20                  25                  30

Gly Gln Leu Lys Leu Ala Thr Gly Leu Arg Asn Val Pro Ser Ile Gly
        35                  40                  45

Glu Arg
    50
```

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

<400> SEQUENCE: 294

000

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300

<400> SEQUENCE: 300

000

<210> SEQ ID NO 301

<400> SEQUENCE: 301

000

<210> SEQ ID NO 302

<400> SEQUENCE: 302

000

<210> SEQ ID NO 303

<400> SEQUENCE: 303

000

<210> SEQ ID NO 304

<400> SEQUENCE: 304

000

<210> SEQ ID NO 305

<400> SEQUENCE: 305

000

<210> SEQ ID NO 306

<400> SEQUENCE: 306

000

<210> SEQ ID NO 307

<400> SEQUENCE: 307

000

<210> SEQ ID NO 308
<211> LENGTH: 44
<212> TYPE: PRT
<213> ORGANISM: Influenza virus A
<220> FEATURE:
<223> OTHER INFORMATION: N-terminal stem segment of Influenza A HA subtype H3(HK68-CON-A)

<400> SEQUENCE: 308

```
Ser Thr Ala Thr Leu Cys Leu Gly His His Ala Val Pro Asn Gly Thr
 1               5                  10                  15

Leu Val Lys Thr Ile Thr Asp Asp Gln Ile Glu Val Thr Asn Ala Thr
            20                  25                  30

Glu Leu Val Gln Ser Ser Ser Thr Gly Lys Ile Cys
        35                  40
```

<210> SEQ ID NO 309
<211> LENGTH: 24
<212> TYPE: PRT
<213> ORGANISM: Influenza virus A
<220> FEATURE:
<223> OTHER INFORMATION: C-terminal stem segment of Influenza A HA subtype H3(HK68-CON-B)

<400> SEQUENCE: 309

```
Cys Lys Tyr Val Lys Gln Asn Thr Leu Lys Leu Ala Thr Gly Met Arg
 1               5                  10                  15

Asn Val Pro Glu Lys Gln Thr Arg
            20
```

<210> SEQ ID NO 310
<211> LENGTH: 97
<212> TYPE: PRT
<213> ORGANISM: Influenza virus A
<220> FEATURE:
<223> OTHER INFORMATION: N-terminal stem segment of Influenza A HA subtype H3(HK68-CON-C)

<400> SEQUENCE: 310

```
Gln Asp Leu Pro Gly Asn Asp Asn Ser Thr Ala Thr Leu Cys Leu Gly
 1               5                  10                  15

His His Ala Val Pro Asn Gly Thr Leu Val Lys Thr Ile Thr Asp Asp
            20                  25                  30

Gln Ile Glu Val Thr Asn Ala Thr Glu Leu Val Gln Ser Ser Ser Thr
        35                  40                  45

Gly Lys Ile Cys Asn Asn Pro His Arg Ile Leu Asp Gly Ile Asp Cys
    50                  55                  60

Thr Leu Ile Asp Ala Leu Leu Gly Asp Pro His Cys Asp Val Phe Gln
65                  70                  75                  80
```

```
Asn Glu Thr Trp Asp Leu Phe Val Glu Arg Ser Lys Ala Phe Ser Asn
                85                  90                  95

Cys


<210> SEQ ID NO 311
<211> LENGTH: 74
<212> TYPE: PRT
<213> ORGANISM: Influenza virus A
<220> FEATURE:
<223> OTHER INFORMATION: C-terminal stem segment of Influenza
      A HA subtype H3(HK68-CON-C)

<400> SEQUENCE: 311

Ala Pro Arg Gly Tyr Phe Lys Met Arg Thr Gly Lys Ser Ser Ile Met
 1               5                  10                  15

Ser Ser Asp Ala Pro Ile Asp Thr Cys Ile Ser Glu Cys Ile Thr Pro
            20                  25                  30

Asn Gly Ser Ile Pro Asn Asp Lys Pro Phe Gln Asn Val Asn Lys Ile
        35                  40                  45

Thr Tyr Gly Ala Cys Pro Lys Tyr Val Lys Gln Asn Thr Leu Lys Leu
    50                  55                  60

Ala Thr Gly Met Arg Asn Val Pro Glu Lys
65                  70


<210> SEQ ID NO 312
<211> LENGTH: 46
<212> TYPE: PRT
<213> ORGANISM: Influenza virus A
<220> FEATURE:
<223> OTHER INFORMATION: N-terminal stem segment of Influenza
      A HA subtype H1(HK68-CON-A)

<400> SEQUENCE: 312

Asp Thr Ile Cys Ile Gly Tyr His Ala Asn Asn Ser Thr Asp Thr Val
 1               5                  10                  15

Asp Thr Val Leu Glu Lys Asn Val Thr Val Thr His Ser Val Asn Leu
            20                  25                  30

Leu Glu Asp Ser His Asn Gly Lys Leu Cys Arg Leu Lys Cys
        35                  40                  45


<210> SEQ ID NO 313
<211> LENGTH: 52
<212> TYPE: PRT
<213> ORGANISM: Influenza virus A
<220> FEATURE:
<223> OTHER INFORMATION: C-terminal stem segment of Influenza
      A HA subtype H1(HK68-CON-A)

<400> SEQUENCE: 313

Cys Lys Cys Gln Thr Pro Leu Gly Ala Ile Asn Ser Ser Leu Pro Tyr
 1               5                  10                  15

Gln Asn Ile His Pro Val Thr Ile Gly Glu Cys Pro Lys Tyr Val Arg
            20                  25                  30

Ser Ala Lys Leu Arg Met Val Thr Gly Leu Arg Asn Asn Pro Ser Ile
        35                  40                  45

Gln Ser Arg Gly
    50


<210> SEQ ID NO 314
<211> LENGTH: 23
<212> TYPE: PRT
```

<213> ORGANISM: Influenza virus A
<220> FEATURE:
<223> OTHER INFORMATION: C-terminal stem segment of Influenza A HA subtype H1(HK68-CON-B)

<400> SEQUENCE: 314

```
Cys Val Arg Ser Ala Lys Leu Arg Met Val Thr Gly Leu Arg Asn Asn
 1               5                  10                  15

Pro Ser Ile Gln Ser Arg Gly
            20
```

<210> SEQ ID NO 315
<211> LENGTH: 94
<212> TYPE: PRT
<213> ORGANISM: Influenza virus A
<220> FEATURE:
<223> OTHER INFORMATION: N-terminal stem segment of Influenza A HA subtype H1(HK68-CON-C)

<400> SEQUENCE: 315

```
Asp Thr Ile Cys Ile Gly Tyr His Ala Asn Asn Ser Thr Asp Thr Val
 1               5                  10                  15

Asp Thr Val Leu Glu Lys Asn Val Thr Val Thr His Ser Val Asn Leu
            20                  25                  30

Leu Glu Asp Ser His Asn Gly Lys Leu Cys Arg Leu Lys Gly Ile Ala
        35                  40                  45

Pro Leu Gln Leu Gly Lys Cys Asn Ile Ala Gly Trp Leu Leu Gly Asn
    50                  55                  60

Pro Glu Cys Asp Pro Leu Leu Pro Val Arg Ser Trp Ser Tyr Ile Val
65                  70                  75                  80

Glu Thr Pro Asn Ser Glu Asn Gly Ile Cys Tyr Pro Gly Cys
                85                  90
```

<210> SEQ ID NO 316
<211> LENGTH: 75
<212> TYPE: PRT
<213> ORGANISM: Influenza virus A
<220> FEATURE:
<223> OTHER INFORMATION: C-terminal stem segment of Influenza A HA subtype H1(HK68-CON-C)

<400> SEQUENCE: 316

```
Ala Phe Ala Leu Ser Arg Gly Phe Gly Ser Gly Ile Ile Thr Ser Asn
 1               5                  10                  15

Ala Ser Met His Glu Cys Asn Thr Lys Cys Gln Thr Pro Leu Gly Ala
            20                  25                  30

Ile Asn Ser Ser Leu Pro Tyr Gln Asn Ile His Pro Val Thr Ile Gly
        35                  40                  45

Glu Cys Pro Lys Tyr Val Arg Ser Ala Lys Leu Arg Met Val Thr Gly
    50                  55                  60

Leu Arg Asn Asn Pro Ser Ile Gln Ser Arg Gly
65                  70                  75
```

<210> SEQ ID NO 317

<400> SEQUENCE: 317

000

<210> SEQ ID NO 318

<400> SEQUENCE: 318

-continued

000

<210> SEQ ID NO 319

<400> SEQUENCE: 319

000

<210> SEQ ID NO 320

<400> SEQUENCE: 320

000

<210> SEQ ID NO 321

<400> SEQUENCE: 321

000

<210> SEQ ID NO 322

<400> SEQUENCE: 322

000

<210> SEQ ID NO 323

<400> SEQUENCE: 323

000

<210> SEQ ID NO 324

<400> SEQUENCE: 324

000

<210> SEQ ID NO 325

<400> SEQUENCE: 325

000

<210> SEQ ID NO 326

<400> SEQUENCE: 326

000

<210> SEQ ID NO 327

<400> SEQUENCE: 327

000

<210> SEQ ID NO 328

<400> SEQUENCE: 328

000

<210> SEQ ID NO 329

<400> SEQUENCE: 329

000

<210> SEQ ID NO 330

<400> SEQUENCE: 330

000

<210> SEQ ID NO 331

<400> SEQUENCE: 331

000

<210> SEQ ID NO 332

<400> SEQUENCE: 332

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338

<400> SEQUENCE: 338

000

<210> SEQ ID NO 339

<400> SEQUENCE: 339

000

<210> SEQ ID NO 340

<400> SEQUENCE: 340

000

<210> SEQ ID NO 341

<400> SEQUENCE: 341

000

<210> SEQ ID NO 342

<400> SEQUENCE: 342

000

<210> SEQ ID NO 343

<400> SEQUENCE: 343

000

<210> SEQ ID NO 344

<400> SEQUENCE: 344

000

<210> SEQ ID NO 345

<400> SEQUENCE: 345

000

<210> SEQ ID NO 346

<400> SEQUENCE: 346

000

<210> SEQ ID NO 347

<400> SEQUENCE: 347

000

<210> SEQ ID NO 348

<400> SEQUENCE: 348

000

<210> SEQ ID NO 349

<400> SEQUENCE: 349

000

<210> SEQ ID NO 350
<211> LENGTH: 25
<212> TYPE: PRT
<213> ORGANISM: Influenza virus A
<220> FEATURE:
<223> OTHER INFORMATION: C-terminal short stem segment of Influenza A HA subtype H1

<400> SEQUENCE: 350

```
Cys Pro Lys Tyr Val Arg Ser Ala Lys Leu Arg Met Val Thr Gly Leu
 1              5                   10                  15

Arg Asn Asn Pro Ser Ile Gln Ser Arg
            20                  25
```

<210> SEQ ID NO 351
<211> LENGTH: 25
<212> TYPE: PRT
<213> ORGANISM: Influenza virus A
<220> FEATURE:
<223> OTHER INFORMATION: C-terminal short stem segment of Influenza
A HA subtype H2

<400> SEQUENCE: 351

Cys Pro Lys Tyr Val Lys Ser Glu Arg Leu Val Leu Ala Thr Gly Leu
1 5 10 15

Arg Asn Val Pro Gln Ile Glu Ser Arg
20 25

<210> SEQ ID NO 352
<211> LENGTH: 25
<212> TYPE: PRT
<213> ORGANISM: Influenza virus A
<220> FEATURE:
<223> OTHER INFORMATION: C-terminal short stem segment of Influenza
A HA subtype H3

<400> SEQUENCE: 352

Cys Pro Lys Tyr Val Lys Gln Asn Thr Leu Lys Leu Ala Thr Gly Met
1 5 10 15

Arg Asn Val Pro Glu Lys Gln Thr Arg
20 25

<210> SEQ ID NO 353
<211> LENGTH: 25
<212> TYPE: PRT
<213> ORGANISM: Influenza virus A
<220> FEATURE:
<223> OTHER INFORMATION: C-terminal short stem segment of Influenza
A HA subtype H4

<400> SEQUENCE: 353

Cys Pro Arg Tyr Val Lys Gln Gly Ser Leu Lys Leu Ala Thr Gly Met
1 5 10 15

Arg Asn Ile Pro Glu Lys Ala Ser Arg
20 25

<210> SEQ ID NO 354
<211> LENGTH: 25
<212> TYPE: PRT
<213> ORGANISM: Influenza virus A
<220> FEATURE:
<223> OTHER INFORMATION: C-terminal short stem segment of Influenza
A HA subtype H5

<400> SEQUENCE: 354

Cys Pro Lys Tyr Val Lys Ser Asp Arg Leu Val Leu Ala Thr Gly Leu
1 5 10 15

Arg Asn Val Pro Gln Arg Lys Lys Arg
20 25

<210> SEQ ID NO 355
<211> LENGTH: 25
<212> TYPE: PRT
<213> ORGANISM: Influenza virus A
<220> FEATURE:
<223> OTHER INFORMATION: C-terminal short stem segment of Influenza
A HA subtype H6

<400> SEQUENCE: 355

```
Cys Pro Lys Tyr Val Lys Ser Glu Ser Leu Arg Leu Ala Thr Gly Leu
 1               5                  10                  15

Arg Asn Val Pro Gln Ile Glu Thr Arg
            20                  25


<210> SEQ ID NO 356
<211> LENGTH: 29
<212> TYPE: PRT
<213> ORGANISM: Influenza virus A
<220> FEATURE:
<223> OTHER INFORMATION: C-terminal short stem segment of Influenza
      A HA subtype H7

<400> SEQUENCE: 356

Cys Pro Arg Tyr Val Lys Gln Glu Ser Leu Leu Leu Ala Thr Gly Met
 1               5                  10                  15

Lys Asn Val Pro Glu Pro Ser Lys Lys Arg Lys Lys Arg
            20                  25


<210> SEQ ID NO 357
<211> LENGTH: 25
<212> TYPE: PRT
<213> ORGANISM: Influenza virus A
<220> FEATURE:
<223> OTHER INFORMATION: C-terminal short stem segment of Influenza
      A HA subtype H8

<400> SEQUENCE: 357

Cys Pro Lys Tyr Val Lys Lys Ala Ser Leu Arg Leu Ala Val Gly Leu
 1               5                  10                  15

Arg Asn Thr Pro Ser Val Glu Pro Arg
            20                  25


<210> SEQ ID NO 358
<211> LENGTH: 25
<212> TYPE: PRT
<213> ORGANISM: Influenza virus A
<220> FEATURE:
<223> OTHER INFORMATION: C-terminal short stem segment of Influenza
      A HA subtype H9

<400> SEQUENCE: 358

Cys Pro Lys Tyr Val Gly Val Lys Ser Leu Lys Leu Pro Val Gly Leu
 1               5                  10                  15

Arg Asn Val Pro Ala Val Ser Ser Arg
            20                  25


<210> SEQ ID NO 359
<211> LENGTH: 26
<212> TYPE: PRT
<213> ORGANISM: Influenza virus A
<220> FEATURE:
<223> OTHER INFORMATION: C-terminal short stem segment of Influenza
      A HA subtype H10

<400> SEQUENCE: 359

Cys Pro Lys Tyr Val Asn Gln Arg Ser Leu Leu Leu Ala Thr Gly Met
 1               5                  10                  15

Arg Asn Val Pro Glu Val Val Gln Gly Arg
            20                  25


<210> SEQ ID NO 360
<211> LENGTH: 25
<212> TYPE: PRT
<213> ORGANISM: Influenza virus A
```

<220> FEATURE:
<223> OTHER INFORMATION: C-terminal short stem segment of Influenza A HA subtype H11

<400> SEQUENCE: 360

Cys Pro Lys Tyr Val Asn Val Lys Ser Leu Lys Leu Ala Thr Gly Pro
1 5 10 15

Arg Asn Val Pro Ala Ile Ala Ser Arg
20 25

<210> SEQ ID NO 361
<211> LENGTH: 25
<212> TYPE: PRT
<213> ORGANISM: Influenza virus A
<220> FEATURE:
<223> OTHER INFORMATION: C-terminal short stem segment of Influenza A HA subtype H12

<400> SEQUENCE: 361

Cys Pro Lys Tyr Ile Pro Ser Gly Ser Leu Lys Leu Ala Ile Gly Leu
1 5 10 15

Arg Asn Val Pro Gln Val Gln Asp Arg
20 25

<210> SEQ ID NO 362
<211> LENGTH: 25
<212> TYPE: PRT
<213> ORGANISM: Influenza virus A
<220> FEATURE:
<223> OTHER INFORMATION: C-terminal short stem segment of Influenza A HA subtype H13

<400> SEQUENCE: 362

Cys Pro Lys Tyr Ile Lys Ser Gly Gln Leu Lys Leu Ala Thr Gly Leu
1 5 10 15

Arg Asn Val Pro Ala Ile Ser Asn Arg
20 25

<210> SEQ ID NO 363
<211> LENGTH: 25
<212> TYPE: PRT
<213> ORGANISM: Influenza virus A
<220> FEATURE:
<223> OTHER INFORMATION: C-terminal short stem segment of Influenza A HA subtype H14

<400> SEQUENCE: 363

Cys Pro Lys Tyr Val Lys Gln Gly Ser Leu Met Leu Ala Thr Gly Met
1 5 10 15

Arg Asn Ile Pro Gly Lys Gln Ala Lys
20 25

<210> SEQ ID NO 364
<211> LENGTH: 26
<212> TYPE: PRT
<213> ORGANISM: Influenza virus A
<220> FEATURE:
<223> OTHER INFORMATION: C-terminal short stem segment of Influenza A HA subtype H15

<400> SEQUENCE: 364

Cys Pro Arg Tyr Val Lys Gln Ser Ser Leu Pro Leu Ala Leu Gly Met
1 5 10 15

Lys Asn Val Pro Glu Lys Ile Arg Thr Arg
20 25

<210> SEQ ID NO 365
<211> LENGTH: 25
<212> TYPE: PRT
<213> ORGANISM: Influenza virus A
<220> FEATURE:
<223> OTHER INFORMATION: C-terminal short stem segment of Influenza A HA subtype H16

<400> SEQUENCE: 365

```
Cys Pro Lys Tyr Ile Lys Ser Gly Gln Leu Lys Leu Ala Thr Gly Leu
 1               5                  10                  15

Arg Asn Val Pro Ser Ile Gly Glu Arg
            20                  25
```

<210> SEQ ID NO 366
<211> LENGTH: 24
<212> TYPE: PRT
<213> ORGANISM: Influenza virus A
<220> FEATURE:
<223> OTHER INFORMATION: C-terminal stem segment of Influenza A HA subtype H1(no Cys)

<400> SEQUENCE: 366

```
Pro Lys Tyr Val Arg Ser Ala Lys Leu Arg Met Val Thr Gly Leu Arg
 1               5                  10                  15

Asn Asn Pro Ser Ile Gln Ser Arg
            20
```

<210> SEQ ID NO 367
<211> LENGTH: 23
<212> TYPE: PRT
<213> ORGANISM: Influenza virus A
<220> FEATURE:
<223> OTHER INFORMATION: C-terminal stem segment of Influenza A HA subtype H1(no Cys-delta 1)

<400> SEQUENCE: 367

```
Lys Tyr Val Arg Ser Ala Lys Leu Arg Met Val Thr Gly Leu Arg Asn
 1               5                  10                  15

Asn Pro Ser Ile Gln Ser Arg
            20
```

<210> SEQ ID NO 368
<211> LENGTH: 22
<212> TYPE: PRT
<213> ORGANISM: Influenza virus A
<220> FEATURE:
<223> OTHER INFORMATION: C-terminal stem segment of Influenza A HA subtype H1(no Cys-delta 3)

<400> SEQUENCE: 368

```
Tyr Val Arg Ser Ala Lys Leu Arg Met Val Thr Gly Leu Arg Asn Asn
 1               5                  10                  15

Pro Ser Ile Gln Ser Arg
            20
```

<210> SEQ ID NO 369
<211> LENGTH: 24
<212> TYPE: PRT
<213> ORGANISM: Influenza virus A
<220> FEATURE:
<223> OTHER INFORMATION: C-terminal stem segment of Influenza A HA subtype H2(no Cys)

<400> SEQUENCE: 369

Pro Lys Tyr Val Lys Ser Glu Arg Leu Val Leu Ala Thr Gly Leu Arg
1 5 10 15

Asn Val Pro Gln Ile Glu Ser Arg
20

<210> SEQ ID NO 370
<211> LENGTH: 23
<212> TYPE: PRT
<213> ORGANISM: Influenza virus A
<220> FEATURE:
<223> OTHER INFORMATION: C-terminal stem segment of Influenza A HA subtype H2(no Cys-delta 1)

<400> SEQUENCE: 370

Lys Tyr Val Lys Ser Glu Arg Leu Val Leu Ala Thr Gly Leu Arg Asn
1 5 10 15

Val Pro Gln Ile Glu Ser Arg
20

<210> SEQ ID NO 371
<211> LENGTH: 22
<212> TYPE: PRT
<213> ORGANISM: Influenza virus A
<220> FEATURE:
<223> OTHER INFORMATION: C-terminal stem segment of Influenza A HA subtype H2(no Cys-delta 3)

<400> SEQUENCE: 371

Tyr Val Lys Ser Glu Arg Leu Val Leu Ala Thr Gly Leu Arg Asn Val
1 5 10 15

Pro Gln Ile Glu Ser Arg
20

<210> SEQ ID NO 372
<211> LENGTH: 24
<212> TYPE: PRT
<213> ORGANISM: Influenza virus A
<220> FEATURE:
<223> OTHER INFORMATION: C-terminal stem segment of Influenza A HA subtype H3(no Cys)

<400> SEQUENCE: 372

Pro Lys Tyr Val Lys Gln Asn Thr Leu Lys Leu Ala Thr Gly Met Arg
1 5 10 15

Asn Val Pro Glu Lys Gln Thr Arg
20

<210> SEQ ID NO 373
<211> LENGTH: 23
<212> TYPE: PRT
<213> ORGANISM: Influenza virus A
<220> FEATURE:
<223> OTHER INFORMATION: C-terminal stem segment of Influenza A HA subtype H3(no Cys-delta 1)

<400> SEQUENCE: 373

Lys Tyr Val Lys Gln Asn Thr Leu Lys Leu Ala Thr Gly Met Arg Asn
1 5 10 15

Val Pro Glu Lys Gln Thr Arg
20

<210> SEQ ID NO 374
<211> LENGTH: 22
<212> TYPE: PRT

```
<213> ORGANISM: Influenza virus A
<220> FEATURE:
<223> OTHER INFORMATION: C-terminal stem segment of Influenza A HA
      subtype H3(no Cys-delta 3)

<400> SEQUENCE: 374

Tyr Val Lys Gln Asn Thr Leu Lys Leu Ala Thr Gly Met Arg Asn Val
1               5                   10                  15

Pro Glu Lys Gln Thr Arg
            20


<210> SEQ ID NO 375
<211> LENGTH: 24
<212> TYPE: PRT
<213> ORGANISM: Influenza virus A
<220> FEATURE:
<223> OTHER INFORMATION: C-terminal stem segment of Influenza A
      HA subtype H4(no Cys)

<400> SEQUENCE: 375

Pro Arg Tyr Val Lys Gln Gly Ser Leu Lys Leu Ala Thr Gly Met Arg
1               5                   10                  15

Asn Ile Pro Glu Lys Ala Ser Arg
            20


<210> SEQ ID NO 376
<211> LENGTH: 23
<212> TYPE: PRT
<213> ORGANISM: Influenza virus A
<220> FEATURE:
<223> OTHER INFORMATION: C-terminal stem segment of Influenza A HA
      subtype H4(no Cys-delta 1)

<400> SEQUENCE: 376

Arg Tyr Val Lys Gln Gly Ser Leu Lys Leu Ala Thr Gly Met Arg Asn
1               5                   10                  15

Ile Pro Glu Lys Ala Ser Arg
            20


<210> SEQ ID NO 377
<211> LENGTH: 22
<212> TYPE: PRT
<213> ORGANISM: Influenza virus A
<220> FEATURE:
<223> OTHER INFORMATION: C-terminal stem segment of Influenza A HA
      subtype H4(no Cys-delta 3)

<400> SEQUENCE: 377

Tyr Val Lys Gln Gly Ser Leu Lys Leu Ala Thr Gly Met Arg Asn Ile
1               5                   10                  15

Pro Glu Lys Ala Ser Arg
            20


<210> SEQ ID NO 378
<211> LENGTH: 24
<212> TYPE: PRT
<213> ORGANISM: Influenza virus A
<220> FEATURE:
<223> OTHER INFORMATION: C-terminal stem segment of Influenza A
      HA subtype H5(no Cys)

<400> SEQUENCE: 378

Pro Lys Tyr Val Lys Ser Asp Arg Leu Val Leu Ala Thr Gly Leu Arg
1               5                   10                  15

Asn Val Pro Gln Arg Lys Lys Arg
```

20

<210> SEQ ID NO 379
<211> LENGTH: 23
<212> TYPE: PRT
<213> ORGANISM: Influenza virus A
<220> FEATURE:
<223> OTHER INFORMATION: C-terminal stem segment of Influenza A HA subtype H5(no Cys-delta 1)

<400> SEQUENCE: 379

```
Lys Tyr Val Lys Ser Asp Arg Leu Val Leu Ala Thr Gly Leu Arg Asn
 1               5                  10                  15

Val Pro Gln Arg Lys Lys Arg
            20
```

<210> SEQ ID NO 380
<211> LENGTH: 22
<212> TYPE: PRT
<213> ORGANISM: Influenza virus A
<220> FEATURE:
<223> OTHER INFORMATION: C-terminal stem segment of Influenza A HA subtype H5(no Cys-delta 3)

<400> SEQUENCE: 380

```
Tyr Val Lys Ser Asp Arg Leu Val Leu Ala Thr Gly Leu Arg Asn Val
 1               5                  10                  15

Pro Gln Arg Lys Lys Arg
            20
```

<210> SEQ ID NO 381
<211> LENGTH: 24
<212> TYPE: PRT
<213> ORGANISM: Influenza virus A
<220> FEATURE:
<223> OTHER INFORMATION: C-terminal stem segment of Influenza A HA subtype H6(no Cys)

<400> SEQUENCE: 381

```
Pro Lys Tyr Val Lys Ser Glu Ser Leu Arg Leu Ala Thr Gly Leu Arg
 1               5                  10                  15

Asn Val Pro Gln Ile Glu Thr Arg
            20
```

<210> SEQ ID NO 382
<211> LENGTH: 23
<212> TYPE: PRT
<213> ORGANISM: Influenza virus A
<220> FEATURE:
<223> OTHER INFORMATION: C-terminal stem segment of Influenza A HA subtype H6(no Cys-delta 1)

<400> SEQUENCE: 382

```
Lys Tyr Val Lys Ser Glu Ser Leu Arg Leu Ala Thr Gly Leu Arg Asn
 1               5                  10                  15

Val Pro Gln Ile Glu Thr Arg
            20
```

<210> SEQ ID NO 383
<211> LENGTH: 22
<212> TYPE: PRT
<213> ORGANISM: Influenza virus A
<220> FEATURE:
<223> OTHER INFORMATION: C-terminal stem segment of Influenza A HA subtype H6(no Cys-delta 3)

<400> SEQUENCE: 383

Tyr Val Lys Ser Glu Ser Leu Arg Leu Ala Thr Gly Leu Arg Asn Val
 1               5                   10                  15

Pro Gln Ile Glu Thr Arg
            20

<210> SEQ ID NO 384
<211> LENGTH: 28
<212> TYPE: PRT
<213> ORGANISM: Influenza virus A
<220> FEATURE:
<223> OTHER INFORMATION: C-terminal stem segment of Influenza A HA subtype H7(no Cys)

<400> SEQUENCE: 384

Pro Arg Tyr Val Lys Gln Glu Ser Leu Leu Leu Ala Thr Gly Met Lys
 1               5                   10                  15

Asn Val Pro Glu Pro Ser Lys Lys Arg Lys Lys Arg
            20                  25

<210> SEQ ID NO 385
<211> LENGTH: 27
<212> TYPE: PRT
<213> ORGANISM: Influenza virus A
<220> FEATURE:
<223> OTHER INFORMATION: C-terminal stem segment of Influenza A HA subtype H7(no Cys-delta 1)

<400> SEQUENCE: 385

Arg Tyr Val Lys Gln Glu Ser Leu Leu Leu Ala Thr Gly Met Lys Asn
 1               5                   10                  15

Val Pro Glu Pro Ser Lys Lys Arg Lys Lys Arg
            20                  25

<210> SEQ ID NO 386
<211> LENGTH: 26
<212> TYPE: PRT
<213> ORGANISM: Influenza virus A
<220> FEATURE:
<223> OTHER INFORMATION: C-terminal stem segment of Influenza A HA subtype H7(no Cys-delta 3)

<400> SEQUENCE: 386

Tyr Val Lys Gln Glu Ser Leu Leu Leu Ala Thr Gly Met Lys Asn Val
 1               5                   10                  15

Pro Glu Pro Ser Lys Lys Arg Lys Lys Arg
            20                  25

<210> SEQ ID NO 387
<211> LENGTH: 24
<212> TYPE: PRT
<213> ORGANISM: Influenza virus A
<220> FEATURE:
<223> OTHER INFORMATION: C-terminal stem segment of Influenza A HA subtype H8(no Cys)

<400> SEQUENCE: 387

Pro Lys Tyr Val Lys Lys Ala Ser Leu Arg Leu Ala Val Gly Leu Arg
 1               5                   10                  15

Asn Thr Pro Ser Val Glu Pro Arg
            20

<210> SEQ ID NO 388
<211> LENGTH: 23

<212> TYPE: PRT
<213> ORGANISM: Influenza virus A
<220> FEATURE:
<223> OTHER INFORMATION: C-terminal stem segment of Influenza A HA subtype H8(no Cys-delta 1)

<400> SEQUENCE: 388

```
Lys Tyr Val Lys Lys Ala Ser Leu Arg Leu Ala Val Gly Leu Arg Asn
 1               5                  10                  15

Thr Pro Ser Val Glu Pro Arg
            20
```

<210> SEQ ID NO 389
<211> LENGTH: 22
<212> TYPE: PRT
<213> ORGANISM: Influenza virus A
<220> FEATURE:
<223> OTHER INFORMATION: C-terminal stem segment of Influenza A HA subtype H8(no Cys-delta 3)

<400> SEQUENCE: 389

```
Tyr Val Lys Lys Ala Ser Leu Arg Leu Ala Val Gly Leu Arg Asn Thr
 1               5                  10                  15

Pro Ser Val Glu Pro Arg
            20
```

<210> SEQ ID NO 390
<211> LENGTH: 24
<212> TYPE: PRT
<213> ORGANISM: Influenza virus A
<220> FEATURE:
<223> OTHER INFORMATION: C-terminal stem segment of Influenza A HA subtype H9(no Cys)

<400> SEQUENCE: 390

```
Pro Lys Tyr Val Gly Val Lys Ser Leu Lys Leu Pro Val Gly Leu Arg
 1               5                  10                  15

Asn Val Pro Ala Val Ser Ser Arg
            20
```

<210> SEQ ID NO 391
<211> LENGTH: 23
<212> TYPE: PRT
<213> ORGANISM: Influenza virus A
<220> FEATURE:
<223> OTHER INFORMATION: C-terminal stem segment of Influenza A HA subtype H9(no Cys-delta 1)

<400> SEQUENCE: 391

```
Lys Tyr Val Gly Val Lys Ser Leu Lys Leu Pro Val Gly Leu Arg Asn
 1               5                  10                  15

Val Pro Ala Val Ser Ser Arg
            20
```

<210> SEQ ID NO 392
<211> LENGTH: 22
<212> TYPE: PRT
<213> ORGANISM: Influenza virus A
<220> FEATURE:
<223> OTHER INFORMATION: C-terminal stem segment of Influenza A HA subtype H9(no Cys-delta 3)

<400> SEQUENCE: 392

```
Tyr Val Gly Val Lys Ser Leu Lys Leu Pro Val Gly Leu Arg Asn Val
 1               5                  10                  15
```

```
Pro Ala Val Ser Ser Arg
            20


<210> SEQ ID NO 393
<211> LENGTH: 25
<212> TYPE: PRT
<213> ORGANISM: Influenza virus A
<220> FEATURE:
<223> OTHER INFORMATION: C-terminal stem segment of Influenza A
      HA subtype H10(no Cys)

<400> SEQUENCE: 393

Pro Lys Tyr Val Asn Gln Arg Ser Leu Leu Leu Ala Thr Gly Met Arg
 1               5                  10                  15

Asn Val Pro Glu Val Val Gln Gly Arg
            20                  25


<210> SEQ ID NO 394
<211> LENGTH: 24
<212> TYPE: PRT
<213> ORGANISM: Influenza virus A
<220> FEATURE:
<223> OTHER INFORMATION: C-terminal stem segment of Influenza A HA
      subtype H10(no Cys-delta 1)

<400> SEQUENCE: 394

Lys Tyr Val Asn Gln Arg Ser Leu Leu Leu Ala Thr Gly Met Arg Asn
 1               5                  10                  15

Val Pro Glu Val Val Gln Gly Arg
            20


<210> SEQ ID NO 395
<211> LENGTH: 23
<212> TYPE: PRT
<213> ORGANISM: Influenza virus A
<220> FEATURE:
<223> OTHER INFORMATION: C-terminal stem segment of Influenza A HA
      subtype H10(no Cys-delta 3)

<400> SEQUENCE: 395

Tyr Val Asn Gln Arg Ser Leu Leu Leu Ala Thr Gly Met Arg Asn Val
 1               5                  10                  15

Pro Glu Val Val Gln Gly Arg
            20


<210> SEQ ID NO 396
<211> LENGTH: 24
<212> TYPE: PRT
<213> ORGANISM: Influenza virus A
<220> FEATURE:
<223> OTHER INFORMATION: C-terminal stem segment of Influenza A
      HA subtype H11(no Cys)

<400> SEQUENCE: 396

Pro Lys Tyr Val Asn Val Lys Ser Leu Lys Leu Ala Thr Gly Pro Arg
 1               5                  10                  15

Asn Val Pro Ala Ile Ala Ser Arg
            20


<210> SEQ ID NO 397
<211> LENGTH: 23
<212> TYPE: PRT
<213> ORGANISM: Influenza virus A
<220> FEATURE:
<223> OTHER INFORMATION: C-terminal stem segment of Influenza A HA
      subtype H11(no Cys-delta 1)
```

```
<400> SEQUENCE: 397

Lys Tyr Val Asn Val Lys Ser Leu Lys Leu Ala Thr Gly Pro Arg Asn
 1              5                   10                  15

Val Pro Ala Ile Ala Ser Arg
            20


<210> SEQ ID NO 398
<211> LENGTH: 22
<212> TYPE: PRT
<213> ORGANISM: Influenza virus A
<220> FEATURE:
<223> OTHER INFORMATION: C-terminal stem segment of Influenza A HA
      subtype H11(no Cys-delta 3)

<400> SEQUENCE: 398

Tyr Val Asn Val Lys Ser Leu Lys Leu Ala Thr Gly Pro Arg Asn Val
 1              5                   10                  15

Pro Ala Ile Ala Ser Arg
            20


<210> SEQ ID NO 399
<211> LENGTH: 24
<212> TYPE: PRT
<213> ORGANISM: Influenza virus A
<220> FEATURE:
<223> OTHER INFORMATION: C-terminal stem segment of Influenza A
      HA subtype H12(no Cys)

<400> SEQUENCE: 399

Pro Lys Tyr Ile Pro Ser Gly Ser Leu Lys Leu Ala Ile Gly Leu Arg
 1              5                   10                  15

Asn Val Pro Gln Val Gln Asp Arg
            20


<210> SEQ ID NO 400
<211> LENGTH: 23
<212> TYPE: PRT
<213> ORGANISM: Influenza virus A
<220> FEATURE:
<223> OTHER INFORMATION: C-terminal stem segment of Influenza A HA
      subtype H12(no Cys-delta 1)

<400> SEQUENCE: 400

Lys Tyr Ile Pro Ser Gly Ser Leu Lys Leu Ala Ile Gly Leu Arg Asn
 1              5                   10                  15

Val Pro Gln Val Gln Asp Arg
            20


<210> SEQ ID NO 401
<211> LENGTH: 22
<212> TYPE: PRT
<213> ORGANISM: Influenza virus A
<220> FEATURE:
<223> OTHER INFORMATION: C-terminal stem segment of Influenza A HA
      subtype H12(no Cys-delta 3)

<400> SEQUENCE: 401

Tyr Ile Pro Ser Gly Ser Leu Lys Leu Ala Ile Gly Leu Arg Asn Val
 1              5                   10                  15

Pro Gln Val Gln Asp Arg
            20


<210> SEQ ID NO 402
```

```
<211> LENGTH: 24
<212> TYPE: PRT
<213> ORGANISM: Influenza virus A
<220> FEATURE:
<223> OTHER INFORMATION: C-terminal stem segment of Influenza A
      HA subtype H13(no Cys)

<400> SEQUENCE: 402

Pro Lys Tyr Ile Lys Ser Gly Gln Leu Lys Leu Ala Thr Gly Leu Arg
 1               5                  10                  15

Asn Val Pro Ala Ile Ser Asn Arg
            20


<210> SEQ ID NO 403
<211> LENGTH: 23
<212> TYPE: PRT
<213> ORGANISM: Influenza virus A
<220> FEATURE:
<223> OTHER INFORMATION: C-terminal stem segment of Influenza A HA
      subtype H13(no Cys-delta 1)

<400> SEQUENCE: 403

Lys Tyr Ile Lys Ser Gly Gln Leu Lys Leu Ala Thr Gly Leu Arg Asn
 1               5                  10                  15

Val Pro Ala Ile Ser Asn Arg
            20


<210> SEQ ID NO 404
<211> LENGTH: 22
<212> TYPE: PRT
<213> ORGANISM: Influenza virus A
<220> FEATURE:
<223> OTHER INFORMATION: C-terminal stem segment of Influenza A HA
      subtype H13(no Cys-delta 3)

<400> SEQUENCE: 404

Tyr Ile Lys Ser Gly Gln Leu Lys Leu Ala Thr Gly Leu Arg Asn Val
 1               5                  10                  15

Pro Ala Ile Ser Asn Arg
            20


<210> SEQ ID NO 405
<211> LENGTH: 24
<212> TYPE: PRT
<213> ORGANISM: Influenza virus A
<220> FEATURE:
<223> OTHER INFORMATION: C-terminal stem segment of Influenza A
      HA subtype H14(no Cys)

<400> SEQUENCE: 405

Pro Lys Tyr Val Lys Gln Gly Ser Leu Met Leu Ala Thr Gly Met Arg
 1               5                  10                  15

Asn Ile Pro Gly Lys Gln Ala Lys
            20


<210> SEQ ID NO 406
<211> LENGTH: 23
<212> TYPE: PRT
<213> ORGANISM: Influenza virus A
<220> FEATURE:
<223> OTHER INFORMATION: C-terminal stem segment of Influenza A HA
      subtype H14(no Cys-delta 1)

<400> SEQUENCE: 406

Lys Tyr Val Lys Gln Gly Ser Leu Met Leu Ala Thr Gly Met Arg Asn
 1               5                  10                  15
```

```
Ile Pro Gly Lys Gln Ala Lys
            20


<210> SEQ ID NO 407
<211> LENGTH: 22
<212> TYPE: PRT
<213> ORGANISM: Influenza virus A
<220> FEATURE:
<223> OTHER INFORMATION: C-terminal stem segment of Influenza A HA
      subtype H14(no Cys-delta 3)

<400> SEQUENCE: 407

Tyr Val Lys Gln Gly Ser Leu Met Leu Ala Thr Gly Met Arg Asn Ile
 1               5                  10                  15

Pro Gly Lys Gln Ala Lys
            20


<210> SEQ ID NO 408
<211> LENGTH: 25
<212> TYPE: PRT
<213> ORGANISM: Influenza virus A
<220> FEATURE:
<223> OTHER INFORMATION: C-terminal stem segment of Influenza A
      HA subtype H15(no Cys)

<400> SEQUENCE: 408

Pro Arg Tyr Val Lys Gln Ser Ser Leu Pro Leu Ala Leu Gly Met Lys
 1               5                  10                  15

Asn Val Pro Glu Lys Ile Arg Thr Arg
            20                  25


<210> SEQ ID NO 409
<211> LENGTH: 24
<212> TYPE: PRT
<213> ORGANISM: Influenza virus A
<220> FEATURE:
<223> OTHER INFORMATION: C-terminal stem segment of Influenza A HA
      subtype H15(no Cys-delta 1)

<400> SEQUENCE: 409

Arg Tyr Val Lys Gln Ser Ser Leu Pro Leu Ala Leu Gly Met Lys Asn
 1               5                  10                  15

Val Pro Glu Lys Ile Arg Thr Arg
            20


<210> SEQ ID NO 410
<211> LENGTH: 23
<212> TYPE: PRT
<213> ORGANISM: Influenza virus A
<220> FEATURE:
<223> OTHER INFORMATION: C-terminal stem segment of Influenza A HA
      subtype H15(no Cys-delta 3)

<400> SEQUENCE: 410

Tyr Val Lys Gln Ser Ser Leu Pro Leu Ala Leu Gly Met Lys Asn Val
 1               5                  10                  15

Pro Glu Lys Ile Arg Thr Arg
            20


<210> SEQ ID NO 411
<211> LENGTH: 24
<212> TYPE: PRT
<213> ORGANISM: Influenza virus A
<220> FEATURE:
<223> OTHER INFORMATION: C-terminal stem segment of Influenza A
```

HA subtype H16(no Cys)

<400> SEQUENCE: 411

Pro Lys Tyr Ile Lys Ser Gly Gln Leu Lys Leu Ala Thr Gly Leu Arg
1 5 10 15

Asn Val Pro Ser Ile Gly Glu Arg
20

<210> SEQ ID NO 412
<211> LENGTH: 23
<212> TYPE: PRT
<213> ORGANISM: Influenza virus A
<220> FEATURE:
<223> OTHER INFORMATION: C-terminal stem segment of Influenza A HA subtype H16(no Cys-delta 1)

<400> SEQUENCE: 412

Lys Tyr Ile Lys Ser Gly Gln Leu Lys Leu Ala Thr Gly Leu Arg Asn
1 5 10 15

Val Pro Ser Ile Gly Glu Arg
20

<210> SEQ ID NO 413
<211> LENGTH: 22
<212> TYPE: PRT
<213> ORGANISM: Influenza virus A
<220> FEATURE:
<223> OTHER INFORMATION: C-terminal stem segment of Influenza A HA subtype H16(no Cys-delta 3)

<400> SEQUENCE: 413

Tyr Ile Lys Ser Gly Gln Leu Lys Leu Ala Thr Gly Leu Arg Asn Val
1 5 10 15

Pro Ser Ile Gly Glu Arg
20

<210> SEQ ID NO 414
<211> LENGTH: 90
<212> TYPE: PRT
<213> ORGANISM: Influenza virus A
<220> FEATURE:
<223> OTHER INFORMATION: N-termianl long stem domain segment of Influenza A HA subtype H1

<400> SEQUENCE: 414

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asp Ser His Asn Gly Lys Leu Cys Arg Leu Lys Gly Ile Ala
35 40 45

Pro Leu Gln Leu Gly Lys Cys Asn Ile Ala Gly Trp Leu Leu Gly Asn
50 55 60

Pro Glu Cys Asp Pro Leu Leu Pro Val Arg Ser Trp Ser Tyr Ile Val
65 70 75 80

Glu Thr Pro Asn Ser Glu Asn Gly Ile Cys
85 90

<210> SEQ ID NO 415
<211> LENGTH: 90
<212> TYPE: PRT
<213> ORGANISM: Influenza virus A
<220> FEATURE:

<223> OTHER INFORMATION: N-termianl long stem domain segment of
      Influenza A HA subtype H2

<400> SEQUENCE: 415

```
Asp Gln Ile Cys Ile Gly Tyr His Ser Asn Asn Ser Thr Glu Lys Val
 1               5                  10                  15

Asp Thr Ile Leu Glu Arg Asn Val Thr Val Thr His Ala Gln Asn Ile
            20                  25                  30

Leu Glu Lys Thr His Asn Gly Lys Leu Cys Lys Leu Asn Gly Ile Pro
        35                  40                  45

Pro Leu Glu Leu Gly Asp Cys Ser Ile Ala Gly Trp Leu Leu Gly Asn
    50                  55                  60

Pro Glu Cys Asp Arg Leu Leu Thr Val Pro Glu Trp Ser Tyr Ile Met
65                  70                  75                  80

Glu Lys Glu Asn Pro Arg Asn Gly Leu Cys
                85                  90
```

<210> SEQ ID NO 416
<211> LENGTH: 97
<212> TYPE: PRT
<213> ORGANISM: Influenza virus A
<220> FEATURE:
<223> OTHER INFORMATION: N-termianl long stem domain segment of
      Influenza A HA subtype H3

<400> SEQUENCE: 416

```
Gln Asp Leu Pro Gly Asn Asp Asn Ser Thr Ala Thr Leu Cys Leu Gly
 1               5                  10                  15

His His Ala Val Pro Asn Gly Thr Leu Val Lys Thr Ile Thr Asp Asp
            20                  25                  30

Gln Ile Glu Val Thr Asn Ala Thr Glu Leu Val Gln Ser Ser Ser Thr
        35                  40                  45

Gly Lys Ile Cys Asn Asn Pro His Arg Ile Leu Asp Gly Ile Asp Cys
    50                  55                  60

Thr Leu Ile Asp Ala Leu Leu Gly Asp Pro His Cys Asp Val Phe Gln
65                  70                  75                  80

Asn Glu Thr Trp Asp Leu Phe Val Glu Arg Ser Lys Ala Phe Ser Asn
                85                  90                  95

Cys
```

<210> SEQ ID NO 417
<211> LENGTH: 93
<212> TYPE: PRT
<213> ORGANISM: Influenza virus A
<220> FEATURE:
<223> OTHER INFORMATION: N-termianl long stem domain segment of
      Influenza A HA subtype H4

<400> SEQUENCE: 417

```
Gln Asn Tyr Thr Gly Asn Pro Val Ile Cys Met Gly His His Ala Val
 1               5                  10                  15

Ala Asn Gly Thr Met Val Lys Thr Leu Ala Asp Asp Gln Val Glu Val
            20                  25                  30

Val Thr Ala Gln Glu Leu Val Glu Ser Gln Asn Leu Pro Glu Leu Cys
        35                  40                  45

Pro Ser Pro Leu Arg Leu Val Asp Gly Gln Thr Cys Asp Ile Ile Asn
    50                  55                  60

Gly Ala Leu Gly Ser Pro Gly Cys Asp His Leu Asn Gly Ala Glu Trp
65                  70                  75                  80
```

```
Asp Val Phe Ile Glu Arg Pro Asn Ala Val Asp Thr Cys
                85                  90


<210> SEQ ID NO 418
<211> LENGTH: 90
<212> TYPE: PRT
<213> ORGANISM: Influenza virus A
<220> FEATURE:
<223> OTHER INFORMATION: N-termianl long stem domain segment of
      Influenza A HA subtype H5

<400> SEQUENCE: 418

Asp Gln Ile Cys Ile Gly Tyr His Ala Asn Lys Ser Thr Lys Gln Val
 1               5                  10                  15

Asp Thr Ile Met Glu Lys Asn Val Thr Val Thr His Ala Gln Asp Ile
            20                  25                  30

Leu Glu Arg Thr His Asn Gly Lys Leu Cys Ser Leu Asn Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Leu Asn Leu Pro Glu Trp Leu Tyr Ile Val
65                  70                  75                  80

Glu Lys Asp Asn Pro Ile Asn Ser Leu Cys
                85                  90


<210> SEQ ID NO 419
<211> LENGTH: 90
<212> TYPE: PRT
<213> ORGANISM: Influenza virus A
<220> FEATURE:
<223> OTHER INFORMATION: N-termianl long stem domain segment of
      Influenza A HA subtype H6

<400> SEQUENCE: 419

Asp Lys Ile Cys Ile Gly Tyr His Ala Asn Asn Ser Thr Thr Gln Ile
 1               5                  10                  15

Asp Thr Ile Leu Glu Lys Asn Val Thr Val Thr His Ser Val Glu Leu
            20                  25                  30

Leu Glu Asn Gln Lys Glu Glu Arg Phe Cys Lys Ile Leu Lys Lys Ala
        35                  40                  45

Pro Leu Asp Leu Lys Gly Cys Thr Ile Glu Gly Trp Ile Leu Gly Asn
    50                  55                  60

Pro Gln Cys Asp Leu Leu Leu Gly Asp Gln Ser Trp Ser Tyr Ile Val
65                  70                  75                  80

Glu Arg Pro Thr Ala Gln Asn Gly Ile Cys
                85                  90


<210> SEQ ID NO 420
<211> LENGTH: 87
<212> TYPE: PRT
<213> ORGANISM: Influenza virus A
<220> FEATURE:
<223> OTHER INFORMATION: N-termianl long stem domain segment of
      Influenza A HA subtype H7

<400> SEQUENCE: 420

Asp Lys Ile Cys Leu Gly His His Ala Val Ser Asn Gly Thr Lys Val
 1               5                  10                  15

Asn Thr Leu Thr Glu Arg Gly Val Glu Val Val Asn Ala Thr Glu Thr
            20                  25                  30
```

```
Val Glu Arg Thr Asn Ile Pro Lys Ile Cys Ser Lys Gly Lys Arg Thr
        35                  40                  45

Thr Asp Leu Gly Gln Cys Gly Leu Leu Gly Thr Ile Thr Gly Pro Pro
    50                  55                  60

Gln Cys Asp Gln Phe Leu Glu Phe Ser Ala Asp Leu Ile Ile Glu Arg
65                  70                  75                  80

Arg Glu Gly Asn Asp Val Cys
                85


<210> SEQ ID NO 421
<211> LENGTH: 90
<212> TYPE: PRT
<213> ORGANISM: Influenza virus A
<220> FEATURE:
<223> OTHER INFORMATION: N-termianl long stem domain segment of
      Influenza A HA subtype H8

<400> SEQUENCE: 421

Asp Arg Ile Cys Ile Gly Tyr Gln Ser Asn Asn Ser Thr Asp Thr Val
 1               5                  10                  15

Asn Thr Leu Ile Glu Gln Asn Val Pro Val Thr Gln Thr Met Glu Leu
            20                  25                  30

Val Glu Thr Glu Lys His Pro Ala Tyr Cys Asn Thr Asp Leu Gly Ala
        35                  40                  45

Pro Leu Glu Leu Arg Asp Cys Lys Ile Glu Ala Val Ile Tyr Gly Asn
    50                  55                  60

Pro Lys Cys Asp Ile His Leu Lys Asp Gln Gly Trp Ser Tyr Ile Val
65                  70                  75                  80

Glu Arg Pro Ser Ala Pro Glu Gly Met Cys
                85                  90


<210> SEQ ID NO 422
<211> LENGTH: 90
<212> TYPE: PRT
<213> ORGANISM: Influenza virus A
<220> FEATURE:
<223> OTHER INFORMATION: N-termianl long stem domain segment of
      Influenza A HA subtype H9

<400> SEQUENCE: 422

Asp Lys Ile Cys Ile Gly Tyr Gln Ser Thr Asn Ser Thr Glu Thr Val
 1               5                  10                  15

Asp Thr Leu Thr Glu Ser Asn Val Pro Val Thr His Thr Lys Glu Leu
            20                  25                  30

Leu His Thr Glu His Asn Gly Met Leu Cys Ala Thr Asp Leu Gly His
        35                  40                  45

Pro Leu Ile Leu Asp Thr Cys Thr Ile Glu Gly Leu Ile Tyr Gly Asn
    50                  55                  60

Pro Ser Cys Asp Ile Leu Leu Gly Gly Lys Glu Trp Ser Tyr Ile Val
65                  70                  75                  80

Glu Arg Ser Ser Ala Val Asn Gly Met Cys
                85                  90


<210> SEQ ID NO 423
<211> LENGTH: 88
<212> TYPE: PRT
<213> ORGANISM: Influenza virus A
<220> FEATURE:
<223> OTHER INFORMATION: N-termianl long stem domain segment of
      Influenza A HA subtype H10
```

<400> SEQUENCE: 423

Leu Asp Arg Ile Cys Leu Gly His His Ala Val Ala Asn Gly Thr Ile
1 5 10 15

Val Lys Thr Leu Thr Asn Glu Gln Glu Glu Val Thr Asn Ala Thr Glu
20 25 30

Thr Val Glu Ser Thr Asn Leu Asn Lys Leu Cys Met Lys Gly Arg Ser
35 40 45

Tyr Lys Asp Leu Gly Asn Cys His Pro Val Gly Met Leu Ile Gly Thr
50 55 60

Pro Val Cys Asp Pro His Leu Thr Gly Thr Trp Asp Thr Leu Ile Glu
65 70 75 80

Arg Glu Asn Ala Ile Ala His Cys
85

<210> SEQ ID NO 424
<211> LENGTH: 90
<212> TYPE: PRT
<213> ORGANISM: Influenza virus A
<220> FEATURE:
<223> OTHER INFORMATION: N-termianl long stem domain segment of Influenza A HA subtype H11

<400> SEQUENCE: 424

Asp Glu Ile Cys Ile Gly Tyr Leu Ser Asn Asn Ser Thr Asp Lys Val
1 5 10 15

Asp Thr Ile Ile Glu Asn Asn Val Thr Val Thr Ser Ser Val Glu Leu
20 25 30

Val Glu Thr Glu His Thr Gly Ser Phe Cys Ser Ile Asn Gly Lys Gln
35 40 45

Pro Ile Ser Leu Gly Asp Cys Ser Phe Ala Gly Trp Ile Leu Gly Asn
50 55 60

Pro Met Cys Asp Glu Leu Ile Gly Lys Thr Ser Trp Ser Tyr Ile Val
65 70 75 80

Glu Lys Pro Asn Pro Thr Asn Gly Ile Cys
85 90

<210> SEQ ID NO 425
<211> LENGTH: 90
<212> TYPE: PRT
<213> ORGANISM: Influenza virus A
<220> FEATURE:
<223> OTHER INFORMATION: N-termianl long stem domain segment of Influenza A HA subtype H12

<400> SEQUENCE: 425

Asp Lys Ile Cys Ile Gly Tyr Gln Thr Asn Asn Ser Thr Glu Thr Val
1 5 10 15

Asn Thr Leu Ser Glu Gln Asn Val Pro Val Thr Gln Val Glu Glu Leu
20 25 30

Val His Arg Gly Ile Asp Pro Ile Leu Cys Gly Thr Glu Leu Gly Ser
35 40 45

Pro Leu Val Leu Asp Asp Cys Ser Leu Glu Gly Leu Ile Leu Gly Asn
50 55 60

Pro Lys Cys Asp Leu Tyr Leu Asn Gly Arg Glu Trp Ser Tyr Ile Val
65 70 75 80

Glu Arg Pro Lys Glu Met Glu Gly Val Cys
85 90

```
<210> SEQ ID NO 426
<211> LENGTH: 90
<212> TYPE: PRT
<213> ORGANISM: Influenza virus A
<220> FEATURE:
<223> OTHER INFORMATION: N-termianl long stem domain segment of
      Influenza A HA subtype H13

<400> SEQUENCE: 426

Asp Arg Ile Cys Val Gly Tyr Leu Ser Thr Asn Ser Ser Glu Arg Val
 1               5                  10                  15

Asp Thr Leu Leu Glu Asn Gly Val Pro Val Thr Ser Ser Ile Asp Leu
            20                  25                  30

Ile Glu Thr Asn His Thr Gly Thr Tyr Cys Ser Leu Asn Gly Val Ser
        35                  40                  45

Pro Val His Leu Gly Asp Cys Ser Phe Glu Gly Trp Ile Val Gly Asn
    50                  55                  60

Pro Ala Cys Thr Ser Asn Phe Gly Ile Arg Glu Trp Ser Tyr Leu Ile
65                  70                  75                  80

Glu Asp Pro Ala Ala Pro His Gly Leu Cys
                85                  90


<210> SEQ ID NO 427
<211> LENGTH: 96
<212> TYPE: PRT
<213> ORGANISM: Influenza virus A
<220> FEATURE:
<223> OTHER INFORMATION: N-termianl long stem domain segment of
      Influenza A HA subtype H14

<400> SEQUENCE: 427

Gln Ile Thr Asn Gly Thr Thr Gly Asn Pro Ile Ile Cys Leu Gly His
 1               5                  10                  15

His Ala Val Glu Asn Gly Thr Ser Val Lys Thr Leu Thr Asp Asn His
            20                  25                  30

Val Glu Val Val Ser Ala Lys Glu Leu Val Glu Thr Asn His Thr Asp
        35                  40                  45

Glu Leu Cys Pro Ser Pro Leu Lys Leu Val Asp Gly Gln Asp Cys His
    50                  55                  60

Leu Ile Asn Gly Ala Leu Gly Ser Pro Gly Cys Asp Arg Leu Gln Asp
65                  70                  75                  80

Thr Thr Trp Asp Val Phe Ile Glu Arg Pro Thr Ala Val Asp Thr Cys
                85                  90                  95


<210> SEQ ID NO 428
<211> LENGTH: 87
<212> TYPE: PRT
<213> ORGANISM: Influenza virus A
<220> FEATURE:
<223> OTHER INFORMATION: N-termianl long stem domain segment of
      Influenza A HA subtype H15

<400> SEQUENCE: 428

Asp Lys Ile Cys Leu Gly His His Ala Val Ala Asn Gly Thr Lys Val
 1               5                  10                  15

Asn Thr Leu Thr Glu Arg Gly Val Glu Val Val Asn Ala Thr Glu Thr
            20                  25                  30

Val Glu Ile Thr Gly Ile Asp Lys Val Cys Thr Lys Gly Lys Lys Ala
        35                  40                  45

Val Asp Leu Gly Ser Cys Gly Ile Leu Gly Thr Ile Ile Gly Pro Pro
    50                  55                  60
```

```
Gln Cys Asp Leu His Leu Glu Phe Lys Ala Asp Leu Ile Ile Glu Arg
65                  70                  75                  80

Arg Asn Ser Ser Asp Ile Cys
                85


<210> SEQ ID NO 429
<211> LENGTH: 90
<212> TYPE: PRT
<213> ORGANISM: Influenza virus A
<220> FEATURE:
<223> OTHER INFORMATION: N-termianl long stem domain segment of
      Influenza A HA subtype H16

<400> SEQUENCE: 429

Asp Lys Ile Cys Ile Gly Tyr Leu Ser Asn Asn Ser Ser Asp Thr Val
 1               5                  10                  15

Asp Thr Leu Thr Glu Asn Gly Val Pro Val Thr Ser Ser Val Asp Leu
            20                  25                  30

Val Glu Thr Asn His Thr Gly Thr Tyr Cys Ser Leu Asn Gly Ile Ser
        35                  40                  45

Pro Ile His Leu Gly Asp Cys Ser Phe Glu Gly Trp Ile Val Gly Asn
    50                  55                  60

Pro Ser Cys Ala Thr Asn Ile Asn Ile Arg Glu Trp Ser Tyr Leu Ile
65                  70                  75                  80

Glu Asp Pro Asn Ala Pro Asn Lys Phe Cys
                85                  90


<210> SEQ ID NO 430
<211> LENGTH: 78
<212> TYPE: PRT
<213> ORGANISM: Influenza virus A
<220> FEATURE:
<223> OTHER INFORMATION: C-termianl long stem domain segment of
      Influenza A HA subtype H1

<400> SEQUENCE: 430

Ala Pro Met Tyr Ala Phe Ala Leu Ser Arg Gly Phe Gly Ser Gly Ile
 1               5                  10                  15

Ile Thr Ser Asn Ala Ser Met His Glu Cys Asn Thr Lys Cys Gln Thr
            20                  25                  30

Pro Leu Gly Ala Ile Asn Ser Ser Leu Pro Tyr Gln Asn Ile His Pro
        35                  40                  45

Val Thr Ile Gly Glu Cys Pro Lys Tyr Val Arg Ser Ala Lys Leu Arg
    50                  55                  60

Met Val Thr Gly Leu Arg Asn Asn Pro Ser Ile Gln Ser Arg
65                  70                  75


<210> SEQ ID NO 431
<211> LENGTH: 78
<212> TYPE: PRT
<213> ORGANISM: Influenza virus A
<220> FEATURE:
<223> OTHER INFORMATION: C-termianl long stem domain segment of
      Influenza A HA subtype H2

<400> SEQUENCE: 431

Ala Pro Glu Tyr Gly Phe Arg Ile Ser Lys Arg Gly Ser Ser Gly Ile
 1               5                  10                  15

Met Lys Thr Glu Gly Thr Leu Glu Asn Cys Glu Thr Lys Cys Gln Thr
            20                  25                  30
```

```
Pro Leu Gly Ala Ile Asn Thr Thr Leu Pro Phe His Asn Val His Pro
        35                  40                  45

Leu Thr Ile Gly Glu Cys Pro Lys Tyr Val Lys Ser Glu Arg Leu Val
    50                  55                  60

Leu Ala Thr Gly Leu Arg Asn Val Pro Gln Ile Glu Ser Arg
65                  70                  75


<210> SEQ ID NO 432
<211> LENGTH: 77
<212> TYPE: PRT
<213> ORGANISM: Influenza virus A
<220> FEATURE:
<223> OTHER INFORMATION: C-termianl long stem domain segment of
      Influenza A HA subtype H3

<400> SEQUENCE: 432

Ala Pro Arg Gly Tyr Phe Lys Met Arg Thr Gly Lys Ser Ser Ile Met
 1               5                  10                  15

Ser Ser Asp Ala Pro Ile Asp Thr Cys Ile Ser Glu Cys Ile Thr Pro
            20                  25                  30

Asn Gly Ser Ile Pro Asn Asp Lys Pro Phe Gln Asn Val Asn Lys Ile
        35                  40                  45

Thr Tyr Gly Ala Cys Pro Lys Tyr Val Lys Gln Asn Thr Leu Lys Leu
    50                  55                  60

Ala Thr Gly Met Arg Asn Val Pro Glu Lys Gln Thr Arg
65                  70                  75


<210> SEQ ID NO 433
<211> LENGTH: 78
<212> TYPE: PRT
<213> ORGANISM: Influenza virus A
<220> FEATURE:
<223> OTHER INFORMATION: C-termianl long stem domain segment of
      Influenza A HA subtype H4

<400> SEQUENCE: 433

Ala Pro Arg Gly His Tyr Lys Leu Asn Asn Gln Lys Lys Ser Thr Ile
 1               5                  10                  15

Leu Asn Thr Ala Ile Pro Ile Gly Ser Cys Val Ser Lys Cys His Thr
            20                  25                  30

Asp Lys Gly Ser Leu Ser Thr Thr Lys Pro Phe Gln Asn Ile Ser Arg
        35                  40                  45

Ile Ala Val Gly Asp Cys Pro Arg Tyr Val Lys Gln Gly Ser Leu Lys
    50                  55                  60

Leu Ala Thr Gly Met Arg Asn Ile Pro Glu Lys Ala Ser Arg
65                  70                  75


<210> SEQ ID NO 434
<211> LENGTH: 78
<212> TYPE: PRT
<213> ORGANISM: Influenza virus A
<220> FEATURE:
<223> OTHER INFORMATION: C-termianl long stem domain segment of
      Influenza A HA subtype H5

<400> SEQUENCE: 434

Ala Pro Arg Tyr Ala Tyr Lys Ile Val Lys Lys Gly Asp Ser Ala Ile
 1               5                  10                  15

Met Lys Ser Gly Leu Ala Tyr Gly Asn Cys Asp Thr Lys Cys Gln Thr
            20                  25                  30

Pro Val Gly Glu Ile Asn Ser Ser Met Pro Phe His Asn Ile His Pro
```

```
        35                  40                  45

His Thr Ile Gly Glu Cys Pro Lys Tyr Val Lys Ser Asp Arg Leu Val
    50                  55                  60

Leu Ala Thr Gly Leu Arg Asn Val Pro Gln Arg Lys Lys Arg
65                  70                  75


<210> SEQ ID NO 435
<211> LENGTH: 79
<212> TYPE: PRT
<213> ORGANISM: Influenza virus A
<220> FEATURE:
<223> OTHER INFORMATION: C-termianl long stem domain segment of
      Influenza A HA subtype H6

<400> SEQUENCE: 435

Ala Pro Trp Tyr Ala Phe Arg Phe Val Ser Thr Ser Asn Lys Gly Ala
 1               5                  10                  15

Val Phe Lys Ser Asn Leu Pro Ile Glu Asn Cys Asp Ala Thr Cys Gln
            20                  25                  30

Thr Val Ala Gly Val Leu Arg Thr Asn Lys Thr Phe Gln Asn Val Ser
        35                  40                  45

Pro Leu Trp Ile Gly Glu Cys Pro Lys Tyr Val Lys Ser Glu Ser Leu
    50                  55                  60

Arg Leu Ala Thr Gly Leu Arg Asn Val Pro Gln Ile Glu Thr Arg
65                  70                  75


<210> SEQ ID NO 436
<211> LENGTH: 81
<212> TYPE: PRT
<213> ORGANISM: Influenza virus A
<220> FEATURE:
<223> OTHER INFORMATION: C-termianl long stem domain segment of
      Influenza A HA subtype H7

<400> SEQUENCE: 436

Ala Pro Asn Arg Ala Ser Phe Leu Arg Gly Lys Ser Met Gly Ile Gln
 1               5                  10                  15

Ser Asp Val Gln Val Asp Ala Asn Cys Glu Gly Glu Cys Tyr His Ser
            20                  25                  30

Gly Gly Thr Ile Thr Ser Arg Leu Pro Phe Gln Asn Ile Asn Ser Arg
        35                  40                  45

Ala Val Gly Lys Cys Pro Arg Tyr Val Lys Gln Glu Ser Leu Leu Leu
    50                  55                  60

Ala Thr Gly Met Lys Asn Val Pro Glu Pro Ser Lys Lys Arg Lys Lys
65                  70                  75                  80

Arg


<210> SEQ ID NO 437
<211> LENGTH: 79
<212> TYPE: PRT
<213> ORGANISM: Influenza virus A
<220> FEATURE:
<223> OTHER INFORMATION: C-termianl long stem domain segment of
      Influenza A HA subtype H8

<400> SEQUENCE: 437

Ala Pro Glu Phe Gly Tyr Leu Leu Lys Gly Glu Ser Tyr Gly Arg Ile
 1               5                  10                  15

Ile Gln Asn Glu Asp Ile Pro Ile Gly Asn Cys Asn Thr Lys Cys Gln
            20                  25                  30
```

```
Thr Tyr Ala Gly Ala Ile Asn Ser Ser Lys Pro Phe Gln Asn Ala Ser
        35                  40                  45

Arg His Tyr Met Gly Glu Cys Pro Lys Tyr Val Lys Lys Ala Ser Leu
    50                  55                  60

Arg Leu Ala Val Gly Leu Arg Asn Thr Pro Ser Val Glu Pro Arg
65                  70                  75


<210> SEQ ID NO 438
<211> LENGTH: 78
<212> TYPE: PRT
<213> ORGANISM: Influenza virus A
<220> FEATURE:
<223> OTHER INFORMATION: C-termianl long stem domain segment of
      Influenza A HA subtype H9

<400> SEQUENCE: 438

Ala Pro Trp Tyr Gly His Val Leu Thr Gly Glu Ser His Gly Arg Ile
 1               5                  10                  15

Leu Lys Thr Asp Leu Asn Asn Gly Asn Cys Val Val Gln Cys Gln Thr
            20                  25                  30

Glu Lys Gly Gly Leu Asn Thr Thr Leu Pro Phe His Asn Ile Ser Lys
        35                  40                  45

Tyr Ala Phe Gly Asn Cys Pro Lys Tyr Val Gly Val Lys Ser Leu Lys
    50                  55                  60

Leu Pro Val Gly Leu Arg Asn Val Pro Ala Val Ser Ser Arg
65                  70                  75


<210> SEQ ID NO 439
<211> LENGTH: 78
<212> TYPE: PRT
<213> ORGANISM: Influenza virus A
<220> FEATURE:
<223> OTHER INFORMATION: C-termianl long stem domain segment of
      Influenza A HA subtype H10

<400> SEQUENCE: 439

Ala Pro Ser Arg Val Ser Lys Leu Thr Gly Arg Asp Leu Gly Ile Gln
 1               5                  10                  15

Ser Glu Ala Leu Ile Asp Asn Ser Cys Glu Ser Lys Cys Phe Trp Arg
            20                  25                  30

Gly Gly Ser Ile Asn Thr Lys Leu Pro Phe Gln Asn Leu Ser Pro Arg
        35                  40                  45

Thr Val Gly Gln Cys Pro Lys Tyr Val Asn Gln Arg Ser Leu Leu Leu
    50                  55                  60

Ala Thr Gly Met Arg Asn Val Pro Glu Val Val Gln Gly Arg
65                  70                  75


<210> SEQ ID NO 440
<211> LENGTH: 78
<212> TYPE: PRT
<213> ORGANISM: Influenza virus A
<220> FEATURE:
<223> OTHER INFORMATION: C-termianl long stem domain segment of
      Influenza A HA subtype H11

<400> SEQUENCE: 440

Ala Pro Arg Tyr Ala Phe Glu Ile Val Ser Val Gly Asn Gly Lys Leu
 1               5                  10                  15

Phe Arg Ser Glu Leu Asn Ile Glu Ser Cys Ser Thr Lys Cys Gln Thr
            20                  25                  30

Glu Ile Gly Gly Ile Asn Thr Asn Lys Ser Phe His Asn Val His Arg
```

```
        35                  40                  45

Asn Thr Ile Gly Asp Cys Pro Lys Tyr Val Asn Val Lys Ser Leu Lys
    50                  55                  60

Leu Ala Thr Gly Pro Arg Asn Val Pro Ala Ile Ala Ser Arg
65                  70                  75


<210> SEQ ID NO 441
<211> LENGTH: 78
<212> TYPE: PRT
<213> ORGANISM: Influenza virus A
<220> FEATURE:
<223> OTHER INFORMATION: C-termianl long stem domain segment of
      Influenza A HA subtype H12

<400> SEQUENCE: 441

Ala Pro Glu Tyr Gly His Leu Ile Thr Gly Lys Ser His Gly Arg Ile
 1               5                  10                  15

Leu Lys Asn Asn Leu Pro Met Gly Gln Cys Val Thr Glu Cys Gln Leu
            20                  25                  30

Asn Glu Gly Val Met Asn Thr Ser Lys Pro Phe Gln Asn Thr Ser Lys
        35                  40                  45

His Tyr Ile Gly Lys Cys Pro Lys Tyr Ile Pro Ser Gly Ser Leu Lys
    50                  55                  60

Leu Ala Ile Gly Leu Arg Asn Val Pro Gln Val Gln Asp Arg
65                  70                  75


<210> SEQ ID NO 442
<211> LENGTH: 78
<212> TYPE: PRT
<213> ORGANISM: Influenza virus A
<220> FEATURE:
<223> OTHER INFORMATION: C-termianl long stem domain segment of
      Influenza A HA subtype H13

<400> SEQUENCE: 442

Ala Pro Arg Tyr Gly Tyr Ile Ile Glu Glu Tyr Gly Lys Gly Arg Ile
 1               5                  10                  15

Phe Gln Ser Arg Ile Arg Met Ser Arg Cys Asn Thr Lys Cys Gln Thr
            20                  25                  30

Ser Val Gly Gly Ile Asn Thr Asn Arg Thr Phe Gln Asn Ile Asp Lys
        35                  40                  45

Asn Ala Leu Gly Asp Cys Pro Lys Tyr Ile Lys Ser Gly Gln Leu Lys
    50                  55                  60

Leu Ala Thr Gly Leu Arg Asn Val Pro Ala Ile Ser Asn Arg
65                  70                  75


<210> SEQ ID NO 443
<211> LENGTH: 78
<212> TYPE: PRT
<213> ORGANISM: Influenza virus A
<220> FEATURE:
<223> OTHER INFORMATION: C-termianl long stem domain segment of
      Influenza A HA subtype H14

<400> SEQUENCE: 443

Ala Pro Arg Gly His Tyr Lys Ile Ser Lys Ser Thr Lys Ser Thr Val
 1               5                  10                  15

Leu Lys Ser Asp Lys Arg Ile Gly Ser Cys Thr Ser Pro Cys Leu Thr
            20                  25                  30

Asp Lys Gly Ser Ile Gln Ser Asp Lys Pro Phe Gln Asn Val Ser Arg
        35                  40                  45
```

```
Ile Ala Ile Gly Asn Cys Pro Lys Tyr Val Lys Gln Gly Ser Leu Met
    50                  55                  60

Leu Ala Thr Gly Met Arg Asn Ile Pro Gly Lys Gln Ala Lys
65                  70                  75


<210> SEQ ID NO 444
<211> LENGTH: 88
<212> TYPE: PRT
<213> ORGANISM: Influenza virus A
<220> FEATURE:
<223> OTHER INFORMATION: C-termianl long stem domain segment of
      Influenza A HA subtype H15

<400> SEQUENCE: 444

Ala Pro Asp Arg Ala Thr Phe Leu Arg Ser Asn Ala Pro Ser Gly Ile
 1               5                  10                  15

Glu Tyr Asn Gly Lys Ser Leu Gly Ile Gln Ser Asp Ala Gln Ile Asp
            20                  25                  30

Glu Ser Cys Glu Gly Glu Cys Phe Tyr Ser Gly Gly Thr Ile Asn Ser
        35                  40                  45

Pro Leu Pro Phe Gln Asn Ile Asp Ser Arg Ala Val Gly Lys Cys Pro
    50                  55                  60

Arg Tyr Val Lys Gln Ser Ser Leu Pro Leu Ala Leu Gly Met Lys Asn
65                  70                  75                  80

Val Pro Glu Lys Ile Arg Thr Arg
                85


<210> SEQ ID NO 445
<211> LENGTH: 78
<212> TYPE: PRT
<213> ORGANISM: Influenza virus A
<220> FEATURE:
<223> OTHER INFORMATION: C-termianl long stem domain segment of
      Influenza A HA subtype H16

<400> SEQUENCE: 445

Ala Pro Arg Tyr Gly Tyr Ile Ile Glu Lys Tyr Gly Thr Gly Arg Ile
 1               5                  10                  15

Phe Gln Ser Gly Val Arg Met Ala Arg Cys Asn Thr Lys Cys Gln Thr
            20                  25                  30

Ser Leu Gly Gly Ile Asn Thr Asn Lys Thr Phe Gln Asn Ile Glu Arg
        35                  40                  45

Asn Ala Leu Gly Asp Cys Pro Lys Tyr Ile Lys Ser Gly Gln Leu Lys
    50                  55                  60

Leu Ala Thr Gly Leu Arg Asn Val Pro Ser Ile Gly Glu Arg
65                  70                  75


<210> SEQ ID NO 446
<211> LENGTH: 89
<212> TYPE: PRT
<213> ORGANISM: Influenza virus A
<220> FEATURE:
<223> OTHER INFORMATION: N-termianl long stem domain segment of
      Influenza A HA subtype H1(No Cys, Ala)

<400> SEQUENCE: 446

Asp Thr Ile Cys Ile Gly Tyr His Ala Asn Asn Ser Thr Asp Thr Val
 1               5                  10                  15

Asp Thr Val Leu Glu Lys Asn Val Thr Val Thr His Ser Val Asn Leu
            20                  25                  30
```

```
Leu Glu Asp Ser His Asn Gly Lys Leu Cys Arg Leu Lys Gly Ile Ala
        35                  40                  45

Pro Leu Gln Leu Gly Lys Cys Asn Ile Ala Gly Trp Leu Leu Gly Asn
    50                  55                  60

Pro Glu Cys Asp Pro Leu Leu Pro Val Arg Ser Trp Ser Tyr Ile Val
65                  70                  75                  80

Glu Thr Pro Asn Ser Glu Asn Gly Ile
                85


<210> SEQ ID NO 447
<211> LENGTH: 89
<212> TYPE: PRT
<213> ORGANISM: Influenza virus A
<220> FEATURE:
<223> OTHER INFORMATION: N-termianl long stem domain segment of
      Influenza A HA subtype H1(No Cys, Ala - Delta 1)

<400> SEQUENCE: 447

Asp Thr Ile Cys Ile Gly Tyr His Ala Asn Asn Ser Thr Asp Thr Val
 1               5                  10                  15

Asp Thr Val Leu Glu Lys Asn Val Thr Val Thr His Ser Val Asn Leu
            20                  25                  30

Leu Glu Asp Ser His Asn Gly Lys Leu Cys Arg Leu Lys Gly Ile Ala
        35                  40                  45

Pro Leu Gln Leu Gly Lys Cys Asn Ile Ala Gly Trp Leu Leu Gly Asn
    50                  55                  60

Pro Glu Cys Asp Pro Leu Leu Pro Val Arg Ser Trp Ser Tyr Ile Val
65                  70                  75                  80

Glu Thr Pro Asn Ser Glu Asn Gly Ile
                85


<210> SEQ ID NO 448
<211> LENGTH: 88
<212> TYPE: PRT
<213> ORGANISM: Influenza virus A
<220> FEATURE:
<223> OTHER INFORMATION: N-termianl long stem domain segment of
      Influenza A HA subtype H1(No Cys, Ala - Delta 3)

<400> SEQUENCE: 448

Asp Thr Ile Cys Ile Gly Tyr His Ala Asn Asn Ser Thr Asp Thr Val
 1               5                  10                  15

Asp Thr Val Leu Glu Lys Asn Val Thr Val Thr His Ser Val Asn Leu
            20                  25                  30

Leu Glu Asp Ser His Asn Gly Lys Leu Cys Arg Leu Lys Gly Ile Ala
        35                  40                  45

Pro Leu Gln Leu Gly Lys Cys Asn Ile Ala Gly Trp Leu Leu Gly Asn
    50                  55                  60

Pro Glu Cys Asp Pro Leu Leu Pro Val Arg Ser Trp Ser Tyr Ile Val
65                  70                  75                  80

Glu Thr Pro Asn Ser Glu Asn Gly
                85


<210> SEQ ID NO 449
<211> LENGTH: 89
<212> TYPE: PRT
<213> ORGANISM: Influenza virus A
<220> FEATURE:
<223> OTHER INFORMATION: N-termianl long stem domain segment of
      Influenza A HA subtype H2(No Cys, Ala)
```

<400> SEQUENCE: 449

Asp Gln Ile Cys Ile Gly Tyr His Ser Asn Asn Ser Thr Glu Lys Val
1 5 10 15

Asp Thr Ile Leu Glu Arg Asn Val Thr Val Thr His Ala Gln Asn Ile
20 25 30

Leu Glu Lys Thr His Asn Gly Lys Leu Cys Lys Leu Asn Gly Ile Pro
35 40 45

Pro Leu Glu Leu Gly Asp Cys Ser Ile Ala Gly Trp Leu Leu Gly Asn
50 55 60

Pro Glu Cys Asp Arg Leu Leu Thr Val Pro Glu Trp Ser Tyr Ile Met
65 70 75 80

Glu Lys Glu Asn Pro Arg Asn Gly Leu
85

<210> SEQ ID NO 450
<211> LENGTH: 89
<212> TYPE: PRT
<213> ORGANISM: Influenza virus A
<220> FEATURE:
<223> OTHER INFORMATION: N-termianl long stem domain segment of Influenza A HA subtype H2(No Cys, Ala - Delta 1)

<400> SEQUENCE: 450

Asp Gln Ile Cys Ile Gly Tyr His Ser Asn Asn Ser Thr Glu Lys Val
1 5 10 15

Asp Thr Ile Leu Glu Arg Asn Val Thr Val Thr His Ala Gln Asn Ile
20 25 30

Leu Glu Lys Thr His Asn Gly Lys Leu Cys Lys Leu Asn Gly Ile Pro
35 40 45

Pro Leu Glu Leu Gly Asp Cys Ser Ile Ala Gly Trp Leu Leu Gly Asn
50 55 60

Pro Glu Cys Asp Arg Leu Leu Thr Val Pro Glu Trp Ser Tyr Ile Met
65 70 75 80

Glu Lys Glu Asn Pro Arg Asn Gly Leu
85

<210> SEQ ID NO 451
<211> LENGTH: 88
<212> TYPE: PRT
<213> ORGANISM: Influenza virus A
<220> FEATURE:
<223> OTHER INFORMATION: N-termianl long stem domain segment of Influenza A HA subtype H2(No Cys, Ala - Delta 3)

<400> SEQUENCE: 451

Asp Gln Ile Cys Ile Gly Tyr His Ser Asn Asn Ser Thr Glu Lys Val
1 5 10 15

Asp Thr Ile Leu Glu Arg Asn Val Thr Val Thr His Ala Gln Asn Ile
20 25 30

Leu Glu Lys Thr His Asn Gly Lys Leu Cys Lys Leu Asn Gly Ile Pro
35 40 45

Pro Leu Glu Leu Gly Asp Cys Ser Ile Ala Gly Trp Leu Leu Gly Asn
50 55 60

Pro Glu Cys Asp Arg Leu Leu Thr Val Pro Glu Trp Ser Tyr Ile Met
65 70 75 80

Glu Lys Glu Asn Pro Arg Asn Gly
85

<210> SEQ ID NO 452
<211> LENGTH: 96
<212> TYPE: PRT
<213> ORGANISM: Influenza virus A
<220> FEATURE:
<223> OTHER INFORMATION: N-termianl long stem domain segment of
      Influenza A HA subtype H3(No Cys, Ala)

<400> SEQUENCE: 452

```
Gln Asp Leu Pro Gly Asn Asp Asn Ser Thr Ala Thr Leu Cys Leu Gly
 1               5                  10                  15

His His Ala Val Pro Asn Gly Thr Leu Val Lys Thr Ile Thr Asp Asp
            20                  25                  30

Gln Ile Glu Val Thr Asn Ala Thr Glu Leu Val Gln Ser Ser Ser Thr
        35                  40                  45

Gly Lys Ile Cys Asn Asn Pro His Arg Ile Leu Asp Gly Ile Asp Cys
    50                  55                  60

Thr Leu Ile Asp Ala Leu Leu Gly Asp Pro His Cys Asp Val Phe Gln
65                  70                  75                  80

Asn Glu Thr Trp Asp Leu Phe Val Glu Arg Ser Lys Ala Phe Ser Asn
                85                  90                  95
```

<210> SEQ ID NO 453
<211> LENGTH: 96
<212> TYPE: PRT
<213> ORGANISM: Influenza virus A
<220> FEATURE:
<223> OTHER INFORMATION: N-termianl long stem domain segment of
      Influenza A HA subtype H3(No Cys, Ala - Delta 1)

<400> SEQUENCE: 453

```
Gln Asp Leu Pro Gly Asn Asp Asn Ser Thr Ala Thr Leu Cys Leu Gly
 1               5                  10                  15

His His Ala Val Pro Asn Gly Thr Leu Val Lys Thr Ile Thr Asp Asp
            20                  25                  30

Gln Ile Glu Val Thr Asn Ala Thr Glu Leu Val Gln Ser Ser Ser Thr
        35                  40                  45

Gly Lys Ile Cys Asn Asn Pro His Arg Ile Leu Asp Gly Ile Asp Cys
    50                  55                  60

Thr Leu Ile Asp Ala Leu Leu Gly Asp Pro His Cys Asp Val Phe Gln
65                  70                  75                  80

Asn Glu Thr Trp Asp Leu Phe Val Glu Arg Ser Lys Ala Phe Ser Asn
                85                  90                  95
```

<210> SEQ ID NO 454
<211> LENGTH: 95
<212> TYPE: PRT
<213> ORGANISM: Influenza virus A
<220> FEATURE:
<223> OTHER INFORMATION: N-termianl long stem domain segment of
      Influenza A HA subtype H3(No Cys, Ala - Delta 3)

<400> SEQUENCE: 454

```
Gln Asp Leu Pro Gly Asn Asp Asn Ser Thr Ala Thr Leu Cys Leu Gly
 1               5                  10                  15

His His Ala Val Pro Asn Gly Thr Leu Val Lys Thr Ile Thr Asp Asp
            20                  25                  30

Gln Ile Glu Val Thr Asn Ala Thr Glu Leu Val Gln Ser Ser Ser Thr
        35                  40                  45

Gly Lys Ile Cys Asn Asn Pro His Arg Ile Leu Asp Gly Ile Asp Cys
    50                  55                  60
```

Thr Leu Ile Asp Ala Leu Leu Gly Asp Pro His Cys Asp Val Phe Gln
65 70 75 80

Asn Glu Thr Trp Asp Leu Phe Val Glu Arg Ser Lys Ala Phe Ser
85 90 95

<210> SEQ ID NO 455
<211> LENGTH: 92
<212> TYPE: PRT
<213> ORGANISM: Influenza virus A
<220> FEATURE:
<223> OTHER INFORMATION: N-termianl long stem domain segment of Influenza A HA subtype H4(No Cys, Ala)

<400> SEQUENCE: 455

Gln Asn Tyr Thr Gly Asn Pro Val Ile Cys Met Gly His His Ala Val
1 5 10 15

Ala Asn Gly Thr Met Val Lys Thr Leu Ala Asp Asp Gln Val Glu Val
20 25 30

Val Thr Ala Gln Glu Leu Val Glu Ser Gln Asn Leu Pro Glu Leu Cys
35 40 45

Pro Ser Pro Leu Arg Leu Val Asp Gly Gln Thr Cys Asp Ile Ile Asn
50 55 60

Gly Ala Leu Gly Ser Pro Gly Cys Asp His Leu Asn Gly Ala Glu Trp
65 70 75 80

Asp Val Phe Ile Glu Arg Pro Asn Ala Val Asp Thr
85 90

<210> SEQ ID NO 456
<211> LENGTH: 92
<212> TYPE: PRT
<213> ORGANISM: Influenza virus A
<220> FEATURE:
<223> OTHER INFORMATION: N-termianl long stem domain segment of Influenza A HA subtype H4(No Cys, Ala - Delta 1)

<400> SEQUENCE: 456

Gln Asn Tyr Thr Gly Asn Pro Val Ile Cys Met Gly His His Ala Val
1 5 10 15

Ala Asn Gly Thr Met Val Lys Thr Leu Ala Asp Asp Gln Val Glu Val
20 25 30

Val Thr Ala Gln Glu Leu Val Glu Ser Gln Asn Leu Pro Glu Leu Cys
35 40 45

Pro Ser Pro Leu Arg Leu Val Asp Gly Gln Thr Cys Asp Ile Ile Asn
50 55 60

Gly Ala Leu Gly Ser Pro Gly Cys Asp His Leu Asn Gly Ala Glu Trp
65 70 75 80

Asp Val Phe Ile Glu Arg Pro Asn Ala Val Asp Thr
85 90

<210> SEQ ID NO 457
<211> LENGTH: 91
<212> TYPE: PRT
<213> ORGANISM: Influenza virus A
<220> FEATURE:
<223> OTHER INFORMATION: N-termianl long stem domain segment of Influenza A HA subtype H4(No Cys, Ala - Delta 3)

<400> SEQUENCE: 457

Gln Asn Tyr Thr Gly Asn Pro Val Ile Cys Met Gly His His Ala Val
1 5 10 15

```
Ala Asn Gly Thr Met Val Lys Thr Leu Ala Asp Asp Gln Val Glu Val
            20                  25                  30

Val Thr Ala Gln Glu Leu Val Glu Ser Gln Asn Leu Pro Glu Leu Cys
        35                  40                  45

Pro Ser Pro Leu Arg Leu Val Asp Gly Gln Thr Cys Asp Ile Ile Asn
    50                  55                  60

Gly Ala Leu Gly Ser Pro Gly Cys Asp His Leu Asn Gly Ala Glu Trp
65                  70                  75                  80

Asp Val Phe Ile Glu Arg Pro Asn Ala Val Asp
                85                  90
```

<210> SEQ ID NO 458
<211> LENGTH: 89
<212> TYPE: PRT
<213> ORGANISM: Influenza virus A
<220> FEATURE:
<223> OTHER INFORMATION: N-termianl long stem domain segment of Influenza A HA subtype H5(No Cys, Ala)

<400> SEQUENCE: 458

```
Asp Gln Ile Cys Ile Gly Tyr His Ala Asn Lys Ser Thr Lys Gln Val
 1               5                  10                  15

Asp Thr Ile Met Glu Lys Asn Val Thr Val Thr His Ala Gln Asp Ile
            20                  25                  30

Leu Glu Arg Thr His Asn Gly Lys Leu Cys Ser Leu Asn Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Leu Asn Leu Pro Glu Trp Leu Tyr Ile Val
65                  70                  75                  80

Glu Lys Asp Asn Pro Ile Asn Ser Leu
                85
```

<210> SEQ ID NO 459
<211> LENGTH: 89
<212> TYPE: PRT
<213> ORGANISM: Influenza virus A
<220> FEATURE:
<223> OTHER INFORMATION: N-termianl long stem domain segment of Influenza A HA subtype H5(No Cys, Ala - Delta 1)

<400> SEQUENCE: 459

```
Asp Gln Ile Cys Ile Gly Tyr His Ala Asn Lys Ser Thr Lys Gln Val
 1               5                  10                  15

Asp Thr Ile Met Glu Lys Asn Val Thr Val Thr His Ala Gln Asp Ile
            20                  25                  30

Leu Glu Arg Thr His Asn Gly Lys Leu Cys Ser Leu Asn Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Leu Asn Leu Pro Glu Trp Leu Tyr Ile Val
65                  70                  75                  80

Glu Lys Asp Asn Pro Ile Asn Ser Leu
                85
```

<210> SEQ ID NO 460
<211> LENGTH: 88
<212> TYPE: PRT
<213> ORGANISM: Influenza virus A
<220> FEATURE:

<223> OTHER INFORMATION: N-termianl long stem domain segment of
Influenza A HA subtype H5(No Cys, Ala - Delta 3)

<400> SEQUENCE: 460

Asp Gln Ile Cys Ile Gly Tyr His Ala Asn Lys Ser Thr Lys Gln Val
1 5 10 15

Asp Thr Ile Met Glu Lys Asn Val Thr Val Thr His Ala Gln Asp Ile
20 25 30

Leu Glu Arg Thr His Asn Gly Lys Leu Cys Ser Leu Asn Gly Val Lys
35 40 45

Pro Leu Ile Leu Arg Asp Cys Ser Val Ala Gly Trp Leu Leu Gly Asn
50 55 60

Pro Met Cys Asp Glu Phe Leu Asn Leu Pro Glu Trp Leu Tyr Ile Val
65 70 75 80

Glu Lys Asp Asn Pro Ile Asn Ser
85

<210> SEQ ID NO 461
<211> LENGTH: 89
<212> TYPE: PRT
<213> ORGANISM: Influenza virus A
<220> FEATURE:
<223> OTHER INFORMATION: N-termianl long stem domain segment of
Influenza A HA subtype H6(No Cys, Ala)

<400> SEQUENCE: 461

Asp Lys Ile Cys Ile Gly Tyr His Ala Asn Asn Ser Thr Thr Gln Ile
1 5 10 15

Asp Thr Ile Leu Glu Lys Asn Val Thr Val Thr His Ser Val Glu Leu
20 25 30

Leu Glu Asn Gln Lys Glu Glu Arg Phe Cys Lys Ile Leu Lys Lys Ala
35 40 45

Pro Leu Asp Leu Lys Gly Cys Thr Ile Glu Gly Trp Ile Leu Gly Asn
50 55 60

Pro Gln Cys Asp Leu Leu Leu Gly Asp Gln Ser Trp Ser Tyr Ile Val
65 70 75 80

Glu Arg Pro Thr Ala Gln Asn Gly Ile
85

<210> SEQ ID NO 462
<211> LENGTH: 89
<212> TYPE: PRT
<213> ORGANISM: Influenza virus A
<220> FEATURE:
<223> OTHER INFORMATION: N-termianl long stem domain segment of
Influenza A HA subtype H6(No Cys, Ala - Delta 1)

<400> SEQUENCE: 462

Asp Lys Ile Cys Ile Gly Tyr His Ala Asn Asn Ser Thr Thr Gln Ile
1 5 10 15

Asp Thr Ile Leu Glu Lys Asn Val Thr Val Thr His Ser Val Glu Leu
20 25 30

Leu Glu Asn Gln Lys Glu Glu Arg Phe Cys Lys Ile Leu Lys Lys Ala
35 40 45

Pro Leu Asp Leu Lys Gly Cys Thr Ile Glu Gly Trp Ile Leu Gly Asn
50 55 60

Pro Gln Cys Asp Leu Leu Leu Gly Asp Gln Ser Trp Ser Tyr Ile Val
65 70 75 80

Glu Arg Pro Thr Ala Gln Asn Gly Ile

85

<210> SEQ ID NO 463
<211> LENGTH: 88
<212> TYPE: PRT
<213> ORGANISM: Influenza virus A
<220> FEATURE:
<223> OTHER INFORMATION: N-termianl long stem domain segment of Influenza A HA subtype H6(No Cys, Ala - Delta 3)

<400> SEQUENCE: 463

Asp Lys Ile Cys Ile Gly Tyr His Ala Asn Asn Ser Thr Thr Gln Ile
1 5 10 15

Asp Thr Ile Leu Glu Lys Asn Val Thr Val Thr His Ser Val Glu Leu
20 25 30

Leu Glu Asn Gln Lys Glu Glu Arg Phe Cys Lys Ile Leu Lys Lys Ala
35 40 45

Pro Leu Asp Leu Lys Gly Cys Thr Ile Glu Gly Trp Ile Leu Gly Asn
50 55 60

Pro Gln Cys Asp Leu Leu Leu Gly Asp Gln Ser Trp Ser Tyr Ile Val
65 70 75 80

Glu Arg Pro Thr Ala Gln Asn Gly
85

<210> SEQ ID NO 464
<211> LENGTH: 86
<212> TYPE: PRT
<213> ORGANISM: Influenza virus A
<220> FEATURE:
<223> OTHER INFORMATION: N-termianl long stem domain segment of Influenza A HA subtype H7(No Cys, Ala)

<400> SEQUENCE: 464

Asp Lys Ile Cys Leu Gly His His Ala Val Ser Asn Gly Thr Lys Val
1 5 10 15

Asn Thr Leu Thr Glu Arg Gly Val Glu Val Val Asn Ala Thr Glu Thr
20 25 30

Val Glu Arg Thr Asn Ile Pro Lys Ile Cys Ser Lys Gly Lys Arg Thr
35 40 45

Thr Asp Leu Gly Gln Cys Gly Leu Leu Gly Thr Ile Thr Gly Pro Pro
50 55 60

Gln Cys Asp Gln Phe Leu Glu Phe Ser Ala Asp Leu Ile Ile Glu Arg
65 70 75 80

Arg Glu Gly Asn Asp Val
85

<210> SEQ ID NO 465
<211> LENGTH: 86
<212> TYPE: PRT
<213> ORGANISM: Influenza virus A
<220> FEATURE:
<223> OTHER INFORMATION: N-termianl long stem domain segment of Influenza A HA subtype H7(No Cys, Ala - Delta 1)

<400> SEQUENCE: 465

Asp Lys Ile Cys Leu Gly His His Ala Val Ser Asn Gly Thr Lys Val
1 5 10 15

Asn Thr Leu Thr Glu Arg Gly Val Glu Val Val Asn Ala Thr Glu Thr
20 25 30

Val Glu Arg Thr Asn Ile Pro Lys Ile Cys Ser Lys Gly Lys Arg Thr
35 40 45

```
Thr Asp Leu Gly Gln Cys Gly Leu Leu Gly Thr Ile Thr Gly Pro Pro
    50                  55                  60

Gln Cys Asp Gln Phe Leu Glu Phe Ser Ala Asp Leu Ile Ile Glu Arg
65                  70                  75                  80

Arg Glu Gly Asn Asp Val
                85


<210> SEQ ID NO 466
<211> LENGTH: 85
<212> TYPE: PRT
<213> ORGANISM: Influenza virus A
<220> FEATURE:
<223> OTHER INFORMATION: N-termianl long stem domain segment of
      Influenza A HA subtype H7(No Cys, Ala - Delta 3)

<400> SEQUENCE: 466

Asp Lys Ile Cys Leu Gly His His Ala Val Ser Asn Gly Thr Lys Val
 1              5                   10                  15

Asn Thr Leu Thr Glu Arg Gly Val Glu Val Val Asn Ala Thr Glu Thr
            20                  25                  30

Val Glu Arg Thr Asn Ile Pro Lys Ile Cys Ser Lys Gly Lys Arg Thr
        35                  40                  45

Thr Asp Leu Gly Gln Cys Gly Leu Leu Gly Thr Ile Thr Gly Pro Pro
    50                  55                  60

Gln Cys Asp Gln Phe Leu Glu Phe Ser Ala Asp Leu Ile Ile Glu Arg
65                  70                  75                  80

Arg Glu Gly Asn Asp
                85


<210> SEQ ID NO 467
<211> LENGTH: 89
<212> TYPE: PRT
<213> ORGANISM: Influenza virus A
<220> FEATURE:
<223> OTHER INFORMATION: N-termianl long stem domain segment of
      Influenza A HA subtype H8(No Cys, Ala)

<400> SEQUENCE: 467

Asp Arg Ile Cys Ile Gly Tyr Gln Ser Asn Asn Ser Thr Asp Thr Val
 1              5                   10                  15

Asn Thr Leu Ile Glu Gln Asn Val Pro Val Thr Gln Thr Met Glu Leu
            20                  25                  30

Val Glu Thr Glu Lys His Pro Ala Tyr Cys Asn Thr Asp Leu Gly Ala
        35                  40                  45

Pro Leu Glu Leu Arg Asp Cys Lys Ile Glu Ala Val Ile Tyr Gly Asn
    50                  55                  60

Pro Lys Cys Asp Ile His Leu Lys Asp Gln Gly Trp Ser Tyr Ile Val
65                  70                  75                  80

Glu Arg Pro Ser Ala Pro Glu Gly Met
                85


<210> SEQ ID NO 468
<211> LENGTH: 89
<212> TYPE: PRT
<213> ORGANISM: Influenza virus A
<220> FEATURE:
<223> OTHER INFORMATION: N-termianl long stem domain segment of
      Influenza A HA subtype H8(No Cys, Ala - Delta 1)

<400> SEQUENCE: 468
```

Asp Arg Ile Cys Ile Gly Tyr Gln Ser Asn Asn Ser Thr Asp Thr Val
1 5 10 15

Asn Thr Leu Ile Glu Gln Asn Val Pro Val Thr Gln Thr Met Glu Leu
20 25 30

Val Glu Thr Glu Lys His Pro Ala Tyr Cys Asn Thr Asp Leu Gly Ala
35 40 45

Pro Leu Glu Leu Arg Asp Cys Lys Ile Glu Ala Val Ile Tyr Gly Asn
50 55 60

Pro Lys Cys Asp Ile His Leu Lys Asp Gln Gly Trp Ser Tyr Ile Val
65 70 75 80

Glu Arg Pro Ser Ala Pro Glu Gly Met
85

<210> SEQ ID NO 469
<211> LENGTH: 88
<212> TYPE: PRT
<213> ORGANISM: Influenza virus A
<220> FEATURE:
<223> OTHER INFORMATION: N-termianl long stem domain segment of Influenza A HA subtype H8(No Cys, Ala - Delta 3)

<400> SEQUENCE: 469

Asp Arg Ile Cys Ile Gly Tyr Gln Ser Asn Asn Ser Thr Asp Thr Val
1 5 10 15

Asn Thr Leu Ile Glu Gln Asn Val Pro Val Thr Gln Thr Met Glu Leu
20 25 30

Val Glu Thr Glu Lys His Pro Ala Tyr Cys Asn Thr Asp Leu Gly Ala
35 40 45

Pro Leu Glu Leu Arg Asp Cys Lys Ile Glu Ala Val Ile Tyr Gly Asn
50 55 60

Pro Lys Cys Asp Ile His Leu Lys Asp Gln Gly Trp Ser Tyr Ile Val
65 70 75 80

Glu Arg Pro Ser Ala Pro Glu Gly
85

<210> SEQ ID NO 470
<211> LENGTH: 89
<212> TYPE: PRT
<213> ORGANISM: Influenza virus A
<220> FEATURE:
<223> OTHER INFORMATION: N-termianl long stem domain segment of Influenza A HA subtype H9(No Cys, Ala)

<400> SEQUENCE: 470

Asp Lys Ile Cys Ile Gly Tyr Gln Ser Thr Asn Ser Thr Glu Thr Val
1 5 10 15

Asp Thr Leu Thr Glu Ser Asn Val Pro Val Thr His Thr Lys Glu Leu
20 25 30

Leu His Thr Glu His Asn Gly Met Leu Cys Ala Thr Asp Leu Gly His
35 40 45

Pro Leu Ile Leu Asp Thr Cys Thr Ile Glu Gly Leu Ile Tyr Gly Asn
50 55 60

Pro Ser Cys Asp Ile Leu Leu Gly Gly Lys Glu Trp Ser Tyr Ile Val
65 70 75 80

Glu Arg Ser Ser Ala Val Asn Gly Met
85

<210> SEQ ID NO 471
<211> LENGTH: 89

```
<212> TYPE: PRT
<213> ORGANISM: Influenza virus A
<220> FEATURE:
<223> OTHER INFORMATION: N-termianl long stem domain segment of
      Influenza A HA subtype H9(No Cys, Ala - Delta 1)

<400> SEQUENCE: 471

Asp Lys Ile Cys Ile Gly Tyr Gln Ser Thr Asn Ser Thr Glu Thr Val
 1               5                  10                  15

Asp Thr Leu Thr Glu Ser Asn Val Pro Val Thr His Thr Lys Glu Leu
            20                  25                  30

Leu His Thr Glu His Asn Gly Met Leu Cys Ala Thr Asp Leu Gly His
        35                  40                  45

Pro Leu Ile Leu Asp Thr Cys Thr Ile Glu Gly Leu Ile Tyr Gly Asn
    50                  55                  60

Pro Ser Cys Asp Ile Leu Leu Gly Gly Lys Glu Trp Ser Tyr Ile Val
65                  70                  75                  80

Glu Arg Ser Ser Ala Val Asn Gly Met
                85


<210> SEQ ID NO 472
<211> LENGTH: 88
<212> TYPE: PRT
<213> ORGANISM: Influenza virus A
<220> FEATURE:
<223> OTHER INFORMATION: N-termianl long stem domain segment of
      Influenza A HA subtype H9(No Cys, Ala - Delta 3)

<400> SEQUENCE: 472

Asp Lys Ile Cys Ile Gly Tyr Gln Ser Thr Asn Ser Thr Glu Thr Val
 1               5                  10                  15

Asp Thr Leu Thr Glu Ser Asn Val Pro Val Thr His Thr Lys Glu Leu
            20                  25                  30

Leu His Thr Glu His Asn Gly Met Leu Cys Ala Thr Asp Leu Gly His
        35                  40                  45

Pro Leu Ile Leu Asp Thr Cys Thr Ile Glu Gly Leu Ile Tyr Gly Asn
    50                  55                  60

Pro Ser Cys Asp Ile Leu Leu Gly Gly Lys Glu Trp Ser Tyr Ile Val
65                  70                  75                  80

Glu Arg Ser Ser Ala Val Asn Gly
                85


<210> SEQ ID NO 473
<211> LENGTH: 87
<212> TYPE: PRT
<213> ORGANISM: Influenza virus A
<220> FEATURE:
<223> OTHER INFORMATION: N-termianl long stem domain segment of
      Influenza A HA subtype H10(No Cys, Ala)

<400> SEQUENCE: 473

Leu Asp Arg Ile Cys Leu Gly His His Ala Val Ala Asn Gly Thr Ile
 1               5                  10                  15

Val Lys Thr Leu Thr Asn Glu Gln Glu Glu Val Thr Asn Ala Thr Glu
            20                  25                  30

Thr Val Glu Ser Thr Asn Leu Asn Lys Leu Cys Met Lys Gly Arg Ser
        35                  40                  45

Tyr Lys Asp Leu Gly Asn Cys His Pro Val Gly Met Leu Ile Gly Thr
    50                  55                  60

Pro Val Cys Asp Pro His Leu Thr Gly Thr Trp Asp Thr Leu Ile Glu
```

```
65                  70                  75                  80

Arg Glu Asn Ala Ile Ala His
                85


<210> SEQ ID NO 474
<211> LENGTH: 87
<212> TYPE: PRT
<213> ORGANISM: Influenza virus A
<220> FEATURE:
<223> OTHER INFORMATION: N-termianl long stem domain segment of
      Influenza A HA subtype H10(No Cys, Ala - Delta 1)

<400> SEQUENCE: 474

Leu Asp Arg Ile Cys Leu Gly His His Ala Val Ala Asn Gly Thr Ile
 1               5                  10                  15

Val Lys Thr Leu Thr Asn Glu Gln Glu Glu Val Thr Asn Ala Thr Glu
            20                  25                  30

Thr Val Glu Ser Thr Asn Leu Asn Lys Leu Cys Met Lys Gly Arg Ser
        35                  40                  45

Tyr Lys Asp Leu Gly Asn Cys His Pro Val Gly Met Leu Ile Gly Thr
    50                  55                  60

Pro Val Cys Asp Pro His Leu Thr Gly Thr Trp Asp Thr Leu Ile Glu
65                  70                  75                  80

Arg Glu Asn Ala Ile Ala His
                85


<210> SEQ ID NO 475
<211> LENGTH: 86
<212> TYPE: PRT
<213> ORGANISM: Influenza virus A
<220> FEATURE:
<223> OTHER INFORMATION: N-termianl long stem domain segment of
      Influenza A HA subtype H10(No Cys, Ala - Delta 3)

<400> SEQUENCE: 475

Leu Asp Arg Ile Cys Leu Gly His His Ala Val Ala Asn Gly Thr Ile
 1               5                  10                  15

Val Lys Thr Leu Thr Asn Glu Gln Glu Glu Val Thr Asn Ala Thr Glu
            20                  25                  30

Thr Val Glu Ser Thr Asn Leu Asn Lys Leu Cys Met Lys Gly Arg Ser
        35                  40                  45

Tyr Lys Asp Leu Gly Asn Cys His Pro Val Gly Met Leu Ile Gly Thr
    50                  55                  60

Pro Val Cys Asp Pro His Leu Thr Gly Thr Trp Asp Thr Leu Ile Glu
65                  70                  75                  80

Arg Glu Asn Ala Ile Ala
                85


<210> SEQ ID NO 476
<211> LENGTH: 89
<212> TYPE: PRT
<213> ORGANISM: Influenza virus A
<220> FEATURE:
<223> OTHER INFORMATION: N-termianl long stem domain segment of
      Influenza A HA subtype H11(No Cys, Ala)

<400> SEQUENCE: 476

Asp Glu Ile Cys Ile Gly Tyr Leu Ser Asn Asn Ser Thr Asp Lys Val
 1               5                  10                  15

Asp Thr Ile Ile Glu Asn Asn Val Thr Val Thr Ser Ser Val Glu Leu
            20                  25                  30
```

Val Glu Thr Glu His Thr Gly Ser Phe Cys Ser Ile Asn Gly Lys Gln
35 40 45

Pro Ile Ser Leu Gly Asp Cys Ser Phe Ala Gly Trp Ile Leu Gly Asn
50 55 60

Pro Met Cys Asp Glu Leu Ile Gly Lys Thr Ser Trp Ser Tyr Ile Val
65 70 75 80

Glu Lys Pro Asn Pro Thr Asn Gly Ile
85

<210> SEQ ID NO 477
<211> LENGTH: 89
<212> TYPE: PRT
<213> ORGANISM: Influenza virus A
<220> FEATURE:
<223> OTHER INFORMATION: N-termianl long stem domain segment of
Influenza A HA subtype H11(No Cys, Ala - Delta 1)

<400> SEQUENCE: 477

Asp Glu Ile Cys Ile Gly Tyr Leu Ser Asn Asn Ser Thr Asp Lys Val
1 5 10 15

Asp Thr Ile Ile Glu Asn Asn Val Thr Val Thr Ser Ser Val Glu Leu
20 25 30

Val Glu Thr Glu His Thr Gly Ser Phe Cys Ser Ile Asn Gly Lys Gln
35 40 45

Pro Ile Ser Leu Gly Asp Cys Ser Phe Ala Gly Trp Ile Leu Gly Asn
50 55 60

Pro Met Cys Asp Glu Leu Ile Gly Lys Thr Ser Trp Ser Tyr Ile Val
65 70 75 80

Glu Lys Pro Asn Pro Thr Asn Gly Ile
85

<210> SEQ ID NO 478
<211> LENGTH: 88
<212> TYPE: PRT
<213> ORGANISM: Influenza virus A
<220> FEATURE:
<223> OTHER INFORMATION: N-termianl long stem domain segment of
Influenza A HA subtype H11(No Cys, Ala - Delta 3)

<400> SEQUENCE: 478

Asp Glu Ile Cys Ile Gly Tyr Leu Ser Asn Asn Ser Thr Asp Lys Val
1 5 10 15

Asp Thr Ile Ile Glu Asn Asn Val Thr Val Thr Ser Ser Val Glu Leu
20 25 30

Val Glu Thr Glu His Thr Gly Ser Phe Cys Ser Ile Asn Gly Lys Gln
35 40 45

Pro Ile Ser Leu Gly Asp Cys Ser Phe Ala Gly Trp Ile Leu Gly Asn
50 55 60

Pro Met Cys Asp Glu Leu Ile Gly Lys Thr Ser Trp Ser Tyr Ile Val
65 70 75 80

Glu Lys Pro Asn Pro Thr Asn Gly
85

<210> SEQ ID NO 479
<211> LENGTH: 89
<212> TYPE: PRT
<213> ORGANISM: Influenza virus A
<220> FEATURE:
<223> OTHER INFORMATION: N-termianl long stem domain segment of
Influenza A HA subtype H12(No Cys, Ala)

<400> SEQUENCE: 479

Asp Lys Ile Cys Ile Gly Tyr Gln Thr Asn Asn Ser Thr Glu Thr Val
1 5 10 15

Asn Thr Leu Ser Glu Gln Asn Val Pro Val Thr Gln Val Glu Glu Leu
20 25 30

Val His Arg Gly Ile Asp Pro Ile Leu Cys Gly Thr Glu Leu Gly Ser
35 40 45

Pro Leu Val Leu Asp Asp Cys Ser Leu Glu Gly Leu Ile Leu Gly Asn
50 55 60

Pro Lys Cys Asp Leu Tyr Leu Asn Gly Arg Glu Trp Ser Tyr Ile Val
65 70 75 80

Glu Arg Pro Lys Glu Met Glu Gly Val
85

<210> SEQ ID NO 480
<211> LENGTH: 89
<212> TYPE: PRT
<213> ORGANISM: Influenza virus A
<220> FEATURE:
<223> OTHER INFORMATION: N-termianl long stem domain segment of Influenza A HA subtype H12(No Cys, Ala - Delta 1)

<400> SEQUENCE: 480

Asp Lys Ile Cys Ile Gly Tyr Gln Thr Asn Asn Ser Thr Glu Thr Val
1 5 10 15

Asn Thr Leu Ser Glu Gln Asn Val Pro Val Thr Gln Val Glu Glu Leu
20 25 30

Val His Arg Gly Ile Asp Pro Ile Leu Cys Gly Thr Glu Leu Gly Ser
35 40 45

Pro Leu Val Leu Asp Asp Cys Ser Leu Glu Gly Leu Ile Leu Gly Asn
50 55 60

Pro Lys Cys Asp Leu Tyr Leu Asn Gly Arg Glu Trp Ser Tyr Ile Val
65 70 75 80

Glu Arg Pro Lys Glu Met Glu Gly Val
85

<210> SEQ ID NO 481
<211> LENGTH: 88
<212> TYPE: PRT
<213> ORGANISM: Influenza virus A
<220> FEATURE:
<223> OTHER INFORMATION: N-termianl long stem domain segment of Influenza A HA subtype H12(No Cys, Ala - Delta 3)

<400> SEQUENCE: 481

Asp Lys Ile Cys Ile Gly Tyr Gln Thr Asn Asn Ser Thr Glu Thr Val
1 5 10 15

Asn Thr Leu Ser Glu Gln Asn Val Pro Val Thr Gln Val Glu Glu Leu
20 25 30

Val His Arg Gly Ile Asp Pro Ile Leu Cys Gly Thr Glu Leu Gly Ser
35 40 45

Pro Leu Val Leu Asp Asp Cys Ser Leu Glu Gly Leu Ile Leu Gly Asn
50 55 60

Pro Lys Cys Asp Leu Tyr Leu Asn Gly Arg Glu Trp Ser Tyr Ile Val
65 70 75 80

Glu Arg Pro Lys Glu Met Glu Gly
85

<210> SEQ ID NO 482
<211> LENGTH: 89
<212> TYPE: PRT
<213> ORGANISM: Influenza virus A
<220> FEATURE:
<223> OTHER INFORMATION: N-termianl long stem domain segment of
Influenza A HA subtype H13(No Cys, Ala)

<400> SEQUENCE: 482

```
Asp Arg Ile Cys Val Gly Tyr Leu Ser Thr Asn Ser Ser Glu Arg Val
 1               5                  10                  15

Asp Thr Leu Leu Glu Asn Gly Val Pro Val Thr Ser Ser Ile Asp Leu
            20                  25                  30

Ile Glu Thr Asn His Thr Gly Thr Tyr Cys Ser Leu Asn Gly Val Ser
        35                  40                  45

Pro Val His Leu Gly Asp Cys Ser Phe Glu Gly Trp Ile Val Gly Asn
    50                  55                  60

Pro Ala Cys Thr Ser Asn Phe Gly Ile Arg Glu Trp Ser Tyr Leu Ile
65                  70                  75                  80

Glu Asp Pro Ala Ala Pro His Gly Leu
                85
```

<210> SEQ ID NO 483
<211> LENGTH: 89
<212> TYPE: PRT
<213> ORGANISM: Influenza virus A
<220> FEATURE:
<223> OTHER INFORMATION: N-termianl long stem domain segment of
Influenza A HA subtype H13(No Cys, Ala - Delta 1)

<400> SEQUENCE: 483

```
Asp Arg Ile Cys Val Gly Tyr Leu Ser Thr Asn Ser Ser Glu Arg Val
 1               5                  10                  15

Asp Thr Leu Leu Glu Asn Gly Val Pro Val Thr Ser Ser Ile Asp Leu
            20                  25                  30

Ile Glu Thr Asn His Thr Gly Thr Tyr Cys Ser Leu Asn Gly Val Ser
        35                  40                  45

Pro Val His Leu Gly Asp Cys Ser Phe Glu Gly Trp Ile Val Gly Asn
    50                  55                  60

Pro Ala Cys Thr Ser Asn Phe Gly Ile Arg Glu Trp Ser Tyr Leu Ile
65                  70                  75                  80

Glu Asp Pro Ala Ala Pro His Gly Leu
                85
```

<210> SEQ ID NO 484
<211> LENGTH: 88
<212> TYPE: PRT
<213> ORGANISM: Influenza virus A
<220> FEATURE:
<223> OTHER INFORMATION: N-termianl long stem domain segment of
Influenza A HA subtype H13(No Cys, Ala - Delta 3)

<400> SEQUENCE: 484

```
Asp Arg Ile Cys Val Gly Tyr Leu Ser Thr Asn Ser Ser Glu Arg Val
 1               5                  10                  15

Asp Thr Leu Leu Glu Asn Gly Val Pro Val Thr Ser Ser Ile Asp Leu
            20                  25                  30

Ile Glu Thr Asn His Thr Gly Thr Tyr Cys Ser Leu Asn Gly Val Ser
        35                  40                  45

Pro Val His Leu Gly Asp Cys Ser Phe Glu Gly Trp Ile Val Gly Asn
```

50                  55                  60

Pro Ala Cys Thr Ser Asn Phe Gly Ile Arg Glu Trp Ser Tyr Leu Ile
65                  70                  75                  80

Glu Asp Pro Ala Ala Pro His Gly
                85

<210> SEQ ID NO 485
<211> LENGTH: 95
<212> TYPE: PRT
<213> ORGANISM: Influenza virus A
<220> FEATURE:
<223> OTHER INFORMATION: N-termianl long stem domain segment of
      Influenza A HA subtype H14(No Cys, Ala)

<400> SEQUENCE: 485

Gln Ile Thr Asn Gly Thr Thr Gly Asn Pro Ile Ile Cys Leu Gly His
 1               5                  10                  15

His Ala Val Glu Asn Gly Thr Ser Val Lys Thr Leu Thr Asp Asn His
            20                  25                  30

Val Glu Val Val Ser Ala Lys Glu Leu Val Glu Thr Asn His Thr Asp
        35                  40                  45

Glu Leu Cys Pro Ser Pro Leu Lys Leu Val Asp Gly Gln Asp Cys His
    50                  55                  60

Leu Ile Asn Gly Ala Leu Gly Ser Pro Gly Cys Asp Arg Leu Gln Asp
65                  70                  75                  80

Thr Thr Trp Asp Val Phe Ile Glu Arg Pro Thr Ala Val Asp Thr
                85                  90                  95

<210> SEQ ID NO 486
<211> LENGTH: 95
<212> TYPE: PRT
<213> ORGANISM: Influenza virus A
<220> FEATURE:
<223> OTHER INFORMATION: N-termianl long stem domain segment of
      Influenza A HA subtype H14(No Cys, Ala - Delta 1)

<400> SEQUENCE: 486

Gln Ile Thr Asn Gly Thr Thr Gly Asn Pro Ile Ile Cys Leu Gly His
 1               5                  10                  15

His Ala Val Glu Asn Gly Thr Ser Val Lys Thr Leu Thr Asp Asn His
            20                  25                  30

Val Glu Val Val Ser Ala Lys Glu Leu Val Glu Thr Asn His Thr Asp
        35                  40                  45

Glu Leu Cys Pro Ser Pro Leu Lys Leu Val Asp Gly Gln Asp Cys His
    50                  55                  60

Leu Ile Asn Gly Ala Leu Gly Ser Pro Gly Cys Asp Arg Leu Gln Asp
65                  70                  75                  80

Thr Thr Trp Asp Val Phe Ile Glu Arg Pro Thr Ala Val Asp Thr
                85                  90                  95

<210> SEQ ID NO 487
<211> LENGTH: 94
<212> TYPE: PRT
<213> ORGANISM: Influenza virus A
<220> FEATURE:
<223> OTHER INFORMATION: N-termianl long stem domain segment of
      Influenza A HA subtype H14(No Cys, Ala - Delta 3)

<400> SEQUENCE: 487

Gln Ile Thr Asn Gly Thr Thr Gly Asn Pro Ile Ile Cys Leu Gly His
 1               5                  10                  15

```
His Ala Val Glu Asn Gly Thr Ser Val Lys Thr Leu Thr Asp Asn His
            20                  25                  30

Val Glu Val Val Ser Ala Lys Glu Leu Val Glu Thr Asn His Thr Asp
        35                  40                  45

Glu Leu Cys Pro Ser Pro Leu Lys Leu Val Asp Gly Gln Asp Cys His
    50                  55                  60

Leu Ile Asn Gly Ala Leu Gly Ser Pro Gly Cys Asp Arg Leu Gln Asp
65                  70                  75                  80

Thr Thr Trp Asp Val Phe Ile Glu Arg Pro Thr Ala Val Asp
                85                  90


<210> SEQ ID NO 488
<211> LENGTH: 86
<212> TYPE: PRT
<213> ORGANISM: Influenza virus A
<220> FEATURE:
<223> OTHER INFORMATION: N-termianl long stem domain segment of
      Influenza A HA subtype H15(No Cys, Ala)

<400> SEQUENCE: 488

Asp Lys Ile Cys Leu Gly His His Ala Val Ala Asn Gly Thr Lys Val
 1               5                  10                  15

Asn Thr Leu Thr Glu Arg Gly Val Glu Val Val Asn Ala Thr Glu Thr
            20                  25                  30

Val Glu Ile Thr Gly Ile Asp Lys Val Cys Thr Lys Gly Lys Lys Ala
        35                  40                  45

Val Asp Leu Gly Ser Cys Gly Ile Leu Gly Thr Ile Ile Gly Pro Pro
    50                  55                  60

Gln Cys Asp Leu His Leu Glu Phe Lys Ala Asp Leu Ile Ile Glu Arg
65                  70                  75                  80

Arg Asn Ser Ser Asp Ile
                85


<210> SEQ ID NO 489
<211> LENGTH: 86
<212> TYPE: PRT
<213> ORGANISM: Influenza virus A
<220> FEATURE:
<223> OTHER INFORMATION: N-termianl long stem domain segment of
      Influenza A HA subtype H15(No Cys, Ala - Delta 1)

<400> SEQUENCE: 489

Asp Lys Ile Cys Leu Gly His His Ala Val Ala Asn Gly Thr Lys Val
 1               5                  10                  15

Asn Thr Leu Thr Glu Arg Gly Val Glu Val Val Asn Ala Thr Glu Thr
            20                  25                  30

Val Glu Ile Thr Gly Ile Asp Lys Val Cys Thr Lys Gly Lys Lys Ala
        35                  40                  45

Val Asp Leu Gly Ser Cys Gly Ile Leu Gly Thr Ile Ile Gly Pro Pro
    50                  55                  60

Gln Cys Asp Leu His Leu Glu Phe Lys Ala Asp Leu Ile Ile Glu Arg
65                  70                  75                  80

Arg Asn Ser Ser Asp Ile
                85


<210> SEQ ID NO 490
<211> LENGTH: 85
<212> TYPE: PRT
<213> ORGANISM: Influenza virus A
```

<220> FEATURE:
<223> OTHER INFORMATION: N-termianl long stem domain segment of Influenza A HA subtype H15(No Cys, Ala - Delta 3)

<400> SEQUENCE: 490

```
Asp Lys Ile Cys Leu Gly His His Ala Val Ala Asn Gly Thr Lys Val
 1               5                  10                  15

Asn Thr Leu Thr Glu Arg Gly Val Glu Val Val Asn Ala Thr Glu Thr
            20                  25                  30

Val Glu Ile Thr Gly Ile Asp Lys Val Cys Thr Lys Gly Lys Lys Ala
        35                  40                  45

Val Asp Leu Gly Ser Cys Gly Ile Leu Gly Thr Ile Ile Gly Pro Pro
    50                  55                  60

Gln Cys Asp Leu His Leu Glu Phe Lys Ala Asp Leu Ile Ile Glu Arg
65                  70                  75                  80

Arg Asn Ser Ser Asp
                85
```

<210> SEQ ID NO 491
<211> LENGTH: 89
<212> TYPE: PRT
<213> ORGANISM: Influenza virus A
<220> FEATURE:
<223> OTHER INFORMATION: N-termianl long stem domain segment of Influenza A HA subtype H16(No Cys, Ala)

<400> SEQUENCE: 491

```
Asp Lys Ile Cys Ile Gly Tyr Leu Ser Asn Asn Ser Ser Asp Thr Val
 1               5                  10                  15

Asp Thr Leu Thr Glu Asn Gly Val Pro Val Thr Ser Ser Val Asp Leu
            20                  25                  30

Val Glu Thr Asn His Thr Gly Thr Tyr Cys Ser Leu Asn Gly Ile Ser
        35                  40                  45

Pro Ile His Leu Gly Asp Cys Ser Phe Glu Gly Trp Ile Val Gly Asn
    50                  55                  60

Pro Ser Cys Ala Thr Asn Ile Asn Ile Arg Glu Trp Ser Tyr Leu Ile
65                  70                  75                  80

Glu Asp Pro Asn Ala Pro Asn Lys Phe
                85
```

<210> SEQ ID NO 492
<211> LENGTH: 89
<212> TYPE: PRT
<213> ORGANISM: Influenza virus A
<220> FEATURE:
<223> OTHER INFORMATION: N-termianl long stem domain segment of Influenza A HA subtype H16(No Cys, Ala - Delta 1)

<400> SEQUENCE: 492

```
Asp Lys Ile Cys Ile Gly Tyr Leu Ser Asn Asn Ser Ser Asp Thr Val
 1               5                  10                  15

Asp Thr Leu Thr Glu Asn Gly Val Pro Val Thr Ser Ser Val Asp Leu
            20                  25                  30

Val Glu Thr Asn His Thr Gly Thr Tyr Cys Ser Leu Asn Gly Ile Ser
        35                  40                  45

Pro Ile His Leu Gly Asp Cys Ser Phe Glu Gly Trp Ile Val Gly Asn
    50                  55                  60

Pro Ser Cys Ala Thr Asn Ile Asn Ile Arg Glu Trp Ser Tyr Leu Ile
65                  70                  75                  80
```

Glu Asp Pro Asn Ala Pro Asn Lys Phe
85

<210> SEQ ID NO 493
<211> LENGTH: 88
<212> TYPE: PRT
<213> ORGANISM: Influenza virus A
<220> FEATURE:
<223> OTHER INFORMATION: N-termianl long stem domain segment of Influenza A HA subtype H16(No Cys, Ala - Delta 3)

<400> SEQUENCE: 493

Asp Lys Ile Cys Ile Gly Tyr Leu Ser Asn Asn Ser Ser Asp Thr Val
1 5 10 15

Asp Thr Leu Thr Glu Asn Gly Val Pro Val Thr Ser Ser Val Asp Leu
20 25 30

Val Glu Thr Asn His Thr Gly Thr Tyr Cys Ser Leu Asn Gly Ile Ser
35 40 45

Pro Ile His Leu Gly Asp Cys Ser Phe Glu Gly Trp Ile Val Gly Asn
50 55 60

Pro Ser Cys Ala Thr Asn Ile Asn Ile Arg Glu Trp Ser Tyr Leu Ile
65 70 75 80

Glu Asp Pro Asn Ala Pro Asn Lys
85

<210> SEQ ID NO 494
<211> LENGTH: 77
<212> TYPE: PRT
<213> ORGANISM: Influenza virus A
<220> FEATURE:
<223> OTHER INFORMATION: C-termianl long stem domain segment of Influenza A HA subtype H1(No Cys, Ala)

<400> SEQUENCE: 494

Pro Met Tyr Ala Phe Ala Leu Ser Arg Gly Phe Gly Ser Gly Ile Ile
1 5 10 15

Thr Ser Asn Ala Ser Met His Glu Cys Asn Thr Lys Cys Gln Thr Pro
20 25 30

Leu Gly Ala Ile Asn Ser Ser Leu Pro Tyr Gln Asn Ile His Pro Val
35 40 45

Thr Ile Gly Glu Cys Pro Lys Tyr Val Arg Ser Ala Lys Leu Arg Met
50 55 60

Val Thr Gly Leu Arg Asn Asn Pro Ser Ile Gln Ser Arg
65 70 75

<210> SEQ ID NO 495
<211> LENGTH: 76
<212> TYPE: PRT
<213> ORGANISM: Influenza virus A
<220> FEATURE:
<223> OTHER INFORMATION: C-termianl long stem domain segment of Influenza A HA subtype H1(No Cys, Ala - Delta 1)

<400> SEQUENCE: 495

Met Tyr Ala Phe Ala Leu Ser Arg Gly Phe Gly Ser Gly Ile Ile Thr
1 5 10 15

Ser Asn Ala Ser Met His Glu Cys Asn Thr Lys Cys Gln Thr Pro Leu
20 25 30

Gly Ala Ile Asn Ser Ser Leu Pro Tyr Gln Asn Ile His Pro Val Thr
35 40 45

Ile Gly Glu Cys Pro Lys Tyr Val Arg Ser Ala Lys Leu Arg Met Val 50 55 60

Thr Gly Leu Arg Asn Asn Pro Ser Ile Gln Ser Arg
65 70 75

<210> SEQ ID NO 496
<211> LENGTH: 75
<212> TYPE: PRT
<213> ORGANISM: Influenza virus A
<220> FEATURE:
<223> OTHER INFORMATION: C-termianl long stem domain segment of Influenza A HA subtype H1(No Cys, Ala - Delta 3)

<400> SEQUENCE: 496

Tyr Ala Phe Ala Leu Ser Arg Gly Phe Gly Ser Gly Ile Ile Thr Ser
1 5 10 15

Asn Ala Ser Met His Glu Cys Asn Thr Lys Cys Gln Thr Pro Leu Gly
20 25 30

Ala Ile Asn Ser Ser Leu Pro Tyr Gln Asn Ile His Pro Val Thr Ile
35 40 45

Gly Glu Cys Pro Lys Tyr Val Arg Ser Ala Lys Leu Arg Met Val Thr
50 55 60

Gly Leu Arg Asn Asn Pro Ser Ile Gln Ser Arg
65 70 75

<210> SEQ ID NO 497
<211> LENGTH: 77
<212> TYPE: PRT
<213> ORGANISM: Influenza virus A
<220> FEATURE:
<223> OTHER INFORMATION: C-termianl long stem domain segment of Influenza A HA subtype H2(No Cys, Ala)

<400> SEQUENCE: 497

Pro Glu Tyr Gly Phe Arg Ile Ser Lys Arg Gly Ser Ser Gly Ile Met
1 5 10 15

Lys Thr Glu Gly Thr Leu Glu Asn Cys Glu Thr Lys Cys Gln Thr Pro
20 25 30

Leu Gly Ala Ile Asn Thr Thr Leu Pro Phe His Asn Val His Pro Leu
35 40 45

Thr Ile Gly Glu Cys Pro Lys Tyr Val Lys Ser Glu Arg Leu Val Leu
50 55 60

Ala Thr Gly Leu Arg Asn Val Pro Gln Ile Glu Ser Arg
65 70 75

<210> SEQ ID NO 498
<211> LENGTH: 76
<212> TYPE: PRT
<213> ORGANISM: Influenza virus A
<220> FEATURE:
<223> OTHER INFORMATION: C-termianl long stem domain segment of Influenza A HA subtype H2(No Cys, Ala - Delta 1)

<400> SEQUENCE: 498

Glu Tyr Gly Phe Arg Ile Ser Lys Arg Gly Ser Ser Gly Ile Met Lys
1 5 10 15

Thr Glu Gly Thr Leu Glu Asn Cys Glu Thr Lys Cys Gln Thr Pro Leu
20 25 30

Gly Ala Ile Asn Thr Thr Leu Pro Phe His Asn Val His Pro Leu Thr
35 40 45

Ile Gly Glu Cys Pro Lys Tyr Val Lys Ser Glu Arg Leu Val Leu Ala
50 55 60

Thr Gly Leu Arg Asn Val Pro Gln Ile Glu Ser Arg
65 70 75

<210> SEQ ID NO 499
<211> LENGTH: 75
<212> TYPE: PRT
<213> ORGANISM: Influenza virus A
<220> FEATURE:
<223> OTHER INFORMATION: C-termianl long stem domain segment of Influenza A HA subtype H2(No Cys, Ala - Delta 3)

<400> SEQUENCE: 499

Tyr Gly Phe Arg Ile Ser Lys Arg Gly Ser Ser Gly Ile Met Lys Thr
1 5 10 15

Glu Gly Thr Leu Glu Asn Cys Glu Thr Lys Cys Gln Thr Pro Leu Gly
20 25 30

Ala Ile Asn Thr Thr Leu Pro Phe His Asn Val His Pro Leu Thr Ile
35 40 45

Gly Glu Cys Pro Lys Tyr Val Lys Ser Glu Arg Leu Val Leu Ala Thr
50 55 60

Gly Leu Arg Asn Val Pro Gln Ile Glu Ser Arg
65 70 75

<210> SEQ ID NO 500
<211> LENGTH: 76
<212> TYPE: PRT
<213> ORGANISM: Influenza virus A
<220> FEATURE:
<223> OTHER INFORMATION: C-termianl long stem domain segment of Influenza A HA subtype H3(No Cys, Ala)

<400> SEQUENCE: 500

Pro Arg Gly Tyr Phe Lys Met Arg Thr Gly Lys Ser Ser Ile Met Ser
1 5 10 15

Ser Asp Ala Pro Ile Asp Thr Cys Ile Ser Glu Cys Ile Thr Pro Asn
20 25 30

Gly Ser Ile Pro Asn Asp Lys Pro Phe Gln Asn Val Asn Lys Ile Thr
35 40 45

Tyr Gly Ala Cys Pro Lys Tyr Val Lys Gln Asn Thr Leu Lys Leu Ala
50 55 60

Thr Gly Met Arg Asn Val Pro Glu Lys Gln Thr Arg
65 70 75

<210> SEQ ID NO 501
<211> LENGTH: 75
<212> TYPE: PRT
<213> ORGANISM: Influenza virus A
<220> FEATURE:
<223> OTHER INFORMATION: C-termianl long stem domain segment of Influenza A HA subtype H3(No Cys, Ala - Delta 1)

<400> SEQUENCE: 501

Arg Gly Tyr Phe Lys Met Arg Thr Gly Lys Ser Ser Ile Met Ser Ser
1 5 10 15

Asp Ala Pro Ile Asp Thr Cys Ile Ser Glu Cys Ile Thr Pro Asn Gly
20 25 30

Ser Ile Pro Asn Asp Lys Pro Phe Gln Asn Val Asn Lys Ile Thr Tyr
35 40 45

Gly Ala Cys Pro Lys Tyr Val Lys Gln Asn Thr Leu Lys Leu Ala Thr
50 55 60

Gly Met Arg Asn Val Pro Glu Lys Gln Thr Arg
65 70 75

<210> SEQ ID NO 502
<211> LENGTH: 74
<212> TYPE: PRT
<213> ORGANISM: Influenza virus A
<220> FEATURE:
<223> OTHER INFORMATION: C-termianl long stem domain segment of Influenza A HA subtype H3(No Cys, Ala - Delta 3)

<400> SEQUENCE: 502

Gly Tyr Phe Lys Met Arg Thr Gly Lys Ser Ser Ile Met Ser Ser Asp
1 5 10 15

Ala Pro Ile Asp Thr Cys Ile Ser Glu Cys Ile Thr Pro Asn Gly Ser
20 25 30

Ile Pro Asn Asp Lys Pro Phe Gln Asn Val Asn Lys Ile Thr Tyr Gly
35 40 45

Ala Cys Pro Lys Tyr Val Lys Gln Asn Thr Leu Lys Leu Ala Thr Gly
50 55 60

Met Arg Asn Val Pro Glu Lys Gln Thr Arg
65 70

<210> SEQ ID NO 503
<211> LENGTH: 77
<212> TYPE: PRT
<213> ORGANISM: Influenza virus A
<220> FEATURE:
<223> OTHER INFORMATION: C-termianl long stem domain segment of Influenza A HA subtype H4(No Cys, Ala)

<400> SEQUENCE: 503

Pro Arg Gly His Tyr Lys Leu Asn Asn Gln Lys Lys Ser Thr Ile Leu
1 5 10 15

Asn Thr Ala Ile Pro Ile Gly Ser Cys Val Ser Lys Cys His Thr Asp
20 25 30

Lys Gly Ser Leu Ser Thr Thr Lys Pro Phe Gln Asn Ile Ser Arg Ile
35 40 45

Ala Val Gly Asp Cys Pro Arg Tyr Val Lys Gln Gly Ser Leu Lys Leu
50 55 60

Ala Thr Gly Met Arg Asn Ile Pro Glu Lys Ala Ser Arg
65 70 75

<210> SEQ ID NO 504
<211> LENGTH: 76
<212> TYPE: PRT
<213> ORGANISM: Influenza virus A
<220> FEATURE:
<223> OTHER INFORMATION: C-termianl long stem domain segment of Influenza A HA subtype H4(No Cys, Ala - Delta 1)

<400> SEQUENCE: 504

Arg Gly His Tyr Lys Leu Asn Asn Gln Lys Lys Ser Thr Ile Leu Asn
1 5 10 15

Thr Ala Ile Pro Ile Gly Ser Cys Val Ser Lys Cys His Thr Asp Lys
20 25 30

Gly Ser Leu Ser Thr Thr Lys Pro Phe Gln Asn Ile Ser Arg Ile Ala
35 40 45

Val Gly Asp Cys Pro Arg Tyr Val Lys Gln Gly Ser Leu Lys Leu Ala
50 55 60

Thr Gly Met Arg Asn Ile Pro Glu Lys Ala Ser Arg

```
65                  70                  75


<210> SEQ ID NO 505
<211> LENGTH: 75
<212> TYPE: PRT
<213> ORGANISM: Influenza virus A
<220> FEATURE:
<223> OTHER INFORMATION: C-termianl long stem domain segment of
      Influenza A HA subtype H4(No Cys, Ala - Delta 3)

<400> SEQUENCE: 505

Gly His Tyr Lys Leu Asn Asn Gln Lys Lys Ser Thr Ile Leu Asn Thr
 1               5                  10                  15

Ala Ile Pro Ile Gly Ser Cys Val Ser Lys Cys His Thr Asp Lys Gly
            20                  25                  30

Ser Leu Ser Thr Thr Lys Pro Phe Gln Asn Ile Ser Arg Ile Ala Val
        35                  40                  45

Gly Asp Cys Pro Arg Tyr Val Lys Gln Gly Ser Leu Lys Leu Ala Thr
    50                  55                  60

Gly Met Arg Asn Ile Pro Glu Lys Ala Ser Arg
65                  70                  75


<210> SEQ ID NO 506
<211> LENGTH: 77
<212> TYPE: PRT
<213> ORGANISM: Influenza virus A
<220> FEATURE:
<223> OTHER INFORMATION: C-termianl long stem domain segment of
      Influenza A HA subtype H5(No Cys, Ala)

<400> SEQUENCE: 506

Pro Arg Tyr Ala Tyr Lys Ile Val Lys Lys Gly Asp Ser Ala Ile Met
 1               5                  10                  15

Lys Ser Gly Leu Ala Tyr Gly Asn Cys Asp Thr Lys Cys Gln Thr Pro
            20                  25                  30

Val Gly Glu Ile Asn Ser Ser Met Pro Phe His Asn Ile His Pro His
        35                  40                  45

Thr Ile Gly Glu Cys Pro Lys Tyr Val Lys Ser Asp Arg Leu Val Leu
    50                  55                  60

Ala Thr Gly Leu Arg Asn Val Pro Gln Arg Lys Lys Arg
65                  70                  75


<210> SEQ ID NO 507
<211> LENGTH: 76
<212> TYPE: PRT
<213> ORGANISM: Influenza virus A
<220> FEATURE:
<223> OTHER INFORMATION: C-termianl long stem domain segment of
      Influenza A HA subtype H5(No Cys, Ala - Delta 1)

<400> SEQUENCE: 507

Arg Tyr Ala Tyr Lys Ile Val Lys Lys Gly Asp Ser Ala Ile Met Lys
 1               5                  10                  15

Ser Gly Leu Ala Tyr Gly Asn Cys Asp Thr Lys Cys Gln Thr Pro Val
            20                  25                  30

Gly Glu Ile Asn Ser Ser Met Pro Phe His Asn Ile His Pro His Thr
        35                  40                  45

Ile Gly Glu Cys Pro Lys Tyr Val Lys Ser Asp Arg Leu Val Leu Ala
    50                  55                  60

Thr Gly Leu Arg Asn Val Pro Gln Arg Lys Lys Arg
65                  70                  75
```

<210> SEQ ID NO 508
<211> LENGTH: 75
<212> TYPE: PRT
<213> ORGANISM: Influenza virus A
<220> FEATURE:
<223> OTHER INFORMATION: C-termianl long stem domain segment of Influenza A HA subtype H5(No Cys, Ala - Delta 3)

<400> SEQUENCE: 508

```
Tyr Ala Tyr Lys Ile Val Lys Lys Gly Asp Ser Ala Ile Met Lys Ser
 1               5                  10                  15

Gly Leu Ala Tyr Gly Asn Cys Asp Thr Lys Cys Gln Thr Pro Val Gly
            20                  25                  30

Glu Ile Asn Ser Ser Met Pro Phe His Asn Ile His Pro His Thr Ile
        35                  40                  45

Gly Glu Cys Pro Lys Tyr Val Lys Ser Asp Arg Leu Val Leu Ala Thr
    50                  55                  60

Gly Leu Arg Asn Val Pro Gln Arg Lys Lys Arg
65                  70                  75
```

<210> SEQ ID NO 509
<211> LENGTH: 78
<212> TYPE: PRT
<213> ORGANISM: Influenza virus A
<220> FEATURE:
<223> OTHER INFORMATION: C-termianl long stem domain segment of Influenza A HA subtype H6(No Cys, Ala)

<400> SEQUENCE: 509

```
Pro Trp Tyr Ala Phe Arg Phe Val Ser Thr Ser Asn Lys Gly Ala Val
 1               5                  10                  15

Phe Lys Ser Asn Leu Pro Ile Glu Asn Cys Asp Ala Thr Cys Gln Thr
            20                  25                  30

Val Ala Gly Val Leu Arg Thr Asn Lys Thr Phe Gln Asn Val Ser Pro
        35                  40                  45

Leu Trp Ile Gly Glu Cys Pro Lys Tyr Val Lys Ser Glu Ser Leu Arg
    50                  55                  60

Leu Ala Thr Gly Leu Arg Asn Val Pro Gln Ile Glu Thr Arg
65                  70                  75
```

<210> SEQ ID NO 510
<211> LENGTH: 77
<212> TYPE: PRT
<213> ORGANISM: Influenza virus A
<220> FEATURE:
<223> OTHER INFORMATION: C-termianl long stem domain segment of Influenza A HA subtype H6(No Cys, Ala - Delta 1)

<400> SEQUENCE: 510

```
Trp Tyr Ala Phe Arg Phe Val Ser Thr Ser Asn Lys Gly Ala Val Phe
 1               5                  10                  15

Lys Ser Asn Leu Pro Ile Glu Asn Cys Asp Ala Thr Cys Gln Thr Val
            20                  25                  30

Ala Gly Val Leu Arg Thr Asn Lys Thr Phe Gln Asn Val Ser Pro Leu
        35                  40                  45

Trp Ile Gly Glu Cys Pro Lys Tyr Val Lys Ser Glu Ser Leu Arg Leu
    50                  55                  60

Ala Thr Gly Leu Arg Asn Val Pro Gln Ile Glu Thr Arg
65                  70                  75
```

```
<210> SEQ ID NO 511
<211> LENGTH: 76
<212> TYPE: PRT
<213> ORGANISM: Influenza virus A
<220> FEATURE:
<223> OTHER INFORMATION: C-termianl long stem domain segment of
      Influenza A HA subtype H6(No Cys, Ala - Delta 3)

<400> SEQUENCE: 511

Tyr Ala Phe Arg Phe Val Ser Thr Ser Asn Lys Gly Ala Val Phe Lys
 1               5                  10                  15

Ser Asn Leu Pro Ile Glu Asn Cys Asp Ala Thr Cys Gln Thr Val Ala
            20                  25                  30

Gly Val Leu Arg Thr Asn Lys Thr Phe Gln Asn Val Ser Pro Leu Trp
        35                  40                  45

Ile Gly Glu Cys Pro Lys Tyr Val Lys Ser Glu Ser Leu Arg Leu Ala
    50                  55                  60

Thr Gly Leu Arg Asn Val Pro Gln Ile Glu Thr Arg
65                  70                  75


<210> SEQ ID NO 512
<211> LENGTH: 80
<212> TYPE: PRT
<213> ORGANISM: Influenza virus A
<220> FEATURE:
<223> OTHER INFORMATION: C-termianl long stem domain segment of
      Influenza A HA subtype H7(No Cys, Ala)

<400> SEQUENCE: 512

Pro Asn Arg Ala Ser Phe Leu Arg Gly Lys Ser Met Gly Ile Gln Ser
 1               5                  10                  15

Asp Val Gln Val Asp Ala Asn Cys Glu Gly Glu Cys Tyr His Ser Gly
            20                  25                  30

Gly Thr Ile Thr Ser Arg Leu Pro Phe Gln Asn Ile Asn Ser Arg Ala
        35                  40                  45

Val Gly Lys Cys Pro Arg Tyr Val Lys Gln Glu Ser Leu Leu Leu Ala
    50                  55                  60

Thr Gly Met Lys Asn Val Pro Glu Pro Ser Lys Lys Arg Lys Lys Arg
65                  70                  75                  80


<210> SEQ ID NO 513
<211> LENGTH: 79
<212> TYPE: PRT
<213> ORGANISM: Influenza virus A
<220> FEATURE:
<223> OTHER INFORMATION: C-termianl long stem domain segment of
      Influenza A HA subtype H7(No Cys, Ala - Delta 1)

<400> SEQUENCE: 513

Asn Arg Ala Ser Phe Leu Arg Gly Lys Ser Met Gly Ile Gln Ser Asp
 1               5                  10                  15

Val Gln Val Asp Ala Asn Cys Glu Gly Glu Cys Tyr His Ser Gly Gly
            20                  25                  30

Thr Ile Thr Ser Arg Leu Pro Phe Gln Asn Ile Asn Ser Arg Ala Val
        35                  40                  45

Gly Lys Cys Pro Arg Tyr Val Lys Gln Glu Ser Leu Leu Leu Ala Thr
    50                  55                  60

Gly Met Lys Asn Val Pro Glu Pro Ser Lys Lys Arg Lys Lys Arg
65                  70                  75
```

<210> SEQ ID NO 514
<211> LENGTH: 78
<212> TYPE: PRT
<213> ORGANISM: Influenza virus A
<220> FEATURE:
<223> OTHER INFORMATION: C-termianl long stem domain segment of Influenza A HA subtype H7(No Cys, Ala - Delta 3)

<400> SEQUENCE: 514

```
Arg Ala Ser Phe Leu Arg Gly Lys Ser Met Gly Ile Gln Ser Asp Val
 1               5                  10                  15

Gln Val Asp Ala Asn Cys Glu Gly Glu Cys Tyr His Ser Gly Gly Thr
            20                  25                  30

Ile Thr Ser Arg Leu Pro Phe Gln Asn Ile Asn Ser Arg Ala Val Gly
        35                  40                  45

Lys Cys Pro Arg Tyr Val Lys Gln Glu Ser Leu Leu Leu Ala Thr Gly
    50                  55                  60

Met Lys Asn Val Pro Glu Pro Ser Lys Lys Arg Lys Lys Arg
65                  70                  75
```

<210> SEQ ID NO 515
<211> LENGTH: 78
<212> TYPE: PRT
<213> ORGANISM: Influenza virus A
<220> FEATURE:
<223> OTHER INFORMATION: C-termianl long stem domain segment of Influenza A HA subtype H8(No Cys, Ala)

<400> SEQUENCE: 515

```
Pro Glu Phe Gly Tyr Leu Leu Lys Gly Glu Ser Tyr Gly Arg Ile Ile
 1               5                  10                  15

Gln Asn Glu Asp Ile Pro Ile Gly Asn Cys Asn Thr Lys Cys Gln Thr
            20                  25                  30

Tyr Ala Gly Ala Ile Asn Ser Ser Lys Pro Phe Gln Asn Ala Ser Arg
        35                  40                  45

His Tyr Met Gly Glu Cys Pro Lys Tyr Val Lys Lys Ala Ser Leu Arg
    50                  55                  60

Leu Ala Val Gly Leu Arg Asn Thr Pro Ser Val Glu Pro Arg
65                  70                  75
```

<210> SEQ ID NO 516
<211> LENGTH: 77
<212> TYPE: PRT
<213> ORGANISM: Influenza virus A
<220> FEATURE:
<223> OTHER INFORMATION: C-termianl long stem domain segment of Influenza A HA subtype H8(No Cys, Ala - Delta 1)

<400> SEQUENCE: 516

```
Glu Phe Gly Tyr Leu Leu Lys Gly Glu Ser Tyr Gly Arg Ile Ile Gln
 1               5                  10                  15

Asn Glu Asp Ile Pro Ile Gly Asn Cys Asn Thr Lys Cys Gln Thr Tyr
            20                  25                  30

Ala Gly Ala Ile Asn Ser Ser Lys Pro Phe Gln Asn Ala Ser Arg His
        35                  40                  45

Tyr Met Gly Glu Cys Pro Lys Tyr Val Lys Lys Ala Ser Leu Arg Leu
    50                  55                  60

Ala Val Gly Leu Arg Asn Thr Pro Ser Val Glu Pro Arg
65                  70                  75
```

<210> SEQ ID NO 517

```
<211> LENGTH: 76
<212> TYPE: PRT
<213> ORGANISM: Influenza virus A
<220> FEATURE:
<223> OTHER INFORMATION: C-termianl long stem domain segment of
      Influenza A HA subtype H8(No Cys, Ala - Delta 3)

<400> SEQUENCE: 517

Phe Gly Tyr Leu Leu Lys Gly Glu Ser Tyr Gly Arg Ile Ile Gln Asn
 1               5                  10                  15

Glu Asp Ile Pro Ile Gly Asn Cys Asn Thr Lys Cys Gln Thr Tyr Ala
            20                  25                  30

Gly Ala Ile Asn Ser Ser Lys Pro Phe Gln Asn Ala Ser Arg His Tyr
        35                  40                  45

Met Gly Glu Cys Pro Lys Tyr Val Lys Lys Ala Ser Leu Arg Leu Ala
    50                  55                  60

Val Gly Leu Arg Asn Thr Pro Ser Val Glu Pro Arg
65                  70                  75


<210> SEQ ID NO 518
<211> LENGTH: 77
<212> TYPE: PRT
<213> ORGANISM: Influenza virus A
<220> FEATURE:
<223> OTHER INFORMATION: C-termianl long stem domain segment of
      Influenza A HA subtype H9(No Cys, Ala)

<400> SEQUENCE: 518

Pro Trp Tyr Gly His Val Leu Thr Gly Glu Ser His Gly Arg Ile Leu
 1               5                  10                  15

Lys Thr Asp Leu Asn Asn Gly Asn Cys Val Val Gln Cys Gln Thr Glu
            20                  25                  30

Lys Gly Gly Leu Asn Thr Thr Leu Pro Phe His Asn Ile Ser Lys Tyr
        35                  40                  45

Ala Phe Gly Asn Cys Pro Lys Tyr Val Gly Val Lys Ser Leu Lys Leu
    50                  55                  60

Pro Val Gly Leu Arg Asn Val Pro Ala Val Ser Ser Arg
65                  70                  75


<210> SEQ ID NO 519
<211> LENGTH: 76
<212> TYPE: PRT
<213> ORGANISM: Influenza virus A
<220> FEATURE:
<223> OTHER INFORMATION: C-termianl long stem domain segment of
      Influenza A HA subtype H9(No Cys, Ala - Delta 1)

<400> SEQUENCE: 519

Trp Tyr Gly His Val Leu Thr Gly Glu Ser His Gly Arg Ile Leu Lys
 1               5                  10                  15

Thr Asp Leu Asn Asn Gly Asn Cys Val Val Gln Cys Gln Thr Glu Lys
            20                  25                  30

Gly Gly Leu Asn Thr Thr Leu Pro Phe His Asn Ile Ser Lys Tyr Ala
        35                  40                  45

Phe Gly Asn Cys Pro Lys Tyr Val Gly Val Lys Ser Leu Lys Leu Pro
    50                  55                  60

Val Gly Leu Arg Asn Val Pro Ala Val Ser Ser Arg
65                  70                  75


<210> SEQ ID NO 520
<211> LENGTH: 75
```

```
<212> TYPE: PRT
<213> ORGANISM: Influenza virus A
<220> FEATURE:
<223> OTHER INFORMATION: C-termianl long stem domain segment of
      Influenza A HA subtype H9(No Cys, Ala - Delta 3)

<400> SEQUENCE: 520

Tyr Gly His Val Leu Thr Gly Glu Ser His Gly Arg Ile Leu Lys Thr
 1               5                  10                  15

Asp Leu Asn Asn Gly Asn Cys Val Val Gln Cys Gln Thr Glu Lys Gly
            20                  25                  30

Gly Leu Asn Thr Thr Leu Pro Phe His Asn Ile Ser Lys Tyr Ala Phe
        35                  40                  45

Gly Asn Cys Pro Lys Tyr Val Gly Val Lys Ser Leu Lys Leu Pro Val
    50                  55                  60

Gly Leu Arg Asn Val Pro Ala Val Ser Ser Arg
65                  70                  75


<210> SEQ ID NO 521
<211> LENGTH: 77
<212> TYPE: PRT
<213> ORGANISM: Influenza virus A
<220> FEATURE:
<223> OTHER INFORMATION: C-termianl long stem domain segment of
      Influenza A HA subtype H10(No Cys, Ala)

<400> SEQUENCE: 521

Pro Ser Arg Val Ser Lys Leu Thr Gly Arg Asp Leu Gly Ile Gln Ser
 1               5                  10                  15

Glu Ala Leu Ile Asp Asn Ser Cys Glu Ser Lys Cys Phe Trp Arg Gly
            20                  25                  30

Gly Ser Ile Asn Thr Lys Leu Pro Phe Gln Asn Leu Ser Pro Arg Thr
        35                  40                  45

Val Gly Gln Cys Pro Lys Tyr Val Asn Gln Arg Ser Leu Leu Leu Ala
    50                  55                  60

Thr Gly Met Arg Asn Val Pro Glu Val Val Gln Gly Arg
65                  70                  75


<210> SEQ ID NO 522
<211> LENGTH: 76
<212> TYPE: PRT
<213> ORGANISM: Influenza virus A
<220> FEATURE:
<223> OTHER INFORMATION: C-termianl long stem domain segment of
      Influenza A HA subtype H10(No Cys, Ala - Delta 1)

<400> SEQUENCE: 522

Ser Arg Val Ser Lys Leu Thr Gly Arg Asp Leu Gly Ile Gln Ser Glu
 1               5                  10                  15

Ala Leu Ile Asp Asn Ser Cys Glu Ser Lys Cys Phe Trp Arg Gly Gly
            20                  25                  30

Ser Ile Asn Thr Lys Leu Pro Phe Gln Asn Leu Ser Pro Arg Thr Val
        35                  40                  45

Gly Gln Cys Pro Lys Tyr Val Asn Gln Arg Ser Leu Leu Leu Ala Thr
    50                  55                  60

Gly Met Arg Asn Val Pro Glu Val Val Gln Gly Arg
65                  70                  75


<210> SEQ ID NO 523
<211> LENGTH: 75
<212> TYPE: PRT
```

<213> ORGANISM: Influenza virus A
<220> FEATURE:
<223> OTHER INFORMATION: C-termianl long stem domain segment of
      Influenza A HA subtype H10(No Cys, Ala - Delta 3)

<400> SEQUENCE: 523

```
Arg Val Ser Lys Leu Thr Gly Arg Asp Leu Gly Ile Gln Ser Glu Ala
 1               5                  10                  15

Leu Ile Asp Asn Ser Cys Glu Ser Lys Cys Phe Trp Arg Gly Gly Ser
            20                  25                  30

Ile Asn Thr Lys Leu Pro Phe Gln Asn Leu Ser Pro Arg Thr Val Gly
        35                  40                  45

Gln Cys Pro Lys Tyr Val Asn Gln Arg Ser Leu Leu Leu Ala Thr Gly
    50                  55                  60

Met Arg Asn Val Pro Glu Val Val Gln Gly Arg
65                  70                  75
```

<210> SEQ ID NO 524
<211> LENGTH: 77
<212> TYPE: PRT
<213> ORGANISM: Influenza virus A
<220> FEATURE:
<223> OTHER INFORMATION: C-termianl long stem domain segment of
      Influenza A HA subtype H11(No Cys, Ala)

<400> SEQUENCE: 524

```
Pro Arg Tyr Ala Phe Glu Ile Val Ser Val Gly Asn Gly Lys Leu Phe
 1               5                  10                  15

Arg Ser Glu Leu Asn Ile Glu Ser Cys Ser Thr Lys Cys Gln Thr Glu
            20                  25                  30

Ile Gly Gly Ile Asn Thr Asn Lys Ser Phe His Asn Val His Arg Asn
        35                  40                  45

Thr Ile Gly Asp Cys Pro Lys Tyr Val Asn Val Lys Ser Leu Lys Leu
    50                  55                  60

Ala Thr Gly Pro Arg Asn Val Pro Ala Ile Ala Ser Arg
65                  70                  75
```

<210> SEQ ID NO 525
<211> LENGTH: 76
<212> TYPE: PRT
<213> ORGANISM: Influenza virus A
<220> FEATURE:
<223> OTHER INFORMATION: C-termianl long stem domain segment of
      Influenza A HA subtype H11(No Cys, Ala - Delta 1)

<400> SEQUENCE: 525

```
Arg Tyr Ala Phe Glu Ile Val Ser Val Gly Asn Gly Lys Leu Phe Arg
 1               5                  10                  15

Ser Glu Leu Asn Ile Glu Ser Cys Ser Thr Lys Cys Gln Thr Glu Ile
            20                  25                  30

Gly Gly Ile Asn Thr Asn Lys Ser Phe His Asn Val His Arg Asn Thr
        35                  40                  45

Ile Gly Asp Cys Pro Lys Tyr Val Asn Val Lys Ser Leu Lys Leu Ala
    50                  55                  60

Thr Gly Pro Arg Asn Val Pro Ala Ile Ala Ser Arg
65                  70                  75
```

<210> SEQ ID NO 526
<211> LENGTH: 75
<212> TYPE: PRT
<213> ORGANISM: Influenza virus A
<220> FEATURE:
<223> OTHER INFORMATION: C-termianl long stem domain segment of Influenza A HA subtype H11(No Cys, Ala - Delta 3)

<400> SEQUENCE: 526

```
Tyr Ala Phe Glu Ile Val Ser Val Gly Asn Gly Lys Leu Phe Arg Ser
 1               5                  10                  15

Glu Leu Asn Ile Glu Ser Cys Ser Thr Lys Cys Gln Thr Glu Ile Gly
            20                  25                  30

Gly Ile Asn Thr Asn Lys Ser Phe His Asn Val His Arg Asn Thr Ile
        35                  40                  45

Gly Asp Cys Pro Lys Tyr Val Asn Val Lys Ser Leu Lys Leu Ala Thr
    50                  55                  60

Gly Pro Arg Asn Val Pro Ala Ile Ala Ser Arg
65                  70                  75
```

<210> SEQ ID NO 527
<211> LENGTH: 77
<212> TYPE: PRT
<213> ORGANISM: Influenza virus A
<220> FEATURE:
<223> OTHER INFORMATION: C-termianl long stem domain segment of Influenza A HA subtype H12(No Cys, Ala)

<400> SEQUENCE: 527

```
Pro Glu Tyr Gly His Leu Ile Thr Gly Lys Ser His Gly Arg Ile Leu
 1               5                  10                  15

Lys Asn Asn Leu Pro Met Gly Gln Cys Val Thr Glu Cys Gln Leu Asn
            20                  25                  30

Glu Gly Val Met Asn Thr Ser Lys Pro Phe Gln Asn Thr Ser Lys His
        35                  40                  45

Tyr Ile Gly Lys Cys Pro Lys Tyr Ile Pro Ser Gly Ser Leu Lys Leu
    50                  55                  60

Ala Ile Gly Leu Arg Asn Val Pro Gln Val Gln Asp Arg
65                  70                  75
```

<210> SEQ ID NO 528
<211> LENGTH: 76
<212> TYPE: PRT
<213> ORGANISM: Influenza virus A
<220> FEATURE:
<223> OTHER INFORMATION: C-termianl long stem domain segment of Influenza A HA subtype H12(No Cys, Ala - Delta 1)

<400> SEQUENCE: 528

```
Glu Tyr Gly His Leu Ile Thr Gly Lys Ser His Gly Arg Ile Leu Lys
 1               5                  10                  15

Asn Asn Leu Pro Met Gly Gln Cys Val Thr Glu Cys Gln Leu Asn Glu
            20                  25                  30

Gly Val Met Asn Thr Ser Lys Pro Phe Gln Asn Thr Ser Lys His Tyr
        35                  40                  45

Ile Gly Lys Cys Pro Lys Tyr Ile Pro Ser Gly Ser Leu Lys Leu Ala
    50                  55                  60

Ile Gly Leu Arg Asn Val Pro Gln Val Gln Asp Arg
65                  70                  75
```

<210> SEQ ID NO 529
<211> LENGTH: 75
<212> TYPE: PRT
<213> ORGANISM: Influenza virus A
<220> FEATURE:

<223> OTHER INFORMATION: C-termianl long stem domain segment of
Influenza A HA subtype H12(No Cys, Ala - Delta 3)

<400> SEQUENCE: 529

```
Tyr Gly His Leu Ile Thr Gly Lys Ser His Gly Arg Ile Leu Lys Asn
 1              5                   10                  15

Asn Leu Pro Met Gly Gln Cys Val Thr Glu Cys Gln Leu Asn Glu Gly
            20                  25                  30

Val Met Asn Thr Ser Lys Pro Phe Gln Asn Thr Ser Lys His Tyr Ile
        35                  40                  45

Gly Lys Cys Pro Lys Tyr Ile Pro Ser Gly Ser Leu Lys Leu Ala Ile
    50                  55                  60

Gly Leu Arg Asn Val Pro Gln Val Gln Asp Arg
65                  70                  75
```

<210> SEQ ID NO 530
<211> LENGTH: 77
<212> TYPE: PRT
<213> ORGANISM: Influenza virus A
<220> FEATURE:
<223> OTHER INFORMATION: C-termianl long stem domain segment of
Influenza A HA subtype H13(No Cys, Ala)

<400> SEQUENCE: 530

```
Pro Arg Tyr Gly Tyr Ile Ile Glu Glu Tyr Gly Lys Gly Arg Ile Phe
 1              5                   10                  15

Gln Ser Arg Ile Arg Met Ser Arg Cys Asn Thr Lys Cys Gln Thr Ser
            20                  25                  30

Val Gly Gly Ile Asn Thr Asn Arg Thr Phe Gln Asn Ile Asp Lys Asn
        35                  40                  45

Ala Leu Gly Asp Cys Pro Lys Tyr Ile Lys Ser Gly Gln Leu Lys Leu
    50                  55                  60

Ala Thr Gly Leu Arg Asn Val Pro Ala Ile Ser Asn Arg
65                  70                  75
```

<210> SEQ ID NO 531
<211> LENGTH: 76
<212> TYPE: PRT
<213> ORGANISM: Influenza virus A
<220> FEATURE:
<223> OTHER INFORMATION: C-termianl long stem domain segment of
Influenza A HA subtype H13(No Cys, Ala - Delta 1)

<400> SEQUENCE: 531

```
Arg Tyr Gly Tyr Ile Ile Glu Glu Tyr Gly Lys Gly Arg Ile Phe Gln
 1              5                   10                  15

Ser Arg Ile Arg Met Ser Arg Cys Asn Thr Lys Cys Gln Thr Ser Val
            20                  25                  30

Gly Gly Ile Asn Thr Asn Arg Thr Phe Gln Asn Ile Asp Lys Asn Ala
        35                  40                  45

Leu Gly Asp Cys Pro Lys Tyr Ile Lys Ser Gly Gln Leu Lys Leu Ala
    50                  55                  60

Thr Gly Leu Arg Asn Val Pro Ala Ile Ser Asn Arg
65                  70                  75
```

<210> SEQ ID NO 532
<211> LENGTH: 75
<212> TYPE: PRT
<213> ORGANISM: Influenza virus A
<220> FEATURE:
<223> OTHER INFORMATION: C-termianl long stem domain segment of -continued Influenza A HA subtype H13(No Cys, Ala - Delta 3)

<400> SEQUENCE: 532

```
Tyr Gly Tyr Ile Ile Glu Glu Tyr Gly Lys Gly Arg Ile Phe Gln Ser
 1               5                  10                  15

Arg Ile Arg Met Ser Arg Cys Asn Thr Lys Cys Gln Thr Ser Val Gly
            20                  25                  30

Gly Ile Asn Thr Asn Arg Thr Phe Gln Asn Ile Asp Lys Asn Ala Leu
        35                  40                  45

Gly Asp Cys Pro Lys Tyr Ile Lys Ser Gly Gln Leu Lys Leu Ala Thr
    50                  55                  60

Gly Leu Arg Asn Val Pro Ala Ile Ser Asn Arg
65                  70                  75
```

<210> SEQ ID NO 533
<211> LENGTH: 77
<212> TYPE: PRT
<213> ORGANISM: Influenza virus A
<220> FEATURE:
<223> OTHER INFORMATION: C-termianl long stem domain segment of
Influenza A HA subtype H14(No Cys, Ala)

<400> SEQUENCE: 533

```
Pro Arg Gly His Tyr Lys Ile Ser Lys Ser Thr Lys Ser Thr Val Leu
 1               5                  10                  15

Lys Ser Asp Lys Arg Ile Gly Ser Cys Thr Ser Pro Cys Leu Thr Asp
            20                  25                  30

Lys Gly Ser Ile Gln Ser Asp Lys Pro Phe Gln Asn Val Ser Arg Ile
        35                  40                  45

Ala Ile Gly Asn Cys Pro Lys Tyr Val Lys Gln Gly Ser Leu Met Leu
    50                  55                  60

Ala Thr Gly Met Arg Asn Ile Pro Gly Lys Gln Ala Lys
65                  70                  75
```

<210> SEQ ID NO 534
<211> LENGTH: 76
<212> TYPE: PRT
<213> ORGANISM: Influenza virus A
<220> FEATURE:
<223> OTHER INFORMATION: C-termianl long stem domain segment of
Influenza A HA subtype H14(No Cys, Ala - Delta 1)

<400> SEQUENCE: 534

```
Arg Gly His Tyr Lys Ile Ser Lys Ser Thr Lys Ser Thr Val Leu Lys
 1               5                  10                  15

Ser Asp Lys Arg Ile Gly Ser Cys Thr Ser Pro Cys Leu Thr Asp Lys
            20                  25                  30

Gly Ser Ile Gln Ser Asp Lys Pro Phe Gln Asn Val Ser Arg Ile Ala
        35                  40                  45

Ile Gly Asn Cys Pro Lys Tyr Val Lys Gln Gly Ser Leu Met Leu Ala
    50                  55                  60

Thr Gly Met Arg Asn Ile Pro Gly Lys Gln Ala Lys
65                  70                  75
```

<210> SEQ ID NO 535
<211> LENGTH: 75
<212> TYPE: PRT
<213> ORGANISM: Influenza virus A
<220> FEATURE:
<223> OTHER INFORMATION: C-termianl long stem domain segment of
Influenza A HA subtype H14(No Cys, Ala - Delta 3)

<400> SEQUENCE: 535

```
Gly His Tyr Lys Ile Ser Lys Ser Thr Lys Ser Thr Val Leu Lys Ser
 1               5                  10                  15

Asp Lys Arg Ile Gly Ser Cys Thr Ser Pro Cys Leu Thr Asp Lys Gly
            20                  25                  30

Ser Ile Gln Ser Asp Lys Pro Phe Gln Asn Val Ser Arg Ile Ala Ile
        35                  40                  45

Gly Asn Cys Pro Lys Tyr Val Lys Gln Gly Ser Leu Met Leu Ala Thr
    50                  55                  60

Gly Met Arg Asn Ile Pro Gly Lys Gln Ala Lys
65                  70                  75
```

<210> SEQ ID NO 536
<211> LENGTH: 87
<212> TYPE: PRT
<213> ORGANISM: Influenza virus A
<220> FEATURE:
<223> OTHER INFORMATION: C-termianl long stem domain segment of Influenza A HA subtype H15(No Cys, Ala)

<400> SEQUENCE: 536

```
Pro Asp Arg Ala Thr Phe Leu Arg Ser Asn Ala Pro Ser Gly Ile Glu
 1               5                  10                  15

Tyr Asn Gly Lys Ser Leu Gly Ile Gln Ser Asp Ala Gln Ile Asp Glu
            20                  25                  30

Ser Cys Glu Gly Glu Cys Phe Tyr Ser Gly Gly Thr Ile Asn Ser Pro
        35                  40                  45

Leu Pro Phe Gln Asn Ile Asp Ser Arg Ala Val Gly Lys Cys Pro Arg
    50                  55                  60

Tyr Val Lys Gln Ser Ser Leu Pro Leu Ala Leu Gly Met Lys Asn Val
65                  70                  75                  80

Pro Glu Lys Ile Arg Thr Arg
                85
```

<210> SEQ ID NO 537
<211> LENGTH: 86
<212> TYPE: PRT
<213> ORGANISM: Influenza virus A
<220> FEATURE:
<223> OTHER INFORMATION: C-termianl long stem domain segment of Influenza A HA subtype H15(No Cys, Ala - Delta 1)

<400> SEQUENCE: 537

```
Asp Arg Ala Thr Phe Leu Arg Ser Asn Ala Pro Ser Gly Ile Glu Tyr
 1               5                  10                  15

Asn Gly Lys Ser Leu Gly Ile Gln Ser Asp Ala Gln Ile Asp Glu Ser
            20                  25                  30

Cys Glu Gly Glu Cys Phe Tyr Ser Gly Gly Thr Ile Asn Ser Pro Leu
        35                  40                  45

Pro Phe Gln Asn Ile Asp Ser Arg Ala Val Gly Lys Cys Pro Arg Tyr
    50                  55                  60

Val Lys Gln Ser Ser Leu Pro Leu Ala Leu Gly Met Lys Asn Val Pro
65                  70                  75                  80

Glu Lys Ile Arg Thr Arg
                85
```

<210> SEQ ID NO 538
<211> LENGTH: 85

```
<212> TYPE: PRT
<213> ORGANISM: Influenza virus A
<220> FEATURE:
<223> OTHER INFORMATION: C-termianl long stem domain segment of
      Influenza A HA subtype H15(No Cys, Ala - Delta 3)

<400> SEQUENCE: 538

Arg Ala Thr Phe Leu Arg Ser Asn Ala Pro Ser Gly Ile Glu Tyr Asn
 1               5                   10                  15

Gly Lys Ser Leu Gly Ile Gln Ser Asp Ala Gln Ile Asp Glu Ser Cys
            20                  25                  30

Glu Gly Glu Cys Phe Tyr Ser Gly Gly Thr Ile Asn Ser Pro Leu Pro
        35                  40                  45

Phe Gln Asn Ile Asp Ser Arg Ala Val Gly Lys Cys Pro Arg Tyr Val
    50                  55                  60

Lys Gln Ser Ser Leu Pro Leu Ala Leu Gly Met Lys Asn Val Pro Glu
65                  70                  75                  80

Lys Ile Arg Thr Arg
                85


<210> SEQ ID NO 539
<211> LENGTH: 77
<212> TYPE: PRT
<213> ORGANISM: Influenza virus A
<220> FEATURE:
<223> OTHER INFORMATION: C-termianl long stem domain segment of
      Influenza A HA subtype H16(No Cys, Ala)

<400> SEQUENCE: 539

Pro Arg Tyr Gly Tyr Ile Ile Glu Lys Tyr Gly Thr Gly Arg Ile Phe
 1               5                   10                  15

Gln Ser Gly Val Arg Met Ala Arg Cys Asn Thr Lys Cys Gln Thr Ser
            20                  25                  30

Leu Gly Gly Ile Asn Thr Asn Lys Thr Phe Gln Asn Ile Glu Arg Asn
        35                  40                  45

Ala Leu Gly Asp Cys Pro Lys Tyr Ile Lys Ser Gly Gln Leu Lys Leu
    50                  55                  60

Ala Thr Gly Leu Arg Asn Val Pro Ser Ile Gly Glu Arg
65                  70                  75


<210> SEQ ID NO 540
<211> LENGTH: 76
<212> TYPE: PRT
<213> ORGANISM: Influenza virus A
<220> FEATURE:
<223> OTHER INFORMATION: C-termianl long stem domain segment of
      Influenza A HA subtype H16(No Cys, Ala - Delta 1)

<400> SEQUENCE: 540

Arg Tyr Gly Tyr Ile Ile Glu Lys Tyr Gly Thr Gly Arg Ile Phe Gln
 1               5                   10                  15

Ser Gly Val Arg Met Ala Arg Cys Asn Thr Lys Cys Gln Thr Ser Leu
            20                  25                  30

Gly Gly Ile Asn Thr Asn Lys Thr Phe Gln Asn Ile Glu Arg Asn Ala
        35                  40                  45

Leu Gly Asp Cys Pro Lys Tyr Ile Lys Ser Gly Gln Leu Lys Leu Ala
    50                  55                  60

Thr Gly Leu Arg Asn Val Pro Ser Ile Gly Glu Arg
65                  70                  75
```

<210> SEQ ID NO 541
<211> LENGTH: 75
<212> TYPE: PRT
<213> ORGANISM: Influenza virus A
<220> FEATURE:
<223> OTHER INFORMATION: C-termianl long stem domain segment of
Influenza A HA subtype H16(No Cys, Ala - Delta 3)

<400> SEQUENCE: 541

Tyr Gly Tyr Ile Ile Glu Lys Tyr Gly Thr Gly Arg Ile Phe Gln Ser
1 5 10 15

Gly Val Arg Met Ala Arg Cys Asn Thr Lys Cys Gln Thr Ser Leu Gly
20 25 30

Gly Ile Asn Thr Asn Lys Thr Phe Gln Asn Ile Glu Arg Asn Ala Leu
35 40 45

Gly Asp Cys Pro Lys Tyr Ile Lys Ser Gly Gln Leu Lys Leu Ala Thr
50 55 60

Gly Leu Arg Asn Val Pro Ser Ile Gly Glu Arg
65 70 75

<210> SEQ ID NO 542
<211> LENGTH: 16
<212> TYPE: PRT
<213> ORGANISM: Artificial Sequence
<220> FEATURE:
<223> OTHER INFORMATION: linker sequence

<400> SEQUENCE: 542

Lys Leu Asn Gly Ser Gly Ile Met Lys Thr Glu Gly Thr Leu Glu Asn
1 5 10 15

<210> SEQ ID NO 543
<211> LENGTH: 5
<212> TYPE: PRT
<213> ORGANISM: Artificial Sequence
<220> FEATURE:
<223> OTHER INFORMATION: linker sequence

<400> SEQUENCE: 543

Asn Asn Ile Asp Thr
1 5

<210> SEQ ID NO 544
<211> LENGTH: 5
<212> TYPE: PRT
<213> ORGANISM: Artificial Sequence
<220> FEATURE:
<223> OTHER INFORMATION: sequence of influenza HA polypeptide

<400> SEQUENCE: 544

Thr Gly Leu Arg Asn
1 5

<210> SEQ ID NO 545
<211> LENGTH: 12
<212> TYPE: PRT
<213> ORGANISM: Artificial Sequence
<220> FEATURE:
<223> OTHER INFORMATION: sequence of influenza HA polypeptide

<400> SEQUENCE: 545

Gly Ile Thr Asn Lys Val Asn Ser Val Ile Glu Lys
1 5 10

<210> SEQ ID NO 546

<211> LENGTH: 5
<212> TYPE: PRT
<213> ORGANISM: Artificial Sequence
<220> FEATURE:
<223> OTHER INFORMATION: linker sequence

<400> SEQUENCE: 546

Asn Asn Ile Asp Thr
 1               5

<210> SEQ ID NO 547
<211> LENGTH: 5
<212> TYPE: PRT
<213> ORGANISM: Artificial Sequence
<220> FEATURE:
<223> OTHER INFORMATION: sequence of influenza HA polypeptide

<400> SEQUENCE: 547

Thr Gly Met Arg Asn
 1               5

<210> SEQ ID NO 548
<211> LENGTH: 12
<212> TYPE: PRT
<213> ORGANISM: Artificial Sequence
<220> FEATURE:
<223> OTHER INFORMATION: sequence of influenza HA polypeptide

<400> SEQUENCE: 548

Gln Ile Asn Gly Lys Leu Asn Arg Leu Ile Glu Lys
 1               5                  10

<210> SEQ ID NO 549
<211> LENGTH: 12
<212> TYPE: PRT
<213> ORGANISM: Artificial Sequence
<220> FEATURE:
<223> OTHER INFORMATION: sequence of influenza HA polypeptide

<400> SEQUENCE: 549

Gln Ile Asn Gly Lys Leu Asn Arg Val Ile Glu Lys
 1               5                  10

<210> SEQ ID NO 550
<211> LENGTH: 94
<212> TYPE: PRT
<213> ORGANISM: Influenza virus B
<220> FEATURE:
<223> OTHER INFORMATION: HA1 N-terminal Stem Segment of Influenza
      B HA construct variant Cys94-Cys143

<400> SEQUENCE: 550

Asp Arg Ile Cys Thr Gly Ile Thr Ser Ser Asn Ser Pro His Val Val
 1               5                  10                  15

Lys Thr Ala Thr Gln Gly Glu Val Asn Val Thr Gly Val Ile Pro Leu
            20                  25                  30

Thr Thr Thr Pro Thr Lys Ser His Phe Ala Asn Leu Lys Gly Thr Gln
        35                  40                  45

Thr Arg Gly Lys Leu Cys Pro Asn Cys Leu Asn Cys Thr Asp Leu Asp
    50                  55                  60

Val Ala Leu Gly Arg Pro Lys Cys Met Gly Thr Ile Pro Ser Ala Lys
65                  70                  75                  80

Ala Ser Ile Leu His Glu Val Lys Pro Val Thr Ser Gly Cys
                85                  90

<210> SEQ ID NO 551
<211> LENGTH: 178
<212> TYPE: PRT
<213> ORGANISM: Influenza virus B
<220> FEATURE:
<223> OTHER INFORMATION: HA1 N-terminal Stem Segment of Influenza B HA construct variant Cys178-Cys272

<400> SEQUENCE: 551

Asp Arg Ile Cys Thr Gly Ile Thr Ser Ser Asn Ser Pro His Val Val
1 5 10 15

Lys Thr Ala Thr Gln Gly Glu Val Asn Val Thr Gly Val Ile Pro Leu
20 25 30

Thr Thr Thr Pro Thr Lys Ser His Phe Ala Asn Leu Lys Gly Thr Gln
35 40 45

Thr Arg Gly Lys Leu Cys Pro Asn Cys Leu Asn Cys Thr Asp Leu Asp
50 55 60

Val Ala Leu Gly Arg Pro Lys Cys Met Gly Thr Ile Pro Ser Ala Lys
65 70 75 80

Ala Ser Ile Leu His Glu Val Lys Pro Val Thr Ser Gly Cys Phe Pro
85 90 95

Ile Met His Asp Arg Thr Lys Ile Arg Gln Leu Pro Asn Leu Leu Arg
100 105 110

Gly Tyr Glu Asn Ile Arg Leu Ser Ala Arg Asn Val Thr Asn Ala Glu
115 120 125

Thr Ala Pro Gly Gly Pro Tyr Ile Val Gly Thr Ser Gly Ser Cys Pro
130 135 140

Asn Val Thr Asn Gly Asn Gly Phe Phe Ala Thr Met Ala Trp Ala Val
145 150 155 160

Pro Lys Asn Lys Thr Ala Thr Asn Pro Leu Thr Val Glu Val Pro Tyr
165 170 175

Ile Cys

<210> SEQ ID NO 552
<211> LENGTH: 54
<212> TYPE: PRT
<213> ORGANISM: Influenza virus B
<220> FEATURE:
<223> OTHER INFORMATION: HA1 N-terminal Stem Segment of Influenza B HA construct variant Cys54-Cys272

<400> SEQUENCE: 552

Asp Arg Ile Cys Thr Gly Ile Thr Ser Ser Asn Ser Pro His Val Val
1 5 10 15

Lys Thr Ala Thr Gln Gly Glu Val Asn Val Thr Gly Val Ile Pro Leu
20 25 30

Thr Thr Thr Pro Thr Lys Ser His Phe Ala Asn Leu Lys Gly Thr Gln
35 40 45

Thr Arg Gly Lys Leu Cys
50

<210> SEQ ID NO 553
<211> LENGTH: 200
<212> TYPE: PRT
<213> ORGANISM: Influenza virus B
<220> FEATURE:
<223> OTHER INFORMATION: HA1 C-terminal Stem Segment of Influenza B HA construct variant Cys94-Cys143

<400> SEQUENCE: 553

Cys Pro Asn Val Thr Asn Gly Asn Gly Phe Phe Ala Thr Met Ala Trp
1 5 10 15

Ala Val Pro Lys Asn Lys Thr Ala Thr Asn Pro Leu Thr Val Glu Val
20 25 30

Pro Tyr Ile Cys Thr Lys Gly Glu Asp Gln Ile Thr Val Trp Gly Phe
35 40 45

His Ser Asp Asp Glu Thr Gln Met Val Lys Leu Tyr Gly Asp Ser Lys
50 55 60

Pro Gln Lys Phe Thr Ser Ser Ala Asn Gly Val Thr Thr His Tyr Val
65 70 75 80

Ser Gln Ile Gly Gly Phe Pro Asn Gln Ala Glu Asp Glu Gly Leu Pro
85 90 95

Gln Ser Gly Arg Ile Val Val Asp Tyr Met Val Gln Lys Pro Gly Lys
100 105 110

Thr Gly Thr Ile Ala Tyr Gln Arg Gly Val Leu Leu Pro Gln Lys Val
115 120 125

Trp Cys Ala Ser Gly Arg Ser Lys Val Ile Lys Gly Ser Leu Pro Leu
130 135 140

Ile Gly Glu Ala Asp Cys Leu His Glu Lys Tyr Gly Gly Leu Asn Lys
145 150 155 160

Ser Lys Pro Tyr Tyr Thr Gly Glu His Ala Lys Ala Ile Gly Asn Cys
165 170 175

Pro Ile Trp Val Lys Thr Pro Leu Lys Leu Ala Asn Gly Thr Lys Tyr
180 185 190

Arg Pro Pro Ala Lys Leu Leu Lys
195 200

<210> SEQ ID NO 554
<211> LENGTH: 71
<212> TYPE: PRT
<213> ORGANISM: Influenza virus B
<220> FEATURE:
<223> OTHER INFORMATION: HA1 C-terminal Stem Segment of Influenza B HA construct variant Cys178-Cys272

<400> SEQUENCE: 554

Cys Ala Ser Gly Arg Ser Lys Val Ile Lys Gly Ser Leu Pro Leu Ile
1 5 10 15

Gly Glu Ala Asp Cys Leu His Glu Lys Tyr Gly Gly Leu Asn Lys Ser
20 25 30

Lys Pro Tyr Tyr Thr Gly Glu His Ala Lys Ala Ile Gly Asn Cys Pro
35 40 45

Ile Trp Val Lys Thr Pro Leu Lys Leu Ala Asn Gly Thr Lys Tyr Arg
50 55 60

Pro Pro Ala Lys Leu Leu Lys
65 70

<210> SEQ ID NO 555
<211> LENGTH: 94
<212> TYPE: PRT
<213> ORGANISM: Influenza virus B
<220> FEATURE:
<223> OTHER INFORMATION: HA1 N-terminal Stem Segment of Influenza B HA construct variant Cys94-Cys143-Cys178-Cys272

<400> SEQUENCE: 555

Asp Arg Ile Cys Thr Gly Ile Thr Ser Ser Asn Ser Pro His Val Val
1 5 10 15

```
Lys Thr Ala Thr Gln Gly Glu Val Asn Val Thr Gly Val Ile Pro Leu
            20                  25                  30

Thr Thr Thr Pro Thr Lys Ser His Phe Ala Asn Leu Lys Gly Thr Gln
        35                  40                  45

Thr Arg Gly Lys Leu Cys Pro Asn Cys Leu Asn Cys Thr Asp Leu Asp
    50                  55                  60

Val Ala Leu Gly Arg Pro Lys Cys Met Gly Thr Ile Pro Ser Ala Lys
65                  70                  75                  80

Ala Ser Ile Leu His Glu Val Lys Pro Val Thr Ser Gly Cys
                85                  90


<210> SEQ ID NO 556
<211> LENGTH: 36
<212> TYPE: PRT
<213> ORGANISM: Influenza virus B
<220> FEATURE:
<223> OTHER INFORMATION: HA1 intermediate Segment of
      Influenza B HA construct variant Cys94-Cys143-Cys178-Cys272

<400> SEQUENCE: 556

Cys Pro Asn Val Thr Asn Gly Asn Gly Phe Phe Ala Thr Met Ala Trp
 1               5                  10                  15

Ala Val Pro Lys Asn Lys Thr Ala Thr Asn Pro Leu Thr Val Glu Val
            20                  25                  30

Pro Tyr Ile Cys
        35


<210> SEQ ID NO 557
<211> LENGTH: 71
<212> TYPE: PRT
<213> ORGANISM: Influenza virus B
<220> FEATURE:
<223> OTHER INFORMATION: HA1 C-terminal Stem Segment
      of Influenza B HA construct variant Cys94-Cys143-Cys178-Cys272

<400> SEQUENCE: 557

Cys Ala Ser Gly Arg Ser Lys Val Ile Lys Gly Ser Leu Pro Leu Ile
 1               5                  10                  15

Gly Glu Ala Asp Cys Leu His Glu Lys Tyr Gly Gly Leu Asn Lys Ser
            20                  25                  30

Lys Pro Tyr Tyr Thr Gly Glu His Ala Lys Ala Ile Gly Asn Cys Pro
        35                  40                  45

Ile Trp Val Lys Thr Pro Leu Lys Leu Ala Asn Gly Thr Lys Tyr Arg
    50                  55                  60

Pro Pro Ala Lys Leu Leu Lys
65                  70


<210> SEQ ID NO 558
<211> LENGTH: 585
<212> TYPE: PRT
<213> ORGANISM: Influenza virus B
<220> FEATURE:
<223> OTHER INFORMATION: representative sequence of influenza virus
      B hemagglutinin (in Fig. 2)

<400> SEQUENCE: 558

Met Lys Ala Ile Ile Val Ile Leu Met Val Val Thr Ser Asn Ala Asp
 1               5                  10                  15

Arg Ile Cys Thr Gly Ile Thr Ser Ser Asn Ser Pro His Val Val Lys
            20                  25                  30
```

-continued

```
Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
        195                 200                 205

His Ser Asp Ser Glu Thr Gln Met Ala Lys Leu Tyr Gly Asp Ser Lys
    210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415
```

-continued

```
Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Ala Val Leu Leu
    450                 455                 460

Ser Asn Glu Thr Phe Asp Ser Leu Asn Ile Thr Ala Ala Ser Leu Asn
465                 470                 475                 480

Asp Asp Gly Leu Asp Asn His Thr Ile Leu Leu Tyr Tyr Ser Thr Ala
                485                 490                 495

Ala Ser Ser Leu Ala Val Thr Leu Met Ile Ala Ile Phe Val Val Tyr
            500                 505                 510

Met Val Ser Arg Asp Asn Val Ser Cys Ser Ile Cys Leu Gly Ile Ile
        515                 520                 525

Asn Ser Glu Asp Glu His Leu Leu Ala Leu Glu Arg Lys Leu Lys Lys
    530                 535                 540

Met Leu Gly Pro Ser Ala Val Glu Ile Gly Asn Gly Cys Phe Glu Thr
545                 550                 555                 560

Lys His Lys Cys Asn Gln Thr Cys Leu Asp Arg Ile Ala Ala Gly Thr
                565                 570                 575

Phe Asp Ala Gly Glu Phe Ser Leu Pro
            580                 585


<210> SEQ ID NO 559
<211> LENGTH: 16
<212> TYPE: PRT
<213> ORGANISM: Artificial Sequence
<220> FEATURE:
<223> OTHER INFORMATION: linker sequence

<400> SEQUENCE: 559

Lys Leu Asn Gly Ser Gly Ile Met Lys Thr Glu Gly Thr Leu Glu Asn
 1               5                  10                  15


<210> SEQ ID NO 560
<211> LENGTH: 4
<212> TYPE: PRT
<213> ORGANISM: Artificial Sequence
<220> FEATURE:
<223> OTHER INFORMATION: linker sequence

<400> SEQUENCE: 560

Gly Gly Gly Gly
 1


<210> SEQ ID NO 561
<211> LENGTH: 5
<212> TYPE: PRT
<213> ORGANISM: Artificial Sequence
<220> FEATURE:
<223> OTHER INFORMATION: linker sequence

<400> SEQUENCE: 561

Gly Gly Gly Gly Gly
 1               5
```